US012209249B2

(12) United States Patent
Xu et al.

(10) Patent No.: US 12,209,249 B2
(45) **Date of Patent: *Jan. 28, 2025**

(54) COMPOSITIONS AND METHODS FOR PRODUCING TOBACCO PLANTS AND PRODUCTS HAVING REDUCED OR ELIMINATED SUCKERS

(71) Applicant: ALTRIA CLIENT SERVICES LLC, Richmond, VA (US)

(72) Inventors: Dongmei Xu, Glen Allen, VA (US); Chengalrayan Kudithipudi, Midlothian, VA (US); Yanxin Shen, Glen Allen, VA (US); Jaemo Yang, Richmond, VA (US); Jesse Frederick, Richmond, VA (US); James Strickland, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/476,495

(22) Filed: Sep. 28, 2023

(65) Prior Publication Data

US 2024/0035042 A1 Feb. 1, 2024

Related U.S. Application Data

(63) Continuation of application No. 16/908,891, filed on Jun. 23, 2020, now Pat. No. 11,807,860, which is a continuation of application No. 15/457,553, filed on Mar. 13, 2017, now Pat. No. 10,731,173.

(60) Provisional application No. 62/399,181, filed on Sep. 23, 2016, provisional application No. 62/307,035, filed on Mar. 11, 2016.

(51) Int. Cl.

| | |
|---|---|
| ***C12N 15/82*** | (2006.01) |
| ***A24B 13/00*** | (2006.01) |
| ***A24B 15/10*** | (2006.01) |
| ***C07K 14/415*** | (2006.01) |

(52) U.S. Cl.
CPC .......... *C12N 15/8261* (2013.01); *A24B 13/00* (2013.01); *A24B 15/10* (2013.01); *C07K 14/415* (2013.01); *C12N 15/827* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 4,091,823 | A | 5/1978 | Kallianos et al. |
| 4,516,590 | A | 5/1985 | Teng |
| 4,528,993 | A | 7/1985 | Sensabaugh, Jr. et al. |
| 4,638,816 | A | 1/1987 | Cox et al. |
| 4,660,577 | A | 4/1987 | Sensabaugh, Jr. et al. |
| 4,732,856 | A | 3/1988 | Fedoroff |
| 4,762,785 | A | 9/1988 | Comai |
| 4,778,987 | A | 10/1988 | Saaski et al. |
| 4,848,373 | A | 7/1989 | Lenkey |
| 4,945,050 | A | 7/1990 | Sanford et al. |
| 4,987,907 | A | 1/1991 | Townsend |
| 5,004,863 | A | 4/1991 | Umbeck |
| 5,013,658 | A | 5/1991 | Dooner et al. |
| 5,085,325 | A | 2/1992 | Jones et al. |
| 5,104,310 | A | 4/1992 | Salt in |
| 5,141,131 | A | 8/1992 | Miller, Jr. et al. |
| 5,149,645 | A | 9/1992 | Hoekema et al. |
| 5,159,135 | A | 10/1992 | Umbeck |
| 5,177,010 | A | 1/1993 | Goldman et al. |
| 5,231,019 | A | 7/1993 | Paszkowski et al. |
| 5,316,931 | A | 5/1994 | Donson et al. |
| 5,372,149 | A | 12/1994 | Roth et al. |
| 5,463,174 | A | 10/1995 | Maloney et al. |
| 5,464,763 | A | 11/1995 | Schilperoort et al. |
| 5,469,976 | A | 11/1995 | Burchell |
| 5,491,081 | A | 2/1996 | Webb |
| 5,563,055 | A | 10/1996 | Townsend et al. |
| 5,565,350 | A | 10/1996 | Kmiec |
| 5,589,367 | A | 12/1996 | Donson et al. |
| 5,659,026 | A | 8/1997 | Baszczynski et al. |
| 5,689,035 | A | 11/1997 | Webb |
| 5,731,181 | A | 3/1998 | Kmiec |
| 5,756,325 | A | 5/1998 | Kmiec |

(Continued)

FOREIGN PATENT DOCUMENTS

| | | |
|---|---|---|
| CN | 001824774 | 8/2006 |
| CN | 104086637 | 10/2014 |

(Continued)

OTHER PUBLICATIONS

Jin, Hailing, et al. "Function of a mitogen-activated protein kinase pathway in N gene-mediated resistance in tobacco." The Plant Journal 33.4 (2003): 719-731. (Year: 2003).*
Benfey et al., 1989, "The CaMV 35S Enhancer Contains At Least Two Domains Which Can Confer Different Developmental and TissueSpecific Patterns", EMBO J, 8(8):2195-2202 (Year: 1989).*
Emery, John F., et al. "Radial patterning of *Arabidopsis* shoots by class III HD-ZIP and KANADI genes." Current Biology 13.20 (2003): 1768-1774. (Year: 2003).*
Bowie, James U., et al. "Deciphering the message in protein sequences: tolerance to amino acid substitutions." Science 247.4948 (1990): 1306-1310. (Year: 1990).*

(Continued)

*Primary Examiner* — Weihua Fan
(74) *Attorney, Agent, or Firm* — Arnold & Porter Kaye Scholer LLP

(57) ABSTRACT

The present disclosure provides the identification of genes involved in sucker growth in tobacco. Also provided are promoters that are preferentially active in tobacco axillary buds. Also provided are modified tobacco plants comprising reduced or no sucker growth. Also provided are methods and compositions for producing modified tobacco plants comprising reduced or no sucker growth.

20 Claims, 26 Drawing Sheets

Specification includes a Sequence Listing.

(56) References Cited

U.S. PATENT DOCUMENTS

| | | | | |
|---|---|---|---|---|
| 5,760,012 | A | 6/1998 | Kmiec et al. | |
| 5,789,156 | A | 8/1998 | Bujard et al. | |
| 5,795,972 | A | 8/1998 | Kmiec | |
| 5,814,618 | A | 9/1998 | Bujard et al. | |
| 5,866,785 | A | 2/1999 | Donson et al. | |
| 5,871,984 | A | 2/1999 | Kmiec | |
| 5,879,918 | A | 3/1999 | Tomes et al. | |
| 5,886,244 | A | 3/1999 | Tomes et al. | |
| 5,889,190 | A | 3/1999 | Donson et al. | |
| 5,889,191 | A | 3/1999 | Turpen | |
| 5,932,782 | A | 8/1999 | Bidney | |
| 5,981,840 | A | 11/1999 | Zhao et al. | |
| 6,072,050 | A | 6/2000 | Bowen et al. | |
| 8,124,851 | B2 | 2/2012 | Dewey et al. | |
| 8,319,011 | B2 | 11/2012 | Xu et al. | |
| 9,187,759 | B2 | 11/2015 | Dewey et al. | |
| 9,228,194 | B2 | 1/2016 | Dewey et al. | |
| 9,228,195 | B2 | 1/2016 | Dewey et al. | |
| 9,247,706 | B2 | 2/2016 | Dewey et al. | |
| 10,731,173 | B2 | 8/2020 | Xu et al. | |
| 2002/0008055 | A1 | 1/2002 | Campbell et al. | |
| 2004/0118422 | A1 | 6/2004 | Lundin et al. | |
| 2005/0057263 | A1 | 3/2005 | Moshe et al. | |
| 2005/0178398 | A1 | 8/2005 | Breslin et al. | |
| 2006/0035221 | A1 | 2/2006 | Bergmann et al. | |
| 2006/0191548 | A1 | 8/2006 | Strickland et al. | |
| 2006/0200878 | A1 | 9/2006 | Lutfiyya et al. | |
| 2009/0249518 | A1 | 10/2009 | Thomas et al. | |
| 2015/0315603 | A1* | 11/2015 | Bovet .................. | A24B 15/245 536/23.6 |
| 2016/0281100 | A1 | 9/2016 | Kudithipudi et al. | |
| 2017/0260535 | A1 | 9/2017 | Xu et al. | |
| 2020/0318129 | A1 | 10/2020 | Xu et al. | |

FOREIGN PATENT DOCUMENTS

| | | | |
|---|---|---|---|
| CN | 107250355 | A | 10/2017 |
| EP | 2383344 | | 11/2011 |
| WO | 0821866 | | 2/1998 |
| WO | WO 1998/05199 | | 2/1998 |
| WO | WO 1998/49350 | | 11/1998 |
| WO | WO 1999/07865 | | 2/1999 |
| WO | WO 99/25921 | | 5/1999 |
| WO | WO 2000/58035 | | 10/2000 |
| WO | WO 2004/041006 | | 5/2004 |
| WO | WO 2006/035221 | A2 | 4/2006 |
| WO | WO 2008/133643 | | 11/2008 |
| WO | WO 2011/027315 | | 3/2011 |
| WO | WO 2016/057515 | A2 | 4/2016 |

OTHER PUBLICATIONS

Jeong, Jin-A., et al. "Transgenic rice plants expressing an active tobacco mitogen-activated protein kinase kinase induce multiple defense responses." The Plant Pathology Journal 24.4 (2008): 375-383. (Year: 2008).*

Lu, Wenjing, et al. "Cotton GhMKK1 induces the tolerance of salt and drought stress, and mediates defence responses to pathogen infection in transgenic Nicotiana benthamiana." PLoS One 8.7 (2013): e68503. (Year: 2013).*

Takabatake, Reona, et al. "MAP Kinases Function Downstream of HSP90 and Upstream of Mitochondria in TMV Resistance Gene N-Mediated Hypersensitive Cell Death." Plant and Cell Physiology 50.6 (2009): 1176-1176. (Year: 2009).*

Akaba et al., "Production of Homo- and Hetero-Dimeric Isozymes from Two Aldehyde Oxidase Genes of *Arabidopsis thaliana," The Journal of Biochemistry,* 126(2), pp. 395-401 (Aug. 1999), available online: https://doi.org/10.1093/oxfordjournals.jbchem.a022463.

Allen et al., "Evolution of microRNA genes by inverted duplication of target gene sequences in *Arabidopsis thaliana," Nature Genetics,* 36, pp. 1282-1290 (Dec. 2004), available online DOI: https://doi.org/10.1038/ng1478.

Allen et al., "microRNA-Directed Phasing during Trans-Acting siRNA Biogenesis in Plants," *Cell,* 121(2), pp. 207-221 (Apr. 2005), available online DOI: https://doi.org/10.1016/j.cell.2005.04.004.

Altschul et al., "Basic local alignment search tool," *Journal of Molecular Biology,* 215(3), pp. 403-410 (Oct. 1990), available online: https://doi.org/10.1016/S0022-2836(05)80360-2.

Altschul et al., "Gapped BLAST and PSI-BLAST: a new generation of protein database search programs," *Nucleic Acids Research,* 25(17), pp. 3389-3402 (Sep. 1997), available online: https://doi.org/10.1093/nar/25.17.3389.

Amaya et al., "Expression of CENTRORADIALIS (CEN) and CEN-like genes in tobacco reveals a conserved mechanism controlling phase change in diverse species," *The Plant Cell,* 11(8), pp. 1405-1418 (Aug. 1999), available online: https://doi.org/10.1105/tpc.11.8.1405.

Avci et al., "Cysteine proteases XCP 1 and XCP2 aid micro-autolysis within the intact central vacuole during xylogenesis in *Arabidopsis* roots," *Plant Journal,* 56(2), pp. 303-315 (Oct. 2008), available online: https://doi.org/10.1111/j.1365-313X.2008.03592.x.

Axtell et al., "A two-hit trigger for siRNA biogenesis in plants," Cell, 127(3), pp. 565-577 (Nov. 2006), available online: https://doi.org/10.1016/j.cell.2006.09.032.

Bartel, "MicroRNAs: Genomics, Biogenesis, Mechanism, and Function," Cell, 116(2), pp. 281-297 (Jan. 2004), available online: https://doi.org/10.1016/S0092-8674(04)00045-5.

Beetham et al., "A tool for functional plant genomics: Chimeric RNA/DNA oligonucleotides cause in vivo gene-specific mutations," *Proc. Natl. Acad. Sci. USA,* 96(15):8774-8778 (Jul. 1999), available online: https://doi.org/10.1073/pnas.96.15.8774.

Bender et al., "*Pseudomonas syringae* phytotoxins: Mode of Action, Regulation, and Biosynthesis by Peptide and Polyketide Synthetases," *Microbiology and Molecular Biology Reviews,* 63(2), pp. 266-292 (Jun. 1999), available online: 10.1128/mmbr.63.2.266-292.1999.

Benfey et al., "The CaMV 35S Enhancer Contains At Least Two Domains Which Can Confer Different Developmental and Tissue-Specific Patterns," *EMBO Journal,* vol. 8, No. 8, pp. 2195-2202 (May 1989) available online DOI: 10.1002/j.1460-2075.1989.tb08342.x.

The Bogdanove laboratory, "TAL Effector Nucleotide Targeter 2.0," Retrieved Aug. 4, 2017 from https://tale-nt.cac.cornell.edu/about, Cornell University.

Boutros et al., "Genome-Wide RNAi Analysis of Growth and Viability in *Drosophila* Cells," *Science,* 303(5659), pp. 832-835 (Feb. 2004), available online: DOI: 10.1126/science.1091266.

Bowie et al., "Deciphering the Message in Protein Sequences: Tolerance to Amino Acid Substitutions," *Science,* vol. 247, No. 4948, pp. 1306-1310 (Mar. 1990) (London, UK) available online: https://www.jstor.org/stable/2873717.

Bowman et al., "Revised North Carolina grade index for flue-cured tobacco," *Tobacco Science,* 32:39-40 (1988), available online: https://www.coresta.org/sites/default/files/abstracts/Tobacco_Science1988_32-10_p. 39-40_ISSN._0082-4523.pdf.

Byrne, "Shoot Meristem Function and Leaf Polarity: The Role of Class III HD-ZIP Genes," *PLoS Genetics,* 2(6):e89 (Jun. 2006), available online: https://doi.org/10.1371/journal.pgen.0020089.

Canevascini et al., "Tissue-specific expression and promoter analysis of the tobacco ltp1 gene," *Plant Physiology,* 112(2), pp. 513-524 (Oct. 1996), available online: https://doi.org/10.1104/pp.112.2.513.

Cermak et al., "Efficient design and assembly of custom TALEN and other TAL effector-based constructs for DNA targeting," *Nucleic Acids Research,* 39(12), e82, 11 pages (Jul. 2011), available online: https://doi.org/10.1093/nar/gkr218.

Chapters 4B and 4C of Tobacco, Production, Chemistry and Technology, Davis & Nielsen, eds., Blackwell Publishing, pp. 70-103, (1999) (Oxford, UK).

Cheng et al., "Auxin Synthesized by the YUCCA Flavin Monooxygenases Is Essential for Embryo genesis and Leaf Formation in *Arabidopsis," The Plant Cell,* 19(8), pp. 2430-3439 (Aug. 2007), available online: https://doi.org/10.1105/tpc.107.053009.

Chinese Search Report issued in corresponding Chinese Patent Application No. 2017800289085, dated Sep. 15, 2022, with English translation.

(56) References Cited

OTHER PUBLICATIONS

Christensen et al., "Sequence analysis and transcriptional regulation by heat shock of polyubiquitin transcripts from maize," *Plant Molecular Biology,* 12, pp. 619-632 (Jun. 1989), available online: https://doi.org/10.1007/BF00044153.
Christensen et al., "Maize polyubiquitin genes: structure, thermal perturbation of expression and transcript splicing, and promoter activity following transfer to protoplasts by electroporation," *Plant Molecular Biology,* 18, pp. 675-689 (Feb. 1992), available online: https://doi.org/10.1007/BF00020010.
Christou et al., "Stable Transformations of Soybean Callus by DNA-Coated Gold Particles," *Plant Physiology,* 87(3), pp. 671-674 (Jul. 1988), available online: https://doi.org/10.1104/pp.87.3.671.
Crone et al., "The differential expression of a heat shock promoter in floral and reproductive tissues," *Plant, Cell and Environment,* 24(8), pp. 869-874 (Aug. 2001), available online: https://doi.org/10.1046/j.1365-3040.2001.00727.x.
Crossway et al., "Overview: Micromanipulation techniques in plant biotechnology," *BioTechniques,* 4(4):320-334 (1986) (London, UK) (electronic copy).
Database WPI Week 201502, XP002769652, CN 104 086 637 A (Univ Southwest) Oct. 8, 2014.
Database WPI Week 200682, XP002769653, CN 1 824 774 A (Jia C) Aug. 30, 2006.
D'Halluin et al., "Transgenic Maize Plants by Tissue Electroporation," *The Plant Cell,* 4(12), pp. 1495-1505 (Dec. 1992), available online: DOI: 10.1105/tpc.4.12.1495.
De Jong et al., "Chemical-induced apoptotic cell death in tomato cells: involvement of caspase-like proteases," *Planta,* 211, pp. 656-662, (Oct. 2000), available online: https://doi.org/10.1007/s004250000341.
Devarenne et al., "Adi3 is a Pdk1-interacting AGC kinase that negatively regulates plant cell death," *The EMBO Journal,* 25, pp. 255-265 (Jan. 2006), available online: https://doi.org/10.1038/sj.emboj.7600910.
De Wet et al. "Exogenous gene transfer in maize (*Zea mays*) using DNA-treated pollen," *The experimental manipulation of ovule tissues,* Chapman, GP, et al.,(eds.), Longman, New York, pp. 197-209, (1985) (electronic copy) (accessed Mar. 13, 2017).
Dietzl et al., "A genome-wide transgenic RNAi library for conditional gene activation in *Drosophila,*" *Nature,* 448, pp. 151-156 (Jul. 2007), available online: https://doi.org/10.1038/nature05954.
Doyle et al., "TAL effector-nucleotide targeter (TALE-NT) 2.0: tools for T AL Effector design and target prediction effector," *Nucleic Acids Research,* 40(W1), pp. W117-W122 (Jul. 2012), available online: https://doi.org/10.1093/nar/gks608.
"Draft for Diplomatic Conference for the Revision of the International Convention for the Protection of New Varieties of Plants," Mar. 4-19, 1991 (Geneva, Switzerland).
Dugas et al., "MicroRNA regulation of gene expression in plants," *Current Opinion in Plant Biology,* 7(5), pp. 512-520 (Oct. 2004), available online: https://doi.org/10.1016/j.pbi.2004.07.011.
Emery et al., "Radial patterning of *Arabidopsis* shoots by class III HD-CIP and KANADI genes," *Current Biology,* 13(20), pp. 1768-1774 (Oct. 2003) (Cambridge, MA) available online DOI: 10.1016/j.cub.2003.09.035.
Escamez et al., "Programmes of cell death and autolysis in tracheary elements: when a suicidal cell arranges its own corpse removal," *Journal of Experimental Botany,* 65(5), pp. 1313-1321 (Mar. 2014), available online: https://doi.org/10.1093/jxb/eru057.
Estruch et al., "Transgenic plants: An emerging approach to pest control," *Nature Biotechnology,* 15:137 (Feb. 1997) available online, DOI: 10.1038/nbt0297-137.
Fedoroff et al., "Cloning of the bronze locus in maize by a simple and generalizable procedure using the transposable controlling element Activator (Ac)," *Proc. Natl. Acad. Sci. USA,* 81(12), pp. 382 5-382 9 (Jun. 1984), available online: https://doi.org/10.1073/pnas.81.12.3825.
Finer et al., "Transformation of soybean via particle bombardment of embryogenic suspension culture tissue," *In Vitro Cellular Developmental Biology—Plant,* 27, pp. 175-182 (Oct. 1991), available online: https://doi.org/10.1007/BF02632213.
Fisher et al., "Topping, Managing Suckers, and Using Ethephon," Flue-Cured Tobacco Information, North Carolina State University, pp. 96-117 (2016), (electronic copy).
Franco-Zorilla et al., "Target mimicry provides a new mechanism for regulation of microRNA activity," *Nature Genetics,* 39, pp. 1033-1037 (Jul. 2007), available online: https://doi.org/10.1038/ng2079.
Gälweiler et al., "Regulation of Polar Auxin Transport by AtPIN1 in *Arabidopsis* vascular tissue," Science, 282(5397), pp. 2226-2230 (Dec. 1998), available online: DOI: 10.1126/science.282.5397.2226.
Gatz et al., "Regulation of a modified CaMV 35S promoter by the Tn10-encoded Tet repressor in transgenic tobacco," *Molecular and General Genetics,* 227, pp. 229-237 (Jun. 1991), available online: https://doi.org/10.1007/BF00259675.
Goehring et al., "Screening and large-scale expression of membrane proteins in mammalian cells for structural studies," *Nature Protocols,* 9, pp. 2574-2585 (Nov. 2014), available online: https://doi.org/10.1038/nprot.2014.173.
Goldman et al., "Female sterile tobacco plants are produced by stigma-specific cell ablation," *The EMBO Journal,* 13, pp. 2976-2984 (Jul. 1994), available online: https://doi.org/10.1002/j.1460-2075.1994.tb06596.x.
Gonzalez-Grandio et al., "BRANCHEDI Promotes Axillary Bud Dormancy in Response to Shade in *Arabidopsis,*" *The Plant Cell,* 25(3), pp. 834-850 (Mar. 2013), available online: https://doi.org/10.1105/tpc.112.108480.
Greb et al., "Molecular analysis of the Lateral Suppressor gene in *Arabidopsis* reveals a conserved control mechanism for axillary meristem formation," *Genes & Development,* 17, pp. 1175-1187 (May 2003), available online: 10.1101/gad.260703.
Greene et al, "Spectrum of Chemically Induced Mutations From a Large-Scale Reverse-Genetic Screen in *Arabidopsis,*" Genetics, 164(2), pp. 731-740 (Jun. 2003), available online: https://doi.org/10.1093/genetics/164.2.731.
Griffiths-Jones et al., "Rfam: an RNA family database," Nucleic Acids Research, 31(1), pp. 439-441 (Jan. 2003), available online: https://doi.org/10.1093/nar/gkg006.
Guevara-Garcia et al., Tissue-specific and wound-inducible pattern of expression of the mannopine synthase promoter is determined by the interaction between positive and negative cis-regulatory elements, Plant Journal, 4(3), pp. 495-505 (Sep. 1993), available online: https://doi.org/10.1046/j.1365- 313X.1993.04030495.x.
Guo et al., "Protein tolerance to random amino acid change," Proc. Natl. Acad. Sci. USA, 101(25), pp. 9205-9210 (Jun. 2004), available online: https://doi.org/10.1073/pnas.0403255101.
Hansen et al., "Wound-inducible and organ-specific expression of ORF13 from Agrobacterium rhizogenes 8196 T-DNA in transgenic tobacco plants," Molecular and General Genetics, 254, pp. 337-343 (Apr. 1997), available online: https://doi.org/10.1007/s004380050424.
Hartley, "Barnase and barstar: two small proteins to fold and fit together," *Trends in Biochemical Sciences,* 14(11), pp. 450-454 (Nov. 1989), available online: https://doi.org/10.1016/0968-0004(89)90104-7.
Hildering et al., "Chimeric structure of tomato plants after seed treatment with EMS and X-rays." *The Use of Induced Mutations in Plant Breeding* (*Supplement to Radiation Botany*), vol. 5, Pergamon Press Ltd., pp. 317-320, with cover page (1965) (London, UK).
Hoekema et al., "A binary plant vector strategy based on separation ofvir- and T-region of the *Agrobacterium tumefaciens Ti-plasmid,*" *Nature,* 303: 179-180 (May 1983), available online: https://doi.org/10.1038/303179a0.
Hormoz, "Amino acid composition of proteins reduces deleterious impact of mutations," *Scientific Reports,* 3(2919), 10 pages (Oct. 2013), available online: https://doi.org/10.1038/srep02919.
Horsch et al., "A simple and General Method for Transferring Genes into Plants," Science, 227(4691), pp. 1229-1231 (Mar. 1985), available online: DOI: 10.1126/science.227.4691.1229.
International Search Report and Written Opinion mailed Jul. 3, 2007, in International Application No. PCT/US2017/022156.

(56) References Cited

OTHER PUBLICATIONS

IUBMB Enzyme Nomenclature (2005), accessed online on Sep. 12, 2019.
Jeong et al., "Transgenic Rice Plants Expressing an Active Tobacco Mitogen-activated Protein Kinase Kinase Induce Multiple Defense Responses," *The Plant Pathology Journal*, 24(4), pp. 375.383 (Nov. 2008) (Seoul, KR) (electronic publication).
Jin et al., "Function of a mitogen-activated protein kinase pathway in N gene-mediated resistance in tobacco," *The Plant Journal*, 33(4), pp. 719-731 (Feb. 2003) available online: https://doi.org/10.1046/j.1365-313X.2003.01664.x.
Jones-Rhoades et al., "Computational Identification of Plant MicroRNAs and their Targets, Including a Stress-Induced miRNA," Molecular Cell, 14(6), pp. 787-799 (Jun. 2004), available online: https://doi.org/10.1016/j.molcel.2004.05.027.
Kaeppler et al., "Silicon carbide fiber-mediated DNA delivery into plant cells," *The Plant Cell Reports*, 9, pp. 415-418 (Dec. 1990), available online: https://doi.org/10.1007/BF00232262.
Kaeppler et al., "Silicon carbide fiber-mediated stable transformation of plant cells," *Theoretical and Applied Genetics*, 84, pp. 560-566 (Aug. 1992), available online: https://doi.org/10.1007/BF00224152.
Katoh et al., "Specific residues at every third position of siRNA shape its efficient RNAi activity," *Nucleic Acids Research*, 35(4):e27, 14 pages (Jan. 2007), available online: https://doi.org/10.1093/nar/gkl1120.
Kawamata et al., "Temporal and Spatial Pattern of Expression of the Pea Phenylalanine Ammonia-Lyase Genel Promoter in Transgenic Tobacco," *Plant and Cell Physiology*, 38(7), pp. 792-803 (Jan. 1997), available online: https://doi.org/10.1093/oxfordjournals.pcp.a029237.
Keller et al., "*Arabidopsis* Regulator of Axillary *Meristemsi* Controls a Leaf Axil Stem Cell Niche and Modulates Vegetative Development," *The Plant Cell*, 18(3), pp. 598-611 (Feb. 2006), available online: https://doi.org/10.1105/tpc.105.038588.
Khvorova et al., "Functional siRNAs and miRNAs Exhibit Strand Bias," *Cell*, 115(2), pp. 209-216 (Oct. 2003), available online: https://doi.org/10.1016/S0092-8674(03)00801-8.
Kim, "MicroRNA biogenesis: coordinated cropping and dicing," *Nature Reviews Molecular Cell Biology*, 6, pp. 376-385 (May 2005), available online: https://doi.org/10.1038/nrm1644.
Lam, "Analysis of Tissue-Specific Elements in the CaMV 35S Promoter," In: Nover, L. (eds) Plant Promoters and Transcription Factors. Results and Problems in Cell Differentiation, 20, pp. 181-196 (1994), available online: https://doi.org/10.1007/978-3-540-48037-2_8.
Last et al., "pEMU: an improved promoter for gene expression in cereal cells," Theoretical and Applied Genetics, 81, pp. 581-588 (May 1991), available online: https://doi.org/10.1007/BF00226722.
Lee et al., "A systematic RN Ai screen identifies a critical role for mitochondria in C. elegans longevity," Nature Genetics, 33, pp. 40-48 (Jan. 2003), available online: https://doi.org/10.1038/ng1056.
Long et al., "A member of the KNOTTED class of homeodomain proteins encoded by the STM gene of *Arabidopsis*," Nature, 379, pp. 66-69 (Jan. 1996), available online: https://doi.org/10.1038/379066a0.
Lu et al., "Cotton GhMKKI Induces the Tolerance of Salt and Drought Stress, and Mediates Defense Responses to Pathogen Infection in Transgenic *Nicotiana benthamiana*," *PLOS ONE*, 8(7), e68503, pp. 1-14 (Jul. 2013) available online: DOI: 10.1371/journal.pone.0068503.
Mallory et al., "MicroRNA control of *Phabulosa* in leaf development: importance of pairing to the microRNA 5' region," *The EMBO Journal*, 23, pp. 3356-3364 (Jul. 2004), available online: https://doi.org/10.1038/sj.emboj.7600340.
Matsuoka et al., "Tissue-specific light-regulated expression directed by the promoter of a C4 gene, maize pyruvate, orthophosphate dikinase, in a C3 plant, rice," *Proc. Natl. Acad. Sci.* USA, 90(20), pp. 9586-9590 (Oct. 1993), available online: https://doi.org/10.1073/pnas.90.20.9586.
Mayo et al., "Genetic transformation of tobacco NT1 cells with Agrobacterium tumefaciens," *Nature Protocols*, 1, pp. 1105-1011 (Aug. 2006), available online: https://doi.org/10.1038/nprot.2006.176.
McCabe et al., "Stable Transformation of Soybean (*Glycine max*) by Particle Acceleration," *Biotechnology*, 6, pp. 923-926 (Aug. 1988), available online: https://doi.org/10.1038/nbt0888-923.
McCallum et al., "Targeted screening for induced mutations," Nature *Biotechnology*, 18, pp. 455-457 (Apr. 2000), available online: https://doi.org/10.1038/74542.
McConnell et al., "Role of *Phabulosa* and *Phavoluta* in determining radial patterning in shoots," *Nature*, 411, pp. 709-713, (Jun. 2001), available online: https://doi.org/10.1038/35079635.
McNellis et al., "Glucocorticoid-inducible expression of a bacterial avirulence gene in transgenic *Arabidopsis* induces hypersensitive cell death," *Plant Journal*, 14(2), pp. 247-257 (Apr. 1998), available online: https://doi.org/10.1046/j.1365-313X.1998.00106.x.
Miller "Memorandum: Proposed Burley Tobacco Grade Index," Legacy Tobacco Document Library, The University of Tennessee Agricultural Experiment Station (Bates Document #523267826-523267833) (Jul. 1988) (Knoxville, USA).
Miller et al., "A grade index for type 22 and 23 fire-cured tobacco," Tobacco Science, Tobacco International, 192(22), pp. 55-57 with cover page, (Dec. 1990) (New York, USA).
Murchison et al., "miRNAs on the move: miRNA biogenesis and the RNAi machinery," *Current Opinion in Cell Biology*, 16(3), pp. 223-229 (Jun. 2004), available online: https://doi.org/10.1016/j.ceb.2004.04.003.
Neu et al., "*Arabidopsis* amidase 1, a member of the amidase signature family," *The FEBS Journal*, 274(13), pp. 3440-3451 (Jul. 2007), available online: https://doi.org/10.1111/j.1742-4658.2007.05876.x.
Odell et al., "Identification of DNA sequences required for activity of the cauliflower mosaic virus 35S promoter," *Nature*, 313, pp. 810-812 (Feb. 1985), available online: https://doi.org/10.1038/313810a0.
Official Standard Grades for Burley Tobacco (U.S. Type 31 and Foreign Type 93), effective Nov. 5, 1990 (55 F.R. 40645).
Official Standard Grades for Flue-Cured Tobacco (U.S. Types 11, 12, 13, 14 and Foreign Type 92), effective Mar. 27, 1989 (54 F.R. 7925).
Official Standard Grades for Pennsylvania Seedleaf Tobacco (U.S. Type 41), effective Jan. 8, 1965 (29 F.R. 16854).
Official Standard Grades for Ohio Cigar-Leaf Tobacco (U.S. Types 42, 43, and 44), effective Dec. 8, 1963 (28 F.R. 11719 and 28 F.R. 11926).
Official Standard Grades for Wisconsin Cigar-Binder Tobacco (U.S. Types 54 and 55), effective Nov. 20, 1969 (34 F.R. 17061).
Official Standard Grades for Georgia and Florida Shade-Grown Cigar-Wrapper Tobacco (U.S. Type 62), Effective Apr. 1971.
Orozco et al., "Localization of Light-Inducible and Tissue-Specific Regions of the Spinach Ribulose Bisphosphate Carboxylase/Oxygenase (Rubisco) Activase Promoter in Transgenic Tobacco Plants," *Plant Molecular Biology*, 23, pp. 1129-1138 (Dec. 1993), available online: https://doi.org/10.1007/BF00042347.
Ortiz-Morea et al., "Global analysis of the sugarcane microtranscriptome reveals a unique composition of small RNAs associated with axillary bud outgrowth," *Journal of Experimental Botany*, 64(8), pp. 2307-2320, (May 2013), available online: https://doi.org/10.1093/jxb/ert089.
Parizotto et al., "In vivo investigation of the transcription, processing, endonucleolytic activity, and functional relevance of the spatial distribution of a plant miRNA," *Genes & Development*, 18, pp. 2237-2242 (Sep. 2004), available online: 10.1101/gad.307804.
Paszkowski et al., "Direct Gene Transfer to Plants," *The EMBO Journal*, 3(12), pp. 2717-2722 (Dec. 1984), available online: https://doi.org/10.1002/j.1460-2075.1984.tb02201.x.
Porta et al., "Use of viral replicons for the expression of genes in plants," *Molecular Biotechnology*, 5, pp. 209-221 (Jun. 1996), available online: https://doi.org/10.1007/BF02900359.
Qi et al., "Comprehensive analysis of differential genes and miRNA profiles for discovery of topping-responsive genes in flue-cured

(56) References Cited

OTHER PUBLICATIONS tobacco roots," *The FEBS Journal,* 279(6), pp. 1054-1070 (Jan. 2012), available online: https://doi.org/10.1111/j.1742-4658.2012.08497.x.
Rajani et al., "The *Arabidopsis* myc/bHLH gene ALCATRAZ enables cell separation in fruit dehiscence," *Current Biology,* 11(24), pp. 1941-1922 (Dec. 2001), available online: https://www.cell.com/current-biology/pdf/S0960-9822(01)00593-0.pdf.
Reynolds et al., "Rational siRNA design for RNA interference," *Nature Biotechnology,* 22, pp. 326-330 (Feb. 2004), available online: https://doi.org/10.1038/nbt936.
Rhoades et al., "Prediction of Plant MicroRNA Targets," *Cell,* 110(4), pp. 513-520 (Aug. 2002), available online: https://doi.org/10.1016/S0092-8674(02)00863-2.
Riggs et al., "Stable transformation of tobacco by electroporation: Evidence for plasmid concatenation," *Proc. Natl. Acad. Sci. USA,* 83(15), pp. 5602-5606 (Aug. 1986), available online: https://doi.org/10.1073/pnas.83.15.5602.
Rinehart et al., "Tissue-Specific and Developmental Regulation of Cotton Gene FbL2A (Demonstration of Promoter Activity in Transgenic Plants)," *Plant Physiology,* 112(3), pp. 1331-1341 (Nov. 1996), available online: https://doi.org/10.1104/p. 112.3.1331.
Russell et al., "Tissue-Specific Expression in Transgenic Maize of Four Endosperm Promoters From Maize and Rice," *Transgenic Research,* 6, pp. 157-168 (Mar. 1997), available online: https://doi.org/10.1023/A:1018429821858.
Schena et al., "A steroid-inducible gene expression system for plant cells," *Proc. Natl. Acad. Sci. USA,* 88(23), pp. 10421-10425 (Dec. 1991), available online: https://doi.org/10.1073/pnas.88.23.10421.
Shillito et al., "[19] Direct gene transfer to protoplasts of dicotyledonous and monocotyledonous plants by a number of methods, including electroporation," *Methods in Enzymology,* 153, pp. 313-336 (Jan. 1987), available online: https://doi.org/10.1016/0076-6879(87)53062-2.
Singh et al., "Cytological characterization of transgenic soybean," *Theoretical and Applied Genetics,* 96, pp. 319-324 (Feb. 1998), available online: https://doi.org/10.1007/s001220050743.
Singh et al., "RNA-sequencing Reveals Global Transcriptomic Changes in Nicotiana tabacum Responding to Topping and Treatment of Axillary-shoot Control Chemicals," *Scientific Reports,* 5(18148), 13 pages (Dec. 2015), available online, DOI: 10.1038/srep18148.
Stepanova et al., "TAA1-Mediated Auxin Biosynthesis Is Essential for Hormone Crosstalk and Plant Development," *Cell,* 133(1), pp. 177-191 (Apr. 2008), available online: https://doi.org/10.1016/j.cell.2008.01.047.
Stirnberg et al., "MAX1 and MAX2 control shoot lateral branching in *Arabidopsis," Development,* 129(5), pp. 1131-1141 (Mar. 2002), available online: https://doi.org/10.1242/dev.129.5.1131.
Sun et al., "Inhibition of tobacco axillary bud differentiation by silencing CUP-Shaped COTYLEDON 3," *African Journal of Biotechnology,* 11(16), pp. 3919-3927 (Feb. 2012), available online, DOI: 10.5897/AJB11.1183.
Sunkar et al., "Novel and Stress-Regulated MicroRNAs and Other Small RNAs from Arabidopsis," *The Plant Cell,* 16(8), pp. 2001-2019 (Aug. 2004), available online: https://doi.org/10.1105/tpc.104.022830.
Takabatake et al., "MAP Kinases Function Downstream of HSP90 and Upstream of Mitochondria in TMV Resistance Gene N-Mediated Hypersensitive Cell Death," *Plant and Cell Physiology,* 48(3), pp. 498-510 (Mar. 2007) (Oxford, UK) available online: https://doi.org/10.1093/pcp/pcm021.
Tanaka, et al., "Studies on Biological Effects of Ion Beams on Lethality, Molecular Nature of Mutation, Mutation Rate, and Spectrum of Mutation Phenotype for Mutation Breeding in Higher Plants," *Journal of Radiation Research,* 51(3), pp. 223-233 (May 2010), available online: https://doi.org/10.1269/jrr.09143.
Tanaka-Ueguchi et al., "Over-expression of a tobacco homeobox gene,NTH15, decreases the expression of a gibberellin biosynthetic gene encoding GA 20-oxidase," *Plant Journal,* 15(3), pp. 391-400 (Aug. 1998), available online: https://doi.org/10.1046/j.1365-313X.1998.00217.x.
Tomes et al., "Direct DNA Transfer into Intact Plant Cells Via Microprojectile Bombardment," *The Plant Cell, Tissue, and Organ Culture: Fundamental Methods,* pp. 197-213 (1995), available online: https://doi.org/10.1007/978-3-642-79048-5_16.
Trobacher et al., "Induction of a ricinosomal-protease and programmed cell Death in tomato endosperm by gibberellic acid," *Planta,* 237, pp. 664-679 (Mar. 2013), available online: https://doi.org/10.1007/s00425-012-1780-1.
Tso "Seed to Smoke," Chapter 1 in Davis and Nielsen (ed.), *Tobacco: Production, Chemistry and Technology,* Blackwell Science Publishing, pp. 1-31 with cover page (Oxford, UK).
Van Camp et al., "Tissue-Specific Activity of Two Manganese Superoxide Dismutase Promoters in Transgenic Tobacco1," *Plant Physiology,* 112(2), pp. 525-535 (Oct. 1996), available online: DOI: 10.1104/pp.112.2.525.
Velten et al., "Isolation of a dual plant promoter fragment from the Ti plasmid of *Agrobacterium tumefaciens," The EMBO Journal,* 3(12), pp. 2723-2730 (Dec. 1984), available online: DOI: 10.1002/j.1460-2075.1984.tb02202.x.
Verkerk, "Chimerism of the tomato plant after seed irradiation with fast neutrons," *Netherlands Journal of Agricultural Science,* 19(4), pp. 197-203 (Mar. 1971), available online: https://doi.org/10.18174/njas.v19i4.17300.
Wang et al., "MicroRNA171c-Targeted SCL6-II, SCL6-III, and SCL6-IV Genes Regulate Shoot Branching in *Arabidopsis," Molecular Plant,* 3(5), pp. 794-806 (Sep. 2010), available online: https://doi.org/10.1093/mp/ssq042.
Watanabe et al., "*Arabidopsis metacaspase* 2d is a positive mediator of cell death induced during biotic and abiotic stresses," *Plant Journal,* 66(6), pp. 969-982 (Mar. 2011), available online: https://doi.org/10.1111/j.1365- 313X.2011.04554.x.
Weising et al., "Foreign Genes in Plants: Transfer, Structure, Expression, and Applications," *Annual Review of Genetics,* 22, pp. 421-477 (Dec. 1988), available online: https://doi.org/10.1146/annurev.ge.22.120188.002225.
Wernsman et al., "Chapter Seventeen: Tobacco" in *Principles of Cultivar Development, Crop Species,* vol. 2 , W. H. Fehr (ed.), MacMillan Publishing Go., Inc., pp. 669-698 with cover page, (1987) (New York, NY).
Wilke et al., "Predicting the Tolerance of Proteins to Random Amino Acid Substitution," *Biophysical Journal,* 89(6), pp. 3714-3720 (Dec. 2005), available online: https://doi.org/10.1529/biophysj.105.062125.
Wu et al., "LcMKK, a novel group A mitogen-activated protein kinase kinase gene in Lycium chinense, confers dehydration and drought tolerance in transgenic tobacco via scavenging ROS and modulating expression of stress-responsive genes," *Plant Growth Regulation,* 76, pp. 269-279 (Jul. 2015), available online: https://doi.org/10.1007/s10725-014-9998-5.
Yadav et al., "WUSCHEL protein movement mediates stem cell homeostasis in the *Arabidopsis* shoot apex," *Genes & Development,* 25, pp. 2025-2030 (Oct. 2011), available online: DOI: 10.1101/gad.17258511.
Yamada et al., "The Transport Inhibitor RESPONSE2 Gene Is Required for Auxin Synthesis and Diverse Aspects of Plant Development," *Plant Physiology,* 151(1), pp. 168-179 (Sep. 2009), available online: https://doi.org/10.1104/pp.109.138859.
Yamamoto et al., "The Promoter of a Pine Photosynthetic Gene Allows Expression of a β-Glucuronidase Reporter Gene in Transgenic Rice Plants in a Light-Independent but Tissue-Specific Manner," *Plant & Cell Physiology,* 35(5), pp. 773-778 (Jan. 1994), available online: https://doi.org/10.1093/oxfordjournals.pcp.a078656.
Yamamoto et al., "Light-Responsive Elements of the Tobacco PSI-D Gene Are Located Both Upstream and Within the Transcribed Region," *Plant Journal,* 12(2), pp. 255-265 (Aug. 1997), available online: https://doi.org/10.1046/j.1365-313X.1997.12020255.x.
Zeng et al., "Both Natural and Designed Micro RNAs Can Inhibit the Expression of Cognate mRNAs When Expressed in Human

(56) References Cited

OTHER PUBLICATIONS

Cells," *Molecular Cell,* 9(6), pp. 1327-1333 (Jun. 2002), available online: https://www.cell.com/molecular-cell/pdf/S1097-2765(02)00541-5.pdf.
Zhang et al., "Transcription Activator-Like Effector Nucleases Enable Efficient Plant Genome Engineering," *Plant Physiology,* 161(1), pp. 20-27 (Jan. 2013), available online: https://doi.org/10.1104/pp.112.205179.
Ma et al., "Expression Of T-CYT Gene In Transgenic Tobacco And Influence Thereof On Growth And Development," *Chinese Journal of Applied and Environmental Biology,* 2(1), pp. 1-7 (Dec. 1996) (electronic publication).
Schmid et al., "Developmental and Environmental Regulation of a Bean Chalcone Synthase Promoter in Transgenic Tobacco," *The Plant Cell,* 2, pp. 619-631 (Jul. 1990) (electronic publication).
Search Report issued in Chinese Patent Application No. 2017800289085, dated Apr. 25, 2022, 7 pages (with English translation).
Search Report issued in Chinese Patent Application No. 2017800289085, dated Sep. 15, 2022, 4 pages (with English translation).
"Q14TB0 • Q14TB0_TOBAC—Mitogen-activated protein kinase 2, NtMEK2," UniProt ID Q14TB0_TOBAC, Integrated Aug. 22, 2006, 2 pages.

* cited by examiner

Control

SEQ ID NO: 96

Seedling

Seedling SAM

SAM　　Axillary Buds 0 hours　0 hours　3 days　5 days　7 days

SAM and Axillary Buds

Axillary Bud

SAM and Axillary Buds

Axillary Bud

Control

SEQ ID NO: 117 (promoter) driving SEQ ID NO: 59

Positive Control (SEQ ID NO: 79)

Negative Control (Empty vector)

SEQ ID NO: 203

SEQ ID NO: 208

SEQ ID NO: 209

SEQ ID NO: 210

SEQ ID NO: 216

SEQ ID NO: 228

SEQ ID NO: 230

SEQ ID NO: 232

COMPOSITIONS AND METHODS FOR PRODUCING TOBACCO PLANTS AND PRODUCTS HAVING REDUCED OR ELIMINATED SUCKERS

CROSS-REFERENCE TO RELATED APPLICATIONS

This application is a continuation application of U.S. patent application Ser. No. 16/908,891, filed Jun. 23, 2020, which is a continuation application of U.S. patent application Ser. No. 15/457,553, filed Mar. 13, 2017, now U.S. Pat. No. 10,731,173, issued Aug. 4, 2020, which claims benefit of U.S. Provisional Patent Application No. 62/307,035, filed Mar. 11, 2016, and U.S. Provisional Patent Application No. 62/399,181, filed Sep. 23, 2016. All the foregoing applications are incorporated by reference in their entireties herein.

FIELD

The present disclosure identifies axillary bud-specific promoters and genes involved in sucker growth. Also provided are methods and compositions related to reducing or eliminating suckers in tobacco plants, their development via breeding or transgenic approaches, and production of tobacco products from those tobacco plants.

INCORPORATION OF SEQUENCE LISTING

An XML sequence listing contained in the file named "P34370US04_SL.TXT" which is 618,777 bytes (measured in MS-Windows®) and created on Sep. 26, 2023, is filed electronically herewith and incorporated by reference in its entirety.

BACKGROUND

Tobacco is a plant species that exhibits exceptionally strong apical dominance. Molecular signals from the shoot apical meristem (SAM) mediate a hormonal signal that effectively inhibits axillary bud growth. Upon removal of the SAM (also known as "topping"), physiological and molecular changes occur, enabling the growth of new shoots (or "suckers") from axillary meristems (buds). Sucker growth results in loss of yield and leaf quality. Suckers have been controlled by manual removal and through the application of chemicals. Maleic hydrazide and flumetralin are routinely used on topped plants to inhibit axillary bud growth ("suckering"). However, labor and chemical agents to control suckers are very expensive. Control of suckering in tobacco through conventional breeding, mutation breeding, and transgenic approaches have been a major objective for several decades but, to date, successful inhibition or elimination of suckering has not been achieved through these approaches. Therefore, development of tobacco traits with limited or no suckering would result in a reduction of the use of chemical agents and would reduce costs and labor associated with tobacco production.

SUMMARY

In one aspect, the present disclosure provides a modified tobacco plant comprising no or reduced suckering compared to a control tobacco plant of the same variety when grown under comparable conditions.

In one aspect, the present disclosure provides a modified tobacco plant, where the modified tobacco plant exhibits:

inhibited or eliminated axillary meristem growth; inhibited or eliminated axillary meristem maintenance; or a combination thereof compared to a control tobacco plant of the same variety when grown under comparable conditions.

In one aspect, the present disclosure provides a plant or seed comprising a recombinant polynucleotide, where the recombinant polynucleotide comprises a promoter that is functional in an L1 layer, an L2 layer, an L3 region, a rib zone, a central zone, a peripheral zone, or any combination thereof, which is operably linked to a structural nucleic acid molecule comprising a nucleic acid sequence, where the nucleic acid sequence encodes a polypeptide having at least 70% sequence identity to a polypeptide selected from the group consisting of SEQ ID NOs: 2, 4, 6, 8, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, the present disclosure provides a recombinant DNA construct comprising a promoter that is functional in an L1 layer, an L2 layer, an L3 region, a rib zone, a central zone, a peripheral zone, or a combination thereof; and a heterologous and operably linked nucleic acid sequence, where the nucleic acid sequence encodes a non-coding RNA or a polypeptide.

In one aspect, the present disclosure provides a method of reducing or eliminating topping-induced suckering in a tobacco plant, where the method comprises transforming a tobacco plant with a recombinant DNA construct comprising a promoter functional in an L1 layer, an L2 layer, an L3 region, a rib zone, a central zone, a peripheral zone, or a combination thereof.

In one aspect, the present disclosure provides a method comprising transforming a tobacco plant with a recombinant DNA construct comprising a heterologous promoter that is functional in an L1 layer, an L2 layer, an L3 region, a rib zone, a central zone, a peripheral zone, or a combination thereof, and is operably linked to a polynucleotide that is transcribed into an RNA molecule that suppresses the level of an endogenous gene, and where the endogenous gene promotes or is required for axillary meristem growth, axillary meristem maintenance, or both.

In one aspect, the present disclosure provides a method for producing a tobacco plant comprising crossing at least one tobacco plant of a first tobacco variety with at least one tobacco plant of a second tobacco variety, where the at least one tobacco plant of the first tobacco variety exhibits no or reduced topping-induced suckering compared to a control tobacco plant of the same variety grown under comparable conditions; and selecting for progeny tobacco plants that exhibit no or reduced topping-induced suckering compared to a control tobacco plant of the same cross grown under comparable conditions.

In one aspect, the present disclosure provides a tobacco plant, or part thereof, comprising a heterologous promoter operably linked to a polynucleotide encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, the present disclosure provides a recombinant DNA construct comprising a heterologous promoter operably linked to a polynucleotide encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, the present disclosure provides a method of growing a modified tobacco plant comprising planting a modified tobacco seed comprising a heterologous promoter that is operably linked to a polynucleotide encoding a polypeptide having at least 70% sequence identity to a polypeptide selected from the group consisting of SEQ ID NOs: 2, 4, 6, 8, 10, 12, 14, 16, 18, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255; and growing the modified tobacco plant from the seed.

In one aspect, the present disclosure provides a method for controlling topping-induced suckering in a plant comprising transforming the plant with a recombinant DNA construct, where the recombinant DNA construct comprises a promoter that is operably linked to a polynucleotide encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, the present disclosure provides a tobacco plant, or part thereof, comprising a heterologous promoter operably linked to a polynucleotide that encodes a non-coding RNA molecule, where the non-coding RNA molecule is capable of binding to an RNA encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, and 255, and where the non-coding RNA molecule suppresses the expression of the polypeptide.

In one aspect, the present disclosure provides a recombinant DNA construct comprising a heterologous axillary meristem-specific promoter operably linked to a polynucleotide that encodes a non-coding RNA molecule, where the non-coding RNA molecule is capable of binding to an RNA encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, and 255, and where the non-coding RNA molecule suppresses the expression of the polypeptide.

In one aspect, the present disclosure provides a method of growing a modified tobacco plant comprising planting a modified tobacco seed comprising a recombinant DNA construct comprising a heterologous promoter that is functional in an L1 layer, an L2 layer, an L3 region, a rib zone, a central zone, a peripheral zone, or a combination thereof, and is operably linked to a polynucleotide that encodes a non-coding RNA molecule, where the non-coding RNA molecule is capable of binding to an RNA encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, and 255, and where the non-coding RNA molecule suppresses the expression of the polypeptide; and growing the modified tobacco plant from the seed.

In one aspect, the present disclosure provides a method for controlling topping-induced suckering in a plant comprising transforming the plant with a recombinant DNA construct, where the recombinant DNA construct comprises a heterologous promoter that is functional in an L1 layer, an L2 layer, an L3 region, a rib zone, a central zone, a peripheral zone, or a combination thereof, and where the promoter is operably linked to a polynucleotide that encodes a non-coding RNA molecule, where the non-coding RNA molecule is capable of binding to an RNA encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, and 255, and where the non-coding RNA molecule suppresses the expression of the polypeptide.

In one aspect, the present disclosure provides a bacterial cell comprising a recombinant DNA construct provided herein.

In one aspect, the present disclosure provides a plant genome comprising a recombinant DNA construct provided herein.

In one aspect, the present disclosure provides a method for manufacturing a modified seed comprising introducing a recombinant DNA construct provided herein into a plant cell; screening a population of plant cells for the recombinant DNA construct; selecting one or more plant cells from the population, generating one or more modified plants from the one or more plant cells; and collecting one or more modified seeds from the one or more modified plants.

In one aspect, the present disclosure provides a method of producing a modified tobacco plant to reduce or eliminate suckering, where the method comprises introducing one or more mutations in one or more tobacco genome loci.

In one aspect, the present disclosure provides a method of producing a modified tobacco plant to reduce or eliminate suckering, where the method comprises introducing one or more mutations in one or more tobacco genome loci, and where tobacco products are made from the modified tobacco plants.

In one aspect, the present disclosure provides a plant or seed comprising a recombinant polynucleotide, where the recombinant polynucleotide comprises a promoter that is functional in an L1 layer, an L2 layer, an L3 region, a rib zone, a central zone, a peripheral zone, or any combination thereof, which is operably linked to a structural nucleic acid molecule comprising a nucleic acid sequence, where the nucleic acid sequence encodes an auxin biosynthesis protein or an auxin transport protein.

In one aspect, the present disclosure provides a recombinant DNA construct comprising a promoter that is functional in an L1 layer, an L2 layer, an L3 region, a rib zone, a central zone, a peripheral zone, or any combination thereof; and a heterologous and operably linked nucleic acid sequence, where the nucleic acid sequence encodes an auxin biosynthesis protein or an auxin transport protein.

In one aspect, the present disclosure provides a recombinant DNA construct comprising a heterologous axillary meristem-specific promoter operably linked to a polynucleotide that encodes an auxin biosynthesis protein or an auxin transport protein.

In one aspect, the present disclosure provides a tobacco plant, or part thereof, comprising a heterologous promoter having at least 90% sequence identity to a polynucleotide selected from the group consisting of SEQ ID NOs: 113-118, 148-160, 204, and fragments thereof operably linked to a polynucleotide encoding an auxin biosynthesis protein or an auxin transport protein.

In one aspect, the present disclosure provides a method for controlling topping-induced suckers in a plant comprising transforming said plant with a recombinant DNA construct, where the recombinant DNA construct comprises a promoter that is operably linked to a polynucleotide encoding an auxin biosynthesis protein or an auxin transport protein.

BRIEF DESCRIPTION OF THE SEQUENCES

SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, and 254 are nucleic acid sequences. SEQ ID NOs: 83-101 are RNAi constructs. SEQ ID NOs: 113-118, 148-160, and 204 are promoter or regulatory nucleic acid sequences. SEQ ID NOs: 119-122 are sequences used in TALEN mutagenesis.

SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255 are polypeptide sequences. Additional descriptions of the SEQ ID NOs provided herein can be found in Table 1.

TABLE 1

Description of sequences

| SEQ ID NO | Sequence Type | Sequence Description | NCBI Accession Number of the Top Hit of A BLAST Search |
|---|---|---|---|
| 1 | Nucleic Acid | Transcription factor CYCLOIDEA-like | XM_009609861.1 |
| 2 | Peptide | Transcription factor CYCLOIDEA-like | |
| 3 | Nucleic Acid | Flower-specific gamma-thionin | P32026.1 |
| 4 | Peptide | Flower-specific gamma-thionin | |
| 5 | Nucleic Acid | Polyphenoloxidase | XP_006347083.1 |
| 6 | Peptide | Polyphenoloxidase | |
| 7 | Nucleic Acid | UDP-glucose:glucosyltransferase | BAG80546.1 |
| 8 | Peptide | UDP-glucose:glucosyltransferase | |
| 9 | Nucleic Acid | Tumor-related protein | BAA05479.1 |
| 10 | Peptide | Tumor-related protein | |
| 11 | Nucleic Acid | Hypothetical protein | CAN66732.1 |
| 12 | Peptide | Hypothetical protein | |
| 13 | Nucleic Acid | TCP1 protein-like gene | FJ194953.1 |
| 14 | Peptide | TCP1 protein-like gene | |
| 15 | Nucleic Acid | Chlorophyllase-2 | EYU43828.1 |
| 16 | Peptide | Chlorophyllase-2 | |
| 17 | Nucleic Acid | AP2/ERF domain-containing transcription factor | XP_006363442.1 |
| 18 | Peptide | AP2/ERF domain-containing transcription factor | |
| 19 | Nucleic Acid | Putative miraculin | XP_006360306.1 |
| 20 | Peptide | Putative miraculin | |
| 21 | Nucleic Acid | Oleosin | XP_004236249.1 |
| 22 | Peptide | Oleosin | |
| 23 | Nucleic Acid | ACC synthase | XP_006356827.1 |
| 24 | Peptide | ACC synthase | |
| 25 | Nucleic Acid | LOB domain-containing protein 18-like | XP_007052037.1 |
| 26 | Peptide | LOB domain-containing protein 18-like | |
| 27 | Nucleic Acid | Vicilin-like antimicrobial peptides cupin super family | XP_006363154.1 |
| 28 | Peptide | Vicilin-like antimicrobial peptides cupin super family | |
| 29 | Nucleic Acid | Abscisic acid insensitive | XP_006341248.1 |
| 30 | Peptide | Abscisic acid insensitive | |
| 31 | Nucleic Acid | Seipin-like | XP_004237589.1 |
| 32 | Peptide | Seipin-like | |
| 33 | Nucleic Acid | Transcription factor CYCLOIDEA-like | XM_009618194.1 |
| 34 | Peptide | Transcription factor CYCLOIDEA-like | |
| 35 | Nucleic Acid | Transcription factor DICHOTOMA-like | XM_009593876.1 |
| 36 | Peptide | Transcription factor DICHOTOMA-like | |
| 37 | Nucleic Acid | Transcription factor CYCLOIDEA-like | XM_009764845.1 |
| 38 | Peptide | Transcription factor CYCLOIDEA-like | |
| 39 | Nucleic Acid | RING-H2 finger protein ATL11-like | XP_004251547.1 |
| 40 | Peptide | RING-H2 finger protein ATL11-like | |

TABLE 1-continued

| Description of sequences | | | |
|---|---|---|---|
| SEQ ID NO | Sequence Type | Sequence Description | NCBI Accession Number of the Top Hit of A BLAST Search |
| 41 | Nucleic Acid | Homeobox-leucine zipper protein ATHB-40-like | XP_004232382.1 |
| 42 | Peptide | Homeobox-leucine zipper protein ATHB-40-like | |
| 43 | Nucleic Acid | Uncharacterized protein- LOC102586855 isoform X1 | XP_006357617.1 |
| 44 | Peptide | Uncharacterized protein- LOC102586855 isoform X1 | |
| 45 | Nucleic Acid | Unknown | CAN63006.1 |
| 46 | Peptide | Unknown | |
| 47 | Nucleic Acid | MADS affecting flowering 5-like isoform X1/X2 | XP_006366525.1 |
| 48 | Peptide | MADS affecting flowering 5-like isoform X1/X2 | |
| 49 | Nucleic Acid | Nuclear transcription factor Y subunit | XP_006351227.1 |
| 50 | Peptide | Nuclear transcription factor Y subunit | |
| 51 | Nucleic Acid | Nuclear transcription factor Y subunit A-7-like | XP_006351229.1 |
| 52 | Peptide | Nuclear transcription factor Y subunit A-7-like | |
| 53 | Nucleic Acid | Transcription factor CYCLOIDEA-like | XM_009767637.1 |
| 54 | Peptide | Transcription factor CYCLOIDEA-like | |
| 55 | Nucleic Acid | *Arabidopsis* cytokinin oxidase | NM_129714.3 |
| 56 | Peptide | *Arabidopsis* cytokinin oxidase | |
| 57 | Nucleic Acid | *Nicotiana tabacum* cytokinin oxidase | XM_009611148.1 |
| 58 | Peptide | *Nicotiana tabacum* cytokinin oxidase | |
| 59 | Nucleic Acid | *Nicotiana tabacum* cytokinin oxidase | XM_009632505.1 |
| 60 | Peptide | *Nicotiana tabacum* cytokinin oxidase | |
| 61 | Nucleic Acid | *Nicotiana tabacum* Isopentenyl transferase gene (IPT-g120126) | XM_009784416.1 |
| 62 | Peptide | *Nicotiana tabacum* Isopentenyl transferase gene (IPT-g120126) | |
| 63 | Nucleic Acid | *Nicotiana tabacum* WUSCHEL (WUS-g151887) | XM_009589135.1 |
| 64 | Peptide | *Nicotiana tabacum* WUSCHEL (WUS-g151887) | |
| 65 | Nucleic Acid | *Nicotiana tabacum* WUSCHEL (WUS-g135280) | XM_009793912.1 |
| 66 | Peptide | *Nicotiana tabacum* WUSCHEL (WUS-g135280) | |
| 67 | Nucleic Acid | *Arabidopsis thaliana* CLAVATA3 (CLV3) | NM_001124926.1 |
| 68 | Peptide | *Arabidopsis thaliana* CLAVATA3 (CLV3) | |
| 69 | Nucleic Acid | *Nicotiana tabacum* CLAVATA3 (Scaffold00010610) | XM_009628563.1 |
| 70 | Peptide | *Nicotiana tabacum* CLAVATA3 (Scaffold00010610) | |
| 71 | Nucleic Acid | *Nicotiana tabacum* LATERAL SUPPRESSOR (g56830) | XM_009619761.1 |
| 72 | Peptide | *Nicotiana tabacum* LATERAL SUPPRESSOR (g56830) | |
| 73 | Nucleic Acid | *Nicotiana tabacum* LATERAL SUPPRESSOR (scafflod0004261) | XM_009766770.1 |
| 74 | Peptide | *Nicotiana tabacum* LATERAL SUPPRESSOR (scafflod0004261) | |
| 75 | Nucleic Acid | *Nicotiana tabacum* REGULATOR OF AXILLARY MERISTEMS (RAX-scaffold0000950) | XM_009802273.1 |
| 76 | Peptide | *Nicotiana tabacum* REGULATOR OF AXILLARY MERISTEMS (RAX-scaffold0000950) | |
| 77 | Nucleic Acid | *Nicotiana tabacum* REGULATOR OF AXILLARY MERISTEMS (RAX-scaffold00001904) | XM_009602411.1 |
| 78 | Peptide | *Nicotiana tabacum* REGULATOR OF AXILLARY MERISTEMS (RAX-scaffold00001904) | |
| 79 | Nucleic Acid | *Bacillus amyloliquefaciens* extracellular ribonuclease (Barnase) | CP009748.1 |
| 80 | Peptide | *Bacillus amyloliquefaciens* extracellular ribonuclease (Barnase) | |
| 81 | Nucleic Acid | *Arabidopsis thaliana* BRANCHED1 | NM_001125184.1 |
| 82 | Peptide | *Arabidopsis thaliana* BRANCHED1 | |
| 83 | Nucleic Acid | RNAi_1 (targeting SEQ ID NO: 1) | |
| 84 | Nucleic Acid | RNAi_2 (targeting SEQ ID NO: 3) | |
| 85 | Nucleic Acid | RNAi_5 (targeting SEQ ID NO: 9) | |
| 86 | Nucleic Acid | RNAi_7 (targeting SEQ ID NO: 13) | |
| 87 | Nucleic Acid | RNAi_8 (targeting SEQ ID NO: 15) | |
| 88 | Nucleic Acid | RNAi_9 (targeting SEQ ID NO: 17) | |
| 89 | Nucleic Acid | RNAi_10 (targeting SEQ ID NO: 19) | |
| 90 | Nucleic Acid | RNAi_12 (targeting SEQ ID NO: 21) | |
| 91 | Nucleic Acid | RNAi_14 (targeting SEQ ID NO: 25) | |
| 92 | Nucleic Acid | RNAi_15 (targeting SEQ ID NO: 27) | |
| 93 | Nucleic Acid | RNAi_16 (targeting SEQ ID NO: 29) | |
| 94 | Nucleic Acid | RNAi_17 (targeting SEQ ID NO: 31) | |
| 95 | Nucleic Acid | RNAi_18 (targeting SEQ ID NO: 35) | |
| 96 | Nucleic Acid | RNAi_26 (targeting SEQ ID NO: 49) | |
| 97 | Nucleic Acid | RNAi_61 (targeting SEQ ID NO: 61) | |
| 98 | Nucleic Acid | RNAi_63 and 65 (targeting SEQ ID NO: 63 and 65) | |
| 99 | Nucleic Acid | RNAi_71 and 73 (targeting SEQ ID NO: 71 and 73) | |
| 100 | Nucleic Acid | RNAi_75 and 77 (targeting SEQ ID NO: 75 and 77) | |

TABLE 1-continued

Description of sequences

| SEQ ID NO | Sequence Type | Sequence Description | NCBI Accession Number of the Top Hit of A BLAST Search |
|---|---|---|---|
| 101 | Nucleic Acid | RNAi_CET-26-6 (targeting SEQ ID NO: 11, 49, 108, 109 and 110) | |
| 102 | Nucleic Acid | RNAi_45-2-7-TDNA-145337-RI (targeting SEQ ID NO: 39) | |
| 103 | Nucleic Acid | RNAi_45-2-7-TDNA-348CDS-RI (targeting SEQ ID NO: 41) | |
| 104 | Nucleic Acid | RNAi_45-2-7-TDNA-131180CDS-RI (targeting SEQ ID NO: 43) | |
| 105 | Nucleic Acid | RNAi_45-2-7-TDNA-22266-RI (targeting SEQ ID NO: 45) | |
| 106 | Nucleic Acid | RNAi_45-2-7-TDNA-53803/75660-RI (targeting SEQ ID NO: 49) | |
| 107 | Nucleic Acid | RNAi_45-2-7-TDNA-21860-RI (targeting SEQ ID NO: 47) | |
| 108 | Nucleic Acid | CEN-like protein 2 (CET2) g114109 | AF145260.1 |
| 109 | Nucleic Acid | CEN-like protein 2 (CET2) g2420 | XM_009596199.1 |
| 110 | Nucleic Acid | CEN-like protein 2 (CET2) Scaffold0003597 CDS | XM_009787775.1 |
| 111 | Nucleic Acid | Transformation cassette | |
| 112 | Nucleic Acid | *Agrobacterium* transformation vector p45-2-7 | |
| 113 | Nucleic Acid | A promoter sequence of a gene encoding SEQ ID NO: 2 (Gene 1) | |
| 114 | Nucleic Acid | A promoter sequence of a gene encoding SEQ ID NO: 8 (Gene 4) | |
| 115 | Nucleic Acid | A promoter sequence of a gene encoding SEQ ID NO: 14 (Gene 7) | |
| 116 | Nucleic Acid | promoter of SEQ ID NO: 275 (Gene 11) | |
| 117 | Nucleic Acid | A promoter sequence of a gene encoding SEQ ID NO: 28 (Gene 15) | |
| 118 | Nucleic Acid | A promoter sequence of a gene encoding SEQ ID NO: 4 (Gene 2) | |
| 119 | Nucleic Acid | Sequence for TALEN donor, which targets a gene encoding SEQ ID NO: 1 | |
| 120 | Nucleic Acid | Sequence for TALEN binding sites, which targets a gene encoding SEQ ID NO: 1 | |
| 121 | Nucleic Acid | Sequence for TALEN, include promoter NO: 118, NO: 113 which targets a gene encoding SEQ ID NO: 13 | |
| 122 | Nucleic Acid | Sequence for TALEN biding sites, which targets a gene encoding SEQ ID NO: 13 | |
| 123 | Nucleic Acid | *Nicotiana tabacum* T2 Rnase | XP_009794914.1 |
| 124 | Nucleic Acid | *Nicotiana tabacum* T2 Rnase | XP_009766067.1 |
| 125 | Nucleic Acid | *Nicotiana tabacum* P1 Rnase | XP_009597823.1 |
| 126 | Nucleic Acid | *Nicotiana tabacum* Rnase | XP_009775662.1 |
| 127 | Nucleic Acid | *Nicotiana tabacum* T2 Rnase | XM_009794797.1 |
| 128 | Nucleic Acid | *Nicotiana tabacum* T2 Rnase | XM_009627900.1 |
| 129 | Nucleic Acid | *Nicotiana tabacum* T2 Rnase | JQ041907.1 |
| 130 | Nucleic Acid | *Nicotiana tabacum* T2 Rnase | XM_009795594.1 |
| 131 | Nucleic Acid | *Nicotiana tabacum* T2 Rnase | XM_009795502.1 |
| 132 | Nucleic Acid | *Nicotiana tabacum* T2 Rnase | XM_009606804.1 |
| 133 | Nucleic Acid | *Nicotiana tabacum* T2 Rnase | XM_009794798.1 |
| 134 | Nucleic Acid | *Nicotiana tabacum* T2 Rnase | AB034638.1 |
| 135 | Nucleic Acid | *Nicotiana tabacum* T2 Rnase | XM_009784762.1 |
| 136 | Nucleic Acid | *Nicotiana tabacum* T2 Rnase | XM_009798107.1 |
| 137 | Nucleic Acid | VPE14 | XM_009773063.1 |
| 138 | Nucleic Acid | VPE15 | XM_009594104.1 |
| 139 | Nucleic Acid | VPE16 | XM_009784979.1 |
| 140 | Nucleic Acid | VPE17 | XM_009765910.1 |
| 141 | Nucleic Acid | VPE4 | XM_009623321.1 |
| 142 | Nucleic Acid | VPE6 | XM_009764257.1 |
| 143 | Nucleic Acid | VPE7 | AB075949.1 |
| 144 | Nucleic Acid | *Nicotiana tabacum* Proteinase | XM_009801188.1 |
| 145 | Nucleic Acid | *Nicotiana tabacum* Proteinase | XM_009792063.1 |
| 146 | Nucleic Acid | *Nicotiana tabacum* Proteinase | XM_009779330.1 |
| 147 | Nucleic Acid | *Nicotiana tabacum* Proteinase | XM_009764284.1 |
| 148 | Nucleic Acid | Thionin 5' upstream regulatory sequence | |
| 149 | Nucleic Acid | *Nicotiana tabacum* Lateral Suppressor1 (LAS1) 5' upstream regulatory sequence | |
| 150 | Nucleic Acid | *Nicotiana tabacum* LAS1 3' downstream regulatory sequence | |
| 151 | Nucleic Acid | *Nicotiana tabacum* LAS2 5' upstream regulatory sequence | |

TABLE 1-continued

Description of sequences

| SEQ ID NO | Sequence Type | Sequence Description | NCBI Accession Number of the Top Hit of A BLAST Search |
|---|---|---|---|
| 152 | Nucleic Acid | *Nicotiana tabacum* LAS2 3' downstream regulatory sequence | |
| 153 | Nucleic Acid | *Nicotiana tabacum* Regulator of Axillary Meristems1 (RAX1) 5' upstream regulatory sequence | |
| 154 | Nucleic Acid | *Nicotiana tabacum* RAX1 3' downstream regulatory sequence | |
| 155 | Nucleic Acid | *Nicotiana tabacum* RAX2 5' upstream regulatory sequence | |
| 156 | Nucleic Acid | *Nicotiana tabacum* RAX2 3' downstream regulatory sequence | |
| 157 | Nucleic Acid | SEQ ID NO: 27 5' upstream regulatory sequence | |
| 158 | Nucleic Acid | SEQ ID NO: 27 3' downstream regulatory sequence | |
| 159 | Nucleic Acid | SEQ ID NO: 27 homolog 5' upstream regulatory sequence | |
| 160 | Nucleic Acid | SEQ ID NO: 27 homolog 3' downstream regulatory sequence | |
| 161 | Peptide | *Nicotiana tabacum* T2 Rnase encoded by SEQ ID NO: 123 | |
| 162 | Peptide | *Nicotiana tabacum* T2 Rnase encoded by SEQ ID NO: 124 | |
| 163 | Peptide | *Nicotiana tabacum* P1 Rnase encoded by SEQ ID NO: 125 | |
| 164 | Peptide | *Nicotiana tabacum* Rnase encoded by SEQ ID NO: 126 | |
| 165 | Peptide | *Nicotiana tabacum* T2 Rnase encoded by SEQ ID NO: 127 | |
| 166 | Peptide | *Nicotiana tabacum* T2 Rnase encoded by SEQ ID NO: 128 | |
| 167 | Peptide | *Nicotiana tabacum* T2 Rnase encoded by SEQ ID NO: 129 | |
| 168 | Peptide | *Nicotiana tabacum* T2 Rnase encoded by SEQ ID NO: 130 | |
| 169 | Peptide | *Nicotiana tabacum* T2 Rnase encoded by SEQ ID NO: 131 | |
| 170 | Peptide | *Nicotiana tabacum* T2 Rnase encoded by SEQ ID NO: 132 | |
| 171 | Peptide | *Nicotiana tabacum* T2 Rnase encoded by SEQ ID NO: 133 | |
| 172 | Peptide | *Nicotiana tabacum* T2 Rnase encoded by SEQ ID NO: 134 | |
| 173 | Peptide | *Nicotiana tabacum* T2 Rnase encoded by SEQ ID NO: 135 | |
| 174 | Peptide | *Nicotiana tabacum* T2 Rnase encoded by SEQ ID NO: 136 | |
| 175 | Peptide | VPE14 encoded by SEQ ID NO: 137 | |
| 176 | Peptide | VPE15 encoded by SEQ ID NO: 138 | |
| 177 | Peptide | VPE16 encoded by SEQ ID NO: 139 | |
| 178 | Peptide | VPE17 encoded by SEQ ID NO: 140 | |
| 179 | Peptide | VPE4 encoded by SEQ ID NO: 141 | |
| 180 | Peptide | VPE6 encoded by SEQ ID NO: 142 | |
| 181 | Peptide | VPE7 encoded by SEQ ID NO: 143 | |
| 182 | Peptide | *Nicotiana tabacum* Proteinase encoded by SEQ ID NO: 144 | |
| 183 | Peptide | *Nicotiana tabacum* Proteinase encoded by SEQ ID NO: 145 | |
| 184 | Peptide | *Nicotiana tabacum* Proteinase encoded by SEQ ID NO: 146 | |
| 185 | Peptide | *Nicotiana tabacum* Proteinase encoded by SEQ ID NO: 147 | |
| 186 | Nucleic Acid | C12866 (Gene 11) | XP_006467846.1 |
| 187 | Peptide | C12866 (Gene 11) | |
| 188 | Nucleic Acid | *Nicotiana tabacum* STM homolog (NTH15) | AB004785 |
| 189 | Peptide | *Nicotiana tabacum* STM homolog (NTH15) | |
| 190 | Nucleic Acid | *Nicotiana tabacum* (Grassy Tillers1) GT1 homolog | |
| 191 | Peptide | *Nicotiana tabacum* (Grassy Tillers1) GT1 homolog | |

TABLE 1-continued

| Description of sequences | | | |
|---|---|---|---|
| SEQ ID NO | Sequence Type | Sequence Description | NCBI Accession Number of the Top Hit of A BLAST Search |
| 192 | Nucleic Acid | *Arabidopsis thaliana* More Axillary Branching1 (MAX1) | AK316903.1 |
| 193 | Peptide | *Arabidopsis thaliana* More Axillary Branching1 (MAX1) | |
| 194 | Nucleic Acid | *Arabidopsis thaliana* MAX2 | AAK97303.1 |
| 195 | Peptide | *Arabidopsis thaliana* MAX2 | |
| 196 | Nucleic Acid | *Nicotiana tabacum* MAX1 homolog | XM_009801023.1 |
| 197 | Peptide | *Nicotiana tabacum* MAX1 homolog | |
| 198 | Nucleic Acid | *Nicotiana tabacum* MAX2 homolog | XM_009625596.1 |
| 199 | Peptide | *Nicotiana tabacum* MAX2 homolog | |
| 200 | Nucleic Acid | *Arabidopsis thaliana* Lateral Suppressor (LAS) | BT026519.1 |
| 201 | Peptide | *Arabidopsis thaliana* Lateral Suppressor (LAS) | |
| 202 | Nucleic Acid | *Arabidopsis thaliana* Regulator of Axillary Meristems (RAX) | AY519628.1 |
| 203 | Peptide | *Arabidopsis thaliana* Regulator of Axillary Meristems (RAX) | |
| 204 | Nucleic Acid | Regulatory region of *Solanum lycopersicum* homolog of SEQ ID NO: 28 | |
| 205 | Nucleic Acid | *Solanum lycopersicum* homolog of SEQ ID NO: 28 | HG975514.1 |
| 206 | Peptide | *Solanum lycopersicum* homolog of SEQ ID NO: 28 | |
| 207 | Nucleic Acid | *Arabidopsis thaliana* ALCATRAZ | |
| 208 | Peptide | *Arabidopsis thaliana* ALCATRAZ | |
| 209 | Nucleic Acid | *Arabidopsis thaliana* VND6 | |
| 210 | Peptide | *Arabidopsis thaliana* VND6 | |
| 211 | Nucleic Acid | *Arabidopsis thaliana* VND7 | |
| 212 | Peptide | *Arabidopsis thaliana* VND7 | |
| 213 | Nucleic Acid | *Solanum lycopersicum* Adi3 | |
| 214 | Peptide | *Solanum lycopersicum* Adi3 | |
| 215 | Nucleic Acid | *Arabidopsis thaliana* XCP1 | |
| 216 | Peptide | *Arabidopsis thaliana* XCP1 | |
| 217 | Nucleic Acid | *Arabidopsis thaliana* XCP2 | |
| 218 | Peptide | *Arabidopsis thaliana* XCP2 | |
| 219 | Nucleic Acid | *Arabidopsis thaliana* Metacaspase 2d (ATMC4) | |
| 220 | Peptide | *Arabidopsis thaliana* Metacaspase 2d (ATMC4) | |
| 221 | Nucleic Acid | *Arabidopsis thaliana* disease resistance protein RPS5 | |
| 222 | Peptide | *Arabidopsis thaliana* disease resistance protein RPS5 | |
| 223 | Nucleic Acid | *Nicotiana tabacum* TMV resistance N gene | |
| 224 | Peptide | *Nicotiana tabacum* TMV resistance N gene | |
| 225 | Nucleic Acid | *Saccharum* spp. mature miRNA159 | |
| 226 | Nucleic Acid | *Nicotiana tabacum* precursor miRNA159 | |
| 227 | Nucleic Acid | *Nicotiana tabacum* mature miRNA159 | |
| 228 | Nucleic Acid | Nicotiana NAC089 | |
| 229 | Peptide | Nicotiana NAC089 | |
| 230 | Nucleic Acid | Nicotiana BAG6 | |
| 231 | Peptide | Nicotiana BAG6 | |
| 232 | Nucleic Acid | Nicotiana mitogen-activated protein kinase kinase 2 (NtMEK2) | |
| 233 | Peptide | Nicotiana mitogen-activated protein kinase kinase 2 (NtMEK2) | |
| 234 | Nucleic Acid | *Arabidopsis thaliana* Flavin monooxygenase (YUCCA1) | |
| 235 | Peptide | *Arabidopsis thaliana* Flavin monooxygenase (YUCCA1) | |
| 236 | Nucleic Acid | *Arabidopsis thaliana* Pin-formed1 (PIN1) | |
| 237 | Peptide | *Arabidopsis thaliana* Pin-formed1 (PIN1) | |
| 238 | Nucleic Acid | *Arabidopsis thaliana* Tryptophan aminotransferase1/Transport inhibitor response2 (TAA1/TIR2) | |
| 239 | Peptide | *Arabidopsis thaliana* Tryptophan aminotransferase1/Transport inhibitor response2 (TAA1/TIR2) | |
| 240 | Nucleic Acid | *Arabidopsis thaliana* Aldehyde oxidase1 (AAO1) | |
| 241 | Peptide | *Arabidopsis thaliana* Aldehyde oxidase1 (AAO1) | |
| 242 | Nucleic Acid | *Arabidopsis thaliana* Indole-3-acetamide hydrolase1 (AMI1) | |

TABLE 1-continued

Description of sequences

| SEQ ID NO | Sequence Type | Sequence Description | NCBI Accession Number of the Top Hit of A BLAST Search |
|---|---|---|---|
| 243 | Peptide | *Arabidopsis thaliana* Indole-3-acetamide hydrolase1 (AMI1) | |
| 244 | Nucleic Acid | Nicotiana Flavin monooxygenase (NtYUCCA-like1) | |
| 245 | Peptide | Nicotiana Flavin monooxygenase (NtYUCCA-like1) | |
| 246 | Nucleic Acid | Nicotiana Flavin monooxygenase (NtYUCCA-like2) | |
| 247 | Peptide | Nicotiana Flavin monooxygenase (NtYUCCA-like2) | |
| 248 | Nucleic Acid | Nicotiana Pin-formed1-like (NtPIN1-like) | |
| 249 | Peptide | Nicotiana Pin-formed1-like (NtPIN1-like) | |
| 250 | Nucleic Acid | Nicotiana Tryptophan aminotransferase1/Transport inhibitor response2-like (NtTAA1/TIR2-like) | |
| 251 | Peptide | Nicotiana Tryptophan aminotransferase1/Transport inhibitor response2-like (NtTAA1/TIR2-like) | |
| 252 | Nucleic Acid | Nicotiana Aldehyde oxidase1-like (NtAAO1-like) | |
| 253 | Peptide | Nicotiana Aldehyde oxidase1-like (NtAAO1-like) | |
| 254 | Nucleic Acid | Nicotiana Indole-3-acetamide hydrolase1-like (NtAMI1-like) | |
| 255 | Peptide | Nicotiana Indole-3-acetamide hydrolase1-like (NtAMI1-like) | |
| 256 | Peptide | 6x Histidine tag | |

BRIEF DESCRIPTION OF THE DRAWINGS

FIG. 3 shows photographs of control tobacco plants and modified tobacco plants that overexpress SEQ ID NO: 81, which encodes *Arabidopsis thaliana* BRANCHED1.

FIG. 5 shows the growth of axillary shoots in control tobacco plants and modified tobacco plants that express SEQ ID NO: 83, an RNAi construct that targets SEQ ID NO: 1 for inhibition.

FIG. 13 shows the expression pattern of Promoter P15 (SEQ ID NO: 117) fused to β-glucuronidase (GUS) in tobacco. Dark areas of GUS accumulation demonstrate where Promoter P15 is active. FIG. 13B shows GUS expression driven by Promoter P15 at the time of topping (0 hours), 7 days after topping, and 10 days after topping. At each time point, exemplary GUS staining of axillary buds from two independent modified tobacco lines is shown.

FIG. 14 shows microscopy photographs displaying the activity of axillary bud-specific promoters fused to green fluorescent protein (GFP).

DETAILED DESCRIPTION

Figure 1:
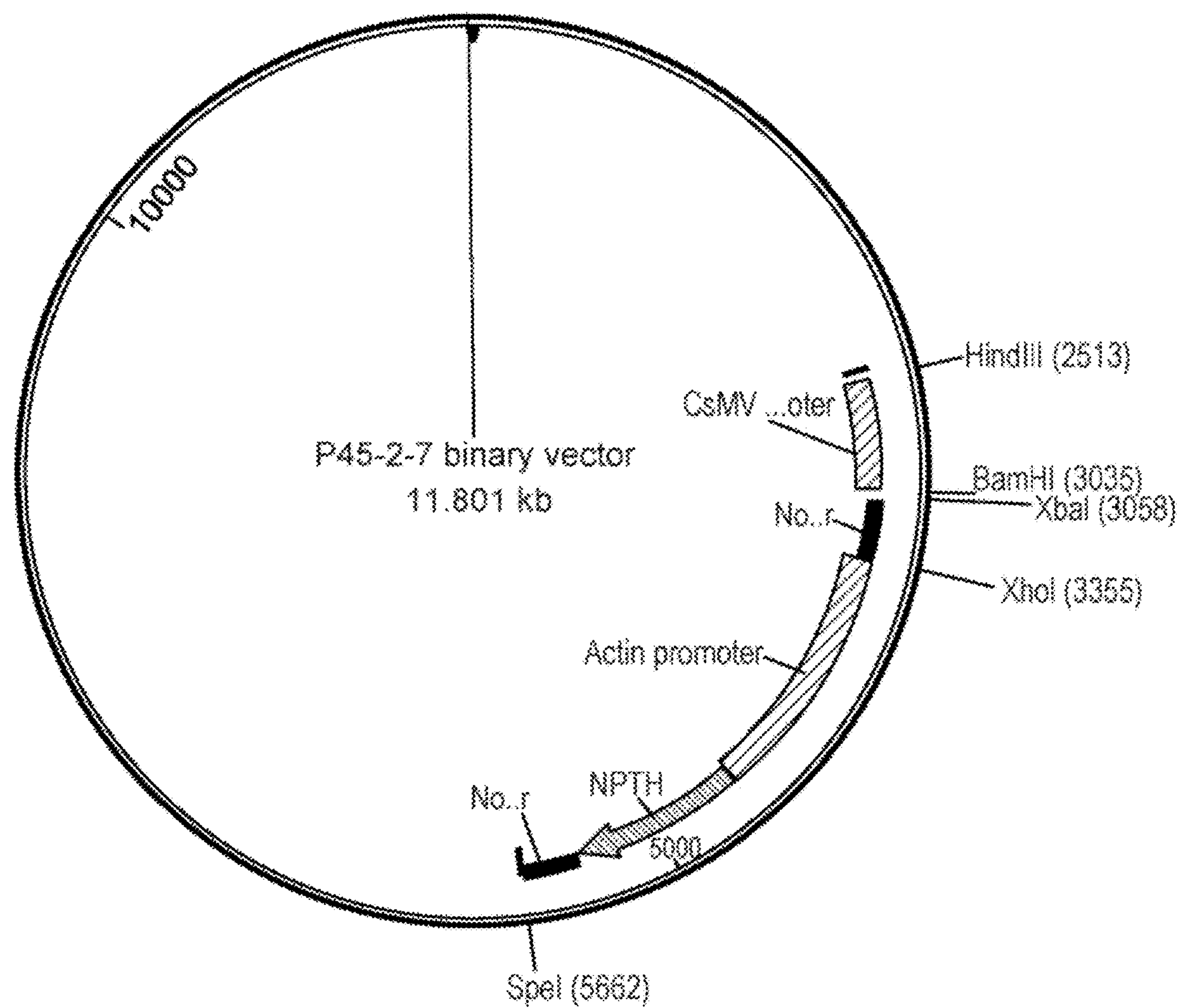
FIG. 1 is a plasmid map of binary vector p45-2-7 (SEQ ID NO: 112).

Unless defined otherwise, technical and scientific terms used herein have the same meaning as commonly understood by one of ordinary skill in the art. One skilled in the art will recognize many methods can be used in the practice of the present disclosure. Indeed, the present disclosure is in no way limited to the methods and materials described. For purposes of the present disclosure, the following terms are defined below.

Any references cited herein, including, e.g., all patents, published patent applications, and non-patent publications, are incorporated by reference in their entirety.

As used herein, the singular form "a," "an," and "the" include plural references unless the context clearly dictates otherwise. For example, the term "a compound" or "at least one compound" may include a plurality of compounds, including mixtures thereof.

The term "about" is used herein to mean approximately, roughly, around, or in the region of. When the term "about" is used in conjunction with a numerical range, it modifies that range by extending the boundaries above and below the numerical values set forth.

As used herein, a tobacco plant can be from any plant from the *Nicotiana tabacum* genus including, but not limited to *Nicotiana tabacum tabacum; Nicotiana tabacum amplexicaulis* PI 271989; *Nicotiana tabacum benthamiana* PI 555478; *Nicotiana tabacum bigelovii* PI 555485; *Nicotiana tabacum debneyi; Nicotiana tabacum excelsior* PI 224063; *Nicotiana tabacum glutinosa PI* 555507; *Nicotiana tabacum goodspeedii* PI 241012; *Nicotiana tabacum gossei* PI 230953; *Nicotiana tabacum hesperis* PI 271991; *Nicotiana tabacum knightiana* PI 555527; *Nicotiana tabacum maritima* PI 555535; *Nicotiana tabacum megalosiphon* PI 555536; *Nicotiana tabacum nudicaulis* PI 555540; *Nicotiana tabacum paniculata* PI 555545; *Nicotiana tabacum plumbaginifolia* PI 555548; *Nicotiana tabacum repanda* PI 555552; *Nicotiana tabacum rustica; Nicotiana tabacum suaveolens* PI 230960; *Nicotiana tabacum sylvestris* PI 555569; *Nicotiana tabacum tomentosa* PI 266379; *Nicotiana tabacum tomentosiformis*; and *Nicotiana tabacum trigonophylla* PI 555572.

In one aspect, this disclosure provides methods and compositions related to modified tobacco plants, seeds, plant components, plant cells, and products made from modified tobacco plants, seeds, plant parts, and plant cells. In one aspect, a modified seed provided herein gives rise to a modified plant provided herein. In one aspect, a modified plant, seed, plant component, plant cell, or plant genome provided herein comprises a recombinant DNA construct provided herein. In another aspect, cured tobacco material or tobacco products provided herein comprise modified tobacco plants, plant components, plant cells, or plant genomes provided herein.

As used herein, "modified" refers to plants, seeds, plant components, plant cells, and plant genomes that have been subjected to mutagenesis, genome editing, genetic transformation, or a combination thereof.

In one aspect, modified tobacco plants provided herein exhibit no or reduced suckering compared to control tobacco plants of the same variety when grown under comparable conditions. In one aspect, modified tobacco plants provided herein exhibit no or reduced topping-induced suckering compared to control tobacco plants of the same variety when grown under comparable conditions. Also provided herein are methods of producing modified tobacco plants that exhibit no or reduced suckering compared to control tobacco plants of the same variety when grown under comparable conditions. In one aspect, methods provided herein produce modified tobacco plants that exhibit no or reduced topping-induced suckering compared to control tobacco plants of the same variety when grown under comparable conditions.

As used herein, "cisgenesis" or "cisgenic" refers to genetic modification of a plant, plant cell, or plant genome in which all components (e.g., promoter, donor nucleic acid, selection gene) have only plant origins (i.e., no non-plant origin components are used). In one aspect, a modified plant, plant cell, or plant genome provided herein is cisgenic. Cisgenic plants, plant cells, and plant genomes provided herein can lead to ready-to-use tobacco lines. In another aspect, a modified tobacco plant provided herein comprises no non-tobacco genetic material or sequences.

As used herein, "suckering" refers to the development and/or growth of axillary (or lateral) buds ("suckers") from axillary meristems that grow between a leaf and the stalk. An axillary bud is an embryonic shoot that comprises an axillary meristem, surrounding leaf tissue, and surrounding stem tissue. In one aspect, suckering is induced by topping a plant.

As used herein, "topping" refers to the removal of the stalk apex, including the SAM, flowers, and up to several adjacent leaves, when a plant is near maturity. Topping a tobacco plant results in the loss of apical dominance. Prior to topping, suckering is largely kept dormant by hormonal signals emanating from the SAM; topping removes the hormonal signals and can allow the outgrowth of suckers ("topping-induced suckering"). Provided suckering is sufficiently controlled, topping increases yield, increases value-per-acre, and results in desirable modifications to physical and chemical properties of tobacco leaves.

As used herein, "comparable growth conditions" refers to similar environmental conditions and/or agronomic practices for growing and making meaningful comparisons between two or more plant genotypes so that neither environmental conditions nor agronomic practices would contribute to, or explain, any differences observed between the two or more plant genotypes. Environmental conditions include, for example, light, temperature, water, humidity, and nutrition (e.g., nitrogen and phosphorus). Agronomic practices include, for example, seeding, clipping, undercutting, transplanting, topping, and suckering. See Chapters 4B and 4C of Tobacco, Production, Chemistry and Technology, Davis & Nielsen, eds., Blackwell Publishing, Oxford (1999), pp. 70-103.

As used herein, "reduced topping-induced suckering" refers to a reduction in the number of suckers; a reduction in the size of suckers (e.g., biomass), and/or a reduction of the impact suckers have on agronomic performance (e.g., yield, quality and overall productivity of the plant) compared to a control plant when grown under comparable conditions. As used herein, a "reduction" in the number of suckers, the size of suckers, and/or the impact suckers have on agronomic performance refers to a statistically significant reduction. As used herein, "statistically significant" refers to a p-value of less than 0.05, a p-value of less than 0.025, a p-value of less than 0.01, or a p-value of less than 0.001 when using an appropriate measure of statistical significance (e.g., a one-tailed two sample t-test).

The present disclosure provides modified tobacco plants with desirable or enhanced properties, e.g., inhibited or reduced sucker growth prior to or after topping. In one aspect, a modified plant provided herein comprises fewer total suckers, smaller suckers, or both compared to a control plant lacking such modification when grown under comparable conditions. In one aspect, smaller suckers of a modified plant provided herein comprise reduced mass, reduced length, reduced diameter, or a combination thereof compared to suckers of a control plant grown under comparable conditions. The diameter of a sucker is measured at the base of the sucker where it adjoins the main stem of the plant.

In one aspect, the mass of suckers of a modified tobacco plant provided herein is at least 10%, at least 15%, at least 20%, at least 25%, at least 30%, at least 35%, at least 40%, at least 45%, at least 50%, at least 60%, at least 70%, at least 80%, at least 90%, or at least 95% reduced compared to the mass of suckers of an unmodified control tobacco plant grown under comparable conditions. In one aspect, the mass of suckers of a modified tobacco plant provided herein is reduced by 1%-25%, 1%-50%, 1%-75%, 1%-100%, 5%-25%, 5%-50%, 5%-75%, 5%-100%, 10%-25%, 10%-50%, 10%-75%, 10%-100%, 25%-50%, 25%-75%, 25%-100%, 50%-75%, or 50%-100% as compared to the mass of suckers of an unmodified control tobacco plant grown under comparable conditions. In another aspect, the length of suckers of a modified tobacco plant provided herein is at least 10%, at least 15%, at least 20%, at least 25%, at least 30%, at least 35%, at least 40%, at least 45%, at least 50%, at least 60%, at least 70%, at least 80%, at least 90%, or at least 95% reduced compared to the length of suckers of an unmodified control tobacco plant grown under comparable conditions. In one aspect, the length of suckers of a modified tobacco plant provided herein is reduced by 1%-25%, 1%-50%, 1%-75%, 1%-100%, 5%-25%, 5%-50%, 5%-75%, 5%-100%, 10%-25%, 10%-50%, 10%-75%, 10%-100%, 25%-50%, 25%-75%, 25%-100%, 50%-75%, or 50%-100% as compared to the length of suckers of an unmodified control tobacco plant grown under comparable conditions. In one aspect, the diameter of suckers of a modified tobacco plant provided herein is at least 10%, at least 15%, at least 20%, at least 25%, at least 30%, at least 35%, at least 40%, at least 45%, at least 50%, at least 60%, at least 70%, at least 80%, at least 90%, or at least 95% reduced compared to the diameter of suckers of an unmodified control tobacco plant grown under comparable conditions. In one aspect, the diameter of suckers of a modified tobacco plant provided herein is reduced by 1%-25%, 1%-50%, 1%-75%, 1%-100%, 5%-25%, 5%-50%, 5%-75%, 5%-100%, 10%-25%, 10%-50%, 10%-75%, 10%-100%, 25%-50%, 25%-75%, 25%-100%, 50%-75%, or 50%-100% as compared to the diameter of suckers of an unmodified control tobacco plant grown under comparable conditions.

In another aspect, a modified tobacco plant provided herein comprises at least 1, at least 2, at least 3, at least 4, at least 5, at least 6, at least 7, at least 8, at least 9, at least 10, at least 15, at least 20, at least 30, at least 40, at least 50, or at least 60 fewer total suckers compared to an unmodified control tobacco plant grown under comparable conditions. In another aspect, a modified tobacco plant provided herein comprises at least 10%, at least 15%, at least 20%, at least 25%, at least 30%, at least 35%, at least 40%, at least 45%, at least 50%, at least 60%, at least 70%, at least 80%, at least 90%, or at least 95% fewer suckers compared to an unmodified control tobacco plant grown under comparable conditions. In one aspect, the number of suckers of a modified tobacco plant provided herein is reduced by 1%-25%, 1%-50%, 1%-75%, 1%-100%, 5%-25%, 5%-50%, 5%-75%, 5%-100%, 10%-25%, 10%-50%, 10%-75%, 10%-100%, 25%-50%, 25%-75%, 25%-100%, 50%-75%, or 50%-100% as compared to the number of suckers of an unmodified control tobacco plant grown under comparable conditions.

Shoot apical and axillary meristems have two main functions: to maintain themselves as a group of pluripotent cells, and to generate lateral above-ground organs of the plant (e.g., stems, leaves, flowers). If a meristem fails to maintain itself, for any reason, it will eventually exhaust its pluripotent cells and cease giving rise to additional organs. In one aspect, a modified tobacco plant provided herein exhibits inhibited or eliminated axillary meristem growth; inhibited or eliminated axillary meristem maintenance; or a combination thereof compared to a control tobacco plant of the same variety when grown under comparable conditions.

In one aspect, a modified tobacco plant provided herein has similar or higher leaf yield compared to a control tobacco plant when grown under comparable conditions. In an aspect, leaf yield is selected from the group consisting of fresh yield, dry yield, and cured yield. In one aspect, a modified tobacco plant provided herein produces a leaf yield mass within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% compared to a control tobacco plant when grown under comparable conditions. In another aspect, a modified tobacco plant provided herein produces a leaf yield mass at least 0.25%, 0.5%, 1%, 2.5%, 5%, 10%, 15%, 20%, 25%, 30%, 40%, 50%, 60%, 70%, 80%, 90%, 100%, or more than 100% higher compared to a control tobacco plant when grown under comparable conditions. In another aspect, a modified tobacco plant provided herein produces a leaf yield mass 0.25%-100%, 0.5%-100%, 1%-100%, 2.5%-100%, 5%-100%, 10%-100%, 15%-100%, 20%-100%, 25%-100%, 30%-100%, 40%-100%, 50%-100%, 60%-100%, 70%-100%, 80%-100%, 90%-100%, 100%-200%, 100%-175%, 100%-150%, 100%-125%, 0.25%-50%, 0.5%-50%, 1%-50%, 2.5%-50%, 5%-50%, 10%-50%, 15%-50%, 20%-50%, 25%-50%, 30%-50%, 40%-50%, 50%-200%, 50%-175%, 50%-150%, 50%-125%, 0.25%-25%, 0.5%-25%, 1%-25%, 2.5%-25%, 5%-25%, 10%-25%, 15%-25%, 20%-25%, 25%-200%, 25%-175%, 25%-150%, or 25%-125% higher compared to a control tobacco plant when grown under comparable conditions. In an aspect, a modified tobacco plant provided herein produces a number of leaves within 75%, within 60%, within 50%, within 45%, within 40%, within 35%, within 30%, within 25%, within 20%, within 15%, within 10%, within 5%, within 4%, within 3%, within 2%, within 1%, or within 0.5% the number of leaves produced by an unmodified control tobacco plant grown under comparable conditions.

In one aspect, a modified tobacco plant provided herein has a similar or comparable plant height compared to a control tobacco plant when grown under comparable conditions. In one aspect, a modified tobacco plant provided herein comprises a height within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% compared to a control tobacco plants when grown under comparable conditions. In another aspect, a modified tobacco plant provided herein comprises a height 0.25%, 0.5%, 1%, 2.5%, 5%, 10%, 15%, 20%, 25%, 30%, 40%, 50%, 60%, 70%, 80%, 90%, 100%, or more than 100% taller compared to a control tobacco plant when grown under comparable conditions. In another aspect, a modified tobacco plant comprises a height 0.25%-100%, 0.5%-100%, 1%-100%, 2.5%-100%, 5%-100%, 10%-100%, 15%-100%, 20%-100%, 25%-100%, 30%-100%, 40%-100%, 50%-100%, 60%-100%, 70%-100%, 80%-100%, 90%-100%, 100%-200%, 100%-175%, 100%-150%, 100%-125%, 0.25%-50%, 0.5%-50%, 1%-50%, 2.5%-50%, 5%-50%, 10%-50%, 15%-50%, 20%-50%, 25%-50%, 30%-50%, 40%-50%, 50%-200%, 50%-175%, 50%-150%, 50%-125%, 0.25%-25%, 0.5%-25%, 1%-25%, 2.5%-25%, 5%-25%, 10%-25%, 15%-25%, 20%-25%, 25%-200%, 25%-175%, 25%-150%, or 25%-125% taller compared to a control tobacco plant when grown under comparable conditions.

In one aspect, a modified tobacco plant provided herein produces leaves that have a similar or higher USDA grade index value compared to a control tobacco plant when grown under comparable conditions. In one aspect, a modified tobacco plant provided herein produces leaves with a USDA grade index value within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% compared to a control tobacco plant when grown under comparable conditions. In one aspect, a modified tobacco plant provided herein is capable of producing leaves having a USDA grade index value of 55 or more, 60 or more, 65 or more, 70 or more, 75 or more, or more, 85 or more, 90 or more, or 95 or more. In one aspect, a modified tobacco plant provided herein produces leaves with a USDA grade index value at least 1, 2, 3, 4, 5, 6, 7, 8, 9, 10, 12, 13, 14, 15, 16, 17, 18, 19, 20, 21, 22, 23, 24, 25, 26, 27, 28, 29, 30, 35, 40, 45, 50, or more than 50 units higher compared to a control tobacco plant when grown under comparable conditions. In one aspect, a modified tobacco plant provided herein produces leaves with a USDA grade index value 1-50, 1-45, 1-40, 1-35, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2, 2-50, 2-45, 2-2-35, 2-30, 2-29, 2-28, 2-27, 2-26, 2-25, 2-24, 2-23, 2-22, 2-21, 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-50, 3-45, 3-40, 3-35, 3-30, 3-29, 3-28, 3-27, 3-26, 3-25, 3-24, 3-23, 3-22, 3-21, 3-20, 3-19, 3-18, 3-17, 3-16, 3-15, 3-14, 3-13, 3-12, 3-11, 3-10, 3-9, 3-8, 3-7, 3-6, 3-5, 3-4, 4-50, 4-45, 4-40, 4-35, 4-30, 4-29, 4-28, 4-27, 4-26, 4-25, 4-24, 4-23, 4-22, 4-21, 4-20, 4-19, 4-18, 4-17, 4-16, 4-15, 4-14, 4-13, 4-12, 4-11, 4-10, 4-9, 4-8, 4-7, 4-6, 4-5, 5-50, 5-45, 5-40, 5-35, 5-30, 5-29, 5-28, 5-27, 5-26, 5-25, 5-24, 5-23, 5-22, 5-21, 5-20, 5-19, 5-18, 5-17, 5-16, 5-15, 5-14, 5-13, 5-12, 5-11, 5-10, 5-9, 5-8, 5-7, 5-6, 10-50, 10-10-30, 10-20, 20-50, 20-30, 20-40, or 20-30 units higher compared to a control tobacco plant when grown under comparable conditions.

Tobacco grades are evaluated based on factors including, but not limited to, the leaf stalk position, leaf size, leaf color, leaf uniformity and integrity, ripeness, texture, elasticity, sheen (related with the intensity and the depth of coloration of the leaf as well as the shine), hygroscopicity (the faculty of the tobacco leaves to absorb and to retain the ambient moisture), and green nuance or cast. Leaf grade can be determined, for example, using an Official Standard Grade published by the Agricultural Marketing Service of the US Department of Agriculture (7 U.S.C. § 511). See, e.g., Official Standard Grades for Burley Tobacco (U.S. Type 31 and Foreign Type 93), effective Nov. 5, 1990 (55 F.R. 40645); Official Standard Grades for Flue-Cured Tobacco (U.S. Types 11, 12, 13, 14 and Foreign Type 92), effective Mar. 27, 1989 (54 F.R. 7925); Official Standard Grades for Pennsylvania Seedleaf Tobacco (U.S. Type 41), effective Jan. 8, 1965 (29 F.R. 16854); Official Standard Grades for Ohio Cigar-Leaf Tobacco (U.S. Types 42, 43, and 44), effective Dec. 8, 1963 (28 F.R. 11719 and 28 F.R. 11926); Official Standard Grades for Wisconsin Cigar-Binder Tobacco (U.S. Types 54 and 55), effective Nov. 20, 1969 (34 F.R. 17061); Official Standard Grades for Wisconsin Cigar-Binder Tobacco (U.S. Types 54 and 55), effective Nov. 20, 1969 (34 F.R. 17061); Official Standard Grades for Georgia and Florida Shade-Grown Cigar-Wrapper Tobacco (U.S. Type 62), Effective April 1971. A USDA grade index value can be determined according to an industry accepted grade index. See, e.g., Bowman et al, *Tobacco Science,* 32:39-40 (1988); Legacy Tobacco Document Library (Bates Document #523267826-523267833, Jul. 1, 1988, Memorandum on the Proposed Burley Tobacco Grade Index); and Miller et al., 1990*, Tobacco Intern.,* 192:55-57 (all foregoing references are incorporated by inference in their entirety). Alternatively, leaf grade can be determined via hyper-spectral imaging. See e.g., WO 2011/027315 (published on Mar. 10, 2011, and incorporated by inference in its entirety).

In one aspect, a modified plant provided herein requires reduced management for controlling suckering compared to a control plant when grown under comparable conditions. As used herein, “management” refers to manually removing suckers, application of chemicals (e.g., maleic hydrazide, flumetralin) to inhibit or remove suckers, or both. In one aspect, a modified plant provided herein requires reduced frequency of manual sucker removal, reduced frequency of chemical application, reduced quantities of chemical application, or a combination thereof, compared to a control plant grown under comparable conditions. See, for example, Fisher et al. “Topping, Managing Suckers, and Using Ethephon,” pages 96-117 In: 2016 Flue-Cured Tobacco Information, North Carolina State University, which is herein incorporated by reference in its entirety. In one aspect, a modified plant provided herein requires manual removal of suckers 10%, 20%, 30%, 40%, 50%, 60%, 70%, 75%, 80%, 85%, 90%, or 95% as frequently as a control plant when grown under comparable conditions. In one aspect, a modified plant provided herein requires manual removal of suckers less than 10%, less than 20%, less than 30%, less than 40%, less than 50%, less than 60%, less than 70%, less than 75%, less than 80%, less than 85%, less than 90%, or less than 95% as frequently as a control plant when grown under comparable conditions. In one aspect, a modified plant provided herein requires manual removal of suckers 10%-95%, 20%-95%, 30%-95%, 40%-95%, 50%-95%, 60%-95%, 70%-95%, 80%-95%, 85%-95%, 90%-95%, 10%-50%, 20%-50%, 30%-50%, 40%-50%, 10%-20%, 10%-30%, 10%-40%, 10%-50%, 10%-60%, 10%-70%, 10%-80%, 10%-85%, or 10%-90% as frequently as a control plant when grown under comparable conditions. In one aspect, a modified plant provided herein requires chemical application to control suckering 10%, 20%, 30%, 40%, 50%, 60%, 70%, 75%, 80%, 85%, 90%, or 95% as frequently as a control plant when grown under comparable conditions. In one aspect, a modified plant provided herein requires chemical application to control suckering less than 10%, less than 20%, less than 30%, less than 40%, less than 50%, less than 60%, less than 70%, less than 75%, less than 80%, less than 85%, less than 90%, or less than 95% as frequently as a control plant when grown under comparable conditions. In one aspect, a modified plant provided herein requires chemical application to control suckering 10%-95%, 20%-95%, 30%-95%, 40%-95%, 50%-95%, 60%-95%, 70%-95%, 80%-95%, 85%-95%, 90%-95%, 10%-50%, 20%-50%, 30%-50%, 40%-50%, 10%-20%, 10%-30%, 10%-40%, 10%-50%, 10%-60%, 10%-70%, 10%-80%, 10%-85%, or 10%-90% as frequently as a control plant when grown under comparable conditions. In one aspect, a modified plant provided herein requires a chemical spray volume of 10%, 20%, 30%, 40%, 50%, 60%, 70%, 75%, 80%, 85%, 90%, or 95% of the volume used to control suckering of a control plant when grown under comparable conditions. In one aspect, a modified plant provided herein requires a chemical spray volume of less than 10%, less than 20%, less than 30%, less than 40%, less than 50%, less than 60%, less than 70%, less than 75%, less than 80%, less than 85%, less than 90%, or less than 95% of the volume used to control suckering of a control plant when grown under comparable conditions. In one aspect, a modified plant provided herein requires a chemical spray volume 10%-95%, 20%-95%, 30%-95%, 40%-95%, 50%-95%, 60%-95%, 70%-95%, 80%-95%, 85%-95%, 90%-95%, 10%-50%, 20%-50%, 30%-50%, 40%-50%, 10%-20%, 10%-30%, 10%-40%, 10%-50%, 10%-60%, 10%-70%, 10%-80%, 10%-85%, 10%-90% less than a control plant when grown under comparable conditions.

Unless specified otherwise, measurements of sucker length, sucker mass, number of suckers, leaf yield, or leaf grade index values mentioned herein for a tobacco plant, variety, cultivar, or line refer to average measurements, including, for example, an average of multiple leaves (e.g., 2, 3, 4, 5, 6, 7, 8, 9, 10, 11, 12, 13, 14, 15, 16, 17, 18, 19, or 20 or more leaves) of a single plant or an average measurement from a population of tobacco plants from a single variety, cultivar, or line. A population of tobacco plants or a collection of tobacco leaves for determining an average measurement (e.g., fresh weight or leaf grading) can be of any size, for example, 5, 10, 20, 25, 30, 35, 40, or 50. Industry-accepted standard protocols are followed for determining average measurements or grade index values.

In one aspect, a modified plant or leaf has a similar leaf chemistry profile compared to a control plant when grown under comparable conditions. Without being limiting, a leaf chemistry profile can comprise the amount of alkaloids (e.g., nicotine, nornicotine, anabasine, anatabine), malic acid, and reducing sugars (e.g., dextrose), or a combination thereof in a tobacco plant or tobacco leaf. In one aspect, a modified plant or leaf provided herein comprises a total alkaloids level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the total alkaloids level of a control plant when grown under comparable conditions. In one aspect, a modified plant or leaf provided herein comprises a nicotine level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the nicotine level of a control plant when grown under comparable conditions. In one aspect, a modified plant or leaf provided herein comprises a nornicotine level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the nornicotine level of a control plant when grown under comparable conditions. In one aspect, a modified plant or leaf provided herein comprises an anabasine level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the anabasine level of a control plant when grown under comparable conditions. In one aspect, a modified plant or leaf provided herein comprises an anatabine level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the anatabine level of a control plant when grown under comparable conditions. In one aspect, a modified plant or leaf provided herein comprises a malic acid level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the malic acid level of a control plant when grown under comparable conditions. In one aspect, a modified plant or leaf provided herein comprises a reducing sugars level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the reducing sugars level of a control plant when grown under comparable conditions. In one aspect, a modified plant or leaf provided herein comprises a dextrose level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the dextrose level of a control plant when grown under comparable conditions.

In one aspect, a modified plant or leaf provided herein comprises no or reduced suckers compared to a control plant and further comprises a nicotine level at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, or at least 99.9% lower than the nicotine level of a control plant when grown under comparable conditions.

In one aspect, a plant component provided herein includes, but is not limited to, a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In further aspects, this disclosure provides tobacco plant cells, tissues, and organs that are not reproductive material and do not mediate the natural reproduction of the plant. In another aspect, this disclosure also provides tobacco plant cells, tissues, and organs that are reproductive material and mediate the natural reproduction of the plant. In another aspect, this disclosure provides tobacco plant cells, tissues, and organs that cannot maintain themselves via photosynthesis. In another aspect, this disclosure provides somatic tobacco plant cells. Somatic cells, contrary to germline cells, do not mediate plant reproduction.

Provided cells, tissues and organs can be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, and vascular tissue. In another aspect, this disclosure provides a tobacco plant chloroplast. In a further aspect, this disclosure provides an epidermal cell, a stomata cell, a leaf hair (trichome), a root hair, or a storage root. In another aspect, this disclosure provides a tobacco protoplast.

Skilled artisans understand that tobacco plants naturally reproduce via seeds, not via asexual reproduction or vegetative propagation. In one aspect, this disclosure provides tobacco endosperm. In another aspect, this disclosure provides a tobacco endosperm cell. In a further aspect, this disclosure provides a male or female sterile tobacco plant, which cannot reproduce without human intervention.

In one aspect, a modified plant, seed, plant part, or plant cell provided herein comprises one or more non-naturally occurring mutations. In one aspect, a mutation provided herein suppresses suckering in a plant. In another aspect, a mutation provided herein suppresses topping-induced suckering in a plant. In still another aspect, a mutation provided herein suppresses suckering in a plant prior to topping. Types of mutations provided herein include, for example, substitutions (point mutations), deletions, insertions, duplications, and inversions. Such mutations are desirably present in the coding region of a gene; however, mutations in a promoter or other regulatory region, an intron, an intron-exon boundary, or an untranslated region of a gene may also be desirable.

In one aspect, methods provided herein are capable of producing a tobacco plant with reduced suckering using mutagenesis. Mutagenesis methods include, without limitation, chemical mutagenesis, for example, treatment of seeds with ethyl methylsulfate (EMS) (Hildering and Verkerk. In, The use of induced mutations in plant breeding. Pergamon Press, pp. 317-320, 1965); or UV-irradiation, X-rays, electron beams, ion beams (e.g., carbon ion beam, helium ion beam, neon ion beam), and fast neutron irradiation (see, for example, Verkerk, *Neth. J. Agric. Sci.* 19:197-203, 1971; Poehlman, Breeding Field Crops, Van Nostrand Reinhold, New York (3. sup. rd ed.), 1987; and Tanaka, *J. Radiat. Res.* 51:223-233, 2010); transposon tagging (Fedoroff et al., 1984; U.S. Pat. Nos. 4,732,856 and 5,013,658); and T-DNA insertion methodologies (Hoekema et al., 1983; U.S. Pat. No. 5,149,645). EMS-induced mutagenesis consists of chemically inducing random point mutations over the length of a genome. Fast neutron mutagenesis consists of exposing seeds to neutron bombardment which causes large deletions through double stranded DNA breakage. Transposon tagging comprises inserting a transposon within an endogenous gene to reduce or eliminate expression of the gene.

In addition, a fast and automatable method for screening for chemically induced mutations, TILLING (Targeting Induced Local Lesions In Genomes), using denaturing HPLC or selective endonuclease digestion of selected PCR products is also applicable to the present disclosure. See, McCallum et al. (2000) *Nat. Biotechnol.* 18:455-457. Mutations that impact gene expression or that interfere with the function of genes provided herein can be determined using methods that are well known in the art. Insertional mutations in gene exons usually result in null-mutants. Mutations in conserved residues can be particularly effective in inhibiting the function of a protein.

The screening and selection of mutagenized tobacco plants can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454) enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

In one aspect, a polynucleotide provided herein comprises at least 1, at least 2, at least 3, at least 4, at least 5, at least 6, at least 7, at least 8, at least 9, at least 10, or more than 10 mutations compared to a naturally existing polynucleotide. In another aspect, a mutation provided herein is positioned within a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, and 254. In one aspect, a mutation provided herein is positioned within a polynucleotide encoding a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, a plant genome provided herein is mutated (edited) by a nuclease selected from the group consisting of a meganuclease, a zinc-finger nuclease (ZFN), a transcription activator-like effector nuclease (TALEN), a CRISPR/Cas9 nuclease, or a CRISPR/Cpf1 nuclease. In another aspect, a plant genome provided herein is mutated by a CRISPR/CasX or a CRISPR/CasY nuclease. As used herein, "editing" or "genome editing" refers to targeted mutagenesis of at least 1, at least 2, at least 3, at least 4, at least 5, at least 6, at least 7, at least 8, at least 9, or at least 10 nucleotides of an endogenous plant genome nucleic acid sequence, or removal or replacement of an endogenous plant genome nucleic acid sequence. In one aspect, an edited nucleic acid sequence provided herein has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with an endogenous nucleic acid sequence. In one aspect, an edited nucleic acid sequence provided herein has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof. In another aspect, an edited nucleic acid sequence provided herein has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with a polynucleotide encoding a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, a nuclease provided herein is used to edit a plant genomic locus encoding a sequence having at least 70%, at least 75%, at least 80%, at least 85%, at least 90%, at least 95%, at least 96%, at least 97%, at least 98%, at least 99% or 100% sequence identity to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof.

In another aspect, a nuclease provided herein is used to edit a plant genomic locus encoding a polypeptide having at least 70%, at least 75%, at least 80%, at least 85%, at least 90%, at least 95%, at least 96%, at least 97%, at least 98%, at least 99% or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In another aspect, a nuclease provided herein is used to edit a plant genome locus encoding a polypeptide having at least 70%, at least 75%, at least 80%, at least 85%, at least 90%, at least 95%, at least 96%, at least 97%, at least 98%, at least 99% or 100% sequence similarity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

Meganucleases, ZFNs, TALENs, CRISPR/Cas9, and CRISPR/Cpf1 induce a double-strand DNA break at a target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of donor nucleic acid sequences by HR. In one aspect, a methods provided herein comprises editing a plant genome with a nuclease provided herein to mutate at least 1, at least 2, at least 3, at least 4, at least 5, at least 6, at least 7, at least 8, at least 9, at least 10, or more than 10 nucleotides in the plant genome via HR with a donor polynucleotide. In one aspect, a mutation provided herein is caused by genome editing using a nuclease. In another aspect, a mutation provided herein is caused by non-homologous end-joining or homologous recombination.

Meganucleases, which are commonly identified in microbes, are unique enzymes with high activity and long recognition sequences (>14 bp) resulting in site-specific digestion of target DNA. Engineered versions of naturally occurring meganucleases typically have extended DNA recognition sequences (for example, 14 to 40 bp).

In one aspect, a meganuclease provided herein edits a polynucleotide having at least 70%, at least 75%, at least 80%, at least 85%, at least 90%, at least 95%, at least 96%, at least 97%, at least 98%, at least 99% or 100% sequence identity to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof. In another aspect, a meganuclease provided herein edits a polynucleotide encoding a polypeptide having at least 70%, at least 75%, at least 80%, at least 85%, at least 90%, at least 95%, at least 96%, at least 97%, at least 98%, at least 99% or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In another aspect, a meganuclease provided herein edits a polynucleotide encoding a polypeptide having at least 70%, at least 75%, at least 80%, at least 85%, at least 90%, at least 95%, at least 96%, at least 97%, at least 98%, at least 99% or 100% sequence similarity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

The engineering of meganucleases can be more challenging than that of ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity.

ZFNs are synthetic proteins consisting of an engineered zinc finger DNA-binding domain fused to the cleavage domain of the FokI restriction endonuclease. ZFNs can be designed to cleave almost any long stretch of double-stranded DNA for modification of the zinc finger DNA-binding domain. ZFNs form dimers from monomers composed of a non-specific DNA cleavage domain of FokI endonuclease fused to a zinc finger array engineered to bind a target DNA sequence.

The DNA-binding domain of a ZFN is typically composed of 3-4 zinc-finger arrays. The amino acids at positions −1, +2, +3, and +6 relative to the start of the zinc finger ∞-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art.

The FokI nuclease domain requires dimerization to cleave DNA and therefore two ZFNs with their C-terminal regions are needed to bind opposite DNA strands of the cleavage site (separated by 5-7 bp). The ZFN monomer can cute the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Without being limited by any scientific theory, because the DNA-binding specificities of zinc finger domains can in principle be re-engineered using one of various methods, customized ZFNs can theoretically be constructed to target nearly any gene sequence. Publicly available methods for engineering zinc finger domains include Context-dependent Assembly (CoDA), Oligomerized Pool Engineering (OPEN), and Modular Assembly.

In one aspect, a ZFN provided herein edits a polynucleotide having at least 70%, at least 75%, at least 80%, at least 85%, at least 90%, at least 95%, at least 96%, at least 97%, at least 98%, at least 99% or 100% sequence identity to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof. In another aspect, a ZFN provided herein edits a polynucleotide encoding a polypeptide having at least 70%, at least 75%, at least 80%, at least 85%, at least 90%, at least 95%, at least 96%, at least 97%, at least 98%, at least 99% or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In another aspect, a ZFN provided herein edits a polynucleotide encoding a polypeptide having at least 70%, at least 75%, at least 80%, at least 85%, at least 90%, at least 95%, at least 96%, at least 97%, at least 98%, at least 99% or 100% sequence similarity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

TALENs are artificial restriction enzymes generated by fusing the transcription activator-like effector (TALE) DNA binding domain to a FokI nuclease domain. When each member of a TALEN pair binds to the DNA sites flanking a target site, the FokI monomers dimerize and cause a double-stranded DNA break at the target site.

The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site.

Transcription activator-like effectors (TALEs) can be engineered to bind practically any DNA sequence. TALE proteins are DNA-binding domains derived from various plant bacterial pathogens of the genus *Xanthomonas*. The X pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

The relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., *Nucleic Acids Research* (2012) 40: W117-122; Cermak et al., *Nucleic Acids Research* (2011). 39:e82; and tale-nt.cac.cornell.edu/about.

In one aspect, a TALEN provided herein edits a polynucleotide having at least 70%, at least 75%, at least 80%, at least 85%, at least 90%, at least 95%, at least 96%, at least 97%, at least 98%, at least 99% or 100% sequence identity to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof. In another aspect, a TALEN provided herein edits a polynucleotide encoding a polypeptide having at least 70%, at least 75%, at least 80%, at least 85%, at least 90%, at least 95%, at least 96%, at least 97%, at least 98%, at least 99% or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In another aspect, a TALEN provided herein edits a polynucleotide encoding a polypeptide having at least 70%, at least 75%, at least 80%, at least 85%, at least 90%, at least 95%, at least 96%, at least 97%, at least 98%, at least 99% or 100% sequence similarity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

A CRISPR/Cas9 system or a CRISPR/Cpf1 system are alternatives to the FokI-based methods ZFN and TALEN. The CRISPR systems are based on RNA-guided engineered nucleases that use complementary base pairing to recognize DNA sequences at target sites.

CRISPR/Cas9 systems are part of the adaptive immune system of bacteria and archaea, protecting them against invading nucleic acids such as viruses by cleaving the foreign DNA in a sequence-dependent manner. The immunity is acquired by the integration of short fragments of the invading DNA known as spacers between two adjacent repeats at the proximal end of a CRISPR locus. The CRISPR arrays, including the spacers, are transcribed during subsequent encounters with invasive DNA and are processed into small interfering CRISPR RNAs (crRNAs) approximately 40 nt in length, which combine with the trans-activating CRISPR RNA (tracrRNA) to activate and guide the Cas9 nuclease. This cleaves homologous double-stranded DNA sequences known as protospacers in the invading DNA. A prerequisite for cleavage is the presence of a conserved protospacer-adjacent motif (PAM) downstream of the target DNA, which usually has the sequence 5-NGG-3 but less frequently NAG. Specificity is provided by the so-called "seed sequence" approximately 12 bases upstream of the PAM, which must match between the RNA and target DNA. Cpf1 acts in a similar manner to Cas9, but Cpf1 does not require a tracrRNA.

In one aspect, an engineered guide RNA provided herein guides a Cas9 or Cpf1 nuclease to a polynucleotide having at least 70%, at least 75%, at least 80%, at least 85%, at least 90%, at least 95%, at least 96%, at least 97%, at least 98%, at least 99% or 100% sequence identity to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof. In another aspect, an engineered guide RNA provided herein guides a Cas9 or Cpf1 nuclease to a polynucleotide encoding a polypeptide having at least 70%, at least 75%, at least 80%, at least 85%, at least 90%, at least 95%, at least 96%, at least 97%, at least 98%, at least 99% or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In another aspect, an engineered guide RNA provided herein guides a Cas9 or Cpf1 nuclease to a polynucleotide encoding a polypeptide having at least 70%, at least 75%, at least 80%, at least 85%, at least 90%, at least 95%, at least 96%, at least 97%, at least 98%, at least 99% or 100% sequence similarity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, a Cas9 or a Cpf1 nuclease provided herein cleaves a polynucleotide having at least 70%, at least 75%, at least 80%, at least 85%, at least 90%, at least 95%, at least 96%, at least 97%, at least 98%, at least 99% or 100% sequence identity to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof. In another aspect, a Cas9 or a Cpf1 nuclease provided herein cleaves a polynucleotide encoding a polypeptide having at least 70%, at least 75%, at least 80%, at least 85%, at least 90%, at least 95%, at least 96%, at least 97%, at least 98%, at least 99% or 100% sequence identity to a polypeptide selected from the group consisting of SEQ ID NOs: 2, 4, 6, 8, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In another aspect, a Cas9 or a Cpf1 nuclease provided herein cleaves a polynucleotide encoding a polypeptide having at least 70%, at least 75%, at least 80%, at least 85%, at least 90%, at least 95%, at least 96%, at least 97%, at least 98%, at least 99% or 100% sequence similarity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, a mutagenesis system provided herein (e.g., chemical mutagenesis, irradiation mutagenesis, transposon mutagenesis, *Agrobacterium*-mediated transformation, a meganuclease, a ZFN, a TALEN, a CRISPR/Cas9 system, a CRISPR/Cpf1 system), or a combination of mutagenesis systems provided herein, is used in a method to introduce one or more mutations to a tobacco gene that is natively expressed in at least one tobacco axillary meristem cell.

In still another aspect, a modified tobacco plant provided herein further comprises one or more mutations in one or more loci encoding a nicotine demethylase (e.g., CYP82E4, CYP82E5, CYP82E10) that confer reduced amounts of nornicotine (See U.S. Pat. Nos. 8,319,011; 8,124,851; 9,187,759; 9,228,194; 9,228,195; 9,247,706) compared to control plant lacking one or more mutations in one or more loci encoding a nicotine demethylase. In another aspect, a tobacco plant provided herein further comprises one or more mutations in a Nic1 locus, a Nic2 locus, or both, which confer reduced amounts of nicotine compared to a control plant lacking one or more mutations in a Nic1 locus, a Nic2 locus, or both.

In one aspect, recombinant DNA constructs or expression cassettes provided herein comprise a promoter selected from the group consisting of a constitutive promoter, an inducible promoter, and a tissue-preferred promoter (for example, without being limiting, a leaf-specific promoter, a root-specific promoter, or a meristem-specific promoter).

In one aspect, a promoter provided herein is an axillary bud-specific promoter. In one aspect, a promoter provided herein is an axillary meristem-specific promoter. In one aspect, an axillary meristem-specific promoter provided herein is functional or preferentially functional in an L1 layer, an L2 layer, an L3 layer, or a combination thereof. Dicot shoot apical and axillary meristems comprise three distinct cell layers: the L1 layer (outermost layer), the L2 layer (middle layer), and the L3 layer (innermost layer). The L1 and L2 layers make up the tunica, and they divide anticlinally (the division plane is perpendicular to the surface of the meristem). The L3 layer, or corpus, divides in all directions. The L1 layer eventually gives rise to epidermal tissue; the L2 layer gives rise to ground tissue (e.g., parenchyma, collenchyma, sclerenchyma); and the L3 layer typically gives rise to vascular tissue (e.g., xylem, phloem)

Shoot apical and axillary meristems can also be divided into three zones: a central zone, a peripheral zone, and a rib zone. Cells from the central zone, comprising parts of the L1, L2, and L3 layers at the peak of the meristem, serve to organize and maintain the meristem; the central zone comprises pluripotent stem cells. The peripheral zone surrounds the central zone and will form organs (e.g., leaf primordia, flower primordia) and undergo morphogenesis; this zone comprises high mitotic activity. The rib zone, or rib meristem, is positioned below the central zone; the rib zone gives rise to stem and vasculature tissue. In one aspect, an axillary meristem-specific promoter provided herein is functional or preferentially functional in a central zone, a peripheral zone, a rib zone, or a combination thereof.

In one aspect, an axillary bud-specific promoter comprises a polynucleotide sequence having at least 60%, at least 70%, at least 75%, at least 80%, at least 85%, at least 90%, at least 95%, at least 96%, at least 97%, at least 98%, at least 99% or 100% sequence identity to a polynucleotide selected from the group consisting of SEQ ID NOs: 113-118, 148-160, 204 and fragments thereof. In another aspect, an axillary meristem-specific promoter comprises a polynucleotide sequence having at least 60%, at least 70%, at least 75%, at least 80%, at least 85%, at least 90%, at least 95%, at least 96%, at least 97%, at least 98%, at least 99% or 100% sequence identity to a polynucleotide selected from the group consisting of SEQ ID NOs: 113-118, 148-160, 204 and fragments thereof. In still another aspect, a promoter active in an L1 layer, an L2 layer, an L3 layer, or a combination thereof comprises a polynucleotide sequence selected from the group consisting of SEQ ID NOs: 113-118, 148-160, 204 and a fragment thereof. In another aspect, a promoter active in a central zone, a peripheral zone, a rib zone, or a combination thereof comprises a polynucleotide sequence selected from the group consisting of SEQ ID NOs: 113-118, 148-160, 204 and a fragment thereof. In one aspect, a promoter fragment provided herein has a length of at least 50, at least 75, at least 100, at least 200, at least 300, at least 400, at least 500, at least 600, at least 700, at least 800, at least 900, at least 1000, at least 1250, at least 1500, at least 1750, at least 2000, at least 2500, at least 3000, at least 3500, at least 4000, at least 4500, or at least 4999 nucleotides. In another aspect, a promoter fragment provided herein has a length of between 50 and 200, between 100 and 200, between 100 and 300, between 100 and 400, between 100 and 500, between 100 and 600, between 100 and 700, between 100 and 800, 100 and 900, between 100 and 1000, between 100 and 2000, between 200 and 300, between 200 and 400, between 200 and 500, between 200 and 600, between 200 and 700, between 200 and 800, between 200 and 900, between 200 and 1000, between 200 and 2000, between 200 and 2500, between 200 and 3000, between 500 and 1000, between 500 and 1500, between 500 and 2000, between 500 and 2500, between 500 and 3000, between 1000 and 2000, between 1000 and 3000, between 1500 and 2000, between 1500 and 2500, between 1500 and 3000, between 2000 and 3000 nucleotides, between 100 and 3500, between 100 and 4000, between 100 and 4500, between 100 and 4999, between 500 and 3500, between 500 and 4000, between 500 and 4500, between 500 and 4999, between 1000 and 3500, between 1000 and 4000, between 1000 and 4500, between 1000 and 4999, between 2000 and 3500, between 2000 and 4000, between 2000 and 4500, between 2000 and 4999, between 3000 and 3500, between 3000 and 4000, between 3000 and 4500, between 3000 and 4999, between 3500 and 4000, between 3500 and 4500, between 3500 and 4999, between 4000 and 4500, between 4000 and 4999, or between 4500 and 4999 nucleotides.

In one aspect, a recombinant DNA construct of the present disclosure comprises a polynucleotide selected from the group consisting of SEQ ID NOs: 113-118, 148-160, 204 and a fragment thereof operably linked to a polynucleotide encoding a polypeptide having at least 70%, at least 75%, at least 80%, at least 85%, at least 90%, at least 95%, at least 96%, at least 97%, at least 98%, at least 99% or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, a recombinant DNA construct of the present disclosure comprises a polynucleotide selected from the group consisting of SEQ ID NOs: 113-118, 148-160, 204 and a fragment thereof operably linked to a polynucleotide encoding a polypeptide having at least 70%, at least 75%, at least 80%, at least 85%, at least 90%, at least 95%, at least 96%, at least 97%, at least 98%, at least 99% or 100% sequence similarity to a polypeptide selected from the group consisting of SEQ ID NOs: 2, 4, 6, 8, 10, 12, 14, 16, 18, 20, 22, 24, 26, 28, 30, 32, 34, 36, 38, 40, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, a recombinant DNA construct of the present disclosure comprises a polynucleotide selected from the group consisting of SEQ ID NOs: 113-118, 148-160, 204 and a fragment thereof operably linked to a polynucleotide having at least 60%, at least 65%, at least 70%, at least 75%, at least 80%, at least 85%, at least 90%, at least 95%, at least 96%, at least 97%, at least 98%, at least 99% or 100% identity to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, and 225-228, 230, 232, 234, 236, 238, 240, 242, 244, 246, 248, 250, 252, 254, and fragments thereof.

In one aspect, a tobacco plant, or part thereof, of the present disclosure comprises a heterologous promoter having at least 90% sequence identity to a polynucleotide selected from the group consisting of SEQ ID NOs: 113-118, 148-160, 204, and fragments thereof operably linked to a polynucleotide encoding an auxin biosynthesis protein or an auxin transport protein.

Exemplary constitutive promoters include the core promoter of the Rsyn7 promoter and other constitutive promoters disclosed in U.S. Pat. No. 6,072,050; the core CaMV 35S promoter (Odell et al. (1985) Nature 313:810-812); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J 3:2723-2730); ALS promoter (U.S. Pat. No. 5,659,026), and the like.

Exemplary chemical-inducible promoters include the tobacco PR-1a promoter, which is activated by salicylic acid. Other chemical-inducible promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2):247-257) and tetracycline-inducible promoters (see, for example, Gatz et al. (1991) Mol. Gen. Genet. 227:229-237, and U.S. Pat. Nos. 5,814,618 and 5,789,156). Additional exemplary promoters that can be used herein are those responsible for heat-regulated gene expression, light-regulated gene expression (for example, the pea rbcS-3A; the maize rbcS promoter; the chlorophyll alb-binding protein gene found in pea; or the Arabssu promoter), hormone-regulated gene expression (for example, the abscisic acid (ABA) responsive sequences from the Em gene of wheat; the ABA-inducible HVA1 and HVA22, and rd29A promoters of barley and *Arabidopsis*; and wound-induced gene expression (for example, of wun1), organ specific gene expression (for example, of the tuber-specific storage protein gene; the 23-kDa zein gene from maize described by; or the French bean (β-phaseolin gene), or pathogen-inducible promoters (for example, the PR-1, prp-1, or (13-1,3 glucanase promoters, the fungal-inducible wirla promoter of wheat, and the nematode-inducible promoters, TobRB7-5A and Hmg-1, of tobacco arid parsley, respectively).

Additional exemplary tissue-preferred promoters include those disclosed in Yamamoto et al. (1997) Plant J. 12(2):255-265; Kawamata et al. (1997) Plant Cell Physiol. 38(7):792-803; Hansen et al. (1997) Mol. Gen. Genet. 254(3):337-343; Russell et al. (1997) Transgenic Res. 6(2):157-168; Rinehart et al. (1996) Plant Physiol. 112(3):1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. Orozco et al. (1993) Plant Mol. Biol. 23(6):1129-1138; Matsuoka et al. (1993) Proc Natl. Acad. Sci. USA 90(20):9586-9590; and Guevara-Garcia et al. (1993) Plant J. 4(3):495-505.

As used herein, "operably linked" refers to a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous. In one aspect, a promoter provided herein is operably linked to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof. In another aspect, a promoter provided herein is operably linked to a polynucleotide encoding a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

As used herein, "heterologous" refers to a sequence that originates from a foreign species, or, if from the same species, is substantially modified from its native form in composition and/or genomic locus by deliberate human intervention. The term also is applicable to nucleic acid constructs, also referred to herein as "polynucleotide constructs" or "nucleotide constructs." In this manner, a "heterologous" nucleic acid construct is intended to mean a construct that originates from a foreign species, or, if from the same species, is substantially modified from its native form in composition and/or genomic locus by deliberate human intervention. Heterologous nucleic acid constructs include, but are not limited to, recombinant nucleotide constructs that have been introduced into a plant or plant part thereof, for example, via transformation methods or subsequent breeding of a transgenic plant with another plant of interest.

In one aspect, a modified plant, seed, plant component, plant cell, or plant genome provided herein comprises a heterologous promoter operably linked to a polynucleotide encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In another aspect, a recombinant DNA construct provided herein comprises a heterologous promoter operably linked to a polynucleotide encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

Enhancer elements are regions of DNA that can be bound by proteins to activate RNA transcription. In one aspect, a promoter sequence provided herein is operably linked to an enhancer element. In another aspect, a polynucleotide selected from the group consisting of SEQ ID NOs: 113-118, 148-160, 204, and a fragment thereof is operably linked to an enhancer element. In one aspect, an enhancer element provided herein is at least 10, at least 25, at least 50, at least 75, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 1100, at least 1200, at least 1300, at least 1400, at least 1500, at least 1750, at least 2000, at least 2500, at least 3000, at least 3500, at least 4000, at least 4500, or at least 5000 nucleotides in length. In one aspect, an enhancer element provided herein is a CsVMV promoter.

Many gene promoters contain cis-regulatory elements that function to regulate gene transcription. Cis-regulatory elements often function by serving as binding sites for transcription factors. In one aspect, a promoter provided herein comprises at least 1, at least 2, at least 3, at least 4, at least 5, or at least 6 cis regulatory elements selected from the group consisting of a bud dormancy element (BDE), an axillary bud growth UP1 element, an axillary bud growth UP2 element, a sucrose responsive element (SRE), a sugar repressive element (SURE), and a bud activation or TCP-binding element (BAE). In another aspect, a recombinant nucleotide provided herein comprises a promoter, where the promoter comprises at least 1, at least 2, at least 3, at least 4, at least 5, or at least 6 cis elements selected from the group consisting of a bud dormancy element (BDE), an axillary bud growth UP1 element, an axillary bud growth UP2 element, a sucrose responsive element (SURE), a sugar repressive element (SRE), and a bud activation or TCP-binding element (BAE).

In one aspect, a promoter provided herein comprises at least 1, at least 2, at least 3, at least 4, at least 5, or at least 6 cis-regulatory elements within 1, 3, 5, 10, 15, 20, 25, 30, 35, 40, 45, 75, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 7500, or 10,000 nucleotides of a transcriptional start site. In another aspect, a promoter provided herein comprises at least 1, at least 2, at least 3, at least 4, at least 5, or at least 6 cis-regulatory elements within 1-10,000, 1-7500, 1-5000, 1-4900, 1-4800, 1-4700, 1-4600, 1-4500, 1-4400, 1-4300, 1-4200, 1-4100, 1-4000, 1-3900, 1-3800, 1-3700, 1-3600, 1-3500, 1-3400, 1-3300, 1-3200, 1-3100, 1-3000, 1-2900, 1-2800, 1-2700, 1-2600, 1-2500, 1-2400, 1-2300, 1-2200, 1-2100, 1-2000, 1-1900, 1-1800, 1-1700, 1-1600, 1-1500, 1-1400, 1-1300, 1-1200, 1-1100, 1-1000, 1-900, 1-800, 1-700, 1-600, 1-500, 1-400, 1-300, 1-200, 1-100, 1-75, 1-50, 1-45, 1-40, 1-35, 1-30, 1-25, 1-20, 1-15, 5-10,000, 5-7500, 5-5000, 5-4900, 5-4800, 5-4700, 5-4600, 5-4500, 5-4400, 5-4300, 5-4200, 5-4100, 5-4000, 5-3900, 5-3800, 5-3700, 5-3600, 5-3500, 5-3400, 5-3300, 5-3200, 5-3000, 5-2900, 5-2800, 5-2700, 5-2600, 5-2500, 5-2400, 5-2300, 5-2200, 5-2100, 5-2000, 5-1900, 5-1800, 5-1700, 5-1600, 5-1500, 5-1400, 5-1300, 5-1200, 5-1100, 5-1000, 5-900, 5-700, 5-600, 5-500, 5-400, 5-300, 5-200, 5-100, 5-75, 5-50, 5-45, 5-40, 5-35, 5-30, 5-25, 20-10,000, 20-7500, 20-5000, 20-4900, 20-4800, 20-4700, 20-4600, 20-4500, 20-4400, 20-4300, 20-4200, 20-4100, 20-4000, 20-3900, 20-3800, 20-3700, 20-3600, 20-3500, 20-3400, 20-3300, 20-3200, 20-3100, 20-3000, 20-2900, 20-2800, 20-2700, 20-2600, 20-2500, 20-2400, 20-2300, 20-2200, 20-2100, 20-2000, 20-1900, 20-1800, 20-1700, 20-1600, 20-1500, 20-1400, 20-1300, 20-1200, 20-1100, 20-1000, 20-900, 20-800, 20-700, 20-600, 20-500, 20-400, 20-300, 20-200, 20-100, 20-75, 20-50, 20-45, 20-40, 20-35, 20-30, 20-25, 50-10,000, 50-7500, 50-5000, 50-4900, 50-4800, 50-4700, 50-4600, 50-4500, 50-4400, 50-4300, 50-4200, 50-4100, 50-4000, 50-3900, 50-3800, 50-3700, 50-3600, 50-3500, 50-3400, 50-3300, 50-3200, 50-3100, 50-3000, 50-2900, 50-2800, 50-2700, 50-2600, 50-2500, 50-2400, 50-2300, 50-2200, 50-2100, 50-2000, 50-1900, 50-1800, 50-1700, 50-1600, 50-1500, 50-1400, 50-1300, 50-1200, 50-1100, 50-1000, 50-900, 50-800, 50-700, 50-600, 50-500, 50-400, 50-300, 50-200, 50-100, 50-75, 100-10,000, 100-7500, 100-5000, 100-4900, 100-4800, 100-4700, 100-4600, 100-4500, 100-4400, 100-4300, 100-4200, 100-4100, 100-4000, 100-3900, 100-3800, 100-3700, 100-3600, 100-3500, 100-3400, 100-3300, 100-3200, 100-3100, 100-3000, 100-2900, 100-2800, 100-2700, 100-2600, 100-2500, 100-2400, 100-2300, 100-2200, 100-2100, 100-2000, 100-1900, 100-1800, 100-1700, 100-1600, 100-1500, 100-1400, 100-1300, 100-1200, 100-1100, 100-1000, 100-900, 100-800, 100-700, 100-600, 100-500, 100-400, 100-300, 100-200, 500-10,000, 500-7500, 500-5000, 500-4900, 500-4800, 500-4700, 500-4600, 500-4500, 500-4400, 500-4300, 500-4200, 500-4100, 500-4000, 500-3900, 500-3800, 500-3700, 500-3600, 500-3500, 500-3400, 500-3300, 500-3200, 500-3100, 500-3000, 500-2900, 500-2800, 500-2700, 500-2600, 500-2500, 500-2400, 500-2300, 500-2200, 500-2100, 500-2000, 500-1900, 500-1800, 500-1700, 500-1600, 500-1500, 500-1400, 500-1300, 500-1200, 500-1100, 500-1000, 500-900, 500-800, 500-700, or 500-600 nucleotides of a transcriptional start site.

In one aspect, a promoter provided herein is functional in an axillary bud cell and comprises at least 1, at least 2, at least 3, at least 4, at least 5, or at least 6 cis-regulatory elements selected from the group consisting of a bud dormancy element (BDE), an axillary bud growth UP1 element, an axillary bud growth UP2 element, a sucrose responsive element (SURE), a sugar repressive element (SRE), and a bud activation or TCP-binding element (BAE).

Also provided herein are the transformation of tobacco plants with recombinant constructs or expression cassettes described herein using any suitable transformation methods known in the art. Methods for introducing polynucleotide sequences into tobacco plants are known in the art and include, but are not limited to, stable transformation methods, transient transformation methods, and virus-mediated methods. "Stable transformation" refers to transformation where the nucleotide construct of interest introduced into a plant integrates into a genome of the plant and is capable of being inherited by the progeny thereof "Transient transformation" is intended to mean that a sequence is introduced into the plant and is only temporally expressed or is only transiently present in the plant.

In one aspect, methods and compositions provided herein comprise the introduction of one or more polynucleotides into one or more plant cells. In one aspect, a plant genome provided herein is modified to include an introduced polynucleotide or recombinant DNA construct. As used herein, "plant genome" refers to a nuclear genome, a mitochondrial genome, or a plastid (e.g., chloroplast) genome of a plant cell. In another aspect, a polynucleotide provided herein is integrated into an artificial chromosome. In one aspect, an artificial chromosome comprising a polynucleotide provided herein is integrated into a plant cell.

In one aspect, a modified plant, seed, plant component, plant cell, or plant genome provided herein comprises one or more transgenes. In one aspect, a transgene provided herein suppresses suckering in a plant. In another aspect, a transgene provided herein suppresses topping-induced suckering in a plant. In still another aspect, a transgene provided herein suppresses suckering in a plant prior to topping. As used herein, a "transgene" refers to a polynucleotide that has been transferred into a genome by any method known in the art. In one aspect, a transgene is an exogenous polynucleotide. In one aspect, a transgene is an endogenous polynucleotide that is integrated into a new genomic locus where it is not normally found.

In one aspect, transgenes provided herein comprise a recombinant DNA construct. In one aspect, recombinant DNA constructs or expression cassettes provided herein can comprise a selectable marker gene for the selection of transgenic cells. Selectable marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, triazolopyrimidines, sulfonylurea (e.g., chlorsulfuron and sulfometuron methyl), and 2,4-dichlorophenoxyacetate (2,4-D). Additional selectable markers include phenotypic markers such as β-galactosidase and fluorescent proteins such as green fluorescent protein (GFP).

In one aspect, methods and compositions provided herein comprise a vector. As used herein, the terms "vector" or "plasmid" are used interchangeably and refer to a circular, double-stranded DNA molecule that is physically separate from chromosomal DNA. In one aspect, a plasmid or vector used herein is capable of replication in vivo. A "transformation vector," as used herein, is a plasmid that is capable of transforming a plant cell. In an aspect, a plasmid provided herein is a bacterial plasmid. In another aspect, a plasmid provided herein is an *Agrobacterium* Ti plasmid or derived from an *Agrobacterium* Ti plasmid.

In one aspect, a plasmid or vector provided herein is a recombinant vector. As used herein, the term "recombinant vector" refers to a vector formed by laboratory methods of genetic recombination, such as molecular cloning. In another aspect, a plasmid provided herein is a synthetic plasmid. As used herein, a "synthetic plasmid" is an artificially created plasmid that is capable of the same functions (e.g., replication) as a natural plasmid (e.g., Ti plasmid). Without being limited, one skilled in the art can create a synthetic plasmid de novo via synthesizing a plasmid by individual nucleotides, or by splicing together nucleic acid molecules from different pre-existing plasmids.

Vectors are commercially available or can be produced by recombinant DNA techniques routine in the art. In one aspect, a vector provided herein comprises all or part of SEQ ID NO: 112. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6×His tag (SEQ ID NO: 256), glutathione S-transferase (GST)).

Suitable methods of introducing polynucleotides (e.g., transgenes, recombinant vectors, recombinant DNA constructs, expression constructs) into plant cells of the present disclosure include microinjection (Crossway et al. (1986) *Biotechniques* 4:320-334), electroporation (Shillito et al. (1987) *Meth. Enzymol.* 153:313-336; Riggs et al. (1986) *Proc. Natl. Acad. Sci. USA* 83:5602-5606), *Agrobacterium*-mediated transformation (U.S. Pat. Nos. 5,149,645, 5,177,010, 5,231,019, 5,463,174, 5,464,763, 5,469,976, 4,762,785, 5,159,135, 5,563,055, and 5,981,840), direct gene transfer (Paszkowski et al. (1984) *EMBO J.* 3:2717-2722), and ballistic particle acceleration (see, for example, U.S. Pat. Nos. 4,945,050, 5,141,131, 5,886,244, 5,879,918, and 5,932,782; Tomes et al. (1995) in *Plant Cell, Tissue, and Organ Culture Fundamental Methods*, ed. Gamborg and Phillips (Springer-Verlag, Berlin); McCabe et al. (1988) Biotechnology 6:923-926). Also see Weissinger et al. (1988) *Ann. Rev. Genet.* 22:421-477; Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation). In one aspect, a bacterial cell provided herein comprises a recombinant DNA construct or recombinant vector provided herein.

In another aspect, recombinant constructs or expression cassettes provided herein may be introduced into plants by contacting plants with a virus or viral nucleic acids. Generally, such methods involve incorporating an expression cassette of the present disclosure within a viral DNA or RNA molecule. It is recognized that promoters for use in the expression cassettes provided herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,866,785, 5,589,367, 5,316,931, and Porta et al. (1996) *Molecular Biotechnology* 5:209-221.

Any plant tissue that can be subsequently propagated using clonal methods, whether by organogenesis or embryogenesis, may be transformed with a recombinant construct or an expression cassette provided herein. By "organogenesis" in intended the process by which shoots and roots are developed sequentially from meristematic centers. By "embryogenesis" is intended the process by which shoots and roots develop together in a concerted fashion (not sequentially), whether from somatic cells or gametes. Exemplary tissues that are suitable for various transformation protocols described herein include, but are not limited to, callus tissue, existing meristematic tissue (e.g., apical meristems, axillary buds, and root meristems) and induced meristem tissue (e.g., cotyledon meristem and hypocotyl meristem), hypocotyls, cotyledons, leaf disks, pollen, embryos, and the like.

In one aspect, this disclosure provides a plant or seed comprising a recombinant polynucleotide, where the recombinant polynucleotide comprises a promoter that is functional in an L1 layer, an L2 layer, an L3 region, a rib zone, a central zone, a peripheral zone, or any combination thereof, which is operably linked to a structural nucleic acid molecule comprising a nucleic acid sequence, where the nucleic acid sequence encodes a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, an auxin biosynthesis protein or an auxin transport protein is selected from the group consisting of SEQ ID NOs: 235, 237, 239, 241, 243, 245, 247, 249, 251, 253, and 255. In another aspect, an auxin biosynthesis protein or an auxin transport protein comprises at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 235, 237, 239, 241, 243, 245, 247, 249, 251, 253, and 255. In another aspect, an auxin biosynthesis protein or an auxin transport protein comprises at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence similarity to a polypeptide selected from the group consisting of SEQ ID NOs: 235, 237, 239, 241, 243, 245, 247, 249, 251, 253, and 255. In one aspect, an auxin biosynthesis protein or an auxin transport protein is encoded by a nucleic acid sequence, where the nucleic acid sequence encodes a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide elected from the group consisting of SEQ ID NOs: 235, 237, 239, 241, 243, 245, 247, 249, 251, 253, and 255.

In one aspect, an auxin biosynthesis protein or an auxin transport protein is encoded by a polynucleotide selected from the group consisting of SEQ ID NOs: 234, 236, 238, 240, 242, 244, 246, 248, 250, 252, and 254. In one aspect, an auxin biosynthesis protein or an auxin transport protein is encoded by a polynucleotide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to a polynucleotide selected from the group consisting of SEQ ID NOs: 234, 236, 238, 240, 242, 244, 246, 248, 250, 252, and 254.

In one aspect, this disclosure provides a plant or seed comprising a recombinant polynucleotide, where the recombinant polynucleotide comprises a promoter that is functional in an L1 layer, an L2 layer, an L3 region, a rib zone, a central zone, a peripheral zone, or a combination thereof, which is operably linked to a structural nucleic acid molecule comprising a nucleic acid sequence, where the nucleic acid sequence encodes an auxin biosynthesis protein or an auxin transport protein.

In another aspect, this disclosure provides a recombinant DNA construct comprising a promoter that is functional in an L1 layer, an L2 layer, an L3 region, a rib zone, a central zone, a peripheral zone, or a combination thereof; and a heterologous and operably linked nucleic acid sequence, where the nucleic acid sequence encodes a non-coding RNA or a polypeptide. In another aspect, this disclosure provides a recombinant DNA construct comprising a promoter that is functional in an L1 later, an L2 layer, an L3 region, a rib zone, a central zone, a peripheral zone, or a combination thereof; and a heterologous and operably linked nucleic acid sequence, where the nucleic acid sequence encodes an auxin biosynthesis protein or an auxin transport protein.

In one aspect, this disclosure provides a recombinant DNA construct comprising a heterologous axillary meristem-specific promoter operably linked to a polynucleotide that encodes an auxin biosynthesis protein or an auxin transport protein.

In one aspect, this disclosure provides a method of reducing or eliminating topping-induced suckering in a tobacco plant comprising transforming a tobacco plant with a recombinant DNA construct comprising a promoter expressing in an L1 layer, an L2 layer, an L3 region, a rib zone, a central zone, a peripheral zone, or a combination thereof. In another aspect, this disclosure provides a method comprising transforming a tobacco plant with a recombinant DNA construct comprising a heterologous promoter that is functional in an L1 layer, an L2 layer, an L3 region, a rib zone, a central zone, a peripheral zone, or a combination thereof, and is operably linked to a polynucleotide that is transcribed into an RNA molecule that suppresses the level of an endogenous gene, and where the endogenous gene promotes or is required for axillary meristem growth, axillary meristem maintenance, or both.

In one aspect, this disclosure provides a method for controlling topping-induced suckering in a plant comprising transforming the plant with a recombinant DNA construct, where the recombinant DNA construct comprises a promoter that is operably linked to a polynucleotide encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, this disclosure provides a method for controlling topping-induced suckers in a plant comprising transforming said plant with a recombinant DNA construct, wherein said recombinant DNA construct comprises a promoter that is operably linked to a polynucleotide encoding an auxin biosynthesis protein or an auxin transport protein.

It is understood that any modified tobacco plant of the present disclosure can further comprise additional agronomically desirable traits, for example, by transformation with a genetic construct or transgene using a technique known in the art. Without limitation, an example of a desired trait is herbicide resistance, pest resistance, disease resistance, high yield, high grade index value, curability, curing quality, mechanical harvestability, holding ability, leaf quality, height, plant maturation (e.g., early maturing, early to medium maturing, medium maturing, medium to late maturing, or late maturing), stalk size (e.g., a small, medium, or a large stalk), or leaf number per plant (e.g., a small (e.g., 5-10 leaves), medium (e.g., 11-15 leaves), or large (e.g., 16-21) number of leaves), or any combination. In one aspect, reduced suckering tobacco plants or seeds provided herein comprise one or more transgenes expressing one or more insecticidal proteins, such as, for example, a crystal protein of *Bacillus thuringiensis* or a vegetative insecticidal protein from *Bacillus cereus*, such as VIP3 (see, for example, Estruch et al. (1997) *Nat. Biotechnol.* 15:137). In another aspect, tobacco plants provided herein further comprise an introgressed trait conferring resistance to brown stem rot (U.S. Pat. No. 5,689,035) or resistance to cyst nematodes (U.S. Pat. No. 5,491,081).

The level and/or activity of polypeptides provided herein may be modulated by employing a polynucleotide that is not capable of directing, in a transformed plant, the expression of a protein or an RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides and recombinogenic oligonucleobases. Such nucleotide constructs and methods of use are known in the art. See, U.S. Pat. Nos. 5,565,350; 5,731,181; 5,756,325; 5,760,012; 5,795,972 and 5,871,984; each of which is incorporated herein by reference as if set forth in its entirety. See also, International Patent Application Publication Nos. WO 98/149350, WO 99/107865 and WO 99/125921; and Beetham et al. (1999) Proc. Natl. Acad. Sci. USA 96:8774-8778; each of which is incorporated herein by reference as if set forth in its entirety.

The present disclosure provides compositions and methods for inhibiting the expression or function of one or more polypeptides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255 in a plant, particularly plants of the *Nicotiana tabacum* genus, including tobacco plants of various commercial varieties.

In one aspect, inhibition of the expression of one or more polypeptides provided herein may be obtained by RNA interference (RNAi) by expression of a polynucleotide provided herein. In one aspect, RNAi comprises expressing a non-coding RNA. As used herein, a "non-coding RNA" is selected from the group consisting of a microRNA (miRNA), a small interfering RNA (siRNA), a trans-acting siRNA (ta-siRNA), a transfer RNA (tRNA), a ribosomal RNA (rRNA), an intron, a hairpin RNA (hpRNA), and an intron-containing hairpin RNA (ihpRNA). In one aspect, a single non-coding RNA provided herein inhibits the expression of at least 1, at least 2, at least 3, at least 4, at least 5, at least 6, at least 7, at least 8, at least 9, at least 10, or more than 10 polypeptides. In one aspect, a non-coding RNA provided herein is stably transformed into a plant genome. In another aspect, a non-coding RNA provided herein is transiently transformed into a plant genome.

In one aspect, this disclosure provides RNA molecules useful for inhibiting the expression or function or one or more polypeptides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In one aspect, an RNA molecule provided herein is a non-coding RNA.

In another aspect, the recombinant DNA construct encodes a double stranded RNA. Also provided are modified tobacco plants or part thereof, cured tobacco material, or tobacco products comprising these recombinant DNA constructs. In one aspect, these transgenic plants, cured tobacco material, or tobacco products comprise reduced suckering compared to a control tobacco plant without the recombinant DNA construct. Further provided are methods of reducing sucker growth of a tobacco plant, the method comprising transforming a tobacco plant with any of these recombinant DNA constructs.

In one aspect, a tobacco plant or part thereof provided herein comprises a heterologous promoter operably linked to a polynucleotide that encodes a non-coding RNA molecule, where the non-coding RNA molecule is capable of binding to an RNA encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 161-185, 187, 189, 191, 193, 195, 197, 199, 224, 229, 231, 233, 245, 247, 249, 251, 253, and 255, and where the non-coding RNA molecule suppresses the expression of the polypeptide.

As used herein, the terms "suppress," "inhibit," "inhibition," and "inhibiting" are defined as any method known in the art or described herein that decreases the expression or function of a gene product of interest (e.g., an mRNA, a protein, a non-coding RNA). "Inhibition" can be in the context of a comparison between two plants, for example, a modified plant versus a control plant. Alternatively, inhibition of expression or function of a target gene product can be in the context of a comparison between plant cells, organelles, organs, tissues, or plant components within the same plant or between different plants, and includes comparisons between developmental or temporal stages within the same plant or plant component or between plants or plant components. "Inhibition" includes any relative decrement of function or production of a gene product of interest, up to and including complete elimination of function or production of that gene product. The term "inhibition" encompasses any method or composition that down-regulates translation and/or transcription of the target gene product or functional activity of the target gene product.

The term "inhibitory sequence" encompasses any polynucleotide or polypeptide sequence capable of inhibiting the expression or function of a gene in a plant, such as full-length polynucleotide or polypeptide sequences, truncated polynucleotide or polypeptide sequences, fragments of polynucleotide or polypeptide sequences, variants of polynucleotide or polypeptide sequences, sense-oriented nucleotide sequences, antisense-oriented nucleotide sequences, the complement of a sense- or antisense-oriented nucleotide sequence, inverted regions of nucleotide sequences, hairpins of nucleotide sequences, double-stranded nucleotide sequences, single-stranded nucleotide sequences, combinations thereof, and the like. The term "polynucleotide sequence" includes sequences of RNA, DNA, chemically modified nucleic acids, nucleic acid analogs, combinations thereof, and the like.

Inhibitory sequences are designated herein by the name of the target gene product. Thus, as a non-limiting example, an "NTH15 inhibitory sequence" refers to an inhibitory sequence that is capable of inhibiting the expression of an NTH15 locus in a plant, for example, at the level of transcription and/or translation, or which is capable of inhibiting the function of a gene product. When the phrase "capable of inhibiting" is used in the context of a polynucleotide inhibitory sequence, it is intended to mean that the inhibitory sequence itself exerts the inhibitory effect; or, where the inhibitory sequence encodes an inhibitory nucleotide molecule (for example, hairpin RNA, miRNA, or double-stranded RNA polynucleotides), or encodes an inhibitory polypeptide (e.g., a polypeptide that inhibits expression or function of the target gene product), following its transcription (for example, in the case of an inhibitory sequence encoding a hairpin RNA, miRNA, or double-stranded RNA polynucleotide) or its transcription and translation (in the case of an inhibitory sequence encoding an inhibitory polypeptide), the transcribed or translated product, respectively, exerts the inhibitory effect on the target gene product (e.g., inhibits expression or function of the target gene product).

An inhibitory sequence provided herein can be a sequence triggering gene silencing via any silencing pathway or mechanism known in the art, including, but not limited to, sense suppression/co-suppression, antisense suppression, double-stranded RNA (dsRNA) interference, hairpin RNA interference and intron-containing hairpin RNA interference, amplicon-mediated interference, ribozymes, small interfering RNA, artificial or synthetic microRNA, and artificial trans-acting siRNA. An inhibitory sequence may range from at least about 20 nucleotides, at least about 50 nucleotides, at least about 70 nucleotides, at least about 100 nucleotides, at least about 150 nucleotides, at least about 200 nucleotides, at least about 250 nucleotides, at least about 300 nucleotides, at least about 350 nucleotides, at least about 400 nucleotides, and up to the full-length polynucleotide encoding the proteins of the present disclosure, depending upon the desired outcome. In one aspect, an inhibitory sequence can be a fragment of between about 50 and about 400 nucleotides, between about 70 and about 350 nucleotides, between about 90 and about 325 nucleotides, between about 90 and about 300 nucleotides, between about 90 and about 275 nucleotides, between about 100 and about 400 nucleotides, between about 100 and about 350 nucleotides, between about 100 and about 325 nucleotides, between about 100 and about 300 nucleotides, between about 125 and about 300 nucleotides, or between about 125 and about 275 nucleotides in length.

In one aspect, the present disclosure provides a recombinant DNA construct comprising a promoter that is functional in a tobacco cell and operably linked to a polynucleotide that encodes an RNA molecule capable of binding to an RNA encoding a polypeptide having an amino acid sequence at least 60%, at least 70%, at least 75%, at least 80%, at least 85%, at least 90%, at least 95%, at least 96%, at least 97%, at least 98%, at least 99%, or 100% identical to an amino acid sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, 255, and fragments thereof. In one aspect, the present disclosure provides a recombinant DNA construct comprising a promoter that is functional in a tobacco cell and operably linked to a polynucleotide having at least 60%, at least 70%, at least 75%, at least 80%, at least 85%, at least 90%, at least 95%, at least 96%, at least 97%, at least 98%, at least 99%, or 100% identical to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof.

In one aspect, the present disclosure provides a recombinant DNA construct comprising a promoter that is functional in a tobacco cell and operably linked to a polynucleotide that encodes an RNA molecule capable of binding to an RNA encoding a polypeptide having an amino acid sequence at least 60%, at least 70%, at least 75%, at least 80%, at least 85%, at least 90%, at least 95%, at least 96%, at least 97%, at least 98%, at least 99%, or 100% identical to an amino acid sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, 255, and fragments thereof, and where the RNA molecule suppresses the expression of the polypeptide. In one aspect, the present disclosure provides a recombinant DNA construct comprising a promoter that is functional in a tobacco cell and operably linked to a polynucleotide having at least 60%, at least 70%, at least 75%, at least 80%, at least 85%, at least 90%, at least 95%, at least 96%, at least 97%, at least 98%, at least 99%, or 100% identical to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof, and where the RNA molecule suppresses the expression of the polynucleotide.

In one aspect, this disclosure provides a recombinant DNA construct comprising a heterologous axillary meristem-specific promoter operably linked to a polynucleotide that encodes a non-coding RNA molecule, where the non-coding RNA molecule is capable of binding to an RNA encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 245, 247, 249, 251, 253, and 255, and where the non-coding RNA molecule suppresses the expression of the polypeptide.

In one aspect, this disclosure provides a method for controlling topping-induced suckering in a plant comprising transforming the plant with a recombinant DNA construct, where the recombinant DNA construct comprises a heterologous promoter that is functional in an L1 layer, an L2 layer, an L3 region, a rib zone, a central zone, a peripheral zone, or a combination thereof, and where the promoter is operably linked to a polynucleotide that encodes a non-coding RNA molecule, where the non-coding RNA molecule is capable of binding to an RNA encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 245, 247, 249, 251, 253, and 255, and where the non-coding RNA molecule suppresses the expression of the polypeptide.

MicroRNAs (miRNAs) are non-protein coding RNAs, generally of between about 19 to about 25 nucleotides (commonly about 20-24 nucleotides in plants), that guide cleavage in trans of target transcripts, negatively regulating the expression of genes involved in various regulation and development pathways (Bartel (2004) Cell, 116:281-297). In some cases, miRNAs serve to guide in-phase processing of siRNA primary transcripts (see Allen et al. (2005) Cell, 121:207-221).

Many microRNA genes (MIR genes) have been identified and made publicly available in a database ("miRBase", available on line at microrna.sanger.ac.uk/sequences; also see Griffiths-Jones et al. (2003) Nucleic Acids Res., 31:439-441). MIR genes have been reported to occur in intergenic regions, both isolated and in clusters in the genome, but can also be located entirely or partially within introns of other genes (both protein-coding and non-protein-coding). For a recent review of miRNA biogenesis, see Kim (2005) Nature Rev. Mol. Cell. Biol., 6:376-385. Transcription of MIR genes can be, at least in some cases, under promotional control of a MIR gene's own promoter. The primary transcript, termed a "pri-miRNA", can be quite large (several kilobases) and can be polycistronic, containing one or more pre-miRNAs (fold-back structures containing a stem-loop arrangement that is processed to the mature miRNA) as well as the usual 5' "cap" and polyadenylated tail of an mRNA. See, for example, FIG. 1 in Kim (2005) Nature Rev. Mol. Cell. Biol., 6:376-385.

Maturation of a mature miRNA from its corresponding precursors (pri-miRNAs and pre-miRNAs) differs significantly between animals and plants. For example, in plant cells, microRNA precursor molecules are believed to be largely processed to the mature miRNA entirely in the nucleus, whereas in animal cells, the pri-miRNA transcript is processed in the nucleus by the animal-specific enzyme Drosha, followed by export of the pre-miRNA to the cytoplasm where it is further processed to the mature miRNA. Mature miRNAs in plants are typically 21 nucleotides in length. For a recent review of miRNA biogenesis in both plants and animals, see Kim (2005) Nature Rev. Mol. Cell. Biol., 6:376-385. Additional reviews on miRNA biogenesis and function are found, for example, in Bartel (2004) Cell, 116:281-297; Murchison and Hannon (2004) Curr. Opin. Cell Biol., 16:223-229; and Dugas and Bartel (2004) Curr Opin. Plant Biol., 7:512-520.

Transgenic expression of miRNAs (whether a naturally occurring sequence or an artificial sequence) can be employed to regulate expression of the miRNA's target gene or genes. Inclusion of a miRNA recognition site in a transgenically expressed transcript is also useful in regulating expression of the transcript; see, for example, Parizotto et al. (2004) Genes Dev., 18:2237-2242. Recognition sites of miRNAs have been validated in all regions of an mRNA, including the 5' untranslated region, coding region, and 3' untranslated region, indicating that the position of the miRNA target site relative to the coding sequence may not necessarily affect suppression (see, e.g., Jones-Rhoades and Bartel (2004). Mol. Cell, 14:787-799, Rhoades et al. (2002) Cell, 110:513-520, Allen et al. (2004) Nat. Genet., 36:1282-1290, Sunkar and Zhu (2004) Plant Cell, 16:2001-2019). Because miRNAs are important regulatory elements in eukaryotes, transgenic suppression of miRNAs is useful for manipulating biological pathways and responses. Finally, promoters of MIR genes can have very specific expression patterns (e.g., cell-specific, tissue-specific, temporally specific, or inducible), and thus are useful in recombinant constructs to induce such specific transcription of a DNA sequence to which they are operably linked. Various utilities of miRNAs, their precursors, their recognition sites, and their promoters are described in detail in U.S. Patent Application Publication 2006/0200878 A1, incorporated by reference herein. Non-limiting examples of these utilities include: (1) the expression of a native miRNA or miRNA precursor sequence to suppress a target gene; (2) the expression of an artificial miRNA or miRNA precursor sequence to suppress a target gene; (3) expression of a transgene with a miRNA recognition site, where the transgene is suppressed when the mature miRNA is expressed; (4) expression of a transgene driven by a miRNA promoter.

Designing an artificial miRNA sequence can be as simple as substituting sequence that is complementary to the intended target for nucleotides in the miRNA stem region of the miRNA precursor, as demonstrated by Zeng et al. (2002) Mol. Cell, 9:1327-1333. One non-limiting example of a general method for determining nucleotide changes in the native miRNA sequence to produce the engineered miRNA precursor includes the following steps: (a) Selecting a unique target sequence of at least 18 nucleotides specific to the target gene, e.g., by using sequence alignment tools such as BLAST (see, for example, Altschul et al. (1990) J. Mol. Biol., 215:403-410; Altschul et al. (1997) Nucleic Acids Res., 25:3389-3402), for example, of both tobacco cDNA and genomic DNA databases, to identify target transcript orthologues and any potential matches to unrelated genes, thereby avoiding unintentional silencing of non-target sequences; (b) Analyzing the target gene for undesirable sequences (e.g., matches to sequences from non-target species), and score each potential 19-mer segment for GC content, Reynolds score (see Reynolds et al. (2004) Nature Biotechnol., 22:326-330), and functional asymmetry characterized by a negative difference in free energy (".DELTA..DELTA.G" or "ΔΔG") (see Khvorova et al. (2003) Cell, 115:209-216). Preferably 19-mers are selected that have all or most of the following characteristics: (1) a Reynolds score>4, (2) a GC content between about 40% to about 60%, (3) a negative ΔΔG, (4) a terminal adenosine, (5) lack of a consecutive run of 4 or more of the same nucleotide; (6) a location near the 3' terminus of the target gene; (7) minimal differences from the miRNA precursor transcript. Positions at every third nucleotide in an siRNA have been reported to be especially important in influencing RNAi efficacy and an algorithm, "siExplorer" is publicly available at rna.chem.t.u-tokyo.ac.jp/siexplorer.htm (see Katoh and Suzuki (2007) Nucleic Acids Res., 10.1093/nar/gkl1120); (c) Determining the reverse complement of the selected 19-mers to use in making a modified mature miRNA. The additional nucleotide at position 20 is preferably matched to the selected target sequence, and the nucleotide at position 21 is preferably chosen to either be unpaired to prevent spreading of silencing on the target transcript or paired to the target sequence to promote spreading of silencing on the target transcript; and (d) transforming the artificial miRNA into a plant.

In one aspect, an artificial miRNA provided herein is complementary to a polynucleotide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 69, 71, 73, 75, 77, 83-160, 186, 188, 190, 196, 198, 223, 225-228, 230, 232, 234, 236, 238, 240, 242, 244, 246, 248, 250, 252, 254, and fragments thereof. In another aspect, an artificial miRNA provided herein is complementary to a polynucleotide encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 72, 74, 76, 78, 161-185, 189, 191, 197, 199, 224, 229, 231, 233, 235, 237, 239, 241, 243, 245, 247, 249, 251, 253, 255. In yet another aspect, an artificial miRNA provided herein is complementary to a polynucleotide encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence similarity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 189, 191, 197, 199, 224, 229, 231, 233, 235, 237, 239, 241, 243, 245, 247, 249, 251, 253, 255.

In one aspect, an artificial miRNA provided herein reduces or eliminates RNA transcription or protein translation of a target gene.

In one aspect, a miRNA or an artificial miRNA provided herein is under the control of a tissue specific promoter. In another aspect, a miRNA or an artificial miRNA provided herein is under the control of a promoter selected from the group consisting of SEQ ID NOs: 113-118, 148-160, 204, and a fragment thereof. In one aspect, a modified plant provided herein comprises an artificial miRNA under the control of a heterologous promoter selected from the group consisting of SEQ ID NOs: 113-118, 148-160, 204, and a fragment thereof.

Plant microRNAs regulate their target genes by recognizing and binding to a near-perfectly complementary sequence (miRNA recognition site) in the target transcript, followed by cleavage of the transcript by RNase III enzymes such as Argonautel. In plants, certain mismatches between a given miRNA recognition site and the corresponding mature miRNA are not tolerated, particularly mismatched nucleotides at positions 10 and 11 of the mature miRNA. Positions within the mature miRNA are given in the 5' to 3' direction. Perfect complementarity between a given miRNA recognition site and the corresponding mature miRNA is usually required at positions 10 and 11 of the mature miRNA. See, for example, Franco-Zorrilla et al. (2007) Nature Genetics, 39:1033-1037; and Axtell et al. (2006) Cell, 127:565-577.

This characteristic of plant miRNAs is exploited to arrive at rules for predicting a "microRNA decoy sequence", i.e., a sequence that can be recognized and bound by an endogenous mature miRNA resulting in base-pairing between the miRNA decoy sequence and the endogenous mature miRNA, thereby forming a cleavage-resistant RNA duplex that is not cleaved because of the presence of mismatches between the miRNA decoy sequence and the mature miRNA. Mismatches include canonical mismatches (e. g., G-A, C-U, C-A) as well as G::U wobble pairs and indels (nucleotide insertions or deletions). In general, these rules define (1) mismatches that are required, and (2) mismatches that are permitted but not required.

Required mismatches include: (a) at least 1 mismatch between the miRNA decoy sequence and the endogenous mature miRNA at positions 9, 10, or 11 of the endogenous mature miRNA, or alternatively, (b) 1, 2, 3, 4, or 5 insertions (i. e., extra nucleotides) at a position in the miRNA decoy sequence corresponding to positions 9, 10, or 11 of the endogenous mature miRNA.

Mismatches that are permitted, but not required, include: (a) 0, 1, or 2 mismatches between the miRNA decoy sequence and the endogenous mature miRNA at positions 1, 2, 3, 4, 5, 6, 7, 8, and 9 of the endogenous mature miRNA, and (b) 0, 1, 2, or 3 mismatches between the miRNA decoy sequence and the endogenous mature miRNA at positions 12 through the last position of the endogenous mature miRNA (i. e., at position 21 of a 21-nucleotide mature miRNA), where each of the mismatches at positions 12 through the last position of the endogenous mature miRNA is adjacent to at least one complementary base-pair (i. e., so that there is not more than 2 contiguous mismatches at positions 12 through the last position of the endogenous mature miRNA).

A miRNA decoy sequence can be of any length as long as it is recognized and bound by an endogenous mature miRNA to form a cleavage-resistant RNA duplex. In one aspect, a miRNA decoy sequence includes between about 18 to about 36 nucleotides. In another aspect, a microRNA decoy provided herein is a small RNA molecule of at least 15, at least 16, at least 17, at least 18, at least 19, at least 20, at least 21, at least 22, at least 23, at least 24, at least 25, at least 26, at least 27, at least 28, at least 29, at least 30, or more than 30 nucleotides that is capable of binding to a mature miRNA. See, for example, WO 2008/133643, which is herein incorporated by reference in its entirety.

In one aspect, an endogenous miRNA is regulated by a miRNA decoy provided herein. A microRNA decoy provided herein is capable of preventing a complementary mature miRNA from binding its native target gene, thereby increasing expression of the target gene.

In another aspect, a recombinant DNA construct provided herein comprises at least 1, at least 2, at least 3, at least 4, at least 5, at least 6, at least 7, at least 8, at least 9, at least 10, or more than 10 miRNA decoys. In one aspect, a miRNA decoy provided herein is under the control of a regulatory sequence selected from the group consisting of SEQ ID NOs: 113-118, 148-160, 204, and a fragment thereof.

In another aspect, an endogenous miRNA target is edited with a site-specific nuclease provided herein to mutate at least one miRNA binding site, thereby rendering the endogenous miRNA target resistant to miRNA-mediated degradation. As used herein, a "miRNA target" refers to a contiguous stretch of at least 18, at least 19, at least 20, at least 21, at least 22, at least 23, at least 24, at least 25, at least 26, at least 27, at least 28, at least 29, at least 30, or more than 30 nucleotides having at least 75%, at least 80%, at least 85%, at least 88%, at least 90%, at least 91%, at least 92%, at least 93%, at least 94%, at least 95%, at least 96%, at least 97%, at least 98%, at least 99% or 100% identity to a mature miRNA. In one aspect, a miRNA target is capable of being hybridized by a mature miRNA, and then cleaved by a mature miRNA/Argonaute RNA-induced silencing complex, under typical cellular conditions.

Also provided herein is cured tobacco material made from tobacco plants or plant components provided herein. "Curing" is the aging process that reduces moisture and brings about the destruction of chlorophyll giving tobacco leaves a golden color and by which starch is converted to sugar. Cured tobacco therefore has a higher reducing sugar content and a lower starch content compared to harvested green leaf. In one aspect, tobacco plants or plant components provided herein can be cured using conventional means, e.g., flue-cured, barn-cured, fire-cured, air-cured or sun-cured. See, for example, Tso (1999, Chapter 1 in Tobacco, Production, Chemistry and Technology, Davis & Nielsen, eds., Blackwell Publishing, Oxford) for a description of different types of curing methods. Cured tobacco is usually aged in a wooden drum (e.g., a hogshead) or cardboard cartons in compressed conditions for several years (e.g., two to five years), at a moisture content ranging from 10% to about 25%. See, U.S. Pat. Nos. 4,516,590 and 5,372,149. Cured and aged tobacco then can be further processed. Further processing includes conditioning the tobacco under vacuum with or without the introduction of steam at various temperatures, pasteurization, and fermentation. Fermentation typically is characterized by high initial moisture content, heat generation, and a 10 to 20% loss of dry weight. See, for example, U.S. Pat. Nos. 4,528,993, 4,660,577, 4,848,373, 5,372,149; U.S. Publication No. 2005/0178398; and Tso (1999, Chapter 1 in Tobacco, Production, Chemistry and Technology, Davis & Nielsen, eds., Blackwell Publishing, Oxford). Cured, aged, and fermented tobacco can be further processed (e.g., cut, shredded, expanded, or blended). See, for example, U.S. Pat. Nos. 4,528,993; 4,660,577; and 4,987,907. In one aspect, the cured tobacco material of the present disclosure is flue-cured, sun-cured, air-cured, or fire-cured.

Tobacco material obtained from modified tobacco lines, varieties or hybrids of the present disclosure can be used to make tobacco products. As used herein, "tobacco product" is defined as any product made or derived from tobacco that is intended for human use or consumption. In an aspect, a tobacco product provided herein comprises cured components from a modified tobacco plant provided herein. In another aspect, a tobacco product provided herein comprises cured tobacco leaves from a modified tobacco plant provided herein.

Tobacco products provided herein include, without limitation, cigarette products (e.g., cigarettes, bidi cigarettes, kreteks), cigar products (e.g., cigars, cigar wrapping tobacco, cigarillos), pipe tobacco products, products derived from tobacco, tobacco-derived nicotine products, smokeless tobacco products (e.g., moist snuff, dry snuff, chewing tobacco, moist smokeless tobacco, fine cut chewing tobacco, long cut chewing tobacco, pouched chewing tobacco), films, chewables (e.g., gum), lozenges, dissolving strips, tabs, tablets, shaped parts, gels, consumable units, insoluble matrices, hollow shapes, reconstituted tobacco, expanded tobacco, and the like. See, for example, U.S. Patent Publication No. US 2006/0191548.

As used herein, "cigarette" refers a tobacco product having a "rod" and "filler". The cigarette "rod" includes the cigarette paper, filter, plug wrap (used to contain filtration materials), tipping paper that holds the cigarette paper (including the filler) to the filter, and all glues that hold these components together. The "filler" includes (1) all tobaccos, including but not limited to reconstituted and expanded tobacco, (2) non-tobacco substitutes (including but not limited to herbs, non-tobacco plant materials and other spices that may accompany tobaccos rolled within the cigarette paper), (3) casings, (4) flavorings, and (5) all other additives (that are mixed into tobaccos and substitutes and rolled into the cigarette).

In one aspect, this disclosure provides nicotine derived from and a method of producing nicotine from a modified tobacco plant provided herein for use in a product.

In one aspect, a method provided herein comprises preparing a tobacco product using a cured tobacco leaf from a modified tobacco plant provided herein.

As used herein, "reconstituted tobacco" refers to a part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars.

As used herein, “expanded tobacco” refers to a part of tobacco filler which is processed through expansion of suitable gases so that the tobacco is “puffed” resulting in reduced density and greater filling capacity. It reduces the weight of tobacco used in cigarettes.

Tobacco products derived from plants of the present disclosure also include cigarettes and other smoking articles, particularly those smoking articles including filter elements, where the rod of smokeable material includes cured tobacco within a tobacco blend. In an aspect, a tobacco product of the present disclosure is selected from the group consisting of a cigarillo, a non-ventilated recess filter cigarette, a vented recess filter cigarette, a bidi cigarette, a cigar, snuff, pipe tobacco, cigar tobacco, cigarette tobacco, chewing tobacco, leaf tobacco, hookah tobacco, shredded tobacco, and cut tobacco. In another aspect, a tobacco product of the present disclosure is a smokeless tobacco product. Smokeless tobacco products are not combusted and include, but not limited to, chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer’s cheek and gum. Snus is a heat treated smokeless tobacco. Dry snuff is finely ground tobacco that is placed in the mouth or used nasally. In a further aspect, a tobacco product of the present disclosure is selected from the group consisting of loose leaf chewing tobacco, plug chewing tobacco, moist snuff, and nasal snuff. In yet another aspect, a tobacco product of the present disclosure is selected from the group consisting of an electronically heated cigarette, an e-cigarette, an electronic vaporing device.

The present disclosure further provides a method manufacturing a tobacco product comprising tobacco material from tobacco plants provided herein. In one aspect, methods provided herein comprise conditioning aged tobacco material made from tobacco plants provided herein to increase its moisture content from between about 12.5% and about 13.5% to about 21%, blending the conditioned tobacco material to produce a desirable blend. In one aspect, the method of manufacturing a tobacco product provided herein further comprises casing or flavoring the blend. Generally, during the casing process, casing or sauce materials are added to blends to enhance their quality by balancing the chemical composition and to develop certain desired flavor characteristics. Further details for the casing process can be found in *Tobacco Production, Chemistry and Technology*, Edited by L. Davis and M. Nielsen, Blackwell Science, 1999.

Tobacco material provided herein can be also processed using methods including, but not limited to, heat treatment (e.g., cooking, toasting), flavoring, enzyme treatment, expansion and/or curing. Both fermented and non-fermented tobaccos can be processed using these techniques. Examples of suitable processed tobaccos include dark air-cured, dark fire cured, burley, flue cured, and cigar filler or wrapper, as well as the products from the whole leaf stemming operation. In one aspect, tobacco fibers include up to 70% dark tobacco on a fresh weight basis. For example, tobacco can be conditioned by heating, sweating and/or pasteurizing steps as described in U.S. Publication Nos. 2004/0118422 or 2005/0178398.

Tobacco material provided herein can be subject to fermentation. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. In addition to modifying the aroma of the leaf, fermentation can change either or both the color and texture of a leaf. Also during the fermentation process, evolution gases can be produced, oxygen can be taken up, the pH can change, and the amount of water retained can change. See, for example, U.S. Publication No. 2005/0178398 and Tso (1999, Chapter 1 in Tobacco, Production, Chemistry and Technology, Davis & Nielsen, eds., Blackwell Publishing, Oxford). Cured, or cured and fermented tobacco can be further processed (e.g., cut, expanded, blended, milled or comminuted) prior to incorporation into the oral product. The tobacco, in some cases, is long cut fermented cured moist tobacco having an oven volatiles content of between 48 and 50 weight percent prior to mixing with a copolymer and, optionally, flavorants and other additives.

In one aspect, tobacco material provided herein can be processed to a desired size. In certain aspects, tobacco fibers can be processed to have an average fiber size of less than 200 micrometers. In one aspect, tobacco fibers are between 75 and 125 micrometers. In another aspect, tobacco fibers are processed to have a size of 75 micrometers or less. In one aspect, tobacco fibers include long cut tobacco, which can be cut or shredded into widths of about 10 cuts/inch up to about 110 cuts/inch and lengths of about 0.1 inches up to about 1 inch. Double cut tobacco fibers can have a range of particle sizes such that about 70% of the double cut tobacco fibers falls between the mesh sizes of −20 mesh and 80 mesh.

Tobacco material provided herein can be processed to have a total oven volatiles content of about 10% by weight or greater; about 20% by weight or greater; about 40% by weight or greater; about 15% by weight to about 25% by weight; about 20% by weight to about 30% by weight; about 30% by weight to about 50% by weight; about 45% by weight to about 65% by weight; or about 50% by weight to about 60% by weight. Those of skill in the art will appreciate that “moist” tobacco typically refers to tobacco that has an oven volatiles content of between about 40% by weight and about 60% by weight (e.g., about 45% by weight to about 55% by weight, or about 50% by weight). As used herein, “oven volatiles” are determined by calculating the percentage of weight loss for a sample after drying the sample in a pre-warmed forced draft oven at 110° C. for 3.25 hours. An oral product can have a different overall oven volatiles content than the oven volatiles content of the tobacco fibers used to make the oral product. The processing steps described herein can reduce or increase the oven volatiles content.

In one aspect, tobacco plants, seeds, plant components, plant cells, and plant genomes provided herein are from a tobacco type selected from the group consisting of flue-cured tobacco, sun-cured tobacco, air-cured tobacco, dark air-cured tobacco, and dark fire-cured tobacco. In another aspect, tobacco plants, seeds, plant components, plant cells, and plant genomes provided herein are from a tobacco type selected from the group consisting of Burley tobacco, Maryland tobacco, bright tobacco, Virginia tobacco, Oriental tobacco, Turkish tobacco, and Galpão tobacco. In one aspect, a tobacco plants or seed provided herein is a hybrid plants or seed. As used herein, a “hybrid” is created by crossing two plants from different varieties or species, such that the progeny comprises genetic material from each parent. Skilled artisans recognize that higher order hybrids can be generated as well. For example, a first hybrid can be made by crossing Variety C with Variety D to create a C×D hybrid, and a second hybrid can be made by crossing Variety E with Variety F to create an E×F hybrid. The first and second hybrids can be further crossed to create the higher order hybrid (C×D)×(E×F) comprising genetic information from all four parent varieties.

Flue-cured tobaccos (also called Virginia of bright tobaccos) amount to approximately 40% of world tobacco production. Flue-cured tobaccos are often also referred to as "bright tobacco" because of the golden-yellow to deep-orange color it reaches during curing. Flue-cured tobaccos have a light, bright aroma and taste. Flue-cured tobaccos are generally high in sugar and low in oils. Major flue-cured tobacco growing countries are Argentina, Brazil, China, India, Tanzania and the U.S. In one aspect, modified tobacco plants or seeds provided herein are in a flue-cured tobacco background selected from the group consisting of CC 13, CC 27, CC 33, CC35, CC 37, CC 65, CC 67, CC 700, GF 318, GL 338, GL 368, GL 939, K 346, K 399, K326, NC 102, NC 196, NC 291, NC 297, NC 299, NC 471, NC 55, NC 606, NC 71, NC 72, NC 92, PVH 1118, PVH 1452, PVH 2110, SPEIGHT 168, SPEIGHT 220, SPEIGHT 225, SPEIGHT 227, SPEIGHT 236, and any variety essentially derived from any one of the foregoing varieties. In another aspect, modified tobacco plants or seeds provided herein are in a flue-cured tobacco background selected from the group consisting of Coker 48, Coker 176, Coker 371-Gold, Coker 319, Coker 347, GL 939, K 149, K326, K 340, K 346, K 358, K 394, K 399, K 730, NC 27NF, NC 37NF, NC 55, NC NC 71, NC 72, NC 82, NC 95, NC 297, NC 606, NC 729, NC 2326, McNair 373, McNair 944, Ox 207, Ox 414 NF, Reams 126, Reams 713, Reams 744, RG 8, RG 11, RG 13, RG 17, RG 22, RG 81, RG H4, RG H51, Speight H-20, Speight G-28, Speight G-58, Speight G-70, Speight G-108, Speight G-111, Speight G-117, Speight 168, Speight 179, Speight NF-3, Va 116, Va 182, and any variety essentially derived from any one of the foregoing varieties. See WO 2004/041006 A1. In further aspects, modified tobacco plants, seeds, hybrids, varieties, or lines provided herein are in any flue cured background selected from the group consisting of K326, K346, and NC196.

Air-cured tobaccos include Burley, Maryland, and dark tobaccos. The common factor is that curing is primarily without artificial sources of heat and humidity. Burley tobaccos are light to dark brown in color, high in oil, and low in sugar. Burley tobaccos are air-cured in barns. Major Burley growing countries are Argentina, Brazil, Italy, Malawi, and the U.S. Maryland tobaccos are extremely fluffy, have good burning properties, low nicotine and a neutral aroma. Major Maryland growing countries include the U.S. and Italy. In one aspect, modified tobacco plants or seeds provided herein are in a Burley tobacco background selected from the group consisting of Clay 402, Clay 403, Clay 502, Ky 14, Ky 907, Ky 910, Ky 8959, NC 2, NC 3, NC 4, NC 5, NC 2000, TN 86, TN 90, TN 97, R 610, R 630, R 711, R 712, NCBH 129, HB4488PLC, PD 7319LC, Bu 21×Ky 10, HB04P, Ky 14×L 8, Kt 200, Newton 98, Pedigo 561, Pf561 and Va 509. In further aspects, modified tobacco plants, seeds, hybrids, varieties, or lines provided herein are in any Burley background selected from the group consisting of TN 90, KT 209, KT 206, KT212, and HB 4488. In another aspect, modified tobacco plants or seeds provided herein are in a Maryland tobacco background selected from the group consisting of Md 10, Md 40, Md 201, Md 609, Md 872 and Md 341.

Dark air-cured tobaccos are distinguished from other types primarily by its curing process which gives dark air-cured tobacco its medium- to dark-brown color and distinct aroma. Dark air-cured tobaccos are mainly used in the production of chewing tobacco and snuff. In one aspect, modified tobacco plants or seeds provided herein are in a dark air-cured tobacco background selected from the group consisting of Sumatra, Jatim, Dominican Cubano, Besuki, One sucker, Green River, Virginia sun-cured, and Paraguan Passado.

Dark fire-cured tobaccos are generally cured with low-burning wood fires on the floors of closed curing barns. Dark fire-cured tobaccos are used for making pipe blends, cigarettes, chewing tobacco, snuff and strong-tasting cigars. Major growing regions for dark fire-cured tobaccos are Tennessee, Kentucky, and Virginia, USA. In one aspect, modified tobacco plants or seeds provided herein are in a dark fire-cured tobacco background selected from the group consisting of Narrow Leaf Madole, Improved Madole, Tom Rosson Madole, Newton's VH Madole, Little Crittenden, Green Wood, Little Wood, Small Stalk Black Mammoth, DT 508, DT 518, DT 592, KY 171, DF 911, DF 485, TN D94, TN D950, VA 309, and VA 359.

Oriental tobaccos are also referred to as Greek, aroma and Turkish tobaccos due to the fact that they are typically grown in eastern Mediterranean regions such as Turkey, Greece, Bulgaria, Macedonia, Syria, Lebanon, Italy, and Romania. The small plant and leaf size, characteristic of today's Oriental varieties, as well as its unique aroma properties are a result of the plant's adaptation to the poor soil and stressful climatic conditions in which it develop over many past centuries. In one aspect, modified tobacco plants or seeds provided herein are in an Oriental tobacco background selected from the group consisting of Izmir, Katerini, Samsun, Basma and Krumovgrad, Trabzon, Thesalian, Tasova, Sinop, Izmit, Hendek, Edirne, Semdinli, Adiyanman, Yayladag, Iskenderun, Duzce, Macedonian, Mavra, Prilep, Bafra, Bursa, Bucak, Bitlis, Balikesir, and any variety essentially derived from any one of the foregoing varieties.

In one aspect, modified tobacco plants, seeds, hybrids, varieties, or lines provided herein are essentially derived from or in the genetic background of BU 64, CC 101, CC 200, CC 13, CC 27, CC 33, CC 35, CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpão, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY 907LC, KTY14×L8 LC, Little Crittenden, McNair 373, McNair 944, male sterile KY 14×L8, Narrow Leaf Madole, MS KY171, Narrow Leaf Madole (phph), MS Narrow Leaf Madole, MS TND950, PD 7302LC, PD 7305LC, PD 7309LC, PD 7312LC, PD 7318LC, PD 7319LC, MSTKS 2002, TKF 2002, TKF 6400, TKF 4028, TKF 4024, KT206LC, KT209LC, KT210LC, KT212LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique', PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, a TR (Tom Rosson) Madole, VA 309, VA 359, or any commercial tobacco variety according to standard tobacco breeding techniques known in the art.

All foregoing mentioned specific varieties of dark air-cured, Burley, Maryland, dark fire-cured, or Oriental type are only listed for exemplary purposes. Any additional dark air-cured, Burley, Maryland, dark fire-cured, Oriental varieties are also contemplated in the present application.

Also provided herein are populations of tobacco plants described herein. In one aspect, a population of tobacco plants provided herein has a planting density of between about 5,000 and about 8000, between about 5,000 and about 7,600, between about 5,000 and about 7,200, between about 5,000 and about 6,800, between about 5,000 and about 6,400, between about 5,000 and about 6,000, between about 5,000 and about 5,600, between about 5,000 and about 5,200, between about and about 8,000, between about 5,600 and about 8,000, between about 6,000 and about 8,000, between about 6,400 and about 8,000, between about 6,800 and about 8,000, between about 7,200 and about 8,000, or between about 7,600 and about 8,000 plants per acre. In another aspect, a population of tobacco plants provided herein is in a soil type with low to medium fertility.

Also provided herein are containers of seeds from tobacco plants described herein. A container of tobacco seeds of the present disclosure may contain any number, weight, or volume of seeds. For example, a container can contain at least, or greater than, about 100, at least, or greater than, about 200, at least, or greater than, about 300, at least, or greater than, about 400, at least, or greater than, about 500, at least, or greater than, about 600, at least, or greater than, about 700, at least, or greater than, about 800, at least, or greater than, about 900, at least, or greater than, about 1000, at least, or greater than, about 1500, at least, or greater than, about 2000, at least, or greater than, about 2500, at least, or greater than, about 3000, at least, or greater than, about 3500, at least, or greater than, or about 4000 or more seeds. Alternatively, the container can contain at least, or greater than, about 1 ounce, at least, or greater than, about 5 ounces, at least, or greater than, about ounces, at least, or greater than, about 1 pound, at least, or greater than, about 2 pounds, at least, or greater than, about 3 pounds, at least, or greater than, about 4 pounds, at least, or greater than, about 5 pounds or more seeds. Containers of tobacco seeds may be any container available in the art. By way of non-limiting example, a container may be a box, a bag, a packet, a pouch, a tape roll, a tube, or a bottle.

The present disclosure also provides methods for breeding tobacco lines, cultivars, or varieties comprising reduced or eliminated suckering. Breeding can be carried out via any known procedures. DNA fingerprinting, SNP mapping, haplotype mapping or similar technologies may be used in a marker-assisted selection (MAS) breeding program to transfer or breed a desirable trait or allele into a tobacco plant. For example, a breeder can create segregating populations in an $F_2$ or backcross generation using $F_1$ hybrid plants provided herein or further crossing the $F_1$ hybrid plants with other donor plants with an agronomically desirable genotype. Plants in the $F_2$ or backcross generations can be screened for a desired agronomic trait or a desirable chemical profile using one of the techniques known in the art or listed herein. Depending on the expected inheritance pattern or the MAS technology used, self-pollination of selected plants before each cycle of backcrossing to aid identification of the desired individual plants can be performed. Backcrossing or other breeding procedure can be repeated until the desired phenotype of the recurrent parent is recovered. In one aspect, a recurrent parent in the present disclosure can be a flue-cured variety, a Burley variety, a dark air-cured variety, a dark fire-cured variety, or an Oriental variety. In another aspect, a recurrent parent can be a modified tobacco plant, line, or variety. Other breeding techniques can be found, for example, in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y., incorporated herein by reference in their entirety.

Results of a plant breeding program using modified tobacco plants described herein includes useful lines, cultivars, varieties, progeny, inbreds, and hybrids of the present disclosure. As used herein, the term "variety" refers to a population of plants that share constant characteristics which separate them from other plants of the same species. A variety is often, although not always, sold commercially. While possessing one or more distinctive traits, a variety is further characterized by a very small overall variation between individuals within that variety. A "pure line" variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972; on Oct. 23, 1978; and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation. A first tobacco variety and a second tobacco variety from which the first variety is essentially derived, are considered as having essentially identical genetic background. A "line" as distinguished from a variety most often denotes a group of plants used non-commercially, for example in plant research. A line typically displays little overall variation between individuals for one or more traits of interest, although there may be some variation between individuals for other traits.

In one aspect, the present disclosure provides a method of producing a tobacco plant comprising crossing at least one tobacco plant of a first tobacco variety with at least one tobacco plant of a second tobacco variety, where the at least one tobacco plant of the first tobacco variety exhibits no or reduced topping-induced suckering compared to a control tobacco plant of the same variety grown under comparable conditions; and selecting for progeny tobacco plants that exhibit no or reduced topping-induced suckering compared to a control tobacco plant of the same cross grown under comparable conditions. In one aspect, a first tobacco variety provided herein comprises modified tobacco plants. In another aspect, a second tobacco variety provided herein comprises modified tobacco plants. In one aspect, a first or second tobacco variety is male sterile. In another aspect, a first or second tobacco variety is cytoplasmically male sterile. In another aspect, a first or second tobacco variety is female sterile. In one aspect, a first or second tobacco variety is an elite variety. In another aspect, a first or second tobacco variety is a hybrid.

In one aspect, the present disclosure provides a method of introgressing one or more transgenes into a tobacco variety, the method comprising: (a) crossing a first tobacco variety comprising one or more transgenes with a second tobacco variety without the one or more transgenes to produce one or more progeny tobacco plants; (b) genotyping the one or more progeny tobacco plants for the one or more transgenes; and (c) selecting a progeny tobacco plant comprising the one or more transgenes. In another aspect, these methods further comprise backcrossing the selected progeny tobacco plant with the second tobacco variety. In further aspects, these methods further comprise: (d) crossing the selected progeny plant with itself or with the second tobacco variety to produce one or more further progeny tobacco plants; and (e) selecting a further progeny tobacco plant comprising the one or more transgenes. In one aspect, the second tobacco variety is an elite variety.

In one aspect, the present disclosure provides a method of introgressing one or more mutations into a tobacco variety, the method comprising: (a) crossing a first tobacco variety comprising one or more mutations with a second tobacco variety without the one or more mutations to produce one or more progeny tobacco plants; (b) genotyping the one or more progeny tobacco plants for the one or more mutations; and (c) selecting a progeny tobacco plant comprising the one or more mutations. In another aspect, these methods further comprise backcrossing the selected progeny tobacco plant with the second tobacco variety. In further aspects, these methods further comprise: (d) crossing the selected progeny plant with itself or with the second tobacco variety to produce one or more further progeny tobacco plants; and (e) selecting a further progeny tobacco plant comprising the one or more mutations. In one aspect, the second tobacco variety is an elite variety.

In one aspect, the present disclosure provides a method of growing a population of modified tobacco plants comprising no or reduced suckering, where the method comprises planting a population of tobacco seeds comprising one or more mutations, one or more transgenes, or both, where the one or more modified tobacco plants exhibit no or reduced suckering compared to control tobacco plants of the same variety when grown under comparable conditions.

In one aspect, the present disclosure provides a method of growing a modified tobacco plant comprising planting a modified tobacco seed comprising a heterologous promoter that is operably linked to a polynucleotide encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, 255; and growing the modified tobacco plant from the seed. In another aspect, this disclosure provides a method of growing a modified tobacco plant comprising planting a modified tobacco seed comprising a recombinant DNA construct comprising a heterologous promoter that is functional in an L1 layer, an L2 layer, an L3 region, a rib zone, a central zone, a peripheral zone, or a combination thereof, and is operably linked to a polynucleotide that encodes a non-coding RNA molecule, where the non-coding RNA molecule is capable of binding to an RNA encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, 255, and where the non-coding RNA molecule suppresses the expression of the polypeptide; and growing the modified tobacco plant the seed. In an aspect, growing comprises germinating a seed. In another aspect, growing comprises placing a seedling in soil, agar, agar-based media, or a hydroponics system. In another aspect, growing comprises providing a seed or plant with water, light (e.g., artificial light, sunlight), fertilizer, a rooting media, or a combination thereof. In an aspect, growing can take place indoors (e.g., a greenhouse) or outdoors (e.g., a field). In one aspect, growing comprises placing a seed or a plant in a container.

In one aspect, this disclosure provides a method for manufacturing a modified seed, comprising introducing a recombinant DNA construct provided herein into a plant cell; screening a population of plant cells for the recombinant DNA construct; selecting one or more plant cells from the population; generating one or more modified plants from the one or more plant cells; and collecting one or more modified seeds from the one or more modified plants.

As used herein, "locus" is a chromosome region where a polymorphic nucleic acid, trait determinant, gene, or marker is located. The loci of this disclosure comprise one or more polymorphisms in a population; e.g., alternative alleles are present in some individuals. As used herein, "allele" refers to an alternative nucleic acid sequence at a particular locus. The length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population. As used herein, a chromosome in a diploid plant is "hemizygous" when only one copy of a locus is present. For example, an inserted transgene is hemizygous when it only inserts into one sister chromosome (i.e., the second sister chromosome does not contain the inserted transgene).

In one aspect, a modified plant, seed, plant component, plant cell, or plant genome is homozygous for a transgene provided herein. In another aspect, a modified plant, seed, plant component, plant cell, or plant genome is heterozygous for a transgene provided herein. In one aspect, a modified plant, seed, plant component, plant cell, or plant genome is hemizygous for a transgene provided herein. In one aspect, a modified plant, seed, plant component, plant cell, or plant genome is homozygous for a mutation provided herein. In another aspect, a modified plant, seed, plant component, plant cell, or plant genome is heterozygous for a mutation provided herein. In one aspect, a modified plant, seed, plant component, plant cell, or plant genome is hemizygous for a mutation provided herein.

As used herein, "introgression" or "introgress" refers to the transmission of a desired allele of a genetic locus from one genetic background to another.

As used herein, "crossed" or "cross" means to produce progeny via fertilization (e.g. cells, seeds or plants) and includes crosses between different plants (sexual) and self-fertilization (selfing).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. The initial cross gives rise to the $F_1$ generation. The term "BC1" refers to the second use of the recurrent parent, "BC2" refers to the third use of the recurrent parent, and so on. In one aspect, a backcross is performed repeatedly, with a progeny individual of each successive backcross generation being itself backcrossed to the same parental genotype.

As used herein, "elite variety" means any variety that has resulted from breeding and selection for superior agronomic performance.

As used herein, "selecting" or "selection" in the context of breeding refer to the act of picking or choosing desired individuals, normally from a population, based on certain pre-determined criteria.

In one aspect, tobacco plants provided herein are hybrid plants. Hybrids can be produced by preventing self-pollination of female parent plants (e.g., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by male sterility (MS), or transgenic male sterility where a transgene inhibits microsporogenesis and/or pollen formation, or self-incompatibility. Female parent plants containing MS are particularly useful. In aspects in which the female parent plants are MS, pollen may be harvested from male fertile plants and applied manually to the stigmas of MS female parent plants, and the resulting $F_1$ seed is harvested. Additionally, female sterile plants can also be used to prevent self-fertilization.

Plants can be used to form single-cross tobacco $F_1$ hybrids. Pollen from a male parent plant is manually transferred to an emasculated female parent plant or a female parent plant that is male sterile to form $F_1$ seed. Alternatively, three-way crosses can be carried out where a single-cross $F_1$ hybrid is used as a female parent and is crossed with a different male parent. As another alternative, double-cross hybrids can be created where the $F_1$ progeny of two different single-crosses are themselves crossed. Self-incompatibility can be used to particular advantage to prevent self-pollination of female parents when forming a double-cross hybrid.

In one aspect, a tobacco variety provided herein is male sterile. In another aspect, a tobacco variety provided herein is cytoplasmic male sterile (CMS). Male sterile tobacco plants may be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y. 761 pp. In another aspect, a tobacco variety provided herein is female sterile. As a non-limiting example, female sterile plants can be made by mutating the STIG1 gene. See, for example, Goldman et al. 1994, *EMBO Journal* 13:2976-2984.

As used herein, the term "sequence identity" or "identity" in the context of two polynucleotide or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity."

The use of the term "polynucleotide" is not intended to limit the present disclosure to polynucleotides comprising DNA. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like.

As used herein, the term "polypeptide" refers to a chain of at least two covalently linked amino acids.

The present disclosure provides recombinant, purified, isolated, or processed nucleic acids and polypeptides. In one aspect, the present disclosure provides a nucleic acid molecule comprising at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or about 100% identity to a sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof. In one aspect, the present disclosure provides a nucleic acid molecule comprising at least 18, at least 19, at least 20, at least 21, at least 22, at least 23, at least 24, at least at least 26, at least 27, at least 28, at least 29, at least 30, or more than 30 contiguous nucleotides identical to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, and 254.

In another aspect, the present disclosure provides a polynucleotide encoding a polypeptide comprising at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, about 98%, at least about 99%, or about 100% sequence identity to a polypeptide sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In another aspect, the present disclosure provides a polynucleotide encoding a polypeptide comprising at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% similarity to a polypeptide sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, the present disclosure provides a polypeptide comprising at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% identity to an amino acid sequence selected from the group consisting of SEQ ID NOs: 2, 4, 6, 8, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In one aspect, the present disclosure provides a polypeptide comprising at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% similarity to an amino acid sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In one aspect, the present disclosure provides a polypeptide comprising at least 10, at least 11, at least 12, at least 13, at least 14, at least 15, at least 16, at least 17, at least 18, at least 19, at least 20, at least 21, at least 22, at least 23, at least 24, at least 25, at least 30, at least 40, at least 50, or more than 50 contiguous amino acid residues identical to an amino acid sequence in a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In another aspect, the present disclosure provides a biologically active variant of a protein having an amino acid sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. A biologically active variant of a protein of the present disclosure may differ from that protein by as few as 1-15 amino acid residues, as few as 10, as few as 9, as few as 8, as few as 7, as few as 6, as few as 5, as few as 4, as few as 3, as few as 2, or as few as 1 amino acid residue. Also provided herein are orthologous genes or proteins of genes or proteins selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. "Orthologs" are genes derived from a common ancestral gene and which are found in different species as a result of speciation. Orthologs may share at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or greater sequence identity or similarity at the nucleotide sequence and/or the amino acid sequence level. Functions of orthologs are often highly conserved among species.

Nucleic acid molecules, polypeptides, or proteins provided herein can be isolated or substantially purified. An "isolated" or "purified" nucleic acid molecule, polypeptide, protein, or biologically active portion thereof, is substantially or essentially free from components that normally accompany or interact with the polynucleotide or protein as found in its naturally occurring environment. For example, an isolated or purified polynucleotide or protein is substantially free of other cellular material, or culture medium when produced by recombinant techniques, or substantially free of chemical precursors or other chemicals when chemically synthesized. In one aspect, an isolated polynucleotide provided herein can contain less than about 5000 nucleotides, less than about 4000 nucleotides, less than about 3000 nucleotides, less than about 2000 nucleotides, less than about 1000 nucleotides, less than about 500 nucleotides, or less than about 100 nucleotides of nucleic acid sequence that naturally flank the polynucleotide in genomic DNA of the cell from which the polynucleotide is derived. In one aspect, an isolated polynucleotide provided herein can contain 100-5000, 500-5000, 1000-5000, 2000-5000, 3000-5000, 4000-5000, 1-500, 1-1000, 1-2000, 1-3000, 1-4000, 1-5000, 100-500, 100-1000, 100-2000, 100-3000, or 100-4000 nucleotides of nucleic acid sequence that naturally flank the polynucleotide in genomic DNA of the cell from which the polynucleotide is derived. In another aspect, an isolated polypeptide provided herein is substantially free of cellular material in preparations having less than about 30%, less than about 20%, less than about 10%, less than about 5%, or less than about 1% (by dry weight) of chemical precursors or non-protein-of-interest chemicals. Fragments of the disclosed polynucleotides and polypeptides encoded thereby are also encompassed by the present invention. Fragments of a polynucleotide may encode polypeptide fragments that retain the biological activity of the native polypeptide. Alternatively, fragments of a polynucleotide that are useful as hybridization probes or PCR primers using methods known in the art generally do not encode fragment polypeptides retaining biological activity. Fragments of a polynucleotide provided herein can range from at least about 20 nucleotides, about 50 nucleotides, about 70 nucleotides, about 100 nucleotides, about 150 nucleotides, about 200 nucleotides, about 250 nucleotides, about 300 nucleotides, and up to the full-length polynucleotide encoding the polypeptides of the invention, depending on the desired outcome.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In one aspect, this disclosure provides methods of detecting recombinant nucleic acids and polypeptides in plant cells. Without being limiting, nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, NY).

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term “label” is intended to encompass the use of direct labels as well as indirect labels. Detectable labels include enzymes, prosthetic groups, fluorescent materials, luminescent materials, bioluminescent materials, and radioactive materials.

The following exemplary, non-limiting embodiments are envisioned:

1. A modified tobacco plant comprising no or reduced suckers compared to a control tobacco plant of the same variety when grown under comparable conditions.
2. The modified tobacco plant of embodiment 1, wherein said suckers is topping-induced suckers.
3. The modified tobacco plant of embodiment 1, wherein said modified tobacco plant comprises one or more mutations.
4. The modified tobacco plant of embodiment 1, wherein said modified tobacco plant comprises one or more transgenes.

The modified tobacco plant of embodiment 3, wherein said one or more mutations suppress suckers.

6. The modified tobacco plant of embodiment 4, wherein said one or more transgenes suppress suckers.
7. The modified tobacco plant of embodiment 3, wherein said one or more mutations suppress topping-induced suckers.
8. The modified tobacco plant of embodiment 4, wherein said one or more transgenes suppress topping-induced suckers.
9. The modified tobacco plant of embodiment 3, wherein said one or more mutations suppress suckers prior to topping.
10. The modified tobacco plant of embodiment 4, wherein said one or more transgenes suppress suckers prior to topping.
11. The modified tobacco plant of embodiment 3, wherein said one or more mutations are selected from the group consisting of an insertion, a deletion, an inversion, a substitution, and a combination thereof.
12. The modified tobacco plant of embodiment 4, wherein said one or more transgenes comprise an axillary meristem-specific promoter.
13. The modified tobacco plant of embodiment 12, wherein said axillary meristem-specific promoter is functional or preferentially functional in an L1 layer, an L2 layer, an L3 region, or a combination thereof.
14. The modified tobacco plant of embodiment 12, wherein said axillary meristem-specific promoter is functional or preferentially functional in a central zone, a peripheral zone, a rib zone, or a combination thereof of an axillary meristem.
15. The modified tobacco plant of embodiment 11, wherein said one or more mutations is introduced via a system selected from the group consisting of chemical mutagenesis, irradiation mutagenesis, transposon mutagenesis, *Agrobacterium*-mediated transformation, a meganuclease, a zinc-finger nuclease (ZFN), a transcription activator-like effector nuclease (TALEN), a clustered regularly-interspaced short palindromic repeats (CRISPR)/Cas9 system, a CRISPR/Cpf1 system, and a combination thereof.
16. The modified tobacco plant of embodiment 11, wherein said one or more mutations are in a gene encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 58, 60, 62, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, 255.
17. The modified tobacco plant of embodiment 3 or 4, wherein said modified tobacco plant has a similar or higher leaf yield compared to said control tobacco plant when grown under comparable conditions.
18. The modified tobacco plant of embodiment 17, wherein said higher leaf yield is at least 1%, 2.5%, 5%, 10%, 15%, or at least 20% higher.
19. The modified tobacco plant of embodiment 3 or 4, wherein said modified tobacco plant has a similar plant height compared to said control tobacco plant when grown under comparable conditions.

20. The modified tobacco plant of embodiment 19, wherein said similar plant height is within 1%, 5%, 10%, 20%, or 25%.
21. The modified tobacco plant of embodiment 3 or 4, wherein said modified tobacco plant has a similar cured leaf chemistry profile compared to said control tobacco plant when grown under comparable conditions.
22. The modified tobacco plant of embodiment 3 or 4, wherein said modified tobacco plant produces cured leaves that have a similar or higher USDA grade index value compared to cured leaves from said control tobacco plant when grown under comparable conditions.
23. The modified tobacco plant of embodiment 1, wherein said reduced topping-induced suckers comprises fewer total suckers, smaller suckers, or both when compared to topping-induced suckers of a control tobacco plant when grown under comparable conditions.
24. The modified tobacco plant of embodiment 23, wherein said smaller suckers comprise reduced mass, reduced length, or both when compared to topping-induced suckers of a control tobacco plant when grown under comparable conditions.
25. The modified tobacco plant of embodiment 3 or 4, wherein said modified tobacco plant requires reduced management for controlling suckers compared to a control tobacco plant when grown under comparable conditions.
26. The modified tobacco plant of embodiment 25, wherein said reduced management comprises reduced manual removal frequency to control suckers, reduced chemical application frequency to control suckers, reduced quantities of chemical application to control suckers, or any combination thereof compared to a control tobacco plant when grown under comparable conditions.
27. The modified tobacco plant of embodiment 26, wherein said reduced manual removal frequency to control suckers comprises less than 10%, less than 20%, less than 30%, less than 40%, less than 50%, less than 60%, less than 70%, less than 75%, less than 80%, less than 85%, less than 90%, or less than 95% as frequently as a control plant when grown under comparable conditions.
28. The modified tobacco plant of embodiment 3 or 4, wherein said modified tobacco plant is homozygous for said one or more transgenes or said one or more mutations.
29. The modified tobacco plant of embodiment 3 or 4, wherein said modified tobacco plant is hemizygous for said one or more transgenes or said one or more mutations.
30. The modified tobacco plant of embodiment 3 or 4, wherein said modified tobacco plant is heterozygous for said one or more transgenes or said one or more mutations.
31. The modified tobacco plant of embodiment 1, wherein said plant is selected from the group consisting of a flue-cured variety, a bright variety, a Burley variety, a Virginia variety, a Maryland variety, a dark variety, an Oriental variety, and a Turkish variety.
32. The modified tobacco plant of embodiment 1, wherein said tobacco plant is selected from the group consisting a BU 64 plant, a CC 101 plant, a CC 200 plant, a CC 13 plant, a CC 27 plant, a CC 33 plant, a CC 35 plant, a CC 37 plant, a CC 65 plant, a CC 67 plant, a CC 301 plant, a CC 400 plant, a CC 500 plant, CC 600 plant, a CC 700 plant, a CC 800 plant, a CC 900 plant, a CC 1063 plant, a Coker 176 plant, a Coker 319 plant, a Coker 371 Gold plant, a Coker 48 plant, a CU 263 plant, a DF911 plant, a Galpao plant, a GL 26H plant, a GL 338 plant, a GL 350 plant, a GL 395 plant, a GL 600 plant, a GL 737 plant, a GL 939 plant, a GL 973 plant, a GF 157 plant, a GF 318 plant, an RJR 901 plant, an HB 04P plant, a K 149 plant, a K 326 plant, a K 346 plant, a K 358 plant, a K394 plant, a K 399 plant, a K 730 plant, an NC 196 plant, an NC 37NF plant, an NC 471 plant, an NC 55 plant, an NC 92 plant, an NC2326 plant, an NC 95 plant, an NC 925 plant, a PVH 1118 plant, a PVH 1452 plant, a PVH 2110 plant, a PVH 2254 plant, a PVH 2275 plant, a VA 116 plant, a VA 119 plant, a KDH 959 plant, a KT 200 plant, a KT204LC plant, a KY 10 plant, a KY 14 plant, a KY 160 plant, a KY 17 plant, a KY 171 plant, a KY 907 plant, a KY 907LC plant, a KTY14×L8 LC plant, a Little Crittenden plant, a McNair 373 plant, a McNair 944 plant, a male sterile KY 14×L8 plant, a Narrow Leaf Madole plant, a MS KY171 plant, a Narrow Leaf Madole (phph) plant, a MS Narrow Leaf Madole plant, a MS TND950 plant, a PD 7302LC plant, a PD 7305LC plant, a PD 7309LC plant, a PD 7312LC plant, a PD 7318LC plant, a PD 7319LC plant, a MSTKS 2002 plant, a TKF 2002 plant, a TKF 6400 plant, a TKF 4028 plant, a TKF 4024 plant, a KT206LC plant, a KT209LC plant, a KT210LC plant, a KT212LC plant, an NC 100 plant, an NC 102 plant, an NC 2000 plant, an NC 291 plant, an NC 297 plant, an NC 299 plant, an NC 3 plant, an NC 4 plant, an NC 5 plant, an NC 6 plant, an NC7 plant, an NC 606 plant, an NC 71 plant, an NC 72 plant, an NC 810 plant, an NC BH 129 plant, an NC 2002 plant, a Neal Smith Madole plant, an OXFORD 207 plant, a 'Perique' plant, a PVH03 plant, a PVH09 plant, a PVH19 plant, a PVH50 plant, a PVH51 plant, an R 610 plant, an R 630 plant, an R 7-11 plant, an R 7-12 plant, an RG 17 plant, an RG 81 plant, an RG H51 plant, an RGH 4 plant, an RGH 51 plant, an RS 1410 plant, a Speight 168 plant, a Speight 172 plant, a Speight 179 plant, a Speight 210 plant, a Speight 220 plant, a Speight 225 plant, a Speight 227 plant, a Speight 234 plant, a Speight G-28 plant, a Speight G-70 plant, a Speight H-6 plant, a Speight H20 plant, a Speight NF3 plant, a TI 1406 plant, a TI 1269 plant, a TN 86 plant, a TN86LC plant, a TN 90 plant, a TN90LC plant, a TN 97 plant, a TN97LC plant, a TN D94 plant, a TN D950 plant, a TR (Tom Rosson) Madole plant, a VA 309 plant, and a VA 359 plant.
33. The modified tobacco plant of embodiment 1, wherein said modified tobacco plant is a hybrid.
34. The modified tobacco plant of embodiment 1, wherein said modified tobacco plant is male sterile or cytoplasmically male sterile (CMS).
35. The modified tobacco plant of embodiment 1, wherein said modified tobacco plant is female sterile.
36. A tobacco leaf of the modified tobacco plant of embodiment 1.
37. The tobacco leaf of embodiment 35, wherein said tobacco leaf is a cured tobacco leaf.
38. The tobacco leaf of embodiment 36, wherein said cured tobacco leaf is air-cured, fire-cured, sun-cured, or flue-cured.
39. A tobacco product comprising cured tobacco material from the modified tobacco plant of embodiment 1.
40. The tobacco product of embodiment 39, wherein said tobacco product is selected from the group consisting of a cigarette, a kretek, a bidi cigarette, a cigar, a cigarillo, a non-ventilated cigarette, a vented recess filter cigarette, pipe tobacco, snuff, chewing tobacco, moist smokeless tobacco, fine cut chewing tobacco, long cut chewing tobacco, pouched chewing tobacco product, gum, a tablet, a lozenge, and a dissolving strip.

41. A seed giving rise to the modified tobacco plant of embodiment 1.

42. A method comprising preparing a tobacco product using a cured tobacco leaf from the modified tobacco plant of embodiment 1.

43. A modified tobacco plant, wherein said modified tobacco plant exhibits:
   a. inhibited or eliminated axillary meristem growth;
   b. inhibited or eliminated axillary meristem maintenance; or
   c. a combination thereof compared to a control tobacco plant of the same variety when grown under comparable conditions.

44. A plant or seed comprising a recombinant polynucleotide, wherein said recombinant polynucleotide comprises:
   a. a promoter that is functional in an L1 layer, an L2 layer, an L3 region, a rib zone, a central zone, a peripheral zone, or any combination thereof, which is operably linked to
   b. a structural nucleic acid molecule comprising a nucleic acid sequence, wherein said nucleic acid sequence encodes a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 58, 60, 62, 68, 72, 74, 76, 78, 80, 82, 161-185, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, 255.

45. The plant or seed of embodiment 43, wherein said promoter comprises a nucleic acid sequence having at least 90% sequence identity to a polynucleotide selected from the group consisting of SEQ ID NOs: 113-118, 148-160, 204 and fragments thereof.

46. The plant or seed of embodiment 43, wherein said plant or seed is a tobacco plant or seed.

47. A recombinant DNA construct comprising:
   a. a promoter that is functional in an L1 layer, an L2 layer, an L3 region, a rib zone, a central zone, a peripheral zone, or a combination thereof; and
   b. a heterologous and operably linked nucleic acid sequence, wherein said nucleic acid sequence encodes a non-coding RNA or a polypeptide.

48. The recombinant DNA construct of embodiment 46, wherein said promoter comprises a nucleic acid sequence having at least 90% sequence identity to a polynucleotide selected from the group consisting of SEQ ID NOs: 113-118, 148-160, 204 and fragments thereof.

49. A method of reducing or eliminating topping-induced suckers in a tobacco plant, said method comprising transforming a tobacco plant with a recombinant DNA construct comprising a promoter functional in an L1 layer, an L2 layer, an L3 region, a rib zone, a central zone, a peripheral zone, or a combination thereof.

50. The method of embodiment 48, wherein said promoter comprises a nucleic acid sequence having at least 90% sequence identity to a polynucleotide selected from the group consisting of SEQ ID NOs: 113-118, 148-160, 204 and fragments thereof.

51. A method comprising transforming a tobacco plant with a recombinant DNA construct comprising a heterologous promoter that is functional in an L1 layer, an L2 layer, an L3 region, a rib zone, a central zone, a peripheral zone, or a combination thereof, and is operably linked to a polynucleotide that is transcribed into an RNA molecule that suppresses the level of an endogenous gene, and wherein said endogenous gene promotes or is required for axillary meristem growth, axillary meristem maintenance, or both.

52. A method for producing a tobacco plant comprising:
   a. crossing at least one tobacco plant of a first tobacco variety with at least one tobacco plant of a second tobacco variety, wherein said at least one tobacco plant of said first tobacco variety exhibits no or reduced topping-induced suckers compared to a control tobacco plant of the same variety grown under comparable conditions; and
   b. selecting for progeny tobacco plants that exhibit no or reduced topping-induced suckers compared to a control tobacco plant of the same cross grown under comparable conditions.

53. A tobacco plant, or part thereof, comprising a heterologous promoter operably linked to a polynucleotide encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 68, 72, 74, 76, 78, 80, 82, 161-185, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, 255.

54. The tobacco plant, or part thereof, of embodiment 52, wherein said promoter comprises a nucleic acid molecule having at least 90% sequence identity to a polynucleotide selected from the group consisting of SEQ ID NOs: 113-118, 148-160, 204 and fragments thereof.

55. The tobacco plant, or part thereof, of embodiment 52, wherein said polynucleotide has at least 90% sequence identity to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 228, 230, 232, 234, 236, 238, 240, 242, 244, 246, 248, 250, 252, and 254.

56. The tobacco plant, or part thereof, of embodiment 52, wherein said polypeptide comprises at least 15 contiguous amino acid residues identical to said polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 68, 70, 72, 74, 76, 78, 80, 82, 161-185, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, 255.

57. A recombinant DNA construct comprising a heterologous promoter operably linked to a polynucleotide encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 58, 60, 62, 68, 70, 72, 74, 76, 78, 80, 82, 161-185, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, 255.

58. A method of growing a modified tobacco plant comprising planting a modified tobacco seed comprising a heterologous promoter that is operably linked to a polynucleotide encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 58, 60, 62, 68, 70, 72, 74, 76, 78, 80, 82, 161-185, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, 255; and growing said modified tobacco plant from said seed.

59. A method for controlling topping-induced suckers in a plant comprising transforming said plant with a recombinant DNA construct, wherein said recombinant DNA construct comprises a promoter that is operably linked to a polynucleotide encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 58, 60, 62, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, 255.

60. A tobacco plant, or part thereof, comprising a heterologous promoter operably linked to a polynucleotide that encodes a non-coding RNA molecule, wherein said non-coding RNA molecule is capable of binding to an RNA encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, 255, and wherein said non-coding RNA molecule suppresses the expression of said polypeptide.

61. The tobacco plant, or part thereof, of embodiment 59, wherein said promoter comprises a nucleic acid sequence having at least 90% sequence identity to a polynucleotide selected from the group consisting of SEQ ID NOs: 113-118, 148-160, 204 and fragments thereof.

62. The tobacco plant, or part thereof, of embodiment 59, wherein said polynucleotide has at least 90% sequence identity to a polynucleotide selected from the group consisting of SEQ ID NOs: 83-101.

63. The tobacco plant, or part thereof, of embodiment 59, wherein said polynucleotide comprises at least 18, 19, 20, 21, 22, 23, 24, 25, 26, 27, 28, 29, 30, or more than 30 contiguous nucleotides identical to a polynucleotide selected from the group consisting of SEQ ID NOs: 83-101.

64. A recombinant DNA construct comprising a heterologous axillary meristem-specific promoter operably linked to a polynucleotide that encodes a non-coding RNA molecule, wherein said non-coding RNA molecule is capable of binding to an RNA encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, 255, and wherein said non-coding RNA molecule suppresses the expression of said polypeptide.

65. A method of growing a modified tobacco plant comprising planting a modified tobacco seed comprising a recombinant DNA construct comprising a heterologous promoter that is functional in an L1 layer, an L2 layer, an L3 region, a rib zone, a central zone, a peripheral zone, or a combination thereof, and is operably linked to a polynucleotide that encodes a non-coding RNA molecule, wherein said non-coding RNA molecule is capable of binding to an RNA encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, 255, and wherein said non-coding RNA molecule suppresses the expression of said polypeptide; and growing said modified tobacco plant from said seed.

66. A method for controlling topping-induced suckers in a plant comprising transforming said plant with a recombinant DNA construct, wherein said recombinant DNA construct comprises a heterologous promoter that is functional in an L1 layer, an L2 layer, an L3 region, a rib zone, a central zone, a peripheral zone, or a combination thereof, and wherein said promoter is operably linked to a polynucleotide that encodes a non-coding RNA molecule, wherein said non-coding RNA molecule is capable of binding to an RNA encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, 255, and wherein said non-coding RNA molecule suppresses the expression of said polypeptide.

67. A bacterial cell comprising the recombinant DNA construct of any one of embodiments 46, 56, or 63.

68. A plant genome comprising the recombinant DNA construct of any one of embodiments 46, 56, or 63.

69. A method for manufacturing a modified seed, said method comprising:
   a. introducing the recombinant DNA construct from any one of embodiments 46, 56, or 63 into a plant cell;
   b. screening a population of plant cells for said recombinant DNA construct;
   c. selecting one or more plant cells from said population;
   d. generating one or more modified plants from said one or more plant cells; and
   e. collecting one or more modified seeds from said one or more modified plants.

70. A method of producing a modified tobacco plant to reduce or eliminate suckers, said method comprising introducing one or more mutations in one or more tobacco genome loci.

71. The method of embodiment 69, wherein said one or more mutations are introduced via a system selected from the group consisting of chemical mutagenesis, irradiation mutagenesis, transposon mutagenesis, *Agrobacterium*-mediated transformation, a meganuclease, a ZFN, a TALEN, a CRISPR/Cas9 system, a CRISPR/Cpf1 system, and a combination thereof.

72. A recombinant DNA construct comprising:
   a. a promoter that is functional in an L1 layer, an L2 layer, an L3 region, a rib zone, a central zone, a peripheral zone, or a combination thereof; and
   b. a heterologous and operably linked to an artificial microRNA, wherein said artificial miRNA has at least 70% identity to an RNA encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, 255, and wherein said artificial microRNA suppresses the expression of said polypeptide.

73. A plant or seed comprising a recombinant polynucleotide, wherein said recombinant polynucleotide comprises:
   a. a promoter that is functional in an L1 layer, an L2 layer, an L3 region, a rib zone, a central zone, a peripheral zone, or any combination thereof, which is operably linked to
   b. a structural nucleic acid molecule comprising a nucleic acid sequence, wherein said nucleic acid sequence encodes an auxin biosynthesis protein or an auxin transport protein.

74. A recombinant DNA construct comprising:
   a. a promoter that is functional in an L1 layer, an L2 layer, an L3 region, a rib zone, a central zone, a peripheral zone, or any combination thereof; and
   b. a heterologous and operably linked nucleic acid sequence, wherein said nucleic acid sequence encodes an auxin biosynthesis protein or an auxin transport protein.

75. A recombinant DNA construct comprising a heterologous axillary meristem-specific promoter operably linked to a polynucleotide that encodes an auxin biosynthesis protein or an auxin transport protein.

76. The recombinant DNA construct of embodiment 74, wherein said auxin biosynthesis protein or auxin transport protein is encoded by a polynucleotide encoding a polypeptide having at least 70% sequence identity to a polypeptide selected from the group consisting of SEQ ID NOs: 235, 237, 239, 241, 243, 245, 247, 249, 251, 253, and 255.

77. A tobacco plant, or part thereof, comprising a heterologous promoter having at least 90% sequence identity to a polynucleotide selected from the group consisting of SEQ ID NOs: 113-118, 148-160, 204, and fragments thereof operably linked to a polynucleotide encoding an auxin biosynthesis protein or an auxin transport protein.

78. The tobacco plant, or part thereof, of embodiment 76, wherein said auxin biosynthesis protein or auxin transport protein is encoded by a polynucleotide encoding a polypeptide having at least 70% sequence identity to a polypeptide selected from the group consisting of SEQ ID NOs: 235, 237, 239, 241, 243, 245, 247, 249, 251, 253, and 255.

79. A method for controlling topping-induced suckers in a plant comprising transforming said plant with a recombinant DNA construct, wherein said recombinant DNA construct comprises a promoter that is operably linked to a polynucleotide encoding an auxin biosynthesis protein or an auxin transport protein.

80. The method of embodiment 78, wherein said auxin biosynthesis protein or auxin transport protein is encoded by a polynucleotide encoding a polypeptide having at least 70% sequence identity to a polypeptide selected from the group consisting of SEQ ID NOs: 235, 237, 239, 241, 243, 245, 247, 249, 251, 253, and 255.

81. The modified tobacco plant of embodiment 23, wherein said fewer total suckers comprises at least 10%, at least 15%, at least 20%, at least 25%, at least 30%, at least 35%, at least 40%, at least 45%, at least 50%, at least 60%, at least 70%, at least 80%, at least 90%, or at least 95% fewer total suckers compared to an unmodified control tobacco plant grown under comparable conditions 82. The modified tobacco plant of embodiment 24, wherein said reduced mass comprises at least 10%, at least 15%, at least 20%, at least 25%, at least 30%, at least 35%, at least 40%, at least 45%, at least 50%, at least 60%, at least 70%, at least 80%, at least 90%, or at least 95% reduced mass compared to the mass of suckers of an unmodified control tobacco plant grown under comparable conditions 83. The modified tobacco plant of embodiment 24, wherein said reduced length comprises at least 10%, at least 15%, at least 20%, at least 25%, at least 30%, at least 35%, at least 40%, at least 45%, at least 50%, at least 60%, at least 70%, at least 80%, at least 90%, or at least 95% reduced length compared to the length of suckers of an unmodified control tobacco plant grown under comparable conditions Having now generally described the disclosure, the same will be more readily understood through reference to the following examples that are provided by way of illustration, and are not intended to be limiting of the present disclosure, unless specified.

EXAMPLES

Example 1. Identification of Topping-Inducible Genes

RNA samples from 4 week old TN90 tobacco plants are obtained from 10 tissue types (axillary buds before topping; axillary buds 2 hours after topping; axillary buds 6 hours after topping; axillary buds 24 hours after topping; axillary buds 72 hours after topping; roots before topping; roots 24 hours after topping; roots 72 hours after topping; young leaf at the time of topping; and shoot apical meristem). The resulting RNA samples (three independently collected samples for each tissue type) are used as starting material for Illumina 1×100 bp sequencing.

Illumina reads are mapped and used to identify a list of candidate genes exhibiting high axillary bud expression. Expression of candidate genes is confirmed using RT-PCR. See U.S. patent application Ser. No. 14/875,928, filed on Oct. 6, 2015, published on Sep. 29, 2016 as US 2016/0281100, which is herein incorporated by reference in its entirety. After confirming candidate genes are differentially expressed in axillary buds, full-length candidate genes are cloned using gene specific primers designed from predicted full-length cDNA sequences (Table 2A). Normalized Illumina read counts for selected loci are provided in Table 2B.

TABLE 2A

Selected full-length candidate tobacco genes exhibiting differential expression in axillary buds

| SEQ ID NO (DNA/peptide) | Coding Sequence | Polynucleotide Length (nucleotides) | Polypeptide Length (amino acids) | Annotation |
|---|---|---|---|---|
| 1/2 | Full length confirmed | 987 | 328 | Transcription factor CYCLOIDEA-like |
| 3/4 | Full length confirmed | 318 | 105 | Flower-specific gamma-thionin |
| 5/6 | Full length confirmed | 1797 | 598 | Polyphenoloxidase |
| 7/8 | Full length confirmed | 1392 | 463 | UDP-glucose:glucosyltransferase |
| 9/10 | Full length confirmed | 405 | 134 | Tumor-related protein |
| 11/12 | Full length confirmed | 630 | 209 | Hypothetical protein |
| 13/14 | Full length confirmed | 1143 | 380 | TCP1 protein-like gene |
| 15/16 | Full length confirmed | 915 | 304 | Chlorophyllase-2 |
| 17/18 | Full length confirmed | 1353 | 450 | AP2/ERF domain-containing transcription factor |
| 19/20 | Full length confirmed | 732 | 243 | Putative miraculin |
| 186/187 | Pseudo gene | 2340 | 87 | (E,E)-geranyllinalool synthase |
| 21/22 | Full length confirmed | 471 | 156 | Oleosin |
| 23/24 | Full length confirmed | 1437 | 478 | ACC synthase |
| 25/26 | Full length confirmed | 645 | 214 | LOB domain-containing protein 18-like |
| 27/28 | Full length confirmed | 2205 | 734 | Vicilin-like antimicrobial peptides cupin super family |
| 29/30 | Full length confirmed | 1302 | 433 | Abscisic acid insensitive |
| 31/32 | Full length confirmed | 1266 | 421 | Seipin-like |
| 33/34 | Full length confirmed | 597 | 198 | Transcription factor CYCLOIDEA-like |
| 35/36 | Full length confirmed | 1038 | 345 | Transcription factor DICHOTOMA-like |
| 37/38 | Full length confirmed | 1014 | 337 | Transcription factor CYCLOIDEA-like |

TABLE 2B

Normalized Illumina read counts for selected candidate genes.

| | Axillary Buds | Axillary Buds After Topping | | | | Roots | Roots After Topping | | Shoot | |
|---|---|---|---|---|---|---|---|---|---|---|
| SEQ ID NO (DNA/Peptide) | Before Topping | 2 hrs | 6 hrs | 24 hrs | 72 hrs | Before Topping | 24 hrs | 72 hrs | Apical Meristem | Young Leaf |
| 1/2 | 1,072 | 998 | 1,346 | 663 | 652 | 7 | 9 | 11 | 180 | 47 |
| 3/4 | 1,387 | 927 | 3,527 | 44,790 | 23,270 | 108 | 90 | 128 | 8,913 | 72 |
| 5/6 | 763 | 1,132 | 1,852 | 5,559 | 2,644 | 110 | 156 | 80 | 513 | 7 |
| 9/10 | 2,342 | 2,357 | 2,992 | 3,143 | 2,190 | 38 | 28 | 27 | 26 | 103 |
| 11/12 | 47 | 29 | 54 | 18 | 17 | 1 | 0 | 0 | 23 | 1 |
| 13/14 | 128 | 131 | 187 | 69 | 54 | 0 | 1 | 1 | 13 | 0 |
| 15/16 | 124 | 308 | 1,619 | 337 | 136 | 217 | 143 | 160 | 88 | 234 |
| 17/18 | 3 | 162 | 186 | 9 | 9 | 22 | 22 | 29 | 6 | 2 |
| 19/20 | 41 | 98 | 334 | 136 | 101 | 1 | 0 | 0 | 50 | 0 |
| 186/187 | 1,479 | 1,486 | 4,216 | 16,176 | 12,228 | 46 | 36 | 33 | 2,144 | 839 |
| 21/22 | 52 | 27 | 81 | 13 | 9 | 2 | 1 | 3 | 5 | 1 |
| 23/24 | 152 | 114 | 135 | 46 | 45 | 2 | 2 | 2 | 1 | 0 |
| 25/26 | 60 | 34 | 22 | 17 | 13 | 2 | 4 | 1 | 30 | 1 |
| 29/30 | 624 | 583 | 1,279 | 300 | 215 | 14 | 9 | 18 | 71 | 9 |
| 31/32 | 176 | 121 | 253 | 95 | 70 | 7 | 1 | 1 | 69 | 27 |
| 33/34 | 268 | 279 | 410 | 231 | 207 | 1 | 1 | 1 | 22 | 11 |

TABLE 2B-continued

Normalized Illumina read counts for selected candidate genes.

| SEQ ID NO (DNA/Peptide) | Axillary Buds Before Topping | Axillary Buds After Topping 2 hrs | 6 hrs | 24 hrs | 72 hrs | Roots Before Topping | Roots After Topping 24 hrs | 72 hrs | Shoot Apical Meristem | Young Leaf |
|---|---|---|---|---|---|---|---|---|---|---|
| 35/36 | 193 | 241 | 366 | 117 | 123 | 2 | 2 | 2 | 13 | 1 |
| 37/38 | 394 | 353 | 505 | 207 | 204 | 2 | 2 | 1 | 34 | 2 |

Example 2. Development of Modified Plants

An expression vector, p45-2-7 (SEQ ID NO: 112; FIG. 1), is used as a backbone to generate multiple transformation vectors (See Examples 6-10 and 13-20). p45-2-7 contains a CsVMV promoter, a NOS terminator, and a cassette comprising a kanamycin selection marker (NPT II) operably linked to an Actin2 promoter and a NOS terminator. Nucleic acid vectors comprising transgenes of interest are introduced into tobacco leaf discs via *Agrobacterium* transformation. See, for example, Mayo et al., 2006, *Nat Protoc.* 1:1105-11 and Horsch et al., 1985, *Science* 227:1229-1231.

Narrow Leaf Madole (NLM) tobacco plants are grown in Magenta™ GA-7 boxes and leaf discs are cut and placed into Petri plates. *Agrobacterium tumefaciens* cells comprising a transformation vector are collected by centrifuging a 20 mL cell suspension in a 50 mL centrifuge tube at 3500 RPM for 10 minutes. The supernatant is removed and the *Agrobacterium tumefaciens* cell pellet is re-suspended in 40 mL liquid re-suspension medium. Tobacco leaves, avoiding the midrib, are cut into eight 0.6 cm discs with a #15 razor blade and placed upside down in a Petri plate. A thin layer of Murashige & Skoog with B5 vitamins liquid re-suspension medium is added to the Petri plate and the leaf discs are poked uniformly with a fine point needle. About 25 mL of the *Agrobacterium tumefaciens* suspension is added to the Petri plate and the leaf discs are incubated in the suspension for 10 minutes.

Leaf discs are transferred to co-cultivation Petri plates (1/2 MS medium) and discs are placed upside down in contact with filter paper overlaid on the co-cultivation TOM medium (MS medium with 20 g/L sucrose; 1 mg/L indole-3-acetic acid; and 2.5 mg/L 6-benzyl aminopurine (BAP)). The Petri plate is sealed with parafilm prior to incubation in dim light (60-80 mE/ms) with 18 hours on, 6 hours off photoperiods at 24 degrees Celsius for three days. After incubation, leaf discs are transferred to regeneration/selection TOM K medium Petri plates (TOM medium plus 300 mg/L kanamycin). Leaf discs are sub-cultured bi-weekly to fresh TOM K medium in dim light with 18 hours on, 6 hours off photoperiods at 24 degrees Celsius until shoots become excisable. Shoots from leaves are removed with forceps and inserted in MS basal medium with 100 mg/L kanamycin. Shoots on MS basal medium with 100 mg/L kanamycin are incubated at 24 degrees Celsius with 18 hours on, 6 hours off photoperiods with high intensity lighting (6080 mE/ms) to induce rooting.

When plantlets containing both shoots and roots grow large enough (e.g., reach approximately half the height of a Magenta™ GA-7 box), they are transferred to soil. Established seedlings are transferred to a greenhouse for further analysis and to set seed. Evaluation of suckering phenotypes is conducted by growing modified plants (T0, T1, T2, or later generations) and control plants to layby stage. Control plants are either NLM plants that have not been transformed or NLM plants that have been transformed with an empty p45-2-7 vector. Plants that have reached layby stage are manually topped (the shoot apical meristem and surrounding tissue is removed), and axillary bud growth is evaluated at specific time points after topping. Observations are typically performed at the time of topping (i.e., 0 hours), 24 hours (i.e., 1 day) after topping, 7-8 days after topping (i.e., one week), and/or 14-15 days (i.e., two weeks) after topping. Observations comprise qualitatively examining the presence or absence of axillary bud growth and overall plant appearance. Observations also comprise quantitatively measuring the fresh weight of all axillary buds at a specific time point after topping and/or measuring the length of all axillary bud outgrowths at a specific time point after topping.

Example 3. Identification of Tobacco Genes that Function in Sucker Development Transformation vectors and modified tobacco plants are generated to over-express full-length coding sequences from tobacco genes (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, and 69).

Figure 2:
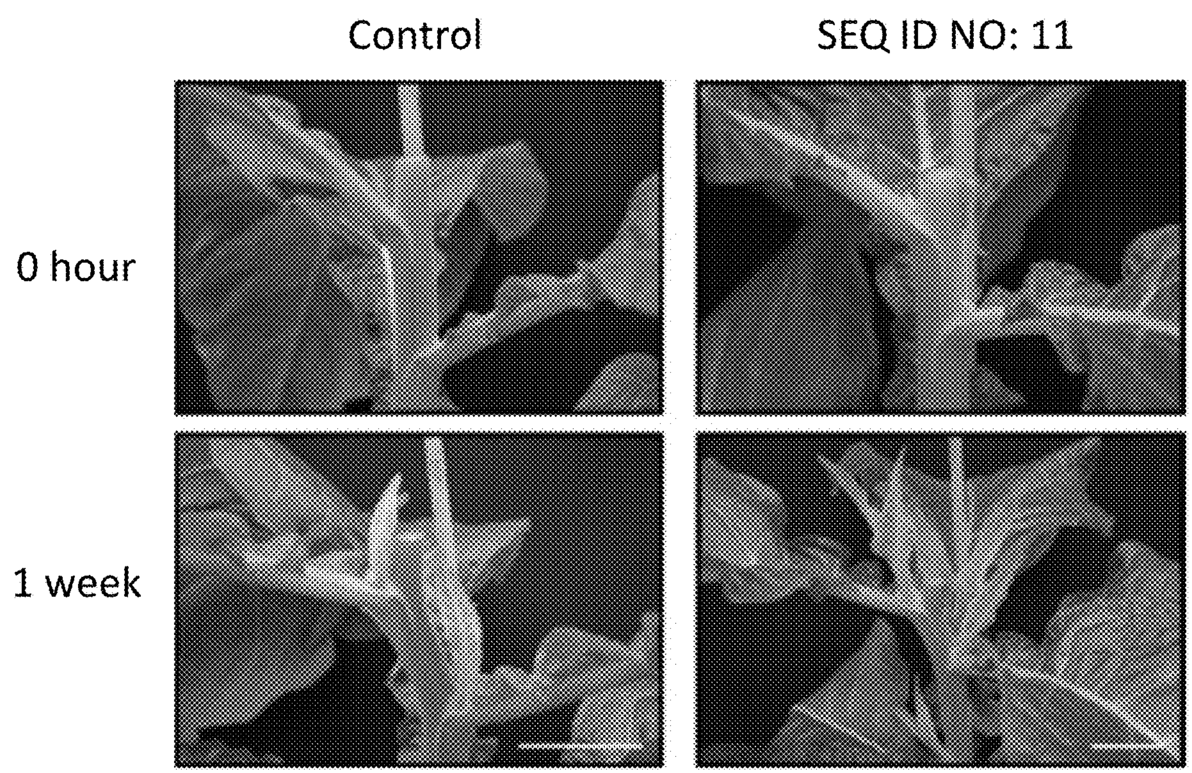
FIG. 2 shows photographs of control tobacco plants and modified tobacco plants that overexpress SEQ ID NO: 11, which encodes a product that promotes sucker growth in tobacco. Plants are shown at the time of topping (0 hour) and one week after topping. Modified plants exhibit increased sucker growth compared to control plants.

As an illustration, SEQ ID NO: 11 is incorporated into a p45-2-7 transformation vector, and modified tobacco plants are generated, according to Example 2. Modified tobacco plants (TO generation) and control tobacco plants are grown to the layby stage, then plants are topped to remove the shoot apical meristem according to Example 2. Sucker growth is evaluated at the time of topping and one week after topping. Overexpression of SEQ ID NO:11 increases bud outgrowth in tobacco, indicating expression of SEQ ID NO: 11 promotes sucker growth (FIG. 2).

Example 4. Expression of Non-Tobacco Origin Genes that Affect Tobacco Sucker Growth Multiple genes have been identified to play a role in sucker growth in non-tobacco species. Transformation vectors and modified tobacco plants are generated to express non-tobacco origin full-length genes (e.g., SEQ ID NOs: 55, 67, 79, and 81). SEQ ID NO: 81 (encoding *Arabidopsis thaliana* BRANCHED1 (BRC1)) is incorporated into a p45-2-7 transformation vector and modified tobacco plants are generated according to Example 2. In *Arabidopsis*, BRC1 is expressed in developing buds, where it functions to arrest bud development. See, for example, González-Grandío et al., 2013, *Plant Cell* 25: 834-850, which is herein incorporated by reference in its entirety.

Figure 3A:
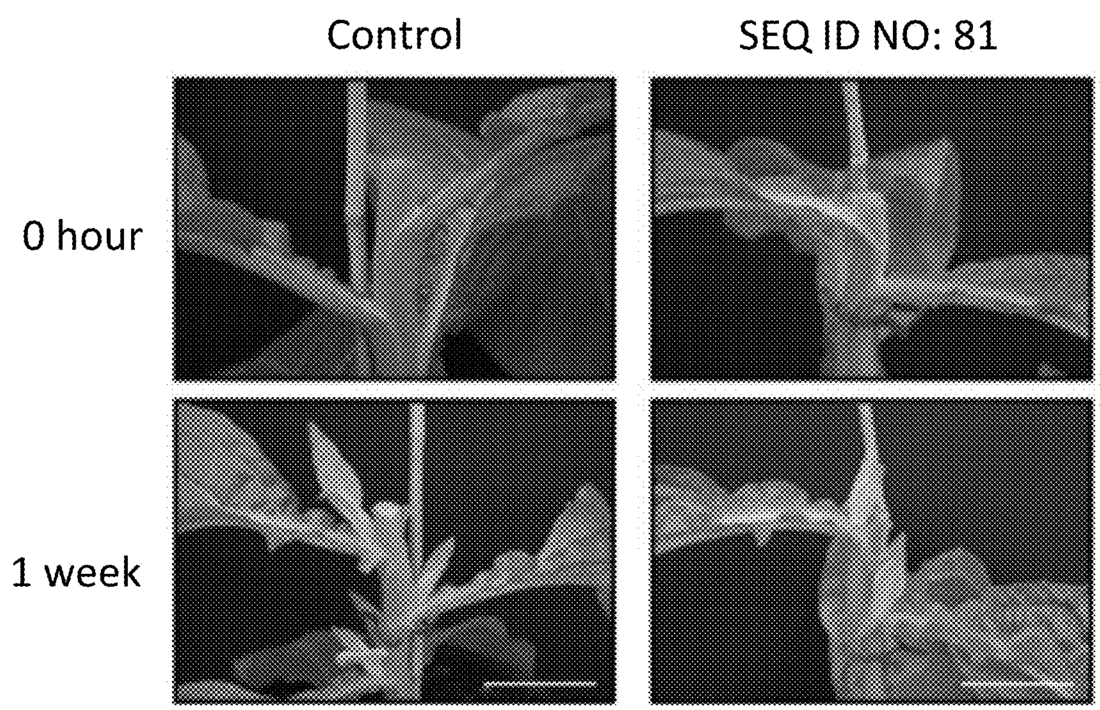
FIG. 3A shows plants at the time of topping (0 hour) and one week after topping. Modified plants exhibit decreased sucker growth compared to control plants.
Figure 3B:
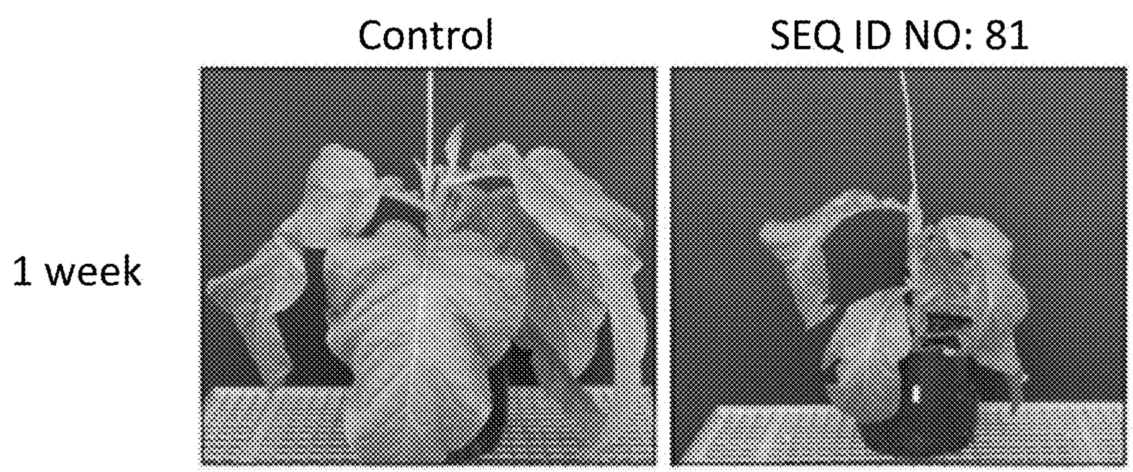
FIG. 3B shows that modified plants overexpressing SEQ ID NO: 81 exhibit stunted growth compared to control plants.

Modified tobacco plants (TO generation) and control tobacco plants are grown to the layby stage, then plants are topped to remove the shoot apical meristem according to Example 2. Sucker growth is evaluated at the time of topping and one week after topping (FIG. 3A). Expression of SEQ ID NO: 81 in tobacco reduces bud outgrowth. These plants also exhibit stunted growth (FIG. 3B).

Example 5. Identification of Native Tobacco Genes that Inhibit Sucker Growth

Transformation vectors and modified tobacco plants are generated to use RNAi to inhibit endogenous tobacco genes (e.g., SEQ ID NOs: 83-107) and identify their role in sucker outgrowth.

Three tobacco genes (SEQ ID NOs: 1, 13, and 35) are identified as TCP-family proteins having homology to *Arabidopsis* BRC1. Transformation vectors and modified tobacco plants are generated according to Example 2; resulting modified tobacco plants are phenotypically evaluated after topping according to Example 2.

Figure 4:
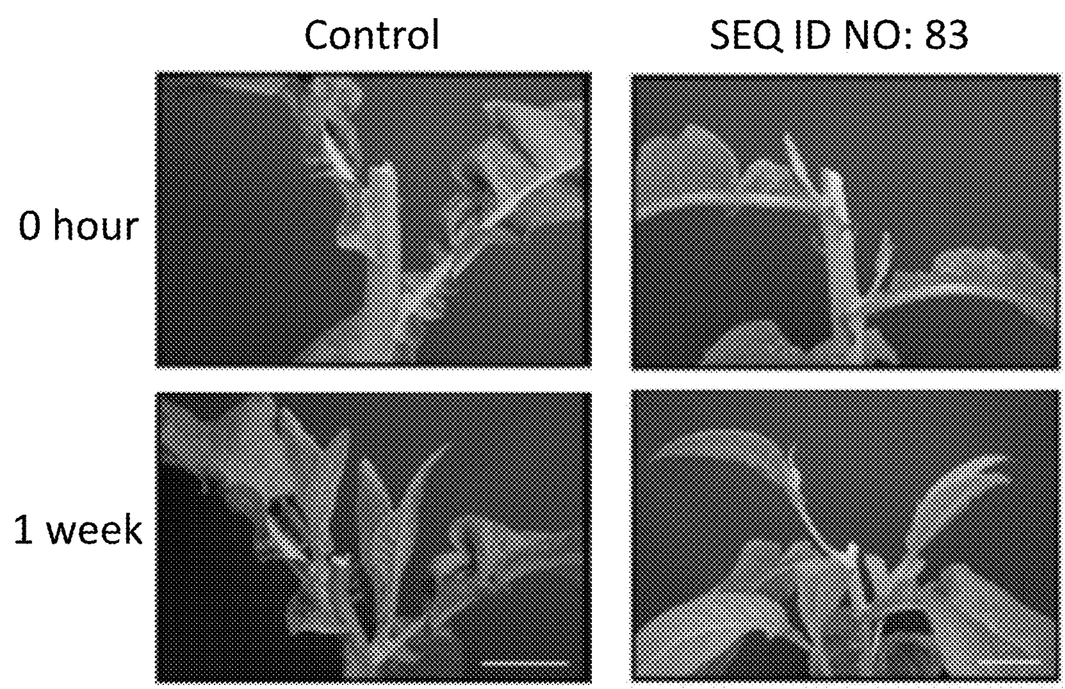
FIG. 4 shows photographs of control tobacco plants and modified tobacco plants that express SEQ ID NO: 83, an RNAi construct that targets SEQ ID NO: 1 for inhibition. Plants are shown at the time of topping (0 hour) and one week after topping. Modified plants exhibit enhanced suckering compared to control plants.
Figure 5A:
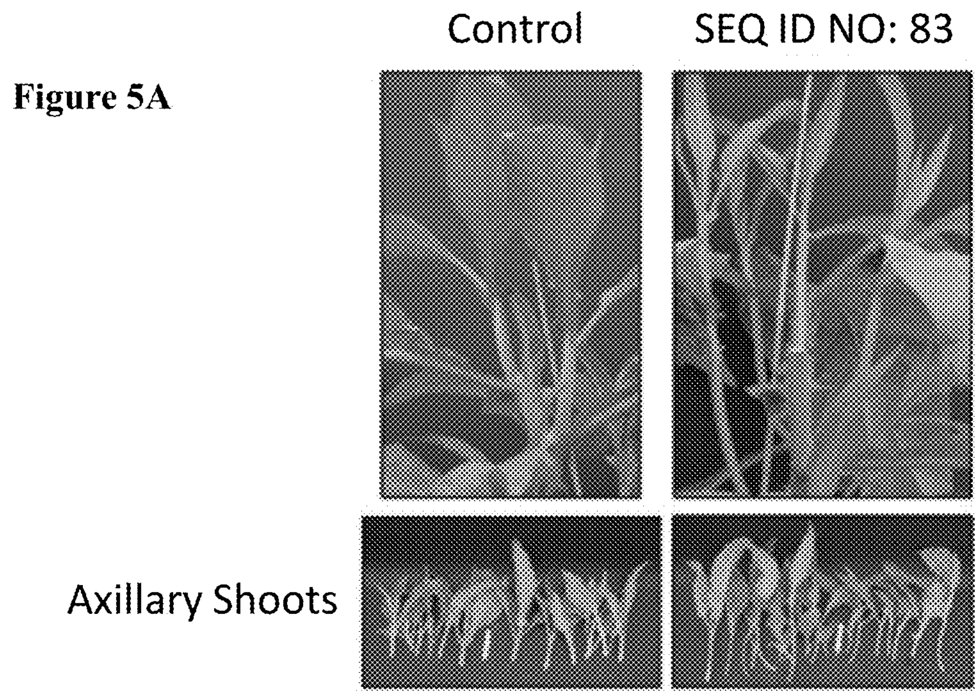
FIG. 5A shows photographs of representative control and modified tobacco plants, as well as all of the axillary shoots from one plant two weeks after topping.
Figure 5B:
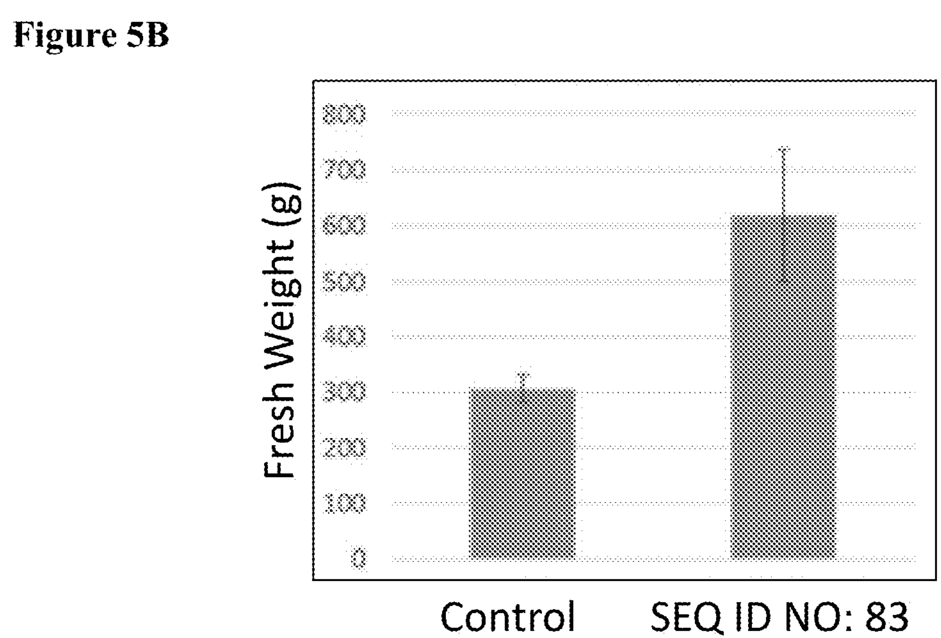
FIG. 5B is a graph displaying the total fresh weight of axillary shoots from control and modified plants two weeks after topping. Modified plants exhibit increased axillary shoot mass compared to control plants.

A first transformation vector comprises SEQ ID NO: 83 inserted into a p45-2-7 backbone for constitutive suppression of native SEQ ID NO: 1 via RNAi, and plants comprising this vector are hereinafter referred to as RNAi_1 plants. RNAi_1 tobacco plants (TO generation) and control tobacco plants are grown to the layby stage, then plants are topped to remove the shoot apical meristem. Sucker growth is evaluated at the time of topping and one week after topping. Bud outgrowth is apparent in RNAi_1 plants prior to topping, and bud outgrowth increases after topping (FIG. 4). RNAi_1 T1 generation plants continue to show increased bud outgrowth (FIGS. 5A and B) at least two weeks after topping. The fresh weight of all axillary shoots two weeks after topping in T1 RNAi_1 plants averages ~600 grams; the fresh weight of all axillary shoots two weeks after topping of control plants is ~300 grams (FIG. 5B). These results indicate SEQ ID NO: 1 functions to inhibit sucker outgrowth in tobacco.

Figure 6:
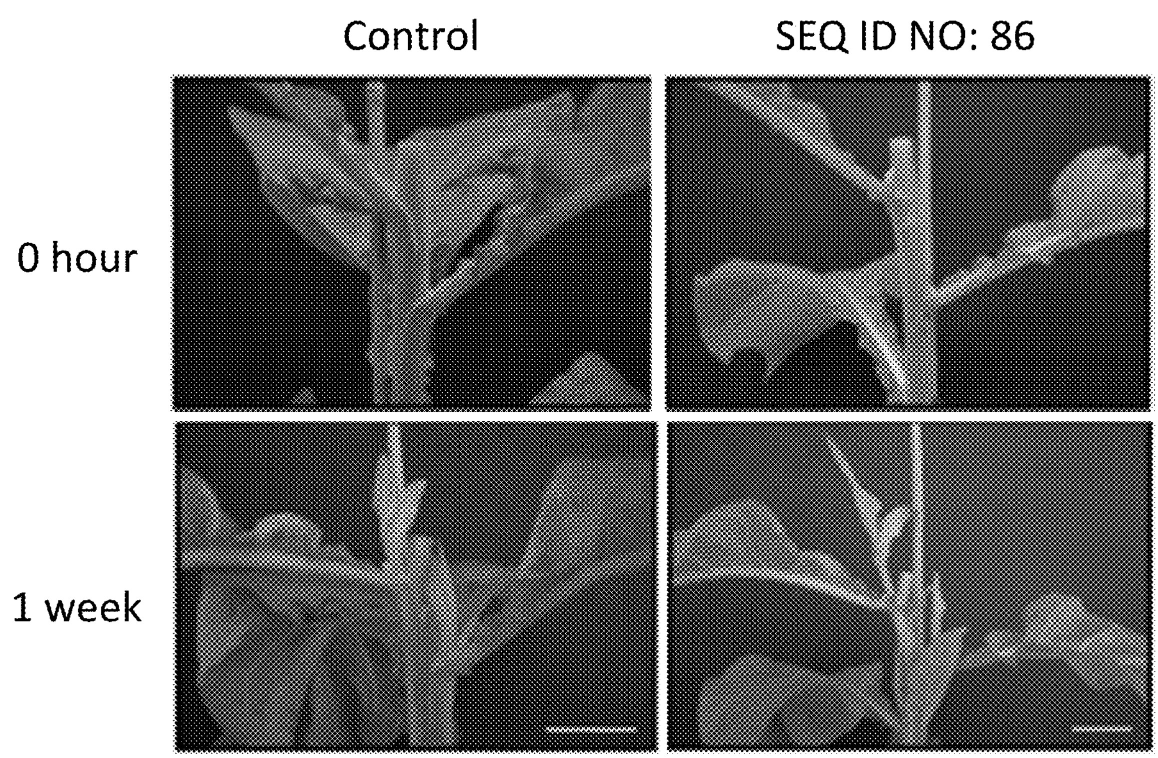
FIG. 6 shows photographs of control tobacco plants and modified tobacco plants that express SEQ ID NO: 86, an RNAi construct that targets SEQ ID NO: 13 for inhibition. Plants are shown at the time of topping (0 hour) and one week after topping. Modified plants exhibit enhanced suckering compared to control plants.
Figure 7:
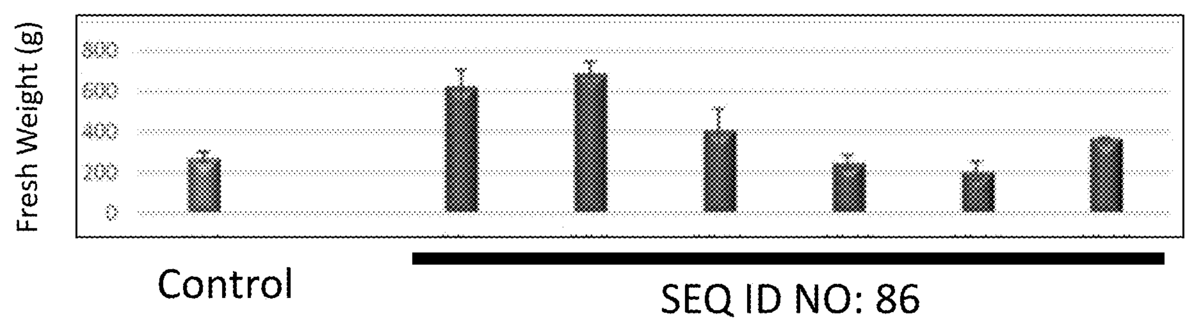
FIG. 7 is a graph displaying the total fresh weight of axillary shoots from control plants and modified tobacco plants that express SEQ ID NO: 86, an RNAi construct that targets SEQ ID NO: 13 for inhibition, two weeks after topping. Data from six independent modified tobacco lines are shown. Modified plants exhibit increased sucker mass compared to control plants.

A second transformation vector comprises SEQ ID NO: 86 inserted into a p45-2-7 backbone. This second transformation vector is designed to repress native SEQ ID NO: 13 via RNAi mechanisms, and plants comprising this vector are hereinafter referred to as RNAi_7 plants. RNAi_7 tobacco plants (TO generation) and control tobacco plants are grown to the layby stage, then plants are topped to remove the shoot apical meristem. Sucker growth is evaluated at the time of topping and one week after topping. Bud outgrowth increases in RNAi_7 plants (FIG. 6). T1 generation RNAi_7 plants continue to show increased bud outgrowth (FIG. 7) at least two weeks after topping. The fresh weight of all axillary shoots two weeks after topping in seven T1 RNAi_7 plant lines average ~600 grams, ~700 grams, ~400 grams, ~250 grams, ~200 grams, and ~375 grams; the fresh weight of all axillary shoots two weeks after topping of control plants is ~300 grams (FIG. 7). These results indicate SEQ ID NO: 13 functions to inhibit sucker outgrowth in tobacco.

Figure 8:
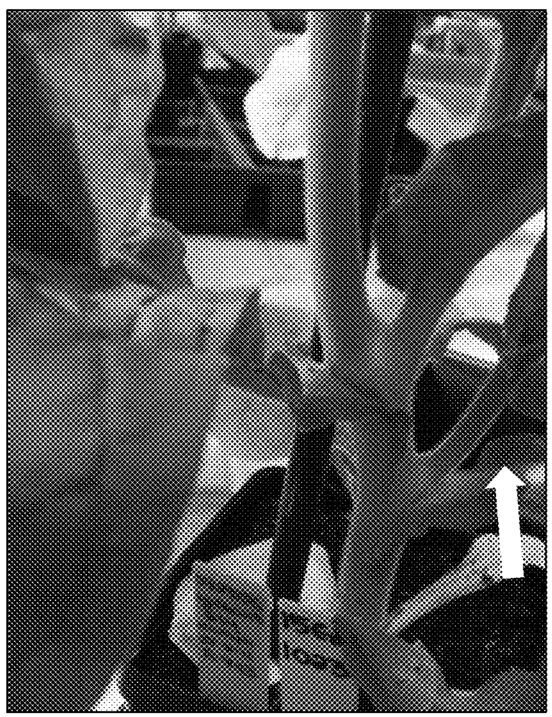
FIG. 8 shows photographs of modified tobacco plants that express SEQ ID NO: 95, an RNAi construct that targets SEQ ID NO: 35 for inhibition. Modified tobacco plants exhibit sucker outgrowth prior to topping. Arrows point to suckers.

A third transformation vector comprises SEQ ID NO: 95 inserted into a p45-2-7 backbone. This third transformation vector is designed to repress native SEQ ID NO: 35 via RNAi mechanisms, and plants comprising this vector are hereinafter referred to as RNAi_18 plants. RNAi_18 plants develop axillary branches at every node prior to topping (FIG. 8). These results indicate SEQ ID NO: 35 functions to inhibit sucker outgrowth in tobacco.

Example 6. Identification of Native Tobacco Genes that Promote Sucker Growth

Some tobacco genes natively function to promote sucker outgrowth. Inhibiting these genes using RNAi constructs decreases sucker outgrowth and positively identifies the genes as promoters of sucker outgrowth in tobacco. Transformation vectors designed to inhibit predicted promoters of sucker outgrowth via RNAi mechanisms are created according to Example 2; modified tobacco plants comprising the transformation vectors are created and phenotypically evaluated according to Example 2.

A transformation vector is created to comprise SEQ ID NO: 101 in a p45-2-7 backbone, which is homologous to a region of CET2, a CENTRORADIALIS (CEN)-like gene from Tobacco (SEQ ID NOs: 108-110). CET genes are not expressed in the shoot apical meristem in tobacco, although CEN is required for shoot apical meristem growth in *Antirrhinum majus*. In tobacco, expression of CEN extends the vegetative phase and delays flowering. See, for example, Amaya et al., 1999, *Plant Cell* 11:1405-1418, which is herein incorporated by reference in its entirety. Plants comprising a transformation vector comprising SEQ ID NO: 101 are hereinafter referred to as RNAi_NtCET2 plants.

Figure 9:
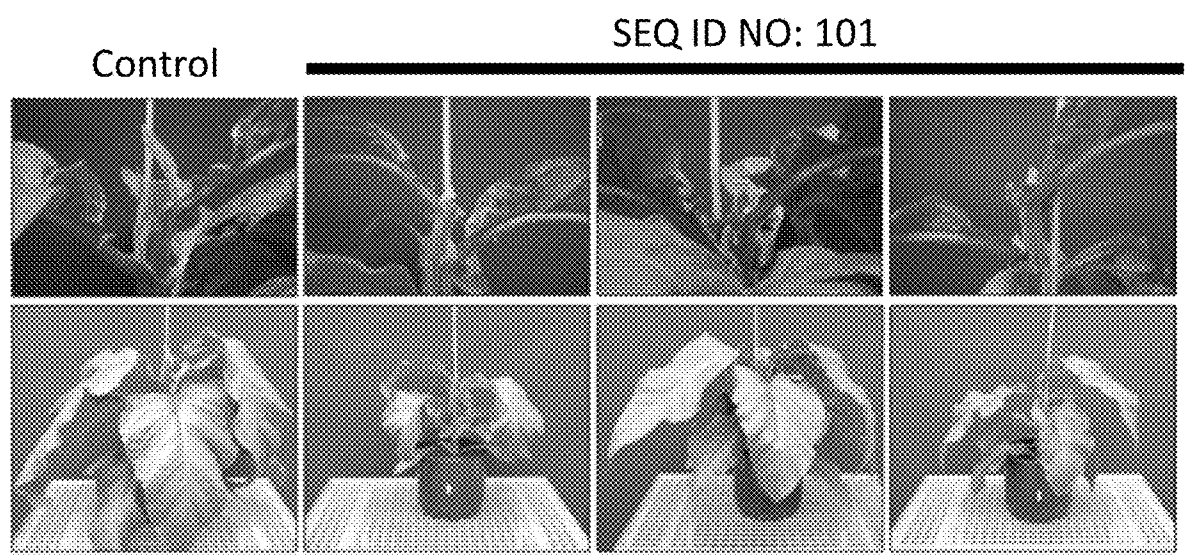
FIG. 9 shows photographs of control tobacco plants and three independent lines of modified tobacco plants that express SEQ ID NO: 101, an RNAi construct that targets tobacco CENTRORADIALIS (SEQ ID NOs: 108-110). Photographs show the apex of a plant (top panel) or an entire plant (lower panel) one week after topping. Sucker growth is reduced in modified plants.

RNAi_NtCET2 plants (TO generation), and control tobacco plants are grown to the layby stage, then plants are topped to remove the shoot apical meristem. Sucker growth is evaluated at the time of topping and one week after topping. Bud outgrowth is reduced in RNAi_NtCET2 plants (FIG. 9), indicating that native NtCET2 promotes sucker outgrowth.

Figure 10:
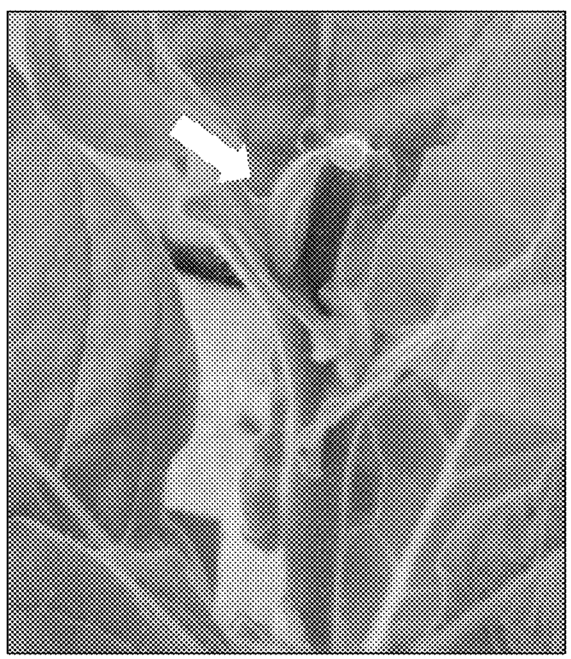
FIG. 10 shows photographs of a control tobacco plant and a modified tobacco plant that expresses SEQ ID NO: 96, an RNAi construct that targets SEQ ID NO: 49 for inhibition. Modified tobacco plants exhibit reduced sucker growth (arrows) compared to control tobacco plants.
Figure 10:
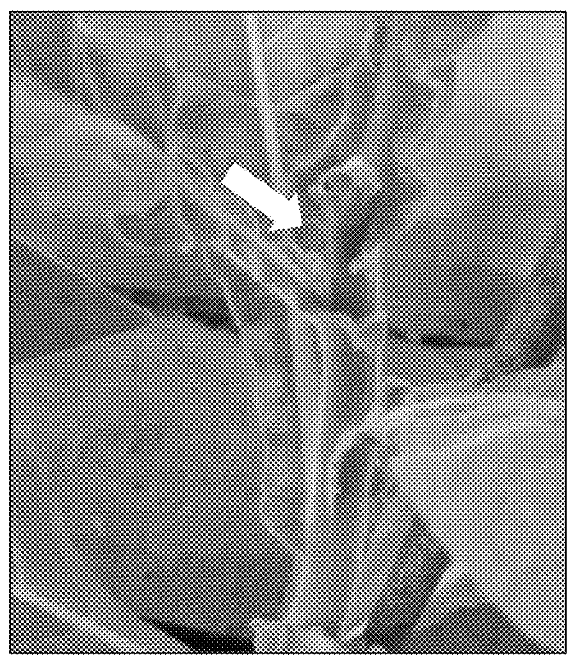

Another transformation vector comprises SEQ ID NO: 96, and plants comprising this vector are hereinafter referred to as RNAi_26 plants. RNAi_26 plants (TO generation) and control tobacco plants are grown to the layby stage, then plants are topped to remove the shoot apical meristem. Sucker growth is evaluated at the time of topping and one week after topping. Bud outgrowth decreases in RNAi_26 plants (FIG. 10), indicating that SEQ ID NO: 49 natively functions to promote sucker outgrowth.

Example 7. Identification of Axillary Bud-Specific Promoters

Expression of SEQ ID NOs: 1, 3, 5, 7, 9, 11, 13, 15, 17, 19, 21, 23, 25, 27, 29, 31, 33, 37, 39, 41, 43, 45, 47, 49, 51, 53, 55, 57, 59, 67, 69, 79, 81, and 83-107 (See Examples 6-8) can be better utilized to reduce or eliminate sucker outgrowth in modified plants if the polynucleotides are expressed in a tissue-dependent manner (e.g., only in the axillary bud). The expression pattern of 28 candidate genes is analyzed, and promoters of the genes having high expression in axillary buds, but low expression in other tissues, are selected (Table 3). Expression patterns of the candidate genes are confirmed by real-time PCR analysis. Six axillary meristem-specific promoters (SEQ ID NOs: 113-118) are cloned by PCR methods from tobacco TN90 genomic DNA using gene-specific primers.

Expression patterns of candidate promoters are analyzed by transformation of tobacco with a chimeric candidate promoter::beta-glucuronidase (GUS) reporter gene within the same plasmid backbone (p45-2-'7) described in Example 2. The chimeric gene is introduced via *Agrobacterium*-mediated transformation into an NLM line. GUS staining is used to identify tissue-specific promoter expression following the method of Crone et al., 2001, *Plant Cell Environ.* 24:869-874.

Briefly, tissue from young seedlings comprising a candidate promoter::GUS transformation construct is placed in cold 90% acetone on ice. When all samples are harvested, samples are placed at room temperature for 20 minutes. Samples are placed back on ice and acetone is removed from the samples. Next, staining buffer (0.2% Triton X-100; 50 mM $NaHPO_4$, pH7.2; 2 mM potassium ferrocyanide) is added to the samples. X-Gluc is added to the staining buffer to a final concentration of 2 mM. Staining buffer is removed from the samples and fresh staining buffer with X-Gluc is added. The samples are then infiltrated under vacuum, on ice, for to 20 minutes. The samples are incubated at 37 degrees Celsius for 2-18 hours before the staining buffer is removed. Samples are washed through an ethanol series (i.e., 10%, 30%, 50%, 70%, 95%) in the dark for 30 minutes per wash. Finally, samples are transferred into 100% ethanol.

Figure 11:
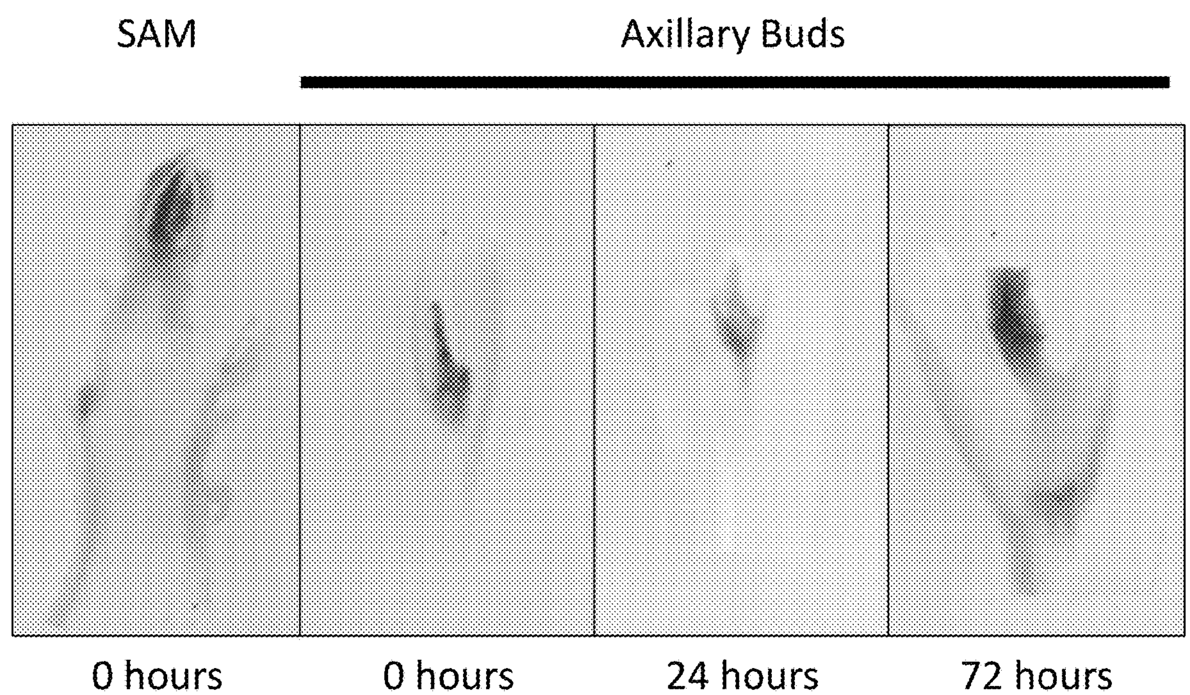
FIG. 11 shows the expression pattern of Promoter P1 (SEQ ID NO: 113) fused to β-glucuronidase (GUS) in a tobacco shoot apical meristem (SAM) at the time of topping (0 hours) and in an axillary bud at 0 hours, 24 hours after topping, and 72 hours after topping. Dark areas of GUS accumulation demonstrate where Promoter P1 is active. Promoter P1 is functional in both shoot apical and axillary buds.
Figure 12:
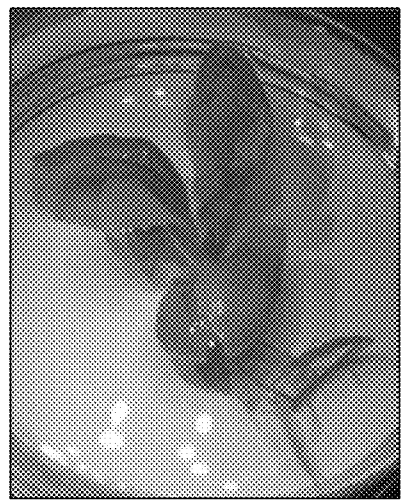
FIG. 12 shows the expression pattern of Promoter P11 (SEQ ID NO: 116) fused to β-glucuronidase (GUS) in a tobacco seedling; a tobacco seedling shoot apical meristem (SAM); a mature SAM at the time of topping (0 hours); and an axillary bud at the time of topping, 3 days after topping, 5 days after topping, and 7 days after topping. Dark areas of GUS accumulation demonstrate where Promoter P11 is active. Promoter P11 is weakly active in axillary buds prior to topping and has higher activity in axillary buds 3 days after topping. Activity of Promoter P11 decreases by 5 and 7 days after topping. Promoter P11 is also active in the SAM prior to topping. No GUS staining is detected in seedlings.
Figure 12:
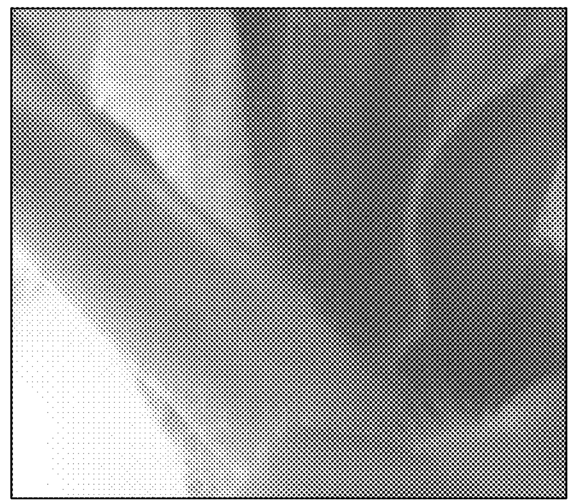
Figure 12:
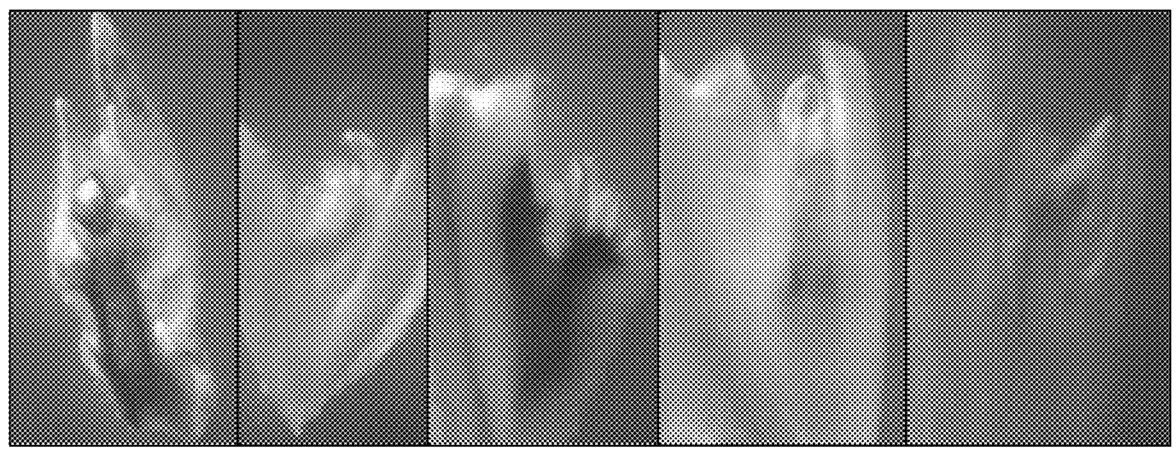

GUS-positive plant tissues are examined with a bright-field microscope (Leica Q500MC; Cambridge, England) at a low magnification and photographed with a digital camera. Results of experiments using three different promoters (SEQ ID NOs: 113, 116, and 117) are shown in FIGS. 11, 12, and 13, respectively. These promoter sequences can be used to drive the expression of a sequence of interest exclusively, or predominantly, within an axillary bud while limiting expression in the rest of the plant.

GUS-positive expression, indicating expression driven by SEQ ID NOs: 113, 116, and 117, is concentrated in axillary buds. Thus, SEQ ID NOs: 113, 116, and 117 are tissue-specific promoters that are active in axillary buds, but not in stem or leaf tissue (FIGS. 11, 12, and 13). The expression of GUS under the direction of SEQ ID NOs: 113 (Promoter P1, hereinafter) and 116 (Promoter P11, hereinafter) decreases after topping, which coincides with the gene expression pattern that is observed for the endogenous genes that are normally regulated by these promoters (FIGS. 11 and 12). Promoter P1 and Promoter P11 are also functional in the tobacco shoot apical meristem. (FIGS. 11 and 12).

Figure 13A:
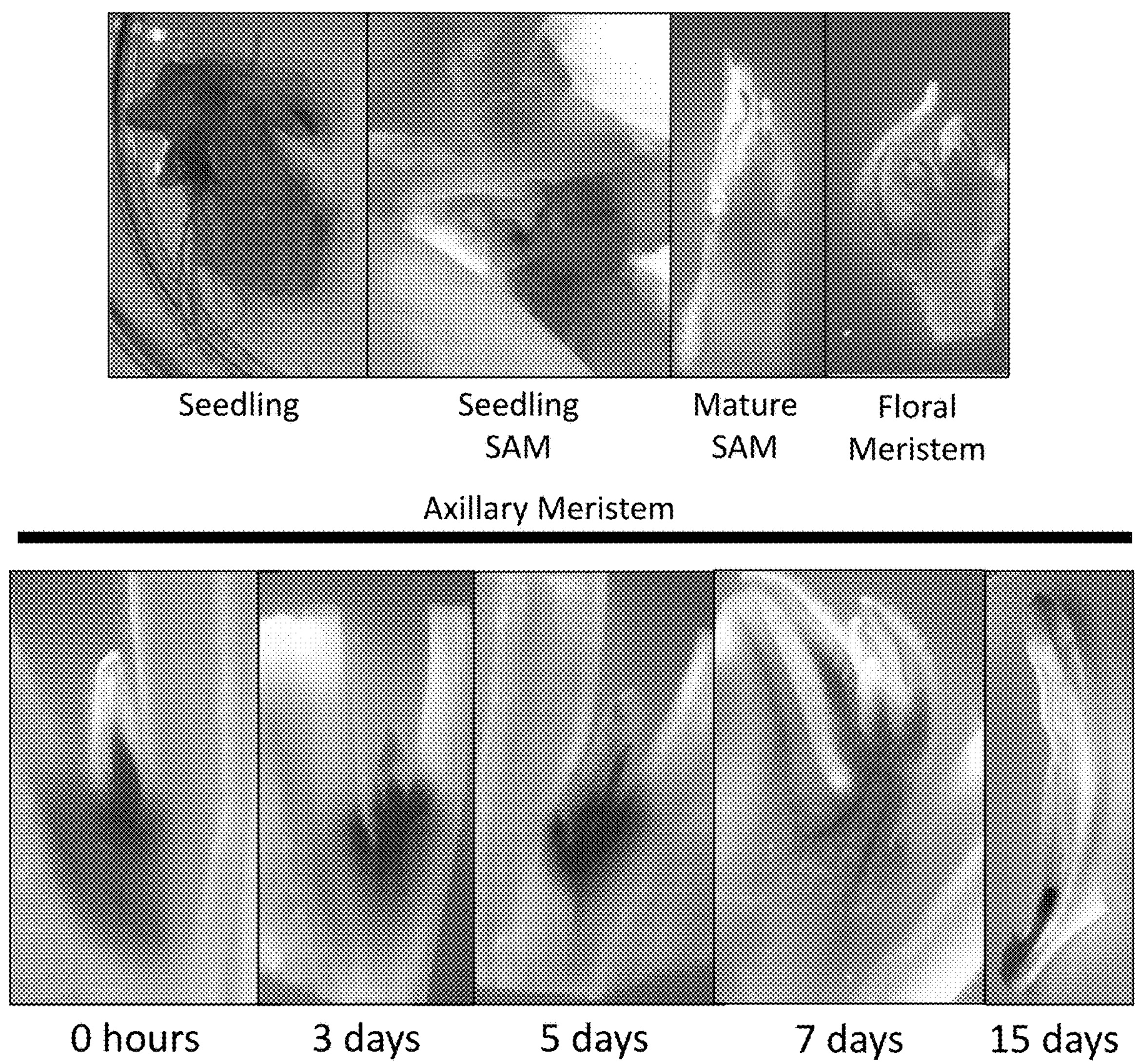
FIG. 13A shows Promoter P15 activity in a tobacco seedling; a tobacco seedling shoot apical meristem (SAM); a mature SAM at the time of topping (0 hours); and an axillary bud at the time of topping, 3 days after topping, 5 days after topping, 7 days after topping, and 15 days after topping. Promoter P15 is not active in seedlings. Promoter P15 is active at the base of the SAM, but it is not active in floral meristems. Promoter P15 exhibits strong activity in axillary buds prior to topping, and the activity is maintained for at least 15 days after topping.
Figure 13B:
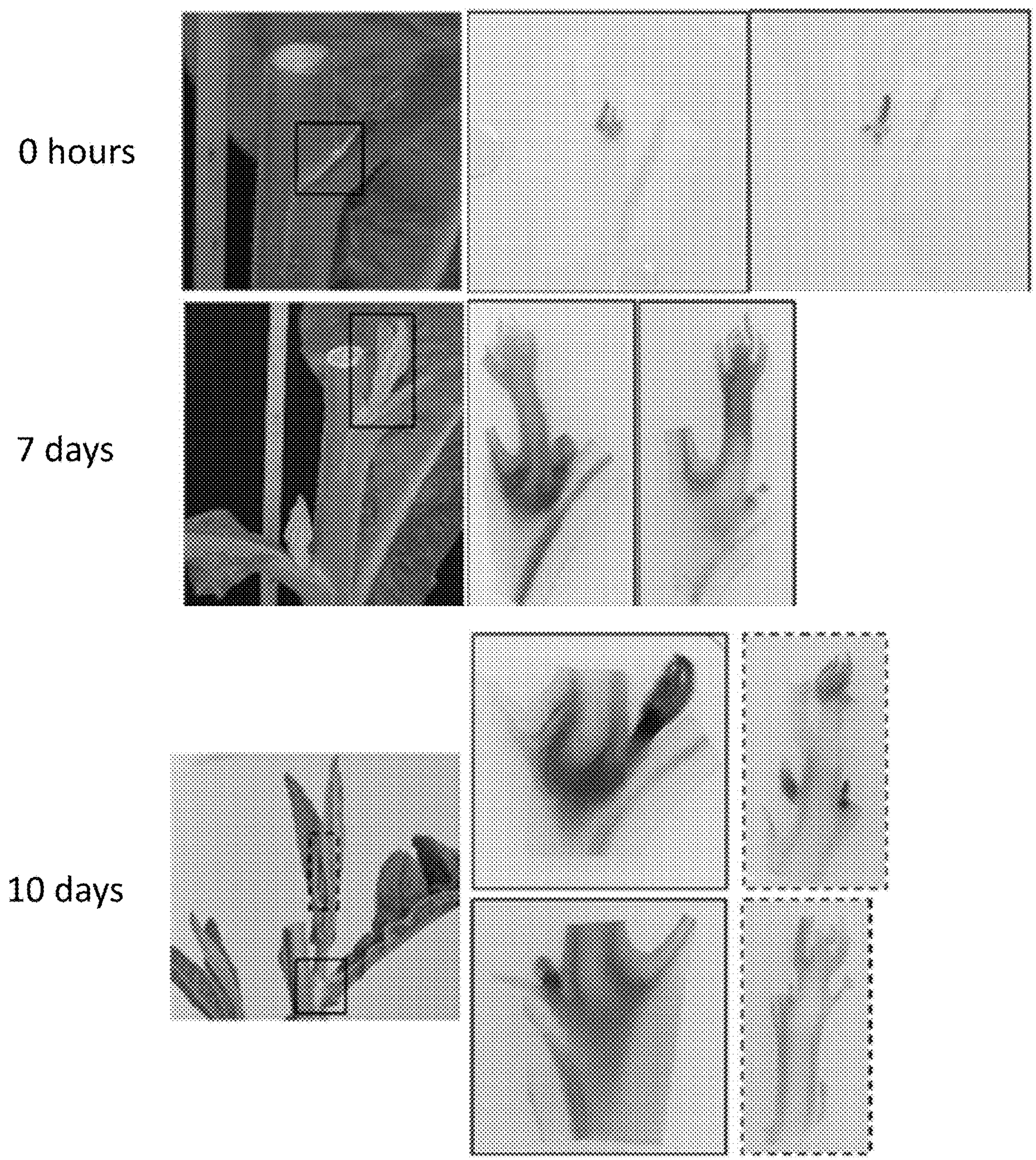
FIG. 13B further demonstrates the axillary bud specificity of Promoter P15.
Figure 13C:
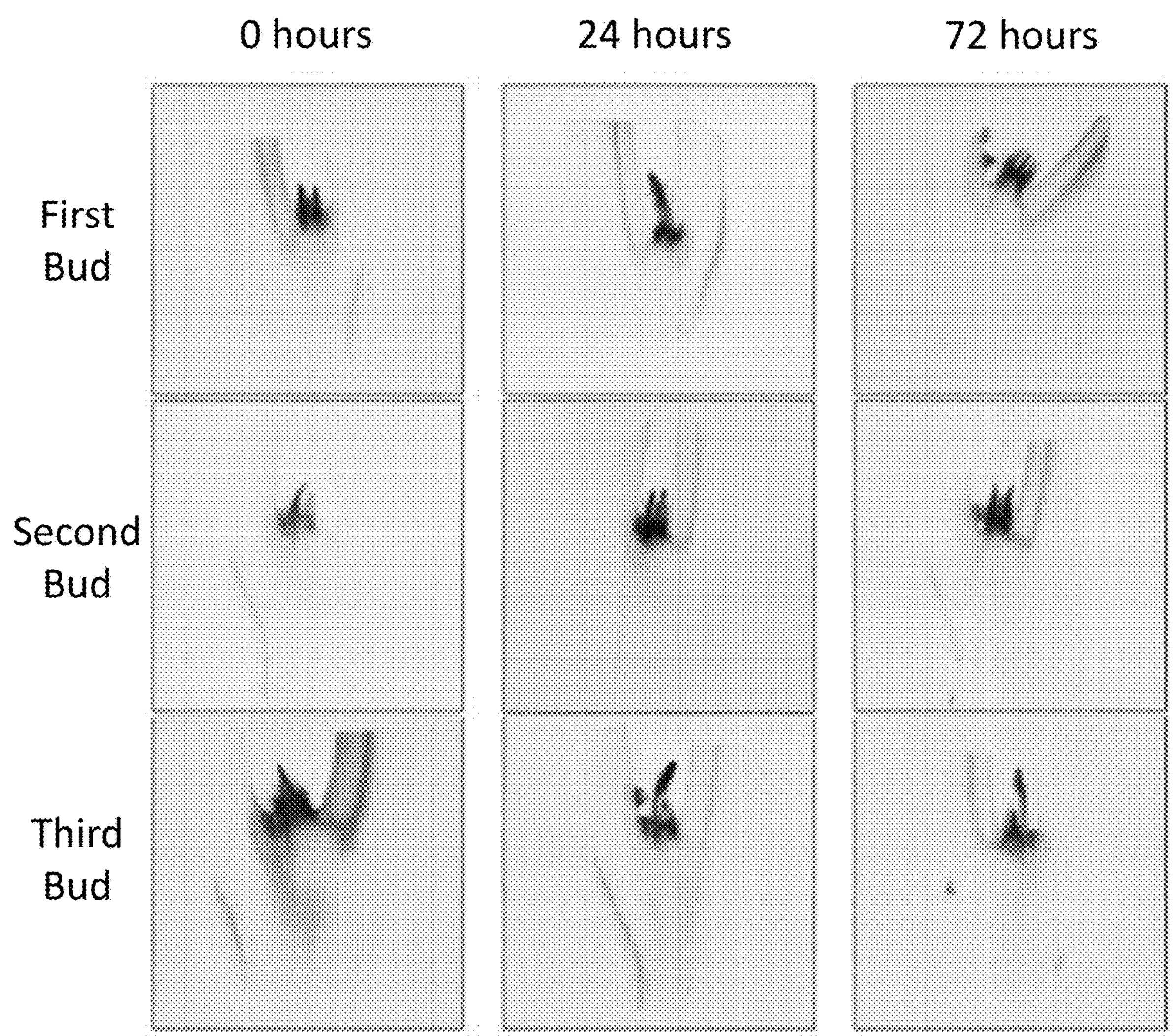
FIG. 13C displays GUS staining in multiple axillary buds from individual plants at the time of topping (0 hours), 24 hours after topping, and 72 hours after topping.

In contrast, SEQ ID NO: 117 (Promoter P15, hereinafter) drives GUS expression in the axillary meristem prior to topping and for at least fifteen days after topping, which coincides with the gene expression pattern that is observed for the endogenous gene that is normally regulated by this promoter (FIGS. 13A-C). Promoter P15 is also functional in the base of the shoot apical meristem (FIG. 13A).

Additional candidate promoters of topping-inducible, and tissue-specific, promoters to control sucker outgrowth include SEQ ID NOs: 148-160 and 204, which represent an axillary bud-specific thionin 5' upstream regulatory sequence (SEQ ID NO: 148); a tobacco lateral suppressor 1 (LAS1) 5' upstream regulatory sequence (SEQ ID NO: 149); a LAS1 3' downstream regulatory sequence (SEQ ID NO: 150); a LAS2 5' upstream regulatory sequence (SEQ ID NO: 151); a LAS2 3' downstream regulatory sequence (SEQ ID NO: 152); a tobacco regulator of axillary meristems1 (RAX1) 5' upstream regulatory sequence (SEQ ID NO: 153); a RAX1 3' downstream regulatory sequence (SEQ ID NO: 154); a RAX2 5' upstream regulatory sequence (SEQ ID NO: 155); a RAX2 3' downstream regulatory sequence (SEQ ID NO: 156); a Promoter P15 5' region (SEQ ID NO: 157); a Promoter P15 3' downstream region, (SEQ ID NO: 158); a 5' upstream regulatory sequence of a P15 homolog (SEQ ID NO: 159); a 3' downstream regulatory sequence of a P15 homolog (SEQ ID NO: 160); and a regulatory region of a P15 homolog from tomato (*Solanum lycopersicum*) (SEQ ID NO: 204). The sequences are cloned by PCR methods from NLM genomic DNA using gene-specific primers. These regulatory sequences are tested for their tissue specificity and developmental regulation as shown for Promoters P1, P11, and P15. The regulatory sequences that exhibit axillary meristem-specific or -preferential expression are used for driving heterologous gene expression and modulating sucker growth.

TABLE 3

Selected clones for promoter analysis

| SEQ ID NO | Length of Promoter |
|---|---|
| 113 | 2248 |
| 114 | 2800 |
| 115 | 3356 |
| 116 | 3150 |
| 117 | 2964 |
| 118 | 941 |
| 148 | 5000 |
| 149 | 5000 |
| 150 | 5000 |
| 151 | 5000 |
| 152 | 5000 |
| 153 | 5000 |
| 154 | 5000 |
| 155 | 5000 |
| 156 | 5000 |
| 157 | 5000 |
| 158 | 5000 |
| 159 | 5000 |
| 160 | 5000 |
| 204 | 5000 |

TABLE 4

Axillary bud-preferred promoter cis-elements

| Cis-regulatory element Name | Cis-regulatory element Nucleotide Sequence |
|---|---|
| Bud Dormancy Element (BDE) | CACGTG |
| Axillary Bud Growth (Up1) | GGCCCAW |
| Axillary Bud Growth (Up2) | AAACCCTA |
| Sucrose Responsive Element (SURE) | AATAGAAAA |
| Sugar Repressive Element (SRE) | TTATCC |
| Bud Activation Element or TCP Binding Element (BAE) | GGCCCAT |

Figure 14A:
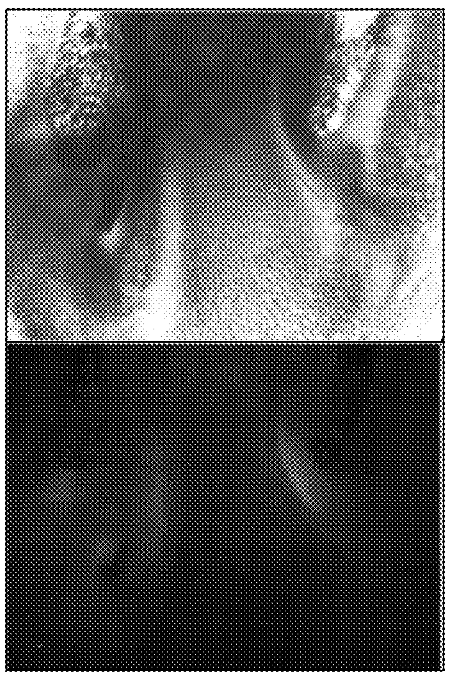
FIG. 14A shows results of a Promoter P15 (SEQ ID NO: 117)::GFP fusion in a shoot apical meristem (SAM) and axillary bud (left panel) and in an axillary bud (right panel). Promoter P15 activity is restricted to axillary buds.
Figure 14B:
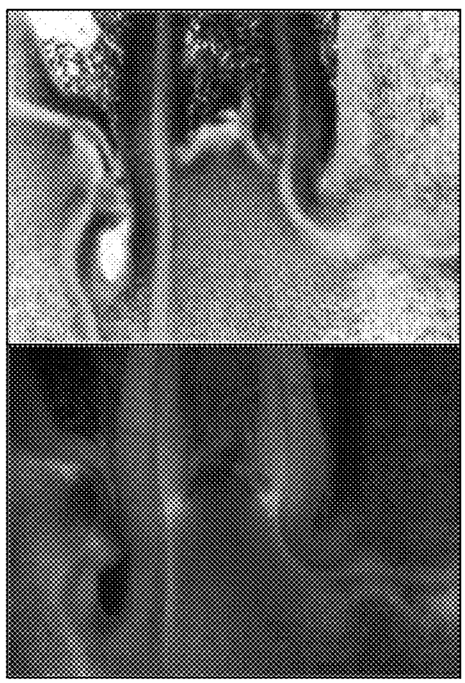
FIG. 14B shows results of a Promoter P1 (SEQ ID NO: 113)::GFP fusion in a shoot apical meristem (SAM) and axillary bud (left panel) and in an axillary bud (right panel).
Figure 14B:
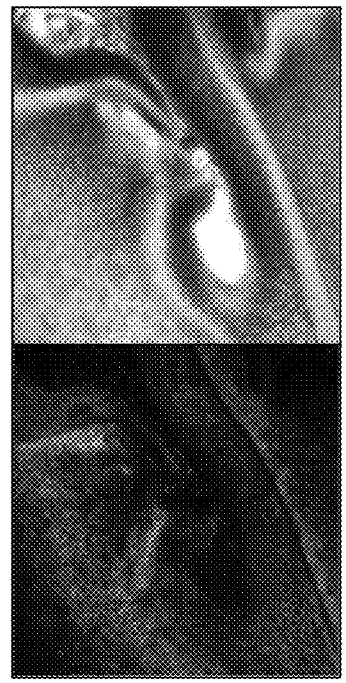

Example 8. Cellular Specificity of Promoter P1, Promoter P15, and Promoter PAB Thionin To analyze the expression pattern of Promoter P1 (SEQ ID NO: 113) and Promoter P15 (SEQ ID NO: 117) at the cellular level in meristem regions, vectors are produced comprising a green fluorescent protein (GFP) gene under the control of either Promoter P1 or Promoter P15 as described in Example 2. The chimeric vectors are introduced into an NLM tobacco plant via *Agrobacterium*-mediated transformation. GFP expression is observed using fluorescence microscopy. Promoter P15 is restricted to tissue within the axillary buds (FIG. 14A). Promoter P1 has a slightly broader expression pattern (FIG. 14B).

Figure 15:
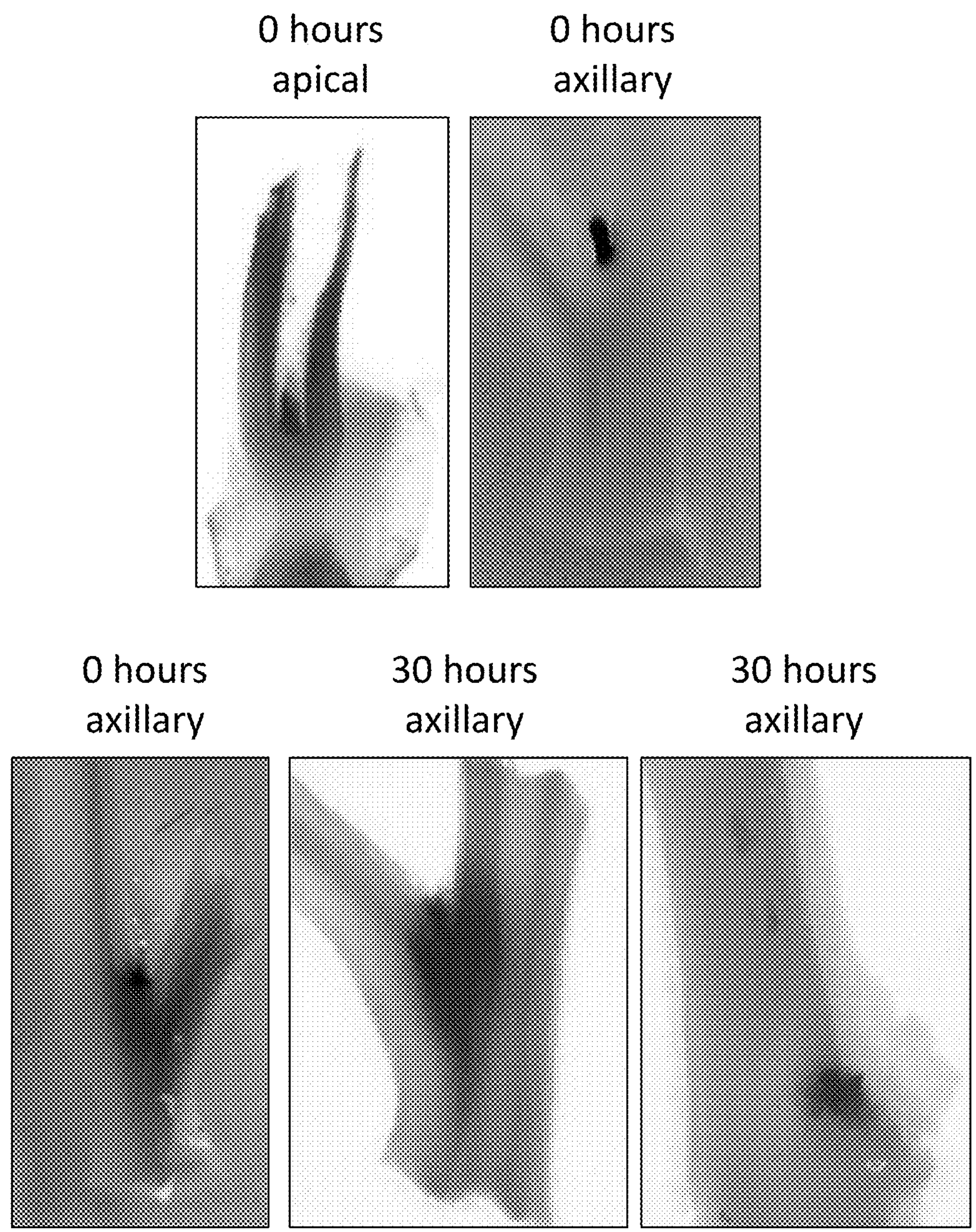
FIG. 15 shows the expression pattern of an axillary bud Thionin promoter (pABTh, SEQ ID NO: 118) fused to β-glucuronidase (GUS) in tobacco apical and axillary meristems at the time of topping (0 hours) and 30 hours after topping. Dark areas of GUS accumulation demonstrate where Promoter P15 is active.

To analyze the expression pattern of a 0.9 kb long Promoter PAB Thionin (pABTh-0.9 kb, SEQ ID NO: 118) at the cellular level in meristem regions, a vector is produced comprising a GUS gene under the control of Promoter PAB Thionin as described in Example 2. The chimeric vector is introduced into an NLM tobacco plant via *Agrobacterium*-mediated transformation. GUS expression is observed in axillary bud tissue and meristem tissue (FIG. 15).

Figure 16:
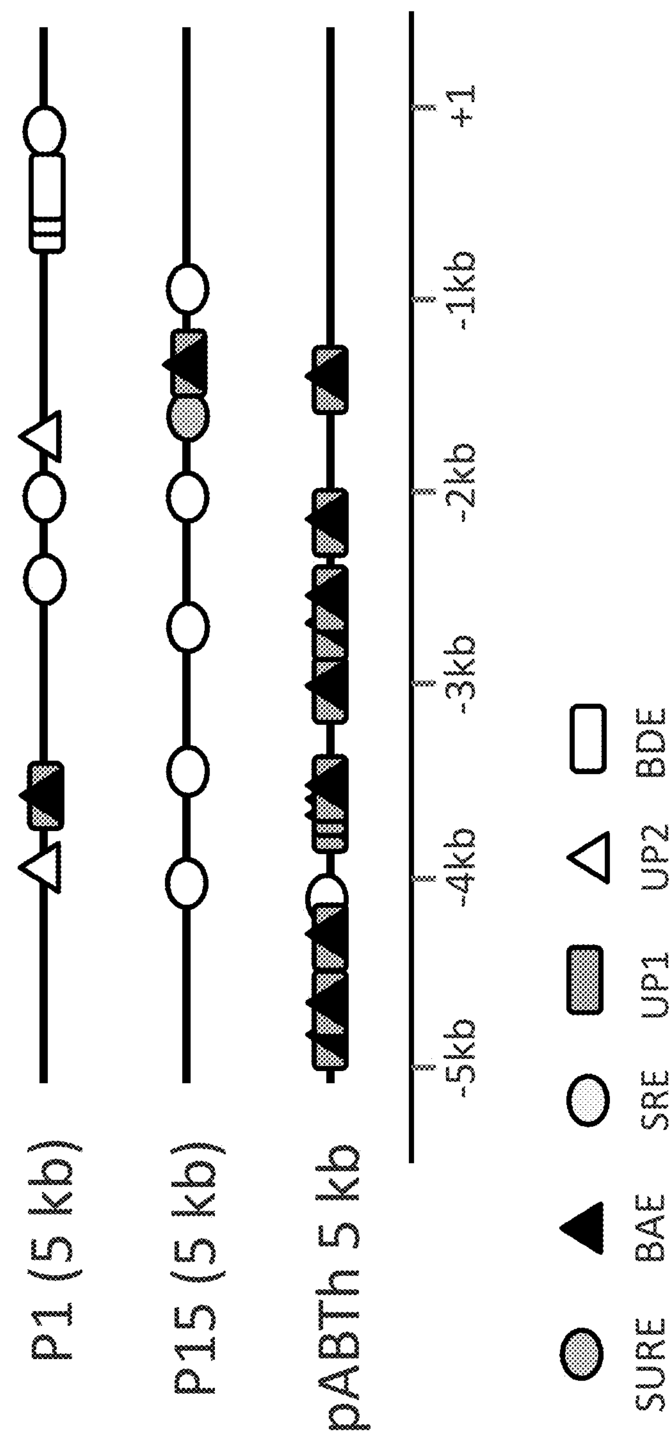
FIG. 16 shows the locations of cis-regulatory elements in Promoter P1 (SEQ ID NO: 113), Promoter P15 (SEQ ID NO: 117), and Promoter pABTh (SEQ ID NO: 118). +1 designates the transcriptional start site.

Promoters P1, P15, and PAB Thionin (pABth-5 kb, SEQ ID NO: 148) are analyzed for similar and/or unique cis-regulatory elements. Six cis-regulatory elements are identified (Table 4) upstream of the transcriptional start sites of the genes natively regulated by Promoters P1, P15, and PAB Thionin (FIG. 16). These cis-regulatory elements can have direct and/or indirect effects towards regulating sucker-specific or meristem-specific expression patterns.

Example 9. Efficacy Testing of Sucker Inhibiting Constructs

After testing of the tissue-specific expression patterns of candidate promoters using promoter::GUS fusion analysis in transgenic plants, vectors and modified plants are constructed as described in Example 2 to express target genes only in axillary buds. Exemplary constructs are shown in Table 5.

TABLE 5

Exemplary constructs for axillary bud-specific expression of a target gene.

| Construct | Promoter SEQ ID NO. | Target Gene SEQ ID NO. |
|---|---|---|
| 1 | 113 | 17 |
| 2 | 113 | 104 |
| 3 | 113 | 7 |
| 4 | 113 | 41 |
| 5 | 113 | 5 |
| 6 | 118 | 17 |
| 7 | 118 | 104 |
| 8 | 118 | 7 |
| 9 | 118 | 41 |
| 10 | 118 | 5 |
| 11 | 115 | 17 |
| 12 | 115 | 104 |
| 13 | 115 | 7 |
| 14 | 115 | 41 |
| 15 | 115 | 5 |
| 16 | 117 | 17 |
| 17 | 117 | 104 |
| 18 | 117 | 7 |
| 19 | 117 | 41 |
| 20 | 117 | 5 |

Efficacy testing for the impact of Constructs 1-20 is carried out under greenhouse and field conditions. Transgenic plants and matched wild type controls are grown to layby stage, then topped and phenotypically evaluated as described in Example 2. Field efficacy testing also determines the type and extent of sucker control chemical application needed under normal agronomical practices.

Example 10. Regulating Axillary Bud Outgrowth Via Overexpressing Genes

Sucker outgrowth can be regulated by modifying the expression of genes and/or genetic pathways that regulate branching. Some genes natively function to restrict bud outgrowth and are defined by mutants with increased branching, for example the *Arabidopsis* BRANCHED1 gene (SEQ ID NO:81) and tobacco homologs (SEQ ID NOs: 1, 13, 35, 37, and 39); and the *Arabidopsis* MORE AXILLARY BRANCHING1 (MAX1) and MAX2 genes (SEQ ID NO: 193 and 195) and tobacco homologs (SEQ ID NO: 197 and 199). See, for example, Stirnberg et al., 2002, Development 129: 1131-1141, which is herein incorporated by reference in its entirety.

Transformation vectors are created to overexpress proteins that restrict sucker outgrowth in tobacco. Separate transformation vectors comprising one of SEQ ID NOs: 1, 13, 35, 37, 39, and 81 are incorporated into p45-2-7 transformation vectors. Additional transformation vectors are created comprising one of SEQ ID NOs: 1, 13, 35, 37, 39, and 81 driven by the axillary bud-specific Promoter P15 (SEQ ID NO: 117). Modified tobacco plants are generated from these transformation vectors according to Example 2. Modified tobacco plants (TO generation) and control tobacco plants are then phenotypically evaluated as described in Example 2. The modified tobacco plants exhibit reduced sucker growth compared to control tobacco plants.

Example 11. Regulating Axillary Bud Outgrowth by Suppressing Genes that Promote Sucker Growth Some genes promote axillary meristem development and are defined by mutants with decreased branching. For example, the *Arabidopsis* LAS gene (SEQ ID NO: 201), and homologs in tobacco (SEQ ID NOs: 71 and 73); and the *Arabidopsis* RAX gene (SEQ ID NO: 203), as well as tobacco homologs (SEQ ID NOs: 75 and 77). See, for example, Greb et al., 2003, *Genes & Development* 17: 1175-1187; and Keller et al., 2006, *Plant Cell* 18: 598-611, both of which are herein incorporated by reference in their entireties.

Transformation vectors comprising RNAi constructs are designed to inhibit tobacco proteins that promote sucker outgrowth. Separate transformation vectors comprise one of SEQ ID NOs: 71, 73, 75, and 77, which are incorporated into p45-2-7 transformation vectors. Additional transformation vectors are created comprising one of SEQ ID NOs: 71, 73, 75, and 77 driven by axillary bud-specific Promoter P15 (SEQ ID NO: 117). These vectors are used to generate modified tobacco plants according to Example 2. Modified tobacco plants and control tobacco plants are then phenotypically evaluated as described in Example 2. The modified tobacco plants exhibit reduced sucker growth compared to control tobacco plants.

Example 12. Regulating Sucker Growth with RNAi, Artificial miRNAs and Gene Overexpression A transformation vector is created in which Promoter P15 (SEQ ID NO: 117) drives the expression of SEQ ID NOs: 81 (BRC1) and 101 (RNAi targeting NtCET2) in a tissue-specific manner. The Promoter P15::BRC1::NtCET2 vector over-expresses BRC1 and inhibits NtCET2 in axillary buds. The transformation vector and modified tobacco plants are generated as described in Example 2.

Figure 17:
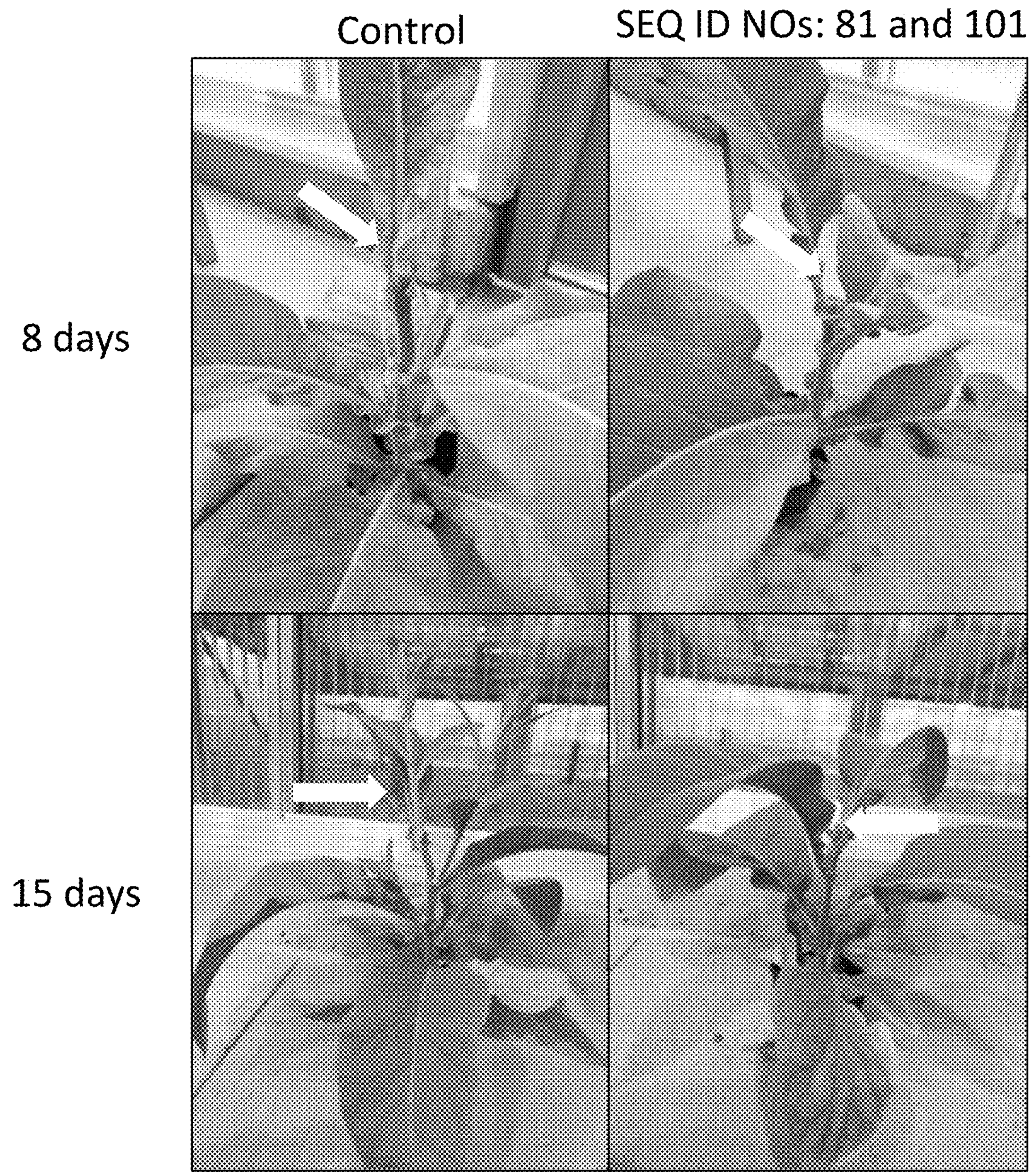
FIG. 17 shows photographs of control tobacco plants and modified tobacco plants that express SEQ ID NO: 81, which encodes *Arabidopsis thaliana* BRANCHED1 and inhibits sucker growth, and SEQ ID NO: 101, an RNAi construct that targets tobacco CENTRORADIALIS and reduces sucker growth, driven by axillary bud-specific Promoter P15 (SEQ ID NO: 117). Plants are shown 8 days after topping and 15 days after topping. Modified plants exhibit reduced sucker growth (arrows) compared to control plants.

Modified tobacco plants (TO generation) having a Promoter P15::BRC1::NtCET2 construct and control tobacco plants are grown to the layby stage, then plants are topped to remove the shoot apical meristem. Sucker growth is evaluated at the time of topping, 8 days after topping, and 15 days after topping (FIG. 17). Expression of SEQ ID NOs: 81 and 101, driven by Promoter P15, eliminates sucker growth in tobacco.

Additional transformation vectors are created in which Promoter P15 (SEQ ID NO: 117) drives the expression of an artificial miRNA designed to reduce the transcription or translation of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 69, 71, 73, 75, 77, 123-147, 186, 188, 190, 196, and 198. The transformation vectors and modified tobacco plants are generated as described in Example 2.

Modified tobacco plants (TO generation) having a Promoter P15::artificial miRNA construct and control tobacco plants are grown to the layby stage, then plants are topped to remove the shoot apical meristem. Modified and control tobacco plants are phenotypically evaluated according to Example 2.

Example 13. Regulating Sucker Growth Via Modifying Cytokinin Synthesis and Distribution Removing the shoot apical meristem releases axillary buds from dormancy and promotes sucker outgrowth. Auxin derived from an intact shoot apical meristem suppresses sucker outgrowth, whereas cytokinin induced by removal of the shoot apical meristem promotes sucker outgrowth.

Figure 18:
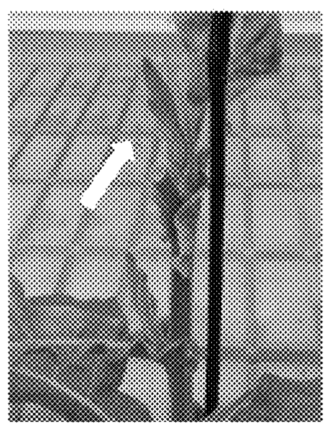
FIG. 18 shows photographs of control plants and a modified tobacco plant that expresses SEQ ID NO: 59 (*Nicotiana tabacum* cytokinin oxidase 13) under the control of Promoter P15 (SEQ ID NO: 117) eight days after topping. Modified plants exhibit reduced sucker growth (arrows) compared to control plants.

Depletion of cytokinin in axillary bud regions by overexpressing genes involved in cytokinin catabolism with an axillary bud specific promoter is used to reduce cytokinin and inhibit axillary meristem outgrowth. For example, *Arabidopsis* cytokinin oxidase (CKX; SEQ ID NO: 55), tobacco CKXs (SEQ ID NOs: 57 and 59); and a tobacco adenosine phosphate-isopentenyltransferase gene (SEQ ID NO: 61) are tested. A transformation vector comprising SEQ ID NO: 59 driven by Promoter P15 (SEQ ID NO: 117) is created according to Example 2. Modified tobacco plants are generated using this vector, and then phenotypically evaluated, according to Example 2. The modified tobacco plants exhibit reduced sucker growth compared to control tobacco plants (FIG. 18).

Example 14. Regulating Sucker Growth Via Inhibition of Axillary Meristem Stem Cell Signaling Shoot meristems comprise stem cells that are continuously replenished through a feedback circuit involving the WUSCHEL (WUS)-*CLAVATA* (CLV) signaling pathway. See, for example, Yadav et al., 2011, *Genes & Development* 25:2025-2030, which is herein incorporated by reference in its entirety. Genes from this pathway include, e.g., WUS (SEQ ID NOs: 63 and 65); CLV1; CLV2; and CLV3 (SEQ ID NOs: 67 and 69). A transformation vector is created comprising SEQ ID NO: 67 driven by Promoter P15 (SEQ ID NO: 117), which causes overexpression of CLV3 in axillary buds. Modified tobacco plants are generated using this transformation vector, and phenotypically evaluated, according to Example 2. The modified tobacco plants exhibit reduced sucker growth compared to control tobacco plants.

Additional transformation vectors are created according to Example 2 to comprise either SEQ ID NO: 63 or 65 driven by Promoter P15 (SEQ ID NO: 117), which inhibit WUS via RNAi. Modified tobacco plants are generated using these transformation vectors, and then phenotypically evaluated, according to Example 2. The modified tobacco plants exhibit reduced sucker growth compared to control tobacco plants.

*Arabidopsis* SHOOT MERISTEMLESS (STM) is a KNOX protein that is essential for shoot meristem formation and maintenance. See, for example, Long et al., 1996, *Nature* 379:66-69, which is herein incorporated by reference in its entirety. NTH15 (SEQ ID NO: 189) is a tobacco homolog of STM that is expressed in tobacco meristems. See, for example, Tanaka-Ueguchi et al., 1998, *Plant Journal* 15:391-400, which is herein incorporated by references in its entirety. A transformation vector is created comprising an RNAi construct that targets SEQ ID NO: 188 for inhibition, driven by Promoter P15 (SEQ ID NO: 117).Modified tobacco plants are generated using these transformation vectors, and then phenotypically evaluated, according to Example 2. The modified tobacco plants exhibit reduced sucker growth compared to control tobacco plants.

Example 15. Screening for Genes to Control Suckers Using Agroinfiltration

Expression of some plant genes (without being limiting, e.g., RNases; proteases; cell cycle genes; transcription factors; kinases; caspases) can elicit a cell death response when expressed at certain times and/or cell types. Identification of such genes is desired, as they can be operably linked to an axillary bud-preferred or axillary bud-specific promoter (e.g., Promoter P15/SEQ ID NO: 117) to reduce or eliminate axillary bud growth and/or development.

Figure 21:
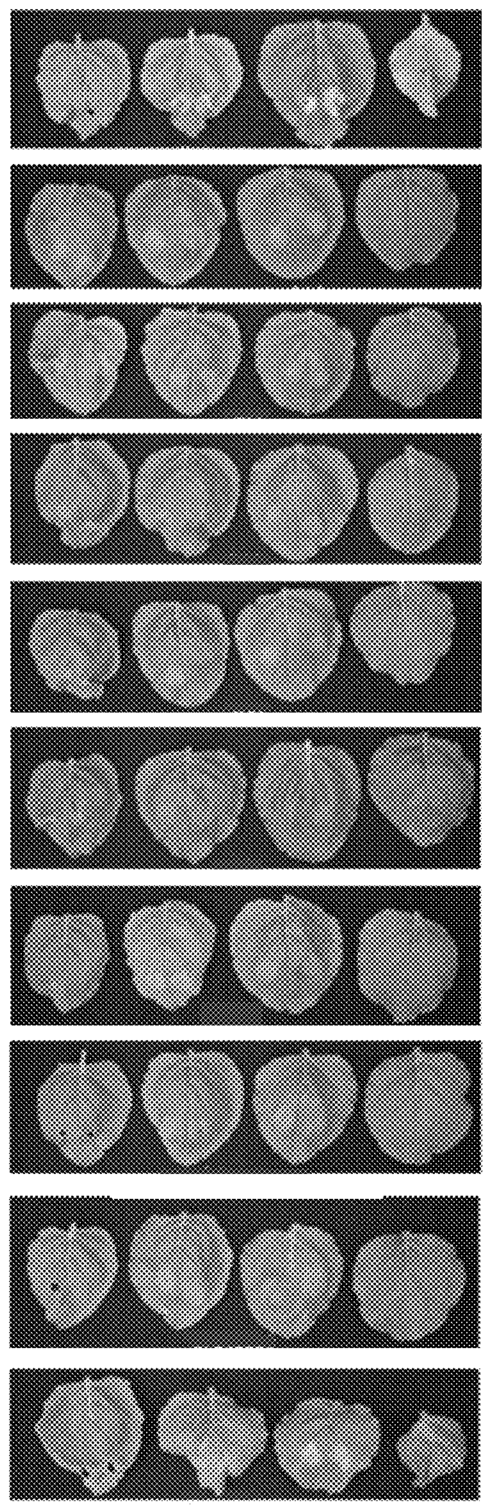
FIG. 21 shows photographs of tobacco leaves subjected to agroinfiltration as described in Example 15. A vector expressing SEQ ID NO: 79 (Barnase) is used as a positive control, and an vector lacking an insert (empty vector) is used as a negative control. Genes of interest are examined ability to induce cellular death in a tobacco leaf according to Example 15. For example, SEQ ID NO: 232 causes cellular death when expressed in a tobacco leaf.

Agroinfiltration is used to transiently express a tobacco genes (e.g., SEQ ID NOs: 201-222, 228, 230, and 232) in tobacco leaves. Plant genes of interest are inserted into a pBIN19 plasmid and transformed into *Agrobacterium tumefaciens* cells. The transformed bacteria are grown in a liquid culture, washed, and suspended in a buffer solution. The buffer solution containing the transformed *A. tumefaciens* cells is injected into one or more living tobacco leaves. Plant leaf phenotypes are then evaluated for presence or absence of cellular death after 5 days. An empty plasmid is used as a negative control, while a plasmid containing a Barnase gene (SEQ ID NO: 79) is used as a positive control. Plant genes inducing cell death in tobacco leaves are used for reducing axillary bud growth and/or development. See, for example, FIG. 21.

*Nicotiana thaliana* mitogen-activated protein kinase kinase 2 (NtMEK2; SEQ ID NO: 232) has been identified as being capable of inducing a cell death response in tobacco. The expression of SEQ ID NO: 232 is directed to axillary buds by driving its expression with Promoter P15 (SEQ ID NO: 117).

Separate transformation vectors are created according to Example 2 to comprise one of SEQ ID NOs: 201-222, 228, 230, and 232 driven by Promoter P15 (SEQ ID NO: 117). Modified tobacco plants are then generated with the Promoter P15::cell death gene vectors, and then phenotypically evaluated, according to Example 2. The modified tobacco plants exhibit reduced sucker growth compared to control tobacco plants.

Example 16. Regulating Sucker Growth Using RNases

The presence of some proteins at elevated levels, in cells where they are not normally expressed, or in subcellular locations where they are not normally located, can induce cell death. Axillary bud specific promoters, such as Promoter P1 (SEQ ID NO: 113) and Promoter P15 (SEQ ID NO: 117) are used to the express heterologous genes that are detrimental to an axillary bud and ultimately result in its death.

Figure 19:
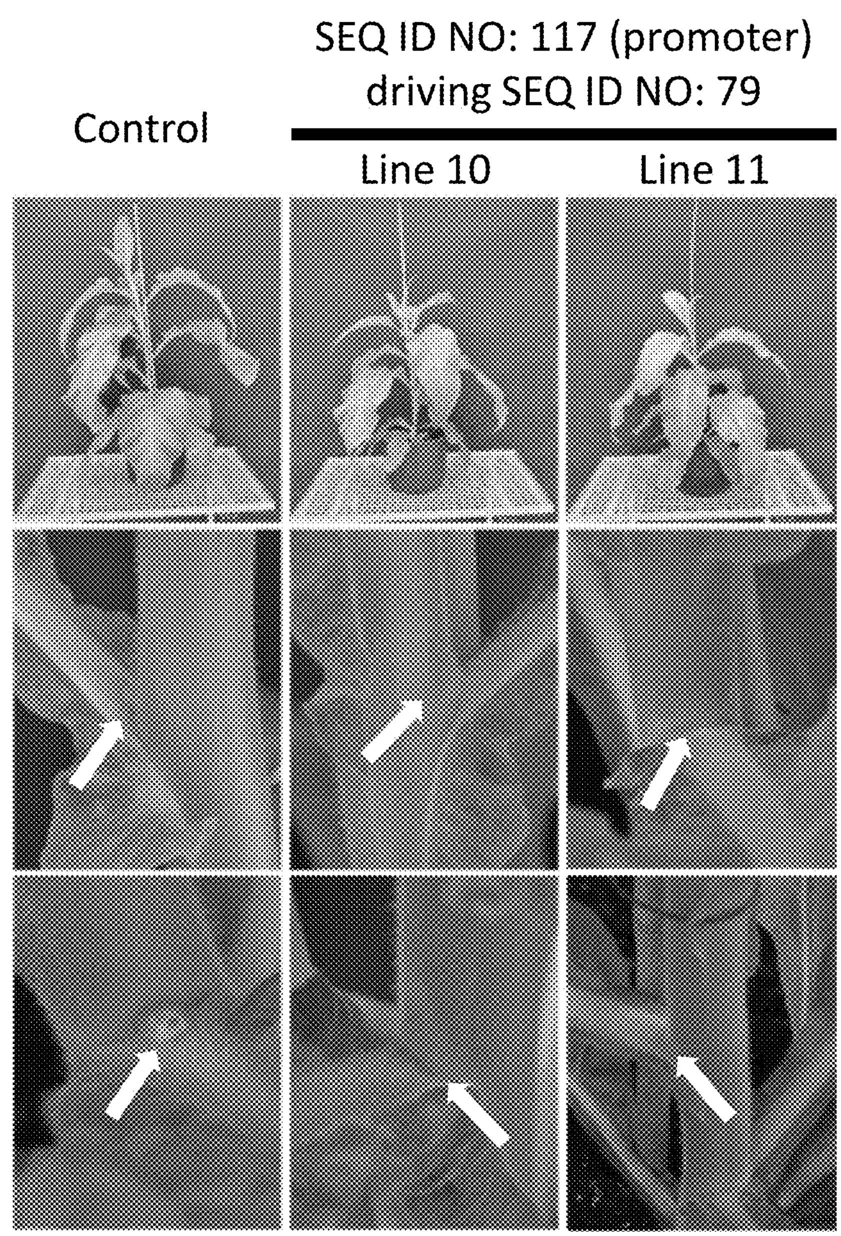
FIG. 19 shows photographs of control plants and two independent lines of modified tobacco plants that express SEQ ID NO: 79 (Barnase) under the control of Promoter P15 (SEQ ID NO: 117). Modified plants exhibit reduced sucker growth (arrows) compared to control plants. No axillary meristem primordia are observed before topping the modified plants.
Figure 20A:
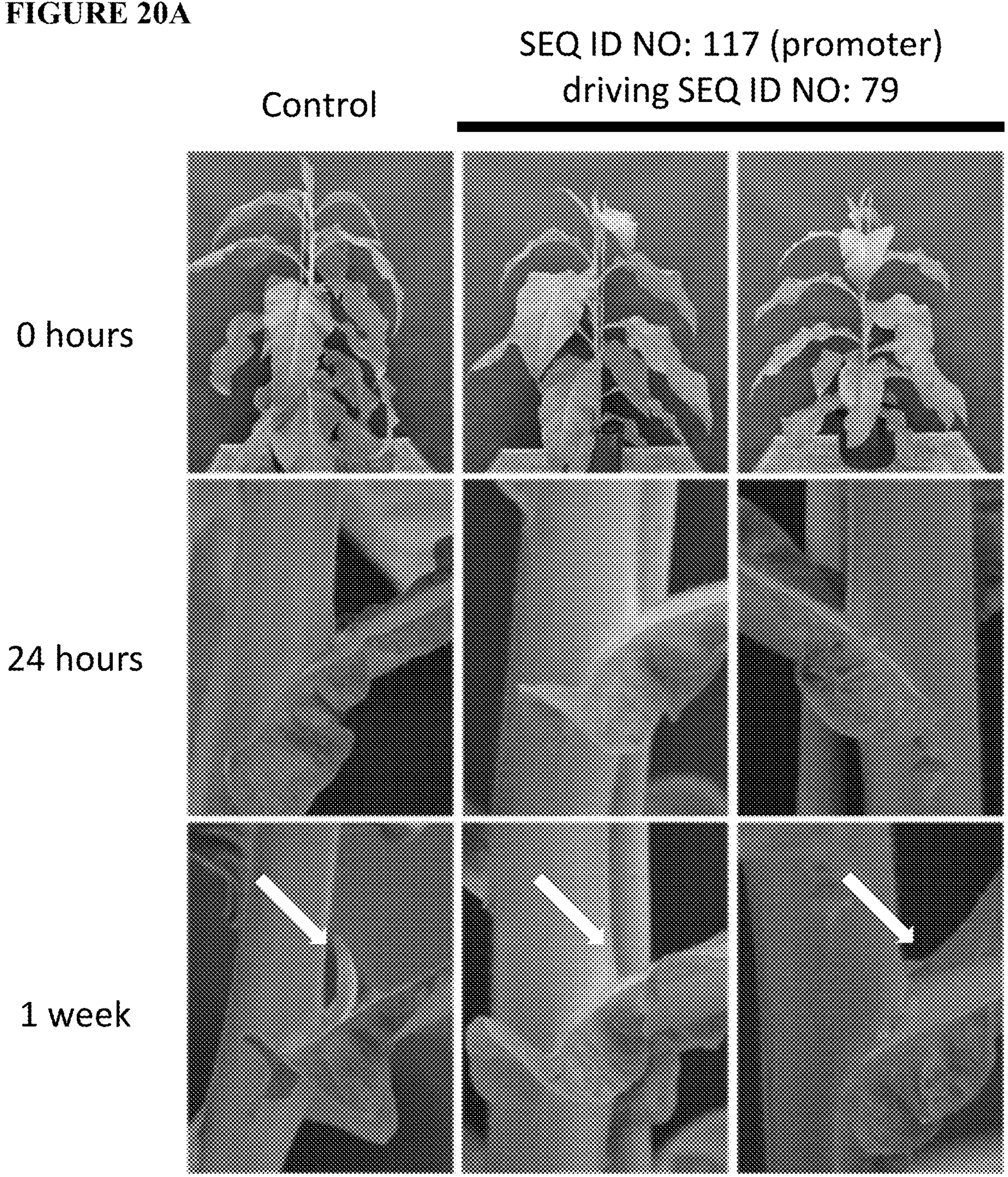
FIG. 20 shows photographs of control plants and two independent lines of modified tobacco plants that express SEQ ID NO: 79 (Barnase) under the control of Promoter P15 (SEQ ID NO: 117). Modified plants exhibit reduced sucker growth (arrows) compared to control plants one week after topping (FIG. 20A), two weeks after topping (FIG. 20B), and three weeks after topping (FIG. 20C).
Figure 20B:
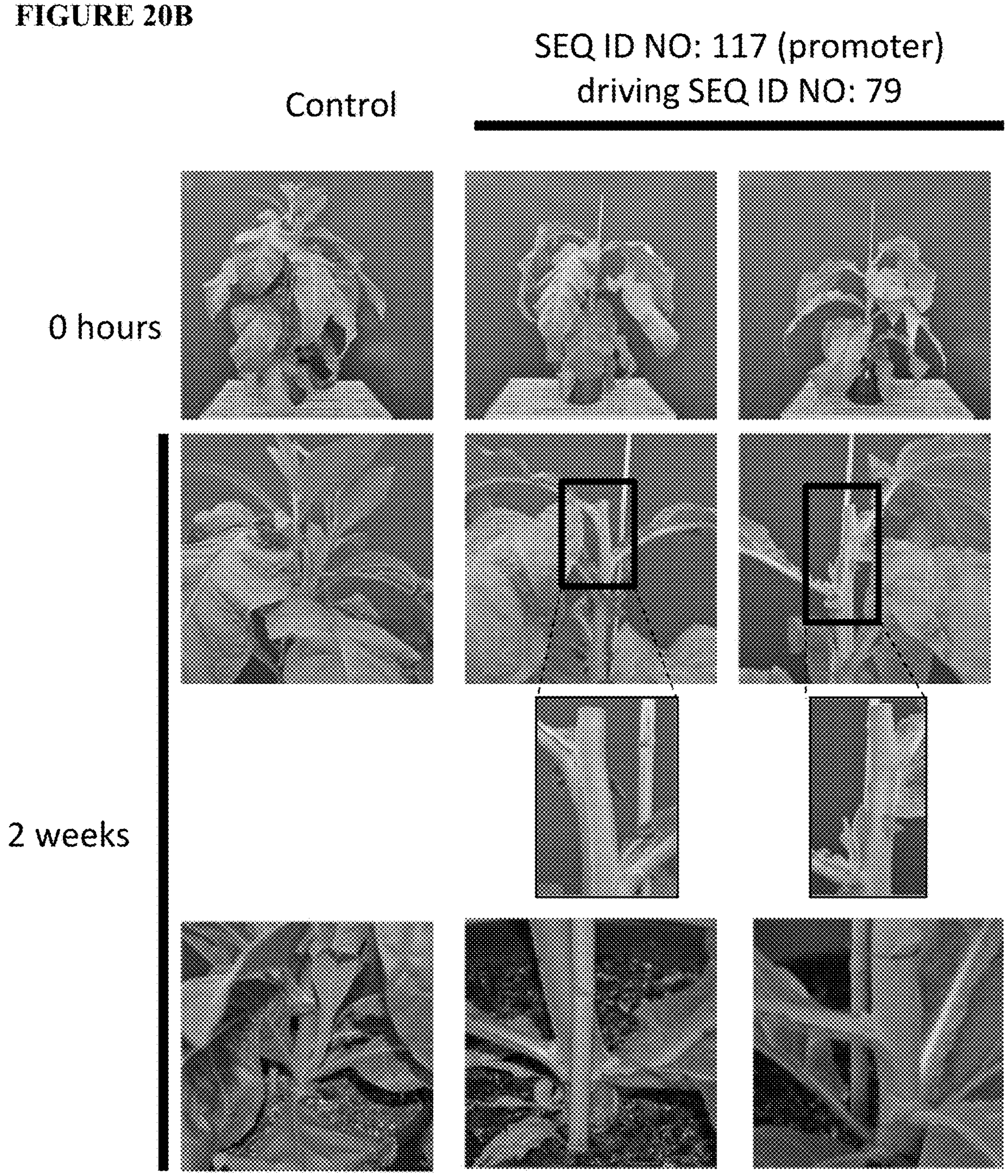
Figure 20C:
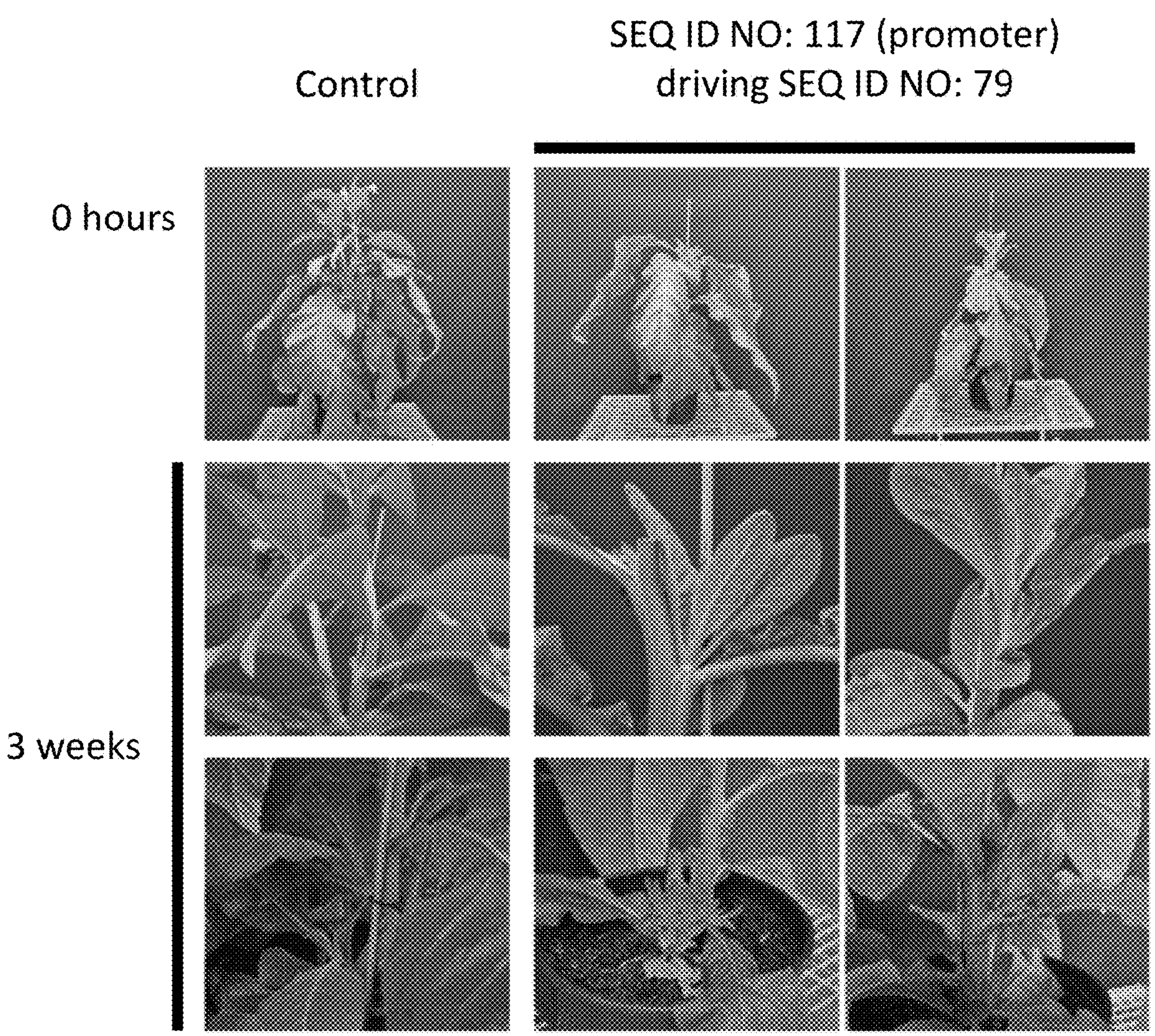

RNA-degrading enzymes, such as the bacterial RNase Barnase (SEQ ID NO: 79; and see, e.g., Hartley, 1989, *Trends in Biochemical Sciences* 14:450-454) are used to induce cellular death in the axillary bud when their expression is driven by Promoter P15 (SEQ ID NO: 117). A transformation vector is created according to Example 2 to comprise SEQ ID NO: 79 driven by Promoter P15 (SEQ ID NO: 117). Modified tobacco plants are then generated with the Promoter P15::Barnase vector according to Example 2. Modified tobacco plants (TO generation) and control tobacco plants are grown to the layby stage, then plants are topped to remove the shoot apical meristem. Sucker growth is observed at the time of topping, 24 hours after topping, one week after topping, two weeks after topping, and three weeks after topping (FIGS. 19 and 20). Expression of SEQ ID NO: 79 driven by Promoter P15 eliminates sucker outgrowth in tobacco.

Additional transformation vectors similar to Promoter P15::Barnase are also created using endogenous tobacco RNases such as: RNase Phy3 (SEQ ID NO: 123), RNase H (SEQ ID NO: 124), RNase P (SEQ ID NO: 125), RNase III (SEQ ID NO: 126), and RNase T2 (SEQ ID NOs: 127-136) in place of Barnase (SEQ ID NO: 79). Each of these vectors is used to generate modified tobacco plants, and to then phenotypically evaluate the tobacco plants, as described in Example 2. The modified tobacco plants exhibit reduced sucker growth compared to control tobacco plants.

Example 17. Regulating Sucker Growth Using Vacuolar Processing Enzymes

Vacuolar processing enzymes (VPEs) are proteases that function in normal plant growth and development, and are also implicated in vacuole-dependent programmed cell death through their caspase-like activity. Eight out of 17 VPE proteins found in the tobacco genome comprise protease domains that contain all the residues required for caspase-like activity (SEQ ID NOs: 137-143). The expression of SEQ ID NOs: 137-143 is directed to axillary buds by driving their expression with Promoter P15 (SEQ ID NO: 117). Expression of proteins encoded by SEQ ID NOs: 137-143 can be further restricted to vacuoles within axillary bud cells by including an N-terminal vacuolar sorting signal.

Separate transformation vectors are created according to Example 2 to comprise one of SEQ ID NOs: 137-143 driven by Promoter P15 (SEQ ID NO: 117). Modified tobacco plants are then generated with the Promoter P15::VPE vectors, and then phenotypically evaluated, according to Example 2. The modified tobacco plants exhibit reduced sucker growth compared to control tobacco plants.

Example 18. Regulating Sucker Growth Using Proteases

Additional plant proteases are expressed in certain tissues to eliminate the cells responsible for axillary shoot meristem development. Proteolytic enzymes are divided into four groups based on their catalytic domain: aspartic proteases, cysteine proteases, metalloproteases, and serine proteases. All of these protease families are found in tobacco and are used to inhibit the development of axillary shoot meristems. For example, an aspartic protease (SEQ ID NO: 144), a cysteine protease (SEQ ID NO: 145), a metalloprotease (SEQ ID NO: 146), or a serine protease (SEQ ID NO: 147) are expressed with a tissue specific promoter (e.g., SEQ ID NOs: 113-118, 148-160, and 204).

Separate transformation vectors are created according to Example 2 to comprise one of SEQ ID NOs: 144-147 driven by Promoter P15 (SEQ ID NO: 117). Modified tobacco plants are then generated with a Promoter P15::protease vector, and then phenotypically evaluated, according to Example 2. The modified tobacco plants exhibit reduced sucker growth compared to control tobacco plants.

Example 19. Genome Editing Using TALEN

Transcription activator-like effector nuclease (TALEN) technology is used to modify commercial tobacco varieties such as TN90, K326 and Narrow Leaf Madole. TALENs enable genetic modification through induction of a double strand break (DSB) in a DNA target sequence. The ensuing DNA break repair by either a non-homologous end joining (NHEJ) or a homology-directed repair (HDR)-mediated pathway is exploited to introduce a desired modification (e.g., gene disruption, gene correction or gene insertion).

PEG-mediated protoplast transformation is used to introduce a TALEN and a donor DNA molecule into a plant cell. Tobacco leaves from 4-8 weeks old tobacco plants from sterile culture are cut into small pieces and transferred into a petri dish containing filter-sterilized enzyme solution containing 1.0% Cellulase onuzuka R10 and 0.5% Macerozym. The leaf strips in the petri dish are vacuum infiltrated for 30 minutes in the dark using a desiccator. After incubation, the digested leaves are resuspended by shaking at 45 R.P.M. for 230 minutes, and then filtered through a sterilized 100 μm nylon filter by collecting in a 50 mL centrifuge tube. The solution is applied to Lymphoprep and separated via centrifugation at 100×g for 10 minutes. Protoplast bands are collected using a pipette, and purified protoplasts are washed with an equal volume of W5n solution containing NaCl, $CaCl_2$, KCl, MES, and glucose, prior to additional centrifugation for 5 minutes at 2000 R.P.M. Protoplast pellets are resuspended at $2\times10^5$/mL in W5n solution, and left on ice for 30 minutes. Next, supernatant is removed and protoplast pellets are resuspended in filter-sterilized MMM solution containing mannitol, $MgCl_2$ and MES.

PEG transfection of tobacco protoplasts is performed according to a method described by Zhang et al. (2013, *Plant Physiology* 161:20-27) with some modifications. A 500 μL aliquot of protoplast suspension is transferred into a 10 mL culture tube and 25 μL (~10 μg) of plasmid DNA is slowly added to the protoplasts suspension. Next, 525 μL PEG solution is added to the protoplast-DNA solution and mixed by carefully tapping the tube. Tubes are incubated for 20 minutes, then 2.5 mL W5n solution is added to stop the reaction. The solution is centrifuged at 100×g for 5 minutes, and washed with protoplast culture media. PEG-treated protoplasts are resuspended in 1 mL culture media containing 0.1 mg/L NAA and 0.5 mg/L BAP, and mixed with 1 mL low-melting agar to make protoplast beads. Protoplast beads are cultured in liquid media, and calli growing from protoplast beads are transferred onto solid shooting media. When shoots are well developed, they are transferred into a Magenta™ GA-7 box for root formation. When root systems are fully developed and shoot growth resumes, plants are transplanted into soil.

Multiple TALEN approaches are used to prevent or reduce sucker growth in tobacco. Instead of randomly inserting a gene into a tobacco genome using conventional transformation methods, TALEN is used for targeted replacement of an endogenous coding sequence. In one example, a coding sequence of interest (e.g., SEQ ID NOs: 123-147) can be placed under the control of an axillary bud-specific promoter sequence (e.g., SEQ ID NOs: 113-118, 148-160, and 204), and the construct can be used with a TALEN to homologously recombine the construct into the endogenous genomic region controlled by the promoter. A TALEN donor sequence is shown in SEQ ID NO:119, and a TALEN target sequence is shown in SEQ ID NO:120.

A second example places an axillary bud-specific promoter and a coding sequence of interest under the control of a native axillary bud-specific promoter to provide two doses of promoter control. A construct including a first promoter (SEQ ID NO:118), a second promoter (SEQ ID NO:113), and a coding sequence (SEQ ID NO:13) is homologously recombined into the genomic region containing native SEQ ID NO: 118 using TALEN, thereby directing expression of the coding sequence by both promoters (SEQ ID NO:118 and 113). A TALEN donor sequence is shown in SEQ ID NO:121.

A third example uses TALEN to disrupt a target gene that promotes sucker growth and/or development. TALEN target sequences are identified for nucleic acid sequences (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 69, 71, 73, 75, 77, 108-110, 123-147, 186, 188, 190, 196, 198) and nucleic acid sequences encoding polypeptides (e.g., SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199). Gene-specific TALENs are designed and introduced into tobacco cells to cause deletions or insertions in an endogenous target gene. For example, potential TALEN target sites in a coding sequence (SEQ ID NO: 11) are identified, and homologous recombination sites within the coding sequence of the gene are selected. A TALEN target sequence is shown in SEQ ID NO:122 (the target sequences are underlined).

Example 20. Additional Methods of Regulating Sucker Growth Using Gene Editing Technologies Gene editing technologies such as CRISPR/Cas9, CRISPR/Cpf1, zinc-finger nucleases (ZFN), and transcription activator-like effector nucleases (TALENs) are used to replace the coding region of an axillary meristem-specific gene with a cell death/axillary shoot suppressor sequence. These gene editing technologies are also used to edit or replace an endogenous promoter sequence to drive its cognate protein expression in axillary buds. For example, an endogenous RNase promoter is edited or replaced so the RNase is only expressed in axillary buds, where it can function to reduce sucker outgrowth via the induction of cell death. Alternatively, the promoter of an axillary meristem regulator gene is mutated (edited) to eliminate regulatory region(s) required for timely expression during sucker activation and/or outgrowth, which can lead to growth defects and/or death of axillary shoots. Gene editing technologies are further used to edit or replace of an endogenous gene that natively functions in axillary buds. An endogenous gene such as NtCET2 is edited so that it no longer makes a functional protein, thereby inhibiting sucker outgrowth. Separate CRISPR/Cas9 or CRISPR/Cpf1 guide RNAs are constructed to recognize and hybridize to the promoter sequence of each one of SEQ ID NOs: 123-147. The engineered guide RNA and a donor polynucleotide comprising Promoter P15 (SEQ ID NO: 117) are provided to a tobacco plant, allowing Promoter P15 to replace the endogenous promoter of SEQ ID NO: 123-147 and restrict expression of endogenous SEQ ID NOs: 123-147 to the axillary bud. The edited tobacco plants exhibit reduced sucker growth compared to control tobacco plants.

Example 21. Development of Novel Mutations Via Random Mutagenesis

Random mutagenesis of tobacco plants are performed using ethyl methanesulfonate (EMS) mutagenesis or fast neutron bombardment. EMS mutagenesis consists of chemically inducing random point mutations. Fast neutron mutagenesis consists of exposing seeds to neutron bombardment which causes large deletions through double stranded DNA breakage.

For EMS mutagenesis, one gram (approximately 10,000 seeds) of Tennessee 90 tobacco (TN90) seeds are washed in 0.1% Tween for fifteen minutes and then soaked in 30 mL of $ddH_2O$ for two hours. One hundred fifty (150) μL of 0.5% EMS (Sigma, Catalogue No. M-0880) is then mixed into the seed/$ddH_2O$ solution and incubated for 8-12 hours (rotating at 30 R.P.M.) under a hood at room temperature (RT; approximately 20° C.). The liquid then is removed from the seeds and mixed into 1 M NaOH overnight for decontamination and disposal. The seeds are then washed twice with 100 mL $ddH_2O$ for 2-4 hours. The washed seeds are then suspended in 0.1% agar solution.

The EMS-treated seeds in the agar solution are evenly spread onto water-soaked Carolina's Choice Tobacco Mix (Carolina Soil Company, Kinston, NC) in flats at ~2000 seeds/flat. The flats are then covered with plastic wrap and placed in a growth chamber. Once the seedlings emerge from the soil, the plastic wrap is punctured to allow humidity to decline gradually. The plastic wrap is completely removed after two weeks. Flats are moved to a greenhouse and fertilized with NPK fertilizer. The seedlings are replugged into a float tray and grown until transplanting size. The plants are subsequently transplanted into a field. During growth, the plants self-pollinate to form M1 seeds. At the mature stage, five capsules are harvested from each plant and individual designations are given to the set of seeds from each plant. This forms the M1 population. A composite of M1 seed from each M0 plant are grown, and plants are phenotypically evaluated as described in Example 2. M1 plants exhibiting enhanced or reduced sucker growth are selected and screened for mutations using DNA sequencing and gene mapping techniques known in the art.

Example 22. Regulating Sucker Growth Using Inducible Promoters

Inducible promoters are also used to express a functional gene in a controlled manner to reduce or eliminate sucker development. These promoters are induced by either a chemical spray or at certain time points (i.e., after topping). Exemplary promoters include alcohol-regulated promoters; tetracycline-regulated promoters; steroid-regulated promoters (e.g., glucocorticoid (See, for example, Schena et al., 1991, *Proceedings of the National Academy of Sciences USA* 88:10421-10425, which is herein incorporated by reference in its entirety); human estrogen; ecdysone); and metal-regulated promoters. For example, an RNase (e.g., SEQ ID NOs: 79 and 123-136), a VPE (e.g., SEQ ID NOs: 137-143), or a protease (e.g., SEQ ID NOs: 144-147) are expressed in a tobacco plant with an inducible promoter.

In one example, a first vector containing a rat glucocorticoid receptor under the control of a constitutive CsVMV promoter and a second vector containing a sequence of interest (e.g., SEQ ID NOs: 83-101) operably linked to one or more glucocorticoid response elements are created according to Example 2. Modified tobacco plants are then generated containing both of these vectors. Dexamethasone is sprayed on the plants to induce the expression of the sequence of interest, then the plants are phenotypically evaluated. The modified tobacco plants exhibit reduced sucker growth compared to control tobacco plants.

In a second example, a first vector containing a rat glucocorticoid receptor under the control of Promoter P15 (SEQ ID NO: 117) and a second vector containing a sequence of interest (e.g., SEQ ID NOs: 79 and 123-147) operably linked to one or more glucocorticoid response elements are created according to Example 2. Modified tobacco plants are then generated containing both of these vectors. Dexamethasone is sprayed on the plants to induce the expression of the sequence of interest, then the plants are phenotypically evaluated. The modified tobacco plants exhibit reduced sucker growth compared to control tobacco plants.

Example 23. Regulating Sucker Growth Using Phytotoxins and Immune Receptors

Tobacco plants are metabolically engineered to produce one or more phytotoxins (e.g., tabtoxin; coronatine; syringomycin; syringopeptin; phaseolotoxin) or immune receptors in an axillary meristem to inhibit cell growth or cell division within the axillary shoot meristem. See, for example, Bender et al., 1999, *Microbiology and Molecular Biology Reviews* 63:266-292, which is herein incorporated by reference in its entirety. As an example, the tabA/tblA genes from *Pseudomonas syringae* required to produce tabtoxin are expressed with a tissue specific promoter (e.g., SEQ ID NOs: 113-118, 148-160, and 204).

Immune receptor genes include wide range of genes. Some examples include *Arabidopsis thaliana* disease resistance protein RPS5 (SEQ ID NO: 222) and tobacco TMV resistance N gene (SEQ ID NO: 224).

A transformation vector is created according to Example 2 to comprise SEQ ID NO: 221 driven by Promoter P15 (SEQ ID NO: 117). Modified tobacco plants are then generated with a Promoter P15::RPS5 vector, and then phenotypically evaluated, according to Example 2. The modified tobacco plants exhibit reduced sucker growth compared to control tobacco plants.

Example 24. Regulating Sucker Growth Using Programmed Cell Death-Inducing Genes

The presence of some proteins at elevated levels, in cells where they are not normally expressed, or in subcellular locations where they are not normally located, can induce cell death. Axillary bud specific promoters, such as Promoter P1 (SEQ ID NO: 113) and Promoter P15 (SEQ ID NO: 117) are used to the express heterologous genes that in axillary bud cells and ultimately result in death of the axillary bud.

Programmed cell death-inducing (PCD-inducing) enzymes (e.g., transcription factors (SEQ ID NOs: 208, 210, and 212), kinases (SEQ ID NO: 214), cysteine proteases (SEQ ID NOs: 216 and 218), and caspases (SEQ ID NO: 220); see Table 6) are used to induce cellular death in the axillary bud when their expression is driven by Promoter P15 (SEQ ID NO: 117). Transformation vectors are created according to Example 2 to comprise SEQ ID NOs: 208, 210, 212, 214, 216, 218, and 220 driven by Promoter P15 (SEQ ID NO: 117). Modified tobacco plants are then generated with the Promoter P15::PCD-inducing enzyme vector according to Example 2. Modified tobacco plants (TO generation) and control tobacco plants are grown to the layby stage, then plants are topped to remove the shoot apical meristem. Sucker growth is observed at the time of topping, 24 hours after topping, and one week after topping. Expression of PCD-inducing enzymes driven by Promoter P15 eliminates sucker outgrowth in tobacco.

TABLE 6

Programmed Cell Death (PCD)-Inducing Genes

| SEQ ID NOs (Nucleic Acid/Protein) | Gene Name | Species | Sequence Description | Sequence Source |
|---|---|---|---|---|
| 207/208 | ALCATRAZ | *Arabidopsis thaliana* | Transcription factor (myc/bHLH), fruit dehiscence | *Current Biology* 2001, 11: 1941-1922 |
| 209/210 | VND6 | *Arabidopsis thaliana* | Transcription factor, PCD- xylogenesis | *JEB* 2014, 65: 1313-1321 |
| 211/212 | VND7 | *Arabidopsis thaliana* | Transcription factor, PCD- xylogenesis | *JEB* 2014, 65: 1313-1321 |
| 213/214 | Adi3 | *Solanum lycopersicum* | AGC kinase, negative regulator, PCD with pathogen attack | *EMBO* 2006, 25: 255-265 |
| 215/216 | XCP1 | *Arabidopsis thaliana* | Cysteine protease, PCD-xylogenesis | *Plant Journal* 2008, 56: 303-315 |
| 217/218 | XCP2 | *Arabidopsis thaliana* | Cysteine protease, PCD-xylogenesis | *Plant Journal* 2008, 56: 303-315 |
| | SlCysEP | *Solanum lycopersicum* | Cysteine protease, ricinosomal protease, PCD-endosperm | *Planta* 2013, 237: 664-679 |
| 219/220 | Metacaspase 2d (ATMC4) | *Arabidopsis thaliana* | Protease, PCD during biotic and abiotic stresses | *Plant Journal* 2011, 66: 969-982 |
| | Caspase-like protease | *Solanum lycopersicum* | PCD, like apoptosis in mammalian cells | *Planta* 2000, 211: 656-662 |

Example 25. Regulating Sucker Growth by Regulating microRNAs miRNAs can be involved in the regulation of axillary bud development. See Ortiz-Morea et al., 2013, *Journal of Experimental Botany* 64:2307-2320; and Wang et al., 2010, *Molecular Plant* 3:794-806, which are herein incorporated by reference in their entireties. To identify miRNAs involved in tobacco sucker development, total RNA samples are extracted from axillary buds and phloem of 4 week old TN90 tobacco plants before topping and several time points after topping (e.g., 2 hours after topping, 6 hours after topping, 24 hours after topping, 72 hours after topping, 96 hours after topping). Small RNA (sRNA) are separated and purified from the total RNAs. The resulting sRNA samples (three independently collected samples for each tissue type) are processed and subjected to Illumina sequencing. The Illumina reads are mapped and used to evaluate the expression profiles of miRNAs and other small RNAs (e.g., small-interfering RNAs (siRNAs), trans-acting siRNAs). Small RNAs, including miRNAs, that exhibit differential expression in axillary buds before and after topping are identified. These sRNAs play a role in the formation or outgrowth of suckers. The identified sRNAs' precursor sequences and genomic sequences are subsequently identified.

Some tobacco sRNAs are associated with reduced sucker development and/or growth. Over-expression of these sRNAs is used to inhibit suckers. sRNAs found to be associated with reduced sucker development and/or growth are placed under the regulation of a promoter functional in an axillary bud (e.g., SEQ ID NOs: 113-118, 148-160, and 204), or a constitutive promoter (e.g., CaMV 35S) according to Example 2.

A transformation vector is created according to Example 2 to comprise sRNAs of interest driven by Promoters P1, P11, P15, or PAB Thionin (SEQ ID NO: 118). Modified tobacco plants are then generated and phenotypically evaluated according to Example 2. The modified tobacco plants exhibit reduced sucker growth compared to control tobacco plants.

miRNAs that promote sucker formation or outgrowth by repressing genes that would otherwise inhibit sucker formation or outgrowth are targeted for regulation by generating constructs comprising at least one miRNA decoy under the regulation of a promoter functional in an axillary bud (e.g., SEQ ID NOs: 113-118, 148-160, and 204), or a constitutive promoter according to Example 2.

A transformation vector is created according to Example 2 to comprise a miRNA decoy driven by Promoters P1, P11, P15, or PAB Thionin (SEQ ID NO: 118). Modified tobacco plants are then generated and phenotypically evaluated, according to Example 2. The modified tobacco plants exhibit reduced sucker growth compared to control tobacco plants.

A further transformation vector is created according to Example 2 to comprise a tobacco miR159 decoy driven by Promoter PAB Thionin (SEQ ID NO: 118). Tobacco mature miR159 (SEQ ID NO: 227) is complementary to at least SEQ ID NOs: 1, 13, and 35, which all function to inhibit sucker growth in tobacco. Preventing miR159-mediated degradation of SEQ ID NOs: 1, 13, and 35 reduces sucker growth. Modified tobacco plants are then generated with an axillary meristem promoter::miR159 decoy vector, and then phenotypically evaluated, according to Example 2. The modified tobacco plants exhibit reduced sucker growth compared to control tobacco plants.

Example 26. Regulating Sucker Growth Via Modifying Auxin Synthesis and Transport Removing the shoot apical meristem releases axillary buds from dormancy and promotes sucker outgrowth. Auxin derived from an intact shoot apical meristem suppresses sucker outgrowth. Typically, cytokinin induced by removal of the shoot apical meristem promotes axillary meristem outgrowth. Without being bound to any scientific theory, maintaining a high auxin:cytokinin ratio in and around axillary buds after removal of the shoot apical meristem can suppress axillary bud outgrowth.

Localized increases in auxin concentration in and around axillary bud regions can suppress sucker outgrowth. Genes related to auxin biosynthesis and/or transport are used to suppress axillary meristem outgrowth when their expression is driven by Promoter P15 (SEQ ID NO: 117) or other promoters functional in axillary buds (e.g., SEQ ID NOs: 113-118, 148-160, 204, and fragments thereof). A transformation vector is created according to Example 2 to comprise SEQ ID NO: 234 (YUCCA1; flavin monooxygenase) driven by Promoter P15 (SEQ ID NO: 117). Modified tobacco plants are then generated with the Promoter P15::YUCCA1 vector according to Example 2. Modified tobacco plants (TO generation) and control tobacco plants are grown to the layby stage, then plants are topped to remove the shoot apical meristem. Sucker growth is observed at the time of topping, 24 hours after topping, one week after topping, two weeks after topping, and three weeks after topping (FIGS. 19 and 20). Expression of SEQ ID NO: 234 driven by Promoter P15 suppresses sucker outgrowth in tobacco.

Additional transformation vectors similar to Promoter P15::YUCCA1 are also created using other auxin biosynthesis and auxin transport genes from *Arabidopsis* such as: PIN-FORMED1 (PIN1; SEQ ID NO: 236); TRYPTOPHAN AMINOTRANSFERASE1/TRANSPORT INHIBITOR RESPONSE2 (TAA1/TIR2; SEQ ID NO: 238); ALDEHYDE OXIDASE1 (AAO1; SEQ ID NO: 240); and INDOLE-3-ACETAMIDE HYDROLASE1 (AMI1; SEQ ID NO: 242). In addition to Promoter P15, several promoters functional in axillary buds (e.g., SEQ ID NOs: 113-118, 148-160, 204, and fragments thereof) are used to drive the expression of auxin biosynthesis and auxin transport genes (e.g., SEQ ID NOs: 234, 236, 238, 240, and 242). Furthermore, tobacco genes homologous to *Arabidopsis* auxin biosynthesis and auxin transport genes (e.g., NtYUCCA-like, SEQ ID NOs:244 and 246; NtPIN1-like, SEQ ID NO:248; NtTAA1/NtTIR2-like, SEQ ID NO:250; NtAAO1-like, SEQ ID NO:252; and NtAMI1-like, SEQ ID NO:254) are included in separate vector constructs with Promoter P15 as well as other promoters (e.g., SEQ ID NOs: 113-118, 148, 160, 204, and fragments thereof) functional in axillary buds.

Each of these vectors is used to generate modified tobacco plants, and to then phenotypically evaluate the tobacco plants, as described in Example 2. The modified tobacco plants exhibit reduced sucker growth compared to control tobacco plants.

TABLE 7

Auxin biosynthesis and auxin transport genes

| SEQ ID NOs (Nucleic Acid/Protein) | Gene Name | Species | Sequence Description | Sequence Source |
|---|---|---|---|---|
| 234/235 | YUCCA1 | *Arabidopsis thaliana* | FLAVIN MONOOXYGENASE | *Plant Cell* 2007, 19: 2430-2439 |
| 236/237 | PIN1 | *Arabidopsis thaliana* | PIN-FORMED1 | *Science* 1998, 282: 2226-2230 |

TABLE 7-continued

| Auxin biosynthesis and auxin transport genes | | | | |
|---|---|---|---|---|
| SEQ ID NOs (Nucleic Acid/Protein) | Gene Name | Species | Sequence Description | Sequence Source |
| 238/239 | TAA1/TIR2 | *Arabidopsis thaliana* | TRYPTOPHAN AMINOTRANSFERASES TRANSPORT INHIBITOR RESPONSE2 | *Cell* 1998, 133: 177-191; *Plant Physiology* 2009, 151: 168-179 |
| 240/241 | AAO1 | *Arabidopsis thaliana* | ALDEHYDE OXIDASE1 | *J Biochem* 1999, 126: 395-401 |
| 242/243 | AMI1 | *Arabidopsis thaliana* | INDOLE-3-ACETAMIDE HYDROLASE | *FEBS J* 2007, 274: 3440-3451 |

SEQUENCE LISTING

```
Sequence total quantity: 256
SEQ ID NO: 1            moltype = DNA  length = 987
FEATURE                 Location/Qualifiers
misc_feature            1..987
                        note = Description of Artificial Sequence: Synthetic
                         polynucleotide
source                  1..987
                        mol_type = other DNA
                        organism = synthetic construct
SEQUENCE: 1
atgtatccgc caagcaacag ctgcaactac agccccattt tcaacatccc ttctccttgt  60
atgcaatatg gagacgaact attcttccaa tattatcctg accatttcct tcaacagcaa  120
caagtgcctt tgatagaaga tcagagtgtt gacatcttag ctgattgcac tgagaatgtt  180
actaacgaag aaactgtcat caatactgat actgtaaaag ttctttatga cacaggagct  240
gttacaaaca gtcagtgttg gggaggaaat gaagaagtag aagaaggccg cgaaaacaaa  300
agaaatgaca tgagaagcac cattagtatt attcatgtac ggaaaaacaa gaaatgttcc  360
aataaagatc gacatagcaa gattaacact gctcgtggcc tcagagaccg aaggatgaga  420
ctttcccttg atgcagctcg caagtttttc agtttacaag acatgttggg gttcgataag  480
gcaagtaaaa ctgtagaatg gttgcttatc aaatcggagt ctgaaatcga agagctagcc  540
aaaggcaata aaggaggagg cattcctaaa caaagctgca gtactactaa tggaattggt  600
gcaattagta ctgcaatatc ctctatttct gagtgtgagg ttatatcagg aactgatgaa  660
tctttctcta ttacttataa aaagaagctg aaaactgcta aaggagcctc gaaaaagacg  720
gctaaaactg ctcgtagagc tgcatttgat cgtcttatta caagggaaac gaggaatcaa  780
gcaagggcta gggctagaga gagaacaaaa ataaagaaaa gcctcggtaa atccaaagag  840
aacagtgctg attactgtaa tttggtggat aattatggag attggagtca atttagtatc  900
ttcaactatc agaaaaatgc agttggaatt tcccatgatc aggtgggttc aataattaaa  960
caacatgatt ttttaggatt tcaatag                                    987

SEQ ID NO: 2            moltype = AA  length = 328
FEATURE                 Location/Qualifiers
REGION                  1..328
                        note = Description of Artificial Sequence: Synthetic
                         polypeptide
source                  1..328
                        mol_type = protein
                        organism = synthetic construct
SEQUENCE: 2
MYPPSNSCNY SPIFNIPSPC MQYGDELFFQ YYPDHFLQQQ QVPLIEDQSV DILADCTENV  60
TNEETVINTD TVKVLYDTGA VTNSQCWGGN EEVEEGRENK RNDMRSTISI IHVRKNKKCS  120
NKDRHSKINT ARGLRDRRMR LSLDAARKFF SLQDMLGFDK ASKTVEWLLI KSESEIEELA  180
KGNKGGGIPK QSCSTTNGIG AISTAISSIS ECEVISGTDE SFSITYKKKL KTAKGASKKT  240
AKTARRAAFD RLITRETRNQ ARARARERTK IKKSLGKSKE NSADYCNLVD NYGDWSQFSI  300
FNYQKNAVGI SHDQVGSIIK QHDFLGFQ                                   328

SEQ ID NO: 3            moltype = DNA  length = 318
FEATURE                 Location/Qualifiers
misc_feature            1..318
                        note = Description of Artificial Sequence: Synthetic
                         polynucleotide
source                  1..318
                        mol_type = other DNA
                        organism = synthetic construct
SEQUENCE: 3
atggctcgct ccttgtgttt catggcattt gcagtcttgg caatgatgct ctttgttgcc  60
tatgaggttc aagctagaga atgcaaaaca gaaagcaata cattccctgg attatgcatt  120
accaaaccac catgcagaaa agcttgtatc agtgagggat ttactgatgg tcattgtagc  180
aaaatcctca gaaggtgcct atgcactaag ccatgtgtgt tcgatgagaa gatgatcaaa  240
acaggagctg aaacttttgc tgaggaagca aaaactttgg ctgcagcttt gcttgaagaa  300
```

```
gagataatgg ataactaa                                                  318

SEQ ID NO: 4            moltype = AA  length = 105
FEATURE                 Location/Qualifiers
REGION                  1..105
                        note = Description of Artificial Sequence: Synthetic
                         polypeptide
source                  1..105
                        mol_type = protein
                        organism = synthetic construct
SEQUENCE: 4
MARSLCFMAF AVLAMMLFVA YEVQARECKT ESNTFPGLCI TKPPCRKACI SEGFTDGHCS  60
KILRRCLCTK PCVFDEKMIK TGAETFAEEA KTLAAALLEE EIMDN                  105

SEQ ID NO: 5            moltype = DNA  length = 1797
FEATURE                 Location/Qualifiers
misc_feature            1..1797
                        note = Description of Artificial Sequence: Synthetic
                         polynucleotide
source                  1..1797
                        mol_type = other DNA
                        organism = synthetic construct
SEQUENCE: 5
atggcttctc ttccccttct caccaccaat gccatctctt catcagcttc ttctttaacc  60
accacacctc tttccaattt gcattcttct cctttcttta caaagacatc aaaagtttcc  120
actatagata agtgcagtaa ctatcgtttc caagtttcat gcaagggtac agaagatgac  180
caaaccatca acacttccaa atcttctgat tcttcaaaca ataagatcat tgatagaaga  240
aacatgctac ttggattagg aggcatttat ggtgctgcta ctcttgttgg tggtcatccc  300
tttgccttcg cggctcctgt gcccggacct gacgtttcca aatgtggtcc tgcagatttg  360
ccaccaggtg cagcaccagt caactgttgt cctccgacaa cggcgaacat catcgacttc  420
caacttccac caccgtcaac caccctccgt acacggccag cagctcattc cgccgatagt  480
gcctatatag agaaattcaa cagagctatt cagctcatga aacaacttcc agataacgat  540
ccacgtagct tcaagcaaca agcaaatgtt cattgtgctt actgtgatgg agcttatgga  600
caactaggtt tcccaagttc tgaactccaa gttcattcct cttggctttt cttccctttc  660
catcgttgtt atctctactt cttcgaaaaa atcttgggaa gtttaataaa tgaccctact  720
ttcgctatcc cattttggaa ctgggatcat cctgatggca tgagacttcc ggccatgtat  780
gcgaaccgta gttcttctct cttcgatcct ctccgtgatc agaagcatca gcctccggtc  840
attgttgatc tcgacttcaa tggagcggat cctaacataa gtaacgctca acaaacttcc  900
cagaatctga caatcatgta taggcaaatg gtctctctag gaagtactcc ggcagctttc  960
ctcggagacc cttaccgtgc cggtggcgaa ccgggtggtg ctgggtccct cgagaacatt  1020
ccacatggaa cggtccatgt ttggaccggt gatagaaccc aacctaattt tgaaaatatg  1080
ggagtttttt atgcagctgg tagagaccct attttctatg ctcatcattc taatattgat  1140
agattgtgga gtgtttggaa aaccctaggt ggaagacgtc aagattttac tgaccctgat  1200
tttttaaatt cttcgttttt gttttacgat gagaaagcac aaatggtacg tattagggta  1260
cgtgactgtt tggatacaac aagacttgga tacgtttatc aaggtgtagt taatccgtgg  1320
ataaattctc gtccaagggc tagggtttca agtgctttga gtagcgtaag gaggcttgct  1380
gaagcaaaag attatttccc aacaaaactt ggccatgtga taagagtaat ggtgaaaagg  1440
ccaaataata aaaagagaaa caaggaggag aaagatgcaa aagaggagtt tttagtggtt  1500
gaagggatag agctggaaac tgatgttttt gtcaagtttg atgtgttgat taatgatgaa  1560
gatgagactg taatttcgcc gaataatgct gagtttgcag gtagttttgt gaacgtgcca  1620
catcttagtc atggtaagag tgacgagaaa cgtaagacta agttgaagtt ggctataact  1680
gagctgctgg aagatttaga tgctgaggat gatgatcatg tggtggtgac ttttgttcca  1740
aagaatggtt ctggtgctgt gaaaattgga ggtgtcaaga ttgtgcttga ggattga     1797

SEQ ID NO: 6            moltype = AA  length = 598
FEATURE                 Location/Qualifiers
REGION                  1..598
                        note = Description of Artificial Sequence: Synthetic
                         polypeptide
source                  1..598
                        mol_type = protein
                        organism = synthetic construct
SEQUENCE: 6
MASLPLLTTN AISSSASSLT TTPLSNLHSS PFFTKTSKVS TIDKCSNYRF QVSCKGTEDD  60
QTINTSKSSD SSNNKIIDRR NMLLGLGGIY GAATLVGGHP FAFAAPVPGP DVSKCGPADL  120
PPGAAPVNCC PPTTANIIDF QLPPPSTTLR TRPAAHSADS AYIEKFNRAI QLMKQLPDND  180
PRSFKQQANV HCAYCDGAYG QLGFPSSELQ VHSSWLFFPF HRCYLYFFEK ILGSLINDPT  240
FAIPFWNWDH PDGMRLPAMY ANRSSSLFDP LRDQKHQPPV IVDLDFNGAD PNISNAQQTS  300
QNLTIMYRQM VSLGSTPAAF LGDPYRAGGE PGGAGSLENI PHGTVHVWTG DRTQPNFENM  360
GVFYAAGRDP IFYAHHSNID RLWSVWKTLG GRRQDFTDPD FLNSSFLFYD EKAQMVRIRV  420
RDCLDTTRLG YVYQGVVNPW INSRPRARVS SALSSVRRLA EAKDYFPTKL GHVIRVMVKR  480
PNNKKRNKEE KDAKEEFLVV EGIELETDVF VKFDVLINDE DETVISPNNA EFAGSFVNVP  540
HLSHGKSDEK RKTKLKLAIT ELLEDLDAED DDHVVVTFVP KNGSGAVKIG GVKIVLED    598

SEQ ID NO: 7            moltype = DNA  length = 1392
FEATURE                 Location/Qualifiers
misc_feature            1..1392
                        note = Description of Artificial Sequence: Synthetic
                         polynucleotide
```

```
source                  1..1392
                        mol_type = other DNA
                        organism = synthetic construct
SEQUENCE: 7
atggtaggca aaagaaatga gcctcatgtc atatttgtac cttacccaag ccaaggtcac  60
attaaccctc ttctccaatt tgcaaaacgc ttatactcca aaggtgtaaa agcaacttta  120
gccactacta aatacacagt caagtctatt aattcaccca acatttcagt tgaagcaatt  180
tctgatggat ttgacgaaag tggtttttcc caagcccaaa aagcagatat atatctcaaa  240
tcattcaaag aaaatggttc aacaactcta tcagaaataa taaaaaatta cgagaattcg  300
acacatccga taagttgcat tgtttatgat tcgtttttac catgggctct tgatgtggct  360
aaaaaacatg ggatttatgg agctgcgttt tttacaaatt cagccactgt ttgtgtagtt  420
tttgctcaca ttcattataa aacattttca ttgccggcga agattgaaga aaatgagcca  480
ttgttattgc ctggattgcc tagtttgtac ccaattgatg ttcctggatt tattagggag  540
cctgaaagtt accctgctta cttagccatg aaaatgagtc aattctctaa tttggaaaat  600
gctgattggg tttttgataa ctcctttcaa gaactagaag gagagatagc aagtggagtt  660
tcaaatattt ggccagcaag gttaattgga ccaatggtgc catcatccta tttagatgac  720
ataatagaag gtgacaaagg gtacggagca agtctatgga aaccacttag tgaagaatgt  780
ctcaaatggc taaaaacaaa gccaaatcaa tcagtaatct acatttcttt tggcagcatg  840
gtatcactca caccacaaca aatggaagaa atggcaaatg ctttaataga cagcaacatg  900
aatttccttt gggttgtaag agaaaccgaa aaaggcaaat tgccaaaaaa attcatagaa  960
tccacaattg gaaaagggtt aattgtgtca tggtgcaatc aattagaaat gctagcaaat  1020
caagccattg gttgttttgt gactcattgt ggatggaatt cgactcttga aggattgagc  1080
cttggcgtgc caatggtggc aatgccacaa tggtctgatc aaatgacgga tgctaaattt  1140
ataggtgaga tttgggaaat tggtgtgagg cctaagttgg ataagtttgg gattgttaga  1200
agagaagagc tattgttttg tttaaaggaa gtaatgggag ggaagaggag ttatgagatt  1260
aggagaaatg ctggaaaatg gaagaacttg gctaagaaag caattagtga aggaggtagc  1320
tcggacaagt ctattaatgt atttgtgaac agtcttagtc tagcatgcca gatgaagaag  1380
tacaagaaat aa                                                     1392

SEQ ID NO: 8            moltype = AA  length = 463
FEATURE                 Location/Qualifiers
REGION                  1..463
                        note = Description of Artificial Sequence: Synthetic
                         polypeptide
source                  1..463
                        mol_type = protein
                        organism = synthetic construct
SEQUENCE: 8
MVGKRNEPHV IFVPYPSQGH INPLLQFAKR LYSKGVKATL ATTKYTVKSI NSPNISVEAI  60
SDGFDESGFS QAQKADIYLK SFKENGSTTL SEIIKNYENS THPISCIVYD SFLPWALDVA  120
KKHGIYGAAF FTNSATVCVV FAHIHYKTFS LPAKIEENEP LLLPGLPSLY PIDVPGFIRE  180
PESYPAYLAM KMSQFSNLEN ADWVFDNSFQ ELEGEIASGV SNIWPARLIG PMVPSSYLDD  240
IIEGDKGYGA SLWKPLSEEC LKWLKTKPNQ SVIYISFGSM VSLTPQQMEE MANALIDSNM  300
NFLWVVRETE KGKLPKKFIE STIGKGLIVS WCNQLEMLAN QAIGCFVTHC GWNSTLEGLS  360
LGVPMVAMPQ WSDQMTDAKF IGEIWEIGVR PKLDKFGIVR REELLFCLKE VMGGKRSYEI  420
RRNAGKWKNL AKKAISEGGS SDKSINVFVN SLSLACQMKK YKK                   463

SEQ ID NO: 9            moltype = DNA  length = 405
FEATURE                 Location/Qualifiers
misc_feature            1..405
                        note = Description of Artificial Sequence: Synthetic
                         polynucleotide
source                  1..405
                        mol_type = other DNA
                        organism = synthetic construct
SEQUENCE: 9
atggcaggga aggttgagaa agtgcttgca gtagtgatgc ttgcaatgct tctgttttcg  60
gagcatttaa tggctgctaa tcatgaaatt aaaacaactg aagataactc tactattagc  120
cctttctgct tagtaaaatg tttatttgga tgtagggggt tgccacctgt acaagcatcc  180
atttgtgctg ctcaatgtta tttaaagtgc cgtgaccaag atgcggccaa tattgctgaa  240
actaagggca taattggtga gactgcatac aaccagtatg atgttggatg tgcccttggc  300
tactgctctg agttcctgtt gaattatgat gagaagaggt tcaagtgctg catggaatac  360
tgccgcgagg acaaaatgat ttgtcctgtt gaggctgcag cttga                 405

SEQ ID NO: 10           moltype = AA  length = 134
FEATURE                 Location/Qualifiers
REGION                  1..134
                        note = Description of Artificial Sequence: Synthetic
                         polypeptide
source                  1..134
                        mol_type = protein
                        organism = synthetic construct
SEQUENCE: 10
MAGKVEKVLA VVMLAMLLFS EHLMAANHEI KTTEDNSTIS PFCLVKCLFG CRGLPPVQAS  60
ICAAQCYLKC RDQDAANIAE TKGIIGETAY NQYDVGCALG YCSEFLLNYD EKRFKCCMEY  120
CREDKMICPV EAAA                                                   134

SEQ ID NO: 11           moltype = DNA  length = 630
FEATURE                 Location/Qualifiers
```

```
misc_feature          1..630
                      note = Description of Artificial Sequence: Synthetic
                       polynucleotide
source                1..630
                      mol_type = other DNA
                      organism = synthetic construct
SEQUENCE: 11
atgaattcaa agaaaaacaa ctcaccaaga aaaaggttga gaaaatatca tacaagaaaa  60
gctcctatta ttagctctta tatggacatg gctgaagcta gaagagaaat tgttcatgct  120
ttacaacttc atcgatcttc atcttcatct ccaactccgt ctattaatag cccaaagaag  180
tacacattat tgggtcaagg agttgtaagc tctcaacaat attactatta ctcaatagtg  240
gaatctatgc ctattcctga accaacatgg tctacaacgg ctccggcaat acttaatgca  300
ctgccaccgc tgccgctgcc gctgccgcca cctccgccgc tgtcttcttc ttccggtgaa  360
gttccagagt ttgaatggtg gatagggttt ttgaagtcgt tggacggcaa gaagagtgct  420
aacaatggtg aagtagtcat agaaaaatat tttcctctag aagaaaatgt tttgatggaa  480
aattcaaaga caggttttgg tcaattagaa catggattaa acagtgagtc tcctaattgt  540
atagataaga atgatgatcc taattaccaa tttccagatg agtggttgat tatccctaca  600
gctgatgatg attatgtact tgagctttaa                                  630

SEQ ID NO: 12         moltype = AA  length = 209
FEATURE               Location/Qualifiers
REGION                1..209
                      note = Description of Artificial Sequence: Synthetic
                       polypeptide
source                1..209
                      mol_type = protein
                      organism = synthetic construct
SEQUENCE: 12
MNSKKNNSPR KRLRKYHTRK APIISSYMDM AEARREIVHA LQLHRSSSSS PTPSINSPKK  60
YTLLGQGVVS SQQYYYYSIV ESMPIPEPTW STTAPAILNA LPPLPLPLPP PPPLSSSSGE  120
VPEFEWWIGF LKSLDGKKSA NNGEVVIEKY FPLEENVLME NSKTGFGQLE HGLNSESPNC  180
IDKNDDPNYQ FPDEWLIIPT ADDDYVLEL                                   209

SEQ ID NO: 13         moltype = DNA  length = 1143
FEATURE               Location/Qualifiers
misc_feature          1..1143
                      note = Description of Artificial Sequence: Synthetic
                       polynucleotide
source                1..1143
                      mol_type = other DNA
                      organism = synthetic construct
SEQUENCE: 13
atgtatccgt caagcaacag ctgtaattac agcctcaata tttcctcctc aaataactta  60
tttcacattc catctccgaa ttctatgcaa tatgaacacg aacttttcca atattttcat  120
gaccatcatc tccttcaacc ccaacaacaa caacaacaac aacaactctt gactacacct  180
gatcattata tggcagcaga ttccaacaaa gacaccgtaa tcagtagtac taatcaagat  240
cctgaagaag ttgaattaca aggccgctgc aagaacaaaa aaggtgacaa taagagacgt  300
gttgcttaca agaaagatag acacagcaag attaacactg ctcacggccc tagagaccga  360
agaatgagac tttctctcga tgtagctcgc aaattttca atttgcaaga cttgcttgga  420
ttcgataagg ctagcaaaac tgtggagtgg ttgctaacaa agtccaaatg tgctgtcaat  480
gagctcgtcc aaggcataaa taaagaaaat tgcgctactg ctaatattgg tgcaattagt  540
acatgctcta ctacatctga gtgtgaagtt gtatcaggaa ttgatgaatc tacaaccact  600
aatgatattc agaagcagtc aaatagaggt aaagtagggg agaagaagaa ggctaataaa  660
ctagttcgta gagctgcatt taatcctgtg gcaaaggaat caagaaagca agctagagcg  720
agggcaaggg agagaacaaa aataaagaaa agctttttaa atattggtga tcagtctatg  780
gcggctgatg atttaaaacg attaggatgt tggagtcttt ttgaaacagg tgaagaatca  840
ggtattcaag gtactaatca tcaaattgaa gaacacacca cgcaccacga ggagcctctt  900
ttggggacta atgagaatgt tgatgattgt aatttggttg ttaccggcaa ctggaaccca  960
tataccatct tcaattatca ccacagtact gaaatttctc acgaggtagg ttttacactt  1020
catttaaatc caagagtaat tcttttagag ttcaagattc tgatattttt tttggtggcg  1080
agacccttc ttatatcaaa gcaaccttca aggtacatac aagattggat aaaccaattc  1140
tga                                                               1143

SEQ ID NO: 14         moltype = AA  length = 380
FEATURE               Location/Qualifiers
REGION                1..380
                      note = Description of Artificial Sequence: Synthetic
                       polypeptide
source                1..380
                      mol_type = protein
                      organism = synthetic construct
SEQUENCE: 14
MYPSSNSCNY SLNISSSNNL FHIPSPNSMQ YEHELFQYFH DHHLLQPQQQ QQQQQLLTTP  60
DHYMAADSNK DTVISSTNQD PEEVELQGRC KNKKGDNKRR VAYKKDRHSK INTAHGPRDR  120
RMRLSLDVAR KFFNLQDLLG FDKASKTVEW LLTKSKCAVN ELVQGINKEN CATANIGAIS  180
TCSTTSECEV VSGIDESTTT NDIQKQSNRG KVGEKKKANK LVRRAAFNPV AKESRKQARA  240
RARERTKIKK SFLNIGDQSM AADDLKRLGC WSLFETGEES GIQGTNHQIE EHTTHHEEPL  300
LGTNENVDDC NLVVTGNWNP YTIFNYHHST EISHEVGFTL HLNPRVILLE FKILIFFLVA  360
RPFLISKQPS RYIQDWINQF                                             380
```

```
SEQ ID NO: 15          moltype = DNA  length = 915
FEATURE                Location/Qualifiers
misc_feature           1..915
                       note = Description of Artificial Sequence: Synthetic
                        polynucleotide
source                 1..915
                       mol_type = other DNA
                       organism = synthetic construct
SEQUENCE: 15
atggaaaagg ttcatgagaa accgctatct ctttataatg gatcattatc tgtttttaga  60
ttaggagatt tggctgtgaa aataacaaag gtgaaaaagg gatcattaaa taatgataat  120
ctttcacccc caacttcatt gttagttgtt tcaccaatca taccaggaac ttatccagtt  180
ttactctttt ttcatggctt cgttctcaag cctatatggt acaagtctct ccttcaacat  240
atttcttccc acggctatat agttgttgct ccacaggttt ctcaaagcga agaagtgaaa  300
aaagcagcca aagttacaga atggttaagt aaagccctcg aatccgtact gccggagaaa  360
gtacagccgg atctactcca gctcgccgtc tccggccaca gcagaggtgg taaaatagca  420
tttgcactag ctttaggata tggcatcaaa tttcaagcac ttctaggaat tgatccagtt  480
gcaggttttt ctccgtccaa ccgatctgct ccaaaaattc ttaaatatat tcctcgtatt  540
ttcgatcaga cggtccctgt ggcggtgatc ggcgctggct tgtcaaacca aagtgcgaat  600
tgtatctttc caccettcgc accaaacggt gtcaaccatt cggagttttt taacgagtcc  660
aaaccacctt gctgttattt tctggctaaa aattatggac atactgatat gttagatgac  720
agaattgctg caattgcgag ttggatttca aagagtggga agggacccaa ggaccttatg  780
agaaaggctg ttggagggat tgttgtggct ttcttgagg ctaaattggg agagaaagtg  840
gataatctaa atgccattgt tcaagaacct tctcttgctc ccatcatcct tgacccagtc  900
atatctgtca aataa                                                   915

SEQ ID NO: 16          moltype = AA  length = 304
FEATURE                Location/Qualifiers
REGION                 1..304
                       note = Description of Artificial Sequence: Synthetic
                        polypeptide
source                 1..304
                       mol_type = protein
                       organism = synthetic construct
SEQUENCE: 16
MEKVHEKPLS LYNGSLSVFR LGDLAVKITK VKKGSLNNDN LSPPTSLLVV SPIIPGTYPV  60
LLFFHGFVLK PIWYKSLLQH ISSHGYIVVA PQVSQSEEVK KAAKVTEWLS KALESVLPEK  120
VQPDLLQLAV SGHSRGGKIA FALALGYGIK FQALLGIDPV AGFSPSNRSA PKILKYIPRI  180
FDQTVPVAVI GAGLSNQSAN CIFPPFAPNG VNHSEFFNES KPPCCYFLAK NYGHTDMLDD  240
RIAAIASWIS KSGKGPKDLM RKAVGGIVVA FLEAKLGEKV DNLNAIVQEP SLAPIILDPV  300
ISVK                                                               304

SEQ ID NO: 17          moltype = DNA  length = 1353
FEATURE                Location/Qualifiers
misc_feature           1..1353
                       note = Description of Artificial Sequence: Synthetic
                        polynucleotide
source                 1..1353
                       mol_type = other DNA
                       organism = synthetic construct
SEQUENCE: 17
atgtgtttgt taataaaggt ggcgaatcca ggagaatccg gcgagcatga cagaattcca  60
tcaacgggag gtgattcaga aagtacaact actaccacag aaggaggaat tccgcagcta  120
tatgaacaat tacaatcaca atcacaatca tttgaagaaa tgttgcggca acaaatacaa  180
caagaaacag agtatttgat gtcttcatct gcaactccta tgttttcacg gtatagtcag  240
acaagggaga tgtcggcaat ggtaacggcg ttaacgcatg tggtatcagg acggagagag  300
ggagagtgga cttacaggcc ggatattagt gccggcgctg ttacgacgtc gtttgctggt  360
ggttcgagta tttattcggc gagttcgccg tcgtcttcaa gttcagggtc atgggctgga  420
cagaagagaa gacgtgatca agaagaaagt gttgctgcag agcaagttca aagggtttat  480
ggagcttttg gtgaatttag aggtggagaa tcatcttcct ctgttaaaac tgaagaagct  540
tcaagcatgg tagcaccacc aaccaccacc agcactacca ccacaaccac cacggcggcg  600
caaacaccac cagaaccagc ggaaggagga ggagctgaag aaacagggga aaggaggagg  660
agatacagag gagtaagaca aaggccatgg ggaaaatggg cagcagaaat aagagatcca  720
cacaaagcag ctagagtttg gttaggcaca tttgatacag ctgaagctgc tgctagagct  780
tatgatgaag ctgcccttag attcagagga aacagagcta aactcaattt ccccgaaaat  840
gtccgcatat taccacaaca acaacagcaa caacctcaag ccacaacaag atcagccatt  900
tccagctcct ccgcagcttc acaattccca ttaatggctg cagcaacaac tccatcacca  960
tttttccaaa cttatcaacc tcagcagcag cagctgcctt ttcagagttc agaaatggtt  1020
agagattatt gggaatactc acagttactt caaaatccag gagagtttca tttacaacaa  1080
cagccttcag ccttgttaga gcaaatgttg tttgcttctt catcaatggg tcttttgcaa  1140
tcacacacat tcccttctta ttcttcatct tcctcattag ctacttcctc tgcagcttct  1200
tcccctgcat atcccctgtt ttactctgct caacaatcac gtttctttca gcccccacaa  1260
agtactcatc aaaatcaaac tagtagcagc agctccagtt ttcctgcacc attttggact  1320
agttcaaccc actacccacc ttcttctagt taa                               1353

SEQ ID NO: 18          moltype = AA  length = 450
FEATURE                Location/Qualifiers
REGION                 1..450
```

```
                         note = Description of Artificial Sequence: Synthetic
                          polypeptide
source                   1..450
                         mol_type = protein
                         organism = synthetic construct
SEQUENCE: 18
MCLLIKVANP GESGEHDRIP STGGDSESTT TTTEGGIPQL YEQLQSQSQS FEEMLRQQIQ  60
QETEYLMSSS ATPMFSRYSQ TREMSAMVTA LTHVVSGRRE GEWTYRPDIS AGAVTTSFAG  120
GSSIYSASSP SSSSSGSWAG QKRRRDQEES VAAEQVQRVY GAFGEFRGGE SSSSVKTEEA  180
SSMVAPPTTT STTTTTTTAA QTPPEPAEGG GAEETGERRR RYRGVRQRPW GKWAAEIRDP  240
HKAARVWLGT FDTAEAAARA YDEAALRFRG NRAKLNFPEN VRILPQQQQQ QPQATTRSAI  300
SSSSAASQFP LMAAATTPSP FFQTYQPQQQ QLPFQSSEMV RDYWEYSQLL QNPGEFHLQQ  360
QPSALLEQML FASSSMGLLQ SHTFPSYSSS SSLATSSAAS SPAYPLFYSA QQSRFFQPPQ  420
STHQNQTSSS SSSFPAPFWT SSTHYPPSSS                                   450

SEQ ID NO: 19            moltype = DNA  length = 732
FEATURE                  Location/Qualifiers
misc_feature             1..732
                         note = Description of Artificial Sequence: Synthetic
                          polynucleotide
source                   1..732
                         mol_type = other DNA
                         organism = synthetic construct
SEQUENCE: 19
atggcacatt tcttctctat aaattcaacg ttagcaggaa cgaataaagc atccaaaaca  60
aatttcacat attcaactca agaaacagaa aaaccaaaaa taaagatcat cttactcttg  120
ttttctcttg cattagttcc cttgtcagcg atggcaactt gcaccactga tactccaaac  180
caagcactat tgagggatgt acacgatata gatggtaacc cccttcaagt aaaagccagg  240
tacttcatat ttccagttat tggcggtggt ggtgtacggc ttgctaatct tggagatcaa  300
gacgaaaacg cttgtgccac agcggtggtg ctatcacgca gtgaagttga caaaggtaaa  360
gcagtcaact tcatacctaa agaccccaaa catgagaaga ttgtggaggc ctcttcagta  420
aacatccagt tttatcttga ttattataag tgtgctaacc taactgtgtg gaaagtagac  480
aactacccta cacttccaag tcgctacacc ataagcacag gtgcaacgcc gggaaatccc  540
ctagagttga atagctggtt tcaaattatg tctcttggtg gctcgacgta taagatagtc  600
ttctgtccct ttggagaatg ccaaaatgtt ggcattgccg aggaaaatgg atataatcgt  660
ttggttctcg cagagaatgc aaaggccttt gttttcataa agcaaggcgg atatggaaag  720
gccgaagcat ga                                                      732

SEQ ID NO: 20            moltype = AA  length = 243
FEATURE                  Location/Qualifiers
REGION                   1..243
                         note = Description of Artificial Sequence: Synthetic
                          polypeptide
source                   1..243
                         mol_type = protein
                         organism = synthetic construct
SEQUENCE: 20
MAHFFSINST LAGTNKASKT NFTYSTQETE KPKIKIILLL FSLALVPLSA MATCTTDTPN  60
QALLRDVHDI DGNPLQVKAR YFIFPVIGGG GVRLANLGDQ DENACATAVV LSRSEVDKGK  120
AVNFIPKDPK HEKIVEASSV NIQFYLDYYK CANLTVWKVD NYPTLPSRYT ISTGATPGNP  180
LELNSWFQIM SLGGSTYKIV FCPFGECQNV GIAEENGYNR LVLAENAKAF VFIKQGGYGK  240
AEA                                                                243

SEQ ID NO: 21            moltype = DNA  length = 471
FEATURE                  Location/Qualifiers
misc_feature             1..471
                         note = Description of Artificial Sequence: Synthetic
                          polynucleotide
source                   1..471
                         mol_type = other DNA
                         organism = synthetic construct
SEQUENCE: 21
atggctgagc aacaccagcg ccaccagcaa cagcagcagc agcagcagat gcaagtgggc  60
cacccgacgg aggcaatcaa gagccttctt cctcaaaggg gtccctctaa atcccaagtc  120
cttgctgtcg tcactctctt ccctgttggt ggggccctcc tctgccttgc tggactgacg  180
ctcgccggaa ctctgatcgg gcttgcagtc gctacgccgg ttttcttact gttcagcccg  240
gttttggtcc ccgctgccct gacaatcgcg ttggccgtca ctggattctt gacttccggc  300
gcctttggaa taacggcgct gtcgtcgctc tcgtggatca ttaactatat gaggagaatc  360
acaggtccag cagcagagca gatggagcat gcaaagcgga gggtgcagga cactgctggt  420
catatgggac agagaggtgg acagaagatt caagaaactg ctagaacttg a           471

SEQ ID NO: 22            moltype = AA  length = 156
FEATURE                  Location/Qualifiers
REGION                   1..156
                         note = Description of Artificial Sequence: Synthetic
                          polypeptide
source                   1..156
                         mol_type = protein
                         organism = synthetic construct
```

```
SEQUENCE: 22
MAEQHQRHQQ QQQQQQMQVG HPTEAIKSLL PQRGPSKSQV LAVVTLFPVG GALLCLAGLT  60
LAGTLIGLAV ATPVFLLFSP VLVPAALTIA LAVTGFLTSG AFGITALSSL SWIINYMRRI  120
TGPAAEQMEH AKRRVQDTAG HMGQRGGQKI QETART                            156

SEQ ID NO: 23          moltype = DNA  length = 1437
FEATURE                Location/Qualifiers
misc_feature           1..1437
                       note = Description of Artificial Sequence: Synthetic
                        polynucleotide
source                 1..1437
                       mol_type = other DNA
                       organism = synthetic construct
SEQUENCE: 23
atggatagtg ataggaggga ttgccacttg aacatgttgt ccaaaatggc tatgtgcaaa  60
tcacacgggc aagactcttc ctatttcata ggatggcaag aatatgagaa gaacccttat  120
catcccattc aaaatccttc tggtattatt cagatgggtc ttgctgagaa tcagctctca  180
ttcgatcttc ttgaatcatg gctcacaaga aaccaagatg taatccagtt tagagaaaat  240
ggaggatcta tgttcagaga cttggctctt ttccaagatt atcatggatt gcaggctttc  300
aagaacgtac tagtgtcatt catgggtgag atcagaagaa ggaaagtaaa atttgatcca  360
gagaagctag tactcacagc tggttcaact tcagcaaacg aaaccctcat attttgctta  420
gctgaacctg gagaagctct ccttcttcca actccttatt atccagggtt tgatagagat  480
ctaaaatgga gaacaggggc tgaaattgta cccatacact gctacagttc aaataacttc  540
agaataactg agtctgccct tgaagatgca tatgaagaag cccaacgact taatttaaga  600
gtcaagggtg tatttatcac aaatccttca aatccactag ggacaaccat gtcacgagac  660
gaattaaaca atcttatcac ctttgccatg gccaaaaata ttcatatagt tagcgacgaa  720
atatacgctg gaacagtttt cgattcgcca aaattcataa gcataatgga agctttaatt  780
gacagaaaac atgaaaaatc caaaatgtgg agtcaagttc acattgtgtc aagtctatca  840
aaagatctag gtctaccagg tttcagaatt gggatgattt attcaaacaa tgaaactctt  900
atagctgctg ctacaaaaat gtcaagtttt ggactcattt catctcaaac tcagtatcta  960
ctatctaaaa ttcttggaga taaaaaattt ataaaacgtt acattaaaga aaacaagaaa  1020
ggattgaaaa agaggaggga aatgcttgtt tccgggttag agaatagtgg gattgagtgt  1080
ttgaaaagta atgctggatt attttgtttt gtggacatga ggcatttgct aaattcaaac  1140
acatttgaag cagaaatgga actgtggaga aaaatactac taagtgatgt tggtttaaat  1200
gtgtctcctg gatcttcttg tcactgtagt gaacctggtt ggtttaaaat ttgttttgca  1260
aatattgccg aagaaactct tgatctcgcg atgcagagga ttaatgattt tgtcagttct  1320
atgaatcttc aacggcgaca gctgatcgcg gcggcgtcgg cgtctagctc aaggaggagg  1380
acacttgcga actgggttgt taagttatct tcaggtgaag gaaaaacata tcgttaa     1437

SEQ ID NO: 24          moltype = AA  length = 478
FEATURE                Location/Qualifiers
REGION                 1..478
                       note = Description of Artificial Sequence: Synthetic
                        polypeptide
source                 1..478
                       mol_type = protein
                       organism = synthetic construct
SEQUENCE: 24
MDSDRRDCHL NMLSKMAMCK SHGQDSSYFI GWQEYEKNPY HPIQNPSGII QMGLAENQLS  60
FDLLESWLTR NQDVIQFREN GGSMFRDLAL FQDYHGLQAF KNVLVSFMGE IRRRKVKFDP  120
EKLVLTAGST SANETLIFCL AEPGEALLLP TPYYPGFDRD LKWRTGAEIV PIHCYSSNNF  180
RITESALEDA YEEAQRLNLR VKGVFITNPS NPLGTTMSRD ELNNLITFAM AKNIHIVSDE  240
IYAGTVFDSP KFISIMEALI DRKHEKSKMW SQVHIVSSLS KDLGLPGFRI GMIYSNNETL  300
IAAATKMSSF GLISSQTQYL LSKILGDKKF IKRYIKENKK GLKKRREMLV SGLENSGIEC  360
LKSNAGLFCF VDMRHLLNSN TFEAEMELWR KILLSDVGLN VSPGSSCHCS EPGWFKICFA  420
NIAEETLDLA MQRINDFVSS MNLQRRQLIA AASASSSRRR TLANWVVKLS SGEGKTYR    478

SEQ ID NO: 25          moltype = DNA  length = 645
FEATURE                Location/Qualifiers
misc_feature           1..645
                       note = Description of Artificial Sequence: Synthetic
                        polynucleotide
source                 1..645
                       mol_type = other DNA
                       organism = synthetic construct
SEQUENCE: 25
atgaacggtg gttcatgtgg tggtgctgat cgtgagtata ataacaataa caacaataat  60
gttgtaggtg gaggaggtgg cgggccttgt ggtgcatgca agtttcttag aagaaaatgt  120
gtgaggggat gcatatttgc accttatttt gattctgatc aaggcactgc tcatttcgct  180
gctgtacata aggtgtttgg tgctagcaat gcctctaaat tgctgctcag aattccagcg  240
cataaacgtc tggatgctgt cgttacactt tgctatgagg ctcttgctag agttagagac  300
cctatctatg gttgtgttgc tcacatcttt actcttcagc aacaggttgt aactttgcaa  360
gctgagttag catatgttca agcccgcctt tctaccctac cacacctacc tatgcgacaa  420
agtccaatta caccaacagg gctgcaatca tcttcagata tcttctgcac tacttcaagc  480
atatcatctt caagtaataa tatggaatat cctcaatttg acataactgc gggtttaagt  540
gattcgttcg atgaaaaaga actggagaac tttgagctcc atacattagc acgagagttg  600
gtttctagac acttacctgg agttagattt agaccttcac cataa                  645

SEQ ID NO: 26          moltype = AA  length = 214
```

```
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 26
MNGGSCGGAD REYNNNNNNN VVGGGGGGPC GACKFLRRKC VRGCIFAPYF DSDQGTAHFA  60
AVHKVFGASN ASKLLLRIPA HKRLDAVVTL CYEALARVRD PIYGCVAHIF TLQQQVVTLQ  120
AELAYVQARL STLPHLPMRQ SPITPTGLQS SSDIFCTTSS ISSSSNNMEY PQFDITAGLS  180
DSFDEKELEN FELHTLAREL VSRHLPGVRF RPSP                              214

SEQ ID NO: 27          moltype = DNA  length = 2205
FEATURE                Location/Qualifiers
misc_feature           1..2205
                       note = Description of Artificial Sequence: Synthetic
                        polynucleotide
source                 1..2205
                       mol_type = other DNA
                       organism = synthetic construct
SEQUENCE: 27
atgtcggata aaaaatctgt ctcgacgcca tttgaatgtt gcagaatctt gtttaagttt  60
ctgctgttta tggttattat cagtaatgtg gcgatccatg taacagcttt gagtgggcga  120
gaaggaataa ccccaagtac ggaatggggt ttggggcctc tggtgaagag aggagaaaga  180
aaactagtag tttcaactga aaatggggag gtctcttcag tcagagtagc tgatggaatc  240
accggttcct atcatcttca gttcatcaca ttggagccca attccctctt ccttcctgtt  300
gttctacatg cagatatggt cttctatgtc cacactgggt cgggaaggct gacttggatg  360
gatgaaactg aacaaaagtc agtggattta agaattggag atgttttcag gttgcccttt  420
ggaactattt tcttcataga gagcaactta gagcctgcgc gacagaaact tagagtttat  480
tccatcttta ccaattcagg ggatgatttg agagagccgt tgtccggacc acactctagc  540
atccgtgata tggttcttgg attcgatagg aaagttctcc aggcggcatt tcatgtacca  600
gaggatgtga tagatgaagt gttgaatggg acagaagtac cagccatcat acatggtgtg  660
cccaagacaa caaaaaagac cctgtgggaa atggaggctc aattcatgaa aagtcttcta  720
ggaaggggtg gtcacggttt ctttgactcc caaagcaata aaaagaagac tgaattgttc  780
aatattttca aagagaaacc agattttgag aattgcaatg gctggagcac tgtaattaca  840
cggaaaaaat tacccgcatt aaagggttcc cacattggta tttatgtagt gaacttaacc  900
aagggatcaa tgatggcgcc acactggaat ccaacggcaa ctgaaatagg aatagcattg  960
caaggagaag gaatggtaag ggtagtttgc tcaagcacgg gaacaaagca aggatgccaa  1020
aacatgaggt ttaaggtgga agaaggagat gtatttgcag tgccaaggtt tcgtcctatg  1080
gctcaaatgg ctttcaacaa caactcattt gtctttgttg gttttagtac aactacaaag  1140
agacatcatc ctcagtacct aacagggaag gcttcagtcc tccgaacact ggataggcaa  1200
atcttggcag cttcctttaa tgtgactaac acaacaatgg atcggattct ggaggcacag  1260
ggtgagtcag tcatactgga gtgtacttct tgtgctgaag aagaagtgag attaatggag  1320
gaagaaagga ggagggcaga ggaggaagaa aggagaaggg aagaagagga ggcaaggcag  1380
agggaggaag aaaggaggag ggaagaagag gaagctagaa ggaaggaaga ggaagaagca  1440
aggaaggctg aagaagaaag aagaaagaga gaggcagaag aagcaagaag acgagaagag  1500
gaggcaacaa gggagaaaga ggaacaaagg aggagacaag aagaagaagc caggagaagg  1560
gaagaggagg aagccagaag gcaagaagaa gaaatcagaa ggagacaaga agaaggggaa  1620
gctaggaaga gagaagagga agaagcagct agaaggcaac aggaggaaga agctgagaga  1680
gaggcagaag aagcgaggac aagagaagag gaagaggcag ctagaaggca gcagggggaa  1740
gaagcacaaa gggaggcaga ggaagcaaga aggagagagg aagaagcagc aaggaggagg  1800
gaggaacaag cgcagagaga ggcggaggaa gcaagtagga gagaggagga agcagcagct  1860
agaaggagac aggaacgaga ggaagcagaa agggaaagac aagcagagga agccaggagg  1920
gagggagagg aaacaaggag acatgaagaa gaagaagaag aagaagagga ggaggaggaa  1980
acaaggagag gagagagggg agaggaggag gaggaaggag gaagaaaaga agaggaggcg  2040
gcaagagagg ccgagaaaag aaggcaagaa gaagcccaga gacaacaaga agcagctagg  2100
agacaggaag aagaaatgga aagaaggcat caagaagaag aaaccgagga agaggagcag  2160
ggtccttacg cacggaggaa aagaacattc cttaaaacag catga                  2205

SEQ ID NO: 28          moltype = AA  length = 734
FEATURE                Location/Qualifiers
REGION                 1..734
                       note = Description of Artificial Sequence: Synthetic
                        polypeptide
source                 1..734
                       mol_type = protein
                       organism = synthetic construct
SEQUENCE: 28
MSDKKSVSTP FECCRILFKF LLFMVIISNV AIHVTALSGR EGITPSTEWG LGPLVKRGER  60
KLVVSTENGE VSSVRVADGI TGSYHLQFIT LEPNSLFLPV VLHADMVFYV HTGSGRLTWM  120
DETEQKSVDL RIGDVFRLPF GTIFFIESNL EPARQKLRVY SIFTNSGDDL REPLSGPHSS  180
IRDMVLGFDR KVLQAAFHVP EDVIDEVLNG TEVPAIIHGV PKTTKKTLWE MEAQFMKSLL  240
GRGGHGFFDS QSNKKKTELF NIFKEKPDFE NCNGWSTVIT RKKLPALKGS HIGIYVVNLT  300
KGSMMAPHWN PTATEIGIAL QGEGMVRVVC SSTGTKQGCQ NMRFKVEEGD VFAVPRFRPM  360
AQMAFNNNSF VFVGFSTTTK RHHPQYLTGK ASVLRTLDRQ ILAASFNVTN TTMDRILEAQ  420
GESVILECTS CAEEEVRLME EERRRAEEEE RRREEEEARQ REEERRREEE EARRKEEEEA  480
RKAEEERRKR EAEEARRREE EATREKEEQR RRQEEEARRR EEEEARRQEE EIRRRQEEGE  540
ARKREEEEAA RRQQEEEAER EAEEARTREE EEAARRQQGE EAQREAEEAR RREEEAARRR  600
```

```
EEQAQREAEE ASRREEEAAA RRRQEREEAE RERQAEEARR EGEETRRHEE EEEEEEEEE  660
TRRGERGEEE EEGGRKEEEA AREAEKRRQE EAQRQQEAAR RQEEEMERRH QEEETEEEEQ  720
GPYARRKRTF LKTA                                                   734

SEQ ID NO: 29          moltype = DNA  length = 1302
FEATURE                Location/Qualifiers
misc_feature           1..1302
                       note = Description of Artificial Sequence: Synthetic
                        polynucleotide
source                 1..1302
                       mol_type = other DNA
                       organism = synthetic construct
SEQUENCE: 29
atgggcgtac cagaatcgga ggtggtgtca caaggtgagg ttgaatcacc attgcaacca  60
gatcaaaacc agcacaagaa ccatcagttc ccgtccctcg gtagacaagc atcgatctac  120
tccctcactc tcgacgaatt ccaacacacc ctatgtgaaa gtggcaagaa tttcgggtcg  180
atgaatatgg atgaattcct taacagcatt tggactgctg aagaaaacca agcccacgca  240
cacgcccatg cccatgccgc gcacgggcat gcgcacgcgc attctcatgc tcatagccaa  300
gcaccaagta caggggaagc cactagcaca ccacattttg cgataggaca gagcaatgtt  360
tcaatggaga aagctattgc caagcagcca agcttgccaa gacagggttc tcttacgctt  420
ccggaacctt tgtgtcggaa aactgtggat gaagtttggt cagaaattca taagagccaa  480
aaagagcaac atcagaataa tgggggcagt gtcccggaca cgggtaattc cgctcaacgg  540
caggttacat ttggcgaaat gacacttgag gatttcttgg tcaaagcagg ggtagtacgc  600
gaacaggaga atgcccctgc acctcctcaa cagcaatcat atatgatgta tcaaaacagc  660
aacaatcccg ctatggccaa tatggctcga cctgttattg gcttaggtgg agtcacgggc  720
agcgttggag ttggcattcc tagctatcca ccacttcctc agaccggggt ggttgaggcc  780
ccaatatacc cggtaagtat gaaaaggggt gccggattcc cacaacagcc aacggctgtt  840
tacggcggga gaatggggaa tggtggcggg gtcgggtatg ggcaagtaca aggagtggcc  900
gggatggggt cgccactaag tccagtgtcg tcggatggat tatgcgttaa tcaagtcgat  960
agcgggggtc aatacgggtt ggaaatggga atgagaggag gaagaaaacg cataatagat  1020
ggtccggtag agaaagtggt ggaaaggagg caaaggagaa tgatcaagaa tagagaatca  1080
gcagcaagat caagagcaag aaagcaggct tacacagtag aacttgaggc agaactgaac  1140
cagctaaaag aagagaatgc acatctgaaa caggccctgg cggagctcga gaggaaaagg  1200
aaacaacagt actttgacga agggaaaatg aaagtgcaaa cgaaagcgca aaaggcgact  1260
aacaaattga gaggtatgag gaggagtttg agttgccctt ga                    1302

SEQ ID NO: 30          moltype = AA  length = 433
FEATURE                Location/Qualifiers
REGION                 1..433
                       note = Description of Artificial Sequence: Synthetic
                        polypeptide
source                 1..433
                       mol_type = protein
                       organism = synthetic construct
SEQUENCE: 30
MGVPESEVVS QGEVESPLQP DQNQHKNHQF PSLGRQASIY SLTLDEFQHT LCESGKNFGS  60
MNMDEFLNSI WTAEENQAHA HAHAHAAHGH AHAHSHAHSQ APSTGEATST PHFAIGQSNV  120
SMEKAIAKQP SLPRQGSLTL PEPLCRKTVD EVWSEIHKSQ KEQHQNNGGS VPDTGNSAQR  180
QVTFGEMTLE DFLVKAGVVR EQENAPAPPQ QQSYMMYQNS NNPAMANMAR PVIGLGGVTG  240
SVGVGIPSYP PLPQTGVVEA PIYPVSMKRG AGFPQQPTAV YGGRMGNGGG VGYGQVQGVA  300
GMGSPLSPVS SDGLCVNQVD SGGQYGLEMG MRGGRKRIID GPVEKVVERR QRRMIKNRES  360
AARSRARKQA YTVELEAELN QLKEENAHLK QALAELERKR KQQYFDEGKM KVQTKAQKAT  420
NKLRGMRRSL SCP                                                    433

SEQ ID NO: 31          moltype = DNA  length = 1266
FEATURE                Location/Qualifiers
misc_feature           1..1266
                       note = Description of Artificial Sequence: Synthetic
                        polynucleotide
source                 1..1266
                       mol_type = other DNA
                       organism = synthetic construct
SEQUENCE: 31
atggaggaaa aagatgaact tgaggaagaa gaagaatatg ttgatgatga aatcaagaac  60
aatttaccag tccaaaactc atcttcaata agttggttca caaaaaatgat atctttacaa  120
gtagagatct tcaccactat cttagtttcc cccatttttct atatcctctc ttttgtatct  180
gacttcaact tcctccgccc tgaagaaacc gaaaagaacg tagctgtagc tgtaaatgct  240
gctgctacag taccttcaaa agtagtacat ggaagtactt tactgctcaa gaaatttggt  300
gttggaattc ttggagctgc ttatgttgga atggttttga caacgttgtt gattttgtcg  360
ggggttctgg gatttgggtt agtgagaatg tgggcggaag agcctgtggt attgagagag  420
aagctgtatt ttgattatgc agatgtttat cctaaggctg ttttttcttt tgctgaatat  480
ggtctggaga attataacca taattttatg atgttgaagc agaagaagaa ttttggtgtg  540
ccagttgggc atacaatgta tgtttctttg tttctactga tgcctgaatc tgatttcaac  600
agagatattg gtgttttcca gttggttgca gaagcgttat cagccgaggg gatcataatg  660
gcaagatcaa gtcatccacg tatgttgcga ttcagaagcc tgccaatccg tctcatgcga  720
gaatttatta tgagtgtgcc cctagtactt ggacttacag ctgaaacaca aaggatgatc  780
attccaatgt taaagcataa ggaaggtatt ccaagaacag aggcaatcaa aataactatg  840
atacctcgag ctggaacgct agccctgccg cagctttatc aatcggagat catattgaag  900
tctcatcctc cttggtataa agacttggca tacaagtgga aatggacatt ctccgtctgg  960
```

```
acctctatgt atatgtatgt tacactgctc ataattctac tcaactggtg cagaccgctc  1020
gtatttccag tgatcgcaac aagctttagg acacgcgttg atgagagttt aacagtggaa  1080
gcatcagaag aaccacaaga gaaagctcga gaagaaagtg atgtgtcgga gtcggtaaga  1140
agatggcggc agagcagaag aaagaggaag gcaatgcttc aacagagtgt ctcgccagag  1200
ttcgcggatg attctgcatc aagcatttct gtgactaggg aggatacagc tgagtcaagc  1260
gagtaa                                                            1266

SEQ ID NO: 32          moltype = AA  length = 421
FEATURE                Location/Qualifiers
REGION                 1..421
                       note = Description of Artificial Sequence: Synthetic
                        polypeptide
source                 1..421
                       mol_type = protein
                       organism = synthetic construct
SEQUENCE: 32
MEEKDELEEE EEYVDDEIKN NLPVQNSSSI SWFTKMISLQ VEIFTTILVS PIFYILSFVS  60
DFNFLRPEET EKNVAVAVNA AATVPSKVVH GSTLLLKKFG VGILGAAYVG MVLTTLLILS  120
GVLGFGLVRM WAEEPVVLRE KLYFDYADVY PKAVFSFAEY GLENYNHNFM MLKQKKNFGV  180
PVGHTMYVSL FLLMPESDFN RDIGVFQLVA EALSAEGIIM ARSSHPRMLR FRSLPIRLMR  240
EFIMSVPLVL GLTAETQRMI IPMLKHKEGI PRTEAIKITM IPRAGTLALP QLYQSEIILK  300
SHPPWYKDLA YKWKWTFSVW TSMYMYVTLL IILLNWCRPL VFPVIATSFR TRVDESLTVE  360
ASEEPQEKAR EESDVSESVR RWRQSRRKRK AMLQQSVSPE FADDSASSIS VTREDTAESS  420
E                                                                 421

SEQ ID NO: 33          moltype = DNA  length = 597
FEATURE                Location/Qualifiers
misc_feature           1..597
                       note = Description of Artificial Sequence: Synthetic
                        polynucleotide
source                 1..597
                       mol_type = other DNA
                       organism = synthetic construct
SEQUENCE: 33
atgtataact caagcaacta cagctgtaat tacaacccca ttttctcatc taatttattc  60
aacatccctt ctccttgtat gcaatatgaa cacgaacttt tcttccaata ttaccatgat  120
caacttcaac agaatcttga cgatacctta gctgagatca gtactgagac tgccattatt  180
aacacggcag attccagcaa agacgaggct ataatcagta gaaatgaact tgaacaagat  240
caggaagcgc gtaagaataa aaagggtaaa gtaagcagca acaagagagt gtctaagaaa  300
gatagacaca gcaagattaa cactgctaaa ggcccgagag accgaagaat aagactttca  360
attgatattg ctcgcaattt tttcaattta caagacatgt tgaggttcga gaaggccagc  420
aaaactctgg agtggttgct tataaagtca aaatctgata tcaaggagct ctccaaaagt  480
cgaataagca aattaagatg tagtactgtt atgggtgcaa atagtgaaac ctccacttct  540
gaatgtgaag ttgtatcagg aattgatgaa tctccatcca atcaaggcaa atgctaa     597

SEQ ID NO: 34          moltype = AA  length = 198
FEATURE                Location/Qualifiers
REGION                 1..198
                       note = Description of Artificial Sequence: Synthetic
                        polypeptide
source                 1..198
                       mol_type = protein
                       organism = synthetic construct
SEQUENCE: 34
MYNSSNYSCN YNPIFSSNLF NIPSPCMQYE HELFFQYYHD QLQQNLDDTL AEISTETAII  60
NTADSSKDEA IISRNELEQD QEARKNKKGK VSSNKRVSKK DRHSKINTAK GPRDRRIRLS  120
IDIARNFFNL QDMLRFEKAS KTLEWLLIKS KSDIKELSKS RISKLRCSTV MGANSETSTS  180
ECEVVSGIDE SPSNQGKC                                               198

SEQ ID NO: 35          moltype = DNA  length = 1038
FEATURE                Location/Qualifiers
misc_feature           1..1038
                       note = Description of Artificial Sequence: Synthetic
                        polynucleotide
source                 1..1038
                       mol_type = other DNA
                       organism = synthetic construct
SEQUENCE: 35
atgtatccgt caagcaacat ctgtaattac aaccccaata tttcctcctc aaataactta  60
tttcacattc catctcctaa ttctatgcaa tatgaacacg aacttttcca atatttccac  120
gaccatcatc tccttcaacc ccaacaacaa caactactct tgactacacc tgatcattac  180
atggcagcag attccaacaa agataccgta atcagtagta ctattaatca actggaaggt  240
cctaaagaag ttgaattaca aggcagctgc aagaacaaaa atggtgaaaa taagagagct  300
gttgcttaca agaaagatag acacagcaag attaatacag ctcacggccc tagagatcga  360
agaatgagac tttctctcga tgttgctcgc aaatttttca atttgcaaga cttgcttgga  420
ttcgataagg ccagcaaaac tgtggagtgg ttgcttacca agtccaaatc tgctatcaat  480
gagctcgtcc aaagtactgc tactggtgca attagtacat cctctacgac atccgagtgt  540
gaagtgatat caggaattga tgaatctaca accactaatg atattcagaa gcagccaaat  600
agaagtaaag taggggagaa gaaaaaggct aataaactag ctcgtagagc tgcatttaat  660
```

```
cctgtggcaa aggaatcaag gaaacaagct agagcgaggg caagggagag aacaaaaata  720
aagaaaagcc ttttaaatat tggtgatcag tctatggcgg ctgatgattt aaaacgatta  780
ggatgttgga gtccttttga aacaggtgaa gaatcaggta ttcaaggcta tagtactaat  840
catcaagtag aagaccaaca cactacgaac cacgaggagc atcttttggg gactaaagag  900
aatgttgatg gctgtaattt ggttgttact ggcaactgga acccatttac tatcttcaac  960
tatcaccaca atactgaaat ttctcacgag caacaattta caaacttcca gttttctggg  1020
aagttttggg aagtttag                                                1038

SEQ ID NO: 36          moltype = AA  length = 345
FEATURE                Location/Qualifiers
REGION                 1..345
                       note = Description of Artificial Sequence: Synthetic
                        polypeptide
source                 1..345
                       mol_type = protein
                       organism = synthetic construct
SEQUENCE: 36
MYPSSNICNY NPNISSSNNL FHIPSPNSMQ YEHELFQYFH DHHLLQPQQQ QLLLTTPDHY  60
MAADSNKDTV ISSTINQLEG PKEVELQGSC KNKNGENKRA VAYKKDRHSK INTAHGPRDR  120
RMRLSLDVAR KFFNLQDLLG FDKASKTVEW LLTKSKSAIN ELVQSTATGA ISTSSTTSEC  180
EVISGIDEST TTNDIQKQPN RSKVGEKKKA NKLARRAAFN PVAKESRKQA RARARERTKI  240
KKSLLNIGDQ SMAADDLKRL GCWSPFETGE ESGIQGYSTN HQVEDQHTTN HEEHLLGTKE  300
NVDGCNLVVT GNWNPFTIFN YHHNTEISHE QQFTNFQFSG KFWEV                  345

SEQ ID NO: 37          moltype = DNA  length = 1014
FEATURE                Location/Qualifiers
misc_feature           1..1014
                       note = Description of Artificial Sequence: Synthetic
                        polynucleotide
source                 1..1014
                       mol_type = other DNA
                       organism = synthetic construct
SEQUENCE: 37
atgtatccgc caagcaatag ctgcaactac agccccattt tcaacatccc ttctccttgt  60
atgcaatatg gagacgaact attcttccaa tattatcatg acgattacct tcaagagcaa  120
caagtaccgt tgatagaaga tcagagtctt gacatcttag ctgagagcac tgagactgtt  180
actaataaca aagaaaccgt catcaattct gatcatagtg taaaagttta taacatagaa  240
actgttacaa acagtcaggg tttgggagga aatgaagaaa aaagagtaga aggccgcgaa  300
aacaaaagag atgatatgag cggcaccatt agtatcattc atggacggaa aaacaagaaa  360
tgttcccata aagatcgaca tagcaagatt agcactgctc gtggccttag agatcgaagg  420
atgagacttt cccttgatgc agctcgcaag tttttcagtt tacaagacat gttggggttc  480
gataaggcaa gtaaaactgt agaatggttg cttaccaaat cggagtctga aatcgaagag  540
ctagctaaag gcaataaaga aggagaatcc cttcctaaac aaagctgcag tactaccaat  600
ggaattggtg caattagtac tgcaatatcc tctatttctg agtgtgaggt tatatcagga  660
actgatgaat cttcttctat tactgataaa aagaagctgg aaactgctaa aggaccgttg  720
aaaaagaagg gtaaaactgc tcgtagagct acatttgatc ctcttattac aagggaatcg  780
aggaatcaag caagggttag ggctagagag cgaacaaaac taaagaaaag ccttagtaaa  840
tccaaagcca tgactcatga gaacagtgct gatgactgta atttggtggt taattttgga  900
gattggagtc aatttagcat cttcaactat cagcaaaatg cagttggaat ttcccatgat  960
cagcagcaat ttacagactt ccaattttgt ggtaataagc tgtgggaagt ctag        1014

SEQ ID NO: 38          moltype = AA  length = 337
FEATURE                Location/Qualifiers
REGION                 1..337
                       note = Description of Artificial Sequence: Synthetic
                        polypeptide
source                 1..337
                       mol_type = protein
                       organism = synthetic construct
SEQUENCE: 38
MYPPSNSCNY SPIFNIPSPC MQYGDELFFQ YYHDDYLQEQ QVPLIEDQSL DILAESTETV  60
TNNKETVINS DHSVKVYNIE TVTNSQGLGG NEEKRVEGRE NKRDDMSGTI SIIHGRKNKK  120
CSHKDRHSKI STARGLRDRR MRLSLDAARK FFSLQDMLGF DKASKTVEWL LTKSESEIEE  180
LAKGNKEGES LPKQSCSTTN GIGAISTAIS SISECEVISG TDESSSITDK KKLETAKGPL  240
KKKGKTARRA TFDPLITRES RNQARVRARE RTKLKKSLSK SKAMTHENSA DDCNLVVNFG  300
DWSQFSIFNY QQNAVGISHD QQQFTDFQFC GNKLWEV                           337

SEQ ID NO: 39          moltype = DNA  length = 867
FEATURE                Location/Qualifiers
misc_feature           1..867
                       note = Description of Artificial Sequence: Synthetic
                        polynucleotide
source                 1..867
                       mol_type = other DNA
                       organism = synthetic construct
SEQUENCE: 39
atgggcctct cacaatatcc agctccagca gatgcaggag tactgtgtgt gattcttgta  60
aacacagcca tatctatttc cattgtcaag gagatagtcc gatcgatcct tcacgttatt  120
ggcatccata tcgcatcatg ggaagattat tcttttgaag gatcatttga atgccgcgga  180
```

```
agcccatcag agtcatacat ggaggagttt agaagccgaa cacctgcatt tcgttatgac  240
tcggtgtgta tctctaacca ccctgagcaa gaatgctctg tgtgcctgac taaattcgag  300
cctgacacag agataaaccg tctctcctgt ggccatgttt tccataagct gtgtctagag  360
aagtggctca agtattggca tgtaacttgc cctctttgca ggaaacacat gatgcctcac  420
gagcaagagg acgatacatg tccaatgtca ttttccagct atgttgcgcg aactctccaa  480
aatgctaccg catttatgtt ggatcctcca aaaatgcact acttttggag gatccgacat  540
gtgcctgatg acattttcgg agaatctgag caacattgct ttccagtagc caactcagag  600
agtttcgagc caactgacat gctagtgcga gtcaacgcag ggttcctgtg gtatctgcac  660
ctgaaagaac ctgcatgtgt agttggtgag cacaagcagc tgtaccttac acttgatgtc  720
tttcgcaatg ctgacggtga agaaggcgtc gaggatggta atggtgccat agttggttgt  780
ggttgttcag ccatccttca gcagattctg cagaagaaat taatagatat gaacaagaaa  840
ttctggattg actatgaggt agagtag                                      867

SEQ ID NO: 40          moltype = AA  length = 288
FEATURE                Location/Qualifiers
REGION                 1..288
                       note = Description of Artificial Sequence: Synthetic
                        polypeptide
source                 1..288
                       mol_type = protein
                       organism = synthetic construct
SEQUENCE: 40
MGLSQYPAPA DAGVLCVILV NTAISISIVK EIVRSILHVI GIHIASWEDY SFEGSFECRG  60
SPSESYMEEF RSRTPAFRYD SVCISNHPEQ ECSVCLTKFE PDTEINRLSC GHVFHKLCLE  120
KWLKYWHVTC PLCRKHMMPH EQEDDTCPMS FSSYVARTLQ NATAFMLDPP KMHYFWRIRH  180
VPDDIFGESE QHCFPVANSE SFEPTDMLVR VNAGFLWYLH LKEPACVVGE HKQLYLTLDV  240
FRNADGEEGV EDGNGAIVGC GCSAILQQIL QKKLIDMNKK FWIDYEVE                288

SEQ ID NO: 41          moltype = DNA  length = 2562
FEATURE                Location/Qualifiers
misc_feature           1..2562
                       note = Description of Artificial Sequence: Synthetic
                        polynucleotide
source                 1..2562
                       mol_type = other DNA
                       organism = synthetic construct
SEQUENCE: 41
atgaatcttc aggtggatga tcaaatgata ctcatttctc agtactatcc tggtatctac  60
actcaagagt taccagaaca aggggaggcg aaacaaagga ggagacgaaa gaagaacaaa  120
ggagaagcaa gtgaggttat gaggaaaaga aagcttagtg aagaacaagt gaatctgctt  180
gaacagagct ttgggaaaga gcacaaactg gagtccgaga ggaaagacaa gcttgcctct  240
gagctggggc ttgatcctag gcaagttgct gtctggtttc agaacagaag ggctagatgg  300
aagaacaaga agttggagga ggaatactct aagttgaagt ctgagcatga cactaacatt  360
gttcataatt gccgtcttga aaatgaggtt ttgaagctga aggaacagtt gtctgaagca  420
gagaaagaga tacaaaggtt gctgatggag agatgtgatg gggttaattc gagcaatagc  480
ccaactactt catcactctc aatggaagca gccaatatgg aacctccttt tcttggggaa  540
tttggaatgg aaggatttga caatacattt tatgtgccag aaaacactta ctctcaggga  600
ttggaatgga atggaccatt ttttgcacct cctgatattg attatgggat cattaggttc  660
cagacattac ccgaccccac tattcctggg cagtatgcga actacacatg gggtagtgaa  720
tcttatacac aattgcttca gtccgttagg cacaagctca acccttctgt tcatttttat  780
gtcattcgag gcattgcact agctatgcaa atatggttgt atgagtgttg ctctaccgtc  840
aacactgata tagctacaag gatttctaat tcaatctctc gcatacttag ctggtcagct  900
agtaaggaca agatatggtt atctgcaatt gaagatagaa tgatcaaacc atcatggatc  960
aagttcacca acataattga agcaccagag gagctttcaa gaatgaattt gccaaataaa  1020
gttgaataca ttcttgaaga agttgaaaca aagtccgagc atccgataga tgctccatct  1080
ccatccgttg gttcagatct tggaactttc aagaaagagg tttttgaaga actagataca  1140
gggcaggtga atgatataaa aattatggag aatgttcctg taggtgttga tttatcttcc  1200
caatttgaag ggcatttgta tgaagagaat gcagagaagg aaactatgca tgtagaatct  1260
ccaaaacaga aagctacaat aagcattcca ggaaaacaaa aaaatgagga gaaggagaca  1320
aaaatacaat ctcacattca agaagagaac gttatacaac aaggagatga ttgttgtgaa  1380
gatttcagtg gtgaatcagc cgactacatt aatataggtg attcagacaa tgactctaga  1440
tctgaaaaaa gagaagtaac acttgatgat tttgagctgc cagagaactt ctcccagatt  1500
attaattctg gggggagaac ttctgttgga cctccaattt tcctcatcaa gcatccattt  1560
actggggtta ttggcgaaga tgttgatcct gacttattgg aagaattcaa taagtggtta  1620
tactttggta tcgatacagt ttcaaagagg aggaaggcgc cttattctgt aaaagataac  1680
cagcttaagc cgtggtatga ttttggagtg gagaaagttg ataaaaatga gaggttttat  1740
actttggtac accccgggca agtcctcaac gatacgcaca ttgatgttat tttatactat  1800
ttgagaaaga gaggaaagta tggtcgtcaa aacaaaatat ggtttacaat cattgattgt  1860
atgttcaaca ctagaattga acaaatttat cagaggtaca tcaatactcc tgccgataag  1920
aagcttgttg ttgtcaaatc ccaagacgtc gtatcagaat acatattggg gtacagatta  1980
ctcgcaaata ttgcattgga tcaagttgat tttgtgatta tgcccataaa cattgtgaaa  2040
aaatttattt ggttgttggt tgtgtttgac attaccgata gggttctata tgtttatgat  2100
tctatgttct cttcacgaaa tcacaacctt gttgaatttg ttgtcaacaa gtttgctgtt  2160
atgatccccc tctacttgtc atgcaccgac ttctatggca agcgtccaga catcaactac  2220
aagaacacaa aagcatacat tgaaaaatgt gttactgacc ctcttgacat tcagtggttg  2280
gtcggtgaga tactccatca aaatgaggga tcacttgact gtagtgtata cgtggctgca  2340
tttacagaat atgtcagcat tggagagcta gcagtttcaa aggaagacct ttctgatatt  2400
gatcaacatc gtagacgcta tggagcgcta ctttgggatt atgataggaa gaagcaagat  2460
actggtgcaa ttagtgagag cgaggtgact ggcagattag caagaagaaa aggtgcacca  2520
```

```
gctgtgaacg agagaacaca agtccggaag aagaagaatt ag                      2562

SEQ ID NO: 42           moltype = AA  length = 853
FEATURE                 Location/Qualifiers
REGION                  1..853
                        note = Description of Artificial Sequence: Synthetic
                         polypeptide
source                  1..853
                        mol_type = protein
                        organism = synthetic construct
SEQUENCE: 42
MNLQVDDQMI LISQYYPGIY TQELPEQGEA KQRRRRKKNK GEASEVMRKR KLSEEQVNLL  60
EQSFGKEHKL ESERKDKLAS ELGLDPRQVA VWFQNRRARW KNKKLEEEYS KLKSEHDTNI  120
VHNCRLENEV LKLKEQLSEA EKEIQRLLME RCDGVNSSNS PTTSSLSMEA ANMEPPFLGE  180
FGMEGFDNTF YVPENTYSQG LEWNGPFFAP PDIDYGIIRF QTLPDPTIPG QYANYTWGSE  240
SYTQLLQSVR HKLNPSVHFY VIRGIALAMQ IWLYECCSTV NTDIATRISN SISRILSWSA  300
SKDKIWLSAI EDRMIKPSWI KFTNIIEAPE ELSRMNLPNK VEYILEEVET KSEHPIDAPS  360
PSVGSDLGTF KKEVFEELDT GQVNDIKIME NVPVGVDLSS QFEGAFDEEN AEKETMHVES  420
PKQKATISIP GKQKNEEKET KIQSHIQEEN VIQQGDDCCE DFSGESADYI NIGDSDNDSR  480
SEKREVTLDD FELPENFSQI INSGGRTSVG PPIFLIKHPF TGVIGEDVDP DLLEEFNKWL  540
YFGIDTVSKR RKAPYSVKDN QLKPWYDFGV EKVDKNERFY TLVHPGQVLN DTHIDVILYY  600
LRKRGKYGRQ NKIWFTIIDC MFNTRIEQIY QRYINTPADK KLVVVKSQDV VSEYILGYRL  660
LANIALDQVD FVIMPINIVK KFYWLLVVFD ITDRVLYVYD SMFSSRNHNL VEFVVNKFAV  720
MIPLYLSCTD FYGKRPDINY KNTKAYIEKC VTDPLDIQWL VGEILHQNEG SLDCSVYVAA  780
FTEYVSIGEL AVSKEDLSDI DQHRRRYGAL LWDYDRKKQD TGAISESEVT GRLARRKGAP  840
AVNERTQVRK KKN                                                      853

SEQ ID NO: 43           moltype = DNA  length = 2790
FEATURE                 Location/Qualifiers
misc_feature            1..2790
                        note = Description of Artificial Sequence: Synthetic
                         polynucleotide
source                  1..2790
                        mol_type = other DNA
                        organism = synthetic construct
SEQUENCE: 43
atgatagtag taagatggtg gatgacaaca ttccaattga cagagctgtt tgtgagttgt  60
ttagttcatt tgacttacgg gctttacata ttcagcacag cagtggccgg tgatgtttcc  120
cagactctga gcgattggct tttcaagcca aatttggaaa ctagccttaa aacagatgat  180
tcaaaaaaga ctaacactga tttgcctcct attgtgttgg ttcatggaat ctttggtttt  240
ggcaaaggga gattgggagg actttcatat ttcgctggtg cagagaaaaa ggatgaaagg  300
gttctagtac cggatttggg ttcacttact agcatttatg acagggcacg tgaattgttt  360
tattatttga aggagggcga ggttgattat ggggaggaac acagtaaggc ttgtgggcat  420
tcccaatttg gacgaattta tgaacaagga cactaccccg agtgggatga agatcatcct  480
attcattttg tgggccattc agctggagca caggttgttc gagtcttgca acagatgctg  540
gctgacaagg cattcaaagg ttacgacaac acttcagaga actgggtgtt aagcctaaca  600
tcattatctg gagcacttaa cgggacaacc cgaacttact ttgatggaat gcaacctgaa  660
gatgggaagt ccttaacgcc cgtatgtttg ctccaacttt gccgcattgg agtaataatt  720
tatgagtggc ttgacattcc cttgctgaag gactattaca actttggctt tgaccacttc  780
agtatgtcct ggaggaaaag tggtatccgg ggttttgttg attgcctttt agggaatggc  840
ggtccatttg cttcgggaga ttggatactt ccagatctta ctatccaggg gtcaatgaag  900
ttgaacagcc acttacgtac atttccgcaa acatactact tcagctatgc taccaagcgt  960
accacacaag taatgggtct tacagttcct tctggcgttc tagggataca tccgctgcta  1020
ttcatcagag tcctgcaaat gagccaatgg cggcatccac aagatgtttc tcctccgtac  1080
aagggctata gggatgaaga ttggtgggac aatgacggtg ctctcaacac catatctatg  1140
acgcacccac gcttgccggt tgaacacccg agtcaccttg tcgttaaaga ttctgattgt  1200
cagcccttgc aacctggcat ctggaatcat caagtttcct cttctgtgca gttgttatca  1260
ccaccattgg ctcgtaggct ttccgtgggg aaatgtgaaa gggaaatatc tgtcattctc  1320
agttatgtta cggaaagatc agctctcacc attagaaacc ccgatggaag ccaacaacaa  1380
accaccaaga tcctctttca ccaccagaag tgcgcatgcc ttccgtctta ctgtgaacgc  1440
ccacgtccaa tggaatttct gggaaggatt tcaagaaatg tagaaggaaa tgatactaag  1500
gctaggattt ctgcagctat tttactagtt tgcattatcc ttcctttgct agcctcagca  1560
tttcttgatc atcttcctga atttctagaa catgattcta gaaataaaga tgtaacaatc  1620
cgtggtgata ataatattgt tcgtgccaat gacaatgact ttactcttcc tcgctcacat  1680
gagaaaaaga atgaaagatc tttaagagaa aagaagtcaa agaagaagaa gcataagaag  1740
aagaagaaca agaagggaaa gaaatcacac aaagataaaa tttttgattt tgaccatatt  1800
tttggaggaa accaacaaga aggagatgaa ttttcccctt atttgcaacc atttgatgtg  1860
cctcaaacaa cagaagaaca agaacagacc gagaattatg atggattacg tgagggattt  1920
taccagaaaa catgtcctca agcagagaat attataagaa atggtctaat cagggccttt  1980
cagaatgact ctaccattgc tgctgcatta cctcgccttc tcttgcatga ttgctttgtc  2040
aatggatgtg atgggtcgat attactagat acaacaccca gtggtgcaag agtggagaag  2100
ttagcaggca caaatggtgc tacagtcaag ggatttgaac tcatagacga gatcaaagcc  2160
gagctcgaga gacaatgccc tggcattgtc tcctgctctg atattttggc atacttgtcg  2220
cgcgatgcct ttgttttatc aggcctcccc aattacaacg tgctaggtgg tcgacgcgat  2280
ggcatggaat ccaatgaagc aaacgttgtt ggaaacctac cacttcctgg cgacacagtg  2340
gatcaaatga ttgatctttt tcaaaagaaa ggcctaaatt cggaagattt ggttgtccta  2400
attggtgcac attcaattgg agtagcccat tgtttcaact tcctttacag attggacgaa  2460
ccagagaagg cacaaatgtt agatccaagg cttgctggag tcatgagatt tatttgtact  2520
aaccaaatga ataccttacc ttttgatccc acaacacagt acaagatgga ttcaattttc  2580
```

```
tacaagcaac taatgatgaa gaaagggttg attgaatcgg atcaaatact ggctcaagat  2640
attagaacga ggggcttggt gcaaaagttt ggtgatgatg aaatgggatg gtttgataag  2700
tttggtaagg ctatgaataa attgggagca attgaagtgc tcactggaaa ccaaggccag  2760
atcaggagac agtgtagagc tgttaactga                                   2790

SEQ ID NO: 44          moltype = AA  length = 929
FEATURE                Location/Qualifiers
REGION                 1..929
                       note = Description of Artificial Sequence: Synthetic
                        polypeptide
source                 1..929
                       mol_type = protein
                       organism = synthetic construct
SEQUENCE: 44
MIVVRWWMTT FQLTELFVSC LVHLTYGLYI FSTAVAGDVS QTLSDWLFKP NLETSLKTDD  60
SKKTNTDLPP IVLVHGIFGF GKGRLGGLSY FAGAEKKDER VLVPDLGSLT SIYDRARELF  120
YYLKGGQVDY GEEHSKACGH SQFGRIYEQG HYPEWDEDHP IHFVGHSAGA QVVRVLQQML  180
ADKAFKGYDN TSENWVLSLT SLSGALNGTT RTYFDGMQPE DGKSLTPVCL LQLCRIGVII  240
YEWLDIPLLK DYYNFGFDHF SMSWRKSGIR GFVDCLLGNG GPFASGDWIL PDLTIQGSMK  300
LNSHLRTFPQ TYYFSYATKR TTQVMGLTVP SGVLGIHPLL FIRVLQMSQW RHPQDVSPPY  360
KGYRDEDWWD NDGALNTISM THPRLPVEHP SHLVVKDSDC QPLQPGIWNH QVSSSVQLLS  420
PPLARRLSVG KCEREISVIL SYVTERSALT IRNPDGSQQQ TTKILFHHQK CACLPSYCER  480
PRPMEFLGRI SRNVEGNDTK ARISAAILLV CIILPLLASA FLDHLPEFLE HDSRNKDVTI  540
RGDNNIVRAN DNDFTLPRSH EKKNERSLRE KKSKKKKHKK KKNKKGKKSH KDKIFDFDHI  600
FGGNQQEGDE FSPYLQPFDV PQTTEEQEQT ENYDGLREGF YQKTCPQAEN IIRNGLIRAF  660
QNDSTIAAAL PRLLLHDCFV NGCDGSILLD TTPSGARVEK LAGTNGATVK GFELIDEIKA  720
ELERQCPGIV SCSDILAYLS RDAFVLSGLP NYNVLGGRRD GMESNEANVV GNLPLPGDTV  780
DQMIDLFQKK GLNSEDLVVL IGAHSIGVAH CFNFLYRLDE PEKAQMLDPR LAGVMRFICT  840
NQMNTLPFDP TTQYKMDSIF YKQLMMKKGL IESDQILAQD IRTRGLVQKF GDDEMGWFDK  900
FGKAMNKLGA IEVLTGNQGQ IRRQCRAVN                                   929

SEQ ID NO: 45          moltype = DNA  length = 2478
FEATURE                Location/Qualifiers
misc_feature           1..2478
                       note = Description of Artificial Sequence: Synthetic
                        polynucleotide
source                 1..2478
                       mol_type = other DNA
                       organism = synthetic construct
SEQUENCE: 45
gtatgtttca gtctcacaga gatcgttcat cgataccaca gccatgtgga agcagaaaaa  60
gagagctctg cagaagtttt ggacaccgag cactctaaat atgcaagctt catgacagtg  120
ggacaactgt tacaaacggt aggaaggcaa ctcgaggaac ctgctgttga tgatctcagt  180
gtaactgacc ttgtccattt ggaaaaccaa ctgccaactg ctctaatgca agtcagatct  240
agcaagacgc atttgatgat tgaatctatc aaaagtcttc gtgagaagga aaaactgctg  300
agtgaagaaa acaaacatct ggagaacaag tacactccag cttacaactt caaatcagca  360
atggctctac ctatcgacct cgaagccggc cttcaagatg aaaccaacaa cttggcgccc  420
ggggccggaa ggctacctga cgacggcaac gaggctcgaa tcgaagaacc cgaaattcga  480
gccgaagtac cattggatat caattcacaa atagctctag aagcgaatca gcgttctgaa  540
ccggaaagaa gcgttcaggg cggtgctcga cccatagccc gagacaccta cagcacgggg  600
gaaatcgggg tcagcttgcg tatgattttc gaaatgttac aagcccaaca agcagcgata  660
gctcagttgc agagccgaac tcatatgcaa agcgggccga actccaatcc gcttcttcga  720
gaagtcaccc ccagaacgga gcccgccgta gtgaaatcaa acgagcagga atcggggacc  780
gctcctgaaa ttgctaaatt gctcgaggaa ctcacaaaac gagtcgaagc caacgacaaa  840
aaagtggaaa cgtataacgc tagggtcgat caaatcccgg gggctccgcc aatgataaaa  900
gggctcgatt cgaaaaaatt catacaaaag cctttttccct cgagcgcggc cccaaaacca  960
atccccaaaa aattccgtat gcccgaaatt cccaaatata acggtacgac cgatcctaac  1020
gaacatgtca cctcctacac atgtgccatc aaaggcaacg atttggagga cgatgagatc  1080
gaatccgtgt tgttgaaaaa gttcggagag accctcgcaa agggagcaat gatctggtat  1140
cacaacttac caccaaattc cattgattct tttgccatgt tagcagattc gttcgtaaaa  1200
gcacatgctg gtgccataaa ggttgcaaca aggaaatcag acctcttcaa agtaaaacaa  1260
aggggtaacg aaatgctgag ggaattcgta tcccgatttc aaatggaacg tatggacttg  1320
ccaccggtca cagacgattg ggccgtacaa gctttcaccc aaggactgaa cgggctaagt  1380
tcgacagcat cacatcggat gaacaacggt tcagcacgtg atacggttcg gaacaaccga  1440
aggactgatc gggggcaaaa ttctcgggga cttatgagca agagcggctt tgataaaatat  1500
gccgatccta tagaagtccc tcgattatcg gagtataact tcaacattga tacatccgcc  1560
atcgtatcgg ccatcggacg catcaaagac accagatggc ctcgacccat gcagaccgat  1620
cctgcccaaa ggaatcccaa tcaaatgtgc gaatatcatg gcacccatgg ccacagaacg  1680
gaagattgca ggcaactaag agaggaagtg gcccgcttat ttaacaaagg acaccttcgg  1740
gaatttctga gtgatagggc gaagaaccat tttaggaaca aggaattcgg caagcaaaac  1800
gagccagaag aaccgcaaca cgtcattcac atgatcatcg gcggcgtcga tgcccctcag  1860
ggaccgatgc ttaaacgcac taaaacatcg attgtgaggg aaaagcgatc tcgaactcaa  1920
gattatacac ccatagggac tttgtccttc agtgatgaag atacagaggg aatcatccaa  1980
ccccataacg atgcactggt aatatccgta ctcatgaata aaactaagat taagcgtgtg  2040
ttaattgatc caggtagctc ggccaatatc atcagatcga gggtcgtaga acagctcggc  2100
ctgcaagatc aggtcgtacc cgcaactctg gttctaaacg gattcaatat ggcatgtgaa  2160
accaccaaag gcgagattac cctaccgata aacgtggccg gaaccatcca ggaaacaaag  2220
tttcacgtga tcgaaggtga tatgagatat aacgcccttt tcggaaggcc gtggatccac  2280
agcatgagag ccgtaccctc gaccctacac caggtcctca aattcccaac atcgggaggt  2340
```

```
gtcaaaatag tgtacggaga acaaccggcc gcaaaggaaa tgttctccgt cgaagaagca  2400
aaatcaatat cctcgtcttc gccgataaaa ggatcaggtt cagaaggaga cacaatcgga  2460
gagcagagcg ccaaatag                                                2478

SEQ ID NO: 46          moltype = AA  length = 825
FEATURE                Location/Qualifiers
REGION                 1..825
                       note = Description of Artificial Sequence: Synthetic
                        polypeptide
source                 1..825
                       mol_type = protein
                       organism = synthetic construct
SEQUENCE: 46
VCFSLTEIVH RYHSHVEAEK ESSAEVLDTE HSKYASFMTV GQLLQTVGRQ LEEPAVDDLS  60
VTDLVHLENQ LPTALMQVRS SKTHLMIESI KSLREKEKLL SEENKHLENK YTPAYNFKSA  120
MALPIDLEAG LQDETNNLAP GAGRLPDDGN EARIEEPEIR AEVPLDINSQ IALEANQRSE  180
PERSVQGGAR PIARDTYSTG EIGVSLRMIF EMLQAQQAAI AQLQSRTHMQ SGPNSNPLLR  240
EVTPRTEPAV VKSNEQESGT APEIAKLLEE LTKRVEANDK KVETYNARVD QIPGAPPMIK  300
GLDSKKFIQK PFPSSAAPKP IPKKFRMPEI PKYNGTTDPN EHVTSYTCAI KGNDLEDDEI  360
ESVLLKKFGE TLAKGAMIWY HNLPPNSIDS FAMLADSFVK AHAGAIKVAT RKSDLFKVKQ  420
RGNEMLREFV SRFQMERMDL PPVTDDWAVQ AFTQGLNGLS STASHRMNNG SARDTVRNNR  480
RTDRGQNSRG LMSKSGFDKY ADPIEVPRLS EYNFNIDTSA IVSAIGRIKD TRWPRPMQTD  540
PAQRNPNQMC EYHGTHGHRT EDCRQLREEV ARLFNKGHLR EFLSDRAKNH FRNKEFGKQN  600
EPEEPQHVIH MIIGGVDAPQ GPMLKRTKTS IVREKRSRTQ DYTPIGTLSF SDEDTEGIIQ  660
PHNDALVISV LMNKTKIKRV LIDPGSSANI IRSRVVEQLG LQDQVVPATL VLNGFNMACE  720
TTKGEITLPI NVAGTIQETK FHVIEGDMRY NALFGRPWIH SMRAVPSTLH QVLKFPTSGG  780
VKIVYGEQPA AKEMFSVEEA KSISSSSPIK GSGSEGDTIG EQSAK                  825

SEQ ID NO: 47          moltype = DNA  length = 1152
FEATURE                Location/Qualifiers
misc_feature           1..1152
                       note = Description of Artificial Sequence: Synthetic
                        polynucleotide
source                 1..1152
                       mol_type = other DNA
                       organism = synthetic construct
SEQUENCE: 47
atgcagtctg tactctggaa cctaaggaag attgaaattc aagataaatt ctgcgatatt  60
gaaaggataa gtcctgcata cctcaacaca aatgacacgg caaagaaaat tcaagaagaa  120
atcaatggct tgcattgtaa actggaggag gctgagggat tattaagaat atttgaacca  180
gatacaaaaa aaattacatc actccatgag cttgatttgt gtgaaaaacg tcttcaggtt  240
gccttgaacc aagttaggca aagaatggaa caactctcca acaatcataa tacatcaagt  300
tatgaagata atatggagca aataaatgca ctccttcaat acatagacaa cacacaaact  360
gaggacacaa aaccctcgtt ggaggaatct ccctatgact tatggctaga gcttgaagat  420
tatagttaca caaactatat taatgacaac aacaatagtc atctctatgc tgcctcagaa  480
acatcttctc ttactcaaag ttctatgagc ctttcttctc caattattta tgatgcaata  540
tcccaaacaa gtataagtgg tgtgactaat tatcataaag aagggacttt tagttcttta  600
actgatgaga attttaagca atcacaacat tcaaccagaa ccttcccaac tctcacttta  660
caaacttcat tcaaatttgc caagcctgaa atggaaactc ccacatctgc actacggccg  720
gtagcgccat atctgcatgt tgaagcaaca gcagcgtgta gccagcaacc agtttcaagt  780
gattattata aagagaacaa tgaactcgac tgcagatttc aacctaaagt tacaacgtct  840
aactatcaaa tgtcccaaaa acgtactgca gaaggaagtt ttagttcctt aactgatgaa  900
agctttaagc aatcacaatg ttcaaccagg atcttcccac ctatcgctcc attacaaact  960
tcattctcat ttgccacgcc tgaaatggaa actccaacct cagcattgcg gccggtggca  1020
ccatatctgc aggctgaagc agcagcatcc tctaaccagc agctaccttc taataatatt  1080
gaagaagaga accatgaaat ctcttggttt cagcctcaaa tgaaaaagtc gaagtatcat  1140
catttagctt ga                                                      1152

SEQ ID NO: 48          moltype = AA  length = 383
FEATURE                Location/Qualifiers
REGION                 1..383
                       note = Description of Artificial Sequence: Synthetic
                        polypeptide
source                 1..383
                       mol_type = protein
                       organism = synthetic construct
SEQUENCE: 48
MQSVLWNLRK IEIQDKFCDI ERISPAYLNT NDTAKKIQEE INGLHCKLEE AEGLLRIFEP  60
DTKKITSLHE LDLCEKRLQV ALNQVRQRME QLSNNHNTSS YEDNMEQINA LLQYIDNTQT  120
EDTKPSLEES PYDLWLELED YSYTNYINDN NNSHLYAASE TSSLTQSSMS LSSPIIYDAI  180
SQTSISGVTN YHKEGTFSSL TDENFKQSQH STRTFPTLTL QTSFKFAKPE METPTSALRP  240
VAPYLHVEAT AACSQQPVSS DYYKENNELD CRFQPKVTTS NYQMSQKRTA EGSFSSLTDE  300
SFKQSQCSTR IFPPIAPLQT SFSFATPEME TPTSALRPVA PYLQAEAAAS SNQQLPSNNI  360
EEENHEISWF QPQMKKSKYH HLA                                          383

SEQ ID NO: 49          moltype = DNA  length = 813
FEATURE                Location/Qualifiers
misc_feature           1..813
                       note = Description of Artificial Sequence: Synthetic
```

```
                         polynucleotide
source                   1..813
                         mol_type = other DNA
                         organism = synthetic construct
SEQUENCE: 49
atgggaactg gtacttatgg agaagtggga cgtacaatac atcaaagatc aggaacacat  60
atacctcaaa ttctcgatcc gcctttgcta ggggatagtg attgcaagcg agaaggcaaa  120
catgtagaat ttatgcctcc aatcatgggt gaaaacttaa aagcagctaa tcaatttgaa  180
ctgatggccc cgtcaattgc attcaaatca tatccctatt cggaggtacc acaatattct  240
ggtggcaatg tggctgctgc atgtggtgaa tctttggtac atcaaaatat agaaagatca  300
gtgcataatg gtagaatgat tttgccaatt gaagtgaagg aggagcctat gtatgtaaat  360
gccaaacaat accatggaat tctaaggcga aggcaacttc gtgcaaaggc tgtgttggag  420
caaaaagtgg ttaaatctag aaagccttat cttcatgaat ctcggcaccg gcatgcgatg  480
agaagagcta gagatggtgg aggccgattt ctcaacacaa aaaagaagat ccaacttcct  540
gctaataata atattaatac aactactcca agtagtaaag gcaaaggttg tgcagcctcg  600
gaagtcagtt ccatggactc tgatttctct caaaattact tgctcaattc tggacatatt  660
ggatcatcca atgctacttc tgttgaagga ttccagttcc aaggaataca taatacagat  720
aatcctcaat tgggttgtca ttatcagtgg aatctcaatg acaaccattg ctattgcatg  780
cagtcaggag cttctaatct ccaaccattt tga                              813

SEQ ID NO: 50            moltype = AA  length = 270
FEATURE                  Location/Qualifiers
REGION                   1..270
                         note = Description of Artificial Sequence: Synthetic
                          polypeptide
source                   1..270
                         mol_type = protein
                         organism = synthetic construct
SEQUENCE: 50
MGTGTYGEVG RTIHQRSGTH IPQILDPPLL GDSDCKREGK HVEFMPPIMG ENLKAANQFE  60
LMAPSIAFKS YPYSEVPQYS GGNVAAACGE SLVHQNIERS VHNGRMILPI EVKEEPMYVN  120
AKQYHGILRR RQLRAKAVLE QKVVKSRKPY LHESRHRHAM RRARDGGGRF LNTKKKIQLP  180
ANNNINTTTP SSKGKGCAAS EVSSMDSDFS QNYLLNSGHI GSSNATSVEG FQFQGIHNTD  240
NPQLGCHYQW NLNDNHCYCM QSGASNLQPF                                  270

SEQ ID NO: 51            moltype = DNA  length = 762
FEATURE                  Location/Qualifiers
misc_feature             1..762
                         note = Description of Artificial Sequence: Synthetic
                          polynucleotide
source                   1..762
                         mol_type = other DNA
                         organism = synthetic construct
SEQUENCE: 51
atgggagctg gtgcttttgg agaagccgga cgtacaatat atcaaaagtc cgatagtgat  60
tgcaagcgag atggcaaacg tgtagaattt atgcctccaa tcatgggtga aaacttaaga  120
gcagctaatc aatttgaact gatgcccccc tcaattgcat tcagatcata tccctattca  180
gaagtaccac aatattctgg tggcaatgtg gctgctgcat ttggcgaatc tacggtacat  240
caaaatatag aaagatcagt gcataatggt agaatgattt tgccacttga agtgaaggag  300
gagcctatgt atgtaaatgc caaacaatac catggaattc taaggcgaag gcaactccgt  360
gcaaaggctg tgttggagca aaaggtggtc aaatctagaa agccttatct tcatgaatct  420
cggcaccggc atgcgatgag aagagctaga gatggtggcg gccgatttct caacacaaag  480
aagaagatcc aacttactac taataataat aataataatg ggaatactaa tgcaactcca  540
agtagtaaag gcaaaggttc ttcagcctca gaagtcagtt ccatggactc ttattctgga  600
catattggat catccaatag tactgctcat gtccagggat ttcagttcca aggaatacat  660
aatacagaaa atcctcaact gggttgtcat tatcagtgga atctcaatga taaccattgc  720
aattgcatgc agtcaggagc ttctaatatc caaccatttt ga                    762

SEQ ID NO: 52            moltype = AA  length = 253
FEATURE                  Location/Qualifiers
REGION                   1..253
                         note = Description of Artificial Sequence: Synthetic
                          polypeptide
source                   1..253
                         mol_type = protein
                         organism = synthetic construct
SEQUENCE: 52
MGAGAFGEAG RTIYQKSDSD CKRDGKRVEF MPPIMGENLR AANQFELMPP SIAFRSYPYS  60
EVPQYSGGNV AAAFGESTVH QNIERSVHNG RMILPLEVKE EPMYVNAKQY HGILRRRQLR  120
AKAVLEQKVV KSRKPYLHES RHRHAMRRAR DGGGRFLNTK KKIQLTTNNN NNNGNTNATP  180
SSKGKGSSAS EVSSMDSYSG HIGSSNSTAH VQGFQFQGIH NTENPQLGCH YQWNLNDNHC  240
NCMQSGASNI QPF                                                    253

SEQ ID NO: 53            moltype = DNA  length = 753
FEATURE                  Location/Qualifiers
misc_feature             1..753
                         note = Description of Artificial Sequence: Synthetic
                          polynucleotide
source                   1..753
```

```
                         mol_type = other DNA
                         organism = synthetic construct
SEQUENCE: 53
atgcaatatg aacacgaatt tttcttccaa tattaccatg atcaacttca acagaatctt  60
gatgatacct tagctgagat cagtactgag actgccatta ttaacacggc agattccaac  120
aaagacgacg ctttaataag tagaaatgaa cttgaacaag aggaaggatg tgagaataaa  180
aagggtaaaa taagcagcaa caagagagtg tctaagaaag atagacacag tgcaaatagt  240
gaatcctcta cttctgaatg tgaagttgta tcagaaattg atgaatctcc atctaatcat  300
aaggcaaatg ctaaaggaaa ttcttgcaac aaggagaagg agaagaagaa gaaggagaag  360
gagaaatcag ttcgtcgagc tgcattttat catccatttg caaaagaatc aaggaaacaa  420
gcaagagaga gggcaaggga gagaacaaaa ctaaagaaaa acttttgtaa atctcatcat  480
ttgaacttaa gatcttggaa tttctccgaa gggggcgaag aatcagcggg atatattagc  540
atgaatcttc cttgtcaaga aatgcaagct gaaatagttg aagaactcac ctcccacaat  600
gagaagcagc ttttattagg gattaaagaa aacattgcta atgattgtaa tttggtggct  660
actggcaatt ggagcccaaa tgccattttc aactatcaac aaaatgctgg aattcctcat  720
gagcatcaaa ttacagacat tccgttttca tga                               753

SEQ ID NO: 54            moltype = AA  length = 250
FEATURE                  Location/Qualifiers
REGION                   1..250
                         note = Description of Artificial Sequence: Synthetic
                          polypeptide
source                   1..250
                         mol_type = protein
                         organism = synthetic construct
SEQUENCE: 54
MQYEHEFFFQ YYHDQLQQNL DDTLAEISTE TAIINTADSN KDDALISRNE LEQEEGCENK  60
KGKISSNKRV SKKDRHSANS ESSTSECEVV SEIDESPSNH KANAKGNSCN KEKEKKKKEK  120
EKSVRRAAFY HPFAKESRKQ ARERARERTK LKKNFCKSHH LNLRSWNFSE GGEESAGYIS  180
MNLPCQEMQA EIVEELTSHN EKQLLLGIKE NIANDCNLVA TGNWSPNAIF NYQQNAGIPH  240
EHQITDIPFS                                                        250

SEQ ID NO: 55            moltype = DNA  length = 1422
FEATURE                  Location/Qualifiers
misc_feature             1..1422
                         note = Description of Artificial Sequence: Synthetic
                          polynucleotide
source                   1..1422
                         mol_type = other DNA
                         organism = synthetic construct
SEQUENCE: 55
atgatgaagc atatagtaca tctgggctcc acctcaaatc ttacagtagc agctagaggc  60
catggtcact cgcttcaagg acaagctcta gctcatcaag gtgttgtcat caaaatggag  120
tcacttcgaa gtcctgatat caggatttat aaggggaagc aaccatatgt tgatgtctca  180
ggtggtgaaa tatggataaa cattctacgc gagactctaa aatacggtct ttcaccaaag  240
tcctggacag actaccttca tttgaccgtt ggaggtacac tatctaatgc tggaatcagc  300
ggtcaagcat tcaagcatgg accccaaatc aacaacgtct accagctaga gattgttaca  360
gggaaaggag aagtcgtaac ctgttctgag aagcggaatt ctgaactttt cttcagtgtt  420
cttggcgggc ttggacagtt tggcataatc acccgggcac ggatctctct tgaaccagca  480
ccgcatatgg ttaaatggat cagggtactc tactctgact ttctgcatt ttcaagggac   540
caagaatatc tgatttcgaa ggagaaaact tttgattacg ttgaaggatt tgtgataatc  600
aatagaacag accttctcaa taattggcga tcgtcattca gtcccaacga ttccacacag  660
gcaagcagat tcaagtcaga tgggaaaact ctttattgcc tagaagtggt caaatatttc  720
aacccagaag aagctagctc tatggatcag gaaactggca agttactttc agagttaaat  780
tatattccat ccactttgtt ttcatctgaa gtgccatata tcgagtttct ggatcgcgtg  840
catatcgcag agagaaaact aagagcaaag ggtttatggg aggttccaca tccctggctg  900
aatctcctga ttcctaagag cagcatatac caatttgcta cagaagtttt caacaacatt  960
ctcacaagca acaacaacgg tcctatcctt atttatccag tcaatcaatc caagtggaag  1020
aaacatacat ctttgataac tccaaatgaa gatatattct atctcgtagc ctttctcccc  1080
tctgcagtgc caaattcctc agggaaaaac gatctagagt acctttgaa acaaaaccaa   1140
agagttatga acttctgcgc agcagcaaac ctcaacgtga agcagtattt gccccattat  1200
gaaactcaaa aagagtggaa atcacacttt ggcaaaagat gggaaacatt tgcacagagg  1260
aaacaagcct acgaccctct agcgattcta gcacctggcc aaagaatatt ccaaaagaca  1320
acaggaaaat tatctcccat ccaactcgca aagtcaaagg caacaggaag tcctcaaagg  1380
taccattacg catcaatact gccgaaacct agaactgtat aa                     1422

SEQ ID NO: 56            moltype = AA  length = 473
FEATURE                  Location/Qualifiers
REGION                   1..473
                         note = Description of Artificial Sequence: Synthetic
                          polypeptide
source                   1..473
                         mol_type = protein
                         organism = synthetic construct
SEQUENCE: 56
MMKHIVHLGS TSNLTVAARG HGHSLQGQAL AHQGVVIKME SLRSPDIRIY KGKQPYVDVS  60
GGEIWINILR ETLKYGLSPK SWTDYLHLTV GGTLSNAGIS GQAFKHGPQI NNVYQLEIVT  120
GKGEVVTCSE KRNSELFFSV LGGLGQFGII TRARISLEPA PHMVKWIRVL YSDFSAFSRD  180
QEYLISKEKT FDYVEGFVII NRTDLLNNWR SSFSPNDSTQ ASRFKSDGKT LYCLEVVKYF  240
```

```
NPEEASSMDQ ETGKLLSELN YIPSTLFSSE VPYIEFLDRV HIAERKLRAK GLWEVPHPWL  300
NLLIPKSSIY QFATEVFNNI LTSNNNGPIL IYPVNQSKWK KHTSLITPNE DIFYLVAFLP  360
SAVPNSSGKN DLEYLLKQNQ RVMNFCAAAN LNVKQYLPHY ETQKEWKSHF GKRWETFAQR  420
KQAYDPLAIL APGQRIFQKT TGKLSPIQLA KSKATGSPQR YHYASILPKP RTV         473

SEQ ID NO: 57           moltype = DNA  length = 1659
FEATURE                 Location/Qualifiers
misc_feature            1..1659
                        note = Description of Artificial Sequence: Synthetic
                         polynucleotide
source                  1..1659
                        mol_type = other DNA
                        organism = synthetic construct
SEQUENCE: 57
atgaagtcac caccaactca tgtcttcttt aaacataaaa gtatgcttct taggttgctt  60
atattcatac taggcatttg ctcaataaac agaactaacc tttgttgtga ccaacctttt  120
gccaccccaa tatcttcttc ttcttctacc ccttcaagtt tttcagtgat tcaatcatca  180
ttgaaacagt taaatattga agggtatttt agtttcaaga atttcgatca cgcggccaaa  240
gactttggca acagatatca cttcttgcca tcggcagttc tgtatccaaa atcagtttct  300
gatatatcat ctaccataaa acatgttttt gacatgggtg ttactacaga cctaactgtt  360
gctgctagag gccatggcca ttctttagaa ggccaagctc aagcttacca aggagtagtg  420
atcaatatgg aatcgcttcg agcgccagca atgcgtttcc acacagggaa tcaagaactg  480
ccttttgttg atgtctctgc aggagaactt tggataaaca tcctgcatga aagtcttaaa  540
cttggattaa caccaaaatc ttggactgat tatcttcacc tcaccgttgg agggactttg  600
tcgaatgccg gaatcagtgg tcaagcattc aaacatggac cacagatcaa taatgtttac  660
caacttgagg ttgtcactgg taaaggagag gtgattactt gttcagagga gaagaatgct  720
gacctgttct atggtgtatt aggaggacta ggccagtttg gtatcatcac aagggctaga  780
attgctcttg aaccagcacc taaaaaggta aagtggatca gagtgctgta ttcagatttc  840
tccacatttt cctatgatca agaacacttg atatcatccg agaactcttt tgactatata  900
gaaggatttg tcattatcaa tagaacagga ttgttaaaca actggaggtc tactttcaat  960
cctaaagatc cacttctagc caaagagttc agttctgagg gaaaagttct gtactgccta  1020
gaagttgcca aatacttcaa tccagaagag acaaccaaaa ctgatcagaa tgttgatgtt  1080
cttttatcaa agttgaatta tatccaatcg acgctgttcc aatcagaagt atcctacgtg  1140
gatttcctcg acagagttca cgtatccgag atgaaacttc aagagaaggg gttatgggat  1200
attcctcatc catggctaaa ccttctaatt ccaaagagca agattcatga ctttgcacga  1260
gaagtttttg ggaagatact taccgacact agccacggtc ctatactcat ctacccagtc  1320
aacaaatcaa agtggagaaa aggaacatca gtagttacac ctgaagaaga tgttatgtat  1380
ctaatagcat ttctatcttc tgccatgcca tcttcaacag gaaaggacgg cgtagaatat  1440
attctaaata agaataagaa gatactaaac ttttgcagaa aagcacatat tggaatgaaa  1500
cagtatttgc cacactacac aacgcaggaa gactggaaag gtcactttgg tccccagtgg  1560
gaaacattta aaggaggaa atctacatat gaccctttgg ctatcctagc tcctggccag  1620
agaattttta gaagagcatc aggcgttcaa caacaatga                       1659

SEQ ID NO: 58           moltype = AA  length = 552
FEATURE                 Location/Qualifiers
REGION                  1..552
                        note = Description of Artificial Sequence: Synthetic
                         polypeptide
source                  1..552
                        mol_type = protein
                        organism = synthetic construct
SEQUENCE: 58
MKSPPTHVFF KHKSMLLRLL IFILGICSIN RTNLCCDQPF ATPISSSSST PSSFSVIQSS  60
LKQLNIEGYF SFKNFDHAAK DFGNRYHFLP SAVLYPKSVS DISSTIKHVF DMGVTTDLTV  120
AARGHGHSLE GQAQAYQGVV INMESLRAPA MRFHTGNQEL PFVDVSAGEL WINILHESLK  180
LGLTPKSWTD YLHLTVGGTL SNAGISGQAF KHGPQINNVY QLEVVTGKGE VITCSEEKNA  240
DLFYGVLGGL GQFGIITRAR IALEPAPKKV KWIRVLYSDF STFSYDQEHL ISSENSFDYI  300
EGFVIINRTG LLNNWRSTFN PKDPLLAKEF SSEGKVLYCL EVAKYFNPEE TTKTDQNVDV  360
LLSKLNYIQS TLFQSEVSYV DFLDRVHVSE MKLQEKGLWD IPHPWLNLLI PKSKIHDFAR  420
EVFGKILTDT SHGPILIYPV NKSKWRKGTS VVTPEEDVMY LIAFLSSAMP SSTGKDGVEY  480
ILNKNKKILN FCRKAHIGMK QYLPHYTTQE DWKGHFGPQW ETFKRRKSTY DPLAILAPGQ  540
RIFRRASGVQ QQ                                                     552

SEQ ID NO: 59           moltype = DNA  length = 1632
FEATURE                 Location/Qualifiers
misc_feature            1..1632
                        note = Description of Artificial Sequence: Synthetic
                         polynucleotide
source                  1..1632
                        mol_type = other DNA
                        organism = synthetic construct
SEQUENCE: 59
atgaaattac catcccattt tttatttaag caaaatgact tgctcctgaa attgcttata  60
ttcatactct gcagttgttc aagcaacaaa aataaactct gctgtaatta tcatcagttt  120
gccacccctg cagtttctac cccctcaagt ttctcactga attatttatc attgaaacaa  180
ttacaacttg aaggttacct taaatttgac aacttagaac atgcagccaa agactttggt  240
aatagatgcc acttccttcc attagcagtt ttgtacccaa aatcagtttc tgatatctct  300
tccactataa aacatgtctt tgaaataggt tccaaaactg atttaactgt tgctgctaga  360
ggccatggcc attctctaga aggtcaagct caagcttatc aaggagtagt gattagtatg  420
```

```
gaatcactac aaacaccagc aatgaaattc aagactggag aattgcctta tgttgatgtt  480
tctgctggag agctttggat taatatcctg aaagaaagtc ttaaacttgg gcttgcacct  540
aaatcttgga ctgattatct tcacctcaca gttggcggca ctttgtctaa tgctggaatc  600
agtggacaag ctttccgcca cggaccgcag atcaataacg tccaacaact tgaagttgtc  660
actggtaaag gagaggtgat tacttgttca gaggagcaga atgcagactt gtttcatggt  720
gtactaggag gactggggca atttggtatt attaccagag caaggattgc tcttgaaaca  780
gcacctaaac aggtcaagtg gattagagtg ctgtattcag atttttccat attttccaat  840
gatcaagagc acttgatatc aactcaggat acatttgact atattgaagg ttttgtcact  900
atcaaccaaa ctggattatt aaataactgg aggtctgctt tcaatcctaa agatccagtt  960
ctagccagca atttcagttc tgagggtaga gttttgttct gcttagaaat tgccaaatac  1020
ttcaatccag aagtcacaga tagtattgat cagaacattg atgtgatctt atcaaagttg  1080
aattatatcc gatccacgct gttcctatca gaagtctcct acacagaatt cctcgacagg  1140
gtgcatgtct ctgagatgaa actccaagaa aatgtttctc atccatggct aaatcttcta  1200
ataccaaaaa gcaggattct tgaatttgca caacaagttt ttggcaagat tcttactgac  1260
actagcaatg gtcctttact catctaccct gtcaacaaat caaagtggag aaaaggaaca  1320
tccatggtta cccctgacga agatgttttt tatctgatcg cgttcctatc ttctgctatg  1380
tcatcttcaa caggaaacga tggactaaga catattcttg ctcagagcaa aaggatactg  1440
aacttttgtg aagaaacaaa tatcggaatg aaacaatatt taccaaatta caagactaag  1500
gaagagtgga aggatcactt tggtcatcaa tgggaagcat ttgctagaag gaaatctaca  1560
tatgaccctt tggcaatact tgctcctggc cagagaattt tcagaagggc agaagcctgt  1620
gaacaacaat aa                                                     1632

SEQ ID NO: 60          moltype = AA  length = 543
FEATURE                Location/Qualifiers
REGION                 1..543
                       note = Description of Artificial Sequence: Synthetic
                        polypeptide
source                 1..543
                       mol_type = protein
                       organism = synthetic construct
SEQUENCE: 60
MKLPSHFLFK QNDLLLKLLI FILCSCSSNK NKLCCNYHQF ATPAVSTPSS FSLNYLSLKQ  60
LQLEGYLKFD NLEHAAKDFG NRCHFLPLAV LYPKSVSDIS STIKHVFEIG SKTDLTVAAR  120
GHGHSLEGQA QAYQGVVISM ESLQTPAMKF KTGELPYVDV SAGELWINIL KESLKLGLAP  180
KSWTDYLHLT VGGTLSNAGI SGQAFRHGPQ INNVQQLEVV TGKGEVITCS EEQNADLFHG  240
VLGGLGQFGI ITRARIALET APKQVKWIRV LYSDFSIFSN DQEHLISTQD TFDYIEGFVT  300
INQTGLLNNW RSAFNPKDPV LASNFSSEGR VLFCLEIAKY FNPEVTDSID QNIDVILSKL  360
NYIRSTLFLS EVSYTEFLDR VHVSEMKLQE NVSHPWLNLL IPKSRILEFA QQVFGKILTD  420
TSNGPLLIYP VNKSKWRKGT SMVTPDEDVF YLIAFLSSAM SSSTGNDGLR HILAQSKRIL  480
NFCEETNIGM KQYLPNYKTK EEWKDHFGHQ WEAFARRKST YDPLAILAPG QRIFRRAEAC  540
EQQ                                                               543

SEQ ID NO: 61          moltype = DNA  length = 960
FEATURE                Location/Qualifiers
misc_feature           1..960
                       note = Description of Artificial Sequence: Synthetic
                        polynucleotide
source                 1..960
                       mol_type = other DNA
                       organism = synthetic construct
SEQUENCE: 61
atgagaaact cttcactaat gtgcaaacaa gtatggccaa ctttgcgaaa tttgcctcaa  60
aaggacaagg ttgtgtttgt gatgggagtc accggcgccg gaaaatcaag actgtcaata  120
gacttagcca ctcaattcag aggagaaata gtgaactccg acaaaataca agtgtacaaa  180
ggtcttgata ttgccactaa caaaatcaca caagaagaac gttgtggtgt accacaccat  240
ctcctaggcg taattgatcc ttacaaagaa ttcaccacca aaaacttctg caacatggct  300
tcacttgcag ttaactctat aaccgaccgc ggtaaacttc cgatcatcgt tggaggttcc  360
aattcgttta tcgaggcgct tgtccacgac aactctcata atttcgtac gaggtatgat  420
tgttgtttcc tatgggtcga tgtgtccatg aacgtactaa attcattttt gtacgaacga  480
gtggacaaaa tgatggagca aggtatgact gacgaagtaa gaagcatgtt caatccaaaa  540
aacacagatt ataccaaagg catacgtaaa gcaattggcg taccagaatt cgatagttat  600
tttcgagctg aattatcaaa ttctgttgac gtggagacgc gcgagaggct actaaaagaa  660
gctattaatg aagtgaagat caataactgt atactagcaa gtaagcaact agagaaaata  720
aagagactca taaatgttaa gggatggaaa attcaaagat tagatgcaac agaagttttt  780
aggaggaaac agagaaatgc agaggaagaa gccgaggaaa tttggaagaa tatggtgatg  840
ggacagagca taaagattgt gggtaaattt ttatgcgaaa ataatcggag caaaatggtt  900
tacagaaatg atgtgacagc cattaagaga gcagcagcgt cggccatagc tcaatattag  960

SEQ ID NO: 62          moltype = AA  length = 319
FEATURE                Location/Qualifiers
REGION                 1..319
                       note = Description of Artificial Sequence: Synthetic
                        polypeptide
source                 1..319
                       mol_type = protein
                       organism = synthetic construct
SEQUENCE: 62
MRNSSLMCKQ VWPTLRNLPQ KDKVVFVMGV TGAGKSRLSI DLATQFRGEI VNSDKIQVYK  60
GLDIATNKIT QEERCGVPHH LLGVIDPYKE FTTKNFCNMA SLAVNSITDR GKLPIIVGGS  120
```

```
NSFIEALVHD NSHNFRTRYD CCFLWVDVSM NVLNSFLYER VDKMMEQGMT DEVRSMFNPK  180
NTDYTKGIRK AIGVPEFDSY FRAELSNSVD VETRERLLKE AINEVKINNC ILASKQLEKI  240
KRLINVKGWK IQRLDATEVF RRKQRNAEEE AEEIWKNMVM GQSIKIVGKF LCENNRSKMV  300
YRNDVTAIKR AAASAIAQY                                               319

SEQ ID NO: 63           moltype = DNA  length = 930
FEATURE                 Location/Qualifiers
misc_feature            1..930
                        note = Description of Artificial Sequence: Synthetic
                         polynucleotide
source                  1..930
                        mol_type = other DNA
                        organism = synthetic construct
SEQUENCE: 63
atggaagctg ctcaacaaca aaaccagcag cactatcttc accaacaaca tttatcaatt  60
ggacaggtgg caaacaacat tgaagatggt gttggtggta atagcagcaa aaacaacagc  120
agcagtttca tgtgcaggca aagtagtacg aggtggacac ccacaactga ccagataaga  180
attttgaagg acctttacta caacaatgga gttaggtctc caactgctga acagattcag  240
aggatctctg ctaagttaag acagtacggt aagattgaag gcaagaatgt gttttattgg  300
tttcagaacc ataaagctcg tgaaaggcaa aagaagaggc ttattgctgc tgctgccact  360
gataacaaca ataatatccc catgcaaatg agaggtgttt ggagatctgc tgatgatccc  420
attcaccaca agtataacaa cactacaggt attcactgtc catcagcttc ttctcatggt  480
gtactagcag ttggacagaa tggaaactat ggttatggaa ctgtagctat ggagaagagc  540
tttagggact gttcaatatc accaggtggt aactccaacg gatcaatggg tcatcaaaac  600
attacatggg ttggagttga tccctacact tctcatcaag cataccettt tcttgaaaag  660
actaaacatt ttgatgaaac cctagacgat tatgaggaac tgcaacaaga agaagaaaat  720
taccaaagag cctctgcttt agaaactctc ccactttttc ccatgcacga agagaacatt  780
tccagtttct gcaacatcaa acatgaatct tcaggcggat tctacacaga atggtatcgt  840
tcagatgatc ataacttggc tgctgcggcc agagcttctc ttgaactcag tctcaactct  900
ttcattggca gatctcctaa ttccccttaa                                   930

SEQ ID NO: 64           moltype = AA  length = 309
FEATURE                 Location/Qualifiers
REGION                  1..309
                        note = Description of Artificial Sequence: Synthetic
                         polypeptide
source                  1..309
                        mol_type = protein
                        organism = synthetic construct
SEQUENCE: 64
MEAAQQQNQQ HYLHQQHLSI GQVANNIEDG VGGNSSKNNS SSFMCRQSST RWTPTTDQIR  60
ILKDLYYNNG VRSPTAEQIQ RISAKLRQYG KIEGKNVFYW FQNHKARERQ KKRLIAAAAT  120
DNNNNIPMQM RGVWRSADDP IHHKYNNTTG IHCPSASSHG VLAVGQNGNY GYGTVAMEKS  180
FRDCSISPGG NSNGSMGHQN ITWVGVDPYT SHQAYPFLEK TKHFDETLDD YEELQQEEEN  240
YQRASALETL PLFPMHEENI SSFCNIKHES SGGFYTEWYR SDDHNLAAAA RASLELSLNS  300
FIGRSPNSP                                                          309

SEQ ID NO: 65           moltype = DNA  length = 822
FEATURE                 Location/Qualifiers
misc_feature            1..822
                        note = Description of Artificial Sequence: Synthetic
                         polynucleotide
source                  1..822
                        mol_type = other DNA
                        organism = synthetic construct
SEQUENCE: 65
atggaagctg cccaacaaca aaaccagcag cactatcttc accaacaaca tttatcaatt  60
ggacaggtga caaacaacat tattgaagat ggtgttggtg gtaatagcag caaaaacaac  120
agcagcagtt tcatgtgcag gcaaagtagt acgaggtgga cacccacaac tgaccagata  180
agaatcttga aggatcttta ctacaacaat ggagttaggt ctccaactgc tgaacagatt  240
cagaggatct ctgctaagtt aagacagtac ggtaagattg aaggcaagaa tgtgttttat  300
tggtttcaga accataaagc tcgtgaaagg caaaagaaga ggcttattgc tgctgctgct  360
actgatagca acaataatat tccccatgcac atgagaggtg tttggagatc tgctgatgat  420
cctatccacc acaagtataa caacactaca ggtattcact gtccatcagc ttcttctcat  480
ggtgtactgg ccgttggaca gaatggaaac tatggttatg gaactttagc tatggaaaag  540
agctttagga ctaaacattt tgatgaaacc ctagtagacg attatgagga actgcaacaa  600
gaagaagaaa attaccaaag agcctctgct ttagaaactc tcccactttt tcccatgcat  660
gaagagaaca tctccagttt ctgcaacatc aaacatgaat cttcaggcgg attctacaca  720
gaatggtacc gttcagatga tcataacttg gctgctgcgg ccagagcttc tcttgaactt  780
agtctcaact ctttcattgg cagatctcct aattcccctt aa                     822

SEQ ID NO: 66           moltype = AA  length = 273
FEATURE                 Location/Qualifiers
REGION                  1..273
                        note = Description of Artificial Sequence: Synthetic
                         polypeptide
source                  1..273
                        mol_type = protein
                        organism = synthetic construct
```

```
SEQUENCE: 66
MEAAQQQNQQ HYLHQQHLSI GQVTNNIIED GVGGNSSKNN SSSFMCRQSS TRWTPTTDQI  60
RILKDLYYNN GVRSPTAEQI QRISAKLRQY GKIEGKNVFY WFQNHKARER QKKRLIAAAA  120
TDSNNNIPMH MRGVWRSADD PIHHKYNNTT GIHCPSASSH GVLAVGQNGN YGYGTLAMEK  180
SFRTKHFDET LVDDYEELQQ EEENYQRASA LETLPLFPMH EENISSFCNI KHESSGGFYT  240
EWYRSDDHNL AAAARASLEL SLNSFIGRSP NSP                              273

SEQ ID NO: 67          moltype = DNA  length = 291
FEATURE                Location/Qualifiers
misc_feature           1..291
                       note = Description of Artificial Sequence: Synthetic
                        polynucleotide
source                 1..291
                       mol_type = other DNA
                       organism = synthetic construct
SEQUENCE: 67
atggattcga agagttttct gctactacta ctactcttct gcttcttgtt ccttcatgat  60
gcttctgatc tcactcaagc tcatgctcac gttcaaggac tttccaaccg caagatgatg  120
atgatgaaaa tggaaagtga atgggttgga gcaaatggag aagcagagaa ggcaaagacg  180
aagggtttag gactacatga agagttaagg actgttcctt cgggacctga cccgttgcac  240
catcatgtga acccaccaag acagccaaga aacaactttc agctcccttg a          291

SEQ ID NO: 68          moltype = AA  length = 96
FEATURE                Location/Qualifiers
REGION                 1..96
                       note = Description of Artificial Sequence: Synthetic
                        polypeptide
source                 1..96
                       mol_type = protein
                       organism = synthetic construct
SEQUENCE: 68
MDSKSFLLLL LLFCFLFLHD ASDLTQAHAH VQGLSNRKMM MMKMESEWVG ANGEAEKAKT  60
KGLGLHEELR TVPSGPDPLH HHVNPPRQPR NNFQLP                           96

SEQ ID NO: 69          moltype = DNA  length = 396
FEATURE                Location/Qualifiers
misc_feature           1..396
                       note = Description of Artificial Sequence: Synthetic
                        polynucleotide
source                 1..396
                       mol_type = other DNA
                       organism = synthetic construct
SEQUENCE: 69
atgtgtattc catatcttga tccgtttgtt tcttactcac ttatagatca acaacttgca  60
tctactgcat ttctgttcgc ttctgaaatg actaatttca ctgccaaacg tttcaccctc  120
ttcctcttgc tgtgtgtttt ggttgtgcaa gaatctcatg ggtgcactag tagctcaaaa  180
tgcatttcac aaaaggaagt tgcttctgtg agaatactaa acagaaaggt tttaggaagc  240
cagcgggctg cttttggaaa gggcttaaat ggaaactaca atcattcagg gaagattaat  300
gacaagtttg ctgattggga gcttagggga attccagctg gtcctgatcc attgcaccac  360
aatggtgcta atccgaagaa accccggact ccataa                           396

SEQ ID NO: 70          moltype = AA  length = 131
FEATURE                Location/Qualifiers
REGION                 1..131
                       note = Description of Artificial Sequence: Synthetic
                        polypeptide
source                 1..131
                       mol_type = protein
                       organism = synthetic construct
SEQUENCE: 70
MCIPYLDPFV SYSLIDQQLA STAFLFASEM TNFTAKRFTL FLLLCVLVVQ ESHGCTSSSK  60
CISQKEVASV RILNRKVLGS QRAAFGKGLN GNYNHSGKIN DKFADWELRG IPAGPDPLHH  120
NGANPKKPRT P                                                      131

SEQ ID NO: 71          moltype = DNA  length = 1158
FEATURE                Location/Qualifiers
misc_feature           1..1158
                       note = Description of Artificial Sequence: Synthetic
                        polynucleotide
source                 1..1158
                       mol_type = other DNA
                       organism = synthetic construct
SEQUENCE: 71
atgttaggat cctttggttc atcatctcaa tctcatgatg aagaagctga tgatcaacgg  60
cggagatgca gttccacttc ccctgcaatc caaatccggc aactactcat tagctgcgcg  120
gagttaatct cacggtccga tttctcggcg gcaaacagac tcctcaccat tttatcaact  180
aactcttccc cttttgccac taatttcttg acacctaatg catcatctaa tgttgttgaa  240
agttcaaatg attcagctct acttcagtca tcctatcttt ccctaaacca agtgacccct  300
tttattagat ttagtcagct aactgctaat caagcgattt tagaagctat taacgataac  360
```

```
caacaagcga tccacatcgt tgattttgat attaatcacg gtgttcaatg gccaccgtta  420
atgcaagcac tagctgatcg ttaccctcct ccaactcttc ggattaccgg tactggaaat  480
gacctcgata cccttcgtag aaccggagat cgtttagcta aatttgctca ctctttaggc  540
cttagatttc agtttcaccc tcttttgatc accaataata atgacaatga tcatgaccct  600
tcaatcattt cttctattgt tcttctccct gatgagacat tagcaatcaa ctgtgtattt  660
tatcttcaca ggctcttaaa agaccgcgaa atgttaagga tttttttgca taggattaaa  720
tccatgaacc ctaaagttgt aacactggcc gagagagaag caaatcataa tcacccactt  780
tttttgcaaa gatttgtgga ggctttggat tattatgcag ctgtctttga ttcattggaa  840
gcaactttgc cgccgagcag tagagagagg atgacagtgg agcaagtttg gttcggaaga  900
gaaattatag atatagtagc agcagaagga gataagagaa gagaaagaca cgagagattc  960
agatcatggg aagtaatgtt gaggagctgt ggatttagca atgttgcttt aagtcctttt  1020
gcactttcac aagctaaact tctcttgaga cttcattacc cttctgaagg ataccagctt  1080
agtgtttcga gtacgagtaa ttctttcttc ttgggttggc aaaatcaacc cctttttttcc  1140
atatcttctt ggcgttaa                                               1158

SEQ ID NO: 72          moltype = AA  length = 385
FEATURE                Location/Qualifiers
REGION                 1..385
                       note = Description of Artificial Sequence: Synthetic
                        polypeptide
source                 1..385
                       mol_type = protein
                       organism = synthetic construct
SEQUENCE: 72
MLGSFGSSSQ SHDEEADDQR RRCSSTSPAI QIRQLLISCA ELISRSDFSA ANRLLTILST  60
NSSPFATNFL TPNASSNVVE SSNDSALLQS SYLSLNQVTP FIRFSQLTAN QAILEAINDN  120
QQAIHIVDFD INHGVQWPPL MQALADRYPP PTLRITGTGN DLDTLRRTGD RLAKFAHSLG  180
LRFQFHPLLI TNNNDNDHDP SIISSIVLLP DETLAINCVF YLHRLLKDRE MLRIFLHRIK  240
SMNPKVVTLA EREANHNHPL FLQRFVEALD YYAAVFDSLE ATLPPSSRER MTVEQVWFGR  300
EIIDIVAAEG DKRRERHERF RSWEVMLRSC GFSNVALSPF ALSQAKLLLR LHYPSEGYQL  360
SVSSTSNSFF LGWQNQPLFS ISSWR                                       385

SEQ ID NO: 73          moltype = DNA  length = 1224
FEATURE                Location/Qualifiers
misc_feature           1..1224
                       note = Description of Artificial Sequence: Synthetic
                        polynucleotide
source                 1..1224
                       mol_type = other DNA
                       organism = synthetic construct
SEQUENCE: 73
atgttaggat cctttggttc atcatctcaa tctcatgatg aagaaactga tgatcaacgg  60
cggagattca gttccacttc ccctgcaatc caaatccggc aactactcat tagctgcgcg  120
gagttaatct cgcggtccga tttctcggcc gcaaacagac tcctcaccat tttatcaact  180
aactcttccc cttttggtga ttcaactgaa agattagtcc atcagttcac tcgcgcactt  240
tctcttcgcc tcaaccgtta tatctcttca gccactaatt tcttgacacc atctaatgtt  300
gttgaaagtt caaatgattc agctctactt cagtcatcct atctttccct aaaccaagtg  360
actcctttca ttagatttag tcagctaact gctaatcaag cgattttgga agctattaac  420
gataaccaac aagcgatcca catcgttgat tttgatatta atcacggtgt tcaatggcca  480
ccgttaatgc aagcactagc tgatcgttac cctcctccaa ctcttcggat taccggtact  540
ggaaatgacc ttgataccct tcgtagaacc ggagatcgtt tagctaaatt tgctcactct  600
ttaggcctta gatttcagtt tcaccctctt ttgattacca ataataatga caatgatcat  660
gacccttcaa taatttcttc tattgttctt ctccctgatg agacattagc tatcaactgt  720
gtattttatc ttcacaggct cttgaaagac cgcgaaaagt taaggatttt tttgcatagg  780
attaaatcca tgaaccctaa agttgtaacg ctggccgaga gagaagcaaa tcataatcac  840
ccactttttt tgcaaagatt tgtggaggct ttggattatt atgcagctgt gtttgattca  900
ttggaagcaa ctttgccacc gagcagtaga gagaggatga cagtggaaca agtttggttc  960
gggagagaaa taattgatat agtagcagca gaaggagata agagaagaga aagacacgag  1020
agattcagat catgggaagt aatgttgagg agctgtggat ttagcaatgt tgctttaagc  1080
ccttttgcac tctcacaagc taaacttctc ttgagacttc attacccatc tgaaggatac  1140
cagcttagtg tttcgagtac gagtaattct ttcttcttgg gttggcaaaa tcaacccctt  1200
ttttccatat cttcttggcg ttaa                                        1224

SEQ ID NO: 74          moltype = AA  length = 407
FEATURE                Location/Qualifiers
REGION                 1..407
                       note = Description of Artificial Sequence: Synthetic
                        polypeptide
source                 1..407
                       mol_type = protein
                       organism = synthetic construct
SEQUENCE: 74
MLGSFGSSSQ SHDEETDDQR RRFSSTSPAI QIRQLLISCA ELISRSDFSA ANRLLTILST  60
NSSPFGDSTE RLVHQFTRAL SLRLNRYISS ATNFLTPSNV VESSNDSALL QSSYLSLNQV  120
TPFIRFSQLT ANQAILEAIN DNQQAIHIVD FDINHGVQWP PLMQALADRY PPPTLRITGT  180
GNDLDTLRRT GDRLAKFAHS LGLRFQFHPL LITNNNDNDH DPSIISSIVL LPDETLAINC  240
VFYLHRLLKD REKLRIFLHR IKSMNPKVVT LAEREANHNH PLFLQRFVEA LDYYAAVFDS  300
LEATLPPSSR ERMTVEQVWF GREIIDIVAA EGDKRRERHE RFRSWEVMLR SCGFSNVALS  360
PFALSQAKLL LRLHYPSEGY QLSVSSTSNS FFLGWQNQPL FSISSWR                407
```

```
SEQ ID NO: 75           moltype = DNA  length = 1014
FEATURE                 Location/Qualifiers
misc_feature            1..1014
                        note = Description of Artificial Sequence: Synthetic
                         polynucleotide
source                  1..1014
                        mol_type = other DNA
                        organism = synthetic construct
SEQUENCE: 75
atggggagag ctccatgttg tgataaagca aatgtgaaga gagggccatg gtctcctgaa  60
gaagatgcta aactcaaaga tttcattcac aaatatggaa ctggtggaaa ttggattgct  120
cttcctcaaa aagctggtct aaagagatgt gggaagagtt gtagattgag atggctaaat  180
tatttaaggc ctaacattaa acatggtgat tttctgagg aagaagatag agttatttgc  240
accttgtatt ccaccattgg aagcaggtgg tcaataatag cagctcaatt accgggaaga  300
actgacaatg atatcaagaa ttactggaat actaagctca agaaaaaacc tatgggatta  360
atgcaatcaa ctaaccaaag aaaatcacca tattttccag ctactaattc tcttcaaacc  420
caaccccaga taaattcaag tctttttaga gacttatatt acaccccaaa taataggcct  480
aatattacag gcctaaatca tcagtccatt tcttctgccc accagacaaa ttttctctac  540
actaataata acatgaactt tcctaatttg ggtgctacaa ataatcaata tccttataat  600
atccaaagtc ataatttact tatgtttgga gaagcaagtt gttcttcatc agatggaagt  660
tgcagccaaa tgagttttgg taaagaaatc aagagagaag aaattatgag taatagttta  720
caacaaggtc aaatttcaag tgttaatgct tttgaagaaa accaccagaa ttttactctt  780
gattatggca atagtagtag taattgggtg gatcaaaaac caaatgtgta ttttggtact  840
actactactc aagtacttca gtatgataat gttgaagaag ttaagcagca gctaacaagt  900
tgtaccaatg gcaacaatgg tagtactatt ggatgtaaca acaacaacag tatgttcgtg  960
ttcaatgatg agaattataa caagtcaaat gagatagaga tgttctatta ctga       1014

SEQ ID NO: 76           moltype = AA  length = 337
FEATURE                 Location/Qualifiers
REGION                  1..337
                        note = Description of Artificial Sequence: Synthetic
                         polypeptide
source                  1..337
                        mol_type = protein
                        organism = synthetic construct
SEQUENCE: 76
MGRAPCCDKA NVKRGPWSPE EDAKLKDFIH KYGTGGNWIA LPQKAGLKRC GKSCRLRWLN  60
YLRPNIKHGD FSEEEDRVIC TLYSTIGSRW SIIAAQLPGR TDNDIKNYWN TKLKKKPMGL  120
MQSTNQRKSP YFPATNSLQT QPQINSSLFR DLYYTPNNRP NITGLNHQSI SSAHQTNFLY  180
TNNNMNFPNL GATNNQYPYN IQSHNLLMFG EASCSSSDGS CSQMSFGKEI KREEIMSNSL  240
QQGQISSVNA FEENHQNFTL DYGNSSSNWV DQKPNVYFGT TTTQVLQYDN VEEVKQQLTS  300
CTNGNNGSTI GCNNNNSMFV FNDENYNKSN EIEMFYY                           337

SEQ ID NO: 77           moltype = DNA  length = 1011
FEATURE                 Location/Qualifiers
misc_feature            1..1011
                        note = Description of Artificial Sequence: Synthetic
                         polynucleotide
source                  1..1011
                        mol_type = other DNA
                        organism = synthetic construct
SEQUENCE: 77
atggggagag ctccatgttg tgataaagca aatgtgaaga gagggccatg gtctcctgaa  60
gaagatgcta aactcaaaga tttcattcac aaatatggaa ctggtggaaa ttggattgct  120
cttccccaaa aagcaggtct aaagagatgt gggaagagtt gtagattgag atggctaaat  180
tatctaaggc ctaatatcaa acatggtgat tttcggagg aagaagatag agttatttgc  240
agcttgtatt ccaccattgg aagcaggtgg tcaataatag cagctcaatt accaggaagg  300
actgacaatg atatcaagaa ttactggaat actaaactca agaaaaagct tatgggatta  360
atgcaatcaa caaaccaaag aaaatcacca tattttccag ctactaattc tcttcaaacc  420
caaccccaga taaattcaag tctttttaga gacttatatt acaacccaaa taataggcct  480
attattacag gcctaaatca gtccatttct tctgcccacc agccaaattt tctctacact  540
aatagtaaca tgaattttcc taatttgggt gctacaaata gtcaatatcc ttataatatt  600
caaagtcata atttacttat gtttggagaa gcaagttgtt cttcatcaga tggaagttgt  660
agccaaatga gttttggcaa agaaatcaag agagaggaaa ttatgagtaa ttgtttacaa  720
caaggtcaaa tttcaagtgt taatgctttt gaagaaaatc agaatttcac tcttgattat  780
ggtaacagta gtagtaattg ggtggatcaa aaaccaaatg tgtattttgg aaatactact  840
actactactc aagtacttca gtatgatgtt gaagaagtta agcagcagct aacaagttgt  900
accaatggca acaatggcag tactattgga tgtaacaaca acaacagtat gttcgtgttc  960
aatgatgaga attataacaa gtcaaatgag atagggatgt tctattactg a           1011

SEQ ID NO: 78           moltype = AA  length = 336
FEATURE                 Location/Qualifiers
REGION                  1..336
                        note = Description of Artificial Sequence: Synthetic
                         polypeptide
source                  1..336
                        mol_type = protein
                        organism = synthetic construct
```

```
SEQUENCE: 78
MGRAPCCDKA NVKRGPWSPE EDAKLKDFIH KYGTGGNWIA LPQKAGLKRC GKSCRLRWLN  60
YLRPNIKHGD FSEEEDRVIC SLYSTIGSRW SIIAAQLPGR TDNDIKNYWN TKLKKKLMGL  120
MQSTNQRKSP YFPATNSLQT QPQINSSLFR DLYYNPNNRP IITGLNQSIS SAHQPNFLYT  180
NSNMNFPNLG ATNSQYPYNI QSHNLLMFGE ASCSSSDGSC SQMSFGKEIK REEIMSNCLQ  240
QGQISSVNAF EENQNFTLDY GNSSSNWVDQ KPNVYFGNTT TTTQVLQYDV EEVKQQLTSC  300
TNGNNGSTIG CNNNNSMFVF NDENYNKSNE IGMFYY                            336

SEQ ID NO: 79          moltype = DNA  length = 495
FEATURE                Location/Qualifiers
source                 1..495
                       mol_type = unassigned DNA
                       organism = Bacillus amyloliquefaciens
SEQUENCE: 79
atgaaaagga atcagcttca catgatgaaa atgggaggta ttgctttgaa aaaacgatta  60
tcgtggattt ccgtttgttt actggtgctt gtctccgcgg cggggatgct gttttcaaca  120
gctgccaaaa cggaaacatc ttctcacaag gcacacacag aagcacaggt tatcaacacg  180
tttgacgggg ttgcggatta tcttcagaca tatcataagc tacctgataa ttacattaca  240
aaatcagaag cacaagccct cggctgggtg gcatcaaaag ggaaccttgc agacgtcgct  300
ccggggaaaa gcatcggcgg agacatcttc tcaaacaggg aaggcaaact cccgggcaaa  360
agcggacgaa catggcgtga agcggatatt aactatacat caggcttcag aaattcagac  420
cggattcttt actcaagcga ctggctgatt tacaaaaacaa cggaccatta tcagaccttt  480
acaaaaatca gataa                                                   495

SEQ ID NO: 80          moltype = AA  length = 164
FEATURE                Location/Qualifiers
source                 1..164
                       mol_type = protein
                       organism = Bacillus amyloliquefaciens
SEQUENCE: 80
MKRNQLHMMK MGGIALKKRL SWISVCLLVL VSAAGMLFST AAKTETSSHK AHTEAQVINT  60
FDGVADYLQT YHKLPDNYIT KSEAQALGWV ASKGNLADVA PGKSIGGDIF SNREGKLPGK  120
SGRTWREADI NYTSGFRNSD RILYSSDWLI YKTTDHYQTF TKIR                  164

SEQ ID NO: 81          moltype = DNA  length = 1290
FEATURE                Location/Qualifiers
source                 1..1290
                       mol_type = unassigned DNA
                       organism = Arabidopsis thaliana
SEQUENCE: 81
atgaacaaca acattttcag tactactacc accatcaatg acgactacat gttattccct  60
tataatgacc attattcctc acaaccattg ctccctttta gcccttcttc ttccattaac  120
gacatcttga ttcactccac ctctaacaca tcaaacaatc atcttgacca tcatcatcaa  180
ttccaacaac cttctccttt ttctcacttc gaatttgccc cggactgcgc cctcctcacc  240
tctttccacc cagaaaacaa tggccatgat gataaccaaa ccatcccaaa cgacaatcat  300
catccatcac ttcactttcc cttgaacaac accattgtag aacaacccac tgagccctcg  360
gaaactataa accttataga agattcccag agaatctcaa cttctcaaga cccaaaaatg  420
aaaaaagcca agaaacccag cagaacggac aggcacagca agatcaaaac ggccaaaggg  480
acacgagatc gtaggatgag actctcgcta gatgtcgcca aagagttgtt tggcttacaa  540
gacatgcttg gatttgacaa agccagcaaa accgttgaat ggttgcttac acaagcaaaa  600
cctgagatca taaagatcgc gacaaccctt tctcaccatg gctgcttcag cagcggcgat  660
gagtctcata tccgatccat ggacacatct tctgatctat gtgaacttgc atccatgtgg  720
acggtcgacg atagaggcag caatactaac acgaccgaaa caagaggaaa caaggtcgat  780
gggagatcga tgagagggaa gagaaagagg ccagaaccgc gaacgcccat tttaaagaag  840
ttgtccaagg aggagagagc gaaagctaga gaaagagcaa agggtagaac aatggagaaa  900
atgatgatga agatgaaagg aagatcacaa ttagtgaaag ttgtggaaga agacgctcat  960
gatcatggtg agataataaa gaataatat agaagccaag tgaatcggag ttcttttgag  1020
atgacacact gcgaagacaa gatcgaagaa ctttgcaaga acgatcgttt tgcagtttgc  1080
aacgaattta tcatgaataa gaaagatcac atttcaaatg aatcttatga cttagtcaac  1140
tacaaaccga actcatcatt cccagtgatt aaccaccatc gcagccaagg agcagctaat  1200
tccattgagc agcatcagtt tacggatctt cattactcct tcggcgcgaa accaagagac  1260
ctcatgcaca actatcaaaa catgtattga                                   1290

SEQ ID NO: 82          moltype = AA  length = 429
FEATURE                Location/Qualifiers
source                 1..429
                       mol_type = protein
                       organism = Arabidopsis thaliana
SEQUENCE: 82
MNNNIFSTTT TINDDYMLFP YNDHYSSQPL LPFSPSSSIN DILIHSTSNT SNNHLDHHHQ  60
FQQPSPFSHF EFAPDCALLT SFHPENNGHD DNQTIPNDNH HPSLHFPLNN TIVEQPTEPS  120
ETINLIEDSQ RISTSQDPKM KKAKKPSRTD RHSKIKTAKG TRDRRMRLSL DVAKELFGLQ  180
DMLGFDKASK TVEWLLTQAK PEIIKIATTL SHHGCFSSGD ESHIRSMDTS SDLCELASMW  240
TVDDRGSNTN TTETRGNKVD GRSMRGKRKR PEPRTPILKK LSKEERAKAR ERAKGRTMEK  300
MMMKMKGRSQ LVKVVEEDAH DHGEIIKNNN RSQVNRSSFE MTHCEDKIEE LCKNDRFAVC  360
NEFIMNKKDH ISNESYDLVN YKPNSSFPVI NHHRSQGAAN SIEQHQFTDL HYSFGAKPRD  420
LMHNYQNMY                                                          429

SEQ ID NO: 83          moltype = DNA  length = 299
```

```
FEATURE                 Location/Qualifiers
misc_feature            1..299
                        note = Description of Artificial Sequence: Synthetic
                         polynucleotide
source                  1..299
                        mol_type = other DNA
                        organism = synthetic construct
SEQUENCE: 83
atgtatccgc caagcaacag ctgcaactac agccccattt tcaacatccc ttctccttgt  60
atgcaatatg gagacgaact attcttccaa tattatcctg accatttcct tcaacagcaa  120
caagtgcctt tgatagaaga tcagagtgtt gacatcttag ctgattgcac tgagaatgtt  180
actaacgaag aaactgtcat caatactgat actgtaaaag ttctttatga cacaggagct  240
gttacaaaca gtcagtgttg gggaggaaat gaagaagtag aagaaggccg cgaaaacaa   299

SEQ ID NO: 84           moltype = DNA  length = 318
FEATURE                 Location/Qualifiers
misc_feature            1..318
                        note = Description of Artificial Sequence: Synthetic
                         polynucleotide
source                  1..318
                        mol_type = other DNA
                        organism = synthetic construct
SEQUENCE: 84
atggctcgct ccttgtgttt catggcattt gcagtcttgg caatgatgct ctttgttgcc  60
tatgaggtgc aagctagaga atgcaaaaca gaaagcaata cattccctgg attatgcatt  120
accaaaccac catgcagaaa agcttgtatc agtgagggat ttactgatgg tcattgtagc  180
aaaatcctca gaaggtgcct atgcactaag ccatgtgtgt ttgatgagaa gatgatcaaa  240
acaggagctg aaactttgc tgaggaagca aaaactttgg ctgcagcttt gcttgaagaa  300
gagataatgg ataactaa                                               318

SEQ ID NO: 85           moltype = DNA  length = 300
FEATURE                 Location/Qualifiers
misc_feature            1..300
                        note = Description of Artificial Sequence: Synthetic
                         polynucleotide
source                  1..300
                        mol_type = other DNA
                        organism = synthetic construct
SEQUENCE: 85
atggcaggga aggttgagaa agtgcttgca gtagtgatgc ttgcaatgct tctgttttcg  60
gagcatttaa tggctgctaa tcatgaaatt aaaacaactg aagataactc tactattagc  120
cctttctgct tagtaaaatg tttatttgga tgtagggggt tgccacctgt acaagcatcc  180
atttgtgctg ctcaatgtta tttaaagtgc cgtgaccaag atgcggccaa tattgctgaa  240
actaagggca taattggtga gactgcatac aaccagtatg atgttggatg tgcccttggc  300

SEQ ID NO: 86           moltype = DNA  length = 300
FEATURE                 Location/Qualifiers
misc_feature            1..300
                        note = Description of Artificial Sequence: Synthetic
                         polynucleotide
source                  1..300
                        mol_type = other DNA
                        organism = synthetic construct
SEQUENCE: 86
atgtatccgt caagcaacag ctgtaattac agcctcaata tttcctcctc aaataactta  60
tttcacattc catctccgaa ttctatgcaa tatgaacacg aacttttcca atattttcat  120
gaccatcatc tccttcaacc ccaacaacaa caacaacaac aacaactctt gactacacct  180
gatcattata tggcagcaga ttccaacaaa gacaccgtaa tcagtagtac taatcaagat  240
cctgaagaag ttgaattaca aggccgctgc aagaacaaaa aaggtgacaa taagagacgt  300

SEQ ID NO: 87           moltype = DNA  length = 362
FEATURE                 Location/Qualifiers
misc_feature            1..362
                        note = Description of Artificial Sequence: Synthetic
                         polynucleotide
source                  1..362
                        mol_type = other DNA
                        organism = synthetic construct
SEQUENCE: 87
atggaaaagg ttcatgagaa accgctatct ctttataatg gatcattatc tgtttttaga  60
ttaggagatt tggctgtgaa aataacaaag gtgaaaaagg gatcattaaa taatgataat  120
ctttcacccc caacttcatt gttagttgtt tcaccaatca taccaggaac ttatccagtt  180
ttactctttt ttcatggctt cgttctcaag cctatatggt acaagtctct ccttcaacat  240
atttcttccc acggctatat agttgttgct ccacaggttt ctcaaagcga agaagtgaaa  300
aaagcagcca aagttacaga atggttaagt aaagccctcg aatccgtact gccggagaaa  360
gt                                                                362

SEQ ID NO: 88           moltype = DNA  length = 300
FEATURE                 Location/Qualifiers
```

```
misc_feature          1..300
                      note = Description of Artificial Sequence: Synthetic
                       polynucleotide
source                1..300
                      mol_type = other DNA
                      organism = synthetic construct
SEQUENCE: 88
atgtgtttgt taataaaggt ggcgaatcca ggagaatccg gcgagcatga cagaattcca  60
tcaacgggag gtgattcaga aagtacaact actaccacag aaggaggaat tccgcagcta  120
tatgaacaat tacaatcaca atcacaatca tttgaagaaa tgttgcggca acaaatacaa  180
caagaaacag agtatttgat gtcttcatct gcaactccta tgttttcacg gtatagtcag  240
acaagggaga tgtcggcaat ggtaacggcg ttaacgcatg tggtatcagg acggagagag  300

SEQ ID NO: 89         moltype = DNA  length = 300
FEATURE               Location/Qualifiers
misc_feature          1..300
                      note = Description of Artificial Sequence: Synthetic
                       polynucleotide
source                1..300
                      mol_type = other DNA
                      organism = synthetic construct
SEQUENCE: 89
atggcacatt tcttctctat aaattcaacg ttagcaggaa cgaataaagc atccaaaaca  60
aatttcacat attcaactca agaaacagaa aaaccaaaaa taaagatcat cttactcttg  120
ttttctcttg cattagttcc cttgtcagcg atggcaactt gcaccactga tactccaaac  180
caagcactat tgagggatgt acacgatata gatggtaacc cccttcaagt aaaagccagg  240
tacttcatat ttccagttat tggcggtggt ggtgtacggc ttgctaatct tggagatcaa  300

SEQ ID NO: 90         moltype = DNA  length = 348
FEATURE               Location/Qualifiers
misc_feature          1..348
                      note = Description of Artificial Sequence: Synthetic
                       polynucleotide
source                1..348
                      mol_type = other DNA
                      organism = synthetic construct
SEQUENCE: 90
atggctgagc aacaccagcg ccaccagcaa cagcagcagc agcagcagat gcaagtgggc  60
cacccgacgg aggcaatcaa gagccttctt cctcaaaggg gtccctctaa atcccaagtc  120
cttgctgtcg tcactctctt ccctgttggt ggggccctcc tctgccttgc tggactgacg  180
ctcgccggaa ctctgatcgg gcttgcagtc gctacgccgg ttttcttact gttcagcccg  240
gttttggtcc ccgctgccct gacaatcgcg ttggccgtca ctggattctt gacttccggc  300
gcctttggaa taacggcgct gtcgtcgctc tcgtggatca ttaactat              348

SEQ ID NO: 91         moltype = DNA  length = 300
FEATURE               Location/Qualifiers
misc_feature          1..300
                      note = Description of Artificial Sequence: Synthetic
                       polynucleotide
source                1..300
                      mol_type = other DNA
                      organism = synthetic construct
SEQUENCE: 91
atgaacggtg gttcatgtgg tggtgctgat cgtgagtata ataacaataa caacaataat  60
gttgtaggtg gaggaggtgg cgggccttgt ggtgcatgca agtttcttag aagaaaatgt  120
gtgaggggat gcatatttgc accttatttt gattctgatc aaggcactgc tcatttcgct  180
gctgtacata aggtgtttgg tgctagcaat gcctctaaat tgctgctcag aattccagcg  240
cataaacgtc tggatgctgt cgttacactt tgctatgagg ctcttgctag agttagagac  300

SEQ ID NO: 92         moltype = DNA  length = 300
FEATURE               Location/Qualifiers
misc_feature          1..300
                      note = Description of Artificial Sequence: Synthetic
                       polynucleotide
source                1..300
                      mol_type = other DNA
                      organism = synthetic construct
SEQUENCE: 92
atgtcggata aaaaatctgt ctcgacgcca tttgaatgtt gcagaatctt gtttaagttt  60
ctgctgttta tggttattat cagtaatgtg gcgatccatg taacagcttt gagtgggcga  120
gaaggaataa ccccaagtac ggaatggggt ttggggcctc tggtgaagag aggagaaaga  180
aaactagtag tttcaactga aaatggggag gtctcttcag tcagagtagc tgatggaatc  240
accggttcct atcatcttca gttcatcaca ttggagccca attccctctt ccttcctgtt  300

SEQ ID NO: 93         moltype = DNA  length = 293
FEATURE               Location/Qualifiers
misc_feature          1..293
                      note = Description of Artificial Sequence: Synthetic
                       polynucleotide
```

```
source                  1..293
                        mol_type = other DNA
                        organism = synthetic construct
SEQUENCE: 93
atgggcgtac cagaatcgga ggtggtgtca caaggtgagg ttgaatcacc attgcaacca  60
gatcaaaacc agcacaagaa ccatcagttc ccgtccctcg gtagacaagc atcgatctac  120
tccctcactc tcgacgaatt ccaacacacc ctatgtgaaa gtggcaagaa tttcgggtcg  180
atgaatatgg atgaattcct aacagcattt ggactgctga agaaaaccaa gcccacgcac  240
acgcccatgc ccatgccgcg cacgggcatg cgcacgcgca ttctcatgct cat         293

SEQ ID NO: 94           moltype = DNA  length = 300
FEATURE                 Location/Qualifiers
misc_feature            1..300
                        note = Description of Artificial Sequence: Synthetic
                         polynucleotide
source                  1..300
                        mol_type = other DNA
                        organism = synthetic construct
SEQUENCE: 94
atggaggaaa aagatgaact tgaggaagaa gaagaatatg ttgatgatga aatcaagaac  60
aatttaccag tccaaaactc atcttcaata agttggttca caaaaatgat atctttacaa  120
gtagagatct tcaccactat cttagtttcc cccattttct atatcctctc ttttgtatct  180
gacttcaact tcctccgccc tgaagaaacc gaaaagaacg tagctgtagc tgtaaatgct  240
gctgctacag taccttcaaa agtagtacat ggaagtactt tactgctcaa gaaatttggt  300

SEQ ID NO: 95           moltype = DNA  length = 300
FEATURE                 Location/Qualifiers
misc_feature            1..300
                        note = Description of Artificial Sequence: Synthetic
                         polynucleotide
source                  1..300
                        mol_type = other DNA
                        organism = synthetic construct
SEQUENCE: 95
atgtataact caagcaacta cagctgtaat tacaacccca ttttctcatc taatttattc  60
aacatccctt ctccttgtat gcaatatgaa cacgaacttt tcttccaata ttaccatgat  120
caacttcaac agaatcttga cgatacctta gctgagatca gtactgagac tgccattatt  180
aacacggcag attccagcaa agacgaggct ataatcagta gaaatgaact tgaacaagat  240
caggaagcgc gtaagaataa aaagggtaaa gtaagcagca acaagagagt gtctaagaaa  300

SEQ ID NO: 96           moltype = DNA  length = 300
FEATURE                 Location/Qualifiers
misc_feature            1..300
                        note = Description of Artificial Sequence: Synthetic
                         polynucleotide
source                  1..300
                        mol_type = other DNA
                        organism = synthetic construct
SEQUENCE: 96
atgggaactg gtacttatgg agaagtggga cgtacaatac atcaaagatc aggaacacat  60
atacctcaaa ttctcgatcc gcctttgcta ggggatagtg attgcaagcg agaaggcaaa  120
catgtagaat ttatgcctcc aatcatgggt gaaaacttaa aagcagctaa tcaatttgaa  180
ctgatggccc cgtcaattgc attcaaatca tatccctatt cggaggtacc acaatattct  240
ggtggcaatg tggctgctgc atgtggtgaa tctttggtac atcaaaatat agaaagatca  300

SEQ ID NO: 97           moltype = DNA  length = 320
FEATURE                 Location/Qualifiers
misc_feature            1..320
                        note = Description of Artificial Sequence: Synthetic
                         polynucleotide
source                  1..320
                        mol_type = other DNA
                        organism = synthetic construct
SEQUENCE: 97
aggacaaggt tgtgtttgtg atgggagtca ccggcgccgg aaaatcaaga ctgtcaatag  60
acttagccac tcaattcaga ggagaaatag tgaactccga caaaatacaa gtgtacaaag  120
gtcttgatat tgccactaac aaaatcacac aagaagaacg ttgtggtgta ccacaccatc  180
tcctaggcgt aattgatcct tacaaagaat tcaccaccaa aaacttctgc aacatggctt  240
cacttgcagt taactctata accgaccgcg gtaaacttcc gatcatcgtt ggaggttcca  300
attcgtttat cgaggcgctt                                              320

SEQ ID NO: 98           moltype = DNA  length = 297
FEATURE                 Location/Qualifiers
misc_feature            1..297
                        note = Description of Artificial Sequence: Synthetic
                         polynucleotide
source                  1..297
                        mol_type = other DNA
                        organism = synthetic construct
```

```
SEQUENCE: 98
gaagatggtg ttggtggtaa tagcagcaaa aacaacagca gcagtttcat gtgcaggcaa  60
agtagtacga ggtggacacc cacaactgac cagataagaa tcttgaagga tctttactac  120
aacaatggag ttaggtctcc aactgctgaa cagattcaga ggatctctgc taagttaaga  180
cagtacggta agattgaagg caagaatgtg ttttattggt ttcagaacca taaagctcgt  240
gaaaggcaaa agaagaggct tattgctgct gctgctactg atagcaacaa taatatt     297

SEQ ID NO: 99          moltype = DNA  length = 339
FEATURE                Location/Qualifiers
misc_feature           1..339
                       note = Description of Artificial Sequence: Synthetic
                        polynucleotide
source                 1..339
                       mol_type = other DNA
                       organism = synthetic construct
SEQUENCE: 99
tctaatgttg ttgaaagttc aaatgattca gctctacttc agtcatccta tctttcccta  60
aaccaagtga ctcctttcat tagatttagt cagctaactg ctaatcaagc gattttggaa  120
gctattaacg ataaccaaca agcgatccac atcgttgatt ttgatattaa tcacggtgtt  180
caatggccac cgttaatgca agcactagct gatcgttacc ctcctccaac tcttcggatt  240
accggtactg gaaatgacct tgataccctt cgtagaaccg gagatcgttt agctaaattt  300
gctcactctt taggccttag atttcagttt caccctctt                        339

SEQ ID NO: 100         moltype = DNA  length = 480
FEATURE                Location/Qualifiers
misc_feature           1..480
                       note = Description of Artificial Sequence: Synthetic
                        polynucleotide
source                 1..480
                       mol_type = other DNA
                       organism = synthetic construct
SEQUENCE: 100
actgacaatg atatcaagaa ttactggaat actaagctca agaaaaaacc tatgggatta  60
atgcaatcaa ctaaccaaag aaaatcacca tattttccag ctactaattc tcttcaaacc  120
caaccccaga taaattcaag tctttttaga gacttatatt acaccccaaa taataggcct  180
aatattacag gcctaaatca tcagtccatt tcttctgccc accagacaaa ttttctctac  240
actaatagta acatgaattt tcctaatttg ggtgctacaa atagtcaata tccttataat  300
attcaaagtc ataatttact tatgtttgga gaagcaagtt gttcttcatc agatggaagt  360
tgtagccaaa tgagttttgg caaagaaatc aagagagagg aaattatgag taattgttta  420
caacaaggtc aaatttcaag tgttaatgct tttgaagaaa atcagaattt cactcttgat  480

SEQ ID NO: 101         moltype = DNA  length = 900
FEATURE                Location/Qualifiers
misc_feature           1..900
                       note = Description of Artificial Sequence: Synthetic
                        polynucleotide
source                 1..900
                       mol_type = other DNA
                       organism = synthetic construct
SEQUENCE: 101
atgaattcaa agaaaaacaa ctcaccaaga aaaaggttga gaaaatatca tacaagaaaa  60
gctcctatta ttagctctta tatggacatg gctgaagcta gaagagaaat tgttcatgct  120
ttacaacttc atcgatcttc atcttcatct ccaactccgt ctattaatag cccaaagaag  180
tacacattat tgggtcaagg agttgtaagc tctcaacaat attactatta ctcaatagtg  240
gaatctatgc ctattcctga accaacatgg tctacaacgg ctccggcaat acttaatgca  300
atgggaactg gtacttatgg agaagtggga cgtacaatac atcaaagatc aggaacacat  360
atacctcaaa ttctcgatcc gcctttgcta ggggatagtg attgcaagcg agaaggcaaa  420
catgtagaat ttatgcctcc aatcatgggt gaaaacttaa aagcagctaa tcaatttgaa  480
ctgatggccc cgtcaattgc attcaaatca tatccctatt cggaggtacc acaatattct  540
ggtggcaatg tggctgctgc atgtggtgaa tctttggtac atcaaaatat agaaagatca  600
atgtctgatc cccttgtgat tggtagagtg attggggaag ttgttgatta tttcactcca  660
agtgttaaga tgtctgttac ttataacagc agcaagcatg tttataatgg gcatgaactc  720
tttccttcct cagtcacctc taaacctagg gttgaagttc atggaggtga tttgagatct  780
ttctttacaa tgatcatgat agacccagat gttcctggtc ctagtgatcc atatctcagg  840
gaacacctac actggattgt cacagacatt ccaggcacta cagattgctc gtttgggaaa  900

SEQ ID NO: 102         moltype = DNA  length = 150
FEATURE                Location/Qualifiers
misc_feature           1..150
                       note = Description of Artificial Sequence: Synthetic
                        polynucleotide
source                 1..150
                       mol_type = other DNA
                       organism = synthetic construct
SEQUENCE: 102
caccacatag attgaacgga gggaataata gtgtagcccc attgggaaac accatattta  60
tataggtaga agaaatactc cagatttaac tagaatttct actgacaaaa gatcttttac  120
actatcaatc acttaaaaga taactacagg                                  150
```

```
SEQ ID NO: 103          moltype = DNA  length = 141
FEATURE                 Location/Qualifiers
misc_feature            1..141
                        note = Description of Artificial Sequence: Synthetic
                         polynucleotide
source                  1..141
                        mol_type = other DNA
                        organism = synthetic construct
SEQUENCE: 103
cactaagctt tcttttcctc ataacctcac ttgcttctcc tttgttcttc tttcgtctcc  60
tcctttgttt cgcctcccct tgttctggta actcttgagt gtagatacca ggatagtact  120
gagaaatgag tatcatttga t                                            141

SEQ ID NO: 104          moltype = DNA  length = 150
FEATURE                 Location/Qualifiers
misc_feature            1..150
                        note = Description of Artificial Sequence: Synthetic
                         polynucleotide
source                  1..150
                        mol_type = other DNA
                        organism = synthetic construct
SEQUENCE: 104
catgaaccaa cacaatagga ggcaaatcag tgttagtctt ttttgaatca tctgttttaa  60
ggctagtttc caaatttggc ttgaaaagcc aatcgctcag agtctgggaa acatcaccgg  120
ccactgaaac agctctgtca attggaatgt                                   150

SEQ ID NO: 105          moltype = DNA  length = 165
FEATURE                 Location/Qualifiers
misc_feature            1..165
                        note = Description of Artificial Sequence: Synthetic
                         polynucleotide
source                  1..165
                        mol_type = other DNA
                        organism = synthetic construct
SEQUENCE: 105
gttatcacaa ttcacaaggg aaagttcata acatgaccac tgtcgaatca aaaagggaaa  60
gttcatatat aatacgctta ggctttgggt ttttcaaatg aagggtagag ttcttcataa  120
acgaaattcc acattgttac ttcatatttc acatattccc gaata                  165

SEQ ID NO: 106          moltype = DNA  length = 153
FEATURE                 Location/Qualifiers
misc_feature            1..153
                        note = Description of Artificial Sequence: Synthetic
                         polynucleotide
source                  1..153
                        mol_type = other DNA
                        organism = synthetic construct
SEQUENCE: 106
ttctccttat acctcctgag taccataatt tacactcatc tatgtccaat gccttacatc  60
ccacccatct aatttcctga acacaagcta cactaatctt ctaatgagcg caaaatacaa  120
cacaaaatta ttgctcgcta gtcaaagata ata                               153

SEQ ID NO: 107          moltype = DNA  length = 180
FEATURE                 Location/Qualifiers
misc_feature            1..180
                        note = Description of Artificial Sequence: Synthetic
                         polynucleotide
source                  1..180
                        mol_type = other DNA
                        organism = synthetic construct
SEQUENCE: 107
tgggacattt gatagttaga cgttgtaact ttaggttgaa atctgcagtc gagttcattg  60
ttctctttat aataatcact tgaaactggt tgctggctac acgctgctgt tgcttcaaca  120
tgcagatatg gcgctaccgg ccgtagtgca gatgtgggag tttccatttc aggcttggca  180

SEQ ID NO: 108          moltype = DNA  length = 560
FEATURE                 Location/Qualifiers
misc_feature            1..560
                        note = Description of Artificial Sequence: Synthetic
                         polynucleotide
source                  1..560
                        mol_type = other DNA
                        organism = synthetic construct
SEQUENCE: 108
attactctta actttaaata gatttcttat atatgggttc aaaaatgtct gatccccttg  60
tgattggtag agtgattggg gaagttgttg attatttcac tccaagtgtt aagatgtctg  120
ttacttataa cagcagcaag catgtttata atgggcatga actctttcct tcctcagtca  180
cctctaaacc tagggttgaa gttcatggag gtgatttgag atctttcttt acaatgatca  240
tgatagaccc agatgttcct ggtcctagtg atccatatct cagggaacac ctacactgga  300
```

```
ttgtcacaga cattccaggc actacagatt gctcgtttgg gaaagaaata gttggctatg  360
aaatgccaag gccaaatatt ggaattcaca ggtttgtatt tctgctgttc aagcagaaga  420
agaggcaaac agtattgact gcacctctct ccagggatcg atttaatacg cgtaaattcg  480
cagaagaaaa tgagcttggg tctcctgttg cagcagtttt cttcaattgc cagagggaaa  540
ctgctgccag aaggcgttga                                              560

SEQ ID NO: 109          moltype = DNA  length = 522
FEATURE                 Location/Qualifiers
misc_feature            1..522
                        note = Description of Artificial Sequence: Synthetic
                         polynucleotide
source                  1..522
                        mol_type = other DNA
                        organism = synthetic construct
SEQUENCE: 109
atggctcaaa tgacagatcc ccttgtgatt agtagggtgg ttggagatgt tgttgattat  60
ttctctccaa gtgttaagat gtgtgttatt tataacccca gtaagcatgt ctataatggg  120
catgaactct ttccatccct tgttacctct aaacctaagg ttgaagttca tggaggtgac  180
atgagatcct tctttacact gatcatgact gaccctgatg ttcctggtcc tagcgatcca  240
tatcttaggg agcacttaca ttgggtaatt acagacattc caggcactac agattcctcg  300
tttggaaaag aagtggtggg ctatgaaatg ccaatgccta acattggaat ccataggttt  360
gtgtttctgc tcttcaagca gaagaagagg caaacagtga gcgcaccatt atccagggac  420
cgattcaata cgcggaaata cgcagaagaa aatgagcttg gctctccagt tgctgctgtt  480
ttcttcaact gccaaaggga aaccgcggcc agaaagcgtt ga                    522

SEQ ID NO: 110          moltype = DNA  length = 453
FEATURE                 Location/Qualifiers
misc_feature            1..453
                        note = Description of Artificial Sequence: Synthetic
                         polynucleotide
source                  1..453
                        mol_type = other DNA
                        organism = synthetic construct
SEQUENCE: 110
atggctcaaa tgagtacaga tccccttgtg attggcaggg tggttggaga tgttgttgat  60
tatttctccc caagtgttaa aatgtctgtt atttgtaacc ccagcaaaca tgtctataat  120
gggcatgaac tctttccatc ctctgttacc tctaaaccta aggttgaagt taacggaggt  180
gacatgacat ccttctttac attgatcatg actgaccctg atgttcctgg tcctagtgat  240
ccatatatta gggagcactt gcactggaaa agaattaagt ggtgggctat gaaatgccaa  300
tgccaaataa aggaatccat aggtttgtgt ttgtgctgtt caagcagaag aaaaggcaaa  360
cagtatgcat tatccaggga ccgattcaat accaatacag ctgctgctgt tttcttcaat  420
tgccaaaggg aaaccgcggc cagaaggcgt tga                               453

SEQ ID NO: 111          moltype = DNA  length = 3155
FEATURE                 Location/Qualifiers
misc_feature            1..3155
                        note = Description of Artificial Sequence: Synthetic
                         polynucleotide
source                  1..3155
                        mol_type = other DNA
                        organism = synthetic construct
SEQUENCE: 111
aagcttccag aaggtaatta tccaagatgt agcatcaaga atccaatgtt tacgggaaaa  60
actatggaag tattatgtga gctcagcaag aagcagatca atatgcggca catatgcaac  120
ctatgttcaa aaatgaagaa tgtacagata caagatccta tactgccaga atacgaagaa  180
gaatacgtag aaattgaaaa agaagaacca ggcgaagaaa agaatcttga agacgtaagc  240
actgacgaca acaatgaaaa gaagaagata aggtcggtga ttgtgaaaga gacatagagg  300
acacatgtaa ggtggaaaat gtaagggcgg aaagtaacct tatcacaaag gaatcttatc  360
ccccactact tatcctttta tatttttccg tgtcattttt gcccttgagt tttcctatat  420
aaggaaccaa gttcggcatt tgtgaaaaca agaaaaaatt tggtgtaagc tattttcttt  480
gaagtactga ggatacaact tcagagaaat ttgtaagttt gtggatcctg caggctagcg  540
tgcactctag actcgacgaa ctgacgagct cgaatttccc cgatcgttca aacatttggc  600
aataaagttt cttaagattg aatcctgttg ccggtcttgc gatgattatc atataatttc  660
tgttgaatta cgttaagcat gtaataatta acatgtaatg catgacgtta tttatgagat  720
gggtttttat gattagagtc ccgcaattat acatttaata cgcgatagaa aacaaaatat  780
agcgcgcaaa ctatgataaa ttatcgcgcg cggtgtcatc tatgttacta gatcgggaat  840
tcctcgagca actattttta tgtatgcaag agtcagcata tgtataattg attcagaatc  900
gttttgacga gttcggatgt agtagtagcc attatttaat gtacatacta atcgtgaata  960
gtgaatatga tgaaacattg tatcttattg tataaatatc cataaacaca tcatgaaaga  1020
cactttcttt cacggtctga attaattatg atacaattct aatagaaaac gaattaaatt  1080
acgttgaatt gtatgaaatc taattgaaca agccaaccac gacgacgact aacgttgcct  1140
ggattgactc ggtttaagtt aaccactaaa aaaacggagc tgtcatgtaa cacgcggatc  1200
gagcaggtca cagtcatgaa gccatcaaag caaaagaact aatccaaggg ctgagatgat  1260
taattagttt aaaaattagt taacacgagg gaaaaggctg tctgacagcc aggtcacgtt  1320
atctttacct gtggtcgaaa tgattcgtgt ctgtcgattt taattatttt tttgaaaggc  1380
cgaaaataaa gttgtaagag ataaacccgc ctatataaat tcatatattt tcctctccgc  1440
tttgaattgt ctcgttgtcc tcctcacttt catcagccgt tttgaatctc cggcgacttg  1500
acagagaaga acaaggaaga agactaagag agaaagtaag agataatcca ggagattcat  1560
tctccgtttt gaatcttcct caatctcatc ttcttccgct ctttctttcc aaggtaatag  1620
```

```
gaactttctg gatctacttt atttgctgga tctcgatctt gttttctcaa tttccttgag  1680
atctggaatt cgtttaattt ggatctgtga acctccacta aatcttttgg ttttactaga  1740
atcgatctaa gttgaccgat cagttagctc gattatagct accagaattt ggcttgacct  1800
tgatggagag atccatgttc atgttacctg ggaaatgatt tgtatatgtg aattgaaatc  1860
tgaactgttg aagttagatt gaatctgaac actgtcaatg ttagattgaa tctgaacact  1920
gtttaaggtt agatgaagtt tgtgtataga ttcttcgaaa ctttaggatt tgtagtgtcg  1980
tacgttgaac agaaagctat ttctgattca atcagggttt atttgactgt attgaactct  2040
ttttgtgtgt ttgcagctca taaaaggtac caaacaatga ttgaacaaga tggattgcac  2100
gcaggttctc cggccgcttg ggtggagagg ctattcggct atgactgggc acaacagaca  2160
atcggctgct ctgatgccgc cgtgttccgg ctgtcagcgc aggggcgccc ggttcttttt  2220
gtcaagaccg acctgtccgg tgccctgaat gaactgcagg acgaggcagc gcggctatcg  2280
tggctggcca cgacgggcgt tccttgcgca gctgtgctcg acgttgtcac tgaagcggga  2340
agggactggc tgctattggg cgaagtgccg gggcaggatc tcctgtcatc tcaccttgct  2400
cctgccgaga aagtatccat catggctgat gcaatgcggc ggctgcatac gcttgatccg  2460
gctacctgcc cattcgacca ccaagcgaaa catcgcatcg agcgagcacg tactcggatg  2520
gaagccggtc ttgtcgatca ggatgatctg gacgaagagc atcaggggct cgcgccagcc  2580
gaactgttcg ccaggctcaa ggcgcgcatg cccgacggcg aggatctcgt cgtgacccat  2640
ggcgatgcct gcttgccgaa tatcatggtg gaaaatggcc gcttttctgg attcatcgac  2700
tgtggccggc tgggtgtggc ggaccgctat caggacatag cgttggctac ccgtgatatt  2760
gctgaagagc ttggcggcga atgggctgac cgcttcctcg tgctttacgg tatcgccgct  2820
cccgattcgc agcgcatcgc cttctatcgc cttcttgacg agttcttttg agcgggactc  2880
tggcgatcgc cccgatcgtt caaacatttg gcaataaagt ttcttaagat tgaatcctgt  2940
tgccggtctt gcgatgatta tcatataatt tctgttgaat tacgttaagc atgtaataat  3000
taacatgtaa tgcatgacgt tatttatgag atgggttttt atgattagag tcccgcaatt  3060
atacatttaa tacgcgatag aaaacaaaat atagcgcgca aactaggata aattatcgcg  3120
cgcggtgtca tctatgttac tagatcggga ctagt                            3155

SEQ ID NO: 112         moltype = DNA  length = 11801
FEATURE                Location/Qualifiers
misc_feature           1..11801
                       note = Description of Artificial Sequence: Synthetic
                        polynucleotide
source                 1..11801
                       mol_type = other DNA
                       organism = synthetic construct
SEQUENCE: 112
tgagcgtcgc aaaggcgctc ggtcttgcct tgctcgtcgg tgatgtactt caccagctcc  60
gcgaagtcgc tcttcttgat ggagcgcatg gggacgtgct tggcaatcac gcgcaccccc  120
cggccgtttt agcggctaaa aaagtcatgg ctctgccctc gggcggacca cgcccatcat  180
gaccttgcca agctcgtcct gcttctcttc gatcttcgcc agcagggcga ggatcgtggc  240
atcaccgaac cgcgccgtgc gcgggtcgtc ggtgagccag agtttcagca ggccgcccag  300
gcggcccagg tcgccattga tgcgggccag ctcgcggacg tgctcatagt ccacgacgcc  360
cgtgattttg tagccctggc cgacggccag caggtaggcc gacaggctca tgccggccgc  420
cgccgccttt tcctcaatcg ctcttcgttc gtctggaagg cagtacacct tgataggtgg  480
gctgcccttc ctggttggct tggtttcatc agccatccgc ttgccctcat ctgttacgcc  540
ggcggtagcc ggccagcctc gcagagcagg attcccgttg agcaccgcca ggtgcgaata  600
agggacagtg aagaaggaac acccgctcgc gggtgggcct acttcaccta tcctgcccgg  660
ctgacgccgt tggatacacc aaggaaagtc tacacgaacc ctttggcaaa atcctgtata  720
tcgtgcgaaa aaggatggat ataccgaaaa aatcgctata atgaccccga agcagggtta  780
tgcagcggaa aagcgccacg cttcccgaag ggagaaaggc ggacaggtat ccggtaagcg  840
gcagggtcgg aacaggagag cgcacgaggg agcttccagg gggaaacgcc tggtatcttt  900
atagtcctgt cgggtttcgc cacctctgac ttgagcgtcg atttttgtga tgctcgtcag  960
gggggcggag cctatggaaa aacgccagca acgcggcctt tttacggttc ctggcctttt  1020
gctggccttt tgctcacatg ttctttcctg cgttatcccc tgattctgtg gataaccgta  1080
ttaccgcctt tgagtgagct gataccgctc gccgcagccg aacgaccgag cgcagcgagt  1140
cagtgagcga ggaagcggaa gagcgccaga aggccgccag agaggccgag cgcggccgtg  1200
aggcttggac gctagggcag ggcatgaaaa agcccgtagc gggctgctac gggcgtctga  1260
cgcggtggaa agggggaggg gatgttgtct acatggctct gctgtagtga gtgggttgcg  1320
ctccggcagc ggtcctgatc aatcgtcacc ctttctcggt ccttcaacgt tcctgacaac  1380
gagcctcctt ttcgccaatc catcgacaat caccgcgagt ccctgctcga acgctgcgtc  1440
cggaccggct tcgtcgaagg cgtctatcgc ggcccgcaac agcggcgaga gcggagcctg  1500
ttcaacggtg ccgccgcgct cgccggcatc gctgtcgccg gcctgctcct caagcacggc  1560
cccaacagtg aagtagctga ttgtcatcag cgcattgacg gcgtccccgg ccgaaaaacc  1620
cgcctcgcag aggaagcgaa gctgcgcgtc ggccgtttcc atctgcggtg cgcccggtcg  1680
cgtgccggca tggatgcgcg cgccatcgcg gtaggcgagc agcgcctgcc tgaagctgcg  1740
ggcattcccg atcagaaatg agcgccagtc gtcgtcggct ctcggcaccg aatgcgtatg  1800
attctccgcc agcatggctt cggccagtgc gtcgagcagc gcccgcttgt tcctgaagtg  1860
ccagtaaagc gccggctgct gaacccccaa ccgttccgcc agtttgcgtg tcgtcagacc  1920
gtctacgccg acctcgttca acaggtccag ggcggcacgg atcactgtat tcggctgcaa  1980
ctttgtcatg cttgacactt tatcactgat aaacataata tgtccaccaa cttatcagtg  2040
ataaagaatc cgcgcgttca atcggaccag cggaggctgg tccggaggcc agacgtgaaa  2100
cccaacatac ccctgatcgt aattctgagc actgtcgcgc tcgacgctgt cggcatcggc  2160
ctgattatgc cggtgctgcc gggcctcctg cgcgatctgg ttcactcgaa cgacgtcacc  2220
gcccactatg gcattctgct ggcgctgtat gcgttggtgc aatttgcctg cgcacctgtg  2280
ctgggcgcgc tgtcggatcg tttcgggcgg cggccaatct tgctcgtctc gctggccggc  2340
gccagatctg gggaaccctg tggttggcat gcacatacaa atggacgaac ggataaacct  2400
tttcacgccc ttttaaatat ccgattattc taataaacgc tcttttctct taggtttacc  2460
cgccaatata tcctgtcaaa cactgatagt ttaaactgaa ggcgggaaac gaagcttcca  2520
gaaggtaatt atccaagatg tagcatcaag aatccaatgt ttacgggaaa aactatggaa  2580
```

-continued

```
gtattatgtg agctcagcaa gaagcagatc aatatgcggc acatatgcaa cctatgttca  2640
aaaatgaaga atgtacagat acaagatcct atactgccag aatacgaaga agaatacgta  2700
gaaattgaaa aagaagaacc aggcgaagaa aagaatcttg aagacgtaag cactgacgac  2760
aacaatgaaa agaagaagat aaggtcggtg attgtgaaag agacatagag gacacatgta  2820
aggtggaaaa tgtaagggcg gaaagtaacc ttatcacaaa ggaatcttat cccccactac  2880
ttatcctttt atatttttcc gtgtcatttt tgcccttgag ttttcctata taaggaacca  2940
agttcggcat ttgtgaaaac aagaaaaaat ttggtgtaag ctattttctt tgaagtactg  3000
aggatacaac ttcagagaaa tttgtaagtt tgtggatcct gcaggctagc gtgcactcta  3060
gactcgacga actgacgagc tcgaatttcc ccgatcgttc aaacatttgg caataaagtt  3120
tcttaagatt gaatcctgtt gccggtcttg cgatgattat catataattt ctgttgaatt  3180
acgttaagca tgtaataatt aacatgtaat gcatgacgtt atttatgaga tgggttttta  3240
tgattagagt cccgcaatta tacatttaat acgcgataga aaacaaaata tagcgcgcaa  3300
actatgataa attatcgcgc gcggtgtcat ctatgttact agatcgggaa ttcctcgagc  3360
aactattttt atgtatgcaa gagtcagcat atgtataatt gattcagaat cgttttgacg  3420
agttcggatg tagtagtagc cattatttaa tgtacatact aatcgtgaat agtgaatatg  3480
atgaaacatt gtatcttatt gtataaatat ccataaacac atcatgaaag acactttctt  3540
tcacggtctg aattaattat gatacaattc taatagaaaa cgaattaaat tacgttgaat  3600
tgtatgaaat ctaattgaac aagccaacca cgacgacgac taacgttgcc tggattgact  3660
cggtttaagt taaccactaa aaaaacggag ctgtcatgta acacgcggat cgagcaggtc  3720
acagtcatga agccatcaaa gcaaaagaac taatccaagg gctgagatga ttaattagtt  3780
taaaaattag ttaacacgag ggaaaaggct gtctgacagc caggtcacgt tatctttacc  3840
tgtggtcgaa atgattcgtg tctgtcgatt ttaattattt ttttgaaagg ccgaaaataa  3900
agttgtaaga gataaacccg cctatataaa ttcatatatt ttcctctccg ctttgaattg  3960
tctcgttgtc ctcctcactt tcatcagccg ttttgaatct ccggcgactt gacagagaag  4020
aacaaggaag aagactaaga gagaaagtaa gagataatcc aggagattca ttctccgttt  4080
tgaatcttcc tcaatctcat cttcttccgc tctttctttc caaggtaata ggaactttct  4140
ggatctactt tatttgctgg atctcgatct tgttttctca atttccttga gatctggaat  4200
tcgtttaatt tggatctgtg aacctccact aaatcttttg gttttactag aatcgatcta  4260
agttgaccga tcagttagct cgattatagc taccagaatt tggcttgacc ttgatggaga  4320
gatccatgtt catgttacct gggaaatgat ttgtatatgt gaattgaaat ctgaactgtt  4380
gaagttagat tgaatctgaa cactgtcaat gttagattga atctgaacac tgtttaaggt  4440
tagatgaagt ttgtgtatag attcttcgaa actttaggat ttgtagtgtc gtacgttgaa  4500
cagaaagcta tttctgattc aatcagggtt tatttgactg tattgaactc tttttgtgtg  4560
tttgcagctc ataaaaggta ccaaacaatg attgaacaag atggattgca cgcaggttct  4620
ccggccgctt gggtggagag gctattcggc tatgactggg cacaacagac aatcggctgc  4680
tctgatgccg ccgtgttccg gctgtcagcg caggggcgcc cggttctttt tgtcaagacc  4740
gacctgtccg gtgccctgaa tgaactgcag gacgaggcag cgcggctatc gtggctggcc  4800
acgacgggcg ttccttgcgc agctgtgctc gacgttgtca ctgaagcggg aagggactgg  4860
ctgctattgg gcgaagtgcc ggggcaggat ctcctgtcat ctcaccttgc tcctgccgag  4920
aaagtatcca tcatggctga tgcaatgcgg cggctgcata cgcttgatcc ggctacctgc  4980
ccattcgacc accaagcgaa acatcgcatc gagcgagcac gtactcggat ggaagccggt  5040
cttgtcgatc aggatgatct ggacgaagag catcaggggc tcgcgccagc cgaactgttc  5100
gccaggctca aggcgcgcat gcccgacggc gaggatctcg tcgtgaccca tggcgatgcc  5160
tgcttgccga atatcatggt ggaaaatggc cgcttttctg gattcatcga ctgtggccgg  5220
ctgggtgtgg cggaccgcta tcaggacata gcgttggcta cccgtgatat tgctgaagag  5280
cttggcggcg aatgggctga ccgcttcctc gtgctttacg gtatcgccgc tcccgattcg  5340
cagcgcatcg ccttctatcg ccttcttgac gagttctttt gagcgggact ctggcgatcg  5400
ccccgatcgt tcaaacattt ggcaataaag tttcttaaga ttgaatcctg ttgccggtct  5460
tgcgatgatt atcatataat ttctgttgaa ttacgttaag catgtaataa ttaacatgta  5520
atgcatgacg ttatttatga gatgggtttt tatgattaga gtcccgcaat tatacattta  5580
atacgcgata gaaaacaaaa tatagcgcgc aaactaggat aaattatcgc gcgcggtgtc  5640
atctatgtta ctagatcggg actagtttac accacaatat atcctgccac cagccagcca  5700
acagctcccc gaccggcagc tcggcacaaa atcaccactc gatacaggca gcccatcagt  5760
ccgggacggc gtcagcggga gagccgttgt aaggcggcag actttgctca tgttaccgat  5820
gctattcgga agaacggcaa ctaagctgcc gggtttgaaa cacggatgat ctcgcggagg  5880
gtagcatgtt gattgtaacg atgacagagc gttgctgcct gtgatcaaat atcatctccc  5940
tcgcagagat ccgaattatc agccttctta ttcatttctc gcttaaccgt gacaggctgt  6000
cgatcttgag aactatgccg acataatagg aaatcgctgg ataaagccgc tgaggaagct  6060
gagtggcgct atttctttag aagtgaacgt tgacgatatc aactccccta tccattgctc  6120
accgaatggt acaggtcggg gacccgaagt tccgactgtc ggcctgatgc atccccggct  6180
gatcgacccc agatctgggg ctgagaaagc ccagtaagga aacaactgta ggttcgagtc  6240
gcgagatccc ccggaaccaa aggaagtagg ttaaacccgc tccgatcagg ccgagccacg  6300
ccaggccgag aacattggtt cctgtaggca tcgggattgg cggatcaaac actaaagcta  6360
ctggaacgag cagaagtcct ccggccgcca gttgccaggc ggtaaaggtg agcagaggca  6420
cgggaggttg ccacttgcgg gtcagcacgg ttccgaacgc catggaaacc gcccccgcca  6480
ggcccgctgc gacgccgaca ggatctagcg ctgcgtttgg tgtcaacacc aacagcgcca  6540
cgcccgcagt tccgcaaata gcccccagga ccgccatcaa tcgtatcggg ctacctagca  6600
gagcggcaga gatgaacacg accatcagcg gctgcacagc gcctaccgtc gccgcgaccc  6660
cgcccggcag gcggtagacc gaaataaaca acaagctcca gaatagcgaa atattaagtg  6720
cgccgaggat gaagatgcgc atccaccaga ttcccgttgg aatctgtcgg acgatcatca  6780
cgagcaataa acccgccggc aacgcccgca gcagcatacc ggcgacccct cggcctcgct  6840
gttcgggctc cacgaaaacg ccggacagat gcgccttgtg agcgtccttg gggccgtcct  6900
cctgtttgaa gaccgacagc ccaatgatct cgccgtcgat gtaggcgccg aatgccacgg  6960
catctcgcaa ccgttcagcg aacgcctcca tgggcttttt ctcctcgtgc tcgtaaacgg  7020
acccgaacat ctctggagct ttcttcaggg ccgacaatcg gatctcgcgg aaatcctgca  7080
cgtcggccgc tccaagccgt cgaatctgag ccttaatcac aattgtcaat tttaatcctc  7140
tgtttatcgg cagttcgtag agcgcgccgt gcgtcccgag cgatactgag cgaagcaagt  7200
gcgtcgagca gtgcccgctt gttcctgaaa tgccagtaaa gcgctggctg ctgaaccccc  7260
agccggaact gaccccacaa ggccctagcg tttgcaatgc accaggtcat cattgaccca  7320
```

```
ggcgtgttcc accaggccgc tgcctcgcaa ctcttcgcag gcttcgccga cctgctcgcg  7380
ccacttcttc acgcgggtgg aatccgatcc gcacatgagg cggaaggttt ccagcttgag  7440
cgggtacggc tcccggtgcg agctgaaata gtcgaacatc cgtcgggccg tcggcgacag  7500
cttgcggtac ttctcccata tgaatttcgt gtagtggtcg ccagcaaaca gcacgacgat  7560
ttcctcgtcg atcaggacct ggcaacggga cgttttcttg ccacggtcca ggacgcggaa  7620
gcggtgcagc agcgacaccg attccaggtg cccaacgcgg tcggacgtga agcccatcgc  7680
cgtcgcctgt aggcgcgaca ggcattcctc ggccttcgtg taataccggc cattgatcga  7740
ccagcccagg tcctggcaaa gctcgtagaa cgtgaaggtg atcggctcgc cgataggggt  7800
gcgcttcgcg tactccaaca cctgctgcca caccagttcg tcatcgtcgg cccgcagctc  7860
gacgccggtg taggtgatct tcacgtcctt gttgacgtgg aaaatgacct tgttttgcag  7920
cgcctcgcgc gggatttttct tgttgcgcgt ggtgaacagg gcagagcggg ccgtgtcgtt  7980
tggcatcgct cgcatcgtgt ccggccacgg cgcaatatcg aacaaggaaa gctgcatttc  8040
cttgatctgc tgcttcgtgt gtttcagcaa cgcggcctgc ttggcctcgc tgacctgttt  8100
tgccaggtcc tcgccggcgg tttttcgctt cttggtcgtc atagttcctc gcgtgtcgat  8160
ggtcatcgac ttcgccaaac ctgccgcctc ctgttcgaga cgacgcgaac gctccacggc  8220
ggccgatggc gcgggcaggg caggggggagc cagttgcacg ctgtcgcgct cgatcttggc  8280
cgtagcttgc tggaccatcg agccgacgga ctggaaggtt tcgcggggcg cacgcatgac  8340
ggtgcggctt gcgatggttt cggcatcctc ggcggaaaac cccgcgtcga tcagttcttg  8400
cctgtatgcc ttccggtcaa acgtccgatt cattcaccct ccttgcggga ttgccccgac  8460
tcacgccggg gcaatgtgcc cttattcctg atttgacccg cctggtgcct tggtgtccag  8520
ataatccacc ttatcggcaa tgaagtcggt cccgtagacc gtctggccgt ccttctcgta  8580
cttggtattc cgaatcttgc cctgcacgaa taccagcgac cccttgccca aatacttgcc  8640
gtgggcctcg gcctgagagc caaaacactt gatgcggaag aagtcggtgc gctcctgctt  8700
gtcgccggca tcgttgcgcc acatctaggt actaaaacaa ttcatccagt aaaatataat  8760
attttatttt ctcccaatca ggcttgatcc ccagtaagtc aaaaaatagc tcgacatact  8820
gttcttcccc gatatcctcc ctgatcgacc ggacgcagaa ggcaatgtca taccacttgt  8880
ccgccctgcc gcttctccca agatcaataa agccacttac tttgccatct ttcacaaaga  8940
tgttgctgtc tcccaggtcg ccgtgggaaa agacaagttc ctcttcgggc ttttccgtct  9000
ttaaaaaatc atacagctcg cgcggatctt taaatggagt gtcttcttcc cagttttcgc  9060
aatccacatc ggccagatcg ttattcagta agtaatccaa ttcggctaag cggctgtcta  9120
agctattcgt atagggacaa tccgatatgt cgatggagtg aaagagcctg atgcactccg  9180
catacagctc gataatcttt tcagggcttt gttcatcttc atactcttcc gagcaaagga  9240
cgccatcggc ctcactcatg agcagattgc tccagccatc atgccgttca aagtgcagga  9300
cctttggaac aggcagcttt ccttccagcc atagcatcat gtccttttcc cgttccacat  9360
cataggtggt ccctttatac cggctgtccg tcatttttaa atataggttt tcattttctc  9420
ccaccagctt atataccttta gcaggagaca ttccttccgt atcttttacg cagcggtatt  9480
tttcgatcag ttttttcaat tccggtgata ttctcatttt agccatttat tatttccttc  9540
ctcttttcta cagtatttaa agatacccca agaagctaat tataacaaga cgaactccaa  9600
ttcactgttc cttgcattct aaaaccttaa ataccagaaa acagcttttt caaagttgtt  9660
ttcaaagttg gcgtataaca tagtatcgac ggagccgatt ttgaaaccac aattatgggt  9720
gatgctgcca acttactgat ttagtgtatg atggtgtttt tgaggtgctc cagtggcttc  9780
tgtgtctatc agctgtccct cctgttcagc tactgacggg gtggtgcgta acggcaaaag  9840
caccgccgga catcagcgct atctctgctc tcactgccgt aaaacatggc aactgcagtt  9900
cacttacacc gcttctcaac ccggtacgca ccagaaaatc attgatatgg ccatgaatgg  9960
cgttggatgc cgggcaacag cccgcattat gggcgttggc ctcaacacga ttttacgtca  10020
cttaaaaaac tcaggccgca gtcggtaacc tcgcgcatac agccgggcag tgacgtcatc  10080
gtctgcgcgg aaatggacga acagtggggc tatgtcgggg ctaaatcgcg ccagcgctgg  10140
ctgttttacg cgtatgacag tctccggaag acggttgttg cgcacgtatt cggtgaacgc  10200
actatggcga cgctggggcg tcttatgagc ctgctgtcac cctttgacgt ggtgatatgg  10260
atgacggatg gctggccgct gtatgaatcc cgcctgaagg gaaagctgca cgtaatcagc  10320
aagcgatata cgcagcgaat tgagcggcat aacctgaatc tgaggcagca cctggcacgg  10380
ctgggacgga agtcgctgtc gttctcaaaa tcggtggagc tgcatgacaa agtcatcggg  10440
cattatctga acataaaaca ctatcaataa gttggagtca ttacccaatt atgatagaat  10500
ttacaagcta taaggttatt gtcctgggtt tcaagcatta gtccatgcaa gtttttatgc  10560
tttgcccatt ctatagatat attgataagc gcgctgccta tgccttgccc cctgaaatcc  10620
ttacatacgg cgatatcttc tatataaaag atatattatc ttatcagtat tgtcaatata  10680
ttcaaggcaa tctgcctcct catcctcttc atcctcttcg tcttggtagc tttttaaata  10740
tggcgcttca tagagtaatt ctgtaaaggt ccaattctcg ttttcatacc tcggtataat  10800
cttacctatc acctcaaatg gttcgctggg tttatcgcac ccccgaacac gagcacggca  10860
cccgcgacca ctatgccaag aatgcccaag gtaaaaattg ccggccccgc catgaagtcc  10920
gtgaatgccc cgacggccga agtgaagggc aggccgccac ccaggccgcc gccctcactg  10980
cccggcacct ggtcgctgaa tgtcgatgcc agcacctgcg gcacgtcaat gcttccgggc  11040
gtcgcgctcg ggctgatcgc ccatcccgtt actgccccga tcccggcaat ggcaaggact  11100
gccagcgctg ccatttttgg ggtgaggccg ttcgcggccg aggggcgcag ccccctggggg  11160
gatgggaggc ccgcgttagc gggccgggag ggttcgagaa gggggggcac ccccccttcgg  11220
cgtgcgcggt cacgcgcaca gggcgcagcc ctggttaaaa acaaggttta taaatattgg  11280
tttaaaagca ggttaaaaga caggttagcg gtggccgaaa aacgggcgga aacccttgca  11340
aatgctggat tttctgcctg tggacagccc ctcaaatgtc aataggtgcg cccctcatct  11400
gtcagcactc tgcccctcaa gtgtcaagga tcgcgcccct catctgtcag tagtcgcgcc  11460
cctcaagtgt caataccgca gggcacttat ccccaggctt gtccacatca tctgtgggaa  11520
actcgcgtaa aatcaggcgt tttcgccgat ttgcgaggct ggccagctcc acgtcgccgg  11580
ccgaaatcga gcctgcccct catctgtcaa cgccgcgccg ggtgagtcgg cccctcaagt  11640
gtcaacgtcc gcccctcatc tgtcagtgag ggccaagttt tccgcgaggt atccacaacg  11700
ccggcggccg cggtgtctcg cacacggctt cgacggcgtt tctggcgcgt ttgcagggcc  11760
atagacggcc gccagcccag cggcgagggc aaccagcccg g                      11801
```

```
SEQ ID NO: 113          moltype = DNA  length = 2499
FEATURE                 Location/Qualifiers
misc_feature            1..2499
```

```
                        note = Description of Artificial Sequence: Synthetic
                         polynucleotide
source                  1..2499
                        mol_type = other DNA
                        organism = synthetic construct
SEQUENCE: 113
tctaggagca aaaaaaaaaa aaaaaaaaaa aacaagtagt agtagtagta gtaaatggaa  60
aaatagagag gcaatttttt ttagtatctt actttatcca ttagcactta aaaaacatag  120
gtttacatgc tctcattgtc acgccaggcc gctaattaaa tggtacattt catcatcccc  180
atttttggc ctcatagtta attatcacaa tttctgaaag caacatcaga acaaccccac  240
atttcttgtg gtcctataat tactgctaga tagtccaaac ccatctgcct atttagggct  300
tgtgaatgag gattgaaaat ggtagagaat atttgcaaag gcatcatgca tatatggaaa  360
agactaaaga gagagttagt gccttgcaaa gcggattctc acagttgtag aaaaggactc  420
accattttca agaatactcc cggcatgaag atggacaatt taatataaaa aacaaagaaa  480
atagtaatta agtgcgttga gatgaatgaa atttatccgc tcttaattga atatggggaa  540
ttgaaagaaa tttctgataa taaattaatg agtcttacat gacgtggatc cgacttaatc  600
tagtctattt aaactaagaa tagataagaa tagagaatat agacaaaaga gaggctcatt  660
ggctagggtt tcaagggagt tccttgaaca taagtggcaa gtacaagcac aaagccaatt  720
tccatggact aaagatgaat aagatgtgtc gtgtggtatg gtgggaaggt gaggaggtat  780
ggggtaattg gagatgctaa acctctctaa aagctctttt gctccaaata tctaaatcca  840
tctctatcac ttttggcgac tgccccaaaa tttgcaactt atgaattaaa gttttaatat  900
ttttaagtta ataaattctg aattaataat ttaacatatt caataaactt tttaaaacaa  960
attacgtata taccatcaaa ctggctgcac catgatcact ttctaaactc acaatgacat  1020
atggatttaa tcaggcacaa agtcatgttg atagaaagag atagtacgga gaatgaagaa  1080
aaaaggtagg ggagagagat ggggtgagtg gggaaaagat agggttctct ttttagtgaa  1140
agcgacaggg tctgagaacc ctaggtcaaa agttgcataa acctctatac aggcttcttc  1200
actcccttac tactaatata ctctcattaa ggcttgaggt ttaattcatt aaaattgtgg  1260
tttaattatt gtatcccctc aaacgaaata attgtccttg tcgaggttag acaatgttgc  1320
gtactatttt caaacgcagt cagccattat tctcctatcc tttacagtcg agattcaaag  1380
acagaaagta gcatgcaagc tgttattaat ttactttgat taggactttg ccaagaaaat  1440
gaagaacctt ttctttttttc ttttaattta gttatcttac aacatgtaat ttttcctagc  1500
aagcaaatac ggtaactttt ttttttattc tcatttaatt tgttggagct attgctactt  1560
tgatgacttc aaccaaatcc tggttggtag gcggagggtg ctgacgatgg aaactacccc  1620
tcttgtccaa atacgataac ctaaaaaata gaataatagc ttattgtact gtgctgcaaa  1680
aattgcattg tcagtataca taattaaaat ctattttgaa tgtgtggagg gcaaagaggg  1740
gtgactggtc tagggttgta gaaatcaggt gggagagaga atggtatttg tctctgtgtc  1800
agctgatatc acgtgaagag gcacaataag aagtccttcg tatccattca cttcccaaaa  1860
ataccggcat tactacaaat atagtactag cacttgcttt ctctatcccc atctttgcta  1920
tttcctttcc ctttccaact ttttggcttt agaattgcaa agatggaggg aattgtggtt  1980
ctttgtatct gtaaaatttt tcctccaagc tccagttgta gctagcttaa tgcgtggacg  2040
cgcgcgcaca cactagaaat ctgcaatcta tatatatatt cacaaggcac tcacatatca  2100
aaaaccacat agacattgta tagagagagc tgtcgttctc aagcagaaaa aatgatatga  2160
tttcatcagc atgtggtcaa ccaaatagtt caattctagt ctttgcttcc tctttctaat  2220
tactgtataa atagagccac aaggacatag aattgagaaa ataaaagaca ataaaaacaa  2280
atctagctac ttaagcgaat gatgatgact ctctctcagt agtcttaact cttaataccc  2340
ttgttttcct tcttgtgctg cagtttgatt ggttaattaa cctaatcaaa agatgtttta  2400
actgtgtttt atccgtcttt ctcaagatct atcttagtcc caccacatag ctccctcaag  2460
ctacagctgc aaaatatata ctatatatat atataacaa                        2499

SEQ ID NO: 114          moltype = DNA  length = 2500
FEATURE                 Location/Qualifiers
misc_feature            1..2500
                        note = Description of Artificial Sequence: Synthetic
                         polynucleotide
source                  1..2500
                        mol_type = other DNA
                        organism = synthetic construct
SEQUENCE: 114
tgacattgct ttggtggttt aagttctcag ccagtatatg cattgtccta ataggtctca  60
catggaagca gcactgagag ttgtaagata cataaaagaa gctcctggct taggtctctt  120
cttgcctgta aaatcttcag atcaactaag tgctttttgt gactcagatt ggggagcatg  180
tatacaaatt agaaggttag ttacagggta cttggtaaag tttgaaagtg ctcttatatc  240
ctggaagtct aagaagcaga gtactgtgtc taggagctct aatgaagctg agtttataag  300
tatggcttca tgtgcagcag aagttacctg gccggtagga ctgttcagtg aacttggtgt  360
caaggttaaa cttcctataa acttggtatg tgatagtaaa gctgcaatcc aaattgcagc  420
aaatccaatc ttccatgaaa gaacaaaaca tattgatata gactgtcact ttgtaaagga  480
aaagctaagt ctaaggatgc taaaaactga gtatgtcaac atgaggatca actggcagat  540
atacttacaa aaggattgtg aagagctcaa catgtacatt tgctgaacaa gctagggttg  600
aagaatctgt atcaaccatc agcttgagag ggagtgttaa tcaacatggt taccactagt  660
ttatttataa agtgtaaatg ctaaaccata gctagtgagt tagttaatag ttagttgagt  720
ttgttataaa tattagtcag ctgtacagtt taacatagct tctctttcag aaatgaaaat  780
tgctcttctc tcatttcctc tcttctagat tcttcttctc cctccttctc ttagctcaga  840
tctctcttat gacagctaac aataaatacg aatatttctt gtaacggttg ctcattgaat  900
gttgtctttc tcaaccgata tctttctttc aagttttccc cccgattcga gtatttttga  960
aactcactca gcaccggtca catattcgta atcggtgcca gctatttgct tactcatatc  1020
ttatttgact tcattgtcac gtgtcagaca gaagtatgtg cgcatatacc atcaagtctc  1080
aatttgaaat aaaatcaact taagcagtta aaagtcaaat ctcttttagt tcggtcttta  1140
aaataataat ttaaataatg aacctataaa acacgcaact cacactgaat ataggggcag  1200
acataaaagc cgaaagactg aattccgaac cggaccgaat tatttcggta tttcgatatc  1260
```

-continued

```
ggtttattca gtatttcggt actatttcgg tataggattt ttagttattc ggtatttcgg  1320
tacgatcctc ggtattgaaa tttcgatatt tcggtatacc gaaataccga ataatttaag  1380
tacaccttcc ttcactgccc agcccgttat caattttcag cccaagtttc taacttgtta  1440
tttctttccc ttagccagta gcctactaag attaagccca acgccccaac ctaacattag  1500
aaattattat aattagaaaa gtataaagaa agtactcaca ttctactgct atgctcatgt  1560
agtgatttct attagaaatt attagaagtg aaggtactgc ccacattttc ttgttgctat  1620
actcattatc acgcaattag aaattttcta atgaattaga attcagtagt tcagcacaga  1680
ggcggatgta gcgtattacc tacgggttca actgaaccta taactttcga cacagagtaa  1740
aaatttatat gtaaaaattc tttaaaattg taaaaatcgt agatatgaac ccataacttt  1800
aaaaatataa tgggtaacat taaaattgaa cccatagaat ttaaatcctg gattcgcctc  1860
tggttcagca ttgtttagtt cacaaaaata tggtacgatg ccgaaccgta tcgaaaccat  1920
accgaaccaa acaagaagat atcgaacaat accgaactac tttggtacag tatttggtat  1980
gcacacttga tatatcgaat accgaaatac cgaaccgtaa ttttcgaata ccgtaccgaa  2040
ataccgaaca ctcacccata actaaacatt aaaaagctag aactcaggtg tttaatgact  2100
aaacggaagt aagatctaga taatccgtca ctctgttgat ttgtaaggct atcgacatgc  2160
aaaagtggaa gcaaaatgga gccgaaattt taacaaaaat gctgaaccaa taccatgaaa  2220
ttgatgaatg gtgggaccct atttcactct tttagaattt gcgtaagacc agaaaataac  2280
ttcaatcgaa atcaaaataa ataccaaccc ttttaggccc caaatcacta cgtgtgattt  2340
gcaaacgtca ttagccttat gtaaacagtg acctcatgcc aacatattat cgcagcctat  2400
aaatcttagt ttacatttca ttttctttca aacacacaca cctcacaata gaactaagtt  2460
gtaagagttt cattttcttt gttctttctc acaaaccaaa                        2500

SEQ ID NO: 115          moltype = DNA  length = 2500
FEATURE                 Location/Qualifiers
misc_feature            1..2500
                        note = Description of Artificial Sequence: Synthetic
                         polynucleotide
source                  1..2500
                        mol_type = other DNA
                        organism = synthetic construct
SEQUENCE: 115
tgccagacag tctaaaattc aaaaatagga cagcccacat cccctccacc ccactagatc  60
tcactacttc ttaattagga cttgtggggg ggagtagagg gatttgcaaa ggcggccgcg  120
gcatgcatat acggaaaaga gaagttagtg gtttgcaaag atgattgtgg aaaagggctt  180
acctaacaat gaagaagagg aagagggtag atggataata ataactcaaa aatagaaaga  240
agagggacaa gtgggggctc aatggctaag gttttaaggg aggtcttgga aacatcatta  300
gcaagtacat gcagtattac caccctacat cagactgtgg ggtctgatgg aatattcttc  360
tactatactc ttttaaatag agggaattaa tgagccttta taatgttgaa atttataaga  420
aaatagtata actttttaaa tctcttaatt atgtatcaaa tcaaatctca tatttaccct  480
ttagtggatc tattcactga agtctgaata aatcgtacca gtaattcata ccgaatgtgt  540
aaataatttg aaagaaagat agacaaggcc tcaatgkcta gggatttgtt agcatcaata  600
gcaagtataa gcagaaatat ataccaccaa ggagtgaggt ggaagaatta agatttactc  660
taatgaaata tatatatcaa gattgagtca tgtgaatgaa gaatttctta gtaccttaaa  720
ttaagcgaat atcacataac agaggtgtaa aaaaacgaaa gatggacaag ctaagtggct  780
ctcaatggct ggggtttaa gggatcggag gtcttgttaa catcagacgg aagtacaatt  840
agagtatata tgctactcta ataatacttg gctacaaaca taaaaaaata tctctatcac  900
tatctctcaa ctcgccatat agacttaatt ggcacaaagt catgctgatg gaaagagata  960
taaggagaat gggaagacaa aaaaaaaagt ggggatagaa agagtgtcca agtagctaga  1020
agggggtggg ggtgggggt gggggagttg ttgttttagt tgtggaagag ataggtttct  1080
ctttttagtg aaagtgacat atatagctag actgagaacc ctggtcaaaa gttgctttgc  1140
cttaacgttt ctaaatgcct gacctctgag aggctatctt ctcctctcat tctctcgacc  1200
cttactgttc atatacccc aaatttgagg tctaatttat ccacactatg gtttcttact  1260
gttgtcttct tctctgaaac aatattgctt gtcgatcttg gacttggcca cgtcaacgtg  1320
taacttcagc aactagggtg actccaagtc atagacagat ctaggtcgac ttctgtgaat  1380
ttaactaaac aaattattta atttcgactc aaaatagata tgtactatat atatatatag  1440
taaacttatt gtgaacttac taacttaaaa ttttcaagtt tgcagtattt tttggaataa  1500
gaaaggggaa aaagaggcag aaaaccccat atttcttcct ctttggagtt gacgctaaag  1560
ggataaagct aacatgcaag ctcttaacaa ataacatact cagtataatc tcacaaatgg  1620
ggtatagaga ggataaaacg tacacaaatc ttaacaatat acacagtgta attccataag  1680
tgagttctgt ggacggtagt agcttacccc ttgcctttaa catgcaagct cttaagcttt  1740
gtatttttat tttgttcttt ctttttggag aggaagaagt ggtggttgaa gactagagat  1800
aaggaagaaa agagaaggat ttttgtcagt tgctatcacg tgaactgaag gggcacaatt  1860
agagagaagt ctatatgctt cacttcccat aaaatcagtt gtaactacaa caagtactaa  1920
gagtgtcccc tccatttct ttctttccct caattccctt tcatactttt aaagcttaat  1980
tccacagcta gaaaaagaag cctttctttt tctctagagg tatttagcaa agatggaagg  2040
acaatattac agctctcttt gtctctacag gtaacaaacc attgcctgtc tttctcaatc  2100
tccagtattt ccagctatct tataatgctt tgagtactcc cacaaaacac atgcattata  2160
gccactagct acatatatat atatatttgt aaaaccacac attaatttag ctgtcattct  2220
caaccaaaaa gctatgttat catcaacata ttgacaaatt acctataatt ccttcccctc  2280
tagctatatg atctatctca ctttattatg cacttaaaaa gttatgttgt ccctctcaaa  2340
agtcttaatt aattaacctt gttttgcatc ttgctgcagc tagctagctt attaaattga  2400
caaactcaga agatgttgtg gttctttcaa cttcaataaa aagctaagag tagtacttgt  2460
gcttgtatat ccgtccttct caagctcaag tcccacttca                        2500

SEQ ID NO: 116          moltype = DNA  length = 3433
FEATURE                 Location/Qualifiers
misc_feature            1..3433
                        note = Description of Artificial Sequence: Synthetic
                         polynucleotide
```

```
source                  1..3433
                        mol_type = other DNA
                        organism = synthetic construct
SEQUENCE: 116
gttggagcta aaaataagag aaatggacaa gtgtcaaatt ctagcgtcca tggtagcgcg  60
acgcactatt gtggcgctag aaatagaaga ccaaaatttc caatgttggc gtcgaccttg  120
cgttgcggta ttttttctat ttcgctaggg acaagattat ttcaacaaaa ggggttctaa  180
acctaatttg gaggatatct aacatacttt gaaggcgaat tcacgtaagg gaatacaaac  240
cacgcttgga aggggctttc aactagtttt tcttctcttc ttttctcttc ctttcatctc  300
attatgtatt agttctaggg ttgttggtac ttacattaac gttatagttt gaagcttgga  360
ttatcttatt attttatcat attggtttat ttattcaatc ttgcgcttga taatttaatt  420
ttaattgatt gatcaccaat taaatactat ctacgaattt aggattgaaa tcgggagaga  480
aaattttaga ttgcatatag gattgagtag agtaagatct tgaacctgaa ttacgaggga  540
acgaatttgc gattaggata taaggatata cctaatcgtc ttgcttggtt actatacggg  600
aattattaat acgttcttat taatcctaat ccactggaat ataggcgttg agttagcttg  660
aacaggcgag tagtacttcg ggagaatact acgagtaata ttaaattgtc aatcaataaa  720
ctagataaat ttataagata gtttaagtaa aaaactcaat gagattgtta gttgacccat  780
aactctgaaa tattttctcc cattagattg tctttaagct tgccggcata gtttttctag  840
ttttctagtt tacaactcta gattagttat agttaacaat cacactttag aaaatcgctt  900
gagtagatta attgttaatt tagttgatag ttaatcataa gtcatcgagg gaacgatact  960
ctacttatca ctttattact tatcgaccac gtatacttga gtgcgtttgg gagcaacaaa  1020
tttttgacgc cgttgccggg acgttagttg atgttttcaa ctagtgaaca aaatgcaaat  1080
atgttatgca attcggtgcc atttacacgt ctatgaggag ttatattaaa gaactttatg  1140
taggatgttg gttggatcct acaagctaaa attatggcta agaaaattgt gaattactaa  1200
taaacttgta ataagataaa aaataatttc ctagaacgta atagaattga agtgagatta  1260
gaccgacacc tcttcgtcgg aaaactatgt tatatatgta ggttatttta tatatatata  1320
tatatatata tataattttc ttggcgttta attttttata ttttgattct tcctactaat  1380
aattctaact ctatcactga attaaacgta caggattcat ttcttataca aaagaggttg  1440
atcattatta ggtctgggca ctgtcagagg ctgaccgata tgagtagttc ttcacatgct  1500
tggcagcaat ttgaactgtg attgcttgag gggcgaaaaa gagagtagaa tctaagttcg  1560
gtaattttta tctgaattct gtatttgtct taaaaattta ttgagtatgc ataaaattat  1620
tattttaaac tcagtaattt aaaaaattta gaattcgaac tcataaattt caaattggga  1680
ctccacctct gattgtttgt aagtggagtt tagggggcaga actagctcaa aagttcggg  1740
ttcgattgaa ctcagtaaat ttgattcaaa gtctatatat ttattgaaaa atcaactaaa  1800
tatgtatata tacaataaat ttcaaattca taaaaattta aatcctgaat taacctaata  1860
gtaaaaccgc agactctaac tagtggtcta gtttagagag tcaaattatg gtttttaaca  1920
accttaaaca agcacaaata cttttccact attggttcaa ttttggttgt taacaacctt  1980
gattggtaat tacgtacttg catgggcatt tgaaaattaa gttacgtacg tgtaaaacgt  2040
tttagagtag tccgtactaa ttaagaacac aaacactgct tgagattttg tggcggaagt  2100
ttgttttgac ttagcatggg taggcccacg aattccccat tttgaataaa agacaacctg  2160
tgctagtcga ttagctatta tttaattact agaatattac ttactccctc ctttttaatt  2220
tagacgattt agtttgactt ggcacaaagt ttaaagaaaa aaaaaagact tttgaaatat  2280
gtggtgttaa aatcttaatg ggcaaaagct aagtggagtc atgatatttg tgtgactata  2340
aaaacttctc attaagaata aagtgagtaa aataaaaaat taaagtcaaa ttatttctaa  2400
atatagaaat atatcattct tttttgaacg gactaatacg gaaagtgtgt catttaaatt  2460
aaaataaata aagtaatatt tatcatatga ttttaacatg taaatatcat acaagtaatc  2520
taatcgtcaa gcgcggatct aataaataag ggacgggtat tttgtttagg ctgtgtatat  2580
ataatttttt aaaatctact aaaaaagaac aaataataga tttgtaaatt agagggatat  2640
ggtagaatct aactataaac ccttaaagtt caaatcttgt atctgcttgt ggtaatagtg  2700
tatatatatt ttttacacgt ttttgttgta tagaactcaa actaaaaagg gcattccagt  2760
gcacaaagca tctcctattc acacacaatt cggtgaaggg ccgcactgta tgcaaggggt  2820
gtgatatcgg cagtctatcc tgatgcaagc atcaatggtt gattccacgg ctcgaatccg  2880
ttacctatag gtcatacgga gataacttta ccgttactcc aagtccccct tctacataaa  2940
acttgcatca atagctgatt tcacgactcg aacccataac ctagttgata cgaagataac  3000
tttaccgttg cttcaaggtc cgtctacaca aaactgatca aattattttc ataaataaag  3060
aagctatcat ttctctataa atagaactag agtccttgca tattccaaca taagtatcag  3120
ttccaggaaa atcaagacat aatctgttag cttttctctt tgccattctc nnnnnnnnat  3180
ggattcctta ccagtctcct ccattgaatc tctagtcatt gagatcaaga aagagatgtt  3240
ctcaaaccaa gaatttaaca cttttgtcac cccaatatct gcctatgaca ctgcttggtt  3300
ggccatgatt tcttataata atcaagaaga agccattaat ggtcattctt tttctggccc  3360
tatgtttaag agttgtttaa attggattct caacaaccaa aatgagcaag gattttgggg  3420
agaatccaat ggt                                                     3433

SEQ ID NO: 117          moltype = DNA  length = 2512
FEATURE                 Location/Qualifiers
misc_feature            1..2512
                        note = Description of Artificial Sequence: Synthetic
                         polynucleotide
source                  1..2512
                        mol_type = other DNA
                        organism = synthetic construct
SEQUENCE: 117
aagctggtac ccttatgttt agtccaagaa aaataaccat acccaaatat aagggtttgt  60
tgaagacgga aatatataaa caaataaaca aatatcatca tatctccgat agtttaaaat  120
tttagattgg atatttcaca caatttatca aaattttcaa aaaaaaattc tactttttct  180
tgcttggaac ttggaagggg aaggggtggt ggtggagata gggcggggca tcttctatct  240
agtctatgtg attaatataa caaaacaaaa agggcgaggc aaaaacatgg atgaatggtg  300
gtccttttct atatttatat ggattgttac gatacgtcga tttcactttg caaaatacca  360
attagattca tttagttatc tttttgatca ctctgctttt actatcatat atatatagga  420
```

```
gtccttccac gtttcgcatg tgtcattgtt tatattttcc atggtcttcc ttccaaatgg  480
ctaaaaaaat ttgacacagt ggtcccaaaa gtttatagaa atagaattca acagtgaggc  540
atatacctat gaattctatt ttacatcttc atcgtataaa atagaatgtg ttataaactt  600
tacctcgtga tgcttacaag gggtgaaaat ataaaagcac tttatagatt tacaagagtc  660
acaccttgat ttatcctaag attttatttt tttacatgcc aaacaatgaa gtatgggaga  720
tccaattgga ataacatcaa atttaataaa attcgaaata gtcagagagc tgtctactga  780
ggtatattga aacttatttt tttttaatag aaaatatcaa atacttagca atatattaaa  840
atgtttcata aattacattg tttaaaccaa gcgttgaaac atatgctgat acgaggtagg  900
cttattgatg aatttataag ggcctcattg gaaaagacga tccaaagcaa tgggctaaaa  960
aattggccca ttttctgcca cccagtgtat ggttattact agtttcaccc acacagattt  1020
gcacttcatt agaggacaat gttgctgaat ttgaaacata agtccattta tctccactgt  1080
acagtccttc ctggagtcca atcctgacca tatcttcatg attttatgta atgtggtgaa  1140
taagcaaagt ttcatgttat gctttgtctc attttatagc aaattcattt cctcataaaa  1200
tttacttcaa aaaagtttcg tttgattttc agaaatcaaa atatgctttt cggtaaccaa  1260
atggttttca attttgttta cgaagaactt aaaactttcc aacaccctac atctatgatt  1320
gcaagttaaa attgcagaaa tatgacactt tttggagtgg tctttatcgt ttaacttcac  1380
ttgcacttta agggcaaaag ttaaaagtgt ttccatgaag caagcgaggg ataacactta  1440
ttaaacttga aattctactc atagaccaaa acaaggacaa aaattcaaga ctatctatgt  1500
gggtaaacgt acgaaaattg ggcttctcca gattagagcc ggaccttgtg gaaagacaga  1560
gaaattcgag gcccacttcc agtttctaag gagattaagc ctatcaaacg atggtccaga  1620
acgaaatatg tctttcttta ttctctacta tatagctgac tcagaatcgt tagaatttgc  1680
aatttcctca taataaaatg tgaggcagta tagattcgaa aacctttgtt gaagattatt  1740
gactcagcta cgcgaaacaa actgtagtat ccaatgtacc gattaacaag cgactggtta  1800
actatgaatt tgttagctcg acaaaatcac cggttaataa tgagtttgtg agttcgataa  1860
aatctaattt tctgatagaa attttatata ttatgcagaa atttaataaa agtagactta  1920
acttatatat tttagcattg actcttttga agtaaaatcc attccatcta aattatgact  1980
tccctacatc gagtaagtaa gttgcgtctg tatcctcatt ttacccactt ttcgctatgc  2040
aattattcaa ggatctttac acaaatagca agccaatatt aattatttat ttttttagt  2100
catatatata aattatacat atattatata cccattaatt atttttaatt taagtgatag  2160
attggacgac tatttggatt aattcttcgt tattcaagat aatagatgtc gtctctaata  2220
catgagctag aagataataa ggattactag gccgaaaggc tgatggaaat gaacaagaag  2280
ataagctcct aaatggaaac agtacggaaa aagtcaaaga gcagtgcatg ggaggaatca  2340
tcagtcagaa aaggaagcca cgtgtcaagt agaaacaagc acgtgtccat gcaaaagcca  2400
cgtaactccc ttccatcaca tcttccttct tcaaaacctc gtgttttact ctctcttttc  2460
tcactgccag tgatcgtcag gactgtgcat gtttgtttaa aaactaaagg ca          2512
```

```
SEQ ID NO: 118          moltype = DNA  length = 941
FEATURE                 Location/Qualifiers
misc_feature            1..941
                        note = Description of Artificial Sequence: Synthetic
                         polynucleotide
source                  1..941
                        mol_type = other DNA
                        organism = synthetic construct
SEQUENCE: 118
tttaaaacgc caaaaaataa gggacggcca tggcgtagca atgactattg ttccgtaggt  60
catttgtgaa ggaccgacaa aattttaggc gatccgggtc cgatttttcg gttctgctca  120
agaaaactcg atctgcacga atagcttata atcaaaccct ttttttttt tcaagaatgt  180
ctaattgatc ctaaaaagac aaccttatat gttccaccat ggcaggatcg gccttattac  240
taagggtttg ccaatagaca cgtttttaac attcaagtaa aaaaaacatt tattcttaat  300
aacccaccta ctatagtacg ttatttggca gtagactacg ttgtacattt gggaccattt  360
ggaacactcg tctttcacga gtcactaatt tttgtgttga atgcataaaa tttgtttttt  420
tctttttcga aattgaacaa ttttatcttc gatcacacct atagtatatt attaccttat  480
tgttagaaaa tattttattt tattattgac tcctaataaa aagtggggta aatttgggtc  540
ttttttttaa agaatgtgaa ctactcattt cactttggtt agaacaaata tgagaagatt  600
tgctaatgac agcaaaatga atagaccaaa agcgtaacga atattaaaaa taaacaattc  660
cgaataactg gttactgaaa attgtggaac tctacatagc cgttgtgagt atggtattgt  720
ttgttcttgt gggcagaata actagttacg gaaaatttat gaatttgctt cacattattt  780
ttttcatttt ctttttgct tcaaaagata agtacaagtt tttatactct tatttcattg  840
cctataaata cctctattga gttactgctc attcacaact ctaaatagca atctttctta  900
ttattaaaat tcctatcctt ttttactcat tcagagaaac g                     941
```

```
SEQ ID NO: 119          moltype = DNA  length = 3013
FEATURE                 Location/Qualifiers
misc_feature            1..3013
                        note = Description of Artificial Sequence: Synthetic
                         polynucleotide
source                  1..3013
                        mol_type = other DNA
                        organism = synthetic construct
SEQUENCE: 119
tttaaaacgc caaaaaataa gggacggcca tggcgtagca atgactattg ttccgtaggt  60
catttgtgaa ggaccgacaa aattttaggc gatccgggtc cgatttttcg gttctgctca  120
agaaaactcg atctgcacga atagcttata atcaaaccct ttttttttt tcaagaatgt  180
ctaattgatc ctaaaaagac aaccttatat gttccaccat ggcaggatcg gccttattac  240
taagggtttg ccaatagaca cgtttttaac attcaagtaa aaaaaacatt tattcttaat  300
aacccaccta ctatagtacg ttatttggca gtagactacg ttgtacattt gggaccattt  360
ggaacactcg tctttcacga gtcactaatt tttgtgttga atgcataaaa tttgtttttt  420
tctttttcga aattgaacaa ttttatcttc gatcacacct atagtatatt attaccttat  480
```

```
tgttagaaaa tattttattt tattattgac tcctaataaa aagtggggta aatttgggtc  540
ttttttttaa agaatgtgaa ctactcattt cactttggtt agaacaaata tgagaagatt  600
tgctaatgac agcaaaatga atagaccaaa agcgtaacga atattaaaaa taaacaattc  660
cgaataactg gttactgaaa attgtggaac tctacatagc cgttgtgagt atggtattgt  720
ttgttcttgt gggcagaata actagttacg gaaaatttat gaatttgctt cacattattt  780
ttttcatttt cttttttgct tcaaaagata agtacaagtt tttatactct tatttcattg  840
cctataaata cctctattga gttactgctc attcacaact ctaaatagca atctttctta  900
ttattaaaat tcctatccta atttactcaa acagagaaac gatgtatccg ccaagcaaca  960
gctgcaacta cagccccatt ttcaacatcc cttctccttg tatgcaatat ggagacgaac  1020
tattcttcca atattatcct gaccatttcc ttcaacagca acaagtgcct ttgatagaag  1080
atcagagtgt tgacatctta gctgattgca ctgagaatgt tactaacgaa gaaactgtca  1140
tcaatactga tactgtaaaa gttctttatg acacaggagc tgttacaaac agtcagtgtt  1200
ggggaggaaa tgaagaagta gaagaaggcc gcgaaaacaa aagaaatgac atgagaagca  1260
ccattagtat tattcatgta cggaaaaaca agaaatgttc caataaagat cgacatagca  1320
agattaacac tgctcgtggc ctcagagacc gaaggatgag actttccctt gatgcagctc  1380
gcaagttttt cagtttacaa gacatgttgg ggttcgataa ggcaagtaaa actgtagaat  1440
ggttgcttat caaatcggag tctgaaatcg aagagctagc caaaggcaat aaaggaggag  1500
gcattcctaa acaaagctgc agtactacta atggaattgg tgcaattagt actgcaatat  1560
cctctatttc tgagtgtgag gttatatcag gaactgatga atctttctct attacttata  1620
aaaagaagct gaaaactgct aaaggagcct cgaaaaagac ggctaaaact gctcgtagag  1680
ctgcatttga tcgtcttatt acaagggaaa cgaggaatca agcaagggct agggctagag  1740
agagaacaaa aataaagaaa agcctcggta aatccaaaga gaacagtgct gattactgta  1800
atttggtgga taattatgga gattggagtc aatttagtat cttcaactat cagaaaaatg  1860
cagttggaat ttcccatgat caggtgggtt caataattaa acaacatgat tttttaggat  1920
ttcaataggc tcgctccttg tgtaacatgg cataagcagt cttggcaatg atgctctttg  1980
ttgcctatgg tttgtctcca tttattcctc taatacccca taaaaataat aaaatataaa  2040
ttacatctac atgactggtt ttgaattatg ataatgaaca tgaagttaca cttcttatga  2100
tttttcaag tacattgtgt tttgattacc gcataaatat ttaagcatgg tcatcttttt  2160
tttgattcat ttgttgttag agtgactaat taatctgtag tatatgtctg gaggcttgag  2220
gaatctgaaa aaatgtgcgt gtttgcatag ttctttcaaa atagtatagg acaatatatt  2280
cttttaaaaa aaggagtccg gtgcacaaag catgtcgcat tgttccgagt aaaagctgca  2340
cccaaagagt gtgatgcaga caacctactc taatacaagc attaatgaac gcgttgctcc  2400
aaggctccgg ccccttcaat atatttcttt atgaaccgtg aatttattca tgtttaaaag  2460
ctttctttca attccatctt ttcttttgtt ctaacatttg ttagtaaacg tgaatgaatg  2520
tagaggttca agctagagaa tgcaaaacag aaagcaatac attccctgga ttatgcatta  2580
ccaaaccacc atgcagaaaa gcttgtatca gtgagggatt tactgatggt cattgtagca  2640
aaatcctcag aaggtgccta tgcactaagc catgtgtgtt tgatgagaag atgatcaaaa  2700
caggagctga aacttttgct gaggaagcaa aaactttggc tgcagctttg cttgaagaag  2760
agataatgga taactaatta gagattagag gaaaggatta attcagtgtc acacataata  2820
aagttgctgc ctttcttaaa aggatagcta atgtattggc ttttagtagc ctttgttacc  2880
ctaaaataag tgtgacatgt caatcctttt gatctagtac caagtttatg tatgttttaa  2940
tgaaaaatga tcttctatgg tcattgcaat cccattatat tccaagaaca aaacttcatt  3000
atttcttgg tcc                                                      3013

SEQ ID NO: 120          moltype = DNA  length = 120
FEATURE                 Location/Qualifiers
misc_feature            1..120
                        note = Description of Artificial Sequence: Synthetic
                         polynucleotide
source                  1..120
                        mol_type = other DNA
                        organism = synthetic construct
SEQUENCE: 120
tagcaatctt tcttattatt aaaattccta tcctttttta ctcattcaga gaaacgatgg  60
ctcgctcctt gtgtttcatg gcatttgcag tcttggcaat gatgctcttt gttgcctatg  120

SEQ ID NO: 121          moltype = DNA  length = 5668
FEATURE                 Location/Qualifiers
misc_feature            1..5668
                        note = Description of Artificial Sequence: Synthetic
                         polynucleotide
source                  1..5668
                        mol_type = other DNA
                        organism = synthetic construct
SEQUENCE: 121
tttaaaacgc caaaaaataa gggacggcca tggcgtagca atgactattg ttccgtaggt  60
catttgtgaa ggaccgacaa aattttaggc gatccgggtc cgatttttcg gttctgctca  120
agaaaactcg atctgcacga atagcttata atcaaaccct tttttttttt tcaagaatgt  180
ctaattgatc ctaaaaagac aaccttatat gttccaccat ggcaggatcg gccttattac  240
taagggtttg ccaatagaca cgtttttaac attcaagtaa aaaaaacatt tattcttaat  300
aacccaccta ctatagtacg ttatttggca gtagactacg ttgtacattt gggaccattt  360
ggaacactcg tctttcacga gtcactaatt tttgtgttga atgcataaaa tttgtttttt  420
tctttttcga aattgaacaa ttttatcttc gatcacacct atagtatatt attaccttat  480
tgttagaaaa tattttattt tattattgac tcctaataaa aagtggggta aatttgggtc  540
ttttttttaa agaatgtgaa ctactcattt cactttggtt agaacaaata tgagaagatt  600
tgctaatgac agcaaaatga atagaccaaa agcgtaacga atattaaaaa taaacaattc  660
cgaataactg gttactgaaa attgtggaac tctacatagc cgttgtgagt atggtattgt  720
ttgttcttgt gggcagaata actagttacg gaaaatttat gaatttgctt cacattattt  780
ttttcatttt cttttttgct tcaaaagata agtacaagtt tttatactct tatttcattg  840
```

```
cctataaata cctctattga gttactgctc attcacaact ctaaatagca atctttctta  900
ttattaaaat tcctatccta atttactcaa acagagaaac gtctaggagc aaaaaaaaaa  960
aaaaaaaaaa aaacaagtag tagtagtagt agtaaatgga aaaatagaga ggcaattttt 1020
tttagtatct tactttatcc attagcactt aaaaaacata ggtttacatg ctctcattgt 1080
cacgccaggc cgctaattaa atggtacatt tcatcatccc catttttttgg cctcatagtt 1140
aattatcaca atttctgaaa gcaacatcag aacaacccca catttcttgt ggtcctataa 1200
ttactgctag atagtccaaa cccatctgcc tatttagggc ttgtgaatga ggattgaaaa 1260
tggtagagaa tatttgcaaa ggcatcatgc atatatggaa aagactaaag agagagttag 1320
tgccttgcaa agcggattct cacagttgta gaaaaggact caccattttc aagaatactc 1380
ccggcatgaa gatggacaat ttaatataaa aaacaaagaa aatagtaatt aagtgcgttg 1440
agatgaatga aatttatccg ctcttaattg aatatgggga attgaaagaa atttctgata 1500
ataaattaat gagtcttaca tgacgtggat ccgacttaat ctagtctatt taaactaaga 1560
atagataaga atagagaata tagacaaaag agaggctcat tggctagggt ttcaagggag 1620
ttccttgaac ataagtggca agtacaagca caaagccaat ttccatggac taaagatgaa 1680
taagatgtgt cgtgtggtat ggtgggaagg tgaggaggta tggggtaatt ggagatgcta 1740
aacctctcta aaagctcttt tgctccaaat atctaaatcc atctctatca cttttggcga 1800
ctgccccaaa atttgcaact tatgaattaa agttttaata tttttaagtt aataaattct 1860
gaattaataa tttaacatat tcaataaact ttttaaaaca aattacgtat ataccatcaa 1920
actggctgca ccatgatcac tttctaaact cacaatgaca tatggattta atcaggcaca 1980
aagtcatgtt gatagaaaga gatagtacgg agaatgaaga aaaaaggtag gggagagaga 2040
tggggtgagt ggggaaaaga tagggttctc tttttagtga aagcgacagg gtctgagaac 2100
cctaggtcaa aagttgcata aacctctata caggcttctt cactccctta ctactaatat 2160
actctcatta aggcttgagg tttaattcat taaaattgtg gtttaattat tgtatcccct 2220
caaacgaaat aattgtcctt gtcgaggtta gacaatgttg cgtactattt tcaaacgcag 2280
tcagccatta ttctcctatc ctttacagtc gagattcaaa gacagaaagt agcatgcaag 2340
ctgttattaa tttactttga ttaggacttt gccaagaaaa tgaagaacct ttcttttttt 2400
cttttaattt agttatctta caacatgtaa tttttcctag caagcaaata cggtaacttt 2460
tttttttatt ctcatttaat ttgttggagc tattgctact ttgatgactt caaccaaatc 2520
ctggttggta ggcggagggt gctgacgatg gaaactaccc ctcttgtcca aatacgataa 2580
cctaaaaaat agaataatag cttattgtac tgtgctgcaa aaattgcatt gtcagtatac 2640
ataattaaaa tctattttga atgtgtggag ggcaaagagg ggtgactggt ctagggttgt 2700
agaaatcagg tgggagagag aatggtattt gtctctgtgt cagctgatat cacgtgaaga 2760
ggcacaataa gaagtccttc gtatccattc acttcccaaa aataccggca ttactacaaa 2820
tatagtacta gcacttgctt tctctatccc catctttgct atttcctttc cctttccaac 2880
tttttggctt tagaattgca aagatggagg gaattgtggt tctttgtatc tgtaaaattt 2940
ttcctccaag ctccagttgt agctagctta atgcgtggac gcgcgcgcac acactagaaa 3000
tctgcaatct atatatatat tcacaaggca ctcacatatc aaaaaccaca tagacattgt 3060
atagagagag ctgtcgttct caagcagaaa aaatgatatg atttcatcag catgtggtca 3120
accaaatagt tcaattctag tctttgcttc ctctttctaa ttactgtata aatagagcca 3180
caaggacata gaattgagaa aataaaagac aataaaaaca aatctagcta cttaagcgaa 3240
tgatgatgac tctctctcag tagtcttaac tcttaatacc cttgttttcc ttcttgtgct 3300
gcagtttgat tggttaatta acctaatcaa aagatgtttt aactgtgttt tatccgtctt 3360
tctcaagatc tatcttagtc ccaccacata gctccctcaa gctacagctg caaaatatat 3420
actatatata tatataacaa atgtatccgt caagcaacag ctgtaattac agcctcaata 3480
tttcctcctc aaataactta tttcacattc catctccgaa ttctatgcaa tatgaacacg 3540
aacttttcca atattttcat gaccatcatc tccttcaacc ccaacaacaa caacaacaac 3600
aacaactctt gactacacct gatcattata tggcagcaga ttccaacaaa gacaccgtaa 3660
tcagtagtac taatcaagat cctgaagaag ttgaattaca aggccgctgc aagaacaaaa 3720
aaggtgacaa taagagacgt gttgcttaca agaaagatag acacagcaag attaacactg 3780
ctcacggccc tagagaccga agaatgagac tttctctcga tgtagctcgc aaattttttca 3840
atttgcaaga cttgcttgga ttcgataagg ctagcaaaac tgtggagtgg ttgctaacaa 3900
agtccaaatg tgctgtcaat gagctcgtcc aaggcataaa taaagaaaat tgcgctactg 3960
ctaatattgg tgcaattagt acatgctcta ctacatctga gtgtgaagtt gtatcaggaa 4020
ttgatgaatc tacaaccact aatgatattc agaagcagtc aaatagaggt aaagtagggg 4080
agaagaagaa ggctaataaa ctagttcgta gagctgcatt taatcctgtg gcaaaggaat 4140
caagaaagca agctagagcg agggcaaggg agagaacaaa aataaagaaa agctttttaa 4200
atattggtga tcagtctatg gcggctgatg atttaaaacg attaggatgt tggagtcttt 4260
ttgaaacagg tgaagaatca ggtattcaag gtactaatca tcaaattgaa gaacacacca 4320
cgcaccacga ggagcctctt ttggggacta atgagaatgt tgatgattgt aatttggttg 4380
ttaccggcaa ctggaaccca tataccatct tcaattatca ccacagtact gaaatttctc 4440
acgaggtagg ttttacactt catttaaatc caagagtaat tcttttagag ttcaagattc 4500
tgatattttt tttggtggcg agaccctttc ttatatcaaa gcaaccttca aggtacatac 4560
aagattggat aaaccaattc tgagctcgct ccttgtgtaa catggcataa gcagtcttgg 4620
caatgatgct ctttgttgcc tatggtttgt ctccatttat tcctctaata ccccataaaa 4680
ataataaaat ataaattaca tctacatgac tggttttgaa ttatgataat gaacatgaag 4740
ttacacttct tatgattttt tcaagtacat tgtgttttga ttaccgcata aatatttaag 4800
catggtcatc ttttttttga ttcatttgtt gttagagtga ctaattaatc tgtagtatat 4860
gtctggaggc ttgaggaatc tgaaaaaatg tgcgtgtttg catagttctt tcaaaatagt 4920
ataggacaat atattctttt aaaaaaagga gtccggtgca caaagcatgt cgcattgttc 4980
cgagtaaaag ctgcacccaa agagtgtgat gcagacaacc tactctaata caagcattaa 5040
tgaacgcgtt gctccaaggc tccggcccct tcaatatatt tctttatgaa ccgtgaattt 5100
attcatgttt aaaagctttc tttcaattcc atcttttctt ttgttctaac atttgttagt 5160
aaacgtgaat gaatgtagag gttcaagcta gagaatgcaa aacagaaagc aatacattcc 5220
ctggattatg cattaccaaa ccaccatgca gaaaagcttg tatcagtgag ggatttactg 5280
atggtcattg tagcaaaatc ctcagaaggt gcctatgcac taagccatgt gtgtttgatg 5340
agaagatgat caaaacagga gctgaaactt ttgctgagga agcaaaaact ttggctgcag 5400
ctttgcttga agaagagata atggataact aattagagat tagaggaaag gattaattca 5460
gtgtcacaca taataaagtt gctgcctttc ttaaaaggat agctaatgta ttggctttta 5520
gtagcctttg ttaccctaaa ataagtgtga catgtcaatc cttttgatct agtaccaagt 5580
```

```
ttatgtatgt tttaatgaaa aatgatcttc tatggtcatt gcaatcccat tatattccaa  5640
gaacaaaact tcattatttt cttggtcc                                      5668

SEQ ID NO: 122          moltype = DNA  length = 210
FEATURE                 Location/Qualifiers
misc_feature            1..210
                        note = Description of Artificial Sequence: Synthetic
                         polynucleotide
source                  1..210
                        mol_type = other DNA
                        organism = synthetic construct
SEQUENCE: 122
atgaattcaa agaaaaacaa ctcaccaaga aaaaggttga gaaaatatca tacaagaaaa  60
gctcctatta ttagctctta tatggacatg gctgaagcta gaagagaaat tgttcatgct  120
ttacaacttc atcgatcttc atcttcatct ccaactccgt ctattaatag cccaaagaag  180
tacacattat tgggtcaagg agttgtaagc                                    210

SEQ ID NO: 123          moltype = DNA  length = 1575
FEATURE                 Location/Qualifiers
misc_feature            1..1575
                        note = Description of Artificial Sequence: Synthetic
                         polynucleotide
source                  1..1575
                        mol_type = other DNA
                        organism = synthetic construct
SEQUENCE: 123
atgattggat acccaaaacg tttcaccttg catggccttt ggccggcaaa cagtactgga  60
tatagtctaa aatgtgctcc acctccagag ggtaccagcg tgtggacaac agacggacag  120
ttacggacag ctcttcaaaa atgttggtat agtctgatcc ggggtcgtcc caattacata  180
ctgtggaaac atgaatggaa ggattatggc tattgctcta gtcatacaat aaaagatact  240
gactacttct gggctgcagt acgaaagcat ggaagaaaca ccaagattgc gggcgatgcg  300
attgttaacg aattgagtga tgcagaaatc agtccgtcaa atgataagga aaggagatgc  360
gagactgaaa gcgatagcag ccatcactac caacattctg aacaccatca acgaagatgg  420
ctgggaagac gacgagaatg cgacaccaaa cggtactccc aggcaaagta tatcacctcc  480
cctcacgaaa gcgtgacggc ttcacgcgaa aagagagcat ccacatccac aattgaggaa  540
gcaccaccag cagtgaagaa actattatta gagtggctga caagcactat aaacaatata  600
ttcgacaaac ctgcccaaaa ggagaatggc aacaccgcac aagcagatat cgtaacaact  660
actggcgagc agcctcttcc tcggacaggt aacacttacc ccactatgga cgcaggggct  720
aagaaggcgg aagccagggt gaacgacata ttcgctgtta ggcaatcgtc tggcgaggga  780
ctcagagact tcctcgcccg atttaacagg gaagaaatcc acaatgccta ttgcgccaag  840
gagagagccg acgatgatga ccttaacggt ccaatccaac ggctgacatc ggttcaagaa  900
gaatcgagaa gtgatcatcg taatgatagt caaagggatc agtcgggccc ccgtctcagc  960
cgagaaagac atcaacacta cgtcagaaca accgtcctgc catctcctcg acacatggaa  1020
gggccgccca ggccgtacat agggacacag cgaaacgaaa gaggtatgcc tccactctta  1080
tccactcaca atttttgtgt ttctccttca aaaatagtgt acgcactaaa gaagctcggc  1140
acgatggtga aatgtccaca aaagatgaag tccggcccaa atactcagaa gttgaatgcc  1200
atttgtgaat ttcaccagga acgaggtcac aaaaccgagg attgcatagg tttgcgacaa  1260
gaggtagtga gaatgttaaa ccaagggaac ttgaaagaac tgatgagtga tcgcggacga  1320
gtcaactttg cccgtggacg cgaactaccc cagggacctc ctaagcctcc ctctccagct  1380
cgcactatcc aaatgatcat cggtggaggc gacgaagcta tgatcaacca tatgaagttc  1440
accaccacgc ataaattgaa acggtcgatg acccacgaac ggtacgacga tttcggagac  1500
agtatcatct tcgataagtc agataccgac ggtttgactt ttccttattt tgaagctatc  1560
gttattactt tatga                                                    1575

SEQ ID NO: 124          moltype = DNA  length = 1032
FEATURE                 Location/Qualifiers
misc_feature            1..1032
                        note = Description of Artificial Sequence: Synthetic
                         polynucleotide
source                  1..1032
                        mol_type = other DNA
                        organism = synthetic construct
SEQUENCE: 124
atgagttgcc agaacagtaa aacagaagaa acggccgacg agcaacacaa taccagcaaa  60
gaccctaaac acaaaccctt ctttgacgtt tacggccctc aggggagggc agatattgtt  120
ttcaatcaac cggaatccaa ttcaactttg aatcttcaag acgtgcaagg tcttgtcaca  180
tgggtgcttg ctgatgggtt catgccgtca tgggctttta tcaaaaaacaa gcctttgatc  240
cctaaagtgg ttatgctgta tgttcctggc cttgatgccg ctctatattt gtcacagtct  300
aaagtgctca aaggtttcaa agaatgctgt ggtattccga ggccagtttt agctctgagc  360
tgtgtatcag atggaaatca gacaatagat gcactcctta cgtacaaatc aaagaggaaa  420
aggaaagaag ctgagcacat ttcaccaata aacaccgagc cttctgaaca aggtgctgag  480
actcccacta tggagcctct atcttttgtt gacctcaaaa aggatatacc atttcccatc  540
agttattaca cacttacgga taaggaacta gaagaaaatg gatactgtta tgaccaacca  600
gaatttcttt cgacgctccc tgctccttca ggaacatctc cacatgaaat tttggccctt  660
gactgcgaga tggttctgct ggataaattg gtcaaaccat caaacaacat tgttgactac  720
aatactaggt atagtggaat tacttgtcag atgttggagg atgtgactac cactcttaaa  780
gatatccagg aggagttctt gaaactggtt tacaaggaga ccattctggt tgggcattcc  840
ttggaaaatg atttgttagc cctgaagatc attcataatt tggtaataga tactgctgtg  900
ttgtacaaac atccaagagg atcctacaaa gctgctcttc gcgttctgag cagaaaattt  960
```

```
ctcggcaggg agatacagga ctcgggcaat gggcatgaca gcattgaaga tgcaaagcta  1020
cactggaact ag                                                      1032

SEQ ID NO: 125         moltype = DNA  length = 2172
FEATURE                Location/Qualifiers
misc_feature           1..2172
                       note = Description of Artificial Sequence: Synthetic
                        polynucleotide
source                 1..2172
                       mol_type = other DNA
                       organism = synthetic construct
SEQUENCE: 125
atggcctcca cctcctacat caccttcaaa ccccttcaac aaactcaact caaactctat  60
tacttcactc actgcagtaa gcattcttca actctgtttc actcttcttt tcatactctc  120
ctttctgcac caacaaaata cacactggaa ccaccaagaa ttttgccctc cattcaagtt  180
aaagcacatg tcactcactt ggaaacaaga ttgtcctttg aaccagagca agaaatatca  240
ggcagtagaa ctaataatga aaatagttct gggttttctt cctttagtcc caaagataag  300
atggttggca tgaaatcttc aagagaaaat ttagataggc actgtcaaac tttagatgaa  360
ttggtgcaat tgttcaagag cagtgcagaa gcttctaata caaaaagtgt gagaggcgaa  420
caggaagatc atggaattaa agtgagtgaa gaagtgaaac actatgcact taaatatggt  480
tttaagatat atgagaagat gcggtcagag aaggtacaaa tgaatgaagc aacccttaca  540
tctgttgcaa gaatggcaat ggcattggga aatggtgaca tggcatttga tgtggtaagg  600
ctaattaaag aatatggaat aaacccgagg ctgcgatctt atggtcctgc cttatctgtt  660
ttctgcaata atggggatgt tgacaaggca tttatggttg aagaacacat gttggagcat  720
ggtgtctatc cagaggaacc cgaactggag gcacttttaa aagtaagtgt agaagctggt  780
aggagtgaga aggtgtacta tttgttgcat aagcttcgag aaggagttcg acaagtctca  840
ccttctactg cagatttgat tgagaagtgg ttcaacagca agatagcttc aagggttggg  900
aaaagaaaat gggatgaaag aaccatacgc gaagctatta aaaatggagg tggtgggtgg  960
catggacaag gctggttggg taatggtaaa tggactgtat cacacgcata tgttgactct  1020
gacggctgct gcaaatgctg tggtgagaag ctggtgacta ttgatcttga tcctgttgaa  1080
actgaaaatt ttgccaagtc agttgcttct atagctgcgc agagagagag aaattcaagc  1140
ttccagaaat ttcaaagatg gcttgactat tatggaccct ttgaagctat tgttgatgga  1200
gcaaatgttg gcctttatag ccaaagaaaa tttaggccat ctagggtcaa tgctattgtc  1260
aacggaattc gccagatgct tccttcgaaa aagtggccgc tgatagtttt gcataataga  1320
cgtattactg gagataagat ggatgaacca ttcaatagag cgtactggct gtatgcagct  1380
ataaaattta agtgcttaat tgtgacgaat gatgaaatga gggaccattt gtttcaactt  1440
ctgggaaatg actttttccc aaagtggaaa gaacggcatc aggtgcattt cagtttctct  1500
gaaacaggtc cagtacttca catgccgcct ccctgttctg ttgtaattca gtcatcggaa  1560
agatttggac cagacagaag gatatatcat ggacggagta gcagaacttt gaaagataaa  1620
gaactatcag ggtctcggga ttcaggatat cccaggttat cggattacaa tttcaatatc  1680
aatttgatag agttggtttc agttatgaga aacatcaagg aagcaaggtt cccgaaacca  1740
attcgatcat actccagtca aaaggatcat tttaaaatta agcgtgtgtt ggttgatcca  1800
ggtagttctg ccaatattat ccaactaagg gtcttagaac aagcaaagct aatcgaagtt  1860
ccgacaatga agcttctggc cgggttcaac ctaacaagcg taacgaccca aggagagatc  1920
gtgttgccta catatgctga aggggtgacg aaatccacct tgttcaaagt tgtggatggc  1980
gatatgggct acaatgtaat tatcggtagg ccatggatcc acaaaaataaa agttgtgcca  2040
tcaacttatg atcaatttct aaattttcct acatcagacg ggattaagca gattagaggt  2100
gatcaacctg ctgcaaggga aatgaatgtt gtcaccttat ctagcagtaa tgcggaggaa  2160
atcaacaaat ag                                                      2172

SEQ ID NO: 126         moltype = DNA  length = 468
FEATURE                Location/Qualifiers
misc_feature           1..468
                       note = Description of Artificial Sequence: Synthetic
                        polynucleotide
source                 1..468
                       mol_type = other DNA
                       organism = synthetic construct
SEQUENCE: 126
atgcagtcgc cggaatcttg cgtcatagtg agttgcccaa ctactctaat agccgacgaa  60
gatgaagagg tggcagatat ggagacatct gttaaggcag tggaggaaat cttgaattac  120
aaattcatta aaccaaaact tcttgaagaa gcccttacgc actcttcttg cattgattct  180
gtttcttatc agcgccttga gttcgttgga gagcaggcgg agttccatgg aggagcaatg  240
aaggcgccga aggttcttgc tgatattgtg gagtctgtgg cggcagctgt atatgtggat  300
tgtggctttg atctgaagaa tctctggctg cttcttctga gaacaaagaa aatgctaact  360
tcacgctgca aggctgcact ccaaaagtta gcttttaaat ctattggtaa gacggatctg  420
aagttgaacc aaatacagag attgatgggg caagcaaaag ctgcatga              468

SEQ ID NO: 127         moltype = DNA  length = 705
FEATURE                Location/Qualifiers
misc_feature           1..705
                       note = Description of Artificial Sequence: Synthetic
                        polynucleotide
source                 1..705
                       mol_type = other DNA
                       organism = synthetic construct
SEQUENCE: 127
atgaaacctc aaaaatcatt gttgatcaag gttcttatta cacaatgttt gttagttctt  60
tgtgttgcac aacaggactt tgatttcttc tactttgttc aacagtggcc agcatcttat  120
```

```
tgtgatacaa gacgtagttg ttgttatccg actaccggaa aacctgatga agattttagc  180
atccatggtc tatggccaaa ctatgaaaat ggtaaatggc ctcaaaactg tgatcgtgaa  240
agctctttgg atgagtcaaa gatctcagat cttataagta caatggaaaa gaattggcca  300
tcattggctt gcccaagtag cgatggtgta agattttgga gtcatgaatg gctaaaacat  360
ggaacctgtt ctgctcttgg tgaacgtgct tactttcaag ctgctcttga cttcaggaaa  420
aaatcaaacc ttcttgaaaa ccttaagaat gcagggatta caccaaggaa tggagaacat  480
tacactttag aaagcattaa aaaggcaata gaagaaggag taggacacag cccttacata  540
gaatgcaatg tggatacaca aggaaatcac cagatttacc aagtttatct ctgtatggac  600
aaaactgcaa cagattttat tgattgccca gttttcccac atggccgagg atgtggttcc  660
aagattgaat tccctccttt ctcctctgac catgatgaat tttaa                  705

SEQ ID NO: 128         moltype = DNA  length = 654
FEATURE                Location/Qualifiers
misc_feature           1..654
                       note = Description of Artificial Sequence: Synthetic
                        polynucleotide
source                 1..654
                       mol_type = other DNA
                       organism = synthetic construct
SEQUENCE: 128
atggcaacta gaagacgaga ggctgacttt gatttcttct actttgttca acagtggccg  60
gcatcttatt gtgacacaag gcgtagttgc tgctatccaa caacgggaaa accagatgaa  120
gattttagca tccatggtct atggccaaac tatgaaaatg gcaaatggcc tcaaaactgc  180
gatcgtgaaa gctctttgga tgaatcagag atctcagatc ttataagtac aatggaaaag  240
aattggccat cgttggcttg cccaagtagt gatggtgtaa gattttggag tcatgaatgg  300
ctaaaacatg ggacctgttc agctcttggc gaacgtgctt actttcaagc tgctcttgac  360
ttcaggaaga aatccaacct tcttgaaaac cttaagaatg cagggattaa tccaaggaat  420
ggagaacatt acactttaga aagcattaaa aaggcaatag aagaaggagt aggacacagc  480
ccttatatag aatgcaatgt ggatacacaa ggaaaccacc agatttacca agtttatctg  540
tgtgtggaca aaactgcaac agattttatt gattgcccag ttttccctcg ggccgagga  600
tgtggttcca agattgaatt ccctcctttc tcctctgacc atgatgaatt ttaa        654

SEQ ID NO: 129         moltype = DNA  length = 483
FEATURE                Location/Qualifiers
misc_feature           1..483
                       note = Description of Artificial Sequence: Synthetic
                        polynucleotide
source                 1..483
                       mol_type = other DNA
                       organism = synthetic construct
SEQUENCE: 129
atgggtgtca ctacctataa ccaagaggtc acaacactag ttgccccaac taggttattc  60
aaagctttgg ttcttgattc tgaaaacctt gtcccaaaat tgatgccaca agttgttaag  120
aacattgaga ttgtagtggg tgatggtgat gcaggaagca tcaagaagat gaactttgtt  180
gaaggttctc ctatcaagta cttgaagcac aagatccatg ttattgatga caagaacttg  240
gtaaccaagt attcactgat cgaaggagat gttttaggtg ataaactgga gttcgttacc  300
tatgatatca aattcgaagc ttcaggaaat ggaggatgta tttgcaagac ttcaactgag  360
taccacacta agggtgatta tgtgtttaaa gaagaagaac actatgaggg caaaaagcaa  420
gccatggaac ttttcaagac tgttgaagat tacctcctcg caaatccttc cgtctatgtt  480
tga                                                                483

SEQ ID NO: 130         moltype = DNA  length = 483
FEATURE                Location/Qualifiers
misc_feature           1..483
                       note = Description of Artificial Sequence: Synthetic
                        polynucleotide
source                 1..483
                       mol_type = other DNA
                       organism = synthetic construct
SEQUENCE: 130
atgggtgttg caatttttac ccaagaattt acatccccta tagcaccaat tcgtttgttt  60
aaagctctaa ttgtggactc aaagtccctc atacccaaac tcttgcctca atttgttgag  120
agtgttgatt tgttacaagg agatggtgga gctggaagta tcgaacaagt gaacttcaca  180
aaaggtagtc cttttgagtt tgtgaaacat agaatagatg aactagataa agaaaatatg  240
gtgtgcaaat acactatgat tgaaggggat gcattggcag ataagtttga ctctatttct  300
tatgaagtaa aatttgaaga gtccaataat ggtggctgta tttgcaagat gacaactgag  360
tatattggaa ttggtgattt tatcgtcaaa gaagaagata tcaaggctgg gaaagatagt  420
gcaattggca tatataaagc tgtggaatct cacctccttc aaaatccaaa cctttatgcg  480
taa                                                                483

SEQ ID NO: 131         moltype = DNA  length = 483
FEATURE                Location/Qualifiers
misc_feature           1..483
                       note = Description of Artificial Sequence: Synthetic
                        polynucleotide
source                 1..483
                       mol_type = other DNA
                       organism = synthetic construct
SEQUENCE: 131
```

```
atgggtgtca ctacctatac tcatgaggtc acaacatcag ttgccccaac taggttattc  60
aaagctattg ttcttgattc tgaaaacctt gtcccaaaat tgatgccaaa agtagttaag  120
aacattgaga ttattgaggg tgatggtggt gctggaagca tcaagaagat gaactttgtt  180
gaaggttctc ctaacaagta cttgaagcac aagatccatg ttattgacga caagaacttg  240
gtgaccaaat attcactgat cgaaggagat gttttaggcg acaaactgga gttcgttact  300
tatgagatca aattcgaagc atctggaaat ggaggatgta tttgcaaaac ttcaactgag  360
taccacacaa agggtgacta tgtatttaaa gaagaagaac acaatgaagg caaaaatcaa  420
gctatggaac ttttcaagac tgttgaagat tacctcctcg ccaatccttc ggtctatgtt  480
taa                                                                483

SEQ ID NO: 132          moltype = DNA  length = 483
FEATURE                 Location/Qualifiers
misc_feature            1..483
                        note = Description of Artificial Sequence: Synthetic
                         polynucleotide
source                  1..483
                        mol_type = other DNA
                        organism = synthetic construct
SEQUENCE: 132
atggctatca cttccttcac tgatgagtac acttgtccta ttcctccatc aagaatcttt  60
aaagcctcca ttattgattc tcacaatttg atgccaaagc taatgccaca agctattaaa  120
agtattgaat ttgttcaggg taatggaggt gctggaagta ttaagcaaat caactttcct  180
gaaggtggca attttaagtc cattaagtat aggattgatg agcttaatga agagaaattt  240
gtttacaaat acactttgat tgaaggtgat gccttggttg ataaactcga aaaaataact  300
tacgaggtga agtttgagca gtcagcagat ggtggttcta tctctaaggt gacaagcaca  360
tattatacgg agggcgattt caagctcaag gaagaagaaa ttaaagcagg caaagagaaa  420
gtcttaggaa tgtataaagc agtagaagtc tatctcctgc agaatcctga tgcatatgct  480
taa                                                                483

SEQ ID NO: 133          moltype = DNA  length = 690
FEATURE                 Location/Qualifiers
misc_feature            1..690
                        note = Description of Artificial Sequence: Synthetic
                         polynucleotide
source                  1..690
                        mol_type = other DNA
                        organism = synthetic construct
SEQUENCE: 133
atggcttcaa attcggccac ttctctgttc ttgacactat ttcttattat acagtgttta  60
tcactcctta ctgctgctca agattttgac tttttctact ttgttcaaca gtggccaggg  120
tcttactgtg acactaaaca aagttgttgc taccccaaaa ctggaaaacc agcatcagat  180
tttggaatcc atggactttg gcctaataac aatgatggct cttacccatc aaactgtgat  240
tctaacagtc cttatgatca atctcaggtt tctgacttaa tcagcagaat gcaacaaaat  300
tggccaactc tagcatgccc aagtggtact ggctcagcat tttggtcaca tgaatgggaa  360
aaacatggca cttgttctga atctattttt gaccaacatg gctatttcaa gaaagctctt  420
gatctcaaaa atcaaattaa tcttttggaa attcttcagg gtgctggaat taaccctgat  480
ggcggatttt atagcttgaa cagcattaaa aatgcgatta acagcgcaat tgggtatact  540
cctggaatcg aatgtaatgt agacgagtcg ggtaatagcc agttatacca ggtttatatt  600
tgtgtcgatg gctcgggttc aaatctcatc gaatgccctg tttttcctag ggaaaaatgt  660
ggctccagca ttgagttccc aacattttaa                                  690

SEQ ID NO: 134          moltype = DNA  length = 690
FEATURE                 Location/Qualifiers
misc_feature            1..690
                        note = Description of Artificial Sequence: Synthetic
                         polynucleotide
source                  1..690
                        mol_type = other DNA
                        organism = synthetic construct
SEQUENCE: 134
atggcttcca attcagccac ttctcggttc ttgacactat ttcttattac gcagtgttta  60
tcagtcctca ctgctgctca agattttgac tttttctact ttgttcaaca gtggccagga  120
tcatactgtg atactaaaca aagttgttgt taccccaaaa ctggaaaacc agcatcagat  180
tttggaatcc atggactttg gccaaataat aatgatggct cttacccatc aaactgtgat  240
tctaacagtc cttatgatca atctcaggtt tctgacttaa ttagcagaat gcaacaaaat  300
tggccaactc tggcatgccc aagtgatact ggctcagcat tttggtcaca tgaatgggaa  360
aaacatggca cttgtgcaga aaatgttttt gaccaacatg gttatttcaa gaaagcactt  420
gatctcaaaa atcaaattaa tcttttggaa attcttcagg gtgctggaat taaccctgat  480
ggtggatttt atagcttgaa caatattaaa aatgcgatta gaagcgcggt tggttatact  540
cctggaattg aatgtaatgt agacgagtct ggtaatagcc agttatacca ggtttatatt  600
tgtgtcgatg gctcgggttc agatctcatc gaatgccctg tttttcctag aggaaaatgt  660
ggctcgagca ttgagttccc aacattctaa                                  690

SEQ ID NO: 135          moltype = DNA  length = 723
FEATURE                 Location/Qualifiers
misc_feature            1..723
                        note = Description of Artificial Sequence: Synthetic
                         polynucleotide
source                  1..723
```

```
                        mol_type = other DNA
                        organism = synthetic construct
SEQUENCE: 135
atgaggtcca tccaacttgt tttggtcaag cttgttatct ttcaatgtat catgttatta  60
catgctcagg attttgattt cttctacttt gctcaacagt ggaatccagc atcatgtgac  120
agcaagataa aatgttgcta cccaacaaat ggaaaaccag cacaagattt tggtattcat  180
gggctctggc caaattacaa caatggctca tttccaaaaa gctgtaacaa aaatgcccgt  240
tatgatgaaa cgcagatttc ggacttgata agtagtatgc agaagaattg gccgacacta  300
tcttgtccat caaacaatgg aacaaggttt tggtctcatg aatggaagaa acatggtact  360
tgttctcttt ctatgctaga tatgcattct tatttccaag ctgctcttgc cttgaaggaa  420
aaggtgaacc tgcttcaatt tctcaataat gcaggtatta aaccagatgg aggattttac  480
agctatgaag caatgaaaga agcaatagaa aaaggcattg gacatactgt tggtgtagaa  540
tgcaatattg atttatttgg gaatcgccag ctttttgagg tttatgtgtg tgttgataaa  600
tgtggttcgg aaatcattga ctgcccaatt gtcccagaaa gtaagagatg caaagaaagt  660
attgaatttg ctgtcttcga atcagaaagt ctccttgatg agaaatctgc ctattcactc  720
tag                                                                723

SEQ ID NO: 136          moltype = DNA  length = 798
FEATURE                 Location/Qualifiers
misc_feature            1..798
                        note = Description of Artificial Sequence: Synthetic
                         polynucleotide
source                  1..798
                        mol_type = other DNA
                        organism = synthetic construct
SEQUENCE: 136
atgagatcca tcaagtttgt cttggtcaag ctcgttatct ttcaatgtat aacgttatta  60
gtacatgcta aggacttaga tttctaccgc cttaccctac agcagtggaa tccagcagca  120
tgctacaata ggattatagg taaatgctgt aacacaacca cgggaagacc agcagaagat  180
tttggtattg ctggactatg gccatcttac aacaatctca catatccaga aaactgtaat  240
aaggcaggcc cttatgatga aacgcaagta agttttgata aaatacagat ctcggacttg  300
ctgagtagta tgcaaaagaa ttggcccaaa atatcttgtc catcaaacaa tggaactagt  360
ctgtgggcta aggaatggaa ggaacgtggt acttgttcta ggctcaacat gcattcttat  420
ttcgaaacag ctcttgatct taaggaaaag ctgaacctga ttcaagatgt taagcgttac  480
ggtacagatc ttacacatgt gcatatgcat ggactcgaac caaatggaca attttaccac  540
tggcgtcaca tcaatgcagc cataaaatta gctattggac atgtgatcgc tatagaatgc  600
aatcttggtt taactgcgga cagccagttt tacagggttc acatatgtgt tgataaatct  660
ggttcggact tcattgactg cccaattaac ctcaccgaaa tctctgagac aacatgttct  720
tcatctacta aatggtctgg ctacgataca gatagtgtcc ttgaagagcg atctgcctat  780
tcttgggcaa ggaaataa                                                798

SEQ ID NO: 137          moltype = DNA  length = 1482
FEATURE                 Location/Qualifiers
misc_feature            1..1482
                        note = Description of Artificial Sequence: Synthetic
                         polynucleotide
source                  1..1482
                        mol_type = other DNA
                        organism = synthetic construct
SEQUENCE: 137
atggggtcct ttagttttgc agtatgtgtt agcttaatgt tgctggttat ggtggttgct  60
attccttttg aacccaaaaa tggcagaagg atagggcggc tgcaccgctg gtgggacccc  120
ttaatacgat cgccggtaga tcgtgatgat gaggtggaag acagcaatag tgttcgttgg  180
gcagttcttg ttgctggttc aaatggatac ggaaattatc ggcatcaggc agatgtatgt  240
catgcttacc agattttgaa aagaggagga ttgaaagatg agaacatagt tgtattcatg  300
tatgatgaca ttgccaaaag tgagctgaat ccaaggcctg gagtcataat caatcatcca  360
aatggcagtg atgtctatgc tggtgtgcca aaggactaca ctggtgagca tgtcactgct  420
gcgaatctgt atgctgtgct tcttggtgat aagagtgctg tgaaaggtgg aagtgggaag  480
gtcatcgata gtaaaccgaa tgacagaata tttctctatt actctgatca tggtggtcca  540
ggggtcctcg ggatgccaaa catgcctttt ctttatgcca aagattttat tgaggccttg  600
aaaaagaagc atgcagcagg gacctacaaa gaaatggtcc tctacattga agcttgtgag  660
agcgggagtg tttttgaggg tatgatgcct gaagacttga acatttatgt gacaacagca  720
tcaaatgccg acgagagcag ctgggggacg tattgcccag gaatggatcc tccacctcca  780
ccagaatata tcacatgttt gggagacttg tatagtgttg catggatgga ggatagtgag  840
tctcacaacc tgaagaagga aacaataaaa caacagtacg agaaggtgaa ggaaagaact  900
tccaacttca acaactataa tgctggatct catgttatgg aatatggaag caaagaaatt  960
aagccagaga aagtatatct gtaccaagga tttgatcctg ccactgcgaa tcttcctgca  1020
aacaagattg attttgcgca cttggaggtt gtcaaccaga gggatgctga tcttctcttc  1080
ttatgggaga gatacaagaa gctagcagac aattcattgg agaaggccaa gcttcggaaa  1140
gagataacgg acacaatgct gcatagacaa catctagacg ggagcgtaga tgcaattgga  1200
gtctttcttt tcggcccaac aaagggttct tctgttctca actctgttag aaaacctggt  1260
ttacctctcg ttgatgattg ggattgccta aaatcgacgg ttcgcctttt cgagctacat  1320
tgtggctcgc taacacaata cgggatgaag cacatgagag catttgcaaa catttgcaac  1380
aatggagtgt ctagagatgc tatggaggaa gcttttatgg ctgcttgcaa tgagcataag  1440
atagaggagt atatcgctgc caaccggggc ttcagcgctt ga                     1482

SEQ ID NO: 138          moltype = DNA  length = 1485
FEATURE                 Location/Qualifiers
misc_feature            1..1485
```

```
                         note = Description of Artificial Sequence: Synthetic
                          polynucleotide
source                   1..1485
                         mol_type = other DNA
                         organism = synthetic construct
SEQUENCE: 138
atggggtcct ttagttttgc agtatgtgta agcttaatgt tgctggttat ggtcgttgct  60
attccttttg aattacccaa aaatggcaga aggatagggc ggctgcaccg ctggtgggac  120
cccttaatac gatcgccggt agatcgtgat gatgagtctg aagacaagga cggtgttcgt  180
tgggcagttc tcgtggctgg ttctaatgga tacggaaatt atcggcatca ggcagatgta  240
tgtcatgctt accagatttt gaaaagagga ggattgaaag atgagaacat agttgtattc  300
atgtatgatg acattgccaa gagtgagcta aatccaagac ccggagtcat aatcaaccat  360
ccaaacggta gtgatgtcta tgctggtgtg ccgaaggatt acactggcga gcatgtcact  420
gcggcgaact tgtatgccgt gcttcttggt gataagagtg ctgtgaaagg tggaagtggg  480
aagatcgtcg atagtaaacc aaatgacaga atatttctct attactctga tcatggtggt  540
ccaggggtgc tcgggatgcc gaacatgcct ttctttatg ccaaagattt tattgaggtc  600
ttgaaaaaga aacatgcagc agggacctac aaagaaatgg tcctctacat tgaagcttgt  660
gagagcggga gtgtttttga gggtatgatg cctgaagact tgaacattta tgtgacaaca  720
gcatcaaatg ccgaagagag cagctggggg acgtattgcc caggaatgga tcctccacct  780
ccaccggaat atatcacatg tttgggagac ttatatagtg ttgcatggat ggaggatagt  840
gagtctcata acctgaagaa ggaaacaata aaacaacagt acgagaaggt gaaggaaaga  900
acttccaact tcaacaacta taatgctgga tctcatgtta tggaatatgg aagcaaagaa  960
attaagccag aaaaagttta tttgtaccaa ggatttgatc ctgccaccgc gaatcttcct  1020
gcaaacaaga ttgcttttgc gcacgtggag gttgtcaacc agagggatgc tgatcttctc  1080
ttcttatggg agagatacaa gaagctagca gacaattcat tggagaaggc caagcttcgg  1140
aaagagataa cggacacaat gctgcataga aaacatctag acgggagcgt agatgcaatt  1200
ggagtctttc ttttcggccc aacaaagggt tcttctgttc tcaactctgt tagagaacct  1260
ggtttacctc tcgttgatga ttgggattgc ctaaaatcga cggttcgcct tttcgagcta  1320
cattgtggtt ctctaacaca atacgggatg aagcacatga gagcatttgc aaacatttgc  1380
aacaatggag tgtcgagaga tgctatggag gaagctttta tggctgcttg caatgagcgt  1440
aagagagagg agtataccgc tgccaaccgg ggcttcagtg cttga                 1485

SEQ ID NO: 139           moltype = DNA  length = 2307
FEATURE                  Location/Qualifiers
misc_feature             1..2307
                         note = Description of Artificial Sequence: Synthetic
                          polynucleotide
source                   1..2307
                         mol_type = other DNA
                         organism = synthetic construct
SEQUENCE: 139
atgtacgatg atattgctaa caatagcgag aaccccagac ctggagtcct catcaataac  60
ccacacggtc aagatgttta tcaaggtgtt cctaaggatt atgtgggtga agatgttaat  120
gctgacaatt ttttcaatgt tatacttgcc aacaaaagtg gtatcactag gggtagtggg  180
aaaattttgg acagtggccc aaatgacaat attttcatct attatactga tcatggtggc  240
cctggaattg tctcaatgcc aactggaatt gtctatgcga acgatctgat taacgtgttg  300
gaaaagaagc atgcttctgg gacatatagt aaaatggtat tttacttgga agcttgtgag  360
tcgggaagca tgtttgatgg tcttcttccc gaaggtctaa atatctatgt cacgactgca  420
tcaaaaccag atgaaaacag ttggggaacg tattgtggtt tgggtcgtgg tgcttgttta  480
gttgagtgtc ctcctcccga gtttgacggt gtttgcttgg gagacttgta cagtgttgct  540
tggatggaag acagtgatgt ccaagatcga caaacttcaa cgttggataa ccagtatgac  600
aggattgcat gcagaactgc agccaaccta acatatggtt cccatgtcat gcaatatggt  660
gatatggagt taagtgttga tgctcttttc cagtatatgg gttctgtttc cacaagccat  720
agtcaagctc ccagtcccat ggcagctgct cccagtccca tggatgccgc gtcattcttg  780
acatcctcag aaaatgtgaa ccaacgtgac actgaacttt tctacttgac atccaaatac  840
caaggtgctc ctgaaggcac taacgaggaa tttgcagctg atcggaagct taatgaggtt  900
gtagcacaaa gaagtcaagt ggataacaac gtaaaacgtc ttggagagct tctgtttgga  960
gtcgaaaaag gtaatgaggt gctgcagagt gttcgacctg ctggacaacc acttgttgac  1020
gattgggatt gccttaaatc ctatgtcaag acattcgagg cacactgtgg aaaattaacc  1080
gcgtacggga agaaacatgt acgtggtatc gccaacatat gcaatgctgg aattgagagt  1140
gaggagatgg ttgatgcaac tgcacaagca tgttcagccg cctctgaaat cggccctaac  1200
tctcctactt ttactcaaac tgattttatt ttacctcctt ctcacccact ctatcttcat  1260
ccttctgaca atcctgaccc cgatatttca caaagtgtta tatactctaa gtctgctaag  1320
agactatggg ataaattgaa ccaaaggtat gggcaagcaa atggtgctaa gatgtatgaa  1380
gttcaaaaag acctaagcac tatatttcaa ggttcttctg atgtaggaag ttatttcact  1440
agggttaaaa gactccagga tgaaatggag tcacttgatg ctgattcctt ttgtgtttgc  1500
gaatgcaaat gtggaggtaa acacaaaatg atcaaaagga tggaaaatca gaaattgatg  1560
cagtttttga tgggtttgaa tgaggagaga ggatatgatc caaaaatgcc atattgtaga  1620
tattgtaaaa agccaggaca tgtaattgag aagtgctata agttacatgg atttccacga  1680
ccttcaaaat cagggaacaa gaatatccga gttgctgcac atgtccattc atcttctgat  1740
gctaagccta acaggtctta tgacaataac atcaatattg ccaacaccat catacctgat  1800
caatacaagc agcacatgac tatccttcaa catattcaag ttggttctaa tgattctcaa  1860
agccaatttg ccacagctaa ttttgcaggt atttttgctt catctgccca tctgatgagt  1920
tgtggtaatt gtacttgttt aagtagtgtt ctaacttctg aaacctggat actagattct  1980
ggaacatcag ttcacatgac atttaacaaa tattcgctta caaatataac aactttatat  2040
gttccctacc tcatcacatt acccaatggg tataaagtca aagtgaccac aattggttct  2100
gtcaaattaa actcttcagt cattttgtcc aaggtgctat atgtgcctac ttttaaatac  2160
aatctcattt tagtccataa gttattagtt gatactttat cattgctatg tttttctcaa  2220
catgcatgtt ttctactaca tggcccttct ctgaggatgc cattgatact tggtaagtgt  2280
```

```
cacaacccaa aatctcaccc atcgtga                                      2307

SEQ ID NO: 140         moltype = DNA  length = 1374
FEATURE                Location/Qualifiers
misc_feature           1..1374
                       note = Description of Artificial Sequence: Synthetic
                        polynucleotide
source                 1..1374
                       mol_type = other DNA
                       organism = synthetic construct
SEQUENCE: 140
atggttcaaa aaaatggtgt tgtttcattc ctagttgtac tttttgtcat agtttgtact  60
gctgagggtc gtaacttgtt ggagagtatt gttgaagatg ataatgcgac tggaactaaa  120
tgggctgtgt tggtagctgg atcaaatgag tgggataatt acagacacca ggcggatgta  180
tgccatgcat atcaactact gaagaaagga ggtctaaaag atgaaaacat catcgtattc  240
atgtacgacg atattgctta taataaaaac aaccctagac ctggagtcat catcaatagc  300
ccccacggcc atgatgttta taaaggagtc cccaaggatt acacaggaaa agattgtaat  360
gctgataact tttcgctgt tatcctggga aacaagagtg ctctaactgg gggcagtgga  420
aaagttgtgg aaaatggtcc aaatgattat atatttatct actacgctga ccacggtgct  480
cctggcctta ttggtatgcc tagtggagat gatgtctatg ccgacgatct gatcaaagtc  540
ctgattaaaa aacacacttt tgggatatat tccaaattgg tattttacat ggaagcttgt  600
gagtctggaa gtatgtttga tggtcttctc ccaaaaggtt tgaacattta cgtaacaaca  660
gcatcaaagc ctgatgaggg cagttgggct acatactgta tttctttagg tgatgaagat  720
gtagtctgct taggagactt gtacagtgtt gcttggttgg aggatagtga tttgcacgat  780
cggcaagttg aaactttgga gaaacagtat cagctggttc gtaagagaac tctaaataat  840
ggtacagtcg aaggctccca tgtcatgcaa tatggtgatt tacatataag tgaggatcct  900
cttttcagat atatgggttc taattctgca aaaaatagtt actatagtac ttctaccaac  960
gatgagtcat ggctaccctc aaggactgtt aatcagcgcg atgttcatct catgcactta  1020
tggtctaagt tccggtctgc tcctgaaggc tctgctagaa aaactgaagc tcaaaggcaa  1080
ttaagggaag ctatatcaca aagagaacac gtagacaaca gtgtgagaca tattggagaa  1140
gttttgtttg gagttgagaa aggtcccgag gtgctgcaga ctgttcgacc tgctggacaa  1200
cccctcgttg atgattggga ctgccttaaa tcctttgtca agatatttga gtcacaatgt  1260
ggaaagctaa ctccctacgg aaggaaacac gttcgtggct ttgctaacct gtgcaatgct  1320
ggaattcgaa gggagcaaat ggctgcagca gctaaacaag catgtccttc ttaa        1374

SEQ ID NO: 141         moltype = DNA  length = 1080
FEATURE                Location/Qualifiers
misc_feature           1..1080
                       note = Description of Artificial Sequence: Synthetic
                        polynucleotide
source                 1..1080
                       mol_type = other DNA
                       organism = synthetic construct
SEQUENCE: 141
atgattcgaa aaaatggtgt tgtgccattc ctagttgcac tttttgtcct agtttgtact  60
gctgagggtc gtaacttgct ggagagtatt gttgaagatg ataatccgac tggaactaaa  120
tgggctgtgt tggtagctgg atcaaatgag tgggataatt acagacacca ggcggatgta  180
tgtcatgcat atcaactact gaagaaagga ggtctaaaag atgaaaacat catcgtattc  240
atgtacgacg atattgctta taataaaaac aaccccagac ctggaattat catcaatagc  300
ccccacggcc atgatgttta taaggagtac ccaagtggga aggttgtgga aaatggtcca  360
aatgattata tctttatcta ctacgctgat catggtgctc ctggccttat tggtatgcct  420
agtggagatg ttgtctatgc cgacgatctg aacagagtcc tgattaaaaa acacactttt  480
ggaacatatt caaaattggt attttacatg gaagcttgtg aatctggaag tatgtttgat  540
ggtttactcc cgaaaggttt aaacatatac gtaacagcag catcaaagcc tgatgagagc  600
agttgggcta cctactgtat tcgtttaggt gatgaagatc aatgcttagg agacttgtac  660
agtgtttctt ggttggagga tagtgatttg cacgatcggc aagttgaaac tttggagaag  720
cagtatcagc tggttcgtaa gagaactcta aacaatggta cagaagaagg ctcccatgtc  780
atgcaatatg gtgatttaca tattagtgag gatcctcttt tcagaatatg ggttctaatt  840
ctgcaaaaaa tagttataat acttcataac aacgacgagt catggctacc ctcaaggact  900
gttaaccagc gcgatgttca tctcatgcat ttatggtcta aggtcaagat atttgagtca  960
caatgtggaa cgttaactcc ctacggaagg aaacacgttc gtggctttgc taacttgtgc  1020
aatgctggaa ttcgaaggga gcaaatggct gcagcagcta aacaagcatg tcctccttaa  1080

SEQ ID NO: 142         moltype = DNA  length = 1062
FEATURE                Location/Qualifiers
misc_feature           1..1062
                       note = Description of Artificial Sequence: Synthetic
                        polynucleotide
source                 1..1062
                       mol_type = other DNA
                       organism = synthetic construct
SEQUENCE: 142
atgataccgg caagaatggc tgatgtatgt cacgcttacc aattactaaa ggatggaggt  60
ctaaaagatg aaaacatcat cgtattcatg tacgatgata ttgctaataa tagggagaac  120
cccagacctg gagtcattat caataaccca catggccatg atgtttacaa aggtgtcccc  180
aaggattatg tgcttgaaga tgttaatgct aacaactttt acaatgttat ccttggaaac  240
aaaagcgctg tagttggggg cagtgggaaa gtagtgaaca gtggtccaaa tgaccatatc  300
ttcatctatt atactgatca tggtggccct ggtgtggttt cgatgccaag tggagaagat  360
gtttacgcta atgatctgat tgatatgttg aaaaagaagc atgcttcagg gacatatgac  420
```

```
agactggtgt tttacttaga agcttgtgag tccggaagca tgtttgatgg tcttcttcct  480
gaaggtctag acatatatgt catgactgca tcagaaccta atgaagatag ttgggcgacg  540
tattgtggtg agggtactcc tgatgatccc tgcttggttg agtgtccccc tcccgagttt  600
cagggtgtgt gcttgggaga tttgtacagt gttgcttgga tggaagatag cacaattgat  660
agacttcttt ttcttacacc acacgatttc tattcatttt tttctgaatg tttgcagcac  720
caaaatgccc ctgaaggctc tgatgagaaa ttcaaagctc atgcgagact tactgaagct  780
atatcacaga gaactcaagt ggacaacaat gtaaaacatc ttggggagct tctttttggt  840
gttgaaaaag gtaatgagat actacacagt gttcgacctg ctggacaacc acttgttgac  900
agctgggatt gccttaagtc ctacgtcaag atatttgagg cacattgtgg aagattaacc  960
tcgtatggaa agaaacacat acgtggtata gccaacatct gcaacgctgg aattgcgagt  1020
gaacaaatgg ctgctacatc tgcacaagca tgttcaagtt ag                    1062

SEQ ID NO: 143         moltype = DNA  length = 1452
FEATURE                Location/Qualifiers
misc_feature           1..1452
                       note = Description of Artificial Sequence: Synthetic
                        polynucleotide
source                 1..1452
                       mol_type = other DNA
                       organism = synthetic construct
SEQUENCE: 143
atgattgttc gctacgttgt gagtgctgtc ttgatcattg gactgtcaat tctcgccgcc  60
gttgagcagg gatgtgctga aattaccgtc ggaagcatta aagttttcag tggtgagtac  120
gatgatgatt caattggtac taaatgggct gtgctggttg ctggatcaag aggttgctgg  180
aattacaggc accaggcaga tgtttgtcac gcatatcagc tgttgaagaa aggtggcctc  240
aaggatgaaa atattattgt gtttatgtat gatgacattg ctcataatcc tgagaatcct  300
aggccaggag tcatcataaa tagccctaat ggtcatgatg tctataaagg agttccaaag  360
gattatacag ggcatcatgt tacagccaac aacgttcttg ctgttatcct tgggaacaaa  420
agcgctctta gtggaggcag tgggaaggtg gtggaaagtg gtccgaatga tcatatcttc  480
atcttctaca gtgatcatgg tggtcctgga gtgcttggga tgcctagtgg cccttatctc  540
tatgctgatg atttaattga tgccttgaaa aggaagcatg cttcagggac atacaaacgc  600
ttagtctttt acattgaggc ttgtgaatct gggagtatat ttgagggcct tctacctgaa  660
ggtcttaata tctgtgcaac aacagcatca aatgctgaag aggacagttg ggaacctac  720
tgtccaggag actatccagg tcctcctcca gaataccaga cctgcttggg tgacttgtac  780
gctgtgtctt ggatggaaga tagtgaaaaa cacaatctcc aaagagaaac tttaggaatg  840
caatatgagc tggttaaaag gagaactgcc aactcgtttc cctatgcaag ttcccatgta  900
atgcaatatg gtgatctgaa gctaatggat gatcctcttt ccctttatat ggggaccaat  960
cccgcaaatg ataattacac ttttctggac gagaattcct cactgctctc tgcaaagcct  1020
gttaaccaac gtgatgcaga tcttttgcat ttctgggaca agttcctcaa ggctcctcaa  1080
ggttctatta ggaaaattga agcccagaag cagctgactg aagctatgtc acacagaatg  1140
cacatagacg acagcattgc acttgttggg aagcttctat tcggaattga gaaaggtcct  1200
gaggtgctga ttagagtcag acctactggc gagcctcttg ttgatgattg ggattgtctt  1260
aaatcctttg taagaacatt tgagacacat tgtggatcat tatcccagta tggaatgaaa  1320
catatgcgtg ctgttgctaa catatgcaac tctggtataa aaatggagca gatagccaaa  1380
gcatcagcac aagcttgtgt gagtattcct tccaactctt ggagttcgct cgacgaggga  1440
tttagtgcat ag                                                      1452

SEQ ID NO: 144         moltype = DNA  length = 474
FEATURE                Location/Qualifiers
misc_feature           1..474
                       note = Description of Artificial Sequence: Synthetic
                        polynucleotide
source                 1..474
                       mol_type = other DNA
                       organism = synthetic construct
SEQUENCE: 144
atgagctatg gtgaccaatc acaaactatt ggtgaccttg cttttgagaa attcacattt  60
ccttctattt ttggaaataa tgttaacatt cttgatgttg tctttggctg cggtcatgac  120
aatagtggca cgttcaacaa ctatacttct gttattattg gcttaggtgg tggtgaagtt  180
tcaattgtca accaattgga taaagaaatc aatggaaaat tctcttattg tttaatcaca  240
attccattac aatcatcaat ttctaatgcc accagtcaca taaattttga tgcagattta  300
gagttgtcgc cttcgagcac gtttgcagaa gtggaggaag atttggtttc tcttacaata  360
gtgccagcag aggaagttgc catttttgga aacttggagc aggcaaattt cctaattgga  420
tatgatcttg ttgccaacaa aatctcctcc ttgccaacag actgcactag ctaa        474

SEQ ID NO: 145         moltype = DNA  length = 867
FEATURE                Location/Qualifiers
misc_feature           1..867
                       note = Description of Artificial Sequence: Synthetic
                        polynucleotide
source                 1..867
                       mol_type = other DNA
                       organism = synthetic construct
SEQUENCE: 145
atgattaata gtcgacaccg tcgaaaatat ggaagtaaag atgaatggaa tatgcgattt  60
gggatttatc aatccaatgt tcaatttatc gacttcttca attccctcaa cctttcttac  120
aacctcactg acaatgcttt tgcagatatg acaaacctcg agtttaattc taaatattta  180
ggttataaga aacgtaaaca ttcaaagcaa ttagcagcac caaatatcac gtgtgacagc  240
tctaaattgc ctatcagtgt cgattggaga aagagtggag ttgtaacacg agtcaaggat  300
```

```
caagaaaatt gtggaagctg ttgggcattc tctgcagtag cagcagttga aggcataaac  360
aagatcaaaa cagggaaatt agtgtcacta tcagaacaac aactagtgga ctgtgatgtt  420
ttctcagaca accaaggatg taacggagga ttcatggaaa aagcttttgc tttcattaat  480
aaaaacggtg gcattacaac tgaaaaaaat tatcattacg taggaaaaga ccagaaatgt  540
aacactacca aagcaaaaca acatgcagtt acaataagtg gctatgaaat ggtagccaaa  600
aatgaggaat ctcttcaagc tgcatttacc aaacaaccta tatcagtggc cattgatgca  660
agtggctatg attttcagct ttgcgctggt ggggtttact ctgttttttt cggaaatagc  720
ctaaatcatg gagtgccatt aattggctat ggtgtagatg atggtgagaa atattggcta  780
gttaagaatt catggggtac tatgtggggt gaagatggtt atatcaaaat taagaggtgg  840
tcaaatgaca aaaaaaggaa cgtgtag                                      867
```

```
SEQ ID NO: 146         moltype = DNA  length = 2121
FEATURE                Location/Qualifiers
misc_feature           1..2121
                       note = Description of Artificial Sequence: Synthetic
                        polynucleotide
source                 1..2121
                       mol_type = other DNA
                       organism = synthetic construct
SEQUENCE: 146
atggccaatt ctctcctctc ttccaacttc atgggttctc aaatctttgt ctctcctccc  60
acccctaaaa caacaaagta tttccatttt cactccaaaa gaaagtcttt aatccctcaa  120
tcaattctca acaaaaaacc caattcagat aattcaaaga atattccttc aaaagctgct  180
ttagctgctt tactcttttc ttcaatcact ccacatgcct atgctcttga taatactacc  240
cctacagtac caacccctca agtgattcaa gctgaagcag ccaatcccac cacttcaaat  300
ccattctctc aaaatataat cttgaatgct ccaaagcctc aagcacagac caatcctgaa  360
cttccagaag tttctcaatg gagatacagt gagttcttga atgctgtaaa gaagggtaaa  420
gttgaaagag tcagattcag taaagacgga actacccttc agcttaatgc tgttgatggc  480
cgtagagcta gtgtaattgt gcctaatgac ccggatttaa ttgacatttt ggctatgaat  540
ggtgttgata tatcagtttc tgaaggtgat tctggtggta atgggttgtt taatttaatt  600
ggaagtttat tccctttttat tgcttttgct ggattgttct atcttttcca gagatctcaa  660
ggtgggcctg gtgggcctgg tgggcttggt gggcccatgg attttggtag atcaaagtcc  720
aagtttcaag aagttcctga aactggagtg tcttttgctg atgttgctgg tgctgatcaa  780
gctaaattgg agttacaaga agtagttgat tttttaaaga atcctgataa gtatacagct  840
ttaggtgcta aaataccaaa agggtgtctt ttggtggacc acctggtaca ggaaagacac  900
ttttggctag agcagttgct ggtgaagctg gtgtaccatt tttctatgtg cagcatcaga  960
gttgttgagt tgtttgttgg tgttggagct tctagagtga gggatttgtt cgagaaggcg  1020
aagtcgaaag cgccttgcat tgtgtttatt gatgagattg atgctgtggg aaggcagaga  1080
ggtgcaggaa tgggaggtgg gaatgatgag agagagcaga ctattaatca actcttgact  1140
gaaatggatg gtttttctgg aaatagtgga gtaattgttt tggctgcaac caataggcct  1200
gatgttcttg attctgcatt gttgagacct gggaggttcg atcgacaagt gactgtcgac  1260
aggcctgatg ttgctggtag aatcaagatt cttcaggtgc attctagagg aaaggccctt  1320
gcaaaggatg tggactttga gaagattgcc aggagaacac cgggtttcac tggtgcagat  1380
ttgcaaaact tgatgaatga agcagcgatc cttgcagcta ggcgtgaact aaaggaaata  1440
agtaaagatg agatatctga tgctttggag aggataattg ctggaccgga gaagaaaaat  1500
gctgttgtct cagaggagaa gaagaagctg gtagcttatc atgaggccgg ccatgccttg  1560
gttggtgcac ttatgcccga gtatgatcct gttgccaaga tatctattat tcctcggggc  1620
caagctggtg gtcttacctt ctttgcccct agcgaagaaa gacttgagtc gggcttgtac  1680
agcaggagct acctagagaa tcaaatggca gttgcacttg gtggaagggt tgctgaggag  1740
gttatttttg gacaagacaa cgtaacaact ggggcatcta acgatttcat gcaagtttca  1800
cgagtggcaa ggcagatggt tgagagatta gggttcagca aaaagatcgg acaggttgcc  1860
attggaggag gtggaggaaa tcctttccta ggtcaacaga tgtcaaccca gaaagactac  1920
tccatggcaa cagccgatgt ggttgatgct gaagtaaggg aattggttga aagagcatat  1980
gaaagggcaa cacagattat cacaacacac attgacatcc tacacaagct tgctcagctg  2040
ttgatagaga aagaaactgt tgatggtgaa gagttcatga gccttttcat cgatggcaag  2100
gccgagctat acatttcatg a                                            2121
```

```
SEQ ID NO: 147         moltype = DNA  length = 2238
FEATURE                Location/Qualifiers
misc_feature           1..2238
                       note = Description of Artificial Sequence: Synthetic
                        polynucleotide
source                 1..2238
                       mol_type = other DNA
                       organism = synthetic construct
SEQUENCE: 147
atgattatag aggtgctcat attgtggcat gcagatgtta ggcataatat atctctaact  60
gcactcagct ctactcagtc cttttacaaa gatgaccttt acattgtttt cttgaaagat  120
catccggtga acgaagaatc gctatttcag agacatatta ttgtcctatc atctttaaag  180
ggaagtgatg gggctgcaac agaatctcat gtttatagct atacaaaaat cttcaatgca  240
tttgcagcaa agctatctca acatgaagtt cacatgttat ccagcatgga tgaagtggtt  300
tctgtcatac caaacagata caggaagcta catactacaa gatcatggga atttattggt  360
ttgcctgcaa ctgcaaaaag aagattgaaa agggagagca acattatcgt gggtgttttc  420
gatacaggga taactcctca atcaaaaagc tttaaggatg atggtcttgg tcctcctcca  480
gtaaaatgga aaggaagttg tggccatttt gcaaattttt ctggatgcaa caacaagctt  540
ataggagcaa gatacttcaa gctggacaaa gttcctgatc caaatgacat attgtcacca  600
attgatgtgc acggccacgg aacacataca tcatccaccc tagcgggaag tatggtgcct  660
gatgcaagct tgtttggtct tgcccgaggg actgcacgtg gagcggttcc ttctgctaga  720
gtggctatgt acaaagtctg ttgggtgacc tcaggttgtg cagatattga cattctagct  780
```

```
gcatttgaag ctgcaattag tgatggtgtg gacttaatat ccatctcaat tggtggtctc  840
agtggtagtt atacaactga tgtgatagcc attggatcat ttcatgccat gagaaaaggg  900
attcttactg tggcttctgc tggaaatgat ggacctaacc tcaacaccgt cgcgaaccat  960
gcaccatgga tgctaactgt agcggctagt ggcattgata gggagttcag gagtaaggtg  1020
gcgttgggaa atgggagaat agtctcaggg attggagtta gcgcgtttga tccaaagaaa  1080
aaattgtatc ctcttacggc gggagtggat atggccaaga gctctgacac tcgagacagt  1140
tcaaggtact gtggtgaagg atcaatggat cctagaaagg taaagggaaa gcttgtttat  1200
tgccagttgg gtacttgggg tgctgattct gttataaaag aacttggagg gatcggcact  1260
atcattgaaa gcgatcagtt tcttgattct gccccaattt tcatggctct tgcaacaata  1320
gttaattcca gcatagggaa aaacattaat aactatatgc attcagagag attaccttca  1380
gcagtaatat acaaatcaca ggaagttaag atcaaagctc catttattgc atcattttca  1440
tcaagaggtc caaatccagg aacaatacgc cttctgaagc ctgatattgc agctccagga  1500
attgacattc tggcttctta caccccccctg aaatcactca ctggtttgaa aggcgatact  1560
caatattcag aattcaccct catgtctggc acttccatgt catgccctca tgttggcggt  1620
gcagctgctt atgtaaagtc ataccatcca gattggtctc cttctgctat taagtctgcc  1680
ctcgtgacta ctgcaagacc tatgagctca aaggtggaca gggaagcaga gttcgcgtat  1740
ggtgctggac aagttaatcc gacgaaagca agaagtcctg gattaattta tgacatggat  1800
gatatgtcat atatccagtt cttatgccat gaaggttaca attcatcatc agtatccagt  1860
ttacttcgac aacgggtaaa ttgctccaca ttgattcctg caaatggtga agatgctatc  1920
aactatccca caatgcagct tggcctaaag agtaatcaag aaccaaccat tggcattttc  1980
aggaggaaag ttaccaatgt tggacaagct atatctgttt ataatgccac tatcagagct  2040
cctaagggag tggatatcac agtaaaacca acgactctct cattcacacg tgcaatgcag  2100
acaagaagtt tcaaggttgt tgtgaaggca aaaccaatgt caaatgctgt aatattgtca  2160
ggttcactca tttggaagag ctcccgccat cttgtaagaa gtcctattgt catatatgat  2220
ccaaaggttt ttgattaa                                                2238
```

```
SEQ ID NO: 148          moltype = DNA  length = 5000
FEATURE                 Location/Qualifiers
misc_feature            1..5000
                        note = Description of Artificial Sequence: Synthetic
                         polynucleotide
source                  1..5000
                        mol_type = other DNA
                        organism = synthetic construct
SEQUENCE: 148
aaaaatatga gaatcgtgcg gaatttcagt tttatggaac taaaacgcca aaaatggagg  60
aacggtcatg gagaggcgat aactaatgtt ccttaggttt ttttagatgg gccgaaaaaa  120
ttttaggcga tacgggtaag gcgtccgaaa cacacgaaaa tttgaaaatc gggcgaattc  180
ttgttttatg acactacaac accaaaaagt atggaagatt atggcgatgc gatgcgatga  240
ataatgttcc ttaggttatt tttgatgggt gacaacattt taggttatac gagaccgggt  300
tcccgggccc acaccagtgg cgtgggctat attgcacacg aaaatatggg aatcgagcga  360
atttctacat ttatggcact aaaatgcaaa acaaaaagga acagtcatgg cgaggcaatg  420
actaatgttc ctagggttat ttagatgggc cggaaaagtt ttaggtgatc ctggtcgtgg  480
cgctcgagcc cacgatggta gtgtgggcac acgaaaatct gggaaccgtg ctgaattcta  540
gttttatggc cttaaaacac caaaaccaac aaagaggaat tctcatggag gggcgatgaa  600
taatgttcct taggttgttt tagatattcc agaaagattt taggtgatcc gggttgcggt  660
gcctgggccc acacccagtg gggtgggcta tagcgcatgc aaatgtggga atcgagcgga  720
attctaattt tatagcccta aaacaccaaa taatgttgaa cggtcatgac acgatgatga  780
ctaatgttcc ttaggttatt tttgatgggc tagcaaaatg ttagaagatt cgggtccggc  840
tgcccgggcc catgccagca caagaaaatc tgggaatcag gcaaattcca tattatggcg  900
attatggcga ggcgatgaat aatattactt agattgtttt ttacaggctg gcagaatttt  960
aggttatcca ggtgcgggcg tctgggcctc tgccggtggc gtgggctgta gtacacaaaa  1020
attagggaat caggtagaat tttagtttta tggccctaaa ataccaaaaa aggaggaaaa  1080
gtcatggcga ggtgatgact aatgtgcctt aggtaatatt ttatgttccg aaaaaaattt  1140
atgtgattca ggtccgggag ctcgtgccca tgcagatggc gtgggctata gcacccgaaa  1200
atctcaaaat catgtggaat tccattttta tggccataaa atgctaaaca taaggaacgg  1260
tcatggagag gcgatggcta atgttcattg ggtcgtattt gataggacgg caaaattata  1320
ggcgattcag gtccggcgcc gggcccatgc agatggcgtg ggctaataat agcacacgaa  1380
aatctgagaa tcgggtggaa ttcatgtttt atggccctaa aacgcaaaaa acaaatgaga  1440
aacggtcatg gcgaggcgat gacaaatgtt ccatgagtca tttttgatgg gccagcaaaa  1500
gtttaggcga ttcggtttcg ggggcccggg cccatgcaga tggcctgggc tattgcacac  1560
gaacaactag gaatctggtg gaattccact tttacagcaa taaaatacca aacaatgaga  1620
aacggttatg gcgaggcgac gactagtgtt ccttaggtcg gtttagatgt ccggaaaaat  1680
aataggcgat cgggtccagg cgtccgggcc tgcgccaatt gcgtgggcca tagcatatga  1740
aaatatggga atcgggtgaa attcgagttt tatggcccta aaatactaaa aaggaggacg  1800
gtcatggcga ggcgatgatt aatgttcctt aggtcacttt ttatgggcag acataatttt  1860
tggcgatctg tgtctgggag accgaggcca tgtaggtagc gtaagctata gcacacgaca  1920
taattccagg tttatggacc taaaacatca aaaatggagg aacggtcatg gtgagccgat  1980
tactaatatt ccttaggtcg ttttggatgg gccgaaaaaa tttagggcga ttcgggtgcg  2040
gacgcccgag cacatacaaa tggtgtgggc tataccacac gaaaatctga ttacctgaca  2100
gaattccagt tttatggccc taaaatgcca aaatcgaaga acggtcatgg tgaggcgatg  2160
actaatgttc ctaaggtcgt tcttgatggg ccgacaaaat tttaggcgat tcgggtgcgg  2220
acgcccaagc acatgtagat ggcgtgggct ataccacacg taaagcaggg aatcgggcgg  2280
aattcaagtt ttatggccct aaaacgccat aaacgaagaa cggttatggc gaggcgatga  2340
ctaatgttcc ttaaatcatt tttgatgggc cgtcaaaatt ttaagcgatt cgggtcaggg  2400
cgccctggtc catgcagatg gcgtagcaca cgaaaatcta agaattgagc agaattctag  2460
ttttatggcc ttaaaacgcc aaggaacgag gaacggtcat gtgaaggcta tgattaatgt  2520
tccttaggtc gtttttaagg gcaggcaaaa ctttaggcta ttcagttctg gacgcccaga  2580
cccatgtaga tggcgtggct atagaacacg aaaatctagg aatcaggcgg aattccagtt  2640
```

```
ttatggtcat aaaatgctaa aaatgaggaa ctgtcatgga gaggcgacaa ctaatattcg  2700
ttgggtcatt tttgatggtc cagcaatatt ttagatgatt cgggtttggg cgcccgggcc  2760
catgcagatg gcatgtgcta ttgcatacac aaatctgtga accgggtgga attcaagttt  2820
tatggcccta aaatacaaaa aaatagagaa acggtcatgg cgatgcgatg gatatgttcc  2880
ataaggcatt tttgatggga tagcaaactt ttaggtgatt ctggtccggg agctagggtc  2940
tatgcagatg gcgtgggcta ttgcacacga aaatttaggt atcggtggaa tttcagtttt  3000
atggccataa aatgcataaa atgagaaacg gttatagcga ggctatgacc agtgtgtcct  3060
taggtcgttt tagatgggct ggcaaaatgt taggcgattt gagtccgggt gcccgggcct  3120
gcgccaattg cgtgggtcat agcatacgaa aatataggaa tcggacgaaa ttctagtttt  3180
atggccctaa aatactaaaa aggaggaact gtcatgacga ggcgatgact aatgtttctt  3240
aggtcgtgtt tgttaggccg gcataatttt aggcgatctg ggtctggacg cccagggtca  3300
tgcaggtagc ataggctgta gcacacgaaa attttgaaat cgggcgaaat tctagtttta  3360
tggccttaaa acgcgaaaaa caaaatgaat ggtcatggag atgcgatgac taatgttcct  3420
taggtcgttc ttgatgggac ggcaaaatgt taggcgattc gggtgtgggc gcctgggcac  3480
atgcatatgg cgtgggccat catagcatat gaaaatatgg gaatcgggca gaatttcagt  3540
tttatggccc taaaacgcca aaaacgaaaa acggccatgg cgaggtgatg actaatattc  3600
cttaggtcat ttctgatagg ccggcaaaat tttagacgat tcgggtaagg acgccctggc  3660
ccatgcagat ggcgtagcac acgaaaatct gggaatcgag aagaattcca gttttatggc  3720
cctaaaatgc gaaataacat ggaacggtca tgtcaaggcg atgattaatt tttcttaggt  3780
tttttttgat gggcaggaaa aatattaggt tatgcccatg cagatggcgt ggctatagca  3840
cacgaaaatc tgggaatcgg gcggaattct agttttatgg ccctaaaacg ccaaaatgtg  3900
aggaacggtc atgtcaaagc aatgattatt attccttagt tcatttttga ttgtcggaca  3960
aaatgttagg caattcgggt ccgttcaccc ggatggatgc atatggtgtg ggctagtaca  4020
cgaaaatctt ggaatcggac ggaattccag ttttatggct ttaaaacgcc aaaaaataag  4080
ggacggccat ggcgtagcaa tgactattgt tccgtaggtc atttgtgaag gaccgacaaa  4140
attttaggcg atccgggtcc gatttttcgg ttctgctcaa gaaaactcga tctgcacgaa  4200
tagcttataa tcaaaccctt tttttttttt caagaatgtc taattgatcc taaaaagaca  4260
accttatatg ttccaccatg gcaggatcgg ccttattact aagggtttgc caatagacac  4320
gtttttaaca ttcaagtaaa aaaaacattt attcttaata acccacctac tatagtacgt  4380
tatttggcag tagactacgt tgtacatttg ggaccatttg gaacactcgt ctttcacgag  4440
tcactaattt ttgtgttgaa tgcataaaat ttgttttttt ctttttcgaa attgaacaat  4500
tttatcttcg atcacaccta tagtatatta ttaccttatt gttagaaaat attttatttt  4560
attattgact cctaataaaa agtggggtaa atttgggtct ttttttttaaa gaatgtgaac  4620
tactcatttc actttggtta gaacaaatat gagaagattt gctaatgaca gcaaaatgaa  4680
tagaccaaaa gcgtaacgaa tattaaaaat aaacaattcc gaataactgg ttactgaaaa  4740
ttgtggaact ctacatagcc gttgtgagta tggtattgtt tgttcttgtg ggcagaataa  4800
ctagttacgg aaaatttatg aatttgcttc acattatttt tttcattttc tttttgctt  4860
caaaagataa gtacaagttt ttatactctt atttcattgc ctataaatac ctctattgag  4920
ttactgctca ttcacaactc taaatagcaa tctttcttat tattaaaatt cctatccttt  4980
tttactcatt cagagaaacg                                              5000
```

```
SEQ ID NO: 149         moltype = DNA  length = 5000
FEATURE                Location/Qualifiers
misc_feature           1..5000
                       note = Description of Artificial Sequence: Synthetic
                        polynucleotide
source                 1..5000
                       mol_type = other DNA
                       organism = synthetic construct
SEQUENCE: 149
gctgatctac aaagggctta gaaagaagta agaaaagaaa tggataaagg aaagggaaag  60
attgcagaat cctcagagct gttgaggaag aggagatgga actggtccat caagaaaggg  120
gtacatcagt ggaggttcct accccaagcc aaaaagccca agacttcctc caagaagtct  180
tcctctgtgt ctgaggctgt tgaacctaca ctagccaaga ggacaagatc tgcagtgaaa  240
acaacaatca aaaatttctg aagatgatga ctggagtgga gaagaagaag aaaatgattc  300
tgagaaggaa caggatagct tgccagtttg gcaaaagaaa gattttaaag ggtagactgc  360
tgaaagacct ggtggaacca ggaatgatga gatgtggatg ctttagctgc tcaggatgga  420
aggacatggt ccttcagatg gatggtaggc tagccagaaa tgagctaatt gaatttatgg  480
caatgtctgg ttaaggatgg catgttagta gcctggtgaa aggagttcaa gtgcagtttg  540
atgcaaagaa actgggagag atcctggaca taccctctga agggtttgat gactatacaa  600
ggcaaaggtg gccctgcctg gactccctcc ctactgctct tgtaattacc aggaggtttt  660
gtgattctga agatgtgaat gaagccaggg ctgtgcagaa aagtgaaatg aggcctgagc  720
acaaggactt gtttgaattt gtcaacaagt gtttattgcc cagacaggag agaagtcaca  780
ttgccaatta catggatcta gttcttatag agtgcctgga gagaggaaag caaatcaatt  840
gtctgccttc attatcaagc tgctcgacag ggttataaat ggctccaagg ctcatgctac  900
tctttatggc tttattctaa ccacagttct ggatagtctc aatgtgcctc taaagaaatg  960
ggaaatgatc tcgagaaagg atcactttgg catcaatact cttcttgctt gtgactatgc  1020
agtcaatgac atcccaaatg aacctggtac atcctagaag acacccatca acagcaaagt  1080
caggactctg gttcaggaat atgtagccaa ggatgctgaa atagctaggc ttttggctcg  1140
tgtgattgaa gtgaaatttg agagggatgg tctcagaact gagcttgaca aagaaaagga  1200
gaaaaatgat ggaattcttc ataacatgct gaaccttctc caagcccaaa cccaaccata  1260
tagttcttcc aagccttagg actcctagct tttgtctcct gaacttgttt agtacctcag  1320
tgacccagat tagggatttt tctatctttt atttttgctc atgatttgga tgtttttctt  1380
tctttttgtg gattgttggt ggcaacatat ctctgtcaat gataactact attttgctct  1440
tgtttaatgt taatttgtcc ttgatatttt aaatatattt tcttgattac tgatgattac  1500
tccatgatta catttgcagt tgccgcagtg gccatgggta cttattaaaa tctgggaatc  1560
acactttgta tgtaacattt cgatgatgcc aaaagggaga agagagttgt gctttacaca  1620
cattctgaaa taagtaatat ttataaccta attaacctgg tccttgatgt taagtgaatt  1680
ttctaagttt agtattgatg gttaagctga gttcttacag gtcccaaata agtaaaaagc  1740
```

```
acagagtttg tcatcatcaa aaaggggaat ttgttggccc aagaacaggt gaagttttga  1800
agatgacaaa agaactcaga catggaccag gtccatcttg tgaagcacag tcatgatcaa  1860
cctatacatg tgagatgcac gtgaaagaga taagtcttac tgattaagca acaatatctc  1920
ttgatctgat cgaaaaggat gaagatagtg ttagagtttg agatcatcat gaactcttcc  1980
acgatagaag agcagcaatt gagtcacaat caaactctga ttactaacct attaaatgtc  2040
agtttgttct cttttacagg aaatacacat acgcaaaagt taaactaaat tgagagcaaa  2100
agagcaaggc gattttgcaa gcaatttatg tggatttgag tgtgcactcc tgaagctact  2160
tgaacgagat agaagaacca gttccatcgt gtctatcttt ttctagttca attgtagtag  2220
gtggtttaaa ttataccttt cagctttcat agaagcaatt gtattagata cctagagtgt  2280
tcaagttata gctaacttga agttgtcgca acagttgagg ttgtgtgcca caacgggatt  2340
agagttaatc cttaggttta taaagagttt ttgtaaaagc tattttggct cagtgatttt  2400
agtggaagtt tgggaaaatc ctactgagtt gtaggtcatg gttttttcac cttttgagcc  2460
aggtgttttc cacgtaaaaa tctccgtgtt ctttatttct gtatttatta ttccgcaatt  2520
agtagtagtt ggaacaccta gaaaaccaag ttcttctata gagtagttaa gcgaaaattg  2580
ggtgccacac aaacacccct ctagtgtggt attgacgctt aaacatcaat tagttaattt  2640
ctggagcaac tagctactag ttgttattaa aatagttagt ttctttgtta gctaatatgt  2700
tgttttggtt gtaaattagt tccggtgtgt agtttggact ttggaagaag acttgtacca  2760
attgtgtttg ttattttctt tggtcttatg aatgctcaca ctaaacatca agttggtatt  2820
tgattttgca tttgaattag aagtagtatt gagacgtgtt gttgctatgc ataagtagta  2880
aaagattggt ttgagcttag ttggtttcgt gataagattg gaaataaaag aaatgtgtca  2940
aagttatgta aaaatcagta aaataggctg ctacctttta atattaccac aagtccacat  3000
ttattttagt tttaaacaat ataaatttgt taaggtaatc ttcttacaat agtctcaact  3060
tttaatttag taacagataa ttgcaaagtc aatccaacta atcatacact acccatatgt  3120
aaaaaaaaaa aaaaaaaaaa aaaaaaaaaa aagtgaacaa tcaatgcaca aaaagaaaaa  3180
aaaatatttt tcttctttaa ttaattccat aacatagtcc ttaaaattag ttaattcttg  3240
ttttagaaaa attgtaacag tctagttaat tctccaaaat gaagcaaaag atttttttc   3300
ttaagtatta cgtcactttt tttattaatc caccaaataa attaaattag atttagttca  3360
ctaaataaac tcaataagat cagatgtttt atttatttta aaaataactc aattacttaa  3420
tcacaaatga tcatgactaa ctcaaaagta atttgtttta acaaaaataa ttaatttcgt  3480
cttaaccgat gtcgggacga ctcattttgg aataaataca taaataaaat ggccaggtcg  3540
cgaggacacg tcatattcca attctttcaa ataagcttgt tatttattaa cttgagtagg  3600
ctccaatttt aggtgcggcg cacgaactaa ggtcggagat attcatcttg gttagcgtaa  3660
gctagggttg ggatattcg  tcctagtttg agattaatta agtcatcaac agtaaaagtg  3720
gacataggca aaacatgaaa accgaataaa gcacaattta tccataatta attcatgcca  3780
aatttaagtt aataaagcaa ctgtgctaga accacggact cggagaatgc tttacacttc  3840
tccccgatca acaaaaatct ttattcggac tttatttttg cagaccgata ataatagagt  3900
caaatcttcc tttgactagg gattcaaata aaaagtgact tggaacatgc aaaaatcaat  3960
tccaagcggg cgaatctgta aacaaaaaat ccttattcaa atttgtcact ttaattgaaa  4020
aactctttaa cccactattc ataacatata tatttttggg gtagaaaagg ggttgacagt  4080
tatgacctac tttatgcatc agtgttcgaa tttattttga tcaacaccct tttggaagag  4140
cgtttgatag aaatggttgg cttaataaac aatcatatta tcatcacctg cggaatcata  4200
tcattaactt ttgaaaatta aaatggtttt caaagacgtt ttgataaaag aattcctatt  4260
gtcgcagttg gaatctacaa gaccaagatg ttgatctagt gctatatttg gagaaagtgc  4320
cttaattaaa aaaaattgtt cattagttgt cttaagattt tttattattt aaaaaaaaat  4380
taagacacaa agaaacacat ttacgagtat atgtcggccg actaatgtga agttcccacg  4440
gacaacccac acatattgtg gtcaagatgg attctatcat aatcaaaagt catcatcaat  4500
tcaattctca tatttggcat ctcaagtaca tgcacaaaag caacttagga tgtaagttta  4560
tatgcacatt cttgaaatag aacctattta tacgtagtac ttaattagtt acagtagtat  4620
tatttattct ctgctacaga gctatggttt atcaaatata tcagattatc atttgttgtg  4680
taggccattt ccttatttgt acttggtatt aattctggca aaagcacaaa actgggaaat  4740
gaggttcttc ttccttaata tgagtcacag attagtacca ctactatagc caagaaaatg  4800
tgaaatcata tagtactaaa tattaatttc agatgccaaa accataaatt tcccctcctc  4860
catcattgaa aacccctctg tcctttcccc tagagagacc ccttttttcct ctctctctcc  4920
ttctcttttt attagacgca tatattctct cttctttctc tttctagggt tttcacctga  4980
aatagtttta tttcggtgat                                              5000
```

```
SEQ ID NO: 150          moltype = DNA  length = 5000
FEATURE                 Location/Qualifiers
misc_feature            1..5000
                        note = Description of Artificial Sequence: Synthetic
                         polynucleotide
source                  1..5000
                        mol_type = other DNA
                        organism = synthetic construct
SEQUENCE: 150
atttaaaacc ctaaaaaaca agatttttat ctatctgcat ggtgaaggac aaagaggtct  60
tcaatctcag gttctttttt tttttttttt ttatatatat atcttgtttg ggtttaaggt  120
tattgggctg atgaatgttt taattttaac ataggtctac ttacgtagta gttataggtt  180
gataatgaga tataattaac taagtctttg tataatgcag atcctgaact taatctttat  240
ttgtattatt tttttttgtt actgaaagat tctgttacca aattttatca gtctatttaa  300
ttagaggcca acgattgtta ggtatgtggc acttcgagtg ggaaatgata tattcccatt  360
aaaggtgtta attaaccacc aaattgttct ttaggtctgt ttgtcatttt gtattaaggt  420
ggatggttta ttatatatat cttctcttta atgctaatca tgcttaactt tttcatttag  480
taccagcaag catatttgtt tactttattg gttattcctt atcaaagtct tcatcttgtt  540
gcttttttttt attgtacttt acaaaagatt tctagtatta atggaaagtg ctcatatttg  600
gaaaaagaca tggccaacaa gaaatgtcta tataccccat ttcttcttct tcttcttttt  660
ttccgaaaat ttcttatttt tgtttttatt tctgtttctt gttgagtgct ttcatggtag  720
aagaagaagt aggagattct tggacatggc tgcatgagaa ttgttaaata accccgtata  780
catacacaag tagtgttggc tgtctttgat atcaaaccat ttattgccct aatttctgcc  840
```

-continued

```
ttttgtcccc tcaacaaaac catcaaagtt ctcaaagagg gtttattctt gtttcccact  900
ttgcccccca cctattaggg ccaccccacc aaagggatct ctctcgtgtc tagtgttttt  960
tcccaaggac caccactcct tttttttct ctaccataac ttcgtccaca ccatcttatt  1020
gtgatatttt cgtttaatga atttgcagcc atgccttcat tcatcatcag aactcagtca  1080
taagcacaga ttctgagaga gtaattaatg aatgaatcag tggtgatttg acgtaaagta  1140
tacatgatta tggtttttag ctgaataagc agagggagaa aatatataca tatataaaca  1200
agtagagtaa aagaatgacg caagattagt accaaaagag tgaaggaaga gatttaatat  1260
tatagggaaa agggaagtag taggtgatac ttgacaggtt gataagatgg ttattactac  1320
aagttgatgt attgacgcta actcacgcaa gagagaccta ctcactgtac aatattttta  1380
caagaataag cgattctttc tctctttact tgcaagaatt gtgtgttgtg tgagttgtat  1440
ggcgcatttt ctaggagcct gtggtagtga tggatgtatt catataatac aatacaatac  1500
atatggaata gatagataga taagatggtg cacgcatgag aggcaattat gcaacttacg  1560
tcaactactt ccatccatcc atcttttctt ccttctgttt ctgtctgata tagtgagtat  1620
atgcttgtgc tggtgttgtg tgcttttctg gcctgggatt ttcctaacac tttagataat  1680
ttaggttccc atcaataata atgtcttttt agaggagcat catcgataga tattcaaata  1740
ttaaacctgg cctagctact atctagggcg tctgctaggt ttttccatta ccctttgtat  1800
atctcttatg tgggaccttt tgtttatgga agaatatgga gtacttttat tcatctcgta  1860
gggtcttgaa tacaagattt tatatatatc actctttaaa aatgaccatc ctaaaattct  1920
tcctctttca tttgcattta ccagaattga tattagtacc taaactagta ctcttcactg  1980
aggccttttg tatttagtcc tattatattt gaatttggca ctatttaaat taaaaaaata  2040
atctacaata aaaaattctt ccctaaacat tacccatcaa atactcacca cctaaggtaa  2100
ctctaccatg tattaatttt ttggatcaaa tctagtgagg attaattctc cacttatgtt  2160
ctttcggaac tggctaagta atcttcaaaa gctagggcat ctccgcagtc atatcgtgcc  2220
ctcccaagta tagcgaccgc ttctatattt tccctgaatt tcatctgtgc tagggcttgt  2280
tttcacgttg atttcaaaca aaggctaaca atttcattga gtaacttttt ctcatttcag  2340
gactcgaacc ttaaacctct gttcaaataa cttctaagaa gtatatatgt atacaatgtt  2400
tgtattcatt gtgacaaagt attatgagtt gtacaacttt cttgtgaaga tagagcataa  2460
tgttaaacaa ggatctatat agagcataat gtcaacaaaa caacaacatc aacccagtaa  2520
tcatcctact aataggattt ggggagggta gagtgtacgt aaaccttacc catacagggg  2580
agggggtaaa gaggttattt tcgggagacc ctcggctcag agacaaaaaa atctataata  2640
acaacagaaa ccagacaaat aatatcagca tcataagaga caacaaataa gtggaatgac  2700
aataattatg ccaataataa cattgaaaaa aataaaatta aaaattaaaa ataaaaatag  2760
tgtgatgaac aaaaatcgct agcagtctta gacaaaacac tatcagacta gctggaacaa  2820
cgaggaaaaa cgctgaagta ccccctaacc tacaacccta atgctcgaca tccacacctc  2880
cctatccagg gtcatgtcct cggaaatctc aaatcgcgtc atgtcctgcc tgatcacctc  2940
gccccattac ttcttaggtc gccctctacc tcttctcata cctgtcaaag ccaaccgtca  3000
cacctcctaa ctggggcatc taggcttctc ggggccggcc agcccgtaga tctaaaagga  3060
tccatccata gcgcccgaac catccacgcc tcgctttccg catcttgtcg tccatgggag  3120
ccacgcccac cttatccagc cttatccagc ctagtgtgcc cccacatcat ctcaacatcc  3180
tcatttcgac tactttcatc ttctggatac aagaattctt gactggccaa cattcagctc  3240
catacaacat ggtcgatcta accaccactc tataaaactt gcctttaaat ttcagtggca  3300
tgttagtatg tttactttag atacaatgtt ttttagagtc ttatagtctt gttagaatac  3360
tatatattat aaaatatgga gacttctggg cacttttgtt ttattttata taagatagga  3420
ttggaatgaa ttcaattgga gggacatgca tgataaatga atattcatgt agccgatata  3480
tgtttgggac tgaaacgaca ttattattgt gaaatatttt acaattgcat ttcacactca  3540
ctgaagtgaa actttgattc cacgtcggtc aatacttagg tgttacggtt tggctgcgag  3600
gggaatcgaa gagagcaaat taattaaagt atttaatgag gaatcatgag ttagttggtg  3660
gaattataat agtcaaatga atgagttatt cgcctgataa tatagttgat agtagtatat  3720
actatatatg ttgatactag ttattggtgg tgacctaatt aagtaaagag aagagaagag  3780
tggttatgta aaggaatcta ggtatagtgg gggatggggg gaggcaaggt taaaagaaag  3840
gtggaaaatc caagaatcct gcttcctcta gtaacatagc atatcctgca attcgtgctt  3900
ttgtttcctc tcacaagata actacttttt tgattaatta ttacatttga cacatacata  3960
caaacctata aaattagaca tccttatgga atcttacgac tccgaacttg tcatatatcc  4020
tttaattatg cttagctttt tgctaaaaac aaaaaggata tccttattcc aaaatgcaac  4080
taggagcatc ttcccacatt tctttttttat gcctctgcat catcaaatcc cataatgccg  4140
cacaacaatt tctttttact taagtatatt ctagcttagc tatttcatac gaataatggg  4200
tatacaaatt tgcttatttt aggttttaaa taccgattta aatatattgg atgggttcaa  4260
cttttaaaat tcttacactg atatacatgc atagaatatg tggaaaactt taatattaat  4320
tacaactgct aaacatttga atggattctt catgccgtgt gctcctttgt tgaagaacac  4380
gtactccctc cgttcgcatt tatttggcac gttttgactt ttcacgcccc ttaagaaata  4440
ataaataaaa tgcataattt atcatgataa acatatcaat ttatgcatat tttattagat  4500
ttgagaaaat aatttgaaat gagtaataaa tactgtgagt ataacaggaa atttttttt  4560
gtcttctctt gatatgcata aaatagcaag taaaaataaa aatctatttt taatataaat  4620
gtcaagtaaa agtgaatgga ggaagtattt ggaagggcga tatcgaataa aaaagttata  4680
ctaataacaa acagcaacaa ttacaagaaa ctgtagagtt ggccagtacc aggtatatat  4740
gtagaatttt ttttatgagg aatttagtga aacgctagct atttcaacac ttcagacata  4800
tcaataccaa ttttatggtt tctcttaggt gttgatagat tctcttttgt cagcaaacat  4860
tatttatgaa atttataata aaatgctgct cttttcgagt ttacattctc cgtcccaata  4920
caatatatac ttgatttgac gaaagaaatg taacaataga atcttaagtc ggaaaaagtc  4980
aaatcaaatt tgaaaaaaat                                              5000

SEQ ID NO: 151          moltype = DNA  length = 5000
FEATURE                 Location/Qualifiers
misc_feature            1..5000
                        note = Description of Artificial Sequence: Synthetic
                         polynucleotide
source                  1..5000
                        mol_type = other DNA
                        organism = synthetic construct
```

```
SEQUENCE: 151
gaaaactaaa aaaagaacta aggcatttac actaggtctt caccggggct cgtcccatca  60
ccagaacccg ttggcctcag gtctcttggc ttctttaatc ttggccgaca ggtcaaaacc  120
tcgggaatgg atatcctcga gggtctctct ctggtatagc cgctttacgt actcggtctt  180
catctttaag cgggcctcag ctatctccac atcagcctta tactgggcca gcatttcctc  240
gacgtcggag gaatcaatag aagttgcctc caacttggat ctcagcgcgt tatattcttg  300
gtcgagggca tcccattccg tgacggctga gttcagctgt gctcggagtt catcatttag  360
ccgagatcac ttgtcggcct tgtcctttgc cacccggagt tggtccttta tcgatgtcaa  420
ctcctctttt gcagcctctt tttccgaagc cagtaggtcc atcctgccct tctacgcctc  480
ggtcgtggcc ttgacctcat ccatctcagc ccgaagccgg tcgatcaggt ctaccttctc  540
ttggacctgg gaagttgcgt tgttagtcac cacgagtagc ttctcatttt tagcctcaaa  600
gatccttacc ttctcgacca agtcagcgtg ctcccacttc atggacaagg cctccttctg  660
agccttttcc agctcggctc agagaattgg gaggtacttg agggcctcgt cttattgttc  720
gctgagagac ctgtaaatgt ccttctcccg gatcagttct ttaagctcga actcaagctg  780
actgatttgc aagagagacc gaaggaagct ttcatgatga agcattcaaa tctgaaatat  840
aataaggtca ttagaatatg cggagcaaat attcgcaaag gatacaaagg atagacgtct  900
tacccggttc aatgcctatt gcacctcgtt gaagaggctc tacgtgccta cttcattcat  960
ctttgcctaa tccttatcgg tcaccaggca acgaaggtag ctggctatgc cgaccggagc  1020
ggacagggct cgggcgtcca tcgggatagt aagaatgacc attctcttac ggtcggggtc  1080
aacacccggg gggagggaac ttcttcacta gtttcgggct caagctcgag ctcggcttgc  1140
tcgctcccga tgacacatcc ttttttggga cctccaggtg accaagcctg gagaagtcct  1200
ccaatgcgac catgtccatg ccatcaaaga acgtgttgag ggcattatct ggacccgacg  1260
ctatctcatt taatttctct ttattagctt gaacctcttc gagcatggac tcagtatagg  1320
acggcgtctc tgcgatgtca atgatactag ctacatcctt cgggacagga gcggcttctc  1380
gataggccat ggactccgtc tctccctctg gttctcgagc tagaggggga tcgacctctt  1440
ggtcaccttt cctggttgcc accttctccc tctcgttgag ggtcgactca tgagcaatga  1500
actcaaggtc gtcatcctca ggataatccc taagccggta gagggaatca gatttcggta  1560
ccctcgactt ggtgctcttt ttgtttttct ggacctggac gaccaccctc ttcttcttca  1620
cctcgacatc cggggagcct gtggatttcc ttttattctt ctttttctct tcccttacgg  1680
cggcctcggg ctgtcccgaa gcggagggtt cagcgagcga ggacggatcc tcgtcctcat  1740
ccaatggctt gagctcggtg gtcatgggtg aacctgtgag aagaaagaag acttagcgat  1800
atattcatca agtatatgaa tgtaatcatt cgggagagag actcactatg ggaacgagcc  1860
tcccatttgc ccttcgagag cttgcgccat acgctcgaag taggacatct atttgcacat  1920
cccctcgatt cactccttga agcaggggaa tgtattagga acctgggcaa ctgctacata  1980
atggcaaata caggcaatta gaaaaaagaa taaaaggaaa tgccagatac tcgagaggga  2040
aaagacttac gggatgcgtt tcactttttg aggaatggta gaaattcgga gaggatgagg  2100
tcttcggttt tcacccgaac gaacctcccc taccaacctc gatctcggtc ctcgtcgatg  2160
ctcgagaacg gagccttgct tgctcggcga acgatcttaa tcaacccctc tcggaagatt  2220
cgaggactgt atagatgaag tagatgttcg agggtgaact gaggtgcttc agtttttgttt  2280
acaaagtgtt ggaggaggat tacgatcctc caaaaggaca ggtgaaggca gaccttgcac  2340
cttttataga tgtcgaggac tatggggtcc accgggacga gcgtgaagga gtaagtgtaa  2400
acacttaggt accccctccac gtgagtggtg atgtctttgt tgggcccggg gacgaccacc  2460
tcctttccct cccagttaca ctctacccga actatgggta gtgtctcctc agtaacagag  2520
catatgtacc tccatgctcc ctcgtctcgg tcctgttgac tggaggcttt ctcgacgttg  2580
aagtcattct cgatagagca gcccccgagt acgaagctct tcaagggagg ctcatgggct  2640
acctcaggaa tggccacctc ggcatttatg gccagattgg aaaataaagg agcggtttgt  2700
tgaggaacga atttgaaagt ttttgctatc gggttctgaa aaatatgaag gtttgaagaa  2760
aaaatatgaa gatttgaaga tagaatggaa atatgaaggt ctgggttgaa gattgaaaga  2820
gaatgtatga agattgagga tgaaggtatg aaaatctaag gagcaatcta tgaagatttg  2880
aaggagttaa aggtatgtaa agaattcaag ggtaaatcaa ggagctctag aatcgaaaag  2940
tggagaagtg aaaaaggggt cggagctttt atagaggaag gacaatcaat gcatgacgtt  3000
tcacattcga ggacagtcaa tcaacggccg atacgtgtcc gatgttagaa cgatgcgact  3060
aatgggacgt ttcattgatc cgtcatctcg gttgtaacgt acgaagaaag gaatcggggt  3120
tcatttatcg cttcccgtcg tttcgataaa tctatcctcc gaaaaacaag gggactatct  3180
gtatacgggt aaaatcaggc aatgtctacc ctgattctcc tataagagaa taaaggggga  3240
gcgcggatcc gcgagattgt aatcgaggac agagacccat cgtatcaaga tccaagaaga  3300
gtgaacgata tatctaacat cagacacggc aaagcgatgt accccggacc gaatataact  3360
cctagacctc gggagaagcg ggggacggtt atgcatgaca gataggagac tgtatactcg  3420
ccctcaatcg gatattacga cgcgaatctc gtcagtaaca attatggatc aataattact  3480
ggaaaaagaa gatttttacc tttttttagac ttatactagg actgaaattc tcgtactata  3540
taaaggtaaa gtttttcttt gatctgacac attgtaacac gcaattcaaa gaaataaaaa  3600
tttgtttttg ccttctaact aatgttaaaa attttgctca cttgttctgt tcttcattca  3660
cgactggact cgaaccgagg gtccaatcga gtacgaggtc actgttcaat ctaagatcat  3720
gcttggtcat aacattgcga ttggtttgat catttatttc gtctttaatt catttatctg  3780
ttatttttaa ttattcgtgt tgaattaaat cacgtatcat ttaaaccgcg tacaaattta  3840
attgttaccc atttttaagg taaacaacta tagacgaaaa aaaaaatata aatattaaat  3900
attatgtttc gaaagataca caatagacaa gaaaagaaaa gaaaaatccc ttataaaatt  3960
tggatttagc ccaccagttt tattgagacg tctttgtgtg ttagttaccc ggcaaaggtt  4020
atgaacctac tttatgcgtc aatgtccgaa tttatttttta tcaacatcct tttggaagag  4080
cttttgatag aaatggttgg cttaattagc aatcatatta tcatcacctg cgctttggtg  4140
ttatatcatt cggaatcata tcattacctt ttgaaattta aaatggtttt caaagacgtt  4200
tcgataaaaa aattcctatt gtcgcagttg gaatctacaa gacgaagatg ttgatctagt  4260
gctatatttg gagaaagtgc cttaattaaa aataaaaaat tgttgatcag ttgtcttaag  4320
attttttatt attaaaaaaa aaaaattaag atacaaagaa acacatttac gagtatatgt  4380
cggccgacta attaatgtga agttccacac ggtcaaccca cacatattgt ggtcaagata  4440
gattctatca taatcaaaag tcattatcga ctcaattttc atatttggca tcttaagtac  4500
atgcacaaaa gctacttagg atgtaagttt ataatcattc attcttgaaa tagaacctat  4560
ttaatagtac ttaattagtt acagtagtat aatttattct ctgctaaaga gctattgttc  4620
atcaaatata tcagattatc ctttgtggtg tagaccattt ccttatttgt acttagtatt  4680
```

```
aattctggca aaagcacaaa actgggaaat gaggttcttc ttcattaatg ttgagtcaag  4740
attagtacta ctactatagc caagaaaatg tgaaatcata tagtactaac tttcccttct  4800
ccctagctac tgataactct aattaatttc agatgccaaa accataaatt tcccctcctc  4860
catcattgaa aacccctttg tcctttcccc ccagacccc ttttcctctc tctctctctc  4920
ctttctcttt ttattagacg catattctct cttctttctc tttctagggt tttcacctga  4980
aatagtttta tttcgttgat                                              5000

SEQ ID NO: 152         moltype = DNA  length = 5000
FEATURE                Location/Qualifiers
misc_feature           1..5000
                       note = Description of Artificial Sequence: Synthetic
                        polynucleotide
source                 1..5000
                       mol_type = other DNA
                       organism = synthetic construct
SEQUENCE: 152
attataaggg aaattaaaac cctaaaaaca agattttatc tatctgcatg gtgaaggaca  60
aagaggtctt caatctcagg ttctttttgt ttttttaact tgtttggata tgaggttatt  120
gagctgatga atgttttaat tttaacatag gcctacttac gtagtagtta taggttgata  180
atgatatata tttaactaag tctttgtata atgcagatcc tgaacttaat ttttattttt  240
attattttgt tgttaatgaa agattctgtt accaaatttt atcagtctat ttaattagag  300
gccaaagatt gttaggtatg tggcacttgg agtgggaaat gatatattcc cattaaaggt  360
gttaattaac caccaaattg ttctttaggt ctgtttgtca ttttgtatta aggtggatgg  420
ttcattatct tctctttaat gctaatcatg cttcaccttt tcatttagta ctagcaagca  480
tatttgttta ctttattggt tattccttat caaagtcttt atcttgttgc ttttttttt  540
attgtacttt acaaaagatt tctggtatta atggaaagtg ctcatatttg gaaaaagaca  600
tggccaacaa gaaaggtgta taccccattt ctttttcttt ttctccaaat ttttttttt  660
tttttttctg tttcttgttg agttctttca tggaagaaga agaagagtag gagattcttg  720
gacatggctg catgagaatt gttattgttt tgtgcactta aataaccccg tatacataca  780
caagtagtgt tggctgtctt tgatattgca ccatttattg ccctaatttc tgccttttgt  840
cccctcaaca aaaccatcaa agttctcaaa tagggtttat tcttgtttcc cactttgccc  900
cccacccatt agggccaccc caccaaaggg atctctctcg tgtctagtgt tttttcccaa  960
ggaccaccac tactttttt tttttctcta ccataacttc cacaccatct tgtgatcttt  1020
cgtttaataa tgattttgca gccatgcctt cgttcatcag aactcggtca taagcacaga  1080
ttctgagaga gtaattaatg aatgaatcag tggtgatttg acttatacat gattatggtt  1140
tttagctcaa taagcagagg gagaaaatat atataaacaa gtaaatctag tagaagaagt  1200
agaagtttta tagctagagt agtgggaaag aatgacgcaa gattagtacc aaaagagtga  1260
aggaagagct ttaatatagg gaaaagggaa gtagtaggtg atacttgaca ggttgataag  1320
atggttacta ctacaagttg atgtattgac gctaactcac gcaagagacc tactcactgt  1380
gcaatattta caagaagcga ttctttctct ctttacttgc aagagttgtg tgttccgagt  1440
tgtatggcgc atatgaacct tttttcatac aatacaatac atatggaata gatagataag  1500
acggtgcacg catgaggcaa ttatgcaact taacatcaac tacttccatc atcttttctt  1560
ccctctgttt ctgtttctgt ttctgtttct gtctgatata ctatatgctt ctctggcctg  1620
gattttccta actcttttga taatttaggt tcccatcaat aatgtctttt tagaggagca  1680
tcatatcgat agatattcaa atattaaacc tggcctaggg ctagggcgtc tgctaggttt  1740
ttgcattact ctttgtatat ctcatctgtg ggaccttttg tttatggaag aatatacttt  1800
tattcatctt gttgggtctt aaattcaaga tttaatatta ctctttaaaa attaatgact  1860
atcctaaaat tcttcctctt ttatttgcat ttacaagaat tgatattagt acctaaaact  1920
cttctctggg gccttttgta tttagtcctt ttatgtttga aattgacact atttaaataa  1980
aacataatct acaataagat gttcttcacc cttcgggttg cccggttggt ttggatggga  2040
tcgattcccc cgatatcttc tgggttgagc atatcgcaca gggcttgtct agtgcggttt  2100
gcattcccta tgtggtttgc attccctatg tggtttgcat gctattatac atgggtttac  2160
ccagtggaca caaagtattc aatacagagt gttcacccga agaacagagg ctgtggcaaa  2220
gattgtaacg gccgcgggtt tcccctctta caaaaaaaaa aatgttcttc cttaaacatt  2280
acccatcaaa gactcaccaa agatagctct accaagtatt atttttggat caaatggcat  2340
ttccacggtc atatctcctc cccccccct cacccccccc cccaaagcta gtgatcactt  2400
ccatattttt tcctgatttc atcggtgctc aaatacttgt tcattcatct tcattccaaa  2460
caaaggcgaa aaacttcact attgagtgct tttttcctat tccaagtgtc aaaccctaaa  2520
cttctagtca aataatatct aagatgtata ctcttatact atgtttgtat tcattatgac  2580
aaagtatgat gagttgtaca attttcttgc ggacttagtg aaaatagagc ataatgttaa  2640
aaaaatattt acatgatatt aattagccgg attaagttta taacgttagt atatatgtct  2700
actttaggta caatacaagt cttatactct tgtcagaatt tatatgtcac aaaatataga  2760
aacttctagc tacttttttt taattttata taatataata ttggaatgaa tttaagtgga  2820
gcaaaagtga atattcatgt agtcgatata ttctaatctg tttggggctg agatgacatg  2880
attgtagtga aatattgtac cattgcattt cacactcact gaactgaaac tttggttcca  2940
cgtcggtgat catttgcatg tttcattagt caatactgtg gctgttatga tttggctgcg  3000
agggggatcg aagagagcac attaaagtat ttaatcagga tttatgagtt gaatgctgtt  3060
agttggcgga attaatagtc aaataatgaa tgagttactc gctgatatag ttaatagtac  3120
tccgtatata tgttgattct agttattggt ggtgacctaa gtaaagagaa tagatgagag  3180
gagtggtggt atgtaaagga atctaggtaa aggggtgggg gtggggggag gcaaagttga  3240
aaagaaaggt ggaaaatcca agaatcctgc ttcctctagt aacatagcat atcctgctat  3300
tcgtgctttt gtttcctctc acaagataac tactttttga ttaattatta catttgacgc  3360
atacaaacct ataaaattaa actaatcaac gacatcctta tggaatctta cgagtccgaa  3420
cttgtcatat atataacttt aaagtacttt gtcacttctt aatatgctcc tttaattgtg  3480
cttagctttt tgctaaaaaa caaaaaggat atccttattc caaaatgcaa ctgggagcat  3540
cttctcactt ttctttttta tgcctctgca tcatcaaatc ccacaatgcc gcacaacaaa  3600
ctcttgttac ttaagtatat attctacttc ataagaataa tgggtataaa aatttgctta  3660
ttttatgttt taaataccac cgaaaattca taagcaaatt caggatttaa atatattaaa  3720
tgaattcaac ttttaaaatt gttgcactta tatatatata tatatatata tatgcatatc  3780
```

```
caagttgagg gatacgggtt cacatgaact catattactt tctctaaacc atgtataaca  3840
atgttatatt ttttcaaaat tatttaaata tatgtgtgtg aacccattct caaaatctct  3900
tatggtgcaa ttattattgg gtgcacatct acaagtgaaa tttgcagctc aaaacctcat  3960
ctgggcggtc ttgttttccg catggagtat aactatatat gtgaaaatta ctagaatttc  4020
aaaatgaata taattttgaa atgttgtggg ttcctggtaa gagactaaag ttaaactcgt  4080
caaatataaa ttctagatcc acctcttcac aatagtgcac ccattctttt gaaattctgg  4140
atctgcctct gttaataata tatatatata tatatatata tatatatata tatatatata  4200
tatatatata taaacacaaa aaaatatgtg gaaaacttta ctattaatta ccactgctaa  4260
acatttgaat ggattcttca tgccgtgtgc tcctttgttg aagaacacgt acttgggagg  4320
gcgagatttc gaataaaaaa gttatactaa taacaaacag caacaattat aagaaaatga  4380
aaataaaagg gaaagagcac tcacataaac tagaaactgt agagttggca agtaccaggt  4440
atatatgtcc ttgaatgttt tttacgagga attgagtaaa acgctagcta tttcaacaca  4500
tatataaaaa gcatcaatac caattttatg gtttctctta ggtgttgata gattctcttt  4560
tgtcagcaaa gttcttgcat taactatatg aaatttataa taaaaatgct gctcttttaa  4620
ttgagtatac atgcagtctc ctaacatata cattctccgt cccgatatat acttgatttg  4680
atgcatttca aaaattaaat gtttgagtgt tttggtgaat tgtgcttgat atagaagtat  4740
ttaaaataag aaagaaatgt aacggcagaa tcttaagtcg aaagtcaaat taaatttgaa  4800
aaataaaaaa taatactctt gatacttact agtactagtc aatgggcagc tctttcggga  4860
ctaaccaaaa gcattattct tattgtttcc ggcatagtat taaaatgtaa caatgcttaa  4920
ttatgttaca aaattaatgt ttttgtggac ttcggaataa tttatttctg aattcgccgg  4980
tgttatcgaa aacatgggga                                              5000

SEQ ID NO: 153          moltype = DNA  length = 5007
FEATURE                 Location/Qualifiers
misc_feature            1..5007
                        note = Description of Artificial Sequence: Synthetic
                         polynucleotide
source                  1..5007
                        mol_type = other DNA
                        organism = synthetic construct
SEQUENCE: 153
tgggggccct ccgcacaagg gaggagctag gggaggcaag aaaattacat gtgtatataa  60
gattaaattt tcttcttctt ttttgtgtat aggataaata tttaattttc ttaatttttt  120
tgcgtagtta ctcttttaat tatttttaac tcctctgaac gcaagtctta cctccgccgc  180
tgactcctct agagaggagg ggtctaaatg catgcaactc aaacgacgaa agggtctttg  240
cctaactaaa ggttccttat tctaatatat ccttctagaa aaggtaatag aagttgattc  300
gaatatcaaa gagagataca tgtcggttac aaaaataatt ctcaagataa tcaatagaca  360
tctctagatt ctcggactta aaagatccat ttagacacat aatcatattt tttttccaaa  420
caatcgtcga aggcagcttg ttgcacaaaa tatttcgtat ttacataagg tttaaggaaa  480
aatcgtactt caaagagtat gatgtagata atacattcta attagggtcg gctctatagg  540
tgtaaggcaa gtgtcttagg ccccaatttt gggaggcccc attttttagt aatactatat  600
attttagagg tttataattt ttttttaaat aattaaataa tatatatagt atttttttac  660
ttttcatata taaaaaagaa aaacttttaa tatattaata aagtaaagat taaaatagta  720
ctaaaaaata gttgtcactt tgatttgatt tgacaacttt actttttgct cttcttccca  780
aataattcct agacccaatc caacatttca attttcatat agaaggatga gacatagtaa  840
cataccttct tcctttcttt tgattcgtgc tcattttgtt tctactagat ttctttcttt  900
ctccaaaact ccaacaagcc aacaactaca tattttgaaa tcaaagtctt caaatttttt  960
gaatcagtta gtcgggtaat atcattctaa ctttttagta ttatttttat ttattattta  1020
ttattttatt aattttacca tgtacatatt gtttaatttt tttagaatat aaatatgtct  1080
acaagaaaat atgcatccgg atattcaaaa atccaaaaga aaagaaaagt tgaaaattta  1140
ataaaatctc aaaaaggagt tctcgagaat ttttgacaaa taataaaaaa actaaatcgc  1200
aaaatgtagg agaatattct gtagatgaac aagtcactaa ctttgagtca gatgataaca  1260
aaattcaaat tgaagaagat gtttatgaga aatctgacga agaaacaaac tttagcctta  1320
ggccctatat taaactttgg ccctaggcct catatgagct tgagtcgccc ctaattctaa  1380
tacaagtatt agtggctact ttcacggctt gtgacttatg gattacaaac aactttacag  1440
ttacgtcaag gctccacgta gttctcaatt tatggagcat atattagatg attaacgcag  1500
ggaaagattc tgctctcctc tgatacatgg ctattattcc tcgtttagtt caaaaaggaa  1560
aaagagggta gtcttgttat attattgggg aatgaattat ggtttcaaac ttttcaaact  1620
taaaggattt tgtacatggt aaaacctaaa ttgacacgta acttggtact ttcaaagaca  1680
cgatctttta cgcgatattt taaataaaga aaagatcaag tcaaaacatg ggccaaaaag  1740
aaaaacccca tgatttttc tgataaaaag ctgctaactt ttagtttgtt ttatccaata  1800
aaacatcttt aacggtctgc ctgctttagt ttaatcctct ttttaagatg taattaagca  1860
taaaatagaa aagggaaaaa aaaggtccat tggattttgg aagaaatttt aagaaagtac  1920
aagaactagt aaagtcattt tgtatagagt atgttaaaaa ggtgagtgac aattcgaaaa  1980
agaaagcatt gataagtcaa tcactaaata aaaaagcaca cctaataatc attcattcaa  2040
aaaaacaaat ttctatgaaa gataatcatt atcataagtc actgcagaaa tcccatatac  2100
agtagagtac caggatttta cgataaggtg ttagcaaact atctattcat tttttgacaa  2160
gcattttatg tttggtcatt tgttgggaaa aattagggag aaatttaaaa atagttagat  2220
ttacaactgg tcattaaaaa tagcccaatt tcaaaagtaa tcgaaattta gccacttttc  2280
atgtaaagat aaatctgagc gaaaatattg ttcaaaaccc ggaaaatacg cccgtatatt  2340
atactggagt tccagcataa gtatgcttga actccagcat attatacggg agttctagga  2400
taactatgtt ggaactccag cataatatgt tggagttcca gcataagtac actagaactc  2460
cagcatatta tacgggagtt ccaacaagta taactgtccc gtataatata ttggagtttg  2520
gagcaccggt gctccagtct cccgtatatt atacaggagt cagcaaagta taccggtcca  2580
gcataatatg ctggagttcg tacacagatg caccgaactc acgtatatta tgcggaaccg  2640
gtctctgttg cagcaaaata gtggctattt ttcattgact tcgtaaacgg tggctatttt  2700
tgaatgacca gtccgaaaac tggctatacc gtgctatttt gacgaaaaat tatcccccca  2760
cccacccacc cacccaaacg caccttacac acattagtgc acatctttta actagttttt  2820
ggttattttt ttatttgatg cccgatattc gtatatggat ttcgattaat tagaattcac  2880
```

```
accgaaacat tctttcttag gattttgtac atacttaata tgcgaataca aaacctatgc  2940
ggaaaggtaa gggaacctat tcatccctct acagtacttg tgataatgtt atactttttt  3000
gaatttaatt tgggagacat gtcaatcttt attttgaaaa aaaaatagaa taaaaccata  3060
gggaaatgaa caatttatct ttcactccta tctcatttta tttgtcttga atttttcaaa  3120
attttgaatt atattttgaa acttcttcaa tttatttttct tggaatcttc agaattcaat  3180
ttaaaattcc aaaattccaa ggatttagct cccgtttggc cacagatttt ggcttcattt  3240
ttttaaaaaa aattttgaaa acattctttg tttatgcaat atgatcatgt tttaggggaa  3300
aaaaattaaa aaaaataaaa aaaaatcaaa ttcccaaaaa ctggttaggc aatttttgga  3360
tgatattttt tcttccactc acaaaacttt aacatgtcca aacacaactt caacttcaaa  3420
aattattttc aacacaattt taaaaactct tttttcaagt ttcaatcaaa tctatatcca  3480
aatgttagct tagtatcaaa taagtgattg aaatcaaatt aaaatcgagt ggtaaataaa  3540
atagaggaga gctcggtaaa ttacaagagt gcggtaaatc ttttctcctt tactctcact  3600
gtagcctatt ctatctgttg taactaataa gtaactgagc tacggaaaaa gtgcctagac  3660
ttttaacttc acaagtataa taaatagaag tcaattcttt cataatattg tttccatcct  3720
atcaaacaga ctttgtctca ctgaccttcc ttctgagtgt gtcttttata tgtcattttt  3780
agtgaatcca tatgatttag agactctaat attccacatg cgggtcttaa tttggtgtat  3840
atgtatatgg taataatttt tgttaggtag ctgtagtatt ctattattgt tatgtattga  3900
ctcatcatgt aaataaagcc ggttagataa ggctagaaaa atatgagtat acctagaaat  3960
tattagcata ttgtttggaa catgtcaaaa atttcaatga cctagctaga gctgtcaatt  4020
agtcaaataa ctttattaat atttacttat gaaaacactt tgaaattctt ggagtttaag  4080
ggaaagacta ctgactaaaa aacaaagcaa aagtctatgc attactatac tatacacagc  4140
acagcatttt ccaatagtat ttgagatgaa tctccaatca gctactgttg ttcttttctt  4200
ttctttattt agtttaagtt ttatgtgttg atggtataca aattatttgc acaatcaaat  4260
ggcttatctg gataatatag gtaaacctct tgtaatcact aattggtaat ctggtaaaaa  4320
taacactatt tctattccaa tttatgtgat caatttcact agacaaaaat ttaagaaaga  4380
aataaatttt ttagaacttg tagtcataaa caagttgtaa catttgtatg gctataattt  4440
ttttaacttg tgatgttaaa catgtcagat tgtttgtgta gctataaaag tttttcatta  4500
ggcgtaaaat taaaaattta gattaaatta ttattaaatt tagaaagagg tcattttttt  4560
tagcgaagta aaaaagaaat cggttcacat aaaccgaaac atagagtaag taatctgtta  4620
tgacaaatta aaaattactt gtagtgtaaa aaaatcttta caacattcgt gtatatactt  4680
aaatcttttt tattttttgg caagagatag ttgttcagca aaagtaagtt agaaataggt  4740
ctgtccttct gactttgtaa ctctgaaatg aaaatttcaa aatcccttct atttttcttt  4800
tccccccccc ccccctcac aaaccccaac tcactcttat ttaataaaaa gctctactta  4860
gaaaagacac ccttgtccat ctgtctatat aggtagaatg agagtaaagg agaaaacata  4920
tcctcctctc catttctgta gacaaagatt ctcaaagaga aacaaattaa acactagaga  4980
gtgagagagt gctataagaa aaagaat                                     5007
```

```
SEQ ID NO: 154         moltype = DNA  length = 5000
FEATURE                Location/Qualifiers
misc_feature           1..5000
                       note = Description of Artificial Sequence: Synthetic
                        polynucleotide
source                 1..5000
                       mol_type = other DNA
                       organism = synthetic construct
SEQUENCE: 154
agaagaaatg actgttgaaa agaaaacaaa tgcaagtacc attaggaaga tttgaaaggg  60
cgtttgggta tgggggttgc caagaagatt cagacttttt ttggggtttt gtgtagttgt  120
ggtagaatta ttattgaatg aaaaaaaaaa acttcctgta ctttaattcg tcagtacata  180
ctacatacta ctacaaagta gttaaaagcc tattctattt gtgctttttt tttcactcga  240
tgttcaataa ttatattggt ttttgattaa atttgaattt gagcaaggaa gatcaacatt  300
ggagggataa attgtttcct aacgaaggcg attacatact tagaacttga actcaatatc  360
tctaattaaa aatgaagtaa tacttataat aactccacca caattcttat tgttgtgcat  420
ttctttataa aatatgtaaa taatgggtca tatatattgt ttaccttttc tattcatata  480
catagatttt aaattaatta tacacatata tataatacat taattattca tatattatat  540
ttttgctagc tatttttagt ttaagcgatt tggtaggcga ctacttgggt taattctttt  600
tttttaatat atatatcaaa ataatgaagc tgtataatac acttaaaaat catatttgaa  660
aggtattaaa tacgacttag gagagttctt aaaccatttt ggaaccttgt ctacgtactt  720
ttatgcaata gctgttttg tttgtctctg ctaaaaccta tgctccccaa ccgtgcacca  780
atcaacttag aagttagaac tcagaaataa atgtaactat actccacaga aagttaaaaa  840
gttttactgt taccattcac tcaaggatca gaaactgaaa gacaaatgaa tcagtgcttc  900
actgttcttc actaaaagaa atactgttta cattagtttc aaaagagttt aatcataaaa  960
acaaatgtac cataaaaagg ggagattatc aacctgaaaa tgaaacagaa catacgttat  1020
atatcaatct atatacggtc gagatcggac tcgtctatta cacgacagat cgggattgaa  1080
acgtaacagt tttgaagatc aaccccgggt tccgtcggac cgaggtacaa ggtcagaatg  1140
cccgttctcg agaacatcga gtccatgacc ccagaatcaa ccctgacccc aaatgagctc  1200
gaggaaacat ccggataacg gaaggcgaaa tatccgtaac cggtcgggta tcacggcatg  1260
aatttcggca cgtaacaatg agaaaccggc taattagcaa atcatggaat tttttacctt  1320
ttatagaatt gtaactaaag tgggattccc ctactatgta aagggggtct gactatttgt  1380
acgggacatt cattaaacgc atcccaaagt aatataatat tattttcttt ttgtaagcta  1440
ttgttctcct gtatctgata ctatttgaat tgcatcaagt tcaagtgaga ctcatttttt  1500
caaggctata attgttcaag tcgcacggtt tgaatttatt cgatcattgt tcgctttaat  1560
tacaattcaa ttcatcgctt tatgtcaaat taatccacat atccttaaaa ccacttacaa  1620
atttaattgt tatcaaattt taagggtaaa cagtttggcg ctcaccgtgg agctaaggat  1680
aatagtggtt gtttgatata gattttcata acacacacta ttttacaatt gttcttcgaa  1740
gtgtctctca tttcaggttt aagctcaaaa tgtcaaactc acaattggca cccctacctg  1800
cacacaatga gtctggtcac catggtgaaa ataacaacat agcacctggt aacgaggtac  1860
cgcccgctga tcccatcaga atttcaatcg cggacccgtt ggacgctaac tcgcatgtgg  1920
ctatcgacat gttacagtct caacaggcga cgatagctca gttacaaaac caaagccgca  1980
```

```
caccgagcag agttgaactc gatccgtccc ggaaaatcac ctgcagggaa gaaccgtccg  2040
cggagaggtc aaatggagat gagtcgggga ctaaccccga gatcataaaa atgcttgagg  2100
aaccgatgat acggattgaa tcaggggaaa agaaaatcga ggcaaatgac aagaaggtaa  2160
aaacttacaa tttcacggtc aaccaaatcc cgggagcacc gccggtactg aaaagcttgg  2220
attccaagaa gttcgtgcaa aaacatttcc ctccgagtgt ggccccgaaa tcgatcccaa  2280
aaacatttat atgcccgaga ttcttaagta taatgggaca accgacccaa acgagtatgt  2340
cacttcttac acatgcccta tcaaagggaa caacttagag gttgatgaga tcgagtctgt  2400
tttgttgaag aaattcggag agaccctgtc aaatggagct atgatatggt atcacttacc  2460
tcctaattct attgactcat ttgcaatgct tgcaaactct ttcgtgaaag cacacgccag  2520
ggctatcaag gtcgagaccc agaagtcgga cctcttcaaa gtaagacaga aggataatga  2580
gatgctcaaa gagtccgtgt cctagtttca aatgaaacag aaggacctac caccggtcgc  2640
tgatgattgg gccgttcaag ctttcaccca aggactcaat gttcgaagct cggtggcttc  2700
acagcagttg aagcaaaatc tgataaagta cccaactgtt atttgggcca atgtgcataa  2760
ccgctatcaa tcaaaaatca aagtcgaaga tgatcaactt gaggctcttt ccgggtcggt  2820
ttaccctgtc agactcgtcg acagaatcaa gagagatatc gaccgtgaac caaggtcaaa  2880
cgtagatcat tactagccat atgatggaga ttggaaaagc aataggtctg ggtgaagttc  2940
tacacagaat gaaaagagaa atgatccagg tcagagcact cgaggactcg caagcaagaa  3000
cgacttcgac aggcctatca ggcctaaaga agcaccaagg ttatcgaaat ataactttaa  3060
tattgatgcg gctgccatcg tatcagctat cagacgcatc aaagatacca aatggcctcg  3120
acctttacaa tccgatccag cccaaaggga tcctaaccaa atgtgcaaat atcatggcac  3180
ttctggccac agaataaagg attgtcgacg gttaagagag gaagtagccc ggttgttcaa  3240
taacgggcac cttcaagaat ttctgagcga ccgagccaag aatcatttta gaaataggga  3300
ttctaacaaa tagaccgaac cagaagaacc tcaacacgtc attaacatga tcatcggtgg  3360
agtcgatgcc cctcaagtgc tgatgttgaa gcgcaccaaa gtgtccatta caagggaaaa  3420
acggactcga gattacatat tagaaggaac cttgtctttc aacgacgagg atgcagaagg  3480
gatcgtgcag cctcacaatg atgcattggt aatatctgta ctcataaata aatctcgagt  3540
taagcgtgtg ttaattgatc caggtagctc aaccaacatc atccgattga gggtcctaga  3600
atggcttggc ctacaagatc aaatcatgcc tgcagtccga gttctaaatg gattcaacat  3660
agcatgcaaa accactaagg gagaaataac attgccggtg aataccacca gaaccatcca  3720
ggaaaccaag ttttatgtga tcgaaggaga catgaggtac aacgctctgt tcgggaggct  3780
aaggatctac agcatgaggg cagcaccctc gactcttcac caagtgttaa agttcccaac  3840
gtcgggaggg atcaaaacaa tctacgggga gcaaccggcc gcaaaagaaa tatttgcagt  3900
cgaagaagag atcccggtat agacactagc aacatcaaag gaaccgagtt cggataagaa  3960
ataataggct aaatagcaat tatcgacacc agccacgacc caatcggata aaaaggggac  4020
tgatgaagat gatgattatg gggttcccag atcttttata gtccctgatg attctgacgc  4080
caccaaatca atggtcgagg agctggaaca ggtcacatta atcgaacgtc tacccaatca  4140
gaaggtatac ctgggcacga ggttaacccc cgagcttagg aaaaactcat tcaatttctt  4200
atagctaaca tagactattt tgcttggtcc catattgata tgacagggat cccaccggag  4260
ataatcattc aaaagctgag cctggacttg aaattctacc cagtcaagca gaaaaggaga  4320
ccccagtcaa aaatcaaaca tgctttcatc aaggacgagt atttgcacaa aactttcaac  4380
atattgaaga agtacaatat gaagctaaac ccggagaaat gtgcattcag agtcggatca  4440
ggtaaattcc tcggattcat ggtatccaat cggggaattg agatcaaccc cgacaagatc  4500
aaatccatca aagatatcac gatcgtggac aacgtgaagg ccgtgcaaag attaatcggc  4560
cgcatagccg ccttggggca atttatctcg agattctcag ataaaagtca ccggttcatt  4620
tcgctactaa agaagaagca caacttttcg tggaccccgg agtgtcaccg ggacttggag  4680
gaactcaagc ggagatagct gcttcacaca acaaaggcaa acgaacaact atacctatac  4740
ttggcagtat cggagatagc ggtaagtgga gtcttggtcc gggaagaaca aggtacacaa  4800
tttccaattt actatgttag caggacccta ggtgaggccg aaactaggta ccctcaccta  4860
gaaatattgg cattcacttt gctaagcgcg tctaggaaac tgaaaccata tttctagtga  4920
catcccatat gtgttgtgat taccaaccaa ttgtggaata taatgtataa acggctactc  4980
tcgggatgat tggccaaatg                                             5000
```

```
SEQ ID NO: 155          moltype = DNA  length = 5002
FEATURE                 Location/Qualifiers
misc_feature            1..5002
                        note = Description of Artificial Sequence: Synthetic
                         polynucleotide
source                  1..5002
                        mol_type = other DNA
                        organism = synthetic construct
SEQUENCE: 155
aatgcagcct cagtcttcaa cataaaaaat cacatgagta tataagatta attttttttt  60
ttttgtatat atgttagatg ttgaatttct tagttgtttt gcgtgtgttt tttttttttt  120
tttttgacct ccctcggtaa aagtcttacc tccggcaact gtctccgcga gagagagggg  180
gtctaaacgc atgtaattat tcaatgattg aaggatggtc tttgcctaaa tactaaaggt  240
tccttattgt ataggtcata ggtgttgatt cgaatatcaa agagagattc ctgtgggtta  300
taaaagtaat tctaagataa taaatactct ttttagaggt gttgttttac tgtaaaatac  360
gtatttggtt aaagtgatag acatatctag attctcagac ataaaagatc catttagaca  420
cataatcata tttttgccag atagttgttg cagctgaaaa ttggagcata tatacttaga  480
agtagcataa cactttactt ccatatagtc ggatggaaaa ttggagtatc atatcttctt  540
ttaattcaca gttaaatctt taaacatatt taataaattt tttaatacaa atataaagtc  600
tatgcaaaag ttattgggtt ggtccaagcc cttaatttcg atctctagct ccgtccccgc  660
atataattct aaaacttctg cttctcctat gatacatggc taatgtttat cgtttagttc  720
aacaagaaaa agagggtagt cttattatat tatgaacggc aaaggtccaa atatgccctt  780
gtactatacg aaattgagta catttgccat ttgttaatac tttagctcaa atataccctt  840
accgtcacgt agttggtcca tatacactac tagaaatccg gtaaaaccga ccaaaaaaac  900
cgaccaactt tggtcggtaa tggccaataa ccgtccaaaa cacgaccatt acgtgtggac  960
ggtattttag gggtcggaaa ggcataccga ccaaagttgg tgtaaattac cgaccaattt  1020
tggtcggtca attaaattaa aaaaaaaccg accaaagttg atcggtattt taattatgta  1080
```

```
atcaaaagat tgaccatctg ggaatcgaac cggggtttgt attgtggcag gatactattc  1140
taccactagg ccattagtgc attttgtttt aagactgttt tttatttgat ttatactctt  1200
taattgtatt ttcgcacgaa aataaccgat caaagttagt cgattttatt aaaaaataaa  1260
attaccgacc aaagttggtc ggtttttaa aatgaccggc cgaattaacc gaccaatttt  1320
ggtcggtttt ttaatattaa tttttattta ttttaattaa aactgaccaa aattggtcgg  1380
tttcttgaaa aaaatttccg ggactcgaaa atagtttttc gcatttttct ccaaagaaaa  1440
ccgaccaaag ttggtcgatt tcgtaaaaaa aaattaaaaa taaaatattt taaaaaaccg  1500
accaactttt gtcggttttt tggtcggtgt tttgaccgac caaagttggt cggtcgacct  1560
tggtcggttt ttgccgaatt tctagtagtg atataccctt agagttacac aattggcaca  1620
tatatgccct tctcaaaacg aaattcaccc aaaaattatg gtttaaactt taaaataata  1680
aaaacatctc aaactttaac aatactcaaa agaccaaaat atttaaatta tttctaaaaa  1740
gataatttaa tgattaaaag cctagagttc aagttgtagt gttataaatt tgagttgtta  1800
gtctttttca tctttttcag ctggacattt tctatttttt ttattaacta tgtaaattag  1860
gggtgtacat ggaacgggtt ggatcgattt ttatcaaaac taaaccaaac cgattatatc  1920
ggtttgaatt gttcggtttt attggttttt tcagattttt tgttacataa atattatttc  1980
aatcttgctt tgttaaattt tttagaacta aatatatgtt cagtaaaact taaaaaattg  2040
acaaacatat gatctatctt gattacctta tgggagaatt ttcttagtaa ttggaattca  2100
tgagttttgt caagtgaaat tggtgacgaa aatagagaag acatcagtaa ttgaggaaat  2160
cggataaggg agaaagaaaa agaaaaaaag aaaaaaagaa gaaagaaaag agaaaggtaa  2220
agaaaaaagc actaataaaa aggaaatagt atttgtaata tactttaata caattaacgt  2280
aagagctaat tagtttgagt ggattccgtt ttgaaaaggg catacatgtg ccaattatat  2340
aactctaagg gcatatatgg accaactatc tgacggtaag ggcatatttg agttaatata  2400
ttaacgaatg acaaatgtgc tcaatttcgt ataatacaag gacatattac attttcccta  2460
ttatgaaatg gttcaaactt aaggatttg tacatggtaa aacctaaatt gacatgtaac  2520
ttggtacttt ccattgggca aagacacgat cttttacgtg atattttaaa tcaagtaaag  2580
atcaagtcgg gccaaaaaga aaaaaaccca tgatttttta agataaaaag ctgctaactt  2640
ttagtttgtt tcatccaata aaacatcttt aacgatctgt ctgctttagt ttaatcctct  2700
ttttaagatg taactaagca tgaaatagaa aaggggaaaa aaaaggacca ttggattttg  2760
gaagaagttt taagaaagta caagaactag taaagtcatt ttgtatagag tatgttaaaa  2820
aggtgagtga caattcgaaa aagagagagc attgataagt caatcaataa aataaaagca  2880
cacctgataa tcattcattc agaaaacaaa tttctatgaa tgataatcat tatcataagt  2940
cactgcagaa atcccatata cagtagagta ccaggatttt acgataaggt gttagcagac  3000
tatctattca tttttgaca accatttac gtttggtcat tttttgggaa acgaactctc  3060
ccaacattct tccaaattac ccccacgcacc ttactgtgca catcttttaa ccaacttctg  3120
gttatttttt cttttgatgt ccgatattcg tatatgaatt cccattaatt ctaagttgca  3180
ccgaaatggt ttttatcaag attttgtata tatttaatat tcgaattcaa aactaatggt  3240
cgaaggtgga agatcgtatc catcccatca taatatttgg ttggtaatat cacacctttt  3300
tgaatttggg agacttgtca atttttattt tgaaaaaaga aaaaaaaaag aaatagaaac  3360
taaaaccata gggaaatgaa caattttatt ttcactccta cctcatttta tttgtcttga  3420
atttttcaat tttgttttga aacttcttca gtttattttc ttggaatctt cagaatttaa  3480
tttgaaattc caaaattcca aggatttagt gtcaaatcag tgcttgaaat taaatttaaa  3540
acgagtggta aataaaatag aggagaactc ggtaaattac aggagtgcgg taaatctttt  3600
ctcctttctt ctctttggag cctactctat tctattgtaa ctaagtaact taactacgaa  3660
aaacgtgcct agacttttaa cttcacaagt ataataaata gaagtcaaat tctttcataa  3720
tattgtttcc atcctatcaa acagactttg cctcactgac tctccttctg agtgtgtctt  3780
ttttatgtca tttttagtga atccaattga tttagagact caaatattcc acatgcgtgt  3840
cttaatttgg tgtatatatg gtaataattt ttgttaggta gctgtagtat tctattattg  3900
ttatgtatta actcatgtaa ataaaagccg gttagataag actagaaaaa atagagtcta  3960
cttagaaatt attagcctat tgtttggaac atgtcaaaaa ttcagtgact cagctagagc  4020
tgtcaattag tcaaataact ttattaatat taacttatga aaacacttgg ggattcttgt  4080
agtttaaggg aaagactact gactgaaaaa caaagcaaaa gtctatgcat tactatatta  4140
tacacaatac agcattttcc aatagtattt tagataaatc tccaatcagc tactgttgtt  4200
cttttctttt ctttttagt ttaagttgta tgtgttgacg gtatacaaat tatttgcaca  4260
attagatggc ttatctagat aatacgtgta aatctattga taatcattaa ttagtaatct  4320
ggtaaaaata atattgcttt tgttctaata taatgtgata tatttgactg ggtacgaaat  4380
ttaaaaaaaa ataagacata tagaacttgt tgtcttaaac aattcataac atttgtgtgg  4440
ctataattct tttgaaactt atggtgttaa acatgtctaa ttgtttgtgt atgtataaaa  4500
gattctcatt aagcgtagga aaatttgaat taaattattt ttttaattta aaaagagatc  4560
actcctttta gagctgactt aaaaagaaat tgattcacat aaactcgcac ggagggaata  4620
agtaatatac tatcaaaaat taaaaatcac ttgtagtgta aaaaaatctt tacaccaatc  4680
gtgtatattc tcaatttttt tttttttt ggcgagaggt agttgttcag caaaagtaag  4740
ttagaaatag gtctgtactt ttgactttgt aactctgaaa tgaaaaattc aaaatctctt  4800
ctttttact gttttaaaaa ctccaactca ctcttattaa tataaagctc tagttagcaa  4860
agacaccctt gtccacttgt ctatatagca agaaagagag taaaggagaa aacatattct  4920
cctctccatt tctgtagaca agattctcaa aaagaaacaa attaaacact agagagtgag  4980
agagaactat aagaaaaaga at                                             5002
```

```
SEQ ID NO: 156          moltype = DNA  length = 5000
FEATURE                 Location/Qualifiers
misc_feature            1..5000
                        note = Description of Artificial Sequence: Synthetic
                         polynucleotide
source                  1..5000
                        mol_type = other DNA
                        organism = synthetic construct
SEQUENCE: 156
agaagaaatg actagctgtt gaaaagagaa aacaaatgta agtacaccat taggaagatt  60
tgaaagggcg tttgggtatg ggggttggca agaagattca aactttttct ggggttttgt  120
gtaattgtgg tggaattatt attattgaaa cttctttact tcaatttaaa tcgtcggtac  180
```

```
atattacgta gttgtagtaa aagccttttc ctttttgtgc tttttttttt ttttcgtgtt  240
cgtattaaga cttcattaaa tccaaatttg catagggacg gtcaacatta gaggaataaa  300
ttgcttccta acaaagacga ttttatactc aagagttcga gcccgaaaaa cgacctctgg  360
ttaagggtaa aaatagtaat tacaataact ccaccacaat ccttattggt gtgcatttct  420
tcattaaata ctccctccaa tccactttaa ttgatttgtt tttggctatt tttatatata  480
ttaaggaatt atcttttagc attaatcaat aatgaaattg accatattaa ccttttagtt  540
cattggaaat ataacaaata ctcctaggct ttttaattca agagcaactt ttaaatccga  600
atttgggcta agaatacaag cttgttcttt tttatctgtt tttcactcgg tgtacgagga  660
ctcaattaaa tccgaatttg agctaagaat acagacatta gaggtaatat gctttctaac  720
aaatgtgact caatgttcag actcagaact cgatatctct ggtaaggatg acatagtact  780
tacaataact ccatcataat ctttataggt atgtatttct ttataaaata tgtaaatagt  840
gttatgattt tttgtatcaa aaatgatgaa gtataatact cttaaaaatc atactccatc  900
cgtttcaatt tatgtgaacg tattttcttt ttagtctgtg ccaaaaagaa tgacctattt  960
ccttatttgg aaataattta cctttatgca atgatttata gtcacacaaa atatatgtgt  1020
ctcattttta accacaagtt caaaagtctt ctatcttttt ttaaactctg tgcccagtca  1080
aatgagttca cataaattaa aacggaggga ataataaaaa tgtattaaag actacttagg  1140
agagttctta aaaaaccatt ttggaacctt gtctacgtac ttttatgcaa taactgctta  1200
agtttgtctc tgctaaaacc tatgctcccc aaccgtgcac caatcagctt agaaatttga  1260
actcaggaat aaatgtaact acactccaca gaaacttaaa aagttttact gttaccattc  1320
actcaaggat cagaactgaa aaacaaaaga atcagtgctt cactaaaaga aatactgttt  1380
acattatttt caaaagagtt taatcattaa aatagatgta ccatcagatt agctaaaaga  1440
taaataatcg ttaaaaaaag gagattatca acttgaaaat gaaacaaatt atatgttata  1500
atatgtcaaa atatactgac agtataaaaa ctcgttaaat gtgttaaatc ctatgaaaaa  1560
actgcccaaa taaatatttg agcttaggtg tcaaatgttg tactcaacaa caataacaac  1620
aacgcattag gatcctacta gtggggtgtc caatgttgta ctattgaaca ttattcaact  1680
aacttttgtt aggtgttcct gtagtttagt gaaattaaag tccactgttc ccctatatat  1740
taatcccaaa ttaattaatc aagtgcagat aaaaatttct cattttctat taatttatta  1800
agtgtaacaa actaaagaaa ttcaagaatc ttgaatgatg agaaagagtc atgcatgtag  1860
aaaaatagat aataatacat ggaaatatat atgtatttgg ggatttgcat ggtagctcaa  1920
agattattgg aaagtgacag gaagataaat caaaatctca gtgttatttc aaaaataaaa  1980
ggcacagatt atttaaataa ttgacagcca gttttataat actatgtggg aggggacaga  2040
gatcaatcca tgtacgtgca tggctaatat taaagtaagg gagaaaaaaa tattaagtta  2100
attgatgatt aaaaatagta aaatttcaga cgtatatcac ggcaatgaag agtttgatct  2160
ttaatatctg tataatggtc cataatatga tggataggcg ttgtttatga tatgattgat  2220
tgatcattga tcattgacta ttgtttcttg aataattaat cagtatggga aagggtccca  2280
ttaaagttga ccatttgctt agcaatatta tcttaggtaa gctccatatt agtttaatcc  2340
acttgcgaat atattccgtc ctcgcaaatc aatatttaca attctttttt ttcagttttc  2400
tatccggtat ctgatacttg cattggtgtt cgacaaaatc tgtattcgcg tcaaaaaatt  2460
tcatattatg gggcaaaatg ctccataata aaagcgactc aatattaggg ctcgaaccaa  2520
tggcggaaac aagattttta ctaagggaat tcaaaaaata aaaacgaaaa cacatgaaga  2580
acctcaggga attcaacatc taatataaat atatgaaata aaaatttgat tctattgtaa  2640
tttgatatac agtgtaattt acaccgtagg ggatttggct aaacctcctt ccgcgtacct  2700
agctccgtcc ctgactcgaa tccgaggtat ttggttaaaa atgaaagagt acttctcata  2760
acctcgtcgg tttttgtttc taatcaatct ttatattgtt aaaacataaa acgtttactt  2820
cctttcttct tcttttaagt tttgaaaatg ataactactt ttgtttgact aatattttgt  2880
agtttttgat gctaatcaat tttgtaaaaa ttactgtact tcaactagcg tttactaccc  2940
cacctcactt taaaaaattc cctaaagaga taacttttttg attaattcat aaactaaatt  3000
gaagaacttt tcaaatgaga gtaagttgaa aatgcatatt atattgtagt atataattgc  3060
aattttgcat aacttaccgt aaaatgttct tccttttaat gatttgttaa tatgggaaat  3120
ttgaactttt ctttctttga aattgtattc ttgtcccatg gtttctatgc aatctcaatc  3180
atcaaattgc aattattttt ttttgttttt tgttggcaaa ttcaggagag cttaggtcag  3240
tgatatatga aaaactattt tttactctta tttattttac cctttactta ttaaagaata  3300
aagtccaaga cgaatagacg atgtacaacg caaatgtaaa aatacaaaaa aatgtttacg  3360
acttcttctc tatttatttt ctacttaatt tacttattaa acaagtactt acttgttaaa  3420
ctagctaatc tgaccaacaa tgtgaaaatg tttgacatta tacatcttga ctttttattt  3480
ctctattatt ttctcgatgg ttacttcaaa tcatagattt gctaatctga ccaatatcgt  3540
ttaacttcaa gtagaacgaa atgaacattt caaggtttta gaaaacagtt gaaattggac  3600
cctaaaataa ataaaatgaa gttattaata ggtttacacc ccaatcttat ctaatgctta  3660
aaacacatag tgtggagcgg aattcattgt cttcacatta ttgtacatta atcatatttt  3720
cttaactaat tctgacgatt atttgtgttc atctaataga aaatgcaaaa gtcattttcc  3780
ttaatacttg gcatctttat agtcaaaata taactcatat ccaatgcaaa agtacagtca  3840
tgcacaacaa tttaaagtat taggagcatt tattagtttc acttgtttat taatgtaaaa  3900
gtacgtagta aaatgaaagg taaactcaaa aatatcacat acatatttta atttgatcga  3960
tcaagtcagc ttgagttctt gaactttgtg aaagcaatat atataatatg aatgaaacac  4020
ttatgcattg cgacattgag agttaattta agaaaatttt accccacaag ttctagcttt  4080
gattgacagg cctagccaca aagtaagata tgcacaattt atcttagtgc ttctatgttg  4140
tgtatcaaaa ctcaacaagt tatgtttagt actcctatga tgtttatcct aatttaaaag  4200
tcaatattaa gtaaataaaa ataaaaataa attaaagtct atgtatgtat tctcttacca  4260
atgcctatag tttaggccca gaacctacca tctccctgcc aacccactac tcttactggt  4320
tttgcagaaa tagttgctga tcaaatcatt tatccaaaga tctagtttca accttaaaga  4380
tggaaggttc gagtcacttg attttgaagt attgacttaa tgatgtactt tctttaacat  4440
aaggtgaaat tagttgtgga cttcatcgat aatctgtcgt taaatcgttt gtagctaact  4500
aaaaatctat cgcgaaatag gattaacgac gaatttttct gtttaactag agaatttttt  4560
cgtcgctaat taattttttt tttttgtagt gagtacatat tagaaagaaa aaaaaaaaaa  4620
aaaaggaaag tgttgaagtc gtaatgtgta caacatatga agtccataac ctgccaggta  4680
caattcttta aagaattaaa atggaagaag aaaggtaaaa gcaaagattg acaacaattt  4740
ttttgtggct cgatgaaaat tattagtgtc aaagaaagaa ataaaggtaa aaaatggcag  4800
aggaaagaat cacctttggg aaatagcccc ttcacaaaga ctagagtcca aaattacaaa  4860
catcaaaaga tctttggtcg gttctactgt ttgcatctct tgttgttgct ttcgtcttgt  4920
```

```
gaaaaatcat tgaggtacta tgtaaattta taatcagttt tttaatctta ttgaaagttt  4980
catagtgaga aggaatttat                                              5000

SEQ ID NO: 157          moltype = DNA  length = 5000
FEATURE                 Location/Qualifiers
misc_feature            1..5000
                        note = Description of Artificial Sequence: Synthetic
                         polynucleotide
source                  1..5000
                        mol_type = other DNA
                        organism = synthetic construct
SEQUENCE: 157
gtactatcag aaaagattta aatctaacct tcgttataat ttgagtccaa atatacccct  60
gatgctatac tattggttca aatatattct tttccattaa gtttgtccaa agtggacatc  120
caatcctacg ttgcactgac atttgatgat gtgggtgtca catggcttgc cacctcagcg  180
ccccaaatcc atatattaga gactaaaatt tgaaatacaa taatttttcg taatggtggc  240
aatagtgatg gaagggaaga aaattttagt ggtggaaaaa aaaaatagaa ggaaggggta  300
aaataggtta tgagcgctga ggtggcatgt cacctcatca aacgtcagtt tttcgtagga  360
ttggatgtcc accttggaca aacttaacag aagatgggta tatttaaacc aatagtatta  420
cggcaatgat atattttgac ccaaagtata acgaaagata tttactcata gtacaacgat  480
acatttcgtc atttaccgaa tttcgaattt acattctcaa agaactcata actttgatgt  540
taactaatta agtttaaact ttagatcacc ctacaattgt tgggagacat atcaaaccca  600
taccattgat atatataaga actttgtaaa actcttttta atatgttagg gtatgtacta  660
gctagcacca tggatagtgc gtgtcaccat tttacagcaa ataatatgcc tcatgaattg  720
gtagggaaag ggtctttaaa gttgaagtgt ttttttcttt ttcttggtag gtagtggggg  780
aggggaaaat aaggggacaa aacacaaaat caatttgagt acaatttaca caagtctcca  840
tatattgata tagtgctgaa aagaaaatata atgttctaag gcaaagggga taacacttag  900
aaattagcca acctcatgtt tcttacaagt ggatgagggt tcgactttgc atttagcatc  960
accttattct ctctaatttt caacaggaca tgttaataaa aggatgacaa tccagattga  1020
caaagttatg aaagtgaaag cactgtaaca tttcattcaa tcatgcaagc atctcccgtt  1080
aatttttcta tcttttggaa tattacgaaa atcaaaccaa ccttttttacg tataagtttc  1140
taatgacatc agggggactc ctgagaaata ttctcactca aggtcgaaaa ggacccttta  1200
ataatgatca atataaattt tttttataat ggtcctttaa tattcgaatc agctcgtaca  1260
catctcaatt tttgtaatga gtacatgtta tccccgacaa tatatatata agataacttt  1320
gccctcaaga atttatatcg acagataaga gatcacataa tatttttgtc tttgttggaa  1380
tgtaaactct acttttatga aattttatta actggtaggt cacatcctac agagctttta  1440
gtcaatgtta ctattattaa gaaggaaaaa aagaagaagc aaaaggaaga tattaacaat  1500
agtataacaa cattcataaa cgtgatttag gaaataaagt atggaaaaat gaatagtgaa  1560
aaaaagtcaa gtacttagga gttaaggttc gtaagttgat gggacagatc gcggtggaaa  1620
aggaagataa gcttcaaaga tacaaaagca aagggggggt gggttgagat tctgagttgt  1680
gattaatacc actcatgaac aaaaagttat gtcatggcac cattcatgag attaagacaa  1740
cggtggaatt aagaatttta ttaaagggag tcaaatttta aaaaaataaa ttcatcaaaa  1800
agttaaagag tatcaatata tatcaatata tatatatata tatatatata tatatatata  1860
tatatattta tattaaatta tctaattaca cagtataatt tttaacgaaa gggtgtcgat  1920
cgacacccctt gaatgcatgt ggccccgcca ctgcattcag agccaactct cccccaaaag  1980
aaaaggcgca aaacaaaagg atttgaaaca gtagttgtgg aggtgattca gccatgcttt  2040
catgactcat caatacctac tttttatgtt tttctttttc ctttttattt tcaggatata  2100
aattttgttg taaactgata taaagaaata aatttactct cttcaaccta ttaagctttt  2160
aggtgaaatt agtaagtcgt acaatttaac atggtgtaga attgatagaa gtcgtagaca  2220
ctcataggtg cactttgtag tgaaaattag gagaaattag ggttcaaaat ccaactaaga  2280
taaaagatgc ttggtaattt cttcacatct gcttagaaat aatctgctta aatttggatg  2340
agcaaagtta tccaatacaa gtgttgctga gaaataatcg gtatctaata gaatagtcga  2400
gatgcacgca aataagtttt gactctactt taacaaaaaa aacaataggc agatgtatcc  2460
aaaattcata tcttatggtc actcgtcaac aaaaatattc cttatgttta gtccaagaaa  2520
aataaccata cccaaatata agggtttgtt gaagacggaa atatataaac aaataaacaa  2580
atatcatcat atctccgata gtttaaaatt ttagattgga tatttcacac aatttatcaa  2640
aattttcaaa aaaaaattct actttttctt gcttggaact tggaagggga aggggtggtg  2700
gtggagatag ggcggggcat cttctatcta gtctatgtga ttaatataac aaaacaaaaa  2760
gggcgaggca aaaacatgga tgaatggtgg tccttttcta tatttatatg gattgttacg  2820
atacgtcgat ttcactttgc aaaataccaa ttagattcat ttagttatct ttttgatcac  2880
tctgctttta ctatcatata tatataggag tccttccacg tttcgcatgt gtcattgttt  2940
atattttcca tggtcttcct tccaaatggc taaaaaaatt tgacacagtg gtcccaaaag  3000
tttatagaaa tagaattcaa cagtgaggca tatacctatg aattctattt tacatcttca  3060
tcgtataaaa tagaatgtgt tataaacttt acctcgtgat gcttacaagg ggtgaaaata  3120
taaaagcact ttatagattt acaagagtca caccttgatt tatcctaaga ttttattttt  3180
ttacatgcca aacaatgaag tatgggagat ccaattggaa taacatcaaa tttaataaaa  3240
ttcgaaatag tcagagagct gtctactgag gtatattgaa acttattttt ttttaataga  3300
aaatatcaaa tacttagcaa tatattaaaa tgtttcataa attacattgt ttaaaccaag  3360
cgttgaaaca tatgctgata cgaggtaggc ttattgatga atttataagg gcctcattgg  3420
aaaagacgat ccaaagcaat gggctaaaaa ttggcccatt ttctgccacc cagtgtatgg  3480
ttattactag tttcacccac acagatttgc acttcattag aggacaatgt tgctgaattt  3540
gaaacataag tccatttatc tccactgtac agtccttcct ggagtccaat cctgaccata  3600
tcttcatgat tttatgtaat gtggtgaata agcaaagttt catgttatgc tttgtctcat  3660
tttatagcaa attcatttcc tcataaaatt tacttcaaaa aagtttcgtt tgattttcag  3720
aaatcaaaat atgcttttcg gtaaccaaat ggttttcaat tttgtttacg aagaacttaa  3780
aactttccaa caccctacat ctatgattgc aagttaaaat tgcagaaata tgacactttt  3840
tggagtggtc tttatcgttt aacttcactt gcactttaag ggcaaaagtt aaaagtgttt  3900
ccatgaagca agcgagggat aacacttatt aaacttgaaa ttctactcat agaccaaaac  3960
aaggacaaaa attcaagact atctatgtgg gtaaacgtac gaaaattggg cttctccaga  4020
```

```
ttagagccgg accttgtgga aagacagaga aattcgaggc ccacttccag tttctaagga  4080
gattaagcct atcaaacgat ggtccagaac gaaatatgtc tttctttatt ctctactata  4140
tagctgactc agaatcgtta gaatttgcaa tttcctcata ataaaatgtg aggcagtata  4200
gattcgaaaa cctttgttga agattattga ctcagctacg cgaaacaaac tgtagtatcc  4260
aatgtaccga ttaacaagcg actggttaac tatgaatttg ttagctcgac aaaatcaccg  4320
gttaataatg agtttgtgag ttcgataaaa tctaattttc tgatagaaat tttatatatt  4380
atgcagaaat ttaataaaag tagacttaac ttatatattt tagcattgac tcttttgaag  4440
taaaatccat tccatctaaa ttatgacttc cctacatcga gtaagtaagt tgcgtctgta  4500
tcctcatttt acccactttt cgctatgcaa ttattcaagg atctttacac aaatagcaag  4560
ccaatattaa ttatttattt tttttagtca tatatataaa ttatacatat attatatacc  4620
cattaattat ttttaattta agtgatagat tggacgacta tttggattaa ttcttcgtta  4680
ttcaagataa tagatgtcgt ctctaataca tgagctagaa gataataagg attactaggc  4740
cgaaaggctg atggaaatga acaagaagat aagctcctaa atggaaacag tacggaaaaa  4800
gtcaaagagc agtgcatggg aggaatcatc agtcagaaaa ggaagccacg tgtcaagtag  4860
aaacaagcac gtgtccatgc aaaagccacg taactccctt ccatcacatc ttccttcttc  4920
aaaacctcgt gttttactct ctcttttctc actgccagtg atcgtcagga ctgtgcatgt  4980
ttgtttaaaa actaaaggca                                              5000

SEQ ID NO: 158         moltype = DNA  length = 5000
FEATURE                Location/Qualifiers
misc_feature           1..5000
                       note = Description of Artificial Sequence: Synthetic
                        polynucleotide
source                 1..5000
                       mol_type = other DNA
                       organism = synthetic construct
SEQUENCE: 158
acatgacccg gttgtctcct ttgtggtgtc tttcagaaca tcgccagtag ttcgttgatg  60
tggtgttgag tgaatacttt ttcaatatat aagcaatttc gtgccttttt tggttcattt  120
tgaggcttat gtaatatatt tgatcatgta atcgtgaata cttcaataaa aggtaactct  180
tcctcagata atgtaaccaa gaataatttc attgaaggga agcggtataa gcataaaggt  240
aactttccct gtgatgaaga atgatgatat caagtaggcg ttgttgatca actttccaaa  300
tgggtggagg gtaagctact tcactgcctt acttcctcta agttcaagtt gggggaggta  360
tgatcgggga ttctctatct tcttgttgaa caagaaaaca gtactactac ttagcatata  420
tagtttcaat caataaatag gaactgtact aacaatcaga gcccttattt tcacttagca  480
tagttgtata ccagttagaa ctcatactgt ggaaacagag actcgtggac tagcaatgcc  540
cttattaaaa actatcatgg atgctctact cattgtctct ccaaacaaca gcactctttc  600
ataaaaaggt acttcatgcg acatccatta atacaagaag ttcaagatac ataacatgca  660
gtaacagaac tcgactcaac ttagacttat cccacatcta gcttgatttt ccatcaaacc  720
agtgtgcgta aaagtaaaac ataactatag aattgatccc atggttaatc acattcacat  780
aacaagcggt tgggataaaa agatggtcag ttctaaggct tcaaaattaa tatagccaat  840
tagtcgaacg gacggtgtgc aatcctagat gacttctatg aaagtgagac gaatcaatct  900
cccaaaagtt tagtacaaag aaataacagc aaccgttcaa acaatctaat acggctacac  960
atattaatct tcacaaatta aacattacaa caaaagcata ctaaattctg aactcagtaa  1020
agattcaaat caacagcacc atattataga cataacaaca ctagtgaatt ggtcatcaaa  1080
gcaacgaaga gcacagaaaa gttcgaaatt taaccaatca cgaacctgat cgaagctctt  1140
gtggaacatc tacacgcttc ctgacttgtg gagacaagag tctcgagtag attcggaaac  1200
tgcccagtct aattttgata cgtattctac aatttcctta ctaaagagaa aaagagaaag  1260
tgtgtgagaa tataaaattg gcgccttctt tcttttggcg ctatttatct agttttagcg  1320
accagttatc atgattttta aagatatttt tagattgcca attttcgctg agaaaaaaag  1380
gaggtaaaag gggtggtagt taaaagtgat aatcaacttt atataagact agtcttaata  1440
tacgtgcgtt gcgcgtgtca taaaaaatat tttaaaaaat atatttgtgt tataatataa  1500
aaattaatac aaatttgcaa gcttcaaaat aatgaattaa tcatatttag gagtttgatc  1560
cactctagtg gtttttggtt catcttgctt cattgtacaa aaaatttgag tatacttcca  1620
attctaagtc gttctattgt tcaaaggaaa aaaagtgtcc taattgctct tcaacttcta  1680
aaatattgcc tatctcttac cttaaatatg aattatcatt tctgcgtcca tatttttttt  1740
ttaaatcaaa attgtctttt tcgttttttt tttttttagaa aactatactc tatagcccac  1800
aaaattttaa tagctcatgt cttttctcac ttacacgaaa tggccctttg gcccaaacat  1860
aatagaccga aatgtctatt ttgtatattt tttgtatagt gacagtctat tttgaatatt  1920
tttttatata atgacagtct attttgtata tatattgtat agtgacggtg gggagtgggt  1980
tgctctagtg gtaagcaccc tccacttcca accaagaggt tgtgagttcg agtcacccca  2040
agagcaaggt ggggagttct tggagggagg gagccgaggg tctatcagaa aagcctctct  2100
accccagggt agaggtaagg tctgcgtaca cactaccctc cacataccct actagtggga  2160
ttatactgga tcgttgttgt tgttgttgtt gtattgtata gtgacggtct atttagtata  2220
taattgtata gtgtttgtat attttttgta tagtgacagt ctattgtata taaattgtac  2280
agtgacagac tattttatat atttttgta tactgacagt ctattttgta tatatgttgt  2340
atagtgacaa tctatttatt actccctccg ttccaattta tgtgaacatg tttgactggg  2400
catgaaattt aagaaaaaat aaagactttt ggaatttgtg gtcctaaaca agtcaaaagg  2460
aggtccagag tatttgtggg gttataaaag cttctcatta agggtacaat tgtaagttta  2520
agctaaatta ttatcaaatt tagaaaaggg tcattctttt tggaacagac caaaaaggaa  2580
ataggttcac ataaactgga acaaatggag tatatttttt gtatagtgag agtctatttt  2640
tcatacttct atgctaagta ttgactttaa acactgttca aacttaaacg tgtctctttc  2700
gcgtgaaatt actctatatt gaactactac aactatttgt gccggatttt gtcaaaaaat  2760
tcaattttcc ggccaagttc gttctgcttc ctcctcccat ccttccaatc ttattctttc  2820
tgccactttt cagcaatagt gatacaacta agatatgttt taaggttttg aactatttgt  2880
gtggaagagt tttatggcat atactttttc tttggtcgtt gagaagagag gtcgacgtcg  2940
ctcatgaaga cattctgccg ccgacgaaac agatcttata gctagccgct agaattattt  3000
taggctataa aatgtatatt ataattttgg actactggat gatatatgtt ttgggccgat  3060
gggctataaa tgaattttgc tcattttttt aacgtgttct ttattagcat aaaaattgca  3120
```

```
ggatgagttt gttactttaa tttcattaat ttactctttt tttgcagaat atacatacat  3180
gaaaagtaac atgtagtaaa tattattatg ttacatatat agtttaaata aaggaaaaag  3240
ttaatgtaag gtagaatttt aattgacttt aaattcctaa attttaggac ttctcaccta  3300
gttcaaataa gtaaatattt aataatcagc atcttagtta atttcaaagt actaaatatt  3360
atgataataa ttaaatgact attttgtcta gtcgaaatct attttttaag ggtaaaaaaa  3420
gcgaacgata tttcgctaag aaccttcgtg cttttaatat aatactagtt tctatgtacg  3480
tgcgttgcac gtaaatcttt agtttatcat ttatatgaaa aaacaataca ttaaatttac  3540
tggaaaatca tatacaaaaa gaccgaataa agccattaat gtgggaacaa tgcaatagta  3600
tcgtcaatgg gaacatgcat tgcacatata ttccgtgtca atagttatct ttgtgaaata  3660
aaaaatgata catgtaattt tatactatca ttcatattat gaataaactt gtttgatttt  3720
taaaatagaa aataataaag agcacgaaaa gttactgcta gtcattaaaa tttgttatga  3780
acattgactc tattatagaa taactcatca agaagaattt taagtgcaat attgaaggat  3840
ttgctttagt ttctaatagt ataaatcgat gtctcttatc ggatcataaa accaaaagaa  3900
ctataatgtc catacaactc cctatgtatg tttacaattt gctttgtgtg tgtaaacatt  3960
agaactttc acctaaatat ctcatacctc ttaagaaaga atccttgctg gatacttttc  4020
ttttggagct tcacaattat aagttaccaa ttaactaatc tctccaagcc tctatttaac  4080
atatacacgt ttatctctgg acgaacaaac aatagatggc gtcgaagatc cactcttcat  4140
cttcctgatt ttcatcaact tccttatgcc tatttatttc ttgttttcag ttaattcgac  4200
aaattaaatt agaacaaaat ccattactgc tggttatcag acaaagaaaa actaaagtaa  4260
ctccttttgc caacaccaat gtagaacata aataagctta aaggtaattt cttttaaatt  4320
ttaggcaaaa cctttatgta aacgaacatt taagccgtgg ctttgccatt ggagttctaa  4380
tacaaatagg acctttagtt ttcaatgact tgaattctac aactaatgaa ctgtttttac  4440
gtttttggat attaatgttg aagacatgat ttaaatatga agggtaaaaa agtcggtcaa  4500
tatttcaggg acatttttgt cgttcaatat ttagcgtgta acattcgtgt ttttataata  4560
atatagatat agatatagat ttctctcccc aaccccgaga ttttttaaaa gtattttaaa  4620
atagggttac tgtgcacata taagaatcag aaatttccag gaccatagca atgagcatta  4680
ttgaacagta gtagtacgta tgtcctttct ggtataggat atgtagcttc attaaaagat  4740
agaaaatgaa aagcgtataa agtttgtgat acatttacta ataaatccaa cgaataaaag  4800
aaatactcgt atataaaagt agaaaagtaa gtgtttgtac tttttataaa aacacaatag  4860
gtggagttga gagggatatg gaaattgcct tggatattat gtaggcatca tgaaccaatt  4920
aatgggacct acaagattaa tgttttggct atccttatct tttattgaca ggcccttcaa  4980
tttaaatcgt tgctgcccaa                                              5000

SEQ ID NO: 159          moltype = DNA  length = 5000
FEATURE                 Location/Qualifiers
misc_feature            1..5000
                        note = Description of Artificial Sequence: Synthetic
                         polynucleotide
source                  1..5000
                        mol_type = other DNA
                        organism = synthetic construct
SEQUENCE: 159
ccgactaaca aaggagtcaa acaatggcga aactagaaat ttacccaagg gtattcaaat  60
ttaaaaaaag tgaaaacaaa ttcctacaaa gggtgtttaa tatgtgttat atacttctaa  120
aacgtaatat ttatctataa acacaatgca atttttcaac gaagagtgat caactgacca  180
ccttataacc gccactggag tcaaacccta gttttctttt ttagcttctt tgtattattg  240
gtagaggtga accattttat acaaacatac atacatatat gtgtgtgtga gagagaaact  300
ttataaaaat agtactatga atattgaata tcgaatttcc attctcaaat aactcataac  360
tttaatgtta actcattgta aaaccttttt tttacatgtt agggtctgta ctagctagca  420
ccatggatag tgcgtgtcac cattttacag caaataatat gcctcatgaa ttggtagggg  480
aagggtcttt aaagttagtg tgtttttttt tctttttctt ggtaggtggt gggggagggg  540
aaaatgaggg gacaaaaaaa atcaattgga gtacaattta cacaagactc cattgtatag  600
tgctgaaaag aaatataatg ttgtaaggca aagaggataa cactttagaa attatagcca  660
acctcatgtt tcttacaagt ggatgagggt tcgactttgc atttagcatc accttattcc  720
ctctaatttt caacaggaca tgttaataaa aggatgacaa tccagattga caaagttatg  780
aaagtgaaag cactgtaaca tttcattcaa tcatgaaaag catctcccat taatttttct  840
atcttttgga atattacgaa aatcaaacca actttttttac gtataaattt ctaatgatgt  900
caggggaact cctgagaaat attctcactc aagttcgaaa aggacccttt aataatgatc  960
aataattttt tttaatggtc gtgtaatatt cgaatcagct cgtacacatt tcaattattg  1020
taacaagtac cttttatccc ccaacaatac atatataagg taacttatca cgtaatattt  1080
ttgtctttgt tggaatgtaa atcctgtttt tataattttt atccacttta ttgaccgcta  1140
ggtcacatct tatggagctt ttttagtcat gataaatatt actattatta agaagggaga  1200
aaaaagcaaa aggaagatat taacattagt ataacaccat tcataaacgt gatttaggaa  1260
ataaagtatg aagaaatgaa tagtgaaaaa agtcaagtac ttaggagtta aggttcgtaa  1320
gtagatggga cagatcgcgg tggaaaagga agagaagctt gaaagataca aaagcaaagg  1380
ggggttgggt tgagattctg agttgtgatt aataccactc atgaagaaaa agatatgtca  1440
tggcaccatt caggacatac agagccaact ctccccccaa aagaaaaggc gcaaaacaaa  1500
aggtttgaaa cagtacttgt ggaggtgatt cagccatgct ttcatgactc atcaatgcct  1560
acttttttttt ctgtttttgt ttttcctttt tattttcagg atataaagtt tgttgttaac  1620
ttaaataaag aaataaaatt actctcttca acctattaag ctttaggtga aattagtaac  1680
tcataaaatt taacatggta tgaattgata gaagtcgtag acacccatag gtgcgctttg  1740
tagtgaaaat tagggttcaa ataagataaa acatgcttga tgatttcttc tcatcggttt  1800
aagtttggat gagcaaagtt atccaataca agtattgccg gtacctaata aaatactcga  1860
gatgcacgca aacaaatttt gacactactg ttaacaataa acaatatgca gctgtccaaa  1920
attaatacta tatcttattg tcactcagtc aacaaaaata ttccttatgt ttagtccaag  1980
aaaaataacc atacccaatt ataagggttt gttgaagaca gaaatatata aataaatgaa  2040
tcatcatatc tccaatagtt taaaatttca aatgggggta tttcacacaa tttatcaaaa  2100
ttttaaataa tttttatact ttttcttgct tggaagggga aggggtggtg gtggagatag  2160
ggcggggcat cttctatcta gtctatgtga ttaatataac taaacaaaaa gggcaaggca  2220
```

```
aaaacatgga tgaatggtgg tccttttcta tatttatatg gattgttacg atacgtcgat  2280
ttcactttgc aaaataccca ctagattcat ttagttttct ttttgatcac tctgcttttt  2340
ctatcatata tataggaagt ccttccacgt ttcgcatgtg tcattgttta tattttccat  2400
ggtcttcctt ccaaatggct aaataatttt gacacagtgg tcccgaaagt ttatagaaat  2460
agaattcaac agtgaggcat atacgtatga attatatttt acatcttcat cgtataaaat  2520
agaatgtgct ataaacttta cctcgtgatg cttacaaggg gtgaaaatat aaaagcactt  2580
tatagattta caagagtcac accttcttga tttatcctaa gattgtattt ttttacatgc  2640
caagcaatga agtatgggag atccaattgg aataacatca aaattaataa gattcgaaat  2700
tgtcagagag ctgtctactg agatacattg aaacttattt cttttgtaca acagaaaata  2760
tcaaatattt agcaacatat taaaatcttc ataaattaca ttgtttaaat cttacgctgt  2820
aacatatgtt gataggaggt aggcctattg atgaatttat aaggtgaaaa tacatggact  2880
agccagtttt cgaactagta attgaaaaaa ggtatattat cacttttagc ccgcgccaga  2940
aattatttat atttggtagt tgaaaaagtg tataaatttg taattttttg tatataacac  3000
acataatgtg tgtgtgagtg tatatatata cacacacaaa aactatatat atttttteta  3060
ttattttgag agtggttata cagtgtcatc tttctaatcg aaaatagcca gcgtttgcaa  3120
tgttattaaa aaaaaatagc cactatttta gctgaaacac ggaaagttcc agcataaatat  3180
atcggatttc agagctcctg catataaact tccagcacat tatgaaattc catcacatta  3240
tgctgaaatt tttccggatt cttaaggtgt tttcattcag attttatctt tacataaaaa  3300
aatggctaaa tttcgattac ttttgaaatt atagctcttt ttcaattact aattataaat  3360
ctgactattt ctgatttttt gcctctggtc aaaatggcat ggcatagtca tttttagggg  3420
tggttattga aaaatagcta gtattcacaa agttattgaa aatagtcatt atttacggcg  3480
aagattaaat cttaacaaat gtacctgagt taaaacacaa aaagttacaa cataatatgt  3540
tggatcatgg aactccttca tgtatgcttc tagcatatta tgttgaaact ccagcacatt  3600
atgaattcca acacattatg tcgaaatctc atatgtaaaa aattcgaact ctggcatatt  3660
atgctggaat tttttcgtat tttttatcag attttatttt cacataacaa agtgactaga  3720
tttcaataac ttttgaaact atgaccaatt ttcaattaat tgtaaatcaa attatttctg  3780
attttttttcc tccagggcaa taatgggact caactttagg caacaaaaaa ctgtttatgt  3840
aggtaaacgc acgaaaattg ggcttctcca gattagagcc gggccttgtg gaaagacaag  3900
aaattcgagg cccacttcta gtttctaagg agattaagcg taaaaatagc actggctagc  3960
cagttttcgg actgatcatt caaaaatagc cagtatttgc aaagtcattg aaaaatagcc  4020
attagtattt tgctgcaaca cgaaaagttc caacataata tattggagat cagtgcacct  4080
atgtatgaac ttccagcata ttatgctgga actccaacac gcggaaagtt ccactataat  4140
atactggaga ttggagcacc ggtgtcaaca aatctatcat ttaataggat ttatggctat  4200
ttttaaatga ccacttgtaa atctgattat tttttaattt ctcccgctta agcctaacca  4260
acgatggtca tgaacgaaat gtctgttttt actctctact atatagctga cccagaatca  4320
ttacaatttg caatttcctc ataataaaat gtgatgtagt atagatttga aaacccttga  4380
agattattaa tttatctttc gcgaaacaaa ctgtagtatc caaggtaccg aatagtaagc  4440
gattggctca caatgagtct gtttgttcga taaaatcatt ggttaataat gagtctctga  4500
gttccataca atctaatgct ctgatagaaa ttttatatat atgcagaaag taataaaaat  4560
agactatgac ttactatatt ttaacattca ctcttttgaa gtaaaatccc ttccgtcaaa  4620
attatgactt cattacacca aattgcgcct gtatactcat tttaccttct cttcactatg  4680
caattattga gataaaaaat ttcgtctcta agacatagct agaggataag gatcttaggc  4740
cgaaacactg atggaactga acaagaagat aatcacctaa atgggaacag tacggaaaaa  4800
gtcaaagagc agtgcatggg aggaatcatc agtcagagaa ggtagccacg tgtcaagtag  4860
aaacaagcac gtgtccatgc aaaagccacg taactccact ccctcatatc ttccttcttc  4920
aaaacctcgt gttttactcc ccctttcctc actgccggtg atcgtcagga ctgtgcatgt  4980
ttgtttaaaa attaaaggcg                                              5000
```

```
SEQ ID NO: 160          moltype = DNA  length = 5000
FEATURE                 Location/Qualifiers
misc_feature            1..5000
                        note = Description of Artificial Sequence: Synthetic
                         polynucleotide
source                  1..5000
                        mol_type = other DNA
                        organism = synthetic construct
SEQUENCE: 160
acatgacccg gttgtctcct tggtggtgtc attcaaaaaa tcgccagtag ttcgttgatg  60
tggtgttgag tgcatacttt ttcaatataa gcaatttcgt gccttttgtt tttccatttt  120
gaggcttatg tagtatattt gatcatgtaa tcgtgaatat ttcaataaaa ggtaactttt  180
ccttagataa tgtgaccaat gatgatctca ttgaagggta tacttttcct gtgaagaaga  240
atgatgatac tcctatcatg taggcgttgt tgatcaactt tcccaatggg tgaagggtaa  300
gctacttcac tgccttactt tttctaagtt caagttggtg gaggtgtgat tggggatcct  360
ttatcttctt gttgaacaag aaaacgctac taattagcaa tgaataggaa ctgtactaac  420
aatcagagcc cttattttca cttagtatag ttgtatgtat accagttaga acctatactc  480
tggaaacagg gactcgtcaa caataaccag aagggtggat tagaaactat catgaattcc  540
ctactcattg tctctccaaa caacaacact cttttataaa aagtgtactg caagaatcat  600
gttatgcttt taaggaatgt gcatcaagat tgaagtatca tgcgacatcc attaacacga  660
gaagttcaag atgcacaacg tgcactaact gaagtcgact caacgtagac ttattccaca  720
tctaacttga tctttcataa aaccggtgtg cgtaaaacat tactatagaa ttgatcccac  780
ggttactcat attcacacaa caagcaattg ggacaaaaag atggtcagtt ctaaggcttc  840
aaaattcata cagccaatta gtcgaacatg cggtgtgcaa tcctagatga cttctatgaa  900
aatgagacca atcaatcttc caaaagttca gtacaaagaa ataacagcaa cccttcaaac  960
aatctaatac aacgacacat attaatcttc acaaattaaa cacaacatca aaagcgtact  1020
agattttgaa ctcggtaaag aatccaaatc aacagcaccg aattatcgac ataataccac  1080
tagtgaatta gtcatcaaag caacgaagag cacagaaaaa gttaagaaat ttaaccaata  1140
acaaacctga tcgaagatct cttagaacat ctacacgctt cccgacttgt ggcgacaaga  1200
gtctcaagta gactcggaag ctgctcagtc taattttaaa tatatattct acactttcct  1260
cgcaaaagag aaaaagagag tgtatgagaa tattaaattg gcgccttttt cttttggcgg  1320
```

```
aattgttcta gttttagcga ccagttatca tgattttact actatgtaaa tcgcaagcat  1380
taaagttata gcaagaaatg agaccgagtg acctaaaaac aatcacattt gtatgtttcg  1440
gttccacgag cagctctggg cggacctagt aggagctcct ttgcactgtt gcaggagtgc  1500
tcaagtacct ttactctctt ggtgactcag acactactgc catatcaatg agaaaaaagg  1560
aggtaaagtg gtagttaaaa gtgataatcc attttatata aaatccctcc ccccgccccc  1620
atacccccgg aattgtaaaa atatttttaa atagtgttac tatgcgcata tactagtcag  1680
aaatttgtag gattacggga ggtagtacgt gcgggtgtac aaaccaaatc ggaaaatcgc  1740
accaaaccga aaagtcaaat caaaaccgat taaaagattc gactagattt ggtttggtat  1800
tgagtaaaac aacccgaatt aaaccgacat ataaatataa atttttatgt atacttttaa  1860
gatttttata tagaatttc tttaagaaaa tatctaaaaa tatttgggat tctcttacgg  1920
gatataatat ttaataaaat atgaagtgct ccatatttat taaccttaaa caatgggtcg  1980
tatgatcact ttcttatcaa gtgttactga aatgcgtcaa tctctttgtt cttccatagt  2040
caagatctat taaattctta tatctttttc gaatttgaag tggttattat tatttaagta  2100
tcatattgac ttttacgttt aattactaaa ttcggttaac cttgaaagtg tatatcaaca  2160
aaaattattg tcggacgact aaaagactaa ctatcatgtg ttattaagta aattcacgca  2220
taagaatatt taatagataa tatatttttc taatttttaa aatttttact aaatatattt  2280
acttataaaa aatttaacaa agtaagattg aaataatatt taagtaacga aaaaccagcc  2340
aaaaccgata tagtttgtgt agtttgattt aaataaaagt cgaacccaac ccgatccatg  2400
tacaccctta atagtacgta tgtcctttct ggcatactgg taggatttgt agctgcatta  2460
aagatagaaa gcgaaaatcg tacaaagttt gtaatactag tacattacta ataaatccaa  2520
cggataaaag aaatatataa aagtagaaaa gtaattggtc tagattttat gaaacacaat  2580
aggtggagtt gagaggggta tggaaattgg cttggatatt atgtaggcat catgaaccat  2640
taatgggacc tacaagatta atgttttgga tatccatatc ttttgttgac aggcccttca  2700
attgaaatct ttgttgccca aaatgattcc actgtcaacc aattataagt tttttgttaa  2760
aaggtttatt gcaccattgc tccactaact tcatgtgcat ttgcaactta ccacacaaga  2820
gagaagaaaa gtttccagta cacaggatta acatttgcta agttgattcg gagttttagt  2880
tagcaaagtt gaaattatca aagacagatt ttgaaactat aagccagtgg atcgctaagg  2940
ggttcctcgt tgataaatac ttattttcat ctggtgttta tactaatcca ataaatatat  3000
aatatatgtc tttacaaata tggttataat taaatcataa ttaattagta cacattgtta  3060
cctcacgtta tcactttacc atgataagag tttggtataa atactggtgg gactaagttt  3120
tttaccttcc tcgtttagtg tctacaagcc taattaggtg aagatggtgc tggatttttt  3180
tttttttttg ttacaagtgt agactacaga aattaaatta ctggtcctat tgtgcaaaat  3240
ttgaattcaa atcttcgtgc atttcagtat gttatttggt acaaaaaaca tggcatttat  3300
ggcttcgcat tgaggaagaa cttgtatata gcttgaatgc tcttgttaca tccaccctcc  3360
ttaaataccc ctagttgatc aacaggcacc aaaaatgtct agacacaaac atgaaccagt  3420
tttatttcta ttctctttat tgtaggtaat tgtttgctgt catcatataa tataagctag  3480
gaagaaaata agtaaaaatc atcagatgtg ataggtcttg aatagagaag caaacctaat  3540
gtagcataat aagaaaggaa gattaggtgg gagaccatta tttatgacct catcccaatt  3600
ttaatcatat ttcattattc caggttacta ctaccaaaca aaaataaacg acaagaataa  3660
tgcataaact tccacaatag ctcattattt atttatcagc cggagtgtat taaagtaatg  3720
atataattag aagacaattg agttgctact taaactgatg ctaacctgac gcgttttcgt  3780
tttccaggta cagtcttcca acatcagatg tcccaattgg agttccaagt caaagtggaa  3840
ttggaaaatg gtaagaaaac tctcagcctt agctgtgaca tagacatcaa taaagtagaa  3900
aaaaatcata agatttcaat gtttgaatgc taagcgacac aaaaatcact aaataatttt  3960
tttcatttct gactaagtct ttatgagcaa aactatttat tacttacaat tttgtgatga  4020
taggagatat caaatactcg tggaatactt gaggtaccca caaagtgatt gagaagttgc  4080
tgttaattaa aaaatccttg catcagatcc cttcagtttg aggtcaaaag cacaatcatg  4140
aaaagccctc tcacagcaca ttcacttgat ccattctatt ttacgtcttt tctctaacta  4200
cgacttaagt tcttctaact tttaatcatt accaccctat taaaacttat ctaaagactg  4260
tttttctctg cttttctcca tatttacctc aacgtctcct tccatatcca agctttggta  4320
ctttttcccc ttgtggtatt gattcaggca tggtcccttc tccaatctta tcaatcaaac  4380
atatactaat aaagtataat ataccaccga ctttggtgtc aaccacgagt tcgggagctt  4440
gtgaaatatg gtggtattta gccaattttt ttctttttaa taaaattgac aattaggaac  4500
caacttgccg gcttcataat aaagtatata gttgaaatgg ttcagaaata ttaaattcaa  4560
ttctataaat tacttggatt cggtccatcc taaaggtggt cacttctagg atcaagcccc  4620
attgttggct aaattttggt tttaaataga ttaattagct tggagtcgaa cagcaagcat  4680
taagtttacc aggtctatga tttagttagg catgaattgt aatacaaaga tgatttatgc  4740
agtgattaat gatatcagga tatatatata taagtattgt tatactataa ataacaacaa  4800
caacaacgac ccagtaaagt cccactaagt ggggtttggg gaaggtagtg tgtacgcaga  4860
ccttatcctt accctgatag ggcagagagg ttgtttccga tagatcctca gctcaggaag  4920
atgaaaataa aacaagaaaa caagaaaaga cagtaaccat agaaataatg acagcatcct  4980
aaaaaccata aaatagatga                                              5000
```

```
SEQ ID NO: 161          moltype = AA  length = 524
FEATURE                 Location/Qualifiers
REGION                  1..524
                        note = Description of Artificial Sequence: Synthetic
                         polypeptide
source                  1..524
                        mol_type = protein
                        organism = synthetic construct
SEQUENCE: 161
MIGYPKRFTL HGLWPANSTG YSLKCAPPPE GTSVWTTDGQ LRTALQKCWY SLIRGRPNYI  60
LWKHEWKDYG YCSSHTIKDT DYFWAAVRKH GRNTKIAGDA IVNELSDAEI SPSNDKERRC  120
ETESDSSHHY QHSEHHQRRW LGRRRECDTK RYSQAKYITS PHESVTASRE KRASTSTIEE  180
APPAVKKLLL EWLTSTINNI FDKPAQKENG NTAQADIVTT TGEQPLPRTG NTYPTMDAGA  240
KKAEARVNDI FAVRQSSGEG LRDFLARFNR EEIHNAYCAK ERADDDDLNG PIQRLTSVQE  300
ESRSDHRNDS QRDQSGPRLS RERHQHYVRT TVLPSPRHME GPPRPYIGTQ RNERGMPPLL  360
STHNFCVSPS KIVYALKKLG TMVKCPQKMK SGPNTQKLNA ICEFHQERGH KTEDCIGLRQ  420
```

```
EVVRMLNQGN LKELMSDRGR VNFARGRELP QGPPKPPSPA RTIQMIIGGG DEAMINHMKF  480
TTTHKLKRSM THERYDDFGD SIIFDKSDTD GLTFPYFEAI VITL                   524

SEQ ID NO: 162          moltype = AA  length = 343
FEATURE                 Location/Qualifiers
REGION                  1..343
                        note = Description of Artificial Sequence: Synthetic
                         polypeptide
source                  1..343
                        mol_type = protein
                        organism = synthetic construct
SEQUENCE: 162
MSCQNSKTEE TADEQHNTSK DPKHKPFFDV YGPQGRADIV FNQPESNSTL NLQDVQGLVT  60
WVLADGFMPS WAFIKNKPLI PKVVMLYVPG LDAALYLSQS KVLKGFKECC GIPRPVLALS  120
CVSDGNQTID ALLTYKSKRK RKEAEHISPI NTEPSEQGAE TPTMEPLSFV DLKKDIPFPI  180
SYYTLTDKEL EENGYCYDQP EFLSTLPAPS GTSPHEILAL DCEMVLLDKL VKPSNNIVDY  240
NTRYSGITCQ MLEDVTTTLK DIQEEFLKLV YKETILVGHS LENDLLALKI IHNLVIDTAV  300
LYKHPRGSYK AALRVLSRKF LGREIQDSGN GHDSIEDAKL HWN                    343

SEQ ID NO: 163          moltype = AA  length = 723
FEATURE                 Location/Qualifiers
REGION                  1..723
                        note = Description of Artificial Sequence: Synthetic
                         polypeptide
source                  1..723
                        mol_type = protein
                        organism = synthetic construct
SEQUENCE: 163
MASTSYITFK PLQQTQLKLY YFTHCSKHSS TLFHSSFHTL LSAPTKYTLE PPRILPSIQV  60
KAHVTHLETR LSFEPEQEIS GSRTNNENSS GFSSFSPKDK MVGMKSSREN LDRHCQTLDE  120
LVQLFKSSAE ASNTKSVRGE QEDHGIKVSE EVKHYALKYG FKIYEKMRSE KVQMNEATLT  180
SVARMAMALG NGDMAFDVVR LIKEYGINPR LRSYGPALSV FCNNGDVDKA FMVEEHMLEH  240
GVYPEEPELE ALLKVSVEAG RSEKVYYLLH KLREGVRQVS PSTADLIEKW FNSKIASRVG  300
KRKWDERTIR EAIKNGGGGW HGQGWLGNGK WTVSHAYVDS DGCCKCCGEK LVTIDLDPVE  360
TENFAKSVAS IAAQRERNSS FQKFQRWLDY YGPFEAIVDG ANVGLYSQRK FRPSRVNAIV  420
NGIRQMLPSK KWPLIVLHNR RITGDKMDEP FNRAYWLYAA IKFKCLIVTN DEMRDHLFQL  480
LGNDFFPKWK ERHQVHFSFS ETGPVLHMPP PCSVVIQSSE RFGPDRRIYH GRSSRTLKDK  540
ELSGSRDSGY PRLSDYNFNI NLIELVSVMR NIKEARFPKP IRSYSSQKDH FKIKRVLVDP  600
GSSANIIQLR VLEQAKLIEV PTMKLLAGFN LTSVTTQGEI VLPTYAEGVT KSTLFKVVDG  660
DMGYNVIIGR PWIHKIKVVP STYDQFLNFP TSDGIKQIRG DQPAAREMNV VTLSSSNAEE  720
INK                                                                723

SEQ ID NO: 164          moltype = AA  length = 155
FEATURE                 Location/Qualifiers
REGION                  1..155
                        note = Description of Artificial Sequence: Synthetic
                         polypeptide
source                  1..155
                        mol_type = protein
                        organism = synthetic construct
SEQUENCE: 164
MQSPESCVIV SCPTTLIADE DEEVADMETS VKAVEEILNY KFIKPKLLEE ALTHSSCIDS  60
VSYQRLEFVG EQAEFHGGAM KAPKVLADIV ESVAAAVYVD CGFDLKNLWL LLLRTKKMLT  120
SRCKAALQKL AFKSIGKTDL KLNQIQRLMG QAKAA                             155

SEQ ID NO: 165          moltype = AA  length = 234
FEATURE                 Location/Qualifiers
REGION                  1..234
                        note = Description of Artificial Sequence: Synthetic
                         polypeptide
source                  1..234
                        mol_type = protein
                        organism = synthetic construct
SEQUENCE: 165
MKPQKSLLIK VLITQCLLVL CVAQQDFDFF YFVQQWPASY CDTRRSCCYP TTGKPDEDFS  60
IHGLWPNYEN GKWPQNCDRE SSLDESKISD LISTMEKNWP SLACPSSDGV RFWSHEWLKH  120
GTCSALGERA YFQAALDFRK KSNLLENLKN AGITPRNGEH YTLESIKKAI EEGVGHSPYI  180
ECNVDTQGNH QIYQVYLCMD KTATDFIDCP VFPHGRGCGS KIEFPPFSSD HDEF        234

SEQ ID NO: 166          moltype = AA  length = 217
FEATURE                 Location/Qualifiers
REGION                  1..217
                        note = Description of Artificial Sequence: Synthetic
                         polypeptide
source                  1..217
                        mol_type = protein
                        organism = synthetic construct
SEQUENCE: 166
MATRRREADF DFFYFVQQWP ASYCDTRRSC CYPTTGKPDE DFSIHGLWPN YENGKWPQNC  60
```

```
DRESSLDESE ISDLISTMEK NWPSLACPSS DGVRFWSHEW LKHGTCSALG ERAYFQAALD  120
FRKKSNLLEN LKNAGINPRN GEHYTLESIK KAIEEGVGHS PYIECNVDTQ GNHQIYQVYL  180
CVDKTATDFI DCPVFPRGRG CGSKIEFPPF SSDHDEF                           217

SEQ ID NO: 167         moltype = AA  length = 160
FEATURE                Location/Qualifiers
REGION                 1..160
                       note = Description of Artificial Sequence: Synthetic
                        polypeptide
source                 1..160
                       mol_type = protein
                       organism = synthetic construct
SEQUENCE: 167
MGVTTYNQEV TTLVAPTRLF KALVLDSENL VPKLMPQVVK NIEIVVGDGD AGSIKKMNFV  60
EGSPIKYLKH KIHVIDDKNL VTKYSLIEGD VLGDKLEFVT YDIKFEASGN GGCICKTSTE  120
YHTKGDYVFK EEEHYEGKKQ AMELFKTVED YLLANPSVYV                        160

SEQ ID NO: 168         moltype = AA  length = 160
FEATURE                Location/Qualifiers
REGION                 1..160
                       note = Description of Artificial Sequence: Synthetic
                        polypeptide
source                 1..160
                       mol_type = protein
                       organism = synthetic construct
SEQUENCE: 168
MGVAIFTQEF TSPIAPIRLF KALIVDSKSL IPKLLPQFVE SVDLLQGDGG AGSIEQVNFT  60
KGSPFEFVKH RIDELDKENM VCKYTMIEGD ALADKFDSIS YEVKFEESNN GGCICKMTTE  120
YIGIGDFIVK EEDIKAGKDS AIGIYKAVES HLLQNPNLYA                        160

SEQ ID NO: 169         moltype = AA  length = 160
FEATURE                Location/Qualifiers
REGION                 1..160
                       note = Description of Artificial Sequence: Synthetic
                        polypeptide
source                 1..160
                       mol_type = protein
                       organism = synthetic construct
SEQUENCE: 169
MGVTTYTHEV TTSVAPTRLF KAIVLDSENL VPKLMPKVVK NIEIIEGDGG AGSIKKMNFV  60
EGSPNKYLKH KIHVIDDKNL VTKYSLIEGD VLGDKLEFVT YEIKFEASGN GGCICKTSTE  120
YHTKGDYVFK EEEHNEGKNQ AMELFKTVED YLLANPSVYV                        160

SEQ ID NO: 170         moltype = AA  length = 160
FEATURE                Location/Qualifiers
REGION                 1..160
                       note = Description of Artificial Sequence: Synthetic
                        polypeptide
source                 1..160
                       mol_type = protein
                       organism = synthetic construct
SEQUENCE: 170
MAITSFTDEY TCPIPPSRIF KASIIDSHNL MPKLMPQAIK SIEFVQGNGG AGSIKQINFP  60
EGGNFKSIKY RIDELNEEKF VYKYTLIEGD ALVDKLEKIT YEVKFEQSAD GGSISKVTST  120
YYTEGDFKLK EEEIKAGKEK VLGMYKAVEV YLLQNPDAYA                        160

SEQ ID NO: 171         moltype = AA  length = 229
FEATURE                Location/Qualifiers
REGION                 1..229
                       note = Description of Artificial Sequence: Synthetic
                        polypeptide
source                 1..229
                       mol_type = protein
                       organism = synthetic construct
SEQUENCE: 171
MASNSATSLF LTLFLIIQCL SLLTAAQDFD FFYFVQQWPG SYCDTKQSCC YPKTGKPASD  60
FGIHGLWPNN NDGSYPSNCD SNSPYDQSQV SDLISRMQQN WPTLACPSGT GSAFWSHEWE  120
KHGTCSESIF DQHGYFKKAL DLKNQINLLE ILQGAGINPD GGFYSLNSIK NAINSAIGYT  180
PGIECNVDES GNSQLYQVYI CVDGSGSNLI ECPVFPRGKC GSSIEFPTF              229

SEQ ID NO: 172         moltype = AA  length = 229
FEATURE                Location/Qualifiers
REGION                 1..229
                       note = Description of Artificial Sequence: Synthetic
                        polypeptide
source                 1..229
                       mol_type = protein
                       organism = synthetic construct
SEQUENCE: 172
```

```
MASNSATSRF LTLFLITQCL SVLTAAQDFD FFYFVQQWPG SYCDTKQSCC YPKTGKPASD  60
FGIHGLWPNN NDGSYPSNCD SNSPYDQSQV SDLISRMQQN WPTLACPSDT GSAFWSHEWE  120
KHGTCAENVF DQHGYFKKAL DLKNQINLLE ILQGAGINPD GGFYSLNNIK NAIRSAVGYT  180
PGIECNVDES GNSQLYQVYI CVDGSGSDLI ECPVFPRGKC GSSIEFPTF             229

SEQ ID NO: 173          moltype = AA  length = 240
FEATURE                 Location/Qualifiers
REGION                  1..240
                        note = Description of Artificial Sequence: Synthetic
                         polypeptide
source                  1..240
                        mol_type = protein
                        organism = synthetic construct
SEQUENCE: 173
MRSIQLVLVK LVIFQCIMLL HAQDFDFFYF AQQWNPASCD SKIKCCYPTN GKPAQDFGIH  60
GLWPNYNNGS FPKSCNKNAR YDETQISDLI SSMQKNWPTL SCPSNNGTRF WSHEWKKHGT  120
CSLSMLDMHS YFQAALALKE KVNLLQFLNN AGIKPDGGFY SYEAMKEAIE KGIGHTVGVE  180
CNIDLFGNRQ LFEVYVCVDK CGSEIIDCPI VPESKRCKES IEFAVFESES LLDEKSAYSL  240

SEQ ID NO: 174          moltype = AA  length = 265
FEATURE                 Location/Qualifiers
REGION                  1..265
                        note = Description of Artificial Sequence: Synthetic
                         polypeptide
source                  1..265
                        mol_type = protein
                        organism = synthetic construct
SEQUENCE: 174
MRSIKFVLVK LVIFQCITLL VHAKDLDFYR LTLQQWNPAA CYNRIIGKCC NTTTGRPAED  60
FGIAGLWPSY NNLTYPENCN KAGPYDETQV SFDKIQISDL LSSMQKNWPK ISCPSNNGTS  120
LWAKEWKERG TCSRLNMHSY FETALDLKEK LNLIQDVKRY GTDLTHVHMH GLEPNGQFYH  180
WRHINAAIKL AIGHVIAIEC NLGLTADSQF YRVHICVDKS GSDFIDCPIN LTEISETTCS  240
SSTKWSGYDT DSVLEERSAY SWARK                                       265

SEQ ID NO: 175          moltype = AA  length = 493
FEATURE                 Location/Qualifiers
REGION                  1..493
                        note = Description of Artificial Sequence: Synthetic
                         polypeptide
source                  1..493
                        mol_type = protein
                        organism = synthetic construct
SEQUENCE: 175
MGSFSFAVCV SLMLLVMVVA IPFEPKNGRR IGRLHRWWDP LIRSPVDRDD EVEDSNSVRW  60
AVLVAGSNGY GNYRHQADVC HAYQILKRGG LKDENIVVFM YDDIAKSELN PRPGVIINHP  120
NGSDVYAGVP KDYTGEHVTA ANLYAVLLGD KSAVKGGSGK VIDSKPNDRI FLYYSDHGGP  180
GVLGMPNMPF LYAKDFIEAL KKKHAAGTYK EMVLYIEACE SGSVFEGMMP EDLNIYVTTA  240
SNADESSWGT YCPGMDPPPP PEYITCLGDL YSVAWMEDSE SHNLKKETIK QQYEKVKERT  300
SNFNNYNAGS HVMEYGSKEI KPEKVYLYQG FDPATANLPA NKIDFAHLEV VNQRDADLLF  360
LWERYKKLAD NSLEKAKLRK EITDTMLHRQ HLDGSVDAIG VFLFGPTKGS SVLNSVRKPG  420
LPLVDDWDCL KSTVRLFELH CGSLTQYGMK HMRAFANICN NGVSRDAMEE AFMAACNEHK  480
IEEYIAANRG FSA                                                    493

SEQ ID NO: 176          moltype = AA  length = 494
FEATURE                 Location/Qualifiers
REGION                  1..494
                        note = Description of Artificial Sequence: Synthetic
                         polypeptide
source                  1..494
                        mol_type = protein
                        organism = synthetic construct
SEQUENCE: 176
MGSFSFAVCV SLMLLVMVVA IPFELPKNGR RIGRLHRWWD PLIRSPVDRD DESEDKDGVR  60
WAVLVAGSNG YGNYRHQADV CHAYQILKRG GLKDENIVVF MYDDIAKSEL NPRPGVIINH  120
PNGSDVYAGV PKDYTGEHVT AANLYAVLLG DKSAVKGGSG KIVDSKPNDR IFLYYSDHGG  180
PGVLGMPNMP FLYAKDFIEV LKKKHAAGTY KEMVLYIEAC ESGSVFEGMM PEDLNIYVTT  240
ASNAEESSWG TYCPGMDPPP PPEYITCLGD LYSVAWMEDS ESHNLKKETI KQQYEKVKER  300
TSNFNNYNAG SHVMEYGSKE IKPEKVYLYQ GFDPATANLP ANKIAFAHVE VVNQRDADLL  360
FLWERYKKLA DNSLEKAKLR KEITDTMLHR KHLDGSVDAI GVFLFGPTKG SSVLNSVREP  420
GLPLVDDWDC LKSTVRLFEL HCGSLTQYGM KHMRAFANIC NNGVSRDAME EAFMAACNER  480
KREEYTAANR GFSA                                                   494

SEQ ID NO: 177          moltype = AA  length = 768
FEATURE                 Location/Qualifiers
REGION                  1..768
                        note = Description of Artificial Sequence: Synthetic
                         polypeptide
source                  1..768
                        mol_type = protein
```

```
                          organism = synthetic construct
SEQUENCE: 177
MYDDIANNSE NPRPGVLINN PHGQDVYQGV PKDYVGEDVN ADNFFNVILA NKSGITRGSG  60
KILDSGPNDN IFIYYTDHGG PGIVSMPTGI VYANDLINVL EKKHASGTYS KMVFYLEACE  120
SGSMFDGLLP EGLNIYVTTA SKPDENSWGT YCGLGRGACL VECPPPEFDG VCLGDLYSVA  180
WMEDSDVQDR QTSTLDNQYD RIACRTAANL TYGSHVMQYG DMELSVDALF QYMGSVSTSH  240
SQAPSPMAAA PSPMDAASFL TSSENVNQRD TELFYLTSKY QGAPEGTNEE FAADRKLNEV  300
VAQRSQVDNN VKRLGELLFG VEKGNEVLQS VRPAGQPLVD DWDCLKSYVK TFEAHCGKLT  360
AYGKKHVRGI ANICNAGIES EEMVDATAQA CSAASEIGPN SPTFTQTDFI LPPSHPLYLH  420
PSDNPDPDIS QSVIYSKSAK RLWDKLNQRY GQANGAKMYE VQKDLSTIFQ GSSDVGSYFT  480
RVKRLQDEME SLDADSFCVC ECKCGGKHKM IKRMENQKLM QFLMGLNEER GYDPKMPYCR  540
YCKKPGHVIE KCYKLHGFPR PSKSGNKNIR VAAHVHSSSD AKPNRSYDNN INIANTIIPD  600
QYKQHMTILQ HIQVGSNDSQ SQFATANFAG IFASSAHLMS CGNCTCLSSV LTSETWILDS  660
GTSVHMTFNK YSLTNITTLY VPYLITLPNG YKVKVTTIGS VKLNSSVILS KVLYVPTFKY  720
NLILVHKLLV DTLSLLCFSQ HACFLLHGPS LRMPLILGKC HNPKSHPS              768

SEQ ID NO: 178         moltype = AA  length = 457
FEATURE                Location/Qualifiers
REGION                 1..457
                       note = Description of Artificial Sequence: Synthetic
                        polypeptide
source                 1..457
                       mol_type = protein
                       organism = synthetic construct
SEQUENCE: 178
MVQKNGVVSF LVVLFVIVCT AEGRNLLESI VEDDNATGTK WAVLVAGSNE WDNYRHQADV  60
CHAYQLLKKG GLKDENIIVF MYDDIAYNKN NPRPGVIINS PHGHDVYKGV PKDYTGKDCN  120
ADNFFAVILG NKSALTGGSG KVVENGPNDY IFIYYADHGA PGLIGMPSGD DVYADDLIKV  180
LIKKHTFGIY SKLVFYMEAC ESGSMFDGLL PKGLNIYVTT ASKPDEGSWA TYCISLGDED  240
VVCLGDLYSV AWLEDSDLHD RQVETLEKQY QLVRKRTLNN GTVEGSHVMQ YGDLHISEDP  300
LFRYMGSNSA KNSYYSTSTN DESWLPSRTV NQRDVHLMHL WSKFRSAPEG SARKTEAQRQ  360
LREAISQREH VDNSVRHIGE VLFGVEKGPE VLQTVRPAGQ PLVDDWDCLK SFVKIFESQC  420
GKLTPYGRKH VRGFANLCNA GIRREQMAAA AKQACPS                           457

SEQ ID NO: 179         moltype = AA  length = 359
FEATURE                Location/Qualifiers
REGION                 1..359
                       note = Description of Artificial Sequence: Synthetic
                        polypeptide
source                 1..359
                       mol_type = protein
                       organism = synthetic construct
SEQUENCE: 179
MIRKNGVVPF LVALFVLVCT AEGRNLLESI VEDDNPTGTK WAVLVAGSNE WDNYRHQADV  60
CHAYQLLKKG GLKDENIIVF MYDDIAYNKN NPRPGIIINS PHGHDVYKEY PSGKVVENGP  120
NDYIFIYYAD HGAPGLIGMP SGDVVYADDL NRVLIKKHTF GTYSKLVFYM EACESGSMFD  180
GLLPKGLNIY VTAASKPDES SWATYCIRLG DEDQCLGDLY SVSWLEDSDL HDRQVETLEK  240
QYQLVRKRTL NNGTEEGSHV MQYGDLHISE DPLFRIWVLI LQKIVIILHN NDESWLPSRT  300
VNQRDVHLMH LWSKVKIFES QCGTLTPYGR KHVRGFANLC NAGIRREQMA AAAKQACPP   359

SEQ ID NO: 180         moltype = AA  length = 301
FEATURE                Location/Qualifiers
REGION                 1..301
                       note = Description of Artificial Sequence: Synthetic
                        polypeptide
source                 1..301
                       mol_type = protein
                       organism = synthetic construct
SEQUENCE: 180
MIPARMADVC HAYQLLKDGG LKDENIIVFM YDDIANNREN PRPGVIINNP HGHDVYKGVP  60
KDYVLEDVNA NNFYNVILGN KSAVVGGSGK VVNSGPNDHI FIYYTDHGGP GVVSMPSGED  120
VYANDLIDML KKKHASGTYD RLVFYLEACE SGSMFDGLLP EGLDIYVMTA SEPNEDSWAT  180
YCGEGTPDDP CLVECPPPEF QGVCLGDLYS VAWMEDSTID RLLFLTPHDF YSFFSECLQH  240
QNAPEGSDEK FKAHARLTEA ISQRTQVDNN VKHLGELLFG VEKGNEILHS VRPAGQPLVD  300
S                                                                  301

SEQ ID NO: 181         moltype = AA  length = 483
FEATURE                Location/Qualifiers
REGION                 1..483
                       note = Description of Artificial Sequence: Synthetic
                        polypeptide
source                 1..483
                       mol_type = protein
                       organism = synthetic construct
SEQUENCE: 181
MIVRYVVSAV LIIGLSILAA VEQGCAEITV GSIKVFSGEY DDDSIGTKWA VLVAGSRGCW  60
NYRHQADVCH AYQLLKKGGL KDENIIVFMY DDIAHNPENP RPGVIINSPN GHDVYKGVPK  120
DYTGHHVTAN NVLAVILGNK SALSGGSGKV VESGPNDHIF IFYSDHGGPG VLGMPSGPYL  180
YADDLIDALK RKHASGTYKR LVFYIEACES GSIFEGLLPE GLNICATTAS NAEEDSWGTY  240
```

```
CPGDYPGPPP EYQTCLGDLY AVSWMEDSEK HNLQRETLGM QYELVKRRTA NSFPYASSHV  300
MQYGDLKLMD DPLSLYMGTN PANDNYTFLD ENSSLLSAKP VNQRDADLLH FWDKFLKAPQ  360
GSIRKIEAQK QLTEAMSHRM HIDDSIALVG KLLFGIEKGP EVLIRVRPTG EPLVDDWDCL  420
KSFVRTFETH CGSLSQYGMK HMRAVANICN SGIKMEQIAK ASAQACVSIP SNSWSSLDEG  480
FSA                                                                483

SEQ ID NO: 182          moltype = AA  length = 157
FEATURE                 Location/Qualifiers
REGION                  1..157
                        note = Description of Artificial Sequence: Synthetic
                         polypeptide
source                  1..157
                        mol_type = protein
                        organism = synthetic construct
SEQUENCE: 182
MSYGDQSQTI GDLAFEKFTF PSIFGNNVNI LDVVFGCGHD NSGTFNNYTS VIIGLGGGEV  60
SIVNQLDKEI NGKFSYCLIT IPLQSSISNA TSHINFDADL ELSPSSTFAE VEEDLVSLTI  120
VPAEEVAIFG NLEQANFLIG YDLVANKISS LPTDCTS                            157

SEQ ID NO: 183          moltype = AA  length = 288
FEATURE                 Location/Qualifiers
REGION                  1..288
                        note = Description of Artificial Sequence: Synthetic
                         polypeptide
source                  1..288
                        mol_type = protein
                        organism = synthetic construct
SEQUENCE: 183
MINSRHRRKY GSKDEWNMRF GIYQSNVQFI DFFNSLNLSY NLTDNAFADM TNLEFNSKYL  60
GYKKRKHSKQ LAAPNITCDS SKLPISVDWR KSGVVTRVKD QENCGSCWAF SAVAAVEGIN  120
KIKTGKLVSL SEQQLVDCDV FSDNQGCNGG FMEKAFAFIN KNGGITTEKN YHYVGKDQKC  180
NTTKAKQHAV TISGYEMVAK NEESLQAAFT KQPISVAIDA SGYDFQLCAG GVYSVFFGNS  240
LNHGVPLIGY GVDDGEKYWL VKNSWGTMWG EDGYIKIKRW SNDKKRNV                288

SEQ ID NO: 184          moltype = AA  length = 706
FEATURE                 Location/Qualifiers
REGION                  1..706
                        note = Description of Artificial Sequence: Synthetic
                         polypeptide
source                  1..706
                        mol_type = protein
                        organism = synthetic construct
SEQUENCE: 184
MANSLLSSNF MGSQIFVSPP TPKTTKYFHF HSKRKSLIPQ SILNKKPNSD NSKNIPSKAA  60
LAALLFSSIT PHAYALDNTT PTVPTPQVIQ AEAANPTTSN PFSQNIILNA PKPQAQTNPE  120
LPEVSQWRYS EFLNAVKKGK VERVRFSKDG TTLQLNAVDG RRASVIVPND PDLIDILAMN  180
GVDISVSEGD SGGNGLFNLI GSLFPFIAFA GLFYLFQRSQ GGPGGPGGLG GPMDFGRSKS  240
KFQEVPETGV SFADVAGADQ AKLELQEVVD FLKNPDKYTA LGAKIPKGCL LVDHLVQERH  300
FWLEQLLVKL VYHFSMCSIR VVELFVGVGA SRVRDLFEKA KSKAPCIVFI DEIDAVGRQR  360
GAGMGGGNDE REQTINQLLT EMDGFSGNSG VIVLAATNRP DVLDSALLRP GRFDRQVTVD  420
RPDVAGRIKI LQVHSRGKAL AKDVDFEKIA RRTPGFTGAD LQNLMNEAAI LAARRELKEI  480
SKDEISDALE RIIAGPEKKN AVVSEEKKKL VAYHEAGHAL VGALMPEYDP VAKISIIPRG  540
QAGGLTFFAP SEERLESGLY SRSYLENQMA VALGGRVAEE VIFGQDNVTT GASNDFMQVS  600
RVARQMVERL GFSKKIGQVA IGGGGGNPFL GQQMSTQKDY SMATADVVDA EVRELVERAY  660
ERATQIITTH IDILHKLAQL LIEKETVDGE EFMSLFIDGK AELYIS                  706

SEQ ID NO: 185          moltype = AA  length = 745
FEATURE                 Location/Qualifiers
REGION                  1..745
                        note = Description of Artificial Sequence: Synthetic
                         polypeptide
source                  1..745
                        mol_type = protein
                        organism = synthetic construct
SEQUENCE: 185
MIIEVLILWH ADVRHNISLT ALSSTQSFYK DDLYIVFLKD HPVNEESLFQ RHIIVLSSLK  60
GSDGAATESH VYSYTKIFNA FAAKLSQHEV HMLSSMDEVV SVIPNRYRKL HTTRSWEFIG  120
LPATAKRRLK RESNIIVGVF DTGITPQSKS FKDDGLGPPP VKWKGSCGHF ANFSGCNNKL  180
IGARYFKLDK VPDPNDILSP IDVHGHGTHT SSTLAGSMVP DASLFGLARG TARGAVPSAR  240
VAMYKVCWVT SGCADIDILA AFEAAISDGV DLISISIGGL SGSYTTDVIA IGSFHAMRKG  300
ILTVASAGND GPNLNTVANH APWMLTVAAS GIDREFRSKV ALGNGRIVSG IGVSAFDPKK  360
KLYPLTAGVD MAKSSDTRDS SRYCGEGSMD PRKVKGKLVY CQLGTWGADS VIKELGGIGT  420
IIESDQFLDS APIFMALATI VNSSIGKNIN NYMHSERLPS AVIYKSQEVK IKAPFIASFS  480
SRGPNPGTIR LLKPDIAAPG IDILASYTPL KSLTGLKGDT QYSEFTLMSG TSMSCPHVGG  540
AAAYVKSYHP DWSPSAIKSA LVTTARPMSS KVDREAEFAY GAGQVNPTKA RSPGLIYDMD  600
DMSYIQFLCH EGYNSSSVSS LLRQRVNCST LIPANGEDAI NYPTMQLGLK SNQEPTIGIF  660
RRKVTNVGQA ISVYNATIRA PKGVDITVKP TTLSFTRAMQ TRSFKVVVKA KPMSNAVILS  720
GSLIWKSSRH LVRSPIVIYD PKVFD                                         745
```

```
SEQ ID NO: 186          moltype = DNA  length = 2372
FEATURE                 Location/Qualifiers
misc_feature            1..2372
                        note = Description of Artificial Sequence: Synthetic
                         polynucleotide
source                  1..2372
                        mol_type = other DNA
                        organism = synthetic construct
SEQUENCE: 186
atggattcct taccagtctc ctccattgaa tctctagtca ttgagatcaa gaaagagatg  60
ttctcaaacc aagaatttaa cacttttgtc accccaatat ctgcctatga cactgcttgg  120
ttggccatga tttcttataa taatcaagaa gaagccatta atggtcattc tttttctggc  180
cctatgttta agagttgttt aaattggatt ctcaacaacc aaaatgagca aggattttgg  240
ggagaatcca atggtgtttg aaatttattc atgctaatac ggaaatactt ctgaaagaga  300
attctcaaca atttccacgt tggttcatca ttgttttccc tgcaatggtt caactttcta  360
aatcagtagg cctggagatt atttttgtga atggatcaga aagattactt tcggacgttg  420
caatgaaaag gaaagtaatt cttgaaagtg aaaagctaat ggacgtgaca gcagggcatg  480
atcaacctct attggcatat ttagagagct tgccaaatta tgttttgaat caaaaagacc  540
aaatcctaaa acatttaagt gaagatggtt ctttgtttca atctccctct gctacagcac  600
aagcattcat ggccacagga aaccaaaaat ctcttgaata tctcatgtcc attgttcata  660
agtgtccaaa tggagtgcag taccttcaat gtttccagtg gatgaagagc taacaaagct  720
ttgcatagtt gaccacattc aaagaatgga ttgtttatct gagagattat acaaggactc  780
attggctttt cgacttctcc gtttgcaagg ctataaaata aatgaaggga agtttttgtt  840
ggtttgttca tcaaccgcag ataagggcct acatagaaaa gaatcaagaa cgttttacgt  900
atgtgatgta caatgtgtac agagctacag atctcatgtt taaaggagaa tctgaaatgg  960
aggaagtacg atcttttgcc agatatttc ttgaacgttc aatgaagctc gtgaacaatg  1020
agggcagctt attacttctt cctacacttc aaaaagtgat taagcatgag ttgaatgttc  1080
catgggttgc tcgactagaa catcttgatc acagattatg gattgaatta agtcaatctc  1140
tccctctttc aattggaaaa tccgcagatt attggttgtc ttgtctgcac aatgacaaat  1200
tgctgaaatt agcagtgcaa aattacgaat ttcggcagtc agtttacagg acggaattgg  1260
aagaactaaa gagagttggt cgaaagagaa aggccttgtg gacattggat ttgggcgaga  1320
gaaaactaca tattcctatt ttgcaagtgc agctagcagc agcagttttc taccttttga  1380
ttcttattat gatgaggaag cttctttaag tgacttgcaa atcttaaccg acgctgtaca  1440
aaggttacat aggtgggatg gaagtaacct tgatggccct agtaagatca tatttgatgc  1500
acttgatgat cttgtgtgtg atgttgctaa gttataccac cttcgacacg caattgacat  1560
caccccagaa cttcgacatg tggcaggaga catttcttgc atggatgatg gaaagtacgt  1620
ggagtaataa tgtagccatg ccatctagga atcaatacct agaaattggc atgatatcaa  1680
tcggtgcaca tattttggtt cttcacgctg cttctcttga aaatccaagc ttgccaaggg  1740
aaaaacttag gccaattaat ggccaatatg aaaatattac aaagttgcta atggccacca  1800
ctcgtttgtt gaatgacatc cagagctatc aacagaaaga atgtgaagta gggaaaatga  1860
actacacatt acttcacatg aatgaaaatc caggggcaca acttgatggt tcaattgaat  1920
ttgtgaaaga gattttggcc aacaagaaga aagaatttct tgaaaatgtt ctaatggatg  1980
gattcaatga tatgccaaag aaatgcaaac ttcttcatct ttcttgccta aatgtatttc  2040
acatgttctt caattcttgc aatttatttg ataccaaagc agcaattctt gaagatataa  2100
tgagagctat ttacgttcct cttcaagaac aaacctcagt tccacctta aaaacttctc  2160
caattttaac acctcaagaa aagaagaaga agaagaagaa gaagattgag aatattccaa  2220
ctaaagtttc tgcttgtctc aatgggaaaa acttcaaaca ccaagttggc attggcataa  2280
gttttgttgg aagtaaagct cctaagaata atccttttgg ttggtataca aaaggatttg  2340
cttcacaaaa gttaagttca tgtttcatat ga                                2372

SEQ ID NO: 187          moltype = AA  length = 86
FEATURE                 Location/Qualifiers
REGION                  1..86
                        note = Description of Artificial Sequence: Synthetic
                         polypeptide
source                  1..86
                        mol_type = protein
                        organism = synthetic construct
SEQUENCE: 187
MDSLPVSSIE SLVIEIKKEM FSNQEFNTFV TPISAYDTAW LAMISYNNQE EAINGHSFSG  60
PMFKSCLNWI LNNQNEQGFW GESNGV                                      86

SEQ ID NO: 188          moltype = DNA  length = 1029
FEATURE                 Location/Qualifiers
misc_feature            1..1029
                        note = Description of Artificial Sequence: Synthetic
                         polynucleotide
source                  1..1029
                        mol_type = other DNA
                        organism = synthetic construct
SEQUENCE: 188
atgggggggg gtggttctag tggaaatact tcttcatgtt taatgggtta tggagatgac  60
aacaacaaca ataacagtgg aaatgcagcc ctatgtcctc ctcctatgat gatgcctcct  120
cctcctatta ataataacaa tggagaaagc agcaataata ttggtggcaa caacaacaac  180
aatatcctgt ttctcccttt tatggccaac aacaacaata atccacatga agacgcaaac  240
tgttcttctt ctagttccat caagtctaag attatggctc atcctcacta ccctcgtctc  300
ttgtctgctt atgtcaattg tcaaaagata ggagctccgc cggaagtggt ggcaaggcta  360
gaggaagtat gtgccacgtc agcaacaata ggccgtaaca gtggcggcat tatcggagaa  420
gatccagcgc tagatcagtt catggaagct tactgtgaaa tgctgacaaa atatgagcaa  480
```

```
gaactttcaa aaccctttaa ggaagccatg gttttcctct caagaattga gtgccagttt  540
aaagctctca ctcttacttc ctcctctgaa tctgttgcag ctctaggtga ggcaatcgat  600
agaaatggat cgtctgaaga ggaggttgat gtgaataacg gtttcatcga ccctcaggct  660
gaagatcaag aactgaaagg tcaattgctg cgcaaataca gtggttactt gggtagcctt  720
aagcaggagt tcatgaagaa gaggaagaaa ggcaagctgc ctaaggaagc aaggcaacaa  780
ctactggact ggtggaccag acattacaaa tggccatatc catcggaatc ccagaagctg  840
gcactggctg aatctacagg attggaccaa aaacaaataa acaactggtt tatcaaccaa  900
aggaaaaggc actggaaacc ttcagaggat atgcagtttg tggtaatgga tgctgctcat  960
ccacattact atatggacaa tgttctcggt aatccttttc caatggatat tacaccaact  1020
ctcctctaa                                                          1029

SEQ ID NO: 189         moltype = AA  length = 342
FEATURE                Location/Qualifiers
REGION                 1..342
                       note = Description of Artificial Sequence: Synthetic
                        polypeptide
source                 1..342
                       mol_type = protein
                       organism = synthetic construct
SEQUENCE: 189
MGGGGSSGNT SSCLMGYGDD NNNNNSGNAA LCPPPMMMPP PPINNNNGES SNNIGGNNNN  60
NILFLPFMAN NNNNPHEDAN CSSSSSIKSK IMAHPHYPRL LSAYVNCQKI GAPPEVVARL  120
EEVCATSATI GRNSGGIIGE DPALDQFMEA YCEMLTKYEQ ELSKPFKEAM VFLSRIECQF  180
KALTLTSSSE SVAALGEAID RNGSSEEEVD VNNGFIDPQA EDQELKGQLL RKYSGYLGSL  240
KQEFMKKRKK GKLPKEARQQ LLDWWTRHYK WPYPSESQKL ALAESTGLDQ KQINNWFINQ  300
RKRHWKPSED MQFVVMDAAH PHYYMDNVLG NPFPMDITPT LL                     342

SEQ ID NO: 190         moltype = DNA  length = 738
FEATURE                Location/Qualifiers
misc_feature           1..738
                       note = Description of Artificial Sequence: Synthetic
                        polynucleotide
source                 1..738
                       mol_type = other DNA
                       organism = synthetic construct
SEQUENCE: 190
atgtataccc cagacactcc ggcgcaagaa ctatatgacg aggaatatta cgacgagcag  60
tcgccggaga agaagcgccg tctcactccc gagcaggtgc acttgctgga gaagagcttt  120
gaggcggaga acaagctgga gccagagcgt aagactcagc tagccaagaa gcttggcctg  180
cagcccaggc aagtggctgt gtggttccaa aaccgccgcg cccggtggaa gaccaagacg  240
ctcgaaaggg attatgatca gctcaaatcc tcttatgact ctcttctctc tgattttgac  300
tccattcgca aagataatga gaagctcaaa gctgaggtgg tttcattgat ggagaagttg  360
caggggaaag tggttggtga agcaggggta ataaatgaaa aatgtgaggt tttggaggta  420
gatgcgctga cccttcaagt gaaggtgaag gcggaggaca ggctgagcag tggcagcggc  480
ggaagtgcgg tggtagatga gcacagtcca cagctggtgg acagtgggga ctcctatttt  540
cacactggtc atatggaaga gtatccacta ggggctggag gatgtaataa tattcctccg  600
cctatggatg gtttgcagtc ggaggaagat gatggtagtg atgacggcgg cggccatggc  660
tacttctgta acgtctttgt ggcggcagag gagcagcaac atgaagaagg agagcctatt  720
gggtggttct ggtcttga                                                738

SEQ ID NO: 191         moltype = AA  length = 245
FEATURE                Location/Qualifiers
REGION                 1..245
                       note = Description of Artificial Sequence: Synthetic
                        polypeptide
source                 1..245
                       mol_type = protein
                       organism = synthetic construct
SEQUENCE: 191
MYTPDTPAQE LYDEEYYDEQ SPEKKRRLTP EQVHLLEKSF EAENKLEPER KTQLAKKLGL  60
QPRQVAVWFQ NRRARWKTKT LERDYDQLKS SYDSLLSDFD SIRKDNEKLK AEVVSLMEKL  120
QGKVVGEAGV INEKCEVLEV DALTLQVKVK AEDRLSSGSG GSAVVDEHSP QLVDSGDSYF  180
HTGHMEEYPL GAGGCNNIPP PMDGLQSEED DGSDDGGGHG YFCNVFVAAE EQQHEEGEPI  240
GWFWS                                                              245

SEQ ID NO: 192         moltype = DNA  length = 1641
FEATURE                Location/Qualifiers
misc_feature           1..1641
                       note = Description of Artificial Sequence: Synthetic
                        polynucleotide
source                 1..1641
                       mol_type = other DNA
                       organism = synthetic construct
SEQUENCE: 192
acacattaaa ctaaagaaga gagaacttta gaggttagag agatgaagac gcaacatcaa  60
tggtgggaag ttcttgatcc attcttgaca caacacgaag ctcttattgc attcttgact  120
tttgcagcgg ttgtaattgt gatttacttg taccgaccct cctggtccgt atgcaatgtt  180
cccggtccaa ccgctatgcc tctagttggt cacttgccct tgatggctaa gtatggtcct  240
gatgtcttct ccgttcttgc taagcaatat ggccctattt tcagatttca gatggggagg  300
```

```
caaccactga taataatagc agaagcagag ctttgcagag aagttgggat aaagaagttc  360
aaagatcttc caaacagaag cattccttcc ccaatctcag cttctcctct tcacaagaaa  420
ggcctcttct tcaccaggga caagagatgg tctaaaatga gaaacaccat cctatctctc  480
tatcagcctt cacatttaac aagtcttatc cctacaatgc atagtttcat cacttctgct  540
actcataatc ttgattctaa accgcgagat atcgtttttct ccaacctctt cctcaaactt  600
accactgata tcatcggaca agcggctttt ggagtcgact tcggtctttc cgggaagaaa  660
ccaatcaaag atgtggaggt gactgatttc ataaaccagc atgtctactc tacaacacaa  720
ctcaagatgg atttatcagg atcactctct atcatcttag gcttactgat tccgattctt  780
caagagccgt ttaggcaggt gttgaagagg ataccgggaa caatggactg gagagtcgag  840
aagactaatg caagactgag tggacaactt aatgagattg tgtcaaagcg agccaaggag  900
gctgagactg actcaaaaga cttcttgtca ttgattttga aagctcgaga gtccgatcct  960
ttcgccaaaa acatcttcac atcggattat attagtgctg tgacttatga gcatcttctt  1020
cttgatgttg agaaacgtct gcttcaagaa attgacgggt ttgggaaccg tgatctgatc  1080
ccgactgctc atgacttaca acacaagttt ccatacctcg atcaggtcat taaagaggct  1140
atgagattct acatggtttc tcctttggtt gcaagggaaa ctgctaaaga agtggagata  1200
ggaggttatt tactcccaaa ggggacatgg gtttggttag cactaggagt tctagcaaag  1260
gaccctaaaa actttccaga accggagaag ttcaagccgg aaagatttga tccgaacgga  1320
gaagaggaga aacatagaca tccatacgct ttcatcccat tcggtatcgg tccacgagcc  1380
tgtgttggac agagatttgc cctgcaagag atcaaactca cattactgca tctctaccgt  1440
aattacattt tcagacattc cctagaaatg gagataccac tgcagcttga ttatggtata  1500
attctcagct tcaagaacgg ggttaagctc agaaccatca aagattctg attcttgaaa  1560
caagtgaaat aaaagcaaga ctgaaattta tatttaaatt caaaactcca atgtagttcc  1620
aaaggaaaaa gaacaattaa c                                            1641
```

```
SEQ ID NO: 193          moltype = AA  length = 522
FEATURE                 Location/Qualifiers
REGION                  1..522
                        note = Description of Artificial Sequence: Synthetic
                         polypeptide
source                  1..522
                        mol_type = protein
                        organism = synthetic construct
SEQUENCE: 193
MKTQHQWWEV LDPFLTQHEA LIAFLTFAAV VIVIYLYRPS WSVCNVPGPT AMPLVGHLPL  60
MAKYGPDVFS VLAKQYGPIF RFQMGRQPLI IIAEAELCRE VGIKKFKDLP NRSIPSPISA  120
SPLHKKGLFF TRDKRWSKMR NTILSLYQPS HLTSLIPTMH SFITSATHNL DSKPRDIVFS  180
NLFLKLTTDI IGQAAFGVDF GLSGKKPIKD VEVTDFINQH VYSTTQLKMD LSGSLSIILG  240
LLIPILQEPF RQVLKRIPGT MDWRVEKTNA RLSGQLNEIV SKRAKEAETD SKDFLSLILK  300
ARESDPFAKN IFTSDYISAV TYEHLLAGSA TTAFTLSSVL YLVSGHLDVE KRLLQEIDGF  360
GNRDLIPTAH DLQHKFPYLD QVIKEAMRFY MVSPLVARET AKEVEIGGYL LPKGTWVWLA  420
LGVLAKDPKN FPEPEKFKPE RFDPNGEEEK HRHPYAFIPF GIGPRACVGQ RFALQEIKLT  480
LLHLYRNYIF RHSLEMEIPL QLDYGIILSF KNGVKLRTIK RF                    522
```

```
SEQ ID NO: 194          moltype = DNA  length = 2329
FEATURE                 Location/Qualifiers
misc_feature            1..2329
                        note = Description of Artificial Sequence: Synthetic
                         polynucleotide
source                  1..2329
                        mol_type = other DNA
                        organism = synthetic construct
SEQUENCE: 194
atctcctctc ttgtagattt gccgcttctc atggcttcca ctactctctc cgacctccct  60
gacgtcatct tatccaccat ttcctctctc gtatccgatt cccgagctcg caactctctc  120
tccctcgtct ctcacaaatt cctcgctctc gaacgatcca ctcgctctca cctcactatc  180
cgtggcaacg ctcgtgatct ctccctcgtc cccgactgtt tccgatcaat ctcacatctc  240
gatctctctt tcctctcccc atggggtcac actcttctcg cttctctccc aatcgatcac  300
cagaaccttc tcgctctccg tctcaaattc tgtttccctt tcgtcgagtc tctaaacgtc  360
tacacacgat ctccgagctc tctcgagctt ctacttcctc aatggccgag aattcgccac  420
atcaagctcc tccgatggca tcaacgagct tctcagatcc ctaccggtgg cgattttgtt  480
cctatttttg aacactgtgg tggtttcctt gagtctttag atctctccaa cttctatcac  540
tggactgaag acttacctcc tgtgcttctc cgctatgctg acgtggcggc gaggcttaca  600
cggttagatc tcttgacggc gtcgttcacc gagggataca aatcaagcga aatcgttagt  660
atcaccaaat cttgccctaa tttgaagact tttcgtgtag cttgtacgtt tgatccgaga  720
tactttgaat tcgtcggaga cgagactctc tccgccgtag ctaccagttc ccctaagtta  780
acgcttctac acatggtgga cacagcttcg ttggcgaatc ctagagctat tccaggtacg  840
gaagctggag attcagctgt cacggcgggg acgctaattg aagttttctc aggtttaccg  900
aatctagagg agctggttct tgacgtagga aaggatgtga agcatagtgg tgtagcttta  960
gaggcattga attctaaatg caagaagtta agagtattga agctaggaca gttccaaggt  1020
gtttgctctg ctacagaatg gaggaggctc gacggtgtgg ctttatgtgg aggattgcag  1080
tcgttgtcga ttaagaattc cggcgatttg actgatatgg gtttggtggc tatagggaga  1140
ggatgttgta agttgactac gtttgagatt caagggtgtg agaatgtaac agtggatgga  1200
ctaagaacaa tggttagtct tcggagtaag actttgactg atgtgagaat ctcttgctgc  1260
aagaatcttg acacagctgc ttctttaaag gcaattgagc cgatttgtga tcggatcaag  1320
agactgcata tagactgtgt gtggtctggt tcagaggacg aggaggtaga aggaagagtg  1380
gaaactagtg aggctgacca cgaagaggag gatgatggtt acgagaggag ccagaagagg  1440
tgcaagtatt cattcgagga agaacactgc tcaactagtg atgtgaatgg attctgttct  1500
gaagatagag tatgggagaa actggagtat ctatctttat ggatcaatgt tggagaattt  1560
ttgacgccat tacctatgac aggactagat gactgtccga atttggaaga gattaggatc  1620
```

```
aagatagaag gagattgcag aggtaaacgc aggccagccg agccagagtt tgggttaagt  1680
tgtctcgctc tctacccaaa gctctcaaag atgcagttag attgcgggga cacaatcggt  1740
ttcgcactga ccgcaccgcc aatgcagatg gatttgagtt tatgggaaag attcttcttg  1800
accggaattg gaagcttgag cttgagcgag cttgattatt ggccaccaca ggatagagat  1860
gttaaccaga ggagtctctc gcttcctgga gcaggtctgt tacaagagtg cctgactttg  1920
aggaagctgt tcatccatgg aacagctcat gagcatttca tgaacttttt gttgagaatc  1980
ccaaacttaa gggatgtaca gcttagagca gactattatc cggcgccgga gaacgatatg  2040
agcacagaga tgagagttgg ttcgtgtagc cgattcgagg accaattgaa cagccgcaac  2100
atcattgact gaaacttgaa gagtgagtta cctacactat tatatctgta ttgacttcag  2160
aaactggtcc attttatttg tatggtcaag agtgttttgt atatgtttgt aagaggaaag  2220
gacaaagact ataatttgcg atgattaatg atatcataaa acaataatcc atttttataa  2280
atgataaaac tcaaatgaag aagccggaga gatctggagt acaaactca             2329

SEQ ID NO: 195         moltype = AA  length = 693
FEATURE                Location/Qualifiers
REGION                 1..693
                       note = Description of Artificial Sequence: Synthetic
                        polypeptide
source                 1..693
                       mol_type = protein
                       organism = synthetic construct
SEQUENCE: 195
MASTTLSDLP DVILSTISSL VSDSRARNSL SLVSHKFLAL ERSTRSHLTI RGNARDLSLV  60
PDCFRSISHL DLSFLSPWGH TLLASLPIDH QNLLALRLKF CFPFVESLNV YTRSPSSLEL  120
LLPQWPRIRH IKLLRWHQRA SQIPTGGDFV PIFEHCGGFL ESLDLSNFYH WTEDLPPVLL  180
RYADVAARLT RLDLLTASFT EGYKSSEIVS ITKSCPNLKT FRVACTFDPR YFEFVGDETL  240
SAVATSSPKL TLLHMVDTAS LANPRAIPGT EAGDSAVTAG TLIEVFSGLP NLEELVLDVG  300
KDVKHSGVAL EALNSKCKKL RVLKLGQFQG VCSATEWRRL DGVALCGGLQ SLSIKNSGDL  360
TDMGLVAIGR GCCKLTTFEI QGCENVTVDG LRTMVSLRSK TLTDVRISCC KNLDTAASLK  420
AIEPICDRIK RLHIDCVWSG SEDEEVEGRV ETSEADHEEE DDGYERSQKR CKYSFEEEHC  480
STSDVNGFCS EDRVWEKLEY LSLWINVGEF LTPLPMTGLD DCPNLEEIRI KIEGDCRGKR  540
RPAEPEFGLS CLALYPKLSK MQLDCGDTIG FALTAPPMQM DLSLWERFFL TGIGSLSLSE  600
LDYWPPQDRD VNQRSLSLPG AGLLQECLTL RKLFIHGTAH EHFMNFLLRI PNLRDVQLRA  660
DYYPAPENDM STEMRVGSCS RFEDQLNSRN IID                               693

SEQ ID NO: 196         moltype = DNA  length = 1110
FEATURE                Location/Qualifiers
misc_feature           1..1110
                       note = Description of Artificial Sequence: Synthetic
                        polynucleotide
source                 1..1110
                       mol_type = other DNA
                       organism = synthetic construct
SEQUENCE: 196
atgggcagac agccactagt tatagtagca gatgcagagc tatgcagaga agttggaata  60
aagaaattca aggacatacc aaatagaagc atcccatctc ccattgcagc atcccctctt  120
catcagaaag gcctattttt tactagggac tccagatggt caacaatgag aaacactatt  180
ctatcagtct accagccatc ttaccttgtt aagttagtgc caatcatgca atcgtttatc  240
gagtcttcaa ctaaaaatct tgattctgag ggagatctca cattctctga tctctccctc  300
aagttagcta ctgatgtaat tggacaagct gcttttgaaa gaacaaacaa gaatttaagc  360
aggaggttag atgagatagt ggcaaagagg atggaggaaa aagatcgcag ttcaaaggac  420
ttcttatcgc ttatactgca ggcaagggag tcagagaagt tagctaagaa tgttttcacc  480
tcagattata tcagtgctgt aacttatgag cacttactgg ctggttctgc aacaacttcc  540
tttacattgt cttctattat ctatttggtt gctggccatc cagaggttga gcagaagttg  600
ctcacggaga tagatgcttt tgggcctaat gatcacatac tcactgccat tgagcttcag  660
cagaaattcc cataccttga tcaggtaatc aaagaagcaa tgaggtgtta tgtcgtctca  720
cccttagttg ccagagaaac atcagctgag gtggagatcg gaggctataa acttcctaag  780
ggcacatggg tttggttggc tcttggagtt cttgctaagg attcaaagaa cttccccgaa  840
ccagagaagt ttagaccaga gaggtttgat ccaagctgtg aagaggaaaa acaaaggcat  900
ccttatgcaa atattccatt tggaataggg ccgcgagcat gcataggaca gaagttctcc  960
atacaagaac ttaaactctc actgattcac ttatatcgca agtacatttt tcgacactct  1020
ccccttatgg aaaagccact ggaacttgag tatggtatag tacttaacta taagcatgga  1080
gtcaaggttt gtgccatcaa gcgtaaatga                                  1110

SEQ ID NO: 197         moltype = AA  length = 369
FEATURE                Location/Qualifiers
REGION                 1..369
                       note = Description of Artificial Sequence: Synthetic
                        polypeptide
source                 1..369
                       mol_type = protein
                       organism = synthetic construct
SEQUENCE: 197
MGRQPLVIVA DAELCREVGI KKFKDIPNRS IPSPIAASPL HQKGLFFTRD SRWSTMRNTI  60
LSVYQPSYLV KLVPIMQSFI ESSTKNLDSE GDLTFSDLSL KLATDVIGQA AFERTNKNLS  120
RRLDEIVAKR MEEKDRSSKD FLSLILQARE SEKLAKNVFT SDYISAVTYE HLLAGSATTS  180
FTLSSIIYLV AGHPEVEQKL LTEIDAFGPN DHILTAIELQ QKFPYLDQVI KEAMRCYVVS  240
PLVARETSAE VEIGGYKLPK GTWVWLALGV LAKDSKNFPE PEKFRPERFD PSCEEEKQRH  300
PYANIPFGIG PRACIGQKFS IQELKLSLIH LYRKYIFRHS PLMEKPLELE YGIVLNYKHG  360
```

```
VKVCAIKRK                                                    369

SEQ ID NO: 198          moltype = DNA  length = 2175
FEATURE                 Location/Qualifiers
misc_feature            1..2175
                        note = Description of Artificial Sequence: Synthetic
                         polynucleotide
source                  1..2175
                        mol_type = other DNA
                        organism = synthetic construct
SEQUENCE: 198
atggctacag ctacacaact tacttgttct accattatta acgacctacc tgatgtgatc  60
ctttctaaca tcatcgccgc aatctccgac gtccgcagcc gcaactccgc cgccctcgtc  120
tgccggaaat gcctcgtcct cgaacgttcc acgcgcgtct ccctcacgct ccgtggcaac  180
gtccgtgacc tcttcatgtt acccacttgc ttcagatccg taactcacct tgacctctcc  240
cttatctctc cttggggtca cccactcctc tctccggtcg acggcgccgg cgcagaagct  300
gacccttccc tcatcgccca ccttctccgc cacgcgtttc cttccgtcac ttccctcgtt  360
gtctacacgc gccacccatt caccctccag cttttgcctc ctctatggcc ccacctaaag  420
gaaatcaagc ttgtgcggtg gcaccagcgt ccccaattag ctactggtga tgaatttaat  480
atgctatttg agaattgccc acagcttaaa tctctagatt tgtcgacttt ttactgctgg  540
acggatgata ttcctacagc acttgaatct catcctatgg ttgcttctaa tctcactagc  600
tttaatctct tgaattccag ttttcctgaa gggtttaagt ctgatgagat taaggtaatt  660
acacaagctt gtcctaattt gaaagagttt aaggttgctt gtatgtttga tcctaggtac  720
attggttttg ttggtgatga aggtttggtt tctatagcta caaactgtac caaattatca  780
gtgcttcatt tggcggacac atcagctttg tccaactcta ggggtgatcc aaatgatgag  840
gggttcaccg aagaggatgc gaagattagt gttggaactt tgattgaggt attttctggt  900
cttccattac ttgaagagct tgttttagat gtttgtaata atgttagaga cacgggtcct  960
gccttggaga ttttgaatag aaaatgtccc aaattgagat cgttgaagtt ggggcaattc  1020
cacggtattt ctgtgccaat tgaatcgaag ttggatgggg ttgctctttg tcaagggctt  1080
caatctctgt cgataagtaa tgtgggggac ttgaatgata tgggtttgat agctattggt  1140
agagggtgtt cgaggttagc caagtttgag attcgaggtt gtaagaagat aactatgagg  1200
ggaatgagga cactagcttc tttgcttagc agaactttgg ttgatgtcaa gatatcttgc  1260
tgcaagaatc ttggagcctc ttcttcattg aaagcattgg aaccgataca aagacggata  1320
caaaagcttc acattgactg tgtgtgggac agcgttgaag aatttgagaa tcttgatggt  1380
aatggatacg ggtttgatct taacaggaat gatggagggg aggcatcaag caactttgct  1440
tgttccgggg acacatttgg atgcgaggaa gatgcttaca tgtttagaca gaagaaaaga  1500
tgcaagttct cctatgatat taatagtttg tatgaggatg tcaatggcca tggcaatgga  1560
tatagtggac gatcatggga taagctgcaa tgcctctctc tttggattgg tgttggtgag  1620
cttttgactc ctttaacaac tgcaggtctt gaagactgtc ctaacttaga ggagatcaag  1680
attagggtgg aaggagattg caggctttgg tcaaaacctt cggagcgggc atttggactg  1740
agcaccctac tactctatcc taagctttcc aagatgcatt tggattgtgg agataccata  1800
ggttatgcac acactgcgcc atcagggcag atggatttga gcttgtggga gaggttttat  1860
ctgtttggga ttggaaattt gagccttgcc gaactagatt actggccacc tcaagatagg  1920
gacgttaacc aaaggtgtct atccctacca gcagctgggc tgctacaaga atgcatcaca  1980
ctcagaaaac tgttcatcca tggaacagcg catgaacatt tcatgatgtt ccttcttaga  2040
atcccaaaca taagagatgt acaactgaga gaggattact atccagcacc agagaatgac  2100
atgagtacag agatgagagc agactccttg agccgctttg aagctgccct aaacaggcgc  2160
ccaatatccg attga                                             2175

SEQ ID NO: 199          moltype = AA  length = 724
FEATURE                 Location/Qualifiers
REGION                  1..724
                        note = Description of Artificial Sequence: Synthetic
                         polypeptide
source                  1..724
                        mol_type = protein
                        organism = synthetic construct
SEQUENCE: 199
MATATQLTCS TIINDLPDVI LSNIIAAISD VRSRNSAALV CRKCLVLERS TRVSLTLRGN  60
VRDLFMLPTC FRSVTHLDLS LISPWGHPLL SPVDGAGAEA DPSLIAHLLR HAFPSVTSLV  120
VYTRHPFTLQ LLPPLWPHLK EIKLVRWHQR PQLATGDEFN MLFENCPQLK SLDLSTFYCW  180
TDDIPTALES HPMVASNLTS FNLLNSSFPE GFKSDEIKVI TQACPNLKEF KVACMFDPRY  240
IGFVGDEGLV SIATNCTKLS VLHLADTSAL SNSRGDPNDE GFTEEDAKIS VGTLIEVFSG  300
LPLLEELVLD VCNNVRDTGP ALEILNRKCP KLRSLKLGQF HGISVPIESK LDGVALCQGL  360
QSLSISNVGD LNDMGLIAIG RGCSRLAKFE IRGCKKITMR GMRTLASLLS RTLVDVKISC  420
CKNLGASSSL KALEPIQRRI QKLHIDCVWD SVEEFENLDG NGYGFDLNRN DGGEASSNFA  480
CSGDTFGCEE DAYMFRQKKR CKFSYDINSL YEDVNGHGNG YSGRSWDKLQ CLSLWIGVGE  540
LLTPLTTAGL EDCPNLEEIK IRVEGDCRLW SKPSERAFGL STLLLYPKLS KMHLDCGDTI  600
GYAHTAPSGQ MDLSLWERFY LFGIGNLSLA ELDYWPPQDR DVNQRCLSLP AAGLLQECIT  660
LRKLFIHGTA HEHFMMFLLR IPNIRDVQLR EDYYPAPEND MSTEMRADSL SRFEAALNRR  720
PISD                                                          724

SEQ ID NO: 200          moltype = DNA  length = 1338
FEATURE                 Location/Qualifiers
misc_feature            1..1338
                        note = Description of Artificial Sequence: Synthetic
                         polynucleotide
source                  1..1338
                        mol_type = other DNA
```

```
                         organism = synthetic construct
SEQUENCE: 200
atgcttactt ccttcaaatc ctctagctcc tcctccgaag atgccaccgc taccaccacc  60
gagaatcctc ctcctttgtg catcgcctcc tcctcggccg caacctccgc ctcacatcac  120
ctccgtcgtc ttcttttcac cgctgcgaat ttcgtctccc agtcaaactt caccgccgct  180
caaaacttac tctcaatcct ctcccttaac tcttctcctc acggcgactc caccgagcga  240
cttgtacacc tcttcactaa agccttgtcc gtacgaatca accgtcagca acaagatcag  300
acggctgaaa cggttgccac gtggacgacg aacgaaatga cgatgagtaa ctccacggtg  360
ttcacgagca gtgtatgcaa agaacagttc ttgtttcgaa ccaagaacaa caattctgac  420
ttcgagtctt gttactatct ttggctaaac caactaacgc cgtttattcg gttcggtcat  480
ttaacggcga accaagctat cctcgacgcg acggagacaa acgataacgg agctctacat  540
atacttgatt tagatatatc acaaggactt caatggcctc cattgatgca agccctagca  600
gagaggtcat caaaccctag cagtccacct ccatctctcc gcataaccgg atgcggtcga  660
gatgtaaccg gattaaaccg aactggagac cggttaaccc ggttcgctga ctctttaggt  720
ctccaattcc agtttcacac gctagtgatc gtagaagaag atctcgccgg actttttgcta  780
cagatccgat tgttagctct ctcagccgta caaggagaga ccattgccgt caattgtgtt  840
cacttcctcc acaaaatatt taacgacgat ggagatatga tcggtcactt cttgtcagcg  900
atcaagagct taaactctag aatcgttaca atggcagaga gagaagctaa tcatggagat  960
cactcgttct tgaatagatt ctctgaggca gtggatcatt acatggcgat ctttgattcg  1020
ttggaagcga cgttgccgcc aaatagccga gagagactaa ccctagagca acggtggttc  1080
ggtaaggaga ttttggatgt tgtggcggcg gaagagacgg agagaaagca aagacatcgg  1140
aggtttgaga tttgggaaga gatgatgaag aggtttggtt tcgttaacgt tcctattgga  1200
agctttgctt tgtctcaagc taagcttctt cttagacttc attatccttc agaaggttat  1260
aatcttcagt tccttaacaa ttctttgttt cttggctggc aaaatcgtcc cctcttctcc  1320
gtttcgtcgt ggaaatga                                                1338

SEQ ID NO: 201          moltype = AA  length = 445
FEATURE                 Location/Qualifiers
REGION                  1..445
                        note = Description of Artificial Sequence: Synthetic
                         polypeptide
source                  1..445
                        mol_type = protein
                        organism = synthetic construct
SEQUENCE: 201
MLTSFKSSSS SSEDATATTT ENPPPLCIAS SSAATSASHH LRRLLFTAAN FVSQSNFTAA  60
QNLLSILSLN SSPHGDSTER LVHLFTKALS VRINRQQQDQ TAETVATWTT NEMTMSNSTV  120
FTSSVCKEQF LFRTKNNNSD FESCYYLWLN QLTPFIRFGH LTANQAILDA TETNDNGALH  180
ILDLDISQGL QWPPLMQALA ERSSNPSSPP PSLRITGCGR DVTGLNRTGD RLTRFADSLG  240
LQFQFHTLVI VEEDLAGLLL QIRLLALSAV QGETIAVNCV HFLHKIFNDD GDMIGHFLSA  300
IKSLNSRIVT MAEREANHGD HSFLNRFSEA VDHYMAIFDS LEATLPPNSR ERLTLEQRWF  360
GKEILDVVAA EETERKQRHR RFEIWEEMMK RFGFVNVPIG SFALSQAKLL LRLHYPSEGY  420
NLQFLNNSLF LGWQNRPLFS VSSWK                                        445

SEQ ID NO: 202          moltype = DNA  length = 990
FEATURE                 Location/Qualifiers
misc_feature            1..990
                        note = Description of Artificial Sequence: Synthetic
                         polynucleotide
source                  1..990
                        mol_type = other DNA
                        organism = synthetic construct
SEQUENCE: 202
atgggaagag ctccgtgttg cgacaagaca aaagtgaagc gagggccttg gtcgcctgaa  60
gaagactcta aacttagaga ttacattgaa aagtatggta atggtggaaa ttggatctct  120
ttccccctca aagccggttt gaggagatgt gggaagagtt gtagactgag gtggctaaac  180
tatttgagac caaacataaa gcatggtgac ttctctgagg aagaagacag gatcattttt  240
agtctcttcg ctgccatagg aagcaggtgg tcaataatag cagctcatct accgggacga  300
acagacaacg acataaaaaa ctattggaac acaaagctaa ggaagaaact cttgtcttct  360
tcctctgatt catcatcatc agccatggct tctccttatc taaaccctat ttctcaggat  420
gtgaaaagac caacctcacc aacaacaatc ccatcttctt cttacaatcc gtatgctgaa  480
aaccctaatc aatacccaac aaaatccctc atctccagca tcaatggctt cgaagctggt  540
gacaaacaga taatttccta tattaaccct aattatcctc aagatctcta tctctcggac  600
agcaacaaca acacctcgaa cgcaaatggt ttcttgctca accacaatat gtgtgatcag  660
tacaagaacc acaccagttt ttcttcagac gtcaatggga taagatcaga gattatgatg  720
aagcaagaag agataatgat gatgatgatg atagaccacc acattgacca gaggacaaaa  780
gggtacaatg gggaattcac acaagggtat tataattact acaatgggca tggggatttg  840
aagcaaatga ttagtggaac aggcactaat tctaacataa acatgggtgg ttcaggttca  900
tcttctagtt cgataagcaa cctagctgag aacaaaagca gtggtagcct cctactagaa  960
tacaaatgct tgccctattt ctactcctag                                   990

SEQ ID NO: 203          moltype = AA  length = 329
FEATURE                 Location/Qualifiers
REGION                  1..329
                        note = Description of Artificial Sequence: Synthetic
                         polypeptide
source                  1..329
                        mol_type = protein
                        organism = synthetic construct
```

```
SEQUENCE: 203
MGRAPCCDKT KVKRGPWSPE EDSKLRDYIE KYGNGGNWIS FPLKAGLRRC GKSCRLRWLN  60
YLRPNIKHGD FSEEEDRIIF SLFAAIGSRW SIIAAHLPGR TDNDIKNYWN TKLRKKLLSS  120
SSDSSSSAMA SPYLNPISQD VKRPTSPTTI PSSSYNPYAE NPNQYPTKSL ISSINGFEAG  180
DKQIISYINP NYPQDLYLSD SNNNTSNANG FLLNHNMCDQ YKNHTSFSSD VNGIRSEIMM  240
KQEEIMMMMM IDHHIDQRTK GYNGEFTQGY YNYYNGHGDL KQMISGTGTN SNINMGGSGS  300
SSSSISNLAE NKSSGSLLLE YKCLPYFYS                                  329

SEQ ID NO: 204          moltype = DNA  length = 5000
FEATURE                 Location/Qualifiers
misc_feature            1..5000
                        note = Description of Artificial Sequence: Synthetic
                         polynucleotide
source                  1..5000
                        mol_type = other DNA
                        organism = synthetic construct
SEQUENCE: 204
aagctagcac catagatagt gggtgtcacc attttacagc aaataatatg cctcaattgg  60
tggagaaagg gtctttaaag ttgaagtgtt tttctttttt tctctttctt tttcttggta  120
ggtggtgggg aaggggaaaa tgaggggaca aaacacgaaa aatcaatttt gatgtataat  180
ttacacaaga ctcaagctaa gtgatagagt tgataaaagg ataacaataa tatgggacac  240
ataaattcat gacgtctccg tttatcggat attttctcaa attgatgtaa catatgtttc  300
aagaagttca aataatgtgt atatagattt atttctataa aatattattt cgaattataa  360
atcttcgact caagaaaaaa taaaaatgtt agatatggca aaggggatag cacttagaca  420
attaggcaac ctcatatttg ttacaagtgg gggtgagggt tcaactttgc attatttagc  480
atcactttgt tatttatttt ttttatataa aatttataga acaggagatg ttaatataag  540
gatgacaatc cagattgaca aagttgtgat agtgatacta ctgtaacatc ttattcaatc  600
atgcaaagca tctcccatta atttgtccat cttttcgaat attacgaaaa tcagacctac  660
ttttttttaca tataattttc tctaatgaca tcacaggaac tactcctgag agaaatattc  720
tcactcaagt ttgaaaacga ctcttaaatt atgataaagt gataactaca atgaccggct  780
aactcttgcg tgcattatga gtgtatatag ttatatgtta tttactctcg tcgtaaatat  840
caagtgcgaa taatatgtat gaaatttaga gaaatgagag taaattagtc gatgttttta  900
atttacgttg tgatttattc gttacttttt gctttctcta aagtcaattt cagtagttcg  960
tggagataca ttagattaaa ttaatctaat ctgttaaata ctacacggta aaaaataaaa  1020
aatatttaaa acgacataaa attttattat caaaataagt aaatcacaaa ttgggggggg  1080
gtttggcttt tttttttttt gtccgaaaat tattatcatc ggtatatata actatgcttc  1140
ttatattata tttttttagt gaaaattcta attttcgtag gcatacattt aattaagata  1200
agtaaatatg atgaataaga acagattgat aaacgtgatt taagaaaaat aaagaaagga  1260
gaaatgaata gtagttccaa tttataaaaa aaagtcaagt acttaggagt taaggttcgt  1320
gagtagatgg gacatatcac ggtggaaaag gtagaagaag cttcaaagat acaaaagaaa  1380
aagaggggtt gagattctgt gttgtgatta atacaattca atcaaagaaa aagatgtgtc  1440
attttggaca tacaactctc cctaaaataa aatgccaata aacacagtac ttgtggacat  1500
catccaccca tccttttatg actcatcaca caaaaaaaac actttttttcc ttcttatttt  1560
tgaagatatt ctatgaagtt tgttgtaaac ttaaacaaaa taaatcaaca aaattgtcct  1620
atctctaaat agaggagttt ttaaaagtta aaaatcaata gaatagatac atgaagtagt  1680
cgaaggagat ttgacatttt attatgtata tatataaaat tattttaatc atatataaaa  1740
aatataattt tctatcaaaa agtgaatcct ttcatatttg tatctccgcc ctatctccaa  1800
atattaagct cacacatgaa aagagcgaga gacgaatgta gcctattggc tatgggttcc  1860
ctcactttcg atatgatgtg tataaaaaaa ttaattgaaa tctcaataaa tattagattt  1920
taacaataag ttaaaaattc aaatcattaa gtggggtctt gatttatttt cttttgtttt  1980
ctttctcaaa ctgatgtttt tattaaggat ttattagaaa aatatttcta tctctcgggg  2040
taggaattaa atttgctatg tgtatatcct accttttgtt aaatttagtt tacagaatta  2100
tcggttaaat atgttagata tgttattatt gttgttacgt ccgaatagac acccataggt  2160
gtagtgtagt caaattaata aaaccatgga atacgatggg atatcaaagt tgataatttt  2220
taactaaaaa aaaatgtcac tagatgattt tttttctct caattgtcta atcttgacag  2280
aaagatgtac ctaatgaaat aataaaagtg caacaaaaaa gaatagacaa atttccaaaa  2340
attgaatctt ttgttggtac tcgtcaacaa gttattcttc atgtctaaat cctaaaaaaa  2400
atatctcctc gtgtaaagac tggtatattg aaaatttaaa ataaattaat acatctaaac  2460
gtatcatatc ttctatataa tataaaattt ttagtgactc gtttcttaca attcaataat  2520
ttagtataaa taatttgtcg attgcgcgga tgaaagaaag gggtggtggt ggagatataa  2580
agtgtgatcg atagggtatc ttgtatgtga ttaatatagc taaacaaaaa ggtgaaaggc  2640
aaaaacatat atgaatggtg gtcctattcc atatttaaat ggattattag gatacgtcga  2700
tttcactttg caaaataccc tctatagatt catatatttt cttttctcat caactttttt  2760
ttctatcata taactagcct tactctggct tctcacgttt cacatgtctc aatgtttatt  2820
tgttttttttt ccactcttgg gcgtctaaag ggtttagaaa aatttgacaa tgtggaccac  2880
ccaaagttta taaaattaga attaaacagt catgaaggca tatacctagg agttccattt  2940
acatcttcac gtataaaatg tgtactttat attaatttta tttatctcat gattcttatt  3000
agagatgata aatgtaacat tttttttttg tttttattaa attttagaag agataacctt  3060
cttgattaat tctatgattt tcctttttta ttacgaaact gaaacttaac aattaactga  3120
gacataacaa acatgaatgt agttcatatc taaattaaca tcaaagccat catatctaac  3180
tcaactaagt tagtcatggt actcttgtga ttgacataaa ttttacaata aactttctta  3240
gctagaacgg actcaccaac aaatataaaa ccacagaaaa aattatatcg aactcaatac  3300
taaacaaaga agtatggaag actaaatatg ttgatacgag gtaggcttat tggtgatttt  3360
acaagggctt atatagcaaa agttgataca aacaaatggg ctaaaaagta aatggcccat  3420
ttattttatt tattttttcc attatcaata cacagatttg cacttcgtta gcggacaatt  3480
ttgggtaaat tatgaaaatt gggcctcttc acaatttaga tcccgaccgt gtggatggat  3540
ggacaaggaa attttaggtc cagttccagt tatattgggg agataaaagg aaaaattacg  3600
tggttaagta atatatatat tagttaatta gttattataa taattatttt agttaattat  3660
tattcgcgat taacattagt gataattatg taggctgaga ttttgagttt gtataatttg  3720
```

```
aaattttaag atataatttc tataactttt atatagtaca attttataaa atattatttg  3780
tataattgat aaaatttaga tgtttgtgtt tgtataaatt tatattttag atttatcaaa  3840
atataactca attattcaaa ctaaccataa tacgtacgaa ttcactcaca aattatacaa  3900
acaatacaat ttgaaccata gctgcaaccc ctaataatgc gagctacgac tataaagtat  3960
aattaaattt atttactata acggatattt gcaaaaattc tccttaggca taaccaataa  4020
tggcccctga acgagttgct cgaaaaagct aattaaagat cattcatttt tggaaaacta  4080
tataaatcag aagactaaaa tatagctttt agcttttcac ttgaaataag ttattttttta  4140
tttaaataaa ttattttgat aattattaaa cactctaata aattaaaaag atgattttta  4200
agtcagattg atcagctttt aagtccatct aaagatgctt taattacatc ttatttttta  4260
aaaaaaatta attattaaaa tttcaaagtt ttcattgctc tcgaagacat ttttttaaat  4320
gtccggtaca ttgtaataat atattattta atggaaggaa agtatagaag gattttttaa  4380
aaaaaataat taagtgataa actttttag aaattataat atgttgtata tttacgttaa  4440
atttcttaat tttttaattt aacatttccc aaaaattttg tgttatccaa atgtccgaat  4500
aacaaccaat taactgacac tgaatttgtg aattttacga gacaaatgtt cttgttaaaa  4560
tttcatatta ggtttcaact gtgagttatt tttggaaatt taaattatgt gtgttgatca  4620
aaatacttta aatatttttt tttcattata tcatgaattt taaatagata tcatatattt  4680
ttaaaagatt tagatttaaa ttttactatt aatatactaa accgacatag ccttaagttg  4740
aaaaaatatc aaattcatcg agggaaaacg aaaattgcaa gtatatttgg ccaaacgaag  4800
cacctgtcca tgaaatgcca cgtaaaaatt ctaagcaaaa atactacaat aagtgcatgg  4860
aatgagacga gcacgtgtca agttgaaaga agcacctgtc catgaaatgc cacgtaactc  4920
acaccttcaa aacctctcca ttgctacaaa tctccatatt tttgtttttt ttttttaaga  4980
aaaagataaa agtactagca                                               5000

SEQ ID NO: 205          moltype = DNA  length = 2058
FEATURE                 Location/Qualifiers
misc_feature            1..2058
                        note = Description of Artificial Sequence: Synthetic
                         polynucleotide
source                  1..2058
                        mol_type = other DNA
                        organism = synthetic construct
SEQUENCE: 205
atgtcggtga aaaattgtat gtcgattcaa tgttgcaaaa tcttgttcaa gtttctactg  60
tttatgatta ttatcatcag tagcgtgttt atcgatgtaa gagctaaaag agaaaatgaa  120
ggttgggaat ggggtttagg tcctctgatt aaaagagcag aaagaaaaac agttatttca  180
actgaaaatg gtgaagtctc atcagtcaca gtagctgatg gaacaaccta tcatcttcaa  240
ttcatcacat tggaacccaa ctccctcttc cttcccgttg ttctacatac agatatggtt  300
ttttatgttc acactgggtc ggggaagcta acttggatga atgaaaatga agagaaatca  360
gtggatttaa gaataggaga tgtattcagg ctgccttttg gatctatttt cttcttagag  420
agtgacttag accctatcag acacaaactt agactttatt ccatttttcc caattcaggc  480
cgagaatcac tgagtgagcc ctactccagc atccgtaaaa tggttcttgg attcgacaag  540
aaagtcctcc aagcggcatt tcatgtacca gaggatgtga tagaagaagt gttggctgga  600
acagaagtac cagccatagt gcacggtgtg ccaaagtcaa ctaagaagaa gaagaactta  660
tgggagatgg aggctcagtt catgaagact gttttaggaa ggggtagtta tagtttcttt  720
gacaaccgaa ggaataaaaa gaagagttct caattgttca atgtattcca agagaaacca  780
gattttgaga attgcaacgg gtggagcacg gtaataaaca ggaagaaatt gccggcgtta  840
aagggctcgc aaattggtat ttacgtagtg aacttaacga aaggatcaat gatggggcca  900
cattggaatc caatggctac tgaaattgga atagcaattc aaggagaagg aatggtgagg  960
gtagtttgct caaagagtgg aacagggtgt aaaaacatga ggtttaaagt ggaagaaggg  1020
gatgtatttg ttgtgccaag gtttgatcct atggctcaaa tggcattcaa taacaattca  1080
tttgtgtttg tggggtttag cacaactaca aagaaacatc atcctcagta cttaacgggg  1140
aaggcatcgg tcctccgaac attggatagg cagatattgg aagcatcttt caatgtgggc  1200
aacacaacaa tgcatcagat tcttgaagca cagggtgatt cagttatact ggagtgtaca  1260
tcttgtgctg aggaagagaa gaggttgatg gaggaagaaa tgaggaagga ggaggaggaa  1320
gcgaagaaga aagaggaggc aagaaaggct gaagaagaga gaagagagaa agaagcagag  1380
gaagaaagga agagacaaga ggaagaagca aggaaaaggg aggaagagga aataaggagg  1440
agacaggaag aagaggaagc taggagaaga caagaggaag aggaagagga aagagagaga  1500
caggaagcta gaaagaaaca agaagaggaa gaagcagcac aaagagaggc agagcaagca  1560
aggagagaag aggaagaagc agaaaaaaga aggcaggagg aggaagaatc aaggagagag  1620
gagaaagcaa gaagaaggca acaggaggaa gcaaggagga gagaggagga agaagcagca  1680
aaaaggcaac atgaggaaga agcagagaga gaggcagagg aagcaagaag gatagaggag  1740
gaagaagcac aaagagaggc agaagaagca aggagaatac aacaggagga agaagcagag  1800
agagcaagga gaagagaaga agaagcagaa acaagaagga aggaggagga ggaggaagaa  1860
tcaaggagac aagaggagga atcaaggagg agtgaagaag aggcagcaag agaggcagag  1920
agggaaaggc aagaggaagc tgaaagacaa gaagaagcta ggagacggga ggaagaaaca  1980
gaagagaggc atcaacaaga agaaaccgag gaagaggagc caggccaacc tgaaatgaac  2040
ggatattcct caaactag                                                 2058

SEQ ID NO: 206          moltype = AA  length = 685
FEATURE                 Location/Qualifiers
REGION                  1..685
                        note = Description of Artificial Sequence: Synthetic
                         polypeptide
source                  1..685
                        mol_type = protein
                        organism = synthetic construct
SEQUENCE: 206
MSVKNCMSIQ CCKILFKFLL FMIIIISSVF IDVRAKRENE GWEWGLGPLI KRAERKTVIS  60
TENGEVSSVT VADGTTYHLQ FITLEPNSLF LPVVLHTDMV FYVHTGSGKL TWMNENEEKS  120
```

```
VDLRIGDVFR LPFGSIFFLE SDLDPIRHKL RLYSIFPNSG RESLSEPYSS IRKMVLGFDK  180
KVLQAAFHVP EDVIEEVLAG TEVPAIVHGV PKSTKKKKNL WEMEAQFMKT VLGRGSYSFF  240
DNRRNKKKSS QLFNVFQEKP DFENCNGWST VINRKKLPAL KGSQIGIYVV NLTKGSMMGP  300
HWNPMATEIG IAIQGEGMVR VVCSKSGTGC KNMRFKVEEG DVFVVPRFDP MAQMAFNNNS  360
FVFVGFSTTT KKHHPQYLTG KASVLRTLDR QILEASFNVG NTTMHQILEA QGDSVILECT  420
SCAEEEKRLM EEEMRKEEEE AKKKEEARKA EEERREKEAE EERKRQEEEA RKREEEEIRR  480
RQEEEEARRR QEEEEEERER QEARKKQEEE EAAQREAEQA RREEEEAEKR RQEEEESRRE  540
EKARRRQQEE ARRREEEEAA KRQHEEEAER EAEEARRIEE EEAQREAEEA RRIQQEEEAE  600
RARRREEEAE TRRKEEEEEE SRRQEEESRR SEEEAAREAE RERQEEAERQ EEARRREEET  660
EERHQQEETE EEEPGQPEMN GYSSN                                        685

SEQ ID NO: 207         moltype = DNA  length = 633
FEATURE                Location/Qualifiers
misc_feature           1..633
                       note = Description of Artificial Sequence: Synthetic
                        polynucleotide
source                 1..633
                       mol_type = other DNA
                       organism = synthetic construct
SEQUENCE: 207
atgggtgatt ctgacgtcgg tgatcgtctt cccccctccat cttcttccga cgaactctcg  60
agctttctcc gacagattct ttcccgtact cctacagctc aaccttcttc accaccgaag  120
agtactaatg tttcctccgc tgagaccttc ttcccttccg tttccggcgg agctgtttct  180
tccgtcggtt atggagtctc tgaaactggc caagacaaat atgctttcga acacaagaga  240
agtggagcta aacagagaaa ttcgttgaag agaaacattg atgctcaatt ccacaacttg  300
tctgaaaaga agaggaggag caagatcaac gagaaaatga aagctttgca gaaactcatt  360
cccaattcca acaagactga taaagcctca atgcttgatg aagctataga atatctgaag  420
cagcttcaac ttcaagtcca gactttagcc gttatgaatg gtttaggctt aaaccctatg  480
cgattaccac aggttccacc tccaactcat acaaggatca atgagacctt agagcaagac  540
ctgaacctag agactcttct cgctgctcct cactcgctgg aaccagctaa aacaagtcaa  600
ggaatgtgct tttccacagc cactctgctt tga                                633

SEQ ID NO: 208         moltype = AA  length = 210
FEATURE                Location/Qualifiers
REGION                 1..210
                       note = Description of Artificial Sequence: Synthetic
                        polypeptide
source                 1..210
                       mol_type = protein
                       organism = synthetic construct
SEQUENCE: 208
MGDSDVGDRL PPPSSSDELS SFLRQILSRT PTAQPSSPPK STNVSSAETF FPSVSGGAVS  60
SVGYGVSETG QDKYAFEHKR SGAKQRNSLK RNIDAQFHNL SEKKRRSKIN EKMKALQKLI  120
PNSNKTDKAS MLDEAIEYLK QLQLQVQTLA VMNGLGLNPM RLPQVPPPTH TRINETLEQD  180
LNLETLLAAP HSLEPAKTSQ GMCFSTATLL                                    210

SEQ ID NO: 209         moltype = DNA  length = 1047
FEATURE                Location/Qualifiers
misc_feature           1..1047
                       note = Description of Artificial Sequence: Synthetic
                        polynucleotide
source                 1..1047
                       mol_type = other DNA
                       organism = synthetic construct
SEQUENCE: 209
atggaaagtc tcgcacacat tcctcccggt tatcgattcc atccgaccga tgaagaactc  60
gttgactatt atctcaagaa caaagttgca ttcccgggaa tgcaagttga tgttatcaaa  120
gatgttgatc tctacaaaat cgagccatgg gacatccaag agttatgtgg aagagggaca  180
ggagaagaga gggaatggta tttctttagc cacaaggaca agaaatatcc aactgggaca  240
cgaaccaata gagcaacggg ctccggattt tggaaagcaa cgggtcgaga caaggccatt  300
tactcaaagc aagagcttgt tgggatgagg aagactcttg tcttttacaa aggtagggcc  360
ccaaatggtc agaaatctga ttggataatg cacgaatacc gtcttgagac cgatgaaaat  420
ggaccgcctc atgaggaagg atgggtggtt tgtcgcgctt tcaagaagaa gctaaccacg  480
atgaactaca acaatccaag aacaatgatg ggatcatcat caggccaaga atctaactgg  540
ttcacgcagc aaatggatgt ggggaatggt aattactatc atcttcctga tctagagagt  600
ccgagaatgt ttcaaggctc atcatcatca tcactatcat cattacatca gaatgatcaa  660
gacccttatg gtgtcgtact cagcactatt aacgcaaccc caactacaat aatgcaacga  720
gatgatggtc atgtgattac caatgatgat gatcatatga tcatgatgaa cacaagtact  780
ggtgatcatc atcaatcagg attactagtc aatgatgatc ataatgatca agtaatggat  840
tggcaaacgc ttgacaagtt tgttgcttct cagctaatca tgagccaaga agaggaagaa  900
gttaacaaag atccatcaga taattcttcg aatgaaacat ttcatcatct ctctgaagag  960
caagctgcaa caatggtttc gatgaatgct tcttcctctt cttctccatg ttccttctac  1020
tcttgggctc aaaatacaca cacgtaa                                       1047

SEQ ID NO: 210         moltype = AA  length = 348
FEATURE                Location/Qualifiers
REGION                 1..348
                       note = Description of Artificial Sequence: Synthetic
                        polypeptide
```

```
source                  1..348
                        mol_type = protein
                        organism = synthetic construct
SEQUENCE: 210
MESLAHIPPG YRFHPTDEEL VDYYLKNKVA FPGMQVDVIK DVDLYKIEPW DIQELCGRGT  60
GEEREWYFFS HKDKKYPTGT RTNRATGSGF WKATGRDKAI YSKQELVGMR KTLVFYKGRA  120
PNGQKSDWIM HEYRLETDEN GPPHEEGWVV CRAFKKKLTT MNYNNPRTMM GSSSGQESNW  180
FTQQMDVGNG NYYHLPDLES PRMFQGSSSS SLSSLHQNDQ DPYGVVLSTI NATPTTIMQR  240
DDGHVITNDD DHMIMMNTST GDHHQSGLLV NDDHNDQVMD WQTLDKFVAS QLIMSQEEEE  300
VNKDPSDNSS NETFHHLSEE QAATMVSMNA SSSSSPCSFY SWAQNTHT          348

SEQ ID NO: 211          moltype = DNA  length = 975
FEATURE                 Location/Qualifiers
misc_feature            1..975
                        note = Description of Artificial Sequence: Synthetic
                         polynucleotide
source                  1..975
                        mol_type = other DNA
                        organism = synthetic construct
SEQUENCE: 211
atggataata taatgcaatc gtcaatgcca ccgggattcc gatttcatcc gacagaggaa  60
gagcttgtgg gttattacct agataggaag atcaattcaa tgaagagtgc tttagatgtc  120
attgtagaga ttgatctcta caaaatggag ccatgggata tacaagcgag gtgtaaacta  180
gggtatgaag agcaaaacga gtggtacttc tttagtcata aggacaggaa gtaccctacc  240
gggactagga ccaaccgagc cactgcggct gggttctgga aagccacggg tagagacaag  300
gcggtactat caaaaaacag tgtcatcgga atgcggaaga cacttgtcta ctacaagggt  360
cgagctccta atggaagaaa gtccgattgg atcatgcacg aataccgtct ccaaaactcc  420
gagcttgccc cggttcagga ggaaggctgg gtggtgtgtc gagcatttag gaagccaatt  480
ccaaaccaga ggccattagg gtacgagcca tggcagaacc agctctacca cgtcgaaagt  540
agtaacaact actcatcttc agtgacaatg aacacgagtc atcatatcgg tgcatcttca  600
tcaagtcata accttaatca aatgctcatg agcaataacc actacaatcc taataataca  660
tcctcatcga tgcatcaata tggcaacatt gagctcccgc agttggacag cccgagcttg  720
tcgcctagtt tagggacgaa taaagatcag aacgagagtt tcgagcaaga agaagagaag  780
agctttaact gtgtggattg gagaacacta gataccttgc ttgagacaca agtcatacat  840
ccgcataacc ctaatattct tatgttcgaa acgcagtcgt ataatccggc gccaagcttc  900
ccttccatgc atcaaagcta taatgaggtc gaagctaata ttcatcattc tcttggatgc  960
ttccctgact cgtaa                                                   975

SEQ ID NO: 212          moltype = AA  length = 324
FEATURE                 Location/Qualifiers
REGION                  1..324
                        note = Description of Artificial Sequence: Synthetic
                         polypeptide
source                  1..324
                        mol_type = protein
                        organism = synthetic construct
SEQUENCE: 212
MDNIMQSSMP PGFRFHPTEE ELVGYYLDRK INSMKSALDV IVEIDLYKME PWDIQARCKL  60
GYEEQNEWYF FSHKDRKYPT GTRTNRATAA GFWKATGRDK AVLSKNSVIG MRKTLVYYKG  120
RAPNGRKSDW IMHEYRLQNS ELAPVQEEGW VVCRAFRKPI PNQRPLGYEP WQNQLYHVES  180
SNNYSSSVTM NTSHHIGASS SSHNLNQMLM SNNHYNPNNT SSSMHQYGNI ELPQLDSPSL  240
SPSLGTNKDQ NESFEQEEEK SFNCVDWRTL DTLLETQVIH PHNPNILMFE TQSYNPAPSF  300
PSMHQSYNEV EANIHHSLGC FPDS                                         324

SEQ ID NO: 213          moltype = DNA  length = 2103
FEATURE                 Location/Qualifiers
misc_feature            1..2103
                        note = Description of Artificial Sequence: Synthetic
                         polynucleotide
source                  1..2103
                        mol_type = other DNA
                        organism = synthetic construct
SEQUENCE: 213
atggaaagga tacctgaagt tagagaatca actaggcagt ttcctatagg ggctaaggtg  60
gctcatactt tctcaacctc caagaaggag gtcggtatta gaggctttcg agattttgac  120
ttggctattc caatacaaac atggaaagga aagacctcct atcaggagga agaagacctg  180
atggtcgatg ctggtacaat caagcgtagt gatgattcac ttgaagatag tggctctaca  240
tcatttcatg gggcgagtca tcctccggaa cctgttgata cagacctaat gagaccagtg  300
tatgtaccaa ttggtcaaaa caaagcagat gggaaatgtc tggtgaaaaa cgtatctttg  360
aagggtcctt tcttggacga tctttcaatc cggatgccaa atgtgaaacc aagcccatcc  420
cttctttcac cggcagagag cttggttgaa gagccaaatg atctaggtgt aatctcctct  480
ccatttacag ttcctcgtcc ttctcaaaac acagaaacca gtctgcctcc tgattccgaa  540
gagaaagaat gtatttggga tgcatcactg cctccaagcg gaaatgtgag tccacttagt  600
agcattgata gtactggtgt tgtgagatct atgagtattg tcaacagttg cacaagcacg  660
tacaggagtg atgtgcttat gagtgatggc atgcttagtg tggacagaaa ctatgagagc  720
acgaaaggga gcattcgagg ggattcactc gaaagtggta aaactagcct tagcagagca  780
agtgacagta gtggacttag tgatgatagt aattggagta acatcactgg cagtgccaat  840
aagcctcaca aggaaatgga tcctagatgg aaggctattc tcgcaattcg ggcacgtgat  900
ggtatattag gcatgagcca ctttaagtta ctcaaaagac ttggttgtgg agacattgga  960
```

```
agtgtttatc tttctgagct tagcgggact cgctgctatt ttgcaatgaa agtgatggat  1020
aaggcatcac ttgcaagcag gaagaaattg acgcgtgctc agacagaaag agaaatccta  1080
cagttattag accatccatt cttgccaaca ttgtacactc attttgagac cgatcgcttc  1140
tcatgtttgg tcatggaata ttgtcctgga ggagatctgc atactctacg acagcgacaa  1200
cctgggaagc atttttcaga atatgctgca aggttttatg cagcagaagt tctattggcg  1260
cttgaatatc tacatatgct tggtgtagtg tacagggatt taaaacctga aaatgttctt  1320
gtgcgtgacg atggccacat tatgctttca gattttgacc tctccttgag atgtgcagtt  1380
tcacctacgc tcataaggat ctcatctgat gatccttcta aacgaggagc tgcattttgt  1440
gtgcagccag cctgtattga gcccacaact gtatgcatgc agccagcatg ctttcttcca  1500
cgtttatttc ctcaaaagag caagaaaaaa acacctaagc ctcgagctga ttctgggttt  1560
caagctaatt caatgcctga gctagttgcg gaacctactt cagcacggtc aatgtcattt  1620
gttgggactc atgaatattt ggcccccgag attatcaagg gagaaggcca tggcagtgca  1680
gttgactggt ggacatttgg tattttcctt catgaactac tctatggaaa gacccctttc  1740
aagggatcag gaaacagggc aactcttttc aatgtagttg gccaacaact taaatttcca  1800
gattctcctg caaccagtta tgccagccgt gatctgatac gtggcttgct tgttaaagag  1860
cctcaaaacc ggcttggggt gaaacgagga gcaactgaga tcaagcaaca tcctttcttt  1920
gaaggtgtta attgggctct aatacgttgc agtacaccac ctgaagtgcc aagacccgtg  1980
gagccagact accctgcgaa gtacgggcaa gtgaaccctg ttggggttgg caataccagt  2040
aaaagagtgg taggggcaga tgcaaagtct gggggtaaat atcttgactt tgagttcttt  2100
tag                                                                2103
```

```
SEQ ID NO: 214          moltype = AA  length = 700
FEATURE                 Location/Qualifiers
REGION                  1..700
                        note = Description of Artificial Sequence: Synthetic
                         polypeptide
source                  1..700
                        mol_type = protein
                        organism = synthetic construct
SEQUENCE: 214
MERIPEVRES TRQFPIGAKV AHTFSTSKKE VGIRGFRDFD LAIPIQTWKG KTSYQEEEDL  60
MVDAGTIKRS DDSLEDSGST SFHGASHPPE PVDTDLMRPV YVPIGQNKAD GKCLVKNVSL  120
KGPFLDDLSI RMPNVKPSPS LLSPAESLVE EPNDLGVISS PFTVPRPSQN TETSLPPDSE  180
EKECIWDASL PPSGNVSPLS SIDSTGVVRS MSIVNSCTST YRSDVLMSDG MLSVDRNYES  240
TKGSIRGDSL ESGKTSLSRA SDSSGLSDDS NWSNITGSAN KPHKGNDPRW KAILAIRARD  300
GILGMSHFKL LKRLGCGDIG SVYLSELSGT RCYFAMKVMD KASLASRKKL TRAQTEREIL  360
QLLDHPFLPT LYTHFETDRF SCLVMEYCPG GDLHTLRQRQ PGKHFSEYAA RFYAAEVLLA  420
LEYLHMLGVV YRDLKPENVL VRDDGHIMLS DFDLSLRCAV SPTLIRISSD DPSKRGAAFC  480
VQPACIEPTT VCMQPACFLP RLFPQKSKKK TPKPRADSGF QANSMPELVA EPTSARSMSF  540
VGTHEYLAPE IIKGEGHGSA VDWWTFGIFL HELLYGKTPF KGSGNRATLF NVVGQQLKFP  600
DSPATSYASR DLIRGLLVKE PQNRLGVKRG ATEIKQHPFF EGVNWALIRC STPPEVPRPV  660
EPDYPAKYGQ VNPVGVGNTS KRVVGADAKS GGKYLDFEFF                        700
```

```
SEQ ID NO: 215          moltype = DNA  length = 1068
FEATURE                 Location/Qualifiers
misc_feature            1..1068
                        note = Description of Artificial Sequence: Synthetic
                         polynucleotide
source                  1..1068
                        mol_type = other DNA
                        organism = synthetic construct
SEQUENCE: 215
atggcttttt ctgcaccatc actttccaaa ttctctcttt tggttgccat ttcagcatca  60
gctctcctct gttgtgcttt tgcccgtgat ttctccattg ttggatacac gccggagcat  120
ttgacaaaca ctgacaagct tctagagctc ttcgagtcat ggatgtcaga acacagcaag  180
gcttacaaaa gcgtggagga gaaggtgcac aggtttgagg ttttcagaga gaatctgatg  240
catatagacc agaggaacaa tgagatcaac agttactggc tcggtttgaa cgagtttgcg  300
gatttgaccc atgaagagtt caaaggaaga tatctaggac ttgcaaagcc acaattctct  360
agaaagagac agccctcagc taacttcagg tacagagata tcacggactt gcctaaatcc  420
gtagactgga gaaagaaagg cgctgtggct cctgtcaagg accagggtca atgtggtagc  480
tgttgggcat tttcaacagt tgcagctgtc gaggggatca accagatcac aacagggaat  540
ctgagttcgc tttcagagca agaactcata gactgtgaca caactttcaa cagtggctgc  600
aatggaggtc tcatggacta cgcattccag tacataattt cgaccggtgg tctccacaaa  660
gaagatgatt acccttatct catggaggaa ggaatttgtc aagagcagaa agaggatgtg  720
gaacgtgtga caatcagcgg ctacgaagat gtccctgaaa atgatgacga aagcctggtg  780
aaggctttag ctcatcagcc agtcagtgtg gctattgagg cttcaggaag agacttccag  840
ttctacaaag gggagtgttt taatggtaaa tgtggaacag acctagacca cggtgtggca  900
gcggttggat atggttcatc aaagggatct gactatgtta ttgtcaagaa ctcatgggga  960
ccaagatggg gagagaaagg gtttattagg atgaagagaa acactggtaa accagaggga  1020
ctctgtggaa tcaacaagat ggcctcatat cctaccaaga ccaagtga               1068
```

```
SEQ ID NO: 216          moltype = AA  length = 355
FEATURE                 Location/Qualifiers
REGION                  1..355
                        note = Description of Artificial Sequence: Synthetic
                         polypeptide
source                  1..355
                        mol_type = protein
                        organism = synthetic construct
```

```
SEQUENCE: 216
MAFSAPSLSK FSLLVAISAS ALLCCAFARD FSIVGYTPEH LTNTDKLLEL FESWMSEHSK  60
AYKSVEEKVH RFEVFRENLM HIDQRNNEIN SYWLGLNEFA DLTHEEFKGR YLGLAKPQFS  120
RKRQPSANFR YRDITDLPKS VDWRKKGAVA PVKDQGQCGS CWAFSTVAAV EGINQITTGN  180
LSSLSEQELI DCDTTFNSGC NGGLMDYAFQ YIISTGGLHK EDDYPYLMEE GICQEQKEDV  240
ERVTISGYED VPENDDESLV KALAHQPVSV AIEASGRDFQ FYKGGVFNGK CGTDLDHGVA  300
AVGYGSSKGS DYVIVKNSWG PRWGEKGFIR MKRNTGKPEG LCGINKMASY PTKTK       355

SEQ ID NO: 217          moltype = DNA  length = 1071
FEATURE                 Location/Qualifiers
misc_feature            1..1071
                        note = Description of Artificial Sequence: Synthetic
                         polynucleotide
source                  1..1071
                        mol_type = other DNA
                        organism = synthetic construct
SEQUENCE: 217
atggctcttt cttcaccttc aagaatcctc tgttttgctc ttgccttatc cgctgcttct  60
ctctccctct ctttcgcttc ttcccacgat tactccatcg ttggatactc ccccgaggat  120
ttggaatctc atgacaaact catagaactc ttcgaaaact ggatctcaaa ttttgagaaa  180
gcttatgaaa ccgttgaaga gaagtttctt aggttcgaag ttttcaagga taatctaaag  240
cacatcgatg agactaacaa gaaagggaaa agctactggc tcgggctcaa cgagtttgcg  300
gatttgagcc atgaggagtt caagaaaatg tatttagggc tcaagactga tatagtgaga  360
cgcgatgaag aaagatctta cgcagagttc gcttacaggg acgtcgaagc tgttcctaag  420
tctgttgact ggagaaagaa aggagctgtg gcggaagtta agaaccaggg ctcttgtgga  480
agttgttggg cgttttcgac agtagcagct gtcgaaggta taaacaagat tgtgacagga  540
aacttgacaa cattgtcaga acaagaactc atagactgtg acacgaccta caacaatggc  600
tgcaacggtg gtctcatgga ctatgccttt gagtacattg ttaagaacgg aggtctacgc  660
aaggaagaag attatcctta ctctatggaa gaaggaactt gcgagatgca aaaggatgaa  720
tctgaaacag taaccattaa tggacaccaa gacgtaccta ctaatgatga gaagagtctc  780
ttgaaggcat tggctcatca gcctctcagt gtcgccattg atgcatctgg tagagagttc  840
cagttctata gcggcggcgt gtttgatggg cggtgcgggg ttgatcttga ccacggtgtg  900
gctgcggttg ggtatggatc aagcaagggt tcagattaca tcattgtgaa gaattcttgg  960
ggaccaaaat ggggagaaaa aggttacatc aggctgaaga ggaacactgg gaaaccagag  1020
ggtctctgtg gaatcaacaa gatggcttct ttccccacca aaactaagtg a           1071

SEQ ID NO: 218          moltype = AA  length = 356
FEATURE                 Location/Qualifiers
REGION                  1..356
                        note = Description of Artificial Sequence: Synthetic
                         polypeptide
source                  1..356
                        mol_type = protein
                        organism = synthetic construct
SEQUENCE: 218
MALSSPSRIL CFALALSAAS LSLSFASSHD YSIVGYSPED LESHDKLIEL FENWISNFEK  60
AYETVEEKFL RFEVFKDNLK HIDETNKKGK SYWLGLNEFA DLSHEEFKKM YLGLKTDIVR  120
RDEERSYAEF AYRDVEAVPK SVDWRKKGAV AEVKNQGSCG SCWAFSTVAA VEGINKIVTG  180
NLTTLSEQEL IDCDTTYNNG CNGGLMDYAF EYIVKNGGLR KEEDYPYSME EGTCEMQKDE  240
SETVTINGHQ DVPTNDEKSL LKALAHQPLS VAIDASGREF QFYSGGVFDG RCGVDLDHGV  300
AAVGYGSSKG SDYIIVKNSW GPKWGEKGYI RLKRNTGKPE GLCGINKMAS FPTKTK      356

SEQ ID NO: 219          moltype = DNA  length = 1257
FEATURE                 Location/Qualifiers
misc_feature            1..1257
                        note = Description of Artificial Sequence: Synthetic
                         polynucleotide
source                  1..1257
                        mol_type = other DNA
                        organism = synthetic construct
SEQUENCE: 219
atgacgaaaa aggcggtgct tattgggatc aattacccag gaaccaaggc ggagttacgg  60
ggatgcgtca acgatgttcg tcgtatgtac aaatgtctcg ttgaacggta cggcttctcc  120
gaggagaaca tcaccgttct catcgacacc gatgaatcct ctactcagcc tactggcaag  180
aacatccgcc gcgcgcttgc tgatctcgtc gaatctgccg attccggcga cgttcttgtc  240
gttcattaca gtggacacgg tacgaggttg ccggctgaga ctggtgaaga cgatgacact  300
ggtttcgacg agtgtattgt tccttgcgac atgaatctga ttactgatga tgattttaga  360
gatcttgtgg acaaggttcc tccaggttgc agaatgacaa tcatttcaga ctcttgtcac  420
agtggtggcc taatcgacga agccaaggag cagattggag agagcactaa gaaagaagcc  480
gaggacgaag atgaatctga agaatcttct tcaagattcg ggtttaggaa gttcttgcgc  540
agcaaagtgg aaggcgccat cgagtctcga gggtttcaca ttggagggaa caagaaggat  600
gaagatgagg cggaagaaat cgagactaag gagattgagc ttgaagacgg agaaacgatc  660
catgccaaag acaaatctct tcctctgcag accttgattg atattctcaa gcagcaaaca  720
gggaatgata atatcgaagt tgggaaaatc aggccaagcc tttttgatgc gtttggtgat  780
gattcgagcc cgaaagtgaa gaagtttatg aaagtgatct taggtaagct tcaggctgga  840
aatggagaag aaggtggatt aatgggaatg cttggcaaat tggcttcagg gtttcttgag  900
ggtaaactaa acgatgaaga ctatgtgaaa cccgctatgc agacacacgt tgggagtaaa  960
gaagaggttt atgctggtgg atcaagaggt tcggttccgc ttccagacag cgggatactg  1020
atcagcggtt gccaaaccga tcagacctct gctgatgcga ctccagcggg gaaaccaact  1080
```

```
gaggcttatg gagcgatgag caattcgata cagacgatat tggaggagac agacggtgag  1140
atatcaaaca gagaaatggt tacaagggct aggaaggcat tgaagaagca agggtttact  1200
cagcagccag gtttgtattg ccatgatggt tatgccaacg ctcctttcat ctgttga     1257

SEQ ID NO: 220         moltype = AA  length = 418
FEATURE                Location/Qualifiers
REGION                 1..418
                       note = Description of Artificial Sequence: Synthetic
                        polypeptide
source                 1..418
                       mol_type = protein
                       organism = synthetic construct
SEQUENCE: 220
MTKKAVLIGI NYPGTKAELR GCVNDVRRMY KCLVERYGFS EENITVLIDT DESSTQPTGK  60
NIRRALADLV ESADSGDVLV VHYSGHGTRL PAETGEDDDT GFDECIVPCD MNLITDDDFR  120
DLVDKVPPGC RMTIISDSCH SGGLIDEAKE QIGESTKKEA EDEDESEESS SRFGFRKFLR  180
SKVEGAIESR GFHIGGNKKD EDEAEEIETK EIELEDGETI HAKDKSLPLQ TLIDILKQQT  240
GNDNIEVGKI RPSLFDAFGD DSSPKVKKFM KVILGKLQAG NGEEGGLMGM LGKLASGFLE  300
GKLNDEDYVK PAMQTHVGSK EEVYAGGSRG SVPLPDSGIL ISGCQTDQTS ADATPAGKPT  360
EAYGAMSNSI QTILEETDGE ISNREMVTRA RKALKKQGFT QQPGLYCHDG YANAPFIC    418

SEQ ID NO: 221         moltype = DNA  length = 2965
FEATURE                Location/Qualifiers
misc_feature           1..2965
                       note = Description of Artificial Sequence: Synthetic
                        polynucleotide
source                 1..2965
                       mol_type = other DNA
                       organism = synthetic construct
SEQUENCE: 221
gtgatcaatt ccagtgtgca caccacttgt ttgatgaatt gtctctgtgg agattttttt  60
ttagatggga ggttgtttct ctgtttcatt gccatgtgat caagtagtga gtcagttctc  120
tcagttgtta tgtgtcaggg gaagttatat tcacaatctc tccaagaatc tggcttctct  180
gcagaaggcc atgcgaatgc tcaaggctcg gcaatatgat gtgataagaa ggttggaaac  240
agaagagttt acagggcgtc aacaaaggct ttcccaagtt caggtatggc ttactagtgt  300
cctaatcatt caaaaccagt ttaatgatct gcttcgtagt aatgaagttg agcttcaaag  360
gttgtgtctt tgtggtttct gctccaaaga tttgaaattg agctatcgtt atgggaaaag  420
agttatcatg atgttgaagg aagttgagag tctcagttct caaggattct ttgatgtggt  480
ttctgaggca actccgtttg ctgatgtgga tgagatccct tttcaaccca caattgttgg  540
tcaggagata atgcttgaaa aggcatggaa ccgtctcatg gaagatggat ccgggatttt  600
gggtctgtac ggtatggggg gagtaggcaa aacgacacta ctcacgaaga tcaacaataa  660
gttttctaaa atagatgaca gatttgatgt tgtgatatgg gttgttgtgt ctagaagttc  720
aacagtccgt aagatacaaa gagacatagc agaaaaggta ggccttgggg gaatggagtg  780
gagcgagaaa aacgataacc agatagccgt tgacatccac aatgtcctta ggagacgaaa  840
gtttgtttta ttgttggatg acatatggga gaaagtgaat ttaaaagcgg ttggagtccc  900
gtatccaagc aaagataacg gatgcaaggt agcattcact actcgttctc gagatgtgtg  960
tgggcgcatg gggttgatg atccgatgga agttagctgt ctacaacccg aagaatcttg  1020
ggatttgttt caaatgaagg ttgggaaaaa tacactggga agtcacccag acattcccgg  1080
acttgctaga aaagtcgcta ggaaatgtcg tggcctacca ttagcactca atgttatcgg  1140
tgaagctatg gcatgcaaaa gaacagtaca tgaatggtgt catgccattg acgttttaac  1200
atcatctgcc atagattttt caggtatgga agatgaaatt ctccatgttt tgaagtatag  1260
ctatgataat ttaaatgggg agctgatgaa atcctgcttc ctctattgct ctctgtttcc  1320
tgaagactat cttattgata aagaggggtt ggtagactac tggataagtg agggattcat  1380
aaatgaaaaa gaaggcagag agaggaatat taaccaaggt tatgagataa ttggtaccct  1440
tgtccgtgca tgtttgttgt tggaggaaga aaggaacaaa tcaaacgtga aaatgcatga  1500
tgtggttcgt gagatggctc tatggatatc atccgatctt gggaagcaaa aggagaaatg  1560
tattgtgcga gctggtgttg ggttacgtga agtaccaaaa gtcaaggatt ggaacactgt  1620
gagaaagatt tctttgatga ataatgagat tgaagagata tttgacagtc acgagtgtgc  1680
tgcacttaca actctatttc tccaaaagaa cgacgtggta aagatctcgg ctgaattctt  1740
tcgatgtatg cctcatctgg tggttttaga tctatcagag aatcagagtc ttaatgaatt  1800
accagaagaa atatcagagc tggcctcttt gagatatttc aacttgtcat atacatgtat  1860
acatcaacta cccgttggtt tatggacatt gaaaaagcta atacatctga atctcgaaca  1920
catgagcagt cttgggagta tattagggat atcaaatttg tggaatttga ggacattggg  1980
actacgagat tccagactgt tgctagatat gagtttagtg aaggagctgc agctcttaga  2040
acatctagaa gttataaccc tagatatatc atcaagtttg gttgcagagc cattgttatg  2100
ctctcaaagg ttggtggaat gtataaaaga ggtagatttt aagtacctta aggaagaatc  2160
agtgagagta ttgactttgc caaccatggg taatctccgc aagctcggga taaaaagatg  2220
tggaatgagg gagataaaga tagagaggac aacttcatca tcgtctcgga acaaaagtcc  2280
cacaactcca tgcttctcaa acctctccag agtctttata gctaaatgcc atggtcttaa  2340
ggatttgacg tggcttttgt ttgctcctaa tcttactttt cttgaagttg ggttctcaaa  2400
ggaagtagag gatataatta gtgaagagaa agctgaggag cattcagcta cgattgttcc  2460
ttttaggaaa ttggagacac tacacctgtt tgaattacgc gggctcaaga gaatctatgc  2520
aaaggctctg cattttccgt gtctgaaagt tatccacgta gaaaaatgtg aaaagctgag  2580
aaagcttcca ttggattcta aaagtgggat cgcgggtgaa gaacttgtca tatattatgg  2640
agagagagaa tggatagaaa gggttgaatg ggaggaccaa gcaactcaac tccgtttctt  2700
accttcatcc aggtggcggt ggagagaaac ataatgaact tcactttctt ctacaaactt  2760
ttgttgtcat ggtctaaaga catttgccgg tgtgtaaatc tcttccttgt ctcttcttgt  2820
ttgcataacc gttctcatcg ttcttttggt tagtgatcat tggatttgta cttatctctt  2880
tctctaaacg atgagtgttt gtttcggctt catagaaaca ttacacagag actcatgaga  2940
```

```
aaatgaataa aaacttgcaa gttcc                                      2965

SEQ ID NO: 222          moltype = AA  length = 889
FEATURE                 Location/Qualifiers
REGION                  1..889
                        note = Description of Artificial Sequence: Synthetic
                         polypeptide
source                  1..889
                        mol_type = protein
                        organism = synthetic construct
SEQUENCE: 222
MGGCFSVSLP CDQVVSQFSQ LLCVRGSYIH NLSKNLASLQ KAMRMLKARQ YDVIRRLETE  60
EFTGRQQRLS QVQVWLTSVL IIQNQFNDLL RSNEVELQRL CLCGFCSKDL KLSYRYGKRV  120
IMMLKEVESL SSQGFFDVVS EATPFADVDE IPFQPTIVGQ EIMLEKAWNR LMEDGSGILG  180
LYGMGGVGKT TLLTKINNKF SKIDDRFDVV IWVVVSRSST VRKIQRDIAE KVGLGGMEWS  240
EKNDNQIAVD IHNVLRRRKF VLLLDDIWEK VNLKAVGVPY PSKDNGCKVA FTTRSRDVCG  300
RMGVDDPMEV SCLQPEESWD LFQMKVGKNT LGSHPDIPGL ARKVARKCRG LPLALNVIGE  360
AMACKRTVHE WCHAIDVLTS SAIDFSGMED EILHVLKYSY DNLNGELMKS CFLYCSLFPE  420
DYLIDKEGLV DYWISEGFIN EKEGRERNIN QGYEIIGTLV RACLLLEEER NKSNVKMHDV  480
VREMALWISS DLGKQKEKCI VRAGVGLREV PKVKDWNTVR KISLMNNEIE EIFDSHECAA  540
LTTLFLQKND VVKISAEFFR CMPHLVVLDL SENQSLNELP EEISELASLR YFNLSYTCIH  600
QLPVGLWTLK KLIHLNLEHM SSLGSILGIS NLWNLRTLGL RDSRLLLDMS LVKELQLLEH  660
LEVITLDISS SLVAEPLLCS QRLVECIKEV DFKYLKEESV RVLTLPTMGN LRKLGIKRCG  720
MREIKIERTT SSSSRNKSPT TPCFSNLSRV FIAKCHGLKD LTWLLFAPNL TFLEVGFSKE  780
VEDIISEEKA EEHSATIVPF RKLETLHLFE LRGLKRIYAK ALHFPCLKVI HVEKCEKLRK  840
LPLDSKSGIA GEELVIYYGE REWIERVEWE DQATQLRFLP SSRWRWRET             889

SEQ ID NO: 223          moltype = DNA  length = 3435
FEATURE                 Location/Qualifiers
misc_feature            1..3435
                        note = Description of Artificial Sequence: Synthetic
                         polynucleotide
source                  1..3435
                        mol_type = other DNA
                        organism = synthetic construct
SEQUENCE: 223
atggcatctt cttcttcttc ttctagatgg agctatgatg ttttcttaag ttttagaggc  60
gaagatactc gaaaaacgtt tacaagtcac ttatacgaag tcttgaatga taagggaata  120
aaaacctttc aagatgataa aaggctagag tacggcgcaa ccatcccagg tgaactctgt  180
aaagctatag aagagtctca atttgccatt gttgtttctc cagagaatta tgcaacatca  240
aggtggtgtt tgaatgaact agtgaagatc atggaatgca aaactcgatt taagcaaact  300
gttataccga tattctatga tgtggatcca tcacatgttc ggaaccaaaa ggagagcttt  360
gcaaaagcct ttgaagaaca tgaaacaaag tataaggatg atgttgaggg aatacaaaga  420
tggaggattg ctttaaatga agcggccaat ctcaaaggct cctgtgataa tcgtgacaag  480
actgatgcag actgtattcg acagattgtt gaccaaatct catccaaatt atgcaagatt  540
tctttatctt atttgcaaaa cattgttgga atagatactc atttagagaa aatagaatcc  600
ttactagaga taggaatcaa tggtgttcgg attatgggga tctggggaat ggggggagtc  660
ggtaaaacaa caatagcaag agctatattt gatactcttt taggaagaat ggatagttcc  720
tatcaatttg atggtgcttg tttccttaag gatattaaag aaaacaaacg tggaatgcat  780
tctttgcaaa atgcccttct ctctgaactt ttaagggaaa aagctaatta caataatgag  840
gaggatggaa agcaccaaat ggctagtaga cttcgttcga agaaggtcct aattgtgctt  900
gatgatatag ataataaaga tcattatttg gagtatttag caggtgatct tgattggttt  960
ggtaatggta gtagaattat tataacaact agagacaagc atttgataga gaagaatgat  1020
ataatatatg aggtgactgc actacccgat catgaatcca ttcaattgtt caaacaacat  1080
gctttcggaa aagaagttcc aaatgagaat tttgagaagc tttcattaga ggtagtaaat  1140
tatgctaaag gccttccttt agccctcaaa gtgtggggtt ctttgctgca taacctacga  1200
ttaactgaat ggaaaagtgc tatagagcac atgaaaaata actcttattc tggaattatt  1260
gataagctca aaataagtta tgatggatta gagcccaaac aacaagagat gtttttagat  1320
atagcatgct tcttgcgagg ggaagaaaaa gattacatcc tacaaatcct tgagagttgt  1380
catattggag ctgaatacgg gttacgtatt ttaattgaca aatctcttgt gttcatctct  1440
gaatataatc aggttcaaat gcatgactta atacaggata tgggtaaata tatagtgaat  1500
tttcaaaaag atcccggaga acgtagcaga ttatggctcg ccaaggaagt cgaagaagtg  1560
atgagcaaca acacagggac catggcaatg gaagcaattt gggtttcttc ttattctagt  1620
actctacgct ttagcaatca ggccgtgaaa aatatgaaaa ggcttagggt atttaacatg  1680
gggaggtcgt cgacacatta tgccatcgat tatctgccca acaacttgcg ttgttttgtt  1740
tgcactaact atccttggga gtcatttcca tctacatttg aactcaaaat gcttgttcac  1800
ctccaactcc gacacaattc tctgcgtcat ttatggacag aaacaaagca tttgccgtct  1860
ctacggagga tagatctcag ctggtctaaa agattgacgc gaacaccaga tttcacgggg  1920
atgccaaatt tggagtatgt gaatttgtat caatgtagta atcttgaaga agttcaccat  1980
tccctgggat gttgcagcaa agtcattggt ttatatttga atgattgtaa aagccttaag  2040
aggtttccat gtgttaacgt ggaatctctt gaatatctgg gtctaagaag ttgcgatagt  2100
ttagagaaat tgccagaaat ctacgggaga atgaagccgg agatacagat tcacatgcaa  2160
ggctctggga taagggaact accatcatct atttttcagt acaaaactca tgttaccaag  2220
ctattgttgt ggaatatgaa aaaccttgta gctcttccaa gcagcatatg taggttgaaa  2280
agtttggtta gtctgagtgt gtcgggttgc tcaaaacttg aaagcttgcc agaagagata  2340
ggggatttag acaacttacg ggtgtttgat gccagtgata ctctaatttt acgacctccg  2400
tcttccatca tacgcttgaa caaacttata atcttgatgt ttcgaggctt caaagatgga  2460
gtgcactttg agttccctcc tgtggctgaa ggattacact cattggaata tctgaatctc  2520
agttactgca atctaataga tggaggactt ccggaagaga ttggatcctt atcctctttg  2580
```

```
aaaaagttgg atctcagtag aaataatttt gagcatttgc cttcaagtat agcccaactt  2640
ggtgctcttc aatccttaga cttaaaagat tgccagaggc ttacacagct accagaactt  2700
cccccagaat taaatgaatt gcatgtagat tgtcatatgg ctctgaaatt tatccattat  2760
ttagtaacaa agagaaagaa actacataga gtgaaacttg atgatgcaca caatgatact  2820
atgtacaatt tgtttgcata taccatgttt cagaatatct cttccatgag gcatgacatc  2880
tctgcttcag attccttgtc actaacagta tttaccggtc aaccgtatcc tgaaaagatc  2940
ccgagttggt tccaccatca gggttgggat agtagtgtat cagtcaattt gcctgaaaat  3000
tggtatatac ctgataaatt cttgggattt gctgtatgtt actctcgtag cttaattgac  3060
acaacagctc acttgattcc cgtatgtgat gacaagatgt cgcgcatgac ccagaaactt  3120
gccttatcag aatgtgatac agaatcatcc aactattcag aatgggatat acatttttc  3180
tttgtacctt ttgctggctt atgggataca tctaaggcaa atggaaaaac accaaatgat  3240
tatgggatta ttaggctatc tttttctgga gaagagaaga tgtatggact tcgtttgttg  3300
tataaagaag gaccagaggt taatgccttg ttacaaatga gggaaaatag caatgaacca  3360
acagaacatt ccactgggat aaggaggact caatataaca acagaacttc cttttatgag  3420
ctcatcaatg ggtga                                                   3435
```

```
SEQ ID NO: 224          moltype = AA  length = 1144
FEATURE                 Location/Qualifiers
REGION                  1..1144
                        note = Description of Artificial Sequence: Synthetic
                         polypeptide
source                  1..1144
                        mol_type = protein
                        organism = synthetic construct
SEQUENCE: 224
MASSSSSSRW SYDVFLSFRG EDTRKTFTSH LYEVLNDKGI KTFQDDKRLE YGATIPGELC  60
KAIEESQFAI VVFSENYATS RWCLNELVKI MECKTRFKQT VIPIFYDVDP SHVRNQKESF  120
AKAFEEHETK YKDDVEGIQR WRIALNEAAN LKGSCDNRDK TDADCIRQIV DQISSKLCKI  180
SLSYLQNIVG IDTHLEKIES LLEIGINGVR IMGIWGMGGV GKTTIARAIF DTLLGRMDSS  240
YQFDGACFLK DIKENKRGMH SLQNALLSEL LREKANYNNE EDGKHQMASR LRSKKVLIVL  300
DDIDNKDHYL EYLAGDLDWF GNGSRIIITT RDKHLIEKND IIYEVTALPD HESIQLFKQH  360
AFGKEVPNEN FEKLSLEVVN YAKGLPLALK VWGSLLHNLR LTEWKSAIEH MKNNSYSGII  420
DKLKISYDGL EPKQQEMFLD IACFLRGEEK DYILQILESC HIGAEYGLRI LIDKSLVFIS  480
EYNQVQMHDL IQDMGKYIVN FQKDPGERSR LWLAKEVEEV MSNNTGTMAM EAIWVSSYSS  540
TLRFSNQAVK NMKRLRVFNM GRSSTHYAID YLPNNLRCFV CTNYPWESFP STFELKMLVH  600
LQLRHNSLRH LWTETKHLPS LRRIDLSWSK RLTRTPDFTG MPNLEYVNLY QCSNLEEVHH  660
SLGCCSKVIG LYLNDCKSLK RFPCVNVESL EYLGLRSCDS LEKLPEIYGR MKPEIQIHMQ  720
GSGIRELPSS IFQYKTHVTK LLLWNMKNLV ALPSSICRLK SLVSLSVSGC SKLESLPEEI  780
GDLDNLRVFD ASDTLILRPP SSIIRLNKLI ILMFRGFKDG VHFEFPPVAE GLHSLEYLNL  840
SYCNLIDGGL PEEIGSLSSL KKLDLSRNNF EHLPSSIAQL GALQSLDLKD CQRLTQLPEL  900
PPELNELHVD CHMALKFIHY LVTKRKKLHR VKLDDAHNDT MYNLFAYTMF QNISSMRHDI  960
SASDSLSLTV FTGQPYPEKI PSWFHHQGWD SSVSVNLPEN WYIPDKFLGF AVCYSRSLID  1020
TTAHLIPVCD DKMSRMTQKL ALSECDTESS NYSEWDIHFF FVPFAGLWDT SKANGKTPND  1080
YGIIRLSFSG EEKMYGLRLL YKEGPEVNAL LQMRENSNEP TEHSTGIRRT QYNNRTSFYE  1140
LING                                                               1144
```

```
SEQ ID NO: 225          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 225
ttggattgaa gggagctctg                                              20
```

```
SEQ ID NO: 226          moltype = DNA  length = 188
FEATURE                 Location/Qualifiers
misc_feature            1..188
                        note = Description of Artificial Sequence: Synthetic
                         polynucleotide
source                  1..188
                        mol_type = other DNA
                        organism = synthetic construct
SEQUENCE: 226
gttttgagag tggagctcct tgaagtccaa cagaggatct aacaggtaag attgagctgc  60
tgacctatgg attcctcagc cctatctatt atttgattgg ataggtttgt gggttgcata  120
tgtcaggagc ttcattgccc taagttggat ccctttttgg attgaaggga gctctacatt  180
catttgac                                                           188
```

```
SEQ ID NO: 227          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
```

```
SEQUENCE: 227
tttggattga agggagctct                                              20

SEQ ID NO: 228         moltype = DNA  length = 1107
FEATURE                Location/Qualifiers
misc_feature           1..1107
                       note = Description of Artificial Sequence: Synthetic
                        polynucleotide
source                 1..1107
                       mol_type = other DNA
                       organism = synthetic construct
SEQUENCE: 228
atggtggatg ggcatgtatc agctggttca agaaatgaga acggtacaac acccagaaat  60
aataatgtgg aaatttcaat agcaacagcg tcatcaatgt ttcctggttt caggttttca  120
ccaacggacg aagaactcat atcatattac ttgaaaaaga aacttgaggg gtctgataag  180
tgtgttgaag ttatttctga ggttgagatt tggaaacatg aaccttggga tttaccagca  240
aaatccgtca ttcaatcaga taatgaatgg ttcttctttt ctcctcgtgg aaggaagtat  300
ccaaacgggt cgcaaagtaa aagggcaact gaatctggtt actggaaggc cacaggaaaa  360
gaacgtaatg tgaaatctgg ttcgaatctc attggcacaa agagaactct ggtgttccac  420
actggtcgag cacctaaagg acagaggaca cattggataa tgcatgaata ttgcatgagc  480
ggaaacacta attatcagga ttctatggtt gtctgccgcc tccggaagaa tagtgagttt  540
catttgaatg acaccccaag aaatcaaagg aatcaactgg ctgctaccgc tactgcaacc  600
gctcagtctg gagcaggaca attgggcagc ttggaattgg tcactgtagg ggattgctgt  660
tgttcaaagg aagggagtag cagtttttat tcccattcgg ttgagcagat tgactctgga  720
tcagaatctg ataaaccaac taaagagttc tctcagcacg attcctctgg ccacttcaag  780
gactgtgatg gcgaggagga ctggtttgct gatataatga aagatgatat cattaagcta  840
gacgaatctt cgttgaatgc ccaacctatt tccatggttc ccagtaggcc tgaatcctcg  900
atatcaactc atgaagctcg agctgcgatg tccggtgtgg ctcctttcca gggcaccgct  960
aatcgaagac tcagactagt aagggaaaaa gtagtggtgt gtccagtaga gggatccaga  1020
atgtatgaag ctaccaaaaa gaataaaatc ggagtgagca taactagttc aggaagatgg  1080
ctgagaaaca tgttttcagt taaatga                                      1107

SEQ ID NO: 229         moltype = AA  length = 368
FEATURE                Location/Qualifiers
REGION                 1..368
                       note = Description of Artificial Sequence: Synthetic
                        polypeptide
source                 1..368
                       mol_type = protein
                       organism = synthetic construct
SEQUENCE: 229
MVDGHVSAGS RNENGTTPRN NNVEISIATA SSMFPGFRFS PTDEELISYY LKKKLEGSDK  60
CVEVISEVEI WKHEPWDLPA KSVIQSDNEW FFFSPRGRKY PNGSQSKRAT ESGYWKATGK  120
ERNVKSGSNL IGTKRTLVFH TGRAPKGQRT HWIMHEYCMS GNTNYQDSMV VCRLRKNSEF  180
HLNDTPRNQR NQLAATATAT AQSGAGQLGS LELVTVGDCC CSKEGSSSFY SHSVEQIDSG  240
SESDKPTKEF SQHDSSGHFK DCDGEEDWFA DIMKDDIIKL DESSLNAQPI SMVPSRPESS  300
ISTHEARAAM SGVAPFQGTA NRRLRLVREK VVVCPVEGSR MYEATKKNKI GVSITSSGRW  360
LRNMFSVK                                                           368

SEQ ID NO: 230         moltype = DNA  length = 3822
FEATURE                Location/Qualifiers
misc_feature           1..3822
                       note = Description of Artificial Sequence: Synthetic
                        polynucleotide
source                 1..3822
                       mol_type = other DNA
                       organism = synthetic construct
SEQUENCE: 230
atgtatccca tgtatgggtt catggacaca catccttacc aaagaaaccg agtacctcac  60
aaccctcctt attatcccca gtttgaaccg aatcatcatc atctgaacat tgatccagct  120
agatctcctg tagcttatga atcctggcct tgtggtggta actatgggca tccttatcca  180
ccgcagtgtc acagttgctg tatccataac aattccccga gccagtgtgc attcggtcct  240
ccttatccct accttccact gcctccctac aacaactgta gcaatccagc atatccggtg  300
atgtatgctg ctaattatgt ttctccccat tttactatgg agcagcctcg gtacgaatat  360
gataagaata tgggaagtgg tcatcacttc tgtggctgtc caaatcatcc atgttatacg  420
aaaggaggga gcaacattaa aatagaagaa caggaccagg ataagaaaaa tgaaagcaat  480
gagtccttgg ttccttttgg gttcaagaat tgtccttatc ctgttctgtg gatgccacct  540
gattatatga tgaatagcgc acacgtgaag cctaatggat ttgaaggtaa acgggatgag  600
gtgaaagatg tgaaaccgta tggtgattgc agatctttcg aacaaccaaa tatctggaat  660
gtatggtctc cttatcaagg gaacaactcg gaattaccaa agcaaagggg agatccaccc  720
agaaaacaac accacgatga tatgaacaag aaacagtttc catttccaat aatctggatg  780
ccttacaaac ctgaggaaat agacggcaaa gttagcaagg agactggtgt tgatcaggag  840
cagacctccc ccttaaaatc taccatacca aagttacatg atgttgaaga ggatagaagc  900
gattctagag aaaatgtagt gaatagagga agtgaaatcc acggaaaggg actgaataaa  960
gattctgtta cgaaaatcat tccagtaagg caaatggagc aaattgagga tgtcttggat  1020
ggaaaaccgg aagatgcttc caaacagcat gatgttgatg ctaaagagaa gaaaaccact  1080
gaagacggtg gcaagaagca gtcgtcttct cctacaaagt catccaagct gccccctgtt  1140
tgtctaagag ttgatcccct gcctaggaaa aaaagcagta acggcagttc taggtcccct  1200
agtcctcctg gtgggaaacg gaaattagta gattcgccaa gtgacagctc caaacctccc  1260
```

```
atcttatcaa atgagaagga gaatgttcat cttgacaaat catccacaac agctacgccg  1320
gagaaaagca tagaagtgga tccaagtgaa ggaaaaagaa aagttgttaa ggttgcccaa  1380
gggactagca aagaagataa acttcaagat caatatacgg ttttccctga tctgaaaggg  1440
aaggcaaggg gccaaagcag tgagggtgat actagtaaag caaccaatga gctcaagcat  1500
caacctgatg gagtagcagc agaacctcag tccaacaatc aaggacatca gattggtgag  1560
gccagagaag cagcgaaggg aaatgcgggt ttagttgtgt acatgaaacc agataggagt  1620
aagctgtctg atgataacgc ggctactgtg attcagtcgg cataccgagg gttcaacgtg  1680
cggagatggg agcctctgaa gaaattaaag cagataacta aaataaagga gcagatggct  1740
gagcttaaaa actgtattca ggctttggag agctcagctg acaacaaaca gatgactatt  1800
ctcacagaag ccataatggg tcttctgctg aagcttgacg ctattcaggg gttacatcca  1860
accgttaggg aatatagaaa atctgtagca aaggagcttg ttagcctgca ggagaagctg  1920
gatcttctga actgtaagaa gcaactggca gaaagtgaac aggctttaac tgctcaatcc  1980
agcggggatg catgcaggac ggtggaagac aacatttcca tgcagggagg ccgagaggtg  2040
ccaaagtttg aacaggatga tgatttagcg cggggagatg aagaaataaa ggtacatgca  2100
aaggagccct gtcaagagca gcctctttgt gcggcagaga cactccccaa ctctcatcac  2160
gtaggcaatg cagaggaagt ggtcggtaaa gaagaaagtg agaacgttga ggaggtggtg  2220
gagaactttt caagtggtgg tgcagtggtg gatgaggcaa cagaatcact ttctgaatct  2280
aaagaaaatt tgaatgataa gtcacctgat gagaatacgg tagtagttga gaaatcagaa  2340
gagcatgaca aagctgaaca atctttgcca aatcctattc cattttctgt agatctgaca  2400
gaaaacttgg gcttagaggt cagaggttgt ggtttgaagg ggaagggtgg aggtgttgat  2460
gaattggaag agctcccgca aggagtcctt gatgaagaga ctagtgttca agggtctact  2520
gagatcagaa aagacgaggt cctccaacat gacaatggaa accttactgc tcatattcct  2580
gaagaaaaag tctctgatac agagaggcga gagcaccacc acttggaagc attaggtgaa  2640
acactagttg ttttggggcc aatgaacatc cacagcagca atggacaaaa agaaaattca  2700
gaagttctgg aaacagataa aacagtacga gttgatgctc cagaacagga gaaagaagat  2760
ctcagaccat taaatgaaga tgggaagatc tctgatgttg atgctaaggt tggtatggaa  2820
gaggatggcg aggaacgtgg acaatgcagc actgggtcag acgcgtttcc aatatactca  2880
caggaagaag caatcaccat gaagcagtct acagatgcca ccaacatgga ggaattggaa  2940
acaactggag ttctgcagga gaaaatgcaa aatgcagtag agagagacat tgaaatcctt  3000
aattcaaaaa aaaccattga agtgtcagca gaacctcaac tatttactgc taccattgac  3060
gaggccaaag aatattatgc tcaggataag cagaatgttg gggaggaaaa tatggaggtg  3120
caaggtgagg aattgcctgc tcgcagtgat gctttggtct ctgtactcaa gagtgaacac  3180
aaagagaata atgtggaggt tgagcagagg catctggagg aaaactttga gatgcaagag  3240
gaagaaccag tggctgctga taaccctgca cctatgaccg aggaaccagt ggatgaaagt  3300
atagtgatga ctgctccaaa atcagaagct gtaactactg agacgcagct gttaggggag  3360
aaagagcttg gtgtagcaga ggaccgcagc acatatccat cgacatgtga tactgtggaa  3420
ggtaattcag ctgatgctgt ctgctctttt ggttctacgc ctaatgaagc acaagtaatg  3480
gatgcaaagg agcttaaaga atggaagaga gtggaaatgt caccatcatc acctactgct  3540
agccaagtat cctttgatag tgatgcattc tcagagagca gtcaaaagct tatagaagag  3600
aatgaaaaat taagggagat gatggagaaa ctaataaaag cagggaaaga acaactcact  3660
gttgtatcca gtctttctgg aagagttaag gacctggaga agagattgtc caggaagaag  3720
aagctgagat tgagacgata tagggtacca agagcaggtt cagtctgtat gaagccattg  3780
aatgactcac tgaaagacag agctgcgggg ttggcaatgt ga                     3822

SEQ ID NO: 231          moltype = AA  length = 1273
FEATURE                 Location/Qualifiers
REGION                  1..1273
                        note = Description of Artificial Sequence: Synthetic
                         polypeptide
source                  1..1273
                        mol_type = protein
                        organism = synthetic construct
SEQUENCE: 231
MYPMYGFMDT HPYQRNRVPH NPPYYPQFEP NHHHLNIDPA RSPVAYESWP CGGNYGHPYP  60
PQCHSCCIHN NSPSQCAFGP PYPYLPLPPY NNCSNPAYPV MYAANYVSPH FTMEQPRYEY  120
DKNMGSGHHF CGCPNHPCYT KGGSNIKIEE QDQDKKNESN ESLVPFGFKN CPYPVLWMPP  180
DYMMNSAHVK PNGFEGKRDE VKDVKPYGDC RSFEQPNIWN VWSPYQGNNS ELPKQRGDPP  240
RKQHHDDMNK KQFPFPIIWM PYKPEEIDGK VSKETGVDQE QTSPLKSTIP KLHDVEEDRS  300
DSRENVVNRG SEIHGKGLNK DSVTKIIPVR QMEQIEDVLD GKPEDASKQH DVDAKEKKTT  360
EDGGKKQSSS PTKSSKLPPV CLRVDPLPRK KSSNGSSRSP SPPGGKRKLV DSPSDSSKPP  420
ILSNEKENVH LDKSSTTATP EKSIEVDPSE GKRKVVKVAQ GTSKEDKLQD QYTVFPDLKG  480
KARGQSSEGD TSKATNELKH QPDGVAAEPQ SNNQGHQIGE AREAAKGNAG LVVYMKPDRS  540
KLSDDNAATV IQSAYRGFNV RRWEPLKKLK QITKIKEQMA ELKNCIQALE SSADNKQMTI  600
LTEAIMGLLL KLDAIQGLHP TVREYRKSVA KELVSLQEKL DLLNCKKQLA ESEQALTAQS  660
SGDACRTVED NISMQGGREV PKFEQDDDLA RGDEEIKVHA KEPCQEQPLC AAETLPNSHH  720
VGNAEEVVGK EESENVEEVV ENFSSGGAVV DEATESLSES KENLNDKSPD ENTVVVEKSE  780
EHDKAEQSLP NPIPFSVDLT ENLGLEVRGC GLKGKGGGVD ELEELPQGVL DEETSVQGST  840
EIRKDEVLQH DNGNLTAHIP EEKVSDTERR EHHHLEALGE TLVVLGPMNI HSSNGQKENS  900
EVLETDKTVR VDAPEQEKED LRPLNEDGKI SDVDAKVGME EDGEERGQCS TGSDAFPIYS  960
QEEAITMKQS TDATNMEELE TTGVLQEKMQ NAVERDIEIL NSKKTIEVSA EPQLFTATID  1020
EAKEYYAQDK QNVGEENMEV QGEELPARSD ALVSVLKSEH KENNVEVEQR HLEENFEMQE  1080
EEPVAADNPA PMTEEPVDES IVMTAPKSEA VTTETQLLGE KELGVAEDRS TYPSTCDTVE  1140
GNSADAVCSF GSTPNEAQVM DAKELKEWKR VEMSPSSPTA SQVSFDSDAF SESSQKLIEE  1200
NEKLREMMEK LIKAGKEQLT VVSSLSGRVK DLEKRLSRKK KLRLRRYRVP RAGSVCMKPL  1260
NDSLKDRAAG LAM                                                     1273

SEQ ID NO: 232          moltype = DNA  length = 1122
FEATURE                 Location/Qualifiers
misc_feature            1..1122
```

```
                         note = Description of Artificial Sequence: Synthetic
                          polynucleotide
source                   1..1122
                         mol_type = other DNA
                         organism = synthetic construct
SEQUENCE: 232
atgcgacctc ttcaaccacc cccaccagcc gccgccgcca ccacctcctc ctccaccacc  60
gcatcaccta tgccccctcc tccttcacgc aaccgtcccc gtcgtcgcac cgatttaact  120
ctccccctc cccaacgtga cccagctctc gccgtacccc tccccctccc ccctacttcc  180
gccccttctt cctcgtcgtc ttcctcttcc tccccactcc ccaccccctt aaacttctcc  240
gaacttgagc gtatcaatcg catcggcagc ggcgctggcg gtacggttta caaagtccta  300
catcgcccca ccggaagact ctacgctctc aaagtcatct acggtaacca cgaggactcc  360
gttcgccttc agatgtgccg tgagatcgag attctccgtg acgtcgacaa ccctaacgtc  420
gttagatgtc acgatatgtt cgatcacaac ggtgaaatcc aagtcctcct tgaattcatg  480
gataaaggct ctctcgaagg gatccacatc cctaaagagt cagctctttc ggatctaacc  540
cgacaagtcc tctcgggtct ctattatctc cacaggcgta agattgtgca cagagatatc  600
aagccctcga atttactaat caactcgagg cgcgaggtga aaattgctga ctttggggtg  660
tcgagagtgc tggcacaaga tatggatcct tgtaatgatt cagttgggac aattgcctat  720
atgagtccag agagaatcaa cacagatctg aatcatggac agtacgatgg gtatgctgga  780
gatatatgga gtcttggtgt tagcatattg gagttttatt tgggaaggtt tccgtttttct  840
gttgggaggt caggtgattg ggctagtctt atgtgcgcca tttgtatgtc gcagccgccg  900
gaggctccgg cgaatgcttc tagagagttc agggacttta ttgcttgctg tttgcagagg  960
gatcctgcac gacggtggac ggcggtgcag ctgttgcgtc atccatttat tacccagaat  1020
agcccagccg ccaccaccac cggtaatatg atgccacttc ctaatcaggt tcatcagcca  1080
gcacatcaat tgttacctcc acctcctcat ttttcttctt aa                    1122

SEQ ID NO: 233           moltype = AA  length = 373
FEATURE                  Location/Qualifiers
REGION                   1..373
                         note = Description of Artificial Sequence: Synthetic
                          polypeptide
source                   1..373
                         mol_type = protein
                         organism = synthetic construct
SEQUENCE: 233
MRPLQPPPPA AAATTSSSTT ASPMPPPPSR NRPRRRTDLT LPLPQRDPAL AVPLPLPPTS  60
APSSSSSSSS SPLPTPLNFS ELERINRIGS GAGGTVYKVL HRPTGRLYAL KVIYGNHEDS  120
VRLQMCREIE ILRDVDNPNV VRCHDMFDHN GEIQVLLEFM DKGSLEGIHI PKESALSDLT  180
RQVLSGLYYL HRRKIVHRDI KPSNLLINSR REVKIADFGV SRVLAQDMDP CNDSVGTIAY  240
MSPERINTDL NHGQYDGYAG DIWSLGVSIL EFYLGRFPFS VGRSGDWASL MCAICMSQPP  300
EAPANASREF RDFIACCLQR DPARRWTAVQ LLRHPFITQN SPAATTTGNM MPLPNQVHQP  360
AHQLLPPPPH FSS                                                    373

SEQ ID NO: 234           moltype = DNA  length = 1245
FEATURE                  Location/Qualifiers
misc_feature             1..1245
                         note = Description of Artificial Sequence: Synthetic
                          polynucleotide
source                   1..1245
                         mol_type = other DNA
                         organism = synthetic construct
SEQUENCE: 234
atggagtctc atcctcacaa caaaactgac cagacccagc atatcatcct cgtacacggt  60
cccatcatca tcggagctgg cccttctggt cttgccactt cagcatgtct ctcgagccgt  120
ggagtccctt ctttgatcct agaacggtcg gattcaatag catctctatg gaaatctaaa  180
acctacgacc gactcagact ccatctccca aaacactttt gccggttacc cctcctggac  240
ttccctgaat attacccaaa atacccttcc aaaaacgagt tcttggccta ccttgagtcc  300
tacgcttccc acttccgcat cgctccaagg ttcaacaaga acgtacaaaa cgcagcttac  360
gattcttcct ccggtttctg gagagtaaag actcatgata acacagagta cctctccaaa  420
tggcttatcg tagccaccgg tgagaacgca gatccatact tccccgagat tccagggaga  480
aagaagtttt ccggcggaaa aatcgttcac gcgagtgagt acaaaagcgg cgaagagttc  540
cggcggcaga aagttttggt tgtcggatgt ggaaattccg gcatggaaat tagcttagac  600
ctcgtccgac ataacgcatc tcctcatctt gttgtccgga acaccgttca tgtgttgcca  660
agggagatac ttggggtatc aacatttgga gttggaatga cacttctcaa atgcttaccc  720
ttaaggctcg ttgacaagtt cttgttattg atggccaatc tttcgtttgg aaataccgac  780
cggttgggcc ttcgccgacc aaaaacgggt ccgcttgagc tgaaaaatgt caccggcaaa  840
agtccggttc tcgatgtcgg agctatgtct ctcatcagat ccggcatgat tcagataatg  900
gaaggtgtaa aggaaataac aaagaaagga gcaaagttta tggatggtca agaaaaggac  960
tttgactcta tcatatttgc cactggttac aaaagcaacg tgcctacttg gcttcaggga  1020
ggtgattttt tcacggacga tgggatgccg aaaacgccgt ttcctaacgg ctggagagga  1080
gggaaaggat tgtacacagt tggttttacg agaagaggac tccttggaac ggcgtctgac  1140
gccgttaaga tcgctggcga aattggtgac cagtggagag acgaaatcaa ggggtccacc  1200
aggaatatgt gcagttctcg ttttgtcttt acctctaaat cctaa                 1245

SEQ ID NO: 235           moltype = AA  length = 414
FEATURE                  Location/Qualifiers
REGION                   1..414
                         note = Description of Artificial Sequence: Synthetic
                          polypeptide
```

```
source                  1..414
                        mol_type = protein
                        organism = synthetic construct
SEQUENCE: 235
MESHPHNKTD QTQHIILVHG PIIIGAGPSG LATSACLSSR GVPSLILERS DSIASLWKSK  60
TYDRLRLHLP KHFCRLPLLD FPEYYPKYPS KNEFLAYLES YASHFRIAPR FNKNVQNAAY  120
DSSSGFWRVK THDNTEYLSK WLIVATGENA DPYFPEIPGR KKFSGGKIVH ASEYKSGEEF  180
RRQKVLVVGC GNSGMEISLD LVRHNASPHL VVRNTVHVLP REILGVSTFG VGMTLLKCLP  240
LRLVDKFLLL MANLSFGNTD RLGLRRPKTG PLELKNVTGK SPVLDVGAMS LIRSGMIQIM  300
EGVKEITKKG AKFMDGQEKD FDSIIFATGY KSNVPTWLQG GDFFTDDGMP KTPFPNGWRG  360
GKGLYTVGFT RRGLLGTASD AVKIAGEIGD QWRDEIKGST RNMCSSRFVF TSKS        414

SEQ ID NO: 236          moltype = DNA  length = 1869
FEATURE                 Location/Qualifiers
misc_feature            1..1869
                        note = Description of Artificial Sequence: Synthetic
                         polynucleotide
source                  1..1869
                        mol_type = other DNA
                        organism = synthetic construct
SEQUENCE: 236
atgattacgg cggcggactt ctaccacgtt atgacggcta tggttccgtt atacgtagct  60
atgatcctcg cttacggctc tgtcaaatgg tggaaaatct tcacaccaga ccaatgctcc  120
ggcataaacc gtttcgtcgc tctcttcgcc gttcctctcc tctctttcca cttcatcgcc  180
gctaacaacc cttacgccat gaacctccgt ttcctcgccg cagattctct ccagaaagtc  240
attgtcctct ctctcctctt cctctggtgc aaactcagcc gcaacggttc tttagattgg  300
accataactc tcttctctct ctcgacactc cccaacactc tagtcatggg gatacctctt  360
ctcaaaggca tgtatggtaa tttctccggc gacctcatgg ttcaaatcgt tgttcttcag  420
tgtatcattt ggtacacact catgctcttt ctctttgagt accgtggagc taagcttttg  480
atctccgagc agtttccaga cacagcagga tctattgttt cgattcatgt tgattccgac  540
attatgtctt tagatggaag acaacctttg gaaactgaag ctgagattaa agaagatggg  600
aagcttcatg ttactgttcg tcgttctaat gcttcaaggt ctgatattta ctcgagaagg  660
tctcaaggct tatctgcgac acctagacct tcgaatctaa ccaacgctga gatatattcg  720
cttcagagtt caagaaaccc aacgccacgt ggctctagtt ttaatcatac tgatttttac  780
tcgatgatgg cttctggtgg tggtcggaac tctaactttg gtcctggaga agctgtgttt  840
ggttctaaag gtcctactcc gagaccttcc aactacgaag aagacggtgg tcctgctaaa  900
ccgacggctg ctggaactgc tgctggagct gggaggtttc attatcaatc tggaggaagt  960
ggtggcggtg gaggagcgca ttatccggcg ccgaacccag ggatgtttc gcccaacact  1020
ggcggtggtg gaggcacggc ggcgaaagga aacgctccgg tggttggtgg gaaaagacaa  1080
gacggaaacg gaagagatct tcacatgttt gtgtggagct caagtgcttc gccggtctca  1140
gatgtgttcg gcggtggagg aggaaaccac cacgccgatt actccaccgc tacgaacgat  1200
catcaaaagg acgttaagat ctctgtacct caggggaata gtaacgacaa ccagtacgtg  1260
gagagggaag agtttagttt cggtaacaaa gacgatgata gcaaagtatt ggcaacggac  1320
ggtgggaaca acataagcaa caaaacgacg caggctaagg tgatgccacc aacaagtgtg  1380
atgacaagac tcattctcat tatggtttgg aggaaactta ttcgtaatcc caactcttac  1440
tccagtttat tcggcatcac ctggtccctc atttccttca agtggaacat tgaaatgcca  1500
gctcttatag caaagtctat ctccatactc tcagatgcag gtctaggcat ggctatgttc  1560
agtcttgggt tgttcatggc gttaaaccca agaataatag cttgtggaaa cagaagagca  1620
gcttttgcgg cggctatgag atttgtcgtt ggacctgccg tcatgctcgt tgcttcttat  1680
gccgttggcc tccgtggcgt cctcctccat gttgccatta tccaggcagc tttgccgcaa  1740
ggaatagtac cgtttgtgtt tgccaaagag tataatgtgc atcctgacat tcttagcact  1800
gcggtgatat ttgggatgtt gatcgcgttg cccataactc ttctctacta cattctcttg  1860
ggtctatga                                                        1869

SEQ ID NO: 237          moltype = AA  length = 622
FEATURE                 Location/Qualifiers
REGION                  1..622
                        note = Description of Artificial Sequence: Synthetic
                         polypeptide
source                  1..622
                        mol_type = protein
                        organism = synthetic construct
SEQUENCE: 237
MITAADFYHV MTAMVPLYVA MILAYGSVKW WKIFTPDQCS GINRFVALFA VPLLSFHFIA  60
ANNPYAMNLR FLAADSLQKV IVLSLLFLWC KLSRNGSLDW TITLFSLSTL PNTLVMGIPL  120
LKGMYGNFSG DLMVQIVVLQ CIIWYTLMLF LFEYRGAKLL ISEQFPDTAG SIVSIHVDSD  180
IMSLDGRQPL ETEAEIKEDG KLHVTVRRSN ASRSDIYSRR SQGLSATPRP SNLTNAEIYS  240
LQSSRNPTPR GSSFNHTDFY SMMASGGGRN SNFGPGEAVF GSKGPTPRPS NYEEDGGPAK  300
PTAAGTAAGA GRFHYQSGGS GGGGGAHYPA PNPGMFSPNT GGGGGTAAKG NAPVVGGKRQ  360
DGNGRDLHMF VWSSSASPVS DVFGGGGGNH HADYSTATND HQKDVKISVP QGNSNDNQYV  420
EREEFSFGNK DDDSKVLATD GGNNISNKTT QAKVMPPTSV MTRLILIMVW RKLIRNPNSY  480
SSLFGITWSL ISFKWNIEMP ALIAKSISIL SDAGLGMAMF SLGLFMALNP RIIACGNRRA  540
AFAAAMRFVV GPAVMLVASY AVGLRGVLLH VAIIQAALPQ GIVPFVFAKE YNVHPDILST  600
AVIFGMLIAL PITLLYYILL GL                                          622

SEQ ID NO: 238          moltype = DNA  length = 1176
FEATURE                 Location/Qualifiers
misc_feature            1..1176
                        note = Description of Artificial Sequence: Synthetic
```

```
                          polynucleotide
source                   1..1176
                         mol_type = other DNA
                         organism = synthetic construct
SEQUENCE: 238
atggtgaaac tggagaactc gaggaaaccc gaaaaaattt cgaacaagaa catccccatg  60
tccgatttcg tggtcaatct ggatcatggt gatccaacgg cgtacgaaga atactggagg  120
aagatgggtg acaggtgtac ggtgacgata cgtggttgtg atctcatgag ttacttcagc  180
gacatgacga acttgtgttg gttccttgag ccagagcttg aagatgcgat caaggacttg  240
cacggtgttg ttggtaacgc tgcgacggag gatcggtaca tagtggttgg gaccggttcg  300
acgcagcttt gtcaagccgc cgtccacgca ctctcttcac tagccaggag tcaacctgtc  360
agcgtcgtcg ccgccgctcc tttttactcc acatatgtgg aggagacgac atatgttcgg  420
tcgggtatgt acaagtggga aggagacgca tggggtttcg acaaaaaggg tccgtacatc  480
gagctagtga cgtcacctaa taaccctgac ggaaccatca gagagacggt ggtgaaccgt  540
ccagacgacg acgaagccaa agtgatccat gactttgctt attactggcc ccactacact  600
cccatcactc gccgtcaaga ccatgacatc atgctcttca ctttctccaa gatcacaggc  660
cacgctgggt cccgtattgg gtgggcattg gtgaaggaca aggaggtagc taagaagatg  720
gttgagtata ttattgtgaa ctcgattggt gtgtctaagg agtcacaggt tcgaacagct  780
aagatactca acgttctaaa ggagacttgt aagagcgagt ccgagtctga gaatttcttc  840
aagtatggtc gtgagatgat gaagaatcgg tgggagaagc tacgtgaagt tgtgaaagag  900
agcgatgctt tcactcttcc caagtaccct gaagcatttt gcaactactt tggaaaatca  960
ctcgaatctt accctgcgtt tgcgtggcta gggacgaagg aagagacgga tctggtaagt  1020
gaattgagga gacacaaggt aatgagcaga gctggagagc gttgtggatc tgacaagaag  1080
catgtccgag tcagcatgct tagtcgtgaa gacgttttca atgtctttct cgagagactc  1140
gccaacatga agctcattaa aagcattgac ctttag                          1176

SEQ ID NO: 239           moltype = AA  length = 391
FEATURE                  Location/Qualifiers
REGION                   1..391
                         note = Description of Artificial Sequence: Synthetic
                          polypeptide
source                   1..391
                         mol_type = protein
                         organism = synthetic construct
SEQUENCE: 239
MVKLENSRKP EKISNKNIPM SDFVVNLDHG DPTAYEEYWR KMGDRCTVTI RGCDLMSYFS  60
DMTNLCWFLE PELEDAIKDL HGVVGNAATE DRYIVVGTGS TQLCQAAVHA LSSLARSQPV  120
SVVAAAPFYS TYVEETTYVR SGMYKWEGDA WGFDKKGPYI ELVTSPNNPD GTIRETVVNR  180
PDDDEAKVIH DFAYYWPHYT PITRRQDHDI MLFTFSKITG HAGSRIGWAL VKDKEVAKKM  240
VEYIIVNSIG VSKESQVRTA KILNVLKETC KSESESENFF KYGREMMKNR WEKLREVVKE  300
SDAFTLPKYP EAFCNYFGKS LESYPAFAWL GTKEETDLVS ELRRHKVMSR AGERCGSDKK  360
HVRVSMLSRE DVFNVFLERL ANMKLIKSID L                               391

SEQ ID NO: 240           moltype = DNA  length = 4107
FEATURE                  Location/Qualifiers
misc_feature             1..4107
                         note = Description of Artificial Sequence: Synthetic
                          polynucleotide
source                   1..4107
                         mol_type = other DNA
                         organism = synthetic construct
SEQUENCE: 240
atgggtgaga aagcgattga cgaagacaaa gtagaagcga tgaagagcag caagacctct  60
cttgttttcg ccattaacgg acaaagattc gagctcgagc tctcttctat tgatccttcc  120
accacactcg tcgatttctt gcgcaacaag actcctttca agagcgtcaa gcttggttgt  180
ggcgaaggtg gttgtggcgc ttgtgttgtt cttctttcaa agtatgatcc attgctcgaa  240
aaagtcgatg aattcacaat tagctcgtgt ctcacgcttc tctgtagcat tgatggctgt  300
tccatcacta cctcagacgg gctcggcaac agcagagtcg gtttccatgc cgtccacgag  360
cgtatcgccg gtttttcatgc cacacaatgc ggtttctgta ctcctggaat gagcgtttcg  420
atgttttctg ctctcttgaa cgctgataag tctcatccac ctcctcgcag cggtttctca  480
aatctcacgg ctgtagaagc tgagaaggct gtgtcaggga atctttgccg gtgtactgga  540
tatagaccgc ttgtggatgc ttgtaagagt tttgcagcgg atgtggatat cgaagatctc  600
ggattcaatg ccttttgcaa gaagggagaa aacagagatg aggttttaag aaggttgcca  660
tgttatgatc atacatcatc tcatgtctgt acatttccgg agttcttgaa gaaggaaatc  720
aagaacgata tgagtcttca ttcaagaaag tatcgatggt caagcccggt tagtgtctca  780
gagcttcaag ggttattaga agtcgagaat ggtttgtcgg ttaagttagt tgcgggtaac  840
acgagcaccg ggtattacaa agaagaaaaa gagaggaagt acgaaagatt tatcgatatc  900
aggaagattc cggagtttac tatggtgaga agtgatgaga aaggagttga attaggagct  960
tgtgtcacta tatcgaaagc tattgaggtt ctaagagagg aaaaaaatgt ttctgtgttg  1020
gcgaaaatcg ctactcatat ggagaaaatt gcaaacagat tcgtgaggaa cacgggaacg  1080
ataggtggaa acattatgat ggctcagaga aaacagtttc cttcggatct tgcaaccata  1140
cttgttgctg ctcaagcaac ggtgaagatc atgactagca gctcgagtca agaacagttc  1200
acattggagg agtttctaca acaacctcct cttgatgcaa aatctcttct tttgagcctc  1260
gagattccat cttggcactc cgcgaagaag aacggttctt cagaagatag tattttgcta  1320
tttgaaactt acagagcagc gcctcgtcct ctaggaaacg cattggcatt tctgaatgcg  1380
gctttctcag ctgaagttac tgaagcactt gatggcattg ttgtaaatga ttgccaatta  1440
gtttttggag cttatgggac caaacatgca cacagggcaa agaaagtaga agagtttctt  1500
acaggaaaag tgatatctga tgaagttttg atggaagcta ttagcttact taaagatgag  1560
atagtacctg ataagggtac ttcgaatccc gggtatagat caagcttggc tgttactttt  1620
```

```
ctcttcgagt tcttcggatc tttaactaaa aaaaacgcta aaacgacaaa cggttggctc  1680
aatggaggat gcaaagagat tggttttgat cagaatgttg aatctttgaa acctgaagct  1740
atgctgtcat ctgcacaaca aatagttgaa aatcaagagc atagtccggt cgggaaaggc  1800
attacaaagg ctggagcttg tctccaagca tctggtgagg ctgtttatgt agacgacatt  1860
cctgctccgg aaaattgtct atacggcgca tttatttaca gtacaatgcc gctagcgcga  1920
attaagggta taaggttcaa gcaaaacaga gttccagaag gagttcttgg cattattact  1980
tacaaagata ttcccaaagg cggcaaaat atcggtacca acggtttctt tacctcggat  2040
cttttgttcg cagaagaagt cactcattgt gcgggtcaga taatcgcctt tttggttgca  2100
gatagtcaaa agcatgcaga tattgcagca aatcttgttg tgatagatta cgacaccaaa  2160
gatttaaaac cacctatact gtccttagaa gaagctgtcg aaaactttag ccttttcgag  2220
gtccctccac ctctgcgtgg ttacccggtt ggtgatatca ccaagggaat ggatgaagct  2280
gaacataaga ttcttggatc aaagataagt ttcgggtcac agtacttctt ctatatggag  2340
acacaaacag ctcttgcagt gccggatgaa gacaactgta tggtggttta tagctcgact  2400
caaacccctg agtttgtaca tcaaaccatc gctggatgtc ttggagttcc tgagaacaat  2460
gtgcgtgtca tcactagaag agttggaggc ggattcggtg ggaaagccgt gaaatcaatg  2520
cctgttgctg cagcttgtgc acttgcagca tccaaaatgc agcgtcctgt gaggacatat  2580
gtgaaccgaa aaacggatat gataactacc ggaggaagac atccgatgaa agtcacatat  2640
agtgttggat tcaaatccaa tggaaagatt actgctttag atgtagaggt gttacttgat  2700
gcagggttaa ccgaagatat aagcccgctt atgccgaagg gaatacaagg agcactaatg  2760
aagtatgatt ggggtgctct gtctttcaat gtgaaagtat gcaaaacaaa cactgtgagc  2820
agaaccgcgc tgagagctcc tggggatgta caaggatcat atataggaga agccatcatt  2880
gaaaaagtag cttcatatct ttcagttgat gttgatgaga tcaggaaggt taatcttcat  2940
acatatgaga gcttaaggtt gtttcacagt gccaaagctg gtgaattttc tgagtatacg  3000
ttaccattgc tttgggacag aatcgatgag ttctcgggat ttaacaagcg gaggaaggtg  3060
gttgaggagt ttaatgcatc aaacaagtgg agaaagagag ggatttcacg tgtgcctgcg  3120
gtttatgcag tgaacatgcg atcaacaccg ggaagagtaa gcgttttggg agatgggtca  3180
atagttgtgg aggttcaagg gattgagata ggacaagggc tttggacaaa ggtgaaacag  3240
atggctgcat attcccttgg tttgatccag tgcggtacta caagtgatga actgcttaaa  3300
aaaatcaggg tcattcaatc cgacacacta agtatggtgc aaggctcaat gactgctggt  3360
agtacaacct ctgaagcgag tagtgaagcg gtaaggattt gctgtgatgg cttagttgaa  3420
aggcttttac cagtcaagac cgctttggtg gagcaaacag gaggacctgt gacttgggat  3480
agtctcatca gtcaggctta tcagcaatcg ataaacatgt ccgttagtag caaatacatg  3540
cctgactcca ctggcgaata cctgaactat ggaattgcag cgagcgaggt tgaagtaaac  3600
gttttgacgg gagaaacaac gatcctgcgt acagatatta tctatgattg tgggaagagt  3660
ctcaatcccg ctgttgattt aggacagatt gaaggagcct ttgttcaagg acttggtttc  3720
ttcatgcttg aagagttcct aatgaactca gacggtctcg tggtaacaga cagcacatgg  3780
acttacaaga tcccaacggt tgacacaatc ccaagacagt ttaatgtgga gattctcaac  3840
agtggacaac acaagaatcg tgttctttca tccaaagctt cgggtgaacc gccattgctt  3900
ttagcggctt ctgttcactg cgcggtacga gcagctgtta aagaagctag gaaacagatc  3960
ctgtcatgga atagtaataa acaagggact gatatgtact tcgaattgcc tgttccagca  4020
acaatgccta ttgtgaagga gttttgtgga cttgatgttg tcgagaaata cttggaatgg  4080
aaaatccagc aaaggaaaaa tgtttga                                      4107
```

```
SEQ ID NO: 241          moltype = AA  length = 1368
FEATURE                 Location/Qualifiers
REGION                  1..1368
                        note = Description of Artificial Sequence: Synthetic
                         polypeptide
source                  1..1368
                        mol_type = protein
                        organism = synthetic construct
SEQUENCE: 241
MGEKAIDEDK VEAMKSSKTS LVFAINGQRF ELELSSIDPS TTLVDFLRNK TPFKSVKLGC  60
GEGGCGACVV LLSKYDPLLE KVDEFTISSC LTLLCSIDGC SITTSDGLGN SRVGFHAVHE  120
RIAGFHATQC GFCTPGMSVS MFSALLNADK SHPPPRSGFS NLTAVEAEKA VSGNLCRCTG  180
YRPLVDACKS FAADVDIEDL GFNAFCKKGE NRDEVLRRLP CYDHTSSHVC TFPEFLKKEI  240
KNDMSLHSRK YRWSSPVSVS ELQGLLEVEN GLSVKLVAGN TSTGYYKEEK ERKYERFIDI  300
RKIPEFTMVR SDEKGVELGA CVTISKAIEV LREEKNVSVL AKIATHMEKI ANRFVRNTGT  360
IGGNIMMAQR KQFPSDLATI LVAAQATVKI MTSSSSQEQF TLEEFLQQPP LDAKSLLLSL  420
EIPSWHSAKK NGSSEDSILL FETYRAAPRP LGNALAFLNA AFSAEVTEAL DGIVVNDCQL  480
VFGAYGTKHA HRAKKVEEFL TGKVISDEVL MEAISLLKDE IVPDKGTSNP GYRSSLAVTF  540
LFEFFGSLTK KNAKTTNGWL NGGCKEIGFD QNVESLKPEA MLSSAQQIVE NQEHSPVGKG  600
ITKAGACLQA SGEAVYVDDI PAPENCLYGA FIYSTMPLAR IKGIRFKQNR VPEGVLGIIT  660
YKDIPKGGQN IGTNGFFTSD LLFAEEVTHC AGQIIAFLVA DSQKHADIAA NLVVIDYDTK  720
DLKPPILSLE EAVENFSLFE VPPPLRGYPV GDITKGMDEA EHKILGSKIS FGSQYFFYME  780
TQTALAVPDE DNCMVVYSST QTPEFVHQTI AGCLGVPENN VRVITRRVGG GFGGKAVKSM  840
PVAAACALAA SKMQRPVRTY VNRKTDMITT GGRHPMKVTY SVGFKSNGKI TALDVEVLLD  900
AGLTEDISPL MPKGIQGALM KYDWGALSFN VKVCKTNTVS RTALRAPGDV QGSYIGEAII  960
EKVASYLSVD VDEIRKVNLH TYESLRLFHS AKAGEFSEYT LPLLWDRIDE FSGFNKRRKV  1020
VEEFNASNKW RKRGISRVPA VYAVNMRSTP GRVSVLGDGS IVVEVQGIEI GQGLWTKVKQ  1080
MAAYSLGLIQ CGTTSDELLK KIRVIQSDTL SMVQGSMTAG STTSEASSEA VRICCDGLVE  1140
RLLPVKTALV EQTGGPVTWD SLISQAYQQS INMSVSSKYM PDSTGEYLNY GIAASEVEVN  1200
VLTGETTILR TDIIYDCGKS LNPAVDLGQI EGAFVQGLGF FMLEEFLMNS DGLVVTDSTW  1260
TYKIPTVDTI PRQFNVEILN SGQHKNRVLS SKASGEPPLL LAASVHCAVR AAVKEARKQI  1320
LSWNSNKQGT DMYFELPVPA TMPIVKEFCG LDVVEKYLEW KIQQRKNV               1368
```

```
SEQ ID NO: 242          moltype = DNA  length = 1278
FEATURE                 Location/Qualifiers
misc_feature            1..1278
```

```
                          note = Description of Artificial Sequence: Synthetic
                           polynucleotide
source                    1..1278
                          mol_type = other DNA
                          organism = synthetic construct
SEQUENCE: 242
atggcgacca ataatgattt tggagctttc attgagaaag ttacaatctc tccaacttct  60
acttcctcgt cgcctccttc tctacagggt cttactttcg ccattaaaga catttttgat  120
gtggaaggac gcgttaccgg ttttggtaac ccggattggt taaggacaca ctcggcagct  180
acttctacag ctccagtagt ttcatctctc ttagaagctg gtgccacagc tttgggtatt  240
accattatgg atgaaatggc ttacagtata aacggagaaa atgcgcatta tgggactccg  300
agaaacccga ttgctttcga tagagtgcct gggggatcat cgagtggctc agccgtagct  360
gtagctgctc gtcttgtgga tttttctatt ggaactgata ccggagggag tgtacgagtt  420
ccagcatctt actgtgggat tttcggtttc cggccatccc acggtgcagt ttccactgtc  480
ggacttactc caatggctca gagcttcgac acagttggat ggtttgctcg ggacacagcc  540
actttgaaac gtgtaggttg cgttctcctg cagcagcatc acttgaaccc catcgaacca  600
tctcaactga ttatcgcgga tgactgcttc aagctgtgta gtgtaccgca tgatctcttg  660
gtgcagcctc tggttggatc cgtggaaaaa tcgtttggag gcaacactgt agtaaagaag  720
gtgaatcttg gagagtacat tggacagaat gttccaagcc ttaaacattt catgacaagt  780
gacgatgtca ctacacaaca agagttctgc attccgtctc tcatggccct atcgagttca  840
atgagattgt tacaaagaca tgaattcaag ataaaccacg gtgcatggat ctcgtcggtg  900
aagccagagt ttggtcctgg aatatcagaa cgaattgagg aagctatcag aacatccgac  960
gagaagatcg accattgccg gtccgtgaaa tctgaactga taacggctct ttcaactttg  1020
ctcggggaga agggtgtgtt ggtgattcca acggtaccag gtcctccacc gcatctccaa  1080
gctaatgtgg ctgcacttga atctttccgc agcagagcct tcagcttgtt gtcgatcgca  1140
ggcgtttctg gattctgtca ggtgagcata ccattggggc tacacgaaaa tcttccggtt  1200
tcggtatcat tggtagctaa gtatggctca gacggttttc ttctgagtct tgtggattcc  1260
cttgctgcat ttatttga                                                1278

SEQ ID NO: 243            moltype = AA  length = 425
FEATURE                   Location/Qualifiers
REGION                    1..425
                          note = Description of Artificial Sequence: Synthetic
                           polypeptide
source                    1..425
                          mol_type = protein
                          organism = synthetic construct
SEQUENCE: 243
MATNNDFGAF IEKVTISPTS TSSSPPSLQG LTFAIKDIFD VEGRVTGFGN PDWLRTHSAA  60
TSTAPVVSSL LEAGATALGI TIMDEMAYSI NGENAHYGTP RNPIAFDRVP GGSSSGSAVA  120
VAARLVDFSI GTDTGGSVRV PASYCGIFGF RPSHGAVSTV GLTPMAQSFD TVGWFARDTA  180
TLKRVGCVLL QQHHLNPIEP SQLIIADDCF KLCSVPHDLL VQPLVGSVEK SFGGNTVVKK  240
VNLGEYIGQN VPSLKHFMTS DDVTTQQEFC IPSLMALSSS MRLLQRHEFK INHGAWISSV  300
KPEFGPGISE RIEEAIRTSD EKIDHCRSVK SELITALSTL LGEKGVLVIP TVPGPPPHLQ  360
ANVAALESFR SRAFSLLSIA GVSGFCQVSI PLGLHENLPV SVSLVAKYGS DGFLLSLVDS  420
LAAFI                                                              425

SEQ ID NO: 244            moltype = DNA  length = 1248
FEATURE                   Location/Qualifiers
misc_feature              1..1248
                          note = Description of Artificial Sequence: Synthetic
                           polynucleotide
source                    1..1248
                          mol_type = other DNA
                          organism = synthetic construct
SEQUENCE: 244
atgggttctt gtaaagaaga agaaaaaact gatcaacaac caaaatggtt atgggttaat  60
ggacctataa tagtaggtgc tggaccttct ggtttagcag tttcagcttc tcttaaagaa  120
aatggagtcc cttcacttat tcttgaaaga agtgattgta ttgcttcttt atggcaacaa  180
aaaacctatg atcgtttaaa acttcatctc cctaaacagt tttgtcaact cccattattt  240
ggttttcctg aaaatttccc taaataccct tcaaaaaaac agttcatttc ttacttagag  300
gattatgcta aacactttgg tataattccc aagtttaaac agtctgtaaa agttgcagaa  360
tttgatcatg ttagtggatt ttggaaggtg gaaactcaag attttttgta tctttcaaag  420
tggttgattg tggctacagg ggaaaatgca gagccagtta taccagaaat tcaagggatt  480
ggtaagttta aaggaacagt aatgcatact agtctttata agtctggtac tgagtttaat  540
aatcaaaggg ttttggtaat tggctgtgga aattctggta tggaagttag cttggacctt  600
tgtagacata atgccatccc tcacatggtc gtcagaaatt ccgtgcatat tttaccaagg  660
gaaatgttag ggatatcaac attttcaata gcaatggcac ttctcaaatg gttgcctata  720
agagttgttg acaagttgct attactagta gccaatttga ccttaggtag cacagataag  780
ttaggtctcc ggcgaccaaa aaccggtcca cttgaactga aaaatgccac cggaaaaact  840
ccggtactcg acgttggtgc attgtcacaa ataagaaatg gaaaaattca gattatgcac  900
ggtgtgaagg agataactaa aataggagca aagtctatag atggaaaaga aggagaattt  960
gattcaataa tcctagcaac tggatacaaa agcaatgttc cttcttggct taagggaact  1020
gacttcttca cagaacaagg gatgccaaaa acaccatttc ctaatggctg gaaaggggaa  1080
aatggattat acacggtggg gtttacaaga agagggcttt tagggactgc aaatgatgca  1140
aaaaacattg ccagggatat tagtgatcaa tggaggaaat acaagggctt ctgcaaaaat  1200
ttttgtactt caagaaatct atcagatagc cagggtatat gtttttag               1248

SEQ ID NO: 245            moltype = AA  length = 415
```

```
FEATURE                Location/Qualifiers
REGION                 1..415
                       note = Description of Artificial Sequence: Synthetic
                        polypeptide
source                 1..415
                       mol_type = protein
                       organism = synthetic construct
SEQUENCE: 245
MGSCKEEEKT DQQPKWLWVN GPIIVGAGPS GLAVSASLKE NGVPSLILER SDCIASLWQQ  60
KTYDRLKLHL PKQFCQLPLF GFPENFPKYP SKKQFISYLE DYAKHFGIIP KFKQSVKVAE  120
FDHVSGFWKV ETQDFLYLSK WLIVATGENA EPVIPEIQGI GKFKGTVMHT SLYKSGTEFN  180
NQRVLVIGCG NSGMEVSLDL CRHNAIPHMV VRNSVHILPR EMLGISTFSI AMALLKWLPI  240
RVVDKLLLLV ANLTLGSTDK LGLRRPKTGP LELKNATGKT PVLDVGALSQ IRNGKIQIMH  300
GVKEITKIGA KSIDGKEGEF DSIILATGYK SNVPSWLKGT DFFTEQGMPK TPFPNGWKGE  360
NGLYTVGFTR RGLLGTANDA KNIARDISDQ WRKYKGFCKN FCTSRNLSDS QGICF       415

SEQ ID NO: 246         moltype = DNA  length = 1167
FEATURE                Location/Qualifiers
misc_feature           1..1167
                       note = Description of Artificial Sequence: Synthetic
                        polynucleotide
source                 1..1167
                       mol_type = other DNA
                       organism = synthetic construct
SEQUENCE: 246
atgggttctt ataaagaaga agaaaaaacc gatcaacaac caaaatggtt atgggttaat  60
ggacctataa tagtaggtgc tggaccttct ggtttagcag tttcagcttg tcttaaagaa  120
aatggagtcc cttcacttat tcttgaaaga agtgattgta ttgcttcttt atggcaacaa  180
aaaacttatg atcgtttaaa acttcatctc cctaaacagt tttgtcaact cccattattt  240
ggttttcctg aaaattttcc taaatacccct tcaaaaaaac tgttcatttc ttacttagag  300
gattatgcta aacactttgg tatagttcct aagtttaaac agtctgttaa agttgcagaa  360
tttgatcatg ttagtggatt ttggaaggta gaaactcaag attttttgta tctttcaaaa  420
tggttgattg tggctacagg agaaaatgca gagccagtaa taccagaaat tcaagggatt  480
gataagttta aaggagcggt gttgcatact agtgtttata agtcaggtac tgagtttaat  540
aatcaaaggg ttttggtaat tggttgtgga aattctggta tggaagttag cttggacctt  600
tgtagacata atgccatccc tcacatggtc gtcagaaatt ctgtgcatat tttaccaagg  660
gaaatgttag ggatatcaac attttcaata gcaatggcac ttctcaaatg gttgcctata  720
agagtagttg acaagttgct gttactagta gcaaatttga ccttaggtag cacagataag  780
ttaggtctcc ggcgaccaaa aaccggtcca cttgaactga aaaatgccac ggaaaaactc  840
gtctcgacgt tgattatgca cggtgtgaag gagataacta aaataggagc aaagtttata  900
gatggaaaag aaggagaata tgattcaata atcttagcaa ctggatacaa aagcaatgtt  960
ccttcttggc ttaagggaac tgacttcttc acagaacaag ggatgccaaa gacaccattt  1020
ccaaatggtt ggaaaggggga aaatggatta tacacagtgg ggtttacaag aagagggctt  1080
ttagggactg caaatgatgc aaaaaaaatt gccagggaca taagtgatca atggaggaaa  1140
tacaagggct tctgcaaaaa cttttga                                    1167

SEQ ID NO: 247         moltype = AA  length = 388
FEATURE                Location/Qualifiers
REGION                 1..388
                       note = Description of Artificial Sequence: Synthetic
                        polypeptide
source                 1..388
                       mol_type = protein
                       organism = synthetic construct
SEQUENCE: 247
MGSYKEEEKT DQQPKWLWVN GPIIVGAGPS GLAVSACLKE NGVPSLILER SDCIASLWQQ  60
KTYDRLKLHL PKQFCQLPLF GFPENFPKYP SKKLFISYLE DYAKHFGIVP KFKQSVKVAE  120
FDHVSGFWKV ETQDFLYLSK WLIVATGENA EPVIPEIQGI DKFKGAVLHT SVYKSGTEFN  180
NQRVLVIGCG NSGMEVSLDL CRHNAIPHMV VRNSVHILPR EMLGISTFSI AMALLKWLPI  240
RVVDKLLLLV ANLTLGSTDK LGLRRPKTGP LELKNATEKL VSTLIMHGVK EITKIGAKFI  300
DGKEGEYDSI ILATGYKSNV PSWLKGTDFF TEQGMPKTPF PNGWKGENGL YTVGFTRRGL  360
LGTANDAKKI ARDISDQWRK YKGFCKNF                                     388

SEQ ID NO: 248         moltype = DNA  length = 1833
FEATURE                Location/Qualifiers
misc_feature           1..1833
                       note = Description of Artificial Sequence: Synthetic
                        polynucleotide
source                 1..1833
                       mol_type = other DNA
                       organism = synthetic construct
SEQUENCE: 248
atgataactt tatctgattt ctaccatgtt atgactgctg ttgtgccact ttatgtggct  60
atgatattag cttatggttc tgttaaatgg tggaagattt tttcacctga ccagtgttct  120
ggtattaaca gatttgttgc acttttcgca gttccacttc tctctttcca ctttatagct  180
gctaataatc cttacactat gaacatacgg ttcattgctg ctgacactct tcagaaactt  240
attgttcttg gagctcttgc tatttgggct aattttagca aaaggggtag tttagaatgg  300
agtataacac tcttttcttt atcaactctt ccaaatactt tagttatggg tattcctttg  360
ttaaaaggaa tgtatggtga tttttcaggg agtttaatgg ttcaaatagt tgtactacag  420
```

```
tgtattattt ggtacacttt gatgcttttt atgtttgagt tcagaggtgc aaggatgctg  480
atctctgagc aatttcctga tactgctggc tcaattgtct caatccatgt tgattctgat  540
gtcatgtcat tagatggtag acaagttttg gaaactgaag ctgaagtgaa agaagatgga  600
aaacttcatg ttactgtgag aaaatcaaat gcctcaaggt ctgatatatt ttcaagaagg  660
tcgcagggat ttcttctac aactccaaga ccatcaaatt taacaaatgc agagatttac  720
tctctacaat cttcaagaaa tccaactcca agagggtcaa gttttaacca tactgatttt  780
tactcaatgg ttgctggtgg gagaaactca aactttggtg caaatgatgt ttatgggatg  840
tcagcttcaa gaggaccaac tcctagacct tcaaattatg aggaagaaag tggaaaatca  900
agatttaatt acaaccatgg agctgcagca caacaaagta atactaataa taatactact  960
cattatccag ctccaaatcc tggtatgttt tcacctagta atggtgcaaa agcagtgggt  1020
tctaacacta ataacaagaa aggtaacaaa ggagaggaag gtggtaaaga tcttcatatg  1080
tttgtttgga gttcaagtgc ttctcctgtt tctgatgtat ttggtggtca tgattatgga  1140
gctaatttag accagaatac agctaaggat gtaagagtac ctatctctcc tggaaaagtt  1200
gaggtgcaaa gaaacaatca agaaaactac atggagagag atgactttag ctttgcaaat  1260
agagatgcag aaatgaatat tcacaaccaa gaaggtgaaa aaggtggaga aaataaagca  1320
aaggttatgc caccaacaag tgtaatgact aggcttatac taattatggt ttggaggaaa  1380
cttattagaa atccaaacac ttattcaagc ttgtttggtc tcacttggtc tctagtttca  1440
ttcaggtgga atttgaagat gcctgctata attgcacagt ccatatctat attgtcagat  1500
gcaggacttg gcatggcaat gttcagtcta ggtctgttta tggctttgca accaaggata  1560
atagcatgtg ggaattctac agcagctttt gctatggctg tgagattcct tacaggtcca  1620
gctgtcatgg cagctgcttc cattgctgtt ggccttcgtg gagttctctt acacgtagcc  1680
attgtacagg cagctctacc ccaaggaatt gtcccctttg tcttcgccaa ggaatacaac  1740
gttcaccctg acattcttag cacgggtgtc atttttggga tgttgattgc cttgccgatt  1800
acactggtct actacatttt gatgggactt taa                                1833
```

```
SEQ ID NO: 249          moltype = AA  length = 610
FEATURE                 Location/Qualifiers
REGION                  1..610
                        note = Description of Artificial Sequence: Synthetic
                         polypeptide
source                  1..610
                        mol_type = protein
                        organism = synthetic construct
SEQUENCE: 249
MITLSDFYHV MTAVVPLYVA MILAYGSVKW WKIFSPDQCS GINRFVALFA VPLLSFHFIA  60
ANNPYTMNIR FIAADTLQKL IVLGALAIWA NFSKRGSLEW SITLFSLSTL PNTLVMGIPL  120
LKGMYGDFSG SLMVQIVVLQ CIIWYTLMLF MFEFRGARML ISEQFPDTAG SIVSIHVDSD  180
VMSLDGRQVL ETEAEVKEDG KLHVTVRKSN ASRSDIFSRR SQGFSSTTPR PSNLTNAEIY  240
SLQSSRNPTP RGSSFNHTDF YSMVAGGRNS NFGANDVYGM SASRGPTPRP SNYEEESGKS  300
RFNYNHGAAA QQSNTNNNTT HYPAPNPGMF SPSNGAKAVG SNTNNKKGNK GEEGGKDLHM  360
FVWSSSASPV SDVFGGHDYG ANLDQNTAKD VRVPISPGKV EVQRNNQENY MERDDFSFAN  420
RDAEMNIHNQ EGEKGGENKA KVMPPTSVMT RLILIMVWRK LIRNPNTYSS LFGLTWSLVS  480
FRWNLKMPAI IAQSISILSD AGLGMAMFSL GLFMALQPRI IACGNSTAAF AMAVRFLTGP  540
AVMAAASIAV GLRGVLLHVA IVQAALPQGI VPFVFAKEYN VHPDILSTGV IFGMLIALPI  600
TLVYYILMGL                                                          610
```

```
SEQ ID NO: 250          moltype = DNA  length = 1191
FEATURE                 Location/Qualifiers
misc_feature            1..1191
                        note = Description of Artificial Sequence: Synthetic
                         polynucleotide
source                  1..1191
                        mol_type = other DNA
                        organism = synthetic construct
SEQUENCE: 250
atgtgtggca cagaggcttg tcttatcaag tgttctccag tcccttgtgt gactcctgaa  60
acaagagaaa atggcactct catcaagtgg gatactctta tcaatcttga tcatggtgat  120
ccagtaatgt atgaatcata ctggcgaaag atgggaaaca ggtgtgacat tacattcagt  180
ggttatcagt cattgagtta ttttgctaac gccaagaact tgtgctggtt ccttgagcca  240
aaactagaag aagagatcaa gaggctgcac aatgtggttg gaaatgcaat tgtggatgat  300
cattatatcg tcgttgggac aggatcaagc cagcttatac aggctgcact ctatgctctt  360
tctcctacag atgaacctga accaatcagt gtagtttcag ctgcaccttt ctattcgtca  420
tatccagaag tgactgattt tgtgcgttca gggctgtaca aatgggcagg agatgcaaga  480
aattttgaga aagatggacc atatattgag ttcattacat ctccaaataa cccagatggg  540
gttactcgag agcctgtagt taatggaatt caagggatat taattcatga tttagcttat  600
tactggccac agtacactgc tattacctct cctgccaaat atgatgttat gctctttaca  660
gtttccaaat gcactggcca tgctggatcc agaattggtt gggctcttgt tagggacaaa  720
gaggtggcta ggaagatgac aaaattcatg gaaattagca caataggggt atcaaaggaa  780
gctcaattga gagctgcaaa gattcttgga ctgatttctg atagctgttt agatcccaca  840
ttggaaaact tctttgagta tagtcaatct cacatgacta aaagatggca gaggttaaga  900
gaagttgtta agagcagtga ccttttcact ctccagaaat atccacttca gtattgccac  960
ttcacaagag acttctatga atcacaccct gcttttgcat ggctaatgtg caaaggaagt  1020
gaagatgacc ttgagaagct tcttaaagga tacaagattc aaacaaggag tggaagaaaa  1080
tttgggagtg atccaaaatg tgttaggata agtatgctga gtagggatga agacttcaac  1140
attttttgc agaggcttat gtctattcaa ggagttacaa atggaaatta a            1191
```

```
SEQ ID NO: 251          moltype = AA  length = 396
FEATURE                 Location/Qualifiers
REGION                  1..396
```

```
                        note = Description of Artificial Sequence: Synthetic
                         polypeptide
source                  1..396
                        mol_type = protein
                        organism = synthetic construct
SEQUENCE: 251
MCGTEACLIK CSPVPCVTPE TRENGTLIKW DTLINLDHGD PVMYESYWRK MGNRCDITFS  60
GYQSLSYFAN AKNLCWFLEP KLEEEIKRLH NVVGNAIVDD HYIVVGTGSS QLIQAALYAL  120
SPTDEPEPIS VVSAAPFYSS YPEVTDFVRS GLYKWAGDAR NFEKDGPYIE FITSPNNPDG  180
VTREPVVNGI QGILIHDLAY YWPQYTAITS PAKYDVMLFT VSKCTGHAGS RIGWALVRDK  240
EVARKMTKFM EISTIGVSKE AQLRAAKILG LISDSCLDPT LENFFEYSQS HMTKRWQRLR  300
EVVKSSDLFT LQKYPLQYCH FTRDFYESHP AFAWLMCKGS EDDLEKLLKG YKIQTRSGRK  360
FGSDPKCVRI SMLSRDEDFN IFLQRLMSIQ GVTNGN                           396

SEQ ID NO: 252          moltype = DNA  length = 4062
FEATURE                 Location/Qualifiers
misc_feature            1..4062
                        note = Description of Artificial Sequence: Synthetic
                         polynucleotide
source                  1..4062
                        mol_type = other DNA
                        organism = synthetic construct
SEQUENCE: 252
atggaacaga aaaaagggaa tttagttttt gcagtaaatg gagagaggtt tgagttgcca  60
aatattgacc cctctactac tttacttcag ttcttgcgtt ctgagacttg tttcaagagt  120
cctaaacttg gttgtggtga aggtggttgt ggggcttgtg ttgttctggt ctcaaagtat  180
gatcctaagc ttaaaaaggt cgaagatttt agcgcgagtt catgccttac acttctttgt  240
agtttaaatg gttactcaat tactacaagt gaaggccttg ggaacaccag agatggtttt  300
cactctattc atgaaagatt tgctggtttc catgcttctc aatgtggctt ttgcactcct  360
ggaatgtgta tgtcattttt ctcagctctt gtcaatgccg ataaaggaaa caagccggat  420
cctccaccag gattttctaa gcttacttca tctgaagctg aaaaggccat agcagggaac  480
ctctgtcggt gcactggata ccggcctatt gctgatgcct gcaagacttt tgctgctgat  540
attgatatag aggatttggg gttcaattct ttttggaaaa agggagattc caaggaattg  600
aaaataagta aattacctcc ttatgatcca accaagaatt ttagtacata tccggagttc  660
ttgaaaagtg aatgcgccac aaatttggac tccacaaggt acccttggta cagtcctact  720
tccattgaag agctgcagag cttgttgaac tccagtgtgg cggataatgg tgcgagcttt  780
aaactggtcg ttggtaatac aggcacaggt tattataagg aaactcagcg atatgatcat  840
tacgttgatc tcaggtatat tcctgaactc tcaatcatca aaagagatca gacaggcatt  900
gaagtgggag caactgtgac tatctctaaa cttatagcat tcttgaaaga ggaaaacaaa  960
gtcaatttgg gtccatatgg gaagctggtg tccgaaaagc tggttaacca catggagaag  1020
attgcttcac catttgttag gaactctgct agtgtgggag gaaatttggt tatggcacaa  1080
aagaatggtt ttccttcaga tattgctaca ttatttcttg gtgtgggtgc taccgttagc  1140
ttgatgaccg gtcatggact tgaaaaactc acatgggagg aattattatc gagaccgcca  1200
atagactcaa ggaccgtgct tctaagtgtt tggatcccat ttaaagaaga gagttctctc  1260
aaaaccttta ctaagttttt gtttgagacc tatcgagctg ctccccgacc tcatgggaat  1320
gcaatagcat atgtaaacgc tgcttttggg gttgatgttt ctctctgcca gaacggcatc  1380
ctgataaacg atatccggct ggcgtttggt gcttatggta caaaacatgc aacaagggct  1440
aaaatggtag aggaatatct aacagggaaa atattaaatg cacatgtttt aagtgaagca  1500
cttaaattag tcaaactagc tgtggtaccg gaagatggga ctttacaccc agagtataga  1560
tcaagcttgg ccgtcagtta tgtttttcag tttctttatc ccttagttga tgttcattct  1620
gctattgtca atggaatcaa tgacatctca ctcgaggaag tttcaaaaag tagtaatgat  1680
agtcagggga gaaaacaaac actactgtct tcttctaagc aggttgtgga atcaagtagc  1740
gagcactatc cagtgggtga accaatgaag aaggttggag ctgccatgca agctgctggt  1800
gaagctgttt atgtagatga cattccgtca ccaccaaact gcctgcacgg agcatttatc  1860
tacagcacaa aaccattagc aggtgtaaaa ggaatccatc ttgagtctaa ttcattaaca  1920
gatggattca ccgacattat tactttcaag gatatcccaa gtggagggtc aaatgtagga  1980
tctattacaa tgtttggtcc tgagccttta ttcgcagacg atctcgcccg atgtgctggc  2040
gacagaattg cagttgcggt tgctgacact cagaggtctg ctgatgtggc tgccacaaca  2100
gcccttgttg aatatgacac tgtaaatgta aattcaccga ttttaactgt cgaggaagct  2160
gttgagaaat ctagcttttt ccaaatcccg ccatttctat atccaaaaca ggttggcgat  2220
ttctcaaaag gaatggctga agctgatcac aagattctct ctgctgaggt aagacttggt  2280
tccgagtact atttttatat ggagacacag actgcccttg caattccaga tgaagacaac  2340
tgtatggttg tttatacttc aagccagtgc cctgagtatg cgcaaaatgt gattgccagt  2400
tgtcttggtg ttcctgaaca caatatccgt gttattacaa gaagggttgg aggtggcttt  2460
gggggcaagg cagtcagagc aatgcctgtt tcgacagcct gtgcacttgc agcatacaag  2520
ttaaggcggc ctgtgaggat aaatgtcaac cggaacagcg acatgataat gacaggagga  2580
agacacccaa tgaaagtaac atacagtgta ggattcaagt caagcggaaa gatcacagca  2640
ttacatcttg atatattgat aaatgctggg atttcggaag atataagccc cctcctacca  2700
tcaaatgtga ttaaagcatt aaagaaatat gattggggtg ccttatcttt tgatgtaaaa  2760
gtatgcaaga cgaatcttac cagcaaatca gctatgcggg cccctgggga ggtgcaagga  2820
tcttatattg ccgaagctat aatggagcat gtagcgagtt tactgtcaaa ggaggtggat  2880
tctgtcagaa ataataatgt tcatacattg gaaagcatta atttattcta tgataacatc  2940
gtaactgaag taggagaata tacgttgcct agtatcatgg ataagttggc cgtgtcctcg  3000
agctttttcc aacgtagcaa gatggtggaa cagtttaacc agaaaaacac atggaagaaa  3060
aagggtattt ctcgactgcc aataatgttt gaagctatgc aacgaccgac cccaggaaaa  3120
gtcagtatcc tgtcggatgg atcaattgtt gtagaggttg gagggattga aatcggccaa  3180
gggctatgga caaaggttag acagatgact gcatatgctc ttggtttaat tgaaagtagt  3240
tggagtgaag aacttgtagg gaaagtacga gtcatacaag cagacagctt aagcttagtg  3300
caaggtgggt atacggctgg aagcactaca tcggaatcaa gctgtgaagc agttagacgt  3360
```

```
tgctgtagtg tcttggttga aagactgact cctctgaaga aacagttgca ggaacaaaat  3420
ggctctcttg attggccaac gctcattcgc caggcacaaa tgcaagcagt aaacttagca  3480
gcaaattctt attatgtacc agaatccagt tccatgagtt atttgaactt tggtgccgct  3540
gtcagtgagg tggatataga tattcttact ggagagactg ccattttgca gtcggatatt  3600
atttacgact gtgggcagag cttgaatcca gctgtcgata tgggacagat tgaaggagct  3660
tatgtacaag gaattggatt ttttatgcat gaagaatatc ttacaaacga cgatgggttg  3720
atggtctcaa atagcacttg gacatacaag atcccaacaa tcgacaccat accccagaat  3780
ttcaacgttc atttggtaaa cagtggacat cacgaaaaac gtgttctctc ttccaaagca  3840
tctggtgaac cgccactgct acttgcagct tcagtccatt gtgcaacaag agcggctgtt  3900
aaagcagcaa gagaacaact caaagtttgg ggcaagctcg acgagtctgc ttcagaattc  3960
tatctggatg ttcctgccat attacctgtt gtgaagacgc agtgtggtct agattatgtg  4020
gagaaatact tagaaagttt actgactcag aaatctaact aa                     4062

SEQ ID NO: 253          moltype = AA  length = 1353
FEATURE                 Location/Qualifiers
REGION                  1..1353
                        note = Description of Artificial Sequence: Synthetic
                         polypeptide
source                  1..1353
                        mol_type = protein
                        organism = synthetic construct
SEQUENCE: 253
MEQKKGNLVF AVNGERFELP NIDPSTTLLQ FLRSETCFKS PKLGCGEGGC GACVVLVSKY  60
DPKLKKVEDF SASSCLTLLC SLNGYSITTS EGLGNTRDGF HSIHERFAGF HASQCGFCTP  120
GMCMSFFSAL VNADKGNKPD PPPGFSKLTS SEAEKAIAGN LCRCTGYRPI ADACKTFAAD  180
IDIEDLGFNS FWKKGDSKEL KISKLPPYDP TKNFSTYPEF LKSECATNLD STRYPWYSPT  240
SIEELQSLLN SSVADNGASF KLVVGNTGTG YYKETQRYDH YVDLRYIPEL SIIKRDQTGI  300
EVGATVTISK LIAFLKEENK VNLGPYGKLV SEKLVNHMEK IASPFVRNSA SVGGNLVMAQ  360
KNGFPSDIAT LFLGVGATVS LMTGHGLEKL TWEELLSRPP IDSRTVLLSV WIPFKEESSL  420
KTFTKFLFET YRAAPRPHGN AIAYVNAAFG VDVSLCQNGI LINDIRLAFG AYGTKHATRA  480
KMVEEYLTGK ILNAHVLSEA LKLVKLAVVP EDGTLHPEYR SSLAVSYVFQ FLYPLVDVHS  540
AIVNGINDIS LEEVSKSSND SQGRKQTLLS SSKQVVESSS EHYPVGEPMK KVGAAMQAAG  600
EAVYVDDIPS PPNCLHGAFI YSTKPLAGVK GIHLESNSLT DGFTDIITFK DIPSGGSNVG  660
SITMFGPEPL FADDLARCAG DRIAVAVADT QRSADVAATT ALVEYDTVNV NSPILTVEEA  720
VEKSSFFQIP PFLYPKQVGD FSKGMAEADH KILSAEVRLG SEYYFYMETQ TALAIPDEDN  780
CMVVYTSSQC PEYAQNVIAS CLGVPEHNIR VITRRVGGGF GGKAVRAMPV STACALAAYK  840
LRRPVRINVN RNSDMIMTGG RHPMKVTYSV GFKSSGKITA LHLDILINAG ISEDISPLLP  900
SNVIKALKKY DWGALSFDVK VCKTNLTSKS AMRAPGEVQG SYIAEAIMEH VASLLSKEVD  960
SVRNNNVHTL ESINLFYDNI VTEVGEYTLP SIMDKLAVSS SFFQRSKMVE QFNQKNTWKK  1020
KGISRLPIMF EAMQRPTPGK VSILSDGSIV VEVGGIEIGQ GLWTKVRQMT AYALGLIESS  1080
WSEELVGKVR VIQADSLSLV QGGYTAGSTT SESSCEAVRR CCSVLVERLT PLKKQLQEQN  1140
GSLDWPTLIR QAQMQAVNLA ANSYYVPESS SMSYLNFGAA VSEVDIDILT GETAILQSDI  1200
IYDCGQSLNP AVDMGQIEGA YVQGIGFFMH EEYLTNDDGL MVSNSTWTYK IPTIDTIPQN  1260
FNVHLVNSGH HEKRVLSSKA SGEPPLLLAA SVHCATRAAV KAAREQLKVW GKLDESASEF  1320
YLDVPAILPV VKTQCGLDYV EKYLESLLTQ KSN                               1353

SEQ ID NO: 254          moltype = DNA  length = 1278
FEATURE                 Location/Qualifiers
misc_feature            1..1278
                        note = Description of Artificial Sequence: Synthetic
                         polynucleotide
source                  1..1278
                        mol_type = other DNA
                        organism = synthetic construct
SEQUENCE: 254
atggagacat gtgaatatgg agctctcatt gagaaattca cactgcaacc aatttgctct  60
tcttcagagc aagtcccctt gaatggctta acctttgccg tgaaagacat atttgatgtg  120
gaaggacata tcactggttt tggaaatcca gactgggcca agacccattc tgcggcaaca  180
tctactgcaa caactgtgct cactcttttg aaggctggtg ctacttgtat tggtaaaact  240
gtcatggatg aaatggctta cagcataaat ggtgaaaatg ttcattatgg cacgcctttg  300
aatcctgttt caccagatcg ggtacctgga gggtcttcaa gtggatctgc agttgcagtc  360
ggtgcaaagc ttgtagattt ctccttaggg actgacactg gaggaagtgt tagagttcct  420
gcatcatatt gtggaattta tggtattcga ccttctcatg gagttgtttc aactgccgga  480
gtcacaccta tggcacaaag ctttgataca gtggggtggt ttgcaaggga tcctctgatc  540
ttaaagcaag ttggaagagt cctacttcaa tctccccaaa tgaaatccgt gcgtccaact  600
aacagtatca ttgcagaaga ctgttttaag ctcctggatt ccaagagtaa ccaattgatt  660
gaagtacttg ttaactcagt ggagaagcta tatggaagtc atatgattaa atacgtgagt  720
gtaggggatt atattgaggg aaatgttcca agtttgaaga aattcatgac gcttggaact  780
ggcaatgatg aatcttacat tccatccttg ctagctctct cagctgccat gcggttgctt  840
caaaggtatg aattcaagga gaatcatgga gaatgggtta gtacagtcaa acctagttta  900
ggtccgggaa tagcagaacg cgtatgggaa gcgctgaagg ccacagatga aaatattgat  960
gtgtgccact ctgtgaaggc tgagcttcga gcagctctca ctgctctcct tggggattct  1020
ggtatacttg caatcccaac tgttcctgga cctccaccaa aactaagaag cgagacaagt  1080
gcattggaag gatttcgtgt taaggctttt agtctgttat caattgctgg agtatctgga  1140
ttttgccagg tcagcatacc tctggggatg caagacaatc ttcctatatc agtttcttta  1200
ctggtaaaac atggttcaga ctggttgctg cttgatgctg ttgaagctat tcacaaagtt  1260
ctcaaggggc aaatctga                                                1278

SEQ ID NO: 255          moltype = AA  length = 425
```

-continued

```
FEATURE                Location/Qualifiers
REGION                 1..425
                       note = Description of Artificial Sequence: Synthetic
                        polypeptide
source                 1..425
                       mol_type = protein
                       organism = synthetic construct
SEQUENCE: 255
METCEYGALI EKFTLQPICS SSEQVPLNGL TFAVKDIFDV EGHITGFGNP DWAKTHSAAT  60
STATTVLTLL KAGATCIGKT VMDEMAYSIN GENVHYGTPL NPVSPDRVPG GSSSGSAVAV  120
GAKLVDFSLG TDTGGSVRVP ASYCGIYGIR PSHGVVSTAG VTPMAQSFDT VGWFARDPLI  180
LKQVGRVLLQ SPQMKSVRPT NSIIAEDCFK LLDSKSNQLI EVLVNSVEKL YGSHMIKYVS  240
VGDYIEGNVP SLKKFMTLGT GNDESYIPSL LALSAAMRLL QRYEFKENHG EWVSTVKPSL  300
GPGIAERVWE ALKATDENID VCHSVKAELR AALTALLGDS GILAIPTVPG PPPKLRSETS  360
ALEGFRVKAF SLLSIAGVSG FCQVSIPLGM QDNLPISVSL LVKHGSDWLL LDAVEAIHKV  420
LKGQI                                                              425

SEQ ID NO: 256         moltype = AA  length = 6
FEATURE                Location/Qualifiers
REGION                 1..6
                       note = Description of Artificial Sequence: Synthetic 6xHis
                        tag
source                 1..6
                       mol_type = protein
                       organism = synthetic construct
SEQUENCE: 256
HHHHHH                                                             6
```

What is claimed is:

1. Cured tobacco material from a modified tobacco plant comprising no or reduced suckers compared to a control tobacco plant of the same variety when grown under comparable conditions, wherein the modified tobacco plant comprises a heterologous axillary meristem-specific promoter functional in a central zone, a peripheral zone, a rib zone, or any combination thereof operably linked to a nucleotide sequence encoding a mitogen-activated protein kinase kinase polypeptide having an amino acid sequence at least 95% identical to SEQ ID NO: 233.

2. The cured tobacco material of claim 1, wherein the cured tobacco material comprises leaf material.

3. The cured tobacco material of claim 1, wherein the cured tobacco material comprises stem material.

4. The cured tobacco material of claim 1, wherein the cured tobacco material is selected from the group consisting of sun-cured tobacco material, flue-cured tobacco material, air-cured tobacco material, and fire-cured tobacco material.

5. The cured tobacco material of claim 1, wherein the mitogen-activated protein kinase kinase polypeptide comprises an amino acid sequence 100% identical to SEQ ID NO: 233.

6. The cured tobacco material of claim 1, wherein the mitogen-activated protein kinase kinase polypeptide is encoded by SEQ ID NO: 232.

7. The cured tobacco material of claim 1, wherein the heterologous axillary meristem-specific promoter comprises a nucleic acid sequence having at least 95% sequence identity to a polynucleotide selected from the group consisting of SEQ ID NOS: 113, 115-118, 148, 149, 151, 153, 155, 157, 159, and 204.

8. The cured tobacco material of claim 1, wherein the modified tobacco plant is of a variety selected from the group consisting of BU 64, CC 101, CC 200, CC 13, CC 27, CC 33, CC 35, CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpão, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY 907LC, KTY14×L8 LC, Little Crittenden, McNair 373, McNair 944, male sterile KY 14×L8, Narrow Leaf Madole, MS KY171, Narrow Leaf Madole (phph), MS Narrow Leaf Madole, MS TND950, PD 7302LC, PD 7305LC, PD 7309LC, PD 7312LC, PD 7318LC, PD 7319LC, MSTKS 2002, TKF 2002, TKF 6400, TKF 4028, TKF 4024, KT206LC, KT209LC, KT210LC, KT212LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique', PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, a TR (Tom Rosson) Madole, VA 309, and VA 359.

9. The cured tobacco material of claim 1, wherein the modified tobacco plant is of a type selected from the group consisting of Burley tobacco, Maryland tobacco, bright tobacco, Virginia tobacco, Oriental tobacco, Turkish tobacco, and Galpão tobacco.

10. A cigarette product, cigar product, pipe tobacco product, or smokeless tobacco product comprising the cured tobacco material of claim 1.

11. Cured tobacco material from a modified tobacco plant comprising a heterologous recombinant polynucleotide, wherein the recombinant polynucleotide comprises: (a) an axillary meristem-specific promoter that is functional in a rib zone, a central zone, a peripheral zone, or any combination thereof, and wherein the axillary meristem-specific promoter is operably linked to (b) a structural nucleic acid molecule comprising a nucleic acid sequence, wherein the nucleic acid sequence encodes a mitogen-activated protein kinase kinase polypeptide at least 95% identical or similar-to the amino acid sequence of SEQ ID NO: 233.

12. The cured tobacco material of claim 11, wherein the cured tobacco material comprises leaf material.

13. The cured tobacco material of claim 11, wherein the cured tobacco material comprises stem material.

14. The cured tobacco material of claim 11, wherein the cured tobacco material is selected from the group consisting of sun-cured tobacco material, flue-cured tobacco material, air-cured tobacco material, and fire-cured tobacco material.

15. The cured tobacco material of claim 11, wherein the mitogen-activated protein kinase kinase polypeptide comprises an amino acid sequence 100% identical to SEQ ID NO: 233.

16. The cured tobacco material of claim 11, wherein the mitogen-activated protein kinase kinase polypeptide is encoded by SEQ ID NO: 232.

17. The cured tobacco material of claim 11, wherein the axillary meristem-specific promoter comprises a nucleic acid sequence having at least 95% sequence identity to a polynucleotide selected from the group consisting of SEQ ID NOs: 113, 115-118, 148, 149, 151, 153, 155, 157, 159, and 204.

18. The cured tobacco material of claim 11, wherein the modified tobacco plant is of a variety selected from the group consisting of BU 64, CC 101, CC 200, CC 13, CC 27, CC 33, CC 35, CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpão, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY 907LC, KTY14×L8 LC, Little Crittenden, McNair 373, McNair 944, male sterile KY 14×L8, Narrow Leaf Madole, MS KY171, Narrow Leaf Madole (phph), MS Narrow Leaf Madole, MS TND950, PD 7302LC, PD 7305LC, PD 7309LC, PD 7312LC, PD 7318LC, PD 7319LC, MSTKS 2002, TKF 2002, TKF 6400, TKF 4028, TKF 4024, KT206LC, KT209LC, KT210LC, KT212LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique', PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, a TR (Tom Rosson) Madole, VA 309, and VA 359.

19. The cured tobacco material of claim 11, wherein the modified tobacco plant is of a type selected from the group consisting of Burley tobacco, Maryland tobacco, bright tobacco, Virginia tobacco, Oriental tobacco, Turkish tobacco, and Galpão tobacco.

20. A cigarette product, cigar product, pipe tobacco product, or smokeless tobacco product comprising the cured tobacco material of claim 11.

* * * * *

UNITED STATES PATENT AND TRADEMARK OFFICE
CERTIFICATE OF CORRECTION

| | | |
|---|---|---|
| PATENT NO. | : 12,209,249 B2 | Page 1 of 1 |
| APPLICATION NO. | : 18/476495 | |
| DATED | : January 28, 2025 | |
| INVENTOR(S) | : Dongmei Xu et al. | |

It is certified that error appears in the above-identified patent and that said Letters Patent is hereby corrected as shown below:

In the Claims

Claim 11, Column 286, Line 66, the phrase "or similar-" should be removed.

Signed and Sealed this
Twenty-fifth Day of March, 2025

Coke Morgan Stewart
*Acting Director of the United States Patent and Trademark Office*